United States Patent
Nagamori et al.

(10) Patent No.: US 12,398,111 B2
(45) Date of Patent: Aug. 26, 2025

(54) TRIAZINE COMPOUNDS AND PHARMACEUTICAL USE THEREOF

(71) Applicant: Japan Tobacco Inc., Tokyo (JP)

(72) Inventors: Hironobu Nagamori, Osaka (JP); Ikuo Mitani, Osaka (JP); Masaki Yamashita, Osaka (JP); Takahiro Hotta, Osaka (JP); Yuichi Nakagawa, Osaka (JP); Masatoshi Ueda, Osaka (JP)

(73) Assignee: Japan Tobacco Inc., Tokyo (JP)

( * ) Notice: Subject to any disclaimer, the term of this patent is extended or adjusted under 35 U.S.C. 154(b) by 719 days.

(21) Appl. No.: 17/575,931

(22) Filed: Jan. 14, 2022

(65) Prior Publication Data

US 2023/0011968 A1    Jan. 12, 2023

Related U.S. Application Data

(63) Continuation of application No. 16/396,503, filed on Apr. 26, 2019, now abandoned, which is a (Continued)

(30) Foreign Application Priority Data

Feb. 20, 2014   (JP) .................... 2014-031035

(51) Int. Cl.
    *C07D 251/22*   (2006.01)
    *A61K 31/53*    (2006.01)
    (Continued)

(52) U.S. Cl.
    CPC ........... *C07D 251/22* (2013.01); *A61K 31/53* (2013.01); *A61K 45/06* (2013.01); *A61P 27/06* (2018.01);
    (Continued)

(58) Field of Classification Search
    CPC .. C07D 251/22; C07D 401/04; C07D 401/10; C07D 401/12; C07D 403/10;
    (Continued)

(56) References Cited

U.S. PATENT DOCUMENTS 3,293,247 A   12/1966   Duennenberger et al.
5,955,060 A   9/1999    Huglin et al.
(Continued)

FOREIGN PATENT DOCUMENTS

BE    661225 A     9/1965
CA    2746427 A1   6/2010
(Continued)

OTHER PUBLICATIONS

Chen et al., "Myeloid cell microsomal prostaglandin E synthase-1 fosters atherogenesis in mice," Proceeding of the National Academy of Sciences, Apr. 21, 2014, 111(18):6826-6833.
(Continued)

*Primary Examiner* — Clinton A Brooks
*Assistant Examiner* — Kendall Nicole Heitmeier
(74) *Attorney, Agent, or Firm* — Fish & Richardson P.C.

(57) ABSTRACT

Provided is a compound having an mPGES-1 inhibitory activity and useful for the prophylaxis or treatment of pain, rheumatism, osteoarthritis, fever, Alzheimer's disease, multiple sclerosis, arteriosclerosis, glaucoma, ocular hypertension, ischemic retinal disease, systemic scleroderma and cancer including colorectal cancer.

A compound represented by the formula [I] or a pharmaceutically acceptable salt thereof:
(Continued)

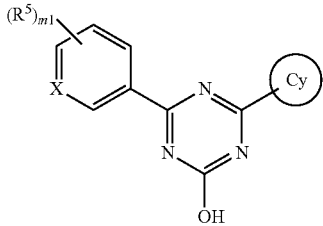

wherein each symbol is as defined in the SPECIFICATION.

10 Claims, 1 Drawing Sheet

Related U.S. Application Data continuation of application No. 14/626,243, filed on Feb. 19, 2015, now abandoned.

(51) Int. Cl.

| | | |
|---|---|---|
| A61K 45/06 | (2006.01) | |
| A61P 9/00 | (2006.01) | |
| A61P 9/10 | (2006.01) | |
| A61P 17/00 | (2006.01) | |
| A61P 19/00 | (2006.01) | |
| A61P 19/02 | (2006.01) | |
| A61P 25/00 | (2006.01) | |
| A61P 25/04 | (2006.01) | |
| A61P 25/28 | (2006.01) | |
| A61P 27/00 | (2006.01) | |
| A61P 27/02 | (2006.01) | |
| A61P 27/06 | (2006.01) | |
| A61P 29/00 | (2006.01) | |
| A61P 35/00 | (2006.01) | |
| A61P 43/00 | (2006.01) | |
| C07D 401/04 | (2006.01) | |
| C07D 401/10 | (2006.01) | |
| C07D 401/12 | (2006.01) | |
| C07D 403/10 | (2006.01) | |
| C07D 405/12 | (2006.01) | |
| C07D 471/10 | (2006.01) | |

(52) U.S. Cl.
CPC ......... *C07D 401/04* (2013.01); *C07D 401/10* (2013.01); *C07D 401/12* (2013.01); *C07D 403/10* (2013.01); *C07D 405/12* (2013.01); *C07D 471/10* (2013.01)

(58) Field of Classification Search
CPC .... C07D 405/12; C07D 471/10; A61K 31/53; A61K 45/06; A61P 27/06; A61P 9/00; A61P 9/10; A61P 17/00; A61P 19/00; A61P 25/28; A61P 29/00; A61P 19/02; A61P 25/00; A61P 25/04; A61P 27/00
See application file for complete search history.

(56) References Cited

U.S. PATENT DOCUMENTS

| | | | |
|---|---|---|---|
| 6,096,753 A | 8/2000 | Spohr et al. | |
| 6,265,405 B1 | 7/2001 | Cox et al. | |
| 6,410,729 B1 | 6/2002 | Spohr et al. | |
| 6,414,149 B1 | 7/2002 | Chu-Moyer et al. | |
| 6,420,385 B1 | 7/2002 | Spohr et al. | |
| 6,465,461 B1 | 10/2002 | Cox et al. | |
| 6,602,875 B2 | 8/2003 | Chu-Moyer et al. | |
| 6,610,698 B2 | 8/2003 | Spohr et al. | |
| 6,649,604 B2 | 11/2003 | Spohr et al. | |
| 6,660,740 B1 | 12/2003 | Chu-Moyer et al. | |
| 6,869,943 B2 | 3/2005 | Chu-Moyer et al. | |
| 6,936,600 B2 | 8/2005 | Chu-Moyer et al. | |
| 8,592,580 B2 | 11/2013 | Lochead et al. | |
| 8,648,200 B2 | 2/2014 | Hughes et al. | |
| 8,716,474 B2 | 5/2014 | Kamimoto et al. | |
| 8,822,521 B2 | 9/2014 | Taggi et al. | |
| 8,871,777 B2 | 10/2014 | Liu et al. | |
| 8,951,999 B2 | 2/2015 | Priepke et al. | |
| 8,952,150 B2 | 2/2015 | Schuster et al. | |
| 9,096,545 B2 | 8/2015 | Gharat et al. | |
| 9,115,121 B2 | 8/2015 | Arnaud et al. | |
| 9,198,433 B2 | 12/2015 | Taggi et al. | |
| 9,439,890 B2 | 9/2016 | Gharat et al. | |
| 10,710,967 B2 * | 7/2020 | Okada ................. | C07D 401/04 |
| 2012/0208839 A1 | 2/2012 | Priepke et al. | |
| 2012/0202806 A1 | 8/2012 | Duerrenberger et al. | |
| 2014/0323436 A1 | 10/2014 | Finkelstein et al. | |
| 2015/0148301 A1 | 5/2015 | Clement-Schatlo et al. | |
| 2015/0266834 A1 | 9/2015 | Nagamori et al. | |
| 2015/0283117 A1 | 10/2015 | Gharat et al. | |
| 2015/0335023 A1 | 11/2015 | Finkelstein et al. | |
| 2016/0339000 A1 | 11/2016 | Gharat et al. | |
| 2017/0057943 A1 | 3/2017 | Mitani et al. | |
| 2018/0200229 A1 | 7/2018 | Gharat et al. | |
| 2020/0087266 A1 | 3/2020 | Nagamori et al. | |
| 2021/0024486 A1 | 1/2021 | Mitani et al. | |

FOREIGN PATENT DOCUMENTS

| | | | | |
|---|---|---|---|---|
| CA | | 2769553 A1 | 3/2011 | |
| CN | | 105586773 A | 5/2016 | |
| IN | 3304/MUM/2013 | | * 10/2013 | |
| JP | | 2002514195 A | 5/2002 | |
| JP | | 2009292754 A | 12/2009 | |
| JP | | 2011525905 A | 9/2011 | |
| JP | | 2012511517 A | 5/2012 | |
| SU | | 220877 A1 | 6/1968 | |
| SU | | 1313854 A1 | 5/1987 | |
| WO | WO 1999/032462 A1 | | 7/1999 | |
| WO | WO 2000/059510 A1 | | 10/2000 | |
| WO | WO 2008/124092 A2 | | 10/2008 | |
| WO | WO 2009/156860 A2 | | 12/2009 | |
| WO | WO 2010/066111 A1 | | 6/2010 | |
| WO | WO 2011/026835 A1 | | 3/2011 | |
| WO | WO 2011/037610 A1 | | 3/2011 | |
| WO | WO 2011/048004 A1 | | 4/2011 | |
| WO | WO 2012/022792 A1 | | 8/2012 | |
| WO | WO 2012/161965 A1 | | 11/2012 | |
| WO | WO 2013/087643 A1 | | 6/2013 | |
| WO | WO 2013/174947 A1 | | 11/2013 | |
| WO | WO 2013/186692 A1 | | 12/2013 | |
| WO | WO-2015059618 A1 * | | 4/2015 | ........... C07D 213/64 |
| WO | WO 2015/125842 A1 | | 8/2015 | |
| ZA | | 9710911 B | 6/1998 | |

OTHER PUBLICATIONS

U.S. Appl. No. 15/228,681, filed Aug. 4, 2016, Gharat et al.
U.S. Appl. No. 16/807,719, filed Mar. 3, 2020, Mitani et al.
Mashkovskiy, "Medicinal Drugs," Doctors Manual, 2001, 1:1-3, 6 pages (with English Translation).
Akitake et al., "Microsomal Prostaglandin E Synthase-I Is Induced in Alzheimer's Disease and Its Deletion Mitigates Alzheimer's Disease-Like Pathology in a Mouse Model", J. Neurosci. Res., 91(7):909-919 (2013).
Alsofrom et al., "A new synthesis of s-triazines," J. Heterocycl. Chem, 1976, 13(4):917-919.
Alvarez-Soria et al., "Long-term NSAID treatment directly decreases COX-2 and mPGES-1 production in the articular cartilage of patients with osteoarthritis," Osteoarthritis and Cartilage, 16(12):1484-1493 (Dec. 2008).
Appendix—Cancer, Jan. 4, 2017, 32 pages.

(56) References Cited

OTHER PUBLICATIONS

Boolbol et al., "Cyclooxygenase-2 Overexpression and Tumor Formation Are Blocked by Sulindac in a Murine Model of Familial Adenomatous Polyposis," Cancer Research, 56:2556-2560 (Jun. 1996).
Brunetti et al., "Synthesis of asymmetrically substituted o-hydroxyphenyl-s-triazines," Helv. Chim. Act, 1972, 55(5):1566-1595 (with English abstract—Abstract on p. 1).
Candelario-Jalil et al., "Ascorbic acid enhances the inhibitory effect of aspirin on neuronal cyclooxygenase-2-mediated prostaglandin $E_2$ production," Journal of Neuroimmunogy, 174(1-2):39-51 (Sep. 2006), Abstract, retrieved on Nov. 4, 2016, Retrieved from <http://www.jni-journal.com/article/S0165-5728(06)00007-5/pdf>, 2 pages.
Castelino, "Lipids and eicosanoids in fibrosis: emerging targets for therapy," Curr Opin Rheumatol., 24(6):649-55 (Nov. 2012), Abstract, retrieved on Nov. 4, 2016, Retrieved from <https://www.ncbi.nlm.nih.gov/pubmed/22810365>, 2 pages.
Cecil Textbook of Medicine, edited by Bennet, J.C., and Plum F., 20th edition, 1:1004-101 (1996).
Chang et al., "Identification and development of mPGES-1 inhibitors: where we are at?," Future Med Chem., 3(15):1909-1934 (Nov. 2011).
Chang et al., "Identification of a Novel Class of Anti-Inflammatory Compounds with Anti-Tumor Activity in Colorectal and Lung Cancers," Invest New Drugs, 30(5):1865-1877 (Oct. 2012).
Cipollone et al., "Overexpression of Functionally Coupled Cyclooxygenase-2 and Prostaglandin E Synthase in Symptomatic Atherosclerotic Plaques as a Basis of Prostaglandin $E_2$-Depending Plaque Instability," Circulation, 104:921-927 (May 2001).
Dallaporta et al., "Towards the Management of Inflammation: Recent Developments of mPGES-1 Inhibitors," Recent patents on CNS Drug Discovery, 5:70-80 (2010).
Dermer et al., Bio/Technology, 12:320 (1994).
Engblom et al., "Microsomal prostaglandin E synthase-1 is the central switch during immune-induced pyresis," Nat Neurosci., 6(11):1137-1138 (2003).
English-Language Translation of International Search Report issued in PCT Application No. PCT/JP2015/054519, published on Aug. 27, 2015, 4 pages.
Fattahi et al., "Positive and negative effects of prostaglandins in Alzheimer's disease," Psychiatry and Clinical Neurosciences, 68:50-60 (May 2013).
Finetti et al., "Pharmacological Inhibition of Microsomal Prostaglandin E Synthase-1 Suppresses Epidermal Growth Factor Receptor-Mediated Tumor Growth and Angiogenesis," PLOS One, 7(7):e40576 (Jul. 2012).
Flach et al., "Topical prostaglandin E2 effects on normal human intraocular pressure", J Ocul. Pharmacol., 4(1):13-18 (1988).
Freshney et al., Culture of Animals Cells, A Manual of Basic Technique, Alan R. Liss, Inc., New York, p. 4, (1983).
Ghassemi et al., "S. 13.3 Pharmacological Inhibition of mPGES-1 Results in Reduced Pro-Fibrotic and Pro-Inflammatory Signalling in Human Scleroderma Fibroblasts," Rheumatology, 51(suppl 2):ii25-ii26 (Feb. 2012).
Goh et al., "Prostaglandin D2 reduces intraocular pressure", Br J Ophthalmol. 72(6):461-464 (Jun. 1988).
Golub et al., Science, 286:531-537 (1999).
Gomez et al., "The role of prostaglandin E2 in human vascular inflammation," PLEFA, 89(2-3):55-63 (Aug. 2013), Abstract, Retrieved Nov. 4, 2016, Retrieved from <http://www.plefa.com/article/S0952-3278(13)00094-X/abstract>, 2 pages.
Gomez-Hernandez et al., "Atorvastatin reduces the expression of prostaglandin E2 receptors in human carotid atherosclerotic plaques and monocytic cells: potential implications for plaque stabilization," J Cardiovasc Pharmacol., 47(1):60-9 (Jan. 2006), Abstract, retrieved on Nov. 4, 2016, Retrieved from <https://www.ncbi.nlm.nih.gov/pubmed/16424787>, 2 pages.
Guo et al., "Misoprostol Reverse Hippocampal Neuron Cyclooxygenase-2 Downstream Signaling Imbalance in Aluminum-Overload Rats," Curr Alzheimer Res., 13(9):1006-1016 (Sep. 2016).
Guo et al., "mPGES-1: A New Target for Drug Development", Progress in Pharmaceutical Sciences, 2008, 32(3):103, Abstract provided.
Hamdy et al., "New pyridone, thioxopyridine, pyrazolopyridine and pyridine derivatives that modulate inflammatory mediators in stimulated RAW 264.7 murine macrophage," EP J Med Chem., 2009, 44:4547-4556.
Hara et al., "Prostaglandin E synthases: Understanding their pathophysiological roles through mouse genetic models," 92(6):651-659 (Jun. 2010), Abstract, retrieved on Nov. 4, 2016, retrieved from <http://www.sciencedirect.com/science/article/pii/S0300908410000519>, 3 pages.
Hassan, "mPGES-1 as a novel target for arthritis," Current Opinion in Rheumatology, 16(5):623-627 (Sep. 2004) Abstract.
He et al., "Molecular Docketing and Competitive Binding Study Discovered Different Binding Modes of Microsomal Prostaglandin E Synthase-1 Inhibitors," J. Chem. Inf. Model., 51(12):3254-61 (2011).
Ikeda-Matsuo et al., "Microsomal prostaglandin E synthase-1 contributes to ischaemic excitotoxicity through prostaglandin $E_2$ $EP_3$ receptors," British Journal of Pharmacology, 160:847-859 (Jan. 2010).
International Search Report in International Application No. PCT/JP2015/054519, mailed May 12, 2015, 5 pages.
International Search Report in International Application No. PCT/JP2016/073879, dated Nov. 15, 2016, 7 pages (English Translation).
Ishikawa et al., "The Friedel-Crafts reaction of chloro-s-triazines with aromatic compounds and the synthesis of their derivatives. III. Reaction with xylenes," Yuki Gosei Kagaku Kyokaishi, 1967, 25(1):55-59 (with English translation of abstract).
Jakobsson et al., "Identification of human prostaglandin E synthase: a microsomal, glutathione-dependent, inducible enzyme, constituting a potential novel drug target," Proc Natl Acad Sci USA., 96(13):7220-7225 (Jun. 1999).
Jongthawin et al., "PGE2 signaling and its biosynthesis-related enzymes in cholangiocarcinoma progression," Tumour Biol., 35(8):8051-64 (Aug. 2014), abstract, retrieved on Nov. 4, 2016, retrieved from <https://www.ncbi.nlm.nih.gov/pubmed/24839005>, 2 pages.
Kakroodi, The role of Microsomal prostaglandin synthase-1 (mPGES-1) and Ephrin B2 in Scleroderma, University of Montreal Ph.D. Dissertation of Parisa Ghassemi Kakroodi, 100 pages, Mar. 2013.
Kamei et al., "Reduced pain hypersensitivity and inflammation in mice lacking microsomal prostaglandin e synthase-1," J Biol. Chem. 279(32):33684-33695 (Aug. 2004).
Kanekura et al., "Cyclooxygenase-2 expression and prostaglandin E2 biosynthesis are enhanced in scleroderma fibroblasts and inhibited by UVA irradiation," J Rheumatol., 28(7): 1568-72 (Jul. 2001), Abstract, Retrieved on Nov. 4, 2016, retrieved from <https://www.ncbi.nlm.nih.gov/pubmed/11469463>, 2 pages.
Kihara et al., "Targeted lipidomics reveals mPGES-1-PGE2 as a therapeutic target for multiple sclerosis," Proc Natl Acad Sci USA., 106(51):21807-21812 (Dec. 2009).
Koeberle et al., " Myrtucommulone, a natural acylphloroglucinol, inhibits microsomal prostaglandin E2 synthase-1," Br J Pharmachol., 156(6):952-961 (Mar. 2009).
Koeberle et al., "Perspective of microsomal prostaglandin E2 synthase-1 as drug target in inflammation-related disorders, " Biochemical Pharmacology, 98(1):1-15 (Nov. 2015), Abstract, retrieved on Nov. 4, 2016, Retrieved from <http://www.sciencedirect.com/science/article/pii/S0006295215003388X>, 4 pages.
Kojima et al., Inflamm Regen., 31(2):157-166 (Mar. 2011).
Korotkova et al., "Characterization of microsomal prostaglandin E synthase 1 inhibitors," Basic Clin Pharmacol Toxicol., 114(1):64-9 (Jan. 2014).
Korotkova et al., "Variants of gene for microsomal prostaglandin E2 synthase show association with disease and severe inflammation in rheumatoid arthritis," Eur. J Hum Genet., 19(8):908-914 (Aug. 2011).
Kothavade et al., "Arzanol, a Potent mPGES-1 Inhibitor: Novel Anti-Inflammatory Agent," The Scientific World Journal, Hindawi Publishing Company, vol. 2013, 9 pages (Sep. 2013).

(56) References Cited

OTHER PUBLICATIONS

Kuroki et al., "Deletion of microsomal prostaglandin E sythase-1 protects neuronal cells from cytotoxic effects of beta-amyloid peptide fragment 31-35," Biochem Biophys Res Commun., 424(3):409-413 (Aug. 2012).
Larsson et al., "Inhibition of microsomal prostaglandin E synthase-1 as targeted therapy in cancer treatment," Prostaglandins Other Lipid Mediat., 120:161-165 (2015).
Lauro et al., "Identification of novel microsomal prostaglandin $E_2$ synthase-1 (mPGES-1) lead inhibitors from fragment Virtual Screening," European Journal of Medical Chemistry, pp. 278-287 (Jan. 2017), Abstract, retrieved on Nov. 4, 2016, retrieved from <http://www.sciencedirect.com/science/article/pii/S0223523416307735>, 3 pages.
Leclerc et al., "Characterization of a new mPGES-1 inhibitor in rat models of inflammation," Prostaglandins Other Lipid Mediat., 102-103:1-12 (Apr.-May 2013), Abstract, retrieved on Nov. 4, 2016, Retrieved from <https://www.ncbi.nlm.nih.gov/pubmed/?term-LeClerc+et.+al.+Prostaglandins+%26+Other+Lipid+Mediators%2C+vol.+102-103%2C+pp.+1-12.>, 2 pages.
Li et al., "[Effect of mPGES-1 inhibitor MK886 on cell cycle of leukemia HL-60 cells]," Zhonqquo Shi Yan Xue Ye Xue Za Zhi, 20(5):1072-6 (Oct. 2012), English Abstract, 2 pages.
Lu et al., "Microsomal Prostaglandin E Synthase-1 Inhibits PTEN and Promotes Experimental Cholangiocarinogenesis and Tumor Progression," Gastroenterology, 140(7):2084-2094 (Jun. 2011).
Luz et al., "Crystal Structures of mPGES-1 Inhibitor Complexes Form a Basis for the Rational Design of Potent Analgesic and Anti-Inflammatory Therapeutics," J. Med. Chem., 58(11):4727-4737 (May 2015), Abstract, retrieved on Nov. 4, 2016, Retrieved from <http://pubs.acs.org/doi/abs/10.1021/acs.jmedchem.5b00330>, 2 pages.
Maione et al., "Anti-inflammatory and analgesic activity of carnosol and carnosic acid in vivo and in vitro and in silico analysis of their target interactions," Br J Pharmacol., (Jul. 2016), Abstract, retrieved on Nov. 4, 2016, Retrieved from <https://www.ncbi.nlm.nih.gov/pubmed/27464306>, 2 pages.
Masuko-Hongo et al., "Up-regulation of microsomal prostaglandin E synthase 1 in osteoarthritic human cartilage: critical roles of the ERK-1/2 and p38 signaling pathways," Arthritis Rheum., 50(9):2829-38 (Sep. 2004).
Mbalaviele et al., "Distinction of microsomal prostaglandin E synthase-1 (mPGES-1) inhibition from cyclooxygenase-2 inhibition in cells using a novel, selective mPGES- 1 inhibitor," Biochem Pharmacol., 79(10):1445-54 (May 2010), Abstract, retrieved on Nov. 4, 2016, Retrieved from <http://www.sciencedirect.com/science/article/pii/S0006295210000109>.
McCann et al., "Mpges-1 null mice are resistant to bleomycin-induced skin fibrosis," Arthritis Res Ther. 13(1):R6 (2011).
Mezzetti et al., "[New insights on the molecular mechanisms of type-1 angiotensin II receptor blockers and their contribution to atherosclerotic plaque stabilization]," Recenti Prog Med., 95(12):586-90 (Dec. 2004), Italian, English Abstract, retrieved on Nov. 4, 2016, Retrieved from <https://www.ncbi.nlm.nih.gov/pubmed/15666492>, 2 pages.
Montine et al., "Elevated CSF prostaglandin E2 levels in patients with probable AD," Neurology, 53(7):1495-8 (Oct. 1999), Abstract, retrieved on Nov. 4, 2016, Retrieved from <https://www.ncbi.nlm.nih.gov/pubmed/10534257>, 2 pages.
Mouawad et al., "Statins Modulate Cyclooxygenase-2 and Microsomal Prostaglandin E Synthase-1 in Human Hepatic Myofibroblasts," J Cell Biochem., 117(5):1176-86 (May 2016), Abstract, retrieved on Nov. 4, 2016, Retrieved from <https://www.ncbi.nlm.nih.gov/pubmed/26477987>, 2 pages.
Nakajima et al., "Effects of prostaglandin E2 on intraocular pressure, anterior chamber depth and blood flow vol. of the iris and the ciliary body in rabbit eyes," Nihon Ganka Gakkai Zasshi, 96(4):455-461 (Apr. 1992).
Nakanishi et al., "mPGES-1 as a Target for Cancer Suppression: A comprehensive invited review" Phopholipase $A_2$ and lipid mediators, Biochimie., 96(6):660-664 (Jun. 2010).
Platas et al., "Conitioned Media from Adipose-Tissue-Derived Mesenchymal Stem Cells Downregulate Degradative Mediators Induced by Interleukin-1β in Osteoarthritic Chondrocytes," Mediators of Inflammation, Hindawi Publishing Corporation, 2013, 11 pages.
Rullah et al., "Inhibition of prostaglandin $E_2$ production synthetic minor prenylated chalcones and flavonoids: Synthesis, biological activity, crystal structure, and in silico evaluation," Bioorganic & Medicinal Chemistry Letters, 24(16):3826-3834 (Aug. 2014), Abstract, retrieved on Nov. 4, 2016, Retrieved from <http://www.sciencedirect.com/science/article/pii/S0960894X14006891>, 3 pages.
Samuelsson et al., "Membrane prostaglandin E synthase-1: novel therapeutic target," Pharmacol Rev., 59(3):207-224 (Sep. 2007).
Sasaki et al., "Microsomal prostaglandin E synthas-1 is involved in multiple steps of colon carcinogenesis," Oncogene., 31(24)2943-2952 (Jun. 2014).
Schaible et al., "Potent inhibition of human 5-lipoxygenase and microsomal prostaglandin $E_2$ synthase-1 by the anti-carcinogenic and anti-inflammatory agent embelin," Biochemical Pharmacology, 86(4):476-486 (Aug. 2013), Abstract, retrieved on Nov. 4, 2016, retrieved from <http://www.sciencedirect.com/science/article/pii/S0006295213002578>, 4 pages.
Sennlaub et al., "Cyclooxygenase-2 in Human and Experimental Ischemic Proliferative Retinopathy," Circulation, 108:198-204 (Jun. 2003).
Sha et al., "Necrosis in DU145 prostate cancer spheroids induces COX-2/mPGES-1-derived PGE2 to promote tumor growth and to inhibit T cell activation," Int J Cancer, 133(7):1578-88 (Oct. 2013), Abstract, retrieved on Nov. 4, 2016, retrieved from <https://www.ncbi.nlm.nih.gov/pubmed/23536473>, 2 pages.
STN Tokyo Search Report Document, RN No. 685121-02-2, dated 2013, 1 page.
Sun et al., "Analysis of meniscal degeneration and meniscal gene expression," BMC Musculoskelet Disord., 11:19 (2010).
Takeuchi et al., "Microsomal prostaglandin E synthase-1 aggravates inflammation and demyelination in a mouse model of multiple sclerosis," Neurochem Int., 62(3):271-80 (2013).
Terzuoli et al., "Inhibition of Hypoxia Inducible Factor-1α by Dihydroxyphenylethanol, a Product from Olive Oil, Blocks Microsomal Prostaglandin-E Synthase-1/Vascular Endothelial Growth Factor Expression and Reduces Tumor Angiogenesis," Clinical Cancer Research, 16(16):4207-4216 (Aug. 2010).
Tian et al., "PGE2-EP3 signaling pathway contributes to protective effects of misprostol on cerebral injury in APP/PSI mice," Oncotarget, 7(18):25304-25314 (Mar. 2016).
Trebino et al., "Impaired inflammatory and pain responses in mice lacking an inducible prostaglandin E synthase," Proc Natl Acad Sci USA., 100(15):9044-9049 (Jul. 2003).
Trebino et al., "Redirection of eicosanoid metabolism in mPGES-1-deficient macrophages," J Biol Chem., 280(17)16579-16585 (Apr. 2005).
Wang et al., "Deletion of microsomal prostaglandin E synthase-I augments prostacyclin and retards atherogenesis," Proc Natl Acad Sci USA., 103(39):14507-14512 (Sep. 2006).
Wang et al., "Targeting Microsomal Prostaglandin E Synthase 1 to Develop Drugs Treating the Inflammatory Diseases", American Journal of Translational Research, 2012, 13(1):391-419.
Xu et al., "MF63 [2-(6-Chloro-1H-phenanthro[9, 10-d]imidazole-2-yl)-isophthalonitrile], a Selective Microsomal Prostaglandin E Synthase-I Inhibitor, Relieves Pyresis and Pain in Preclinical Models of Inflammation, " JPET., 326:754-763 (2008).
Yang et al., "Distinct Roles of Central and Peripheral Prostaglandin $E_2$ and EP Subtypes in Blood Pressure Regulation," American Journal of Hypertension, 25(10):1042-1049 (2012), Abstract, retrieved on Nov. 4, 2016, Retrieved from <http://ajh.oxfordjournals.org/content/25/10/1042.abstract>, 2 pages.

(56) References Cited

OTHER PUBLICATIONS

Yanni et al., "The role of PGE2 receptor EP4 in pathologic ocular angiogenesis," Invest Ophthalmol Vis Sci., 50(11):5479-5486 (Nov. 2009).

* cited by examiner

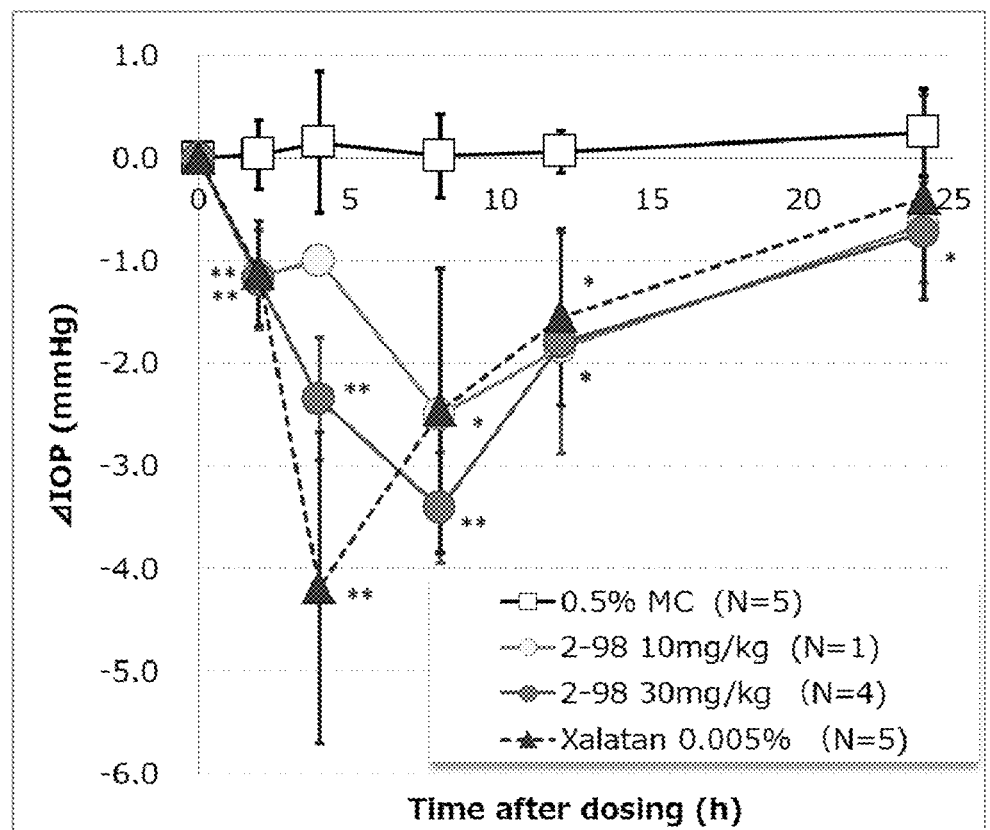
Mean±SD: *:P <0.05, **:P <0.01

TRIAZINE COMPOUNDS AND PHARMACEUTICAL USE THEREOF

TECHNICAL FIELD OF THE INVENTION

The present invention relates to a triazine compound having a microsomal prostaglandin E2 synthase-1 (mPGES-1) inhibitory activity or a pharmaceutically acceptable salt thereof, a pharmaceutical composition containing same, pharmaceutical use thereof and the like.

BACKGROUND OF THE INVENTION

Non-steroidal anti-inflammatory drugs (NSAIDs) are often used for the treatment of diseases accompanying inflammation, fever and pain, for example, rheumatism, osteoarthritis, headache and the like. NSAIDs show an anti-inflammatory action, an antipyretic action and an analgesic action by preventing production of prostanoids by inhibiting cyclooxygenase (COX).

COX includes two isoforms of COX-1 which is ubiquitously distributed and constitutively expressed, and COX-2 which expression is induced by various pro-inflammatory stimulations, for example, cytokines such as interleukin-1β (IL-1β) and the like. COX-1 and COX-2 are enzymes that convert arachidonic acid derived from cell membrane phospholipids to prostaglandin H2 (PGH2) which is a prostanoid precursor. Specific prostanoid synthases are responsible for the conversion of PGH2 to respective prostanoids (prostaglandin E2 (PGE2), prostaglandin F2α (PGF2α), prostaglandin I2 (PGI2), prostaglandin D2 (PGD2), thromboxane A2 (TXA2) etc.). These prostanoids have various physiological activities, for example, induction/suppression of inflammation, vasodilation/vasoconstriction, bronchodilation/bronchoconstriction, induction of/awakening from sleep, development of fever and the like. PGE2 is the most commonly existing prostaglandin in living organisms, and is known to be deeply involved in inflammation, pain and fever. Therefore, suppression of PGE2 production is considered the main action mechanism of NSAIDs.

Inhibition of COX-1 or COX-2 suppresses all prostanoids production in the downstream thereof. This is considered to cause side effects of NSAIDs. Since NSAIDs that non-selectively inhibit COX also suppress production of PGE2 by COX-1 and PGE2 protectively acts on stomach mucosal injury, NSAIDs are considered to suppress secretion of gastric mucus and gastric mucosal blood flow, thereby increasing the risk of stomach perforations, bleeding and the like. While COX-2 selective inhibitors suppress production of PGI2 having a vasodilation action and a platelet aggregation inhibitory action in vascular endothelial cells, they do not suppress production of TXA2 which is a blood coagulation factor produced by platelet COX-1. Therefore, they are considered to disrupt the balance of the blood coagulation system to increase the risk of cardiovascular disorder.

Microsomal prostaglandin E2 synthase-1 (mPGES-1) is an enzyme that catalyzes the final step of PGE2 biosynthesis, and belongs to the membrane-associated proteins in eicosanoid and glutathione metabolism family (MAPEG family). The human mPGES-1 gene was cloned in 1999, and indicated to be constitutively expressed in placenta, prostate, testis and mammary gland (non-patent document 1). In other organs, human mPGES-1 gene expression is induced by various pro-inflammatory stimulations, conjugated with COX-2. For example, inflammatory cytokine IL-1β and Tumor Necrosis Factor-α (TNF α) induce mPGES-1 expression in synovial cell, osteoblast, endothelial cell, orbital fibroblast, gingival cell, chondrocyte, endothelial cell, myocardial cell and the like. For example, Lipopolysaccharide (LPS), which is a bacterial endotoxin, induces mPGES-1 expression in macrophage, smooth muscle and the like.

mPGES-1 inhibitor is considered to selectively suppress PGE2 production only in the topical site of inflammation or tissues where mPGES-1 is expressed, and does not suppress production of prostanoids (PGI2, PGD2, PGF2α, TXA2 etc.) other than PGE2 (non-patent documents 2, 3). Therefore, mPGES-1 inhibitor is considered to be a medicament having an efficacy equivalent to that of NSAIDs but free of side effects of NSAIDs derived from a decreased production of prostanoids other than PGE2.

It is also known that when one of the metabolism pathways downstream from PGH2 is shut off in the arachidonic acid cascade, PGH2 is converted to prostanoids other than the shut-off pathway, or shunt occurs. That is, it is known that while the production amount of PGE2 in macrophage derived from mPGES-1 knockout mice stimulated with LPS becomes lower than the PGE2 production amount in macrophage derived from wild-type (WT) mice stimulated with LPS, the production amounts of TXB2, PGI2, PGD2 and PGF2α in macrophage derived from mPGES-1 knockout mice stimulated with LPS increase beyond the production amounts thereof in macrophage derived from WT mice stimulated with LPS (non-patent document 4). Since mPGES-1 inhibitor increases production of other prostanoids while suppressing the PGE2 production, it is considered to be effective even for diseases different from those treated by NSAIDs.

Use of mPGES-1 inhibitor is described below.

(1) Pain

In mPGES-1 knockout mice, intraperitoneal PGE2 production amount and nociceptive response per unit time significantly decrease as compared to WT mice, in the evaluation of nociceptive response by LPS stimulation which is an acute inflammatory pain model. Therefore, mPGES-1 inhibitor is considered to be an analgesic for acute inflammatory pain (non-patent documents 3, 6).

(2) Rheumatism mPGES-1 gene of Swedish females contains some single nucleotide polymorphisms that increase the onset risk and severity of rheumatism. An increase in the mPGES-1 expression is immunohistologically confirmed in the synovium of rheumatism patients showing single nucleotide polymorphism (Reference SNP ID number: rs23202821) that increases severity, as compared to patients free of mutation (non-patent document 5). In mPGES-1 knockout mice, intraarticular infiltration of inflammatory cells, articular destruction and tumentia of the four limbs are markedly suppressed in a collagen-induced arthritis model, which is an animal model of rheumatism, as compared to WT mice (non-patent document 6). Therefore, mPGES-1 inhibitor is considered to be a therapeutic drug for rheumatism.

(3) Osteoarthritis mRNA expression of mPGES-1 increases in meniscus cells of osteoarthritis patients (non-patent document 7). mPGES-1 inhibitor reduces nociceptive responses in osteoarthritis model using monoiodoacetic acid, as compared to WT mice (patent document 1). Therefore, mPGES-1 inhibitor is considered to be a therapeutic drug for osteoarthritis.

(4) Fever

In mPGES-1 knockout mice, body temperature elevation due to LPS stimulation is suppressed as compared to WT mice (non-patent document 8). Therefore, mPGES-1 inhibitor is considered to be an antipyretic drug.

(5) Alzheimer's Disease

Long-term use of NSAIDs mitigates the onset and progression of Alzheimer's disease. Under amyloid β peptide treatment, PGE2 production in the primary culture brain neuron of mPGES-1 knockout mice is suppressed, compared to the brain neuron of WT mice, and nerve cell death does not occur (non-patent document 9). Therefore, mPGES-1 inhibitor is considered to be a therapeutic drug for Alzheimer's disease.

(6) Multiple Sclerosis

EP4 gene of multiple sclerosis patients contains some single nucleotide polymorphisms that increase the onset risk (Reference SNP ID numbers: rs9292777, rs4613763, rs1044063, rs6896969). In macrophage present in the periventricular demyelinating lesion of multiple sclerosis patients, expression of mPGES-1 protein is confirmed. In mPGES-1 knockout mice, PGE2 production in the spinal cord of experimental autoimmune encephalomyelitis model mice, which is an animal model of multiple sclerosis, is suppressed, and progression of paralysis is suppressed, as compared to WT mice, (non-patent document 10). Therefore, mPGES-1 inhibitor is considered to be a therapeutic drug for multiple sclerosis.

(7) Arteriosclerosis

In mPGES-1 knockout mice, PGE2 production in vascular endothelial cells of high-fat fed low density lipoprotein (LDL) receptor deficient mice, which is an atherosclerosis model, decreases, and atheroma formation is delayed as compared to WT mice. In vascular endothelial cells, production of PGI2, which is known to have a platelet function suppressive action, increases (non-patent document 11). Therefore, mPGES-1 inhibitor is considered to be a prophylactic or therapeutic drug for arteriosclerosis.

(8) Glaucoma, Ocular Hypertension

Glaucoma is a disease showing a characteristic change in the optic nerve and the field of vision. Optic nerve disorder can be generally improved or suppressed by sufficiently decreasing the intraocular pressure. Glaucoma can be categorized into open angle glaucoma and closed angle glaucoma.

mPGES-1 gene is constitutively highly expressed in human conjunctiva (GEO accession No: GSE2513 (Gene Expression Omnibus)). In the retina of glaucoma patients, expression of mPGES-1 increases as compared to healthy individuals. In the retina of high intraocular pressure dogs and high intraocular pressure mice, which are glaucoma models, expression of mPGES-1 increases as compared to normal animals (GEO accession No: human GSE2378, dog GSE21879, mouse GSE3554).

When PGE2 is instilled into the eyes of healthy individuals, the intraocular pressure increases, along with the expansion of blood vessels, for 2 hours after instillation (non-patent document 12). When PGE2 is administered to rabbits subconjunctivally, the intraocular pressure increases due to dilatation of ciliary body and increase in the aqueous humor production (non-patent document 13). PGF2α and PGD2, which are prostaglandins that may increase when mPGES-1 is inhibited, decrease the intraocular pressure of rabbit (non-patent document 14). PGF2α formulations increase outflow of aqueous humor and are used as therapeutic drugs for glaucoma that decrease the intraocular pressure. PGI2 does not show a clear action on the intraocular pressure of rabbits. That is, the intraocular pressure is considered to decrease since decrease of PGE2 suppresses aqueous humor production by mPGES-1 inhibition, and/or since increased PGD2 and PGF2α promote outflow of aqueous humor due to shunt. Also, PGE2 promotes expression of vascular endothelial growth factor (VEGF) from retina (non-patent document 15). Since VEGF produced in retina transfers to the anterior ocular segment to cause angiogenesis glaucoma, which is increase of the intraocular pressure that is caused by obstruction of corner angle due to angiogenesis in iris, mPGES-1 inhibitor is considered to show an improvement or prophylactic effect on angiogenesis glaucoma as well. Furthermore, considering an anti-inflammatory action by the inhibition of PGE2 production, mPGES-1 inhibitor is applicable to patients having intraocular inflammation, who require careful administration of the existing prostaglandin formulations (latanoprost etc.). Therefore, mPGES-1 inhibitor is considered to be a therapeutic drug also effective for glaucoma having various background diseases.

(9) Ischemic Retinal Disease

Excessive secretion of VEGF plays a key role in ischemic retinal diseases such as diabetic retinopathy, diabetic macular edema, retinal vein occlusion and the like. Since PGE2 promotes expression of VEGF (non-patent document 15), mPGES-1 inhibitor is considered to improve these diseases.

(10) Systemic Scleroderma

Expression of mPGES-1 increases in the skin of systemic scleroderma patients, as compared to healthy individuals. Similarly, expression of mPGES-1 increases in the skin of bleomycin induced scleroderma model mice, which is a systemic scleroderma model, as compared to the skin of normal mice. As compared to WT mice, mPGES-1 knockout mice showed a decrease in the accumulation of macrophage in the dermal lesion of bleomycin induced scleroderma model mice, and mitigation of cutaneous thickening, deposition of extracellular matrix and increase in the collagen content (non-patent document 16). Therefore, mPGES-1 inhibitor is considered to be a therapeutic drug for systemic scleroderma.

(11) Cancer

In mPGES-1 knockout mice, the polyp number and size were markedly suppressed in azoxymethane-induced colorectal cancer model mice, which are animal model of colorectal cancer, as compared to WT mice. In mPGES-1 knockout mice, PGE2 production in large intestinal tumor tissue decreased and production amount of PGI2 that inhibits adhesion of cancer cells and PGD2 that induces cell death via peroxisome proliferator-activated receptor γ (PPARγ) increased, as compared to WT mice. When colorectal cancer or lung cancer cells were transplanted into the spleen of mPGES-1 knockout mice, the post-transplantation weight of spleen tumor and the rate of metastasis to the liver decreased as compared to WT mice. Growth of lung cancer cells was decreased when they ware co-cultured in vitro with mPGES-1 knockout mice-derived bone marrow macrophages compared to when they ware co-cultured with WT mice-derived bone marrow macrophages, which indicates that host macrophage-derived PGE2 is involved in cancer cell growth (non-patent document 17). Therefore, mPGES-1 inhibitor is considered to be an anticancer drug that suppresses the growth and metastasis of cancer including colorectal cancer.

(12) Disease for which Suppression of PGE2 Production is Effective

As inflammatory symptoms and/or pain relating to the conditions thereof, for which NSAIDs are effective, for example, arthritis, gout, nephrolithiasis, urolithiasis, headache, menstrual pain, toothache, lumbago, muscular pain, periarthritis scapulohumeralis, cervical syndrome, temporomandibular disorder, and postoperative or posttraumatic inflammation and pain, and inflammation and pain after tooth extraction can be mentioned. Besides these, acute and chronic non-bacterial inflammation of eye can be mentioned and, for example, uveitis, allergic conjunctivitis and postoperative inflammation and ophthalmalgia in intraocular operation can be mentioned.

The main mechanism for the efficacy of NSAIDs is considered to be the suppression of PGE2 production, which is an inflammation promoting substance. Since mPGES-1 inhibitor also has a suppressive action on the PGE2 production, it is considered to be a therapeutic drug for these diseases.

The mPGES-1 inhibitor is considered to be beneficial for the prophylaxis or treatment of pain, rheumatism, osteoarthritis, fever, Alzheimer's disease, multiple sclerosis, arteriosclerosis, glaucoma, ocular hypertension, ischemic retinal disease, systemic scleroderma, cancer including colorectal cancer and diseases for which suppression of PGE2 production is effective.

Document List

Patent Document patent document 1: WO 2012/161965

Non-Patent Documents non-patent document 1: JAKOBSSON, P J et al. Identification of human prostaglandin E synthase: a microsomal, glutathione-dependent, inducible enzyme, constituting a potential novel drug target. Proc Natl Acad Sci USA. Jun. 22, 1999, Vol. 96, No. 13, pages 7220-7225.

non-patent document 2: SAMUELSSON, B et al. Membrane prostaglandin E synthase-1: a novel therapeutic target. Pharmacol Rev. Sep 2007, Vol. 59, No. 3, pages 207-224.

non-patent document 3: KAMEI, D et al. Reduced pain hypersensitivity and inflammation in mice lacking microsomal prostaglandin e synthase-1. J Biol Chem. Aug. 6, 2004, Vol. 279, No. 32, pages 33684-33695.

non-patent document 4: TREBINO, C E et al. Redirection of eicosanoid metabolism in mPGES-1-deficient macrophages. J Biol Chem. Apr. 29, 2005, Vol. 280, No. 17, pages 16579-16585.

non-patent document 5: KOROTKOVA, M et al. Variants of gene for microsomal prostaglandin E2 synthase show association with disease and severe inflammation in rheumatoid arthritis. Eur J Hum Genet. Aug 2011, Vol. 19, No. 8, pages 908-914.

non-patent document 6: TREBINO, C E et al. Impaired inflammatory and pain responses in mice lacking an inducible prostaglandin E synthase. Proc Natl Acad Sci USA. Jul. 22, 2003, Vol. 100, No. 15, pages 9044-9049.

non-patent document 7: SUN, Y et al. Analysis of meniscal degeneration and meniscal gene expression. BMC Musculoskelet Disord. 2010, Vol. 11, pages 19.

non-patent document 8: ENGBLOM, D et al. Microsomal prostaglandin E synthase-1 is the central switch during immune-induced pyresis. Nat Neurosci. Nov 2003, Vol. 6, No. 11, pages 1137-1138.

non-patent document 9: KUROKI, Y et al. Deletion of microsomal prostaglandin E synthase-1 protects neuronal cells from cytotoxic effects of beta-amyloid peptide fragment 31-35. Biochem Biophys Res Commun. Aug. 3, 2012, Vol. 424, No. 3, pages 409-413.

non-patent document 10: KIHARA, Y et al. Targeted lipidomics reveals mPGES-1-PGE2 as a therapeutic target for multiple sclerosis. Proc Natl Acad Sci USA. Dec. 22, 2009, Vol. 106, No. 51, pages 21807-21812.

non-patent document 11: WANG, M et al. Deletion of microsomal prostaglandin E synthase-1 augments prostacyclin and retards atherogenesis. Proc Natl Acad Sci USA. Sep. 26, 2006, Vol. 103, No. 39, pages 14507-14512.

non-patent document 12: FLACH, A J et al. Topical prostaglandin E2 effects on normal human intraocular pressure. J Ocul Pharmacol. Spring 1988, Vol. 4, No. 1, pages 13-18.

non-patent document 13: NAKAJIMA, T et al. [Effects of prostaglandin E2 on intraocular pressure, anterior chamber depth and blood flow volume of the iris and the ciliary body in rabbit eyes]. Nihon Ganka Gakkai Zasshi. Apr 1992, Vol. 96, No. 4, pages 455-461.

non-patent document 14: GOH, Y et al. Prostaglandin D2 reduces intraocular pressure. Br J Ophthalmol. Jun 1988, Vol. 72, No. 6, pages 461-464.

non-patent document 15: YANNI, S E et al. The role of PGE2 receptor EP4 in pathologic ocular angiogenesis. Invest Ophthalmol Vis Sci. Nov 2009, Vol. 50, No. 11, pages 5479-5486.

non-patent document 16: MCCANN, M R et al. mPGES-1 null mice are resistant to bleomycin-induced skin fibrosis. Arthritis Res Ther. 2011, Vol. 13, No. 1, pages R6.

non-patent document 17: SASAKI, Y et al. Microsomal prostaglandin E synthase-1 is involved in multiple steps of colon carcinogenesis. Oncogene. Jun. 14, 2012, Vol. 31, No. 24, pages 2943-2952.

SUMMARY OF THE INVENTION

The present invention aims to provide a triazine compound having an mPGES-1 inhibitory activity or a pharmaceutically acceptable salt thereof, a pharmaceutical composition containing same, and pharmaceutical use thereof and the like. As the target disease, for example, pain, rheumatism, osteoarthritis, fever, Alzheimer's disease, multiple sclerosis, arteriosclerosis, glaucoma, ocular hypertension, ischemic retinal disease, systemic scleroderma, cancer including colorectal cancer and diseases for which suppression of PGE2 production is effective can be mentioned.

The present inventors have found a triazine compound having an mPGES-1 inhibitory activity, which is represented by the following formula [I], and completed the present invention.

Accordingly, the present invention is as follows.

A compound represented by the formula [I] or a pharmaceutically acceptable salt thereof:

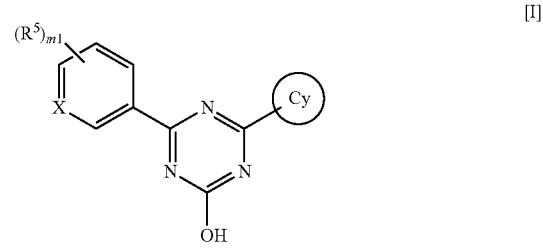

wherein
X is CH or N,
ring Cy is
the formula:

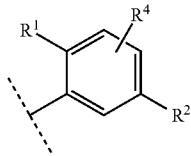

or
the formula:

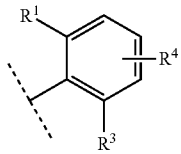

{wherein $R^1$ is
(1) halogen,
(2) $C_{1-6}$ alkyl,
(3) cyano or
(4) halo$C_{1-4}$ alkyl,
$R^2$ is
(1) halogen,
(2) hydroxy,
(3) carboxy,
(4) $C_{1-6}$ alkyl,
(5) $C_{1-6}$ alkoxy,
(6) halo$C_{1-4}$ alkoxy,
(7) halo$C_{1-4}$ alkyl,
(8) $C_{1-6}$ alkyl-carbonyl,
(9) —C(O)$NR^{a1}R^{a2}$ ($R^{a1}$ and $R^{a2}$ are each independently hydrogen or $C_{1-6}$ alkyl) or
(10) —$(C_nH_{2n})$—$R^b$
(n is 1, 2, 3 or 4, —$(C_nH_{2n})$— may be straight or branched chain, and
$R^b$ is
(a) hydroxy,
(b) carboxy,
(c) $C_{1-6}$ alkoxy,
(d) $C_{1-6}$ alkyl-carbonyloxy,
(e) —C(O)$NR^{b1}R^{b2}$ ($R^{b1}$ and $R^{b2}$ are each independently hydrogen or $C_{1-6}$ alkyl),
(f) —OC(O)$NR^{b3}R^{b4}$ ($R^{b3}$ and $R^{b4}$ are each independently hydrogen or $C_{1-6}$ alkyl),
(g) —$NR^{b5}C(O)NR^{b6}R^{b7}$ ($R^{b5}$, $R^{b6}$ and $R^{b7}$ are each independently hydrogen or $C_{1-6}$ alkyl),
(h) —$NR^{b8}R^{b9}$ ($R^{b8}$ and $R^{b9}$ are each independently hydrogen, $C_{1-6}$ alkyl or halo$C_{1-4}$ alkyl),
(i) —$NR^{b10}S(O)_2R^{b11}$ ($R^{b10}$ and $R^{b11}$ are each independently hydrogen, $C_{1-6}$ alkyl or $C_{3-7}$ cycloalkyl),
(j) —$NR^{b12}C(O)OR^{b13}$ ($R^{b12}$ is hydrogen or $C_{1-6}$ alkyl, and $R^{b13}$ is $C_{1-6}$ alkyl),
(k) —$NR^{b14}C(O)R^{b15}$ ($R^{b14}$ is hydrogen or $C_{1-6}$ alkyl, and $R^{b15}$ is
(i) $C_{6-10}$ aryl,
(ii) $C_{1-8}$ alkyl (said $C_{1-8}$ alkyl is optionally substituted by 1, 2 or 3 substituents selected from the group consisting of hydroxy, halo$C_{1-4}$ alkyl, $C_{1-6}$ alkoxy and $C_{6-10}$ aryl)

(iii) adamantyl or
(iv) $C_{3-7}$ cycloalkyl (said $C_{3-7}$ cycloalkyl is optionally substituted by 1, 2, 3 or 4 substituents selected from the group consisting of $C_{1-6}$ alkyl, halogen, hydroxyl $C_{1-6}$ alkyl and halo $C_{1-4}$ alkyl, and/or optionally form a fused ring with a benzene ring), or
$R^{b14}$ and $R^{b15}$ optionally form a 4-, 5- or 6-membered lactam together with the nitrogen atom the nitrogen atom that $R^{b14}$ is bonded to and the carbon atom that $R^{b15}$ is bonded to (said lactam is optionally substituted by 1, 2 or 3 $C_{1-6}$ alkyls, and/or optionally form a fused ring with a benzene ring),
(l) the formula:

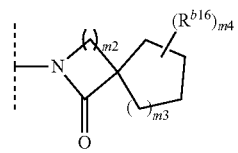

wherein m2 and m3 are each independently 1, 2 or 3, m4 is 0, 1, 2, 3 or 4, $R^{b16}$ is $C_{1-6}$ alkyl or $C_{1-6}$ alkoxy, and when m4 is 2, 3 or 4, each $R^{b16}$ is selected independently, or
(m) the formula:

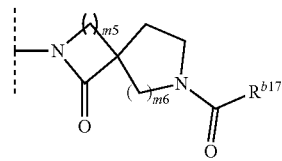

wherein m5 and m6 are each independently 1, 2 or 3, and $R^{b17}$ is $C_{1-6}$ alkyl or $C_{1-6}$ alkoxy)),
$R^3$ is
(1) halogen,
(2) hydroxy,
(3) $C_{1-6}$ alkyl or
(4) —$OR^c$ {$R^c$ is $C_{1-6}$ alkyl optionally substituted by 1, 2 or 3 substituents selected from the group consisting of the following (a) to (f);
(a) halogen,
(b) hydroxy,
(c) $C_{1-6}$ alkoxy,
(d) —C(O)$NR^{c1}R^{c2}$ ($R^{c1}$ and $R^{c2}$ are each independently hydrogen or $C_{1-6}$ alkyl),
(e) $C_{6-10}$ aryl (said $C_{6-10}$ aryl is optionally substituted by 1, 2 or 3 substituents selected from the group consisting of
(i) halogen,
(ii) hydroxy,
(iii) $C_{1-6}$ alkyl,
(iv) $C_{1-6}$ alkoxy, and
(v) halo$C_{1-4}$ alkyl), and
(f) 5- or 6-membered heteroaryl containing 1, 2 or 3 nitrogen atoms, oxygen atoms or sulfur atoms (said heteroaryl is optionally substituted by 1, 2 or 3 substituents selected from the group consisting of
(i) halogen,
(ii) hydroxy,
(iii) $C_{1-6}$ alkyl,
(iv) $C_{1-6}$ alkoxy, and
(v) halo$C_{1-4}$ alkyl)}, and R⁴ is
(1) hydrogen,
(2) halogen,
(3) $C_{1-6}$ alkyl or
(4) $C_{1-6}$ alkoxy},
R⁵ is
(1) halogen,
(2) hydroxy,
(3) $C_{1-6}$ alkylsulfanyl,
(4) $C_{1-6}$ alkyl (said $C_{1-6}$ alkyl is optionally substituted by 1, 2 or 3 substituents selected from the group consisting of halogen, $C_{6-10}$ aryl and $C_{1-6}$ alkoxy),
(5) $C_{3-7}$ cycloalkyl,
(6) —OR$^d$ {R$^d$ is
(a) $C_{2-6}$ alkynyl,
(b) $C_{3-7}$ cycloalkyl optionally substituted by 1, 2 or 3 $C_{1-6}$ alkyls or
(c) $C_{1-8}$ alkyl (said $C_{1-8}$ alkyl is optionally substituted by 1, 2 or 3 substituents selected from the group consisting of the following (i) to (v);
(i) halogen,
(ii) $C_{6-10}$ aryl,
(iii) $C_{1-6}$ alkoxy,
(iv) $C_{3-7}$ cycloalkyl (said $C_{3-7}$ cycloalkyl is optionally substituted by 1, 2 or 3 substituents selected from the group consisting of $C_{1-6}$ alkyl and haloC$_{1-4}$ alkyl), and
(v) 4-, 5- or 6-membered saturated heterocyclyl containing 1, 2 or 3 nitrogen atoms, oxygen atoms or sulfur atoms (said saturated heterocyclyl is optionally substituted by 1, 2 or 3 substituents selected from the group consisting of $C_{1-6}$ alkyl and haloC$_{1-4}$ alkyl))} or
(7) the formula:

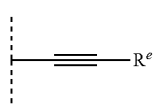

wherein R$^e$ is
(a) $C_{1-6}$ alkyl,
(b) $C_{3-7}$ cycloalkyl,
(c) 5- or 6-membered heteroaryl containing 1, 2 or 3 nitrogen atoms, oxygen atoms or sulfur atoms, or
(d) $C_{6-10}$ aryl (said $C_{6-10}$ aryl is optionally substituted by 1, 2 or 3 substituents selected from the group consisting of
(i) halogen,
(ii) $C_{1-6}$ alkyl,
(iii) haloC$_{1-4}$ alkyl,
(iv) $C_{1-6}$ alkoxy, and
(v) haloC$_{1-4}$ alkoxy), and
m1 is 0, 1, 2 or 3 and, when m1 is 2 or 3, each R⁵ is selected independently,
excluding 4,6-bis-(2,5-dimethyl-phenyl)-1,3,5-triazin-2-ol.

[02]
The compound of [01] or a pharmaceutically acceptable salt thereof, wherein ring Cy is the formula:

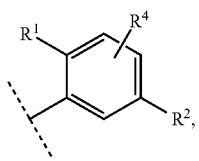

wherein R¹, R² and R⁴ are as defined in [01].

[03]
The compound of [01] or a pharmaceutically acceptable salt thereof, wherein ring Cy is the formula:

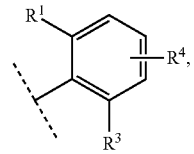

wherein R¹, R³ and R⁴ are as defined in [01].

[04]
The compound of any of [01] to [03] or a pharmaceutically acceptable salt thereof, wherein X is CH.

[05]
The compound of any of [01] to [03] or a pharmaceutically acceptable salt thereof, wherein X is N.

[06]
The compound of any of [01] to [05] or a pharmaceutically acceptable salt thereof, wherein R¹ is
(1) chloro,
(2) methyl,
(3) cyano or
(4) trifluoromethyl.

[07]
The compound of any of [01] to [06] or a pharmaceutically acceptable salt thereof, wherein R⁴ is hydrogen.

[08]
The compound of any of [01], [02] and [04] to [07] or a pharmaceutically acceptable salt thereof, wherein R² is —(C$_n$H$_{2n}$)—R$^b$ (n is 1 or 2, —(C$_n$H$_{2n}$)— may be straight or branched chain, and R$^b$ is
(a) —C(O)NR$^{b1}$R$^{b2}$,
(b) —NR$^{b5}$C(O)NR$^{b6}$R$^{b7}$,
(c) —NR$^{b10}$S(O)$_2$R$^{b11}$ or
(d) —NR$^{b14}$C(O)R$^{b15}$
(R$^{b1}$, R$^{b2}$, R$^{b5}$, R$^{b6}$, R$^{b7}$, R$^{b10}$, R$^{b11}$, R$^{b14}$, and R$^{b15}$ are as defined in [01]))

[09]
The compound of [08] or a pharmaceutically acceptable salt thereof, wherein R² is —CH$_2$—R$^b$ (R$^b$ is as defined in [08])

[10]
The compound of any of [01] and [03] to [09] or a pharmaceutically acceptable salt thereof, wherein R³ is
(1) halogen,
(2) hydroxy,
(3) $C_{1-6}$ alkyl or
(4) —OR$^c${R$^c$ is $C_{1-6}$ alkyl optionally substituted by 1, 2 or 3 substituents selected from the group consisting of the following (a) to (f)
(a) halogen,
(b) hydroxy,
(c) $C_{1-6}$ alkoxy,
(d) —C(O)NR$^{c1}$R$^{c2}$ (R$^{c1}$ and R$^{c2}$ are each independently hydrogen or $C_{1-6}$ alkyl),
(e) phenyl (said phenyl is optionally substituted by 1, 2 or 3 substituents selected from the group consisting of
(i) halogen,
(ii) hydroxy,
(iii) $C_{1-6}$ alkyl,
(iv) $C_{1-6}$ alkoxy, and
(v) haloC$_{1-4}$ alkyl), and (f) pyridyl (said pyridyl is optionally substituted by 1, 2 or 3 substituents selected from the group consisting of
(i) halogen,
(ii) hydroxy,
(iii) $C_{1-6}$ alkyl,
(iv) $C_{1-6}$ alkoxy, and
(v) halo$C_{1-4}$ alkyl)}.

[11]

The compound of any of [01] to [10] or a pharmaceutically acceptable salt thereof, wherein m1 is 1, and $R^5$ is the formula:

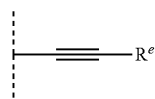

wherein $R^e$ is as defined in [01]

[12]

A compound selected from the following formulas:

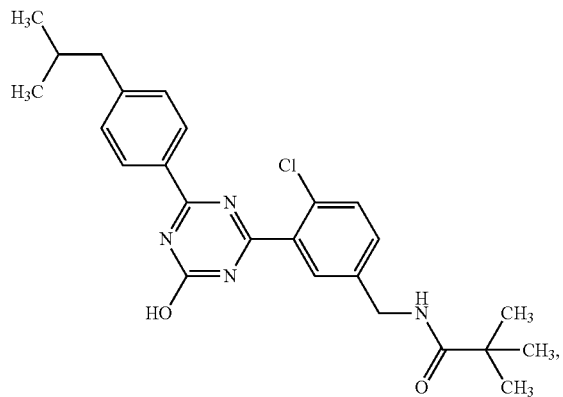

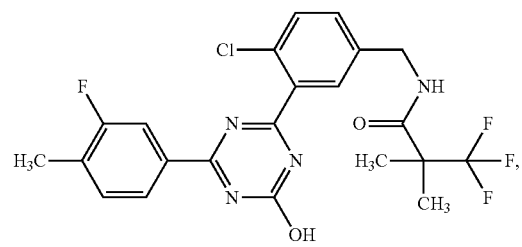

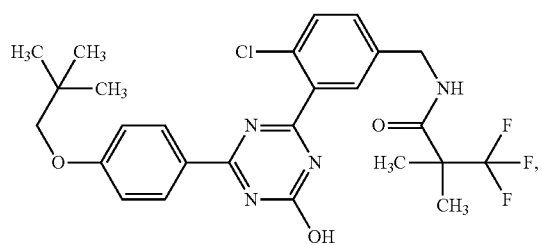

-continued

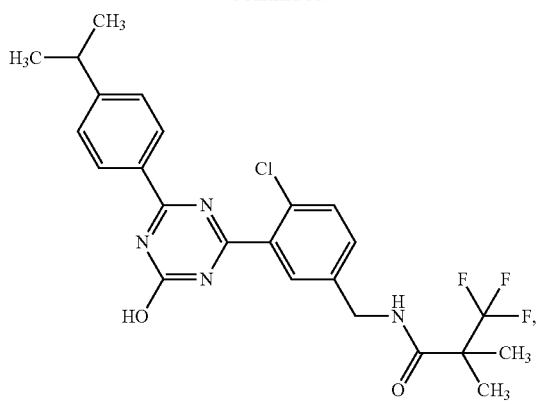

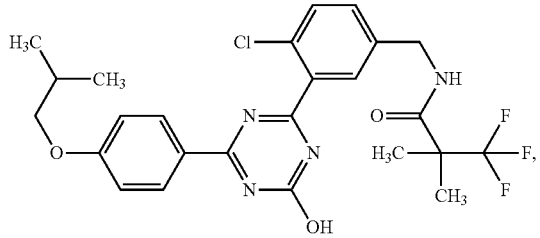

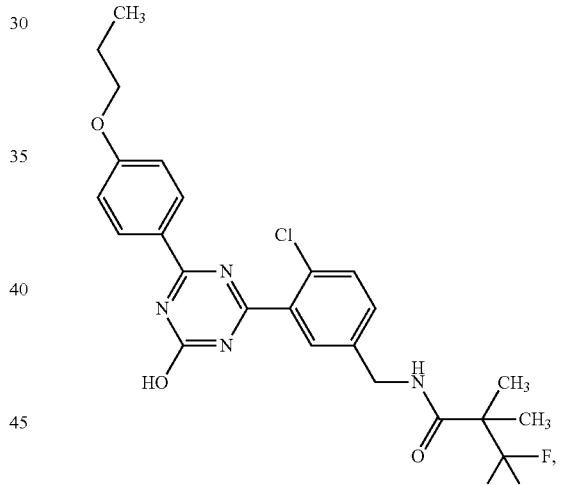

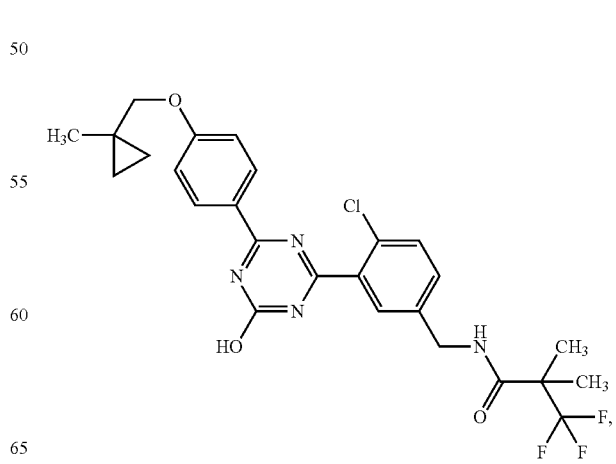

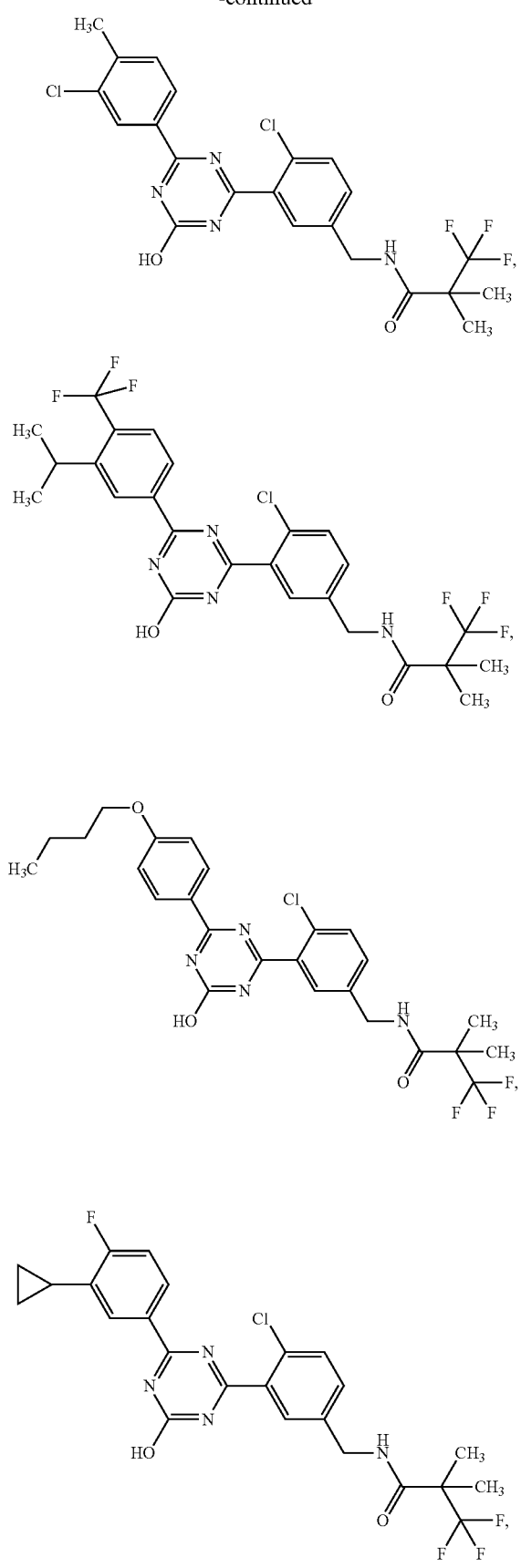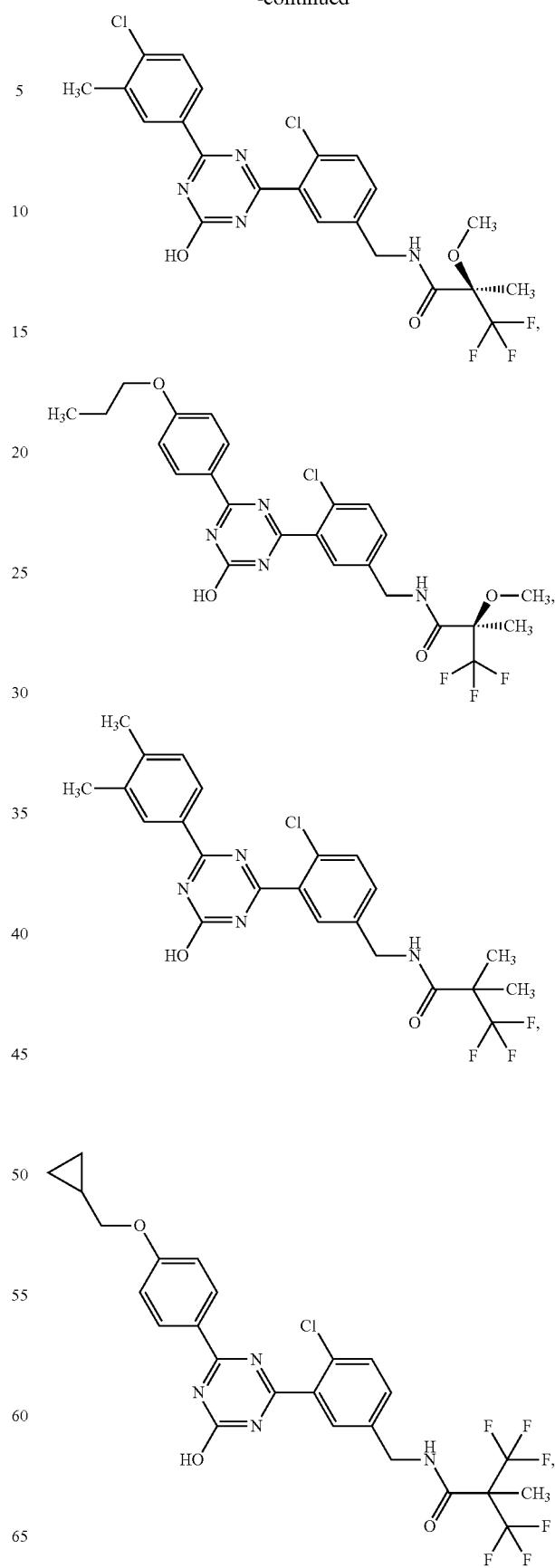

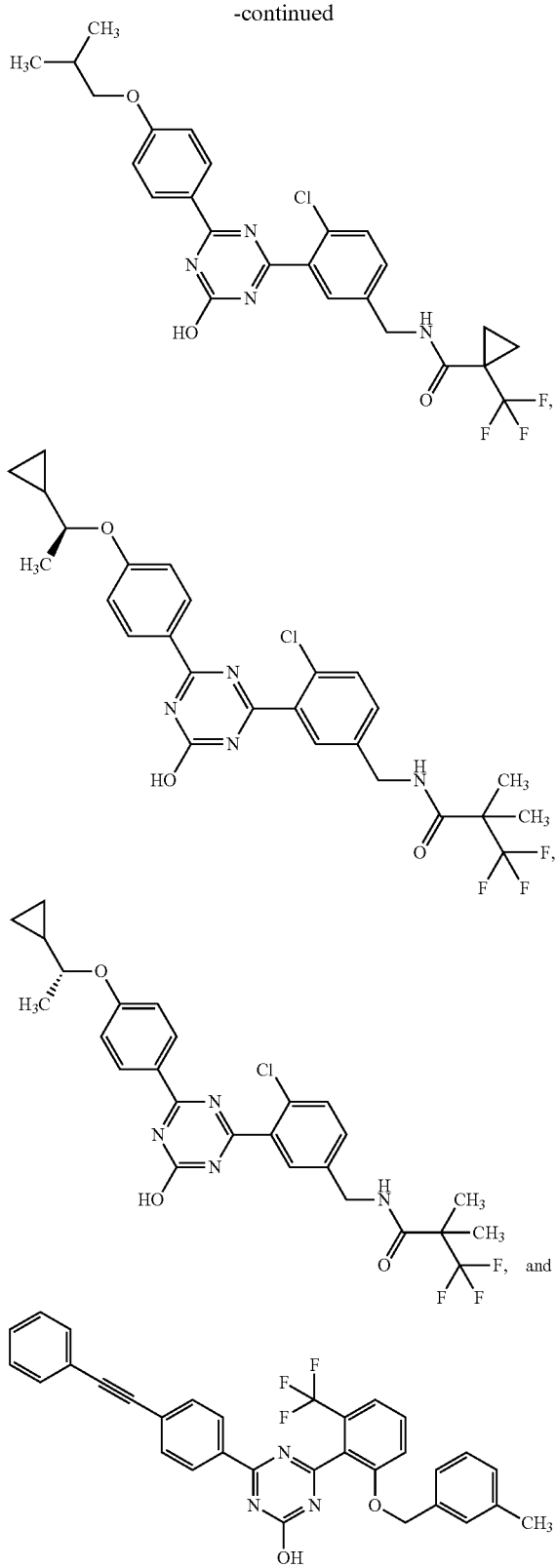

or a pharmaceutically acceptable salt thereof.

[13]
A pharmaceutical composition comprising the compound of any of [01] to [12] or a pharmaceutically acceptable salt thereof, and a pharmaceutically acceptable carrier.

[14]
An mPGES-1 inhibitor comprising the compound of any of [01] to [12] or a pharmaceutically acceptable salt thereof.

[15]
A therapeutic or prophylactic agent for pain, rheumatism, fever, osteoarthritis, arteriosclerosis, Alzheimer's disease, multiple sclerosis, glaucoma, ocular hypertension, ischemic retinal disease, systemic scleroderma, cancer or a disease for which suppression of PGE2 production is effective, comprising the compound of any of [01] to [12] or a pharmaceutically acceptable salt thereof.

[16]
A therapeutic or prophylactic agent for glaucoma or ocular hypertension, comprising the compound of any of [01] to [12] or a pharmaceutically acceptable salt thereof, and one or more kinds of other therapeutic agents for glaucoma in combination.

[17]
A method of inhibiting mPGES-1, comprising administering a pharmaceutically effective amount of the compound of any of [01] to [12] or a pharmaceutically acceptable salt thereof to a human.

[18]
A method of treating or preventing pain, rheumatism, fever, osteoarthritis, arteriosclerosis, Alzheimer's disease, multiple sclerosis, glaucoma, ocular hypertension, ischemic retinal disease, systemic scleroderma, cancer or a disease for which suppression of PGE2 production is effective, which method comprising administering a pharmaceutically effective amount of the compound of any of [01] to [12] or a pharmaceutically acceptable salt thereof to a human.

[19]
The method of [18] for treating or preventing glaucoma or ocular hypertension, further comprising administering a pharmaceutically effective amount of one or more kinds of other therapeutic agents for glaucoma to the human.

[20]
Use of the compound of any of [01] to [12] or a pharmaceutically acceptable salt thereof for the production of an mPGES-1 inhibitor.

[21]
Use of the compound of any of [01] to [12] or a pharmaceutically acceptable salt thereof for the production of a therapeutic or prophylactic agent for pain, rheumatism, fever, osteoarthritis, arteriosclerosis, Alzheimer's disease, multiple sclerosis, glaucoma, ocular hypertension, ischemic retinal disease, systemic scleroderma, cancer or a disease for which suppression of PGE2 production is effective.

Effect of the Invention

The compound of the present invention is effective as a therapeutic or prophylactic agent for pain, rheumatism, fever, osteoarthritis, arteriosclerosis, Alzheimer's disease, multiple sclerosis, glaucoma, ocular hypertension, ischemic retinal disease, systemic scleroderma, cancer including colorectal cancer, a disease for which suppression of PGE2 production is effective and the like.

BRIEF DESCRIPTION OF THE DRAWINGS

FIG. 1 shows effect of a test article (compounds of Example 2-98), a reference article (Xalatan (registered trademark)) or a vehicle (methylcellulose, MC) on the intraocular pressure immediately before and after administration in *Macaca fascicularis*.

DESCRIPTION OF EMBODIMENTS

The definitions of the terms used in the present invention are as follows.

The "halogen" is fluoro, chloro, bromo or iodo.

The "$C_{1-6}$ alkyl" means straight chain or branched chain alkyl having 1 to 6 carbon atoms. Examples thereof include methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl, 2-ethylbutyl and the like.

The "$C_{1-8}$ alkyl" means straight chain or branched chain alkyl having 1 to 8 carbon atoms. Examples thereof include methyl, ethyl, propyl, isopropyl, 1,1-dimethylpropyl, 1-ethyl-propyl, 1-methyl-1-ethyl-propyl, butyl, isobutyl, sec-butyl, tert-butyl, 1-methyl-1-propyl-butyl, pentyl, isopentyl, neopentyl, 1-ethylpropyl, hexyl, isohexyl, 1,1-dimethylbutyl, 2,2-dimethylbutyl, 3,3-dimethylbutyl, 2-ethylbutyl and the like.

The "$C_{1-6}$ alkoxy" means alkoxy wherein the alkyl moiety is the above-defined "$C_{1-6}$ alkyl". Examples thereof include methoxy, ethoxy, propoxy, isopropoxy, butoxy, isobutoxy, sec-butoxy, tert-butoxy, pentyloxy, isopentyloxy, neopentyloxy, 1,2-dimethylpropyloxy, 1-ethylpropyloxy, hexyloxy, isohexyloxy, 1,2,2-trimethylpropyloxy, 1,1-dimethylbutyloxy, 2,2-dimethylbutyloxy, 3,3-dimethylbutyloxy, 2-ethylbutyloxy and the like.

The "halo$C_{1-4}$ alkyl" means straight chain or branched chain alkyl having 1-4 carbon atoms, which is substituted by 1 to 9 the above-defined "halogens". When it is substituted by plural halogens, respective halogens may be the same or different. Examples thereof include 2-fluoroethyl, 2-chloroethyl, 2-bromoethyl, 3-fluoropropyl, 3-chloropropyl, 4-fluorobutyl, 4-chlorobutyl, 1,1-difluoroethyl, 1,1-difluoropropyl, 1,1-difluoro-2-methylpropyl, trifluoromethyl, 2,2,2-trifluoroethyl, 3,3,3-trifluoropropyl, 4,4,4-trifluorobutyl, pentafluoroethyl, 2,2,2-trifluoro-1-trifluoromethyl-ethyl and the like.

The "halo$C_{1-4}$ alkoxy" means alkoxy wherein the alkyl moiety is the above-defined "halo$C_{1-4}$ alkyl". Examples thereof include fluoromethoxy, chloromethoxy, bromomethoxy, 2-fluoroethoxy, 2-chloroethoxy, 2-bromoethoxy, 3-fluoropropoxy, 3-chloropropoxy, 4-fluorobutoxy, 4-chlorobutoxy, 1,1-difluoroethoxy, 2,2-difluoroethoxy, 1,1-difluoropropoxy, 2,2-difluoropropoxy, 3,3-difluoropropoxy, 1,1-difluoro-2-methylpropoxy, trifluoromethoxy, 2,2,2-trifluoroethoxy, 3,3,3-trifluoropropoxy, 4,4,4-trifluorobutoxy, pentafluoroethoxy, 2,2,2-trifluoro-1-trifluoromethyl-ethoxy and the like.

The "hydroxy$C_{1-6}$ alkyl" means the above-defined "$C_{1-6}$ alkyl" substituted by 1 or 2 hydroxy. Examples thereof include hydroxymethyl, 2-hydroxyethyl, 1-hydroxy-1-methylethyl, 1,2-dihydroxyethyl, 3-hydroxypropyl, 1-hydroxy-2,2-dimethylpropyl, 4-hydroxybutyl, 1-hydroxy-2,2-dimethylbutyl, 5-hydroxypentyl, 6-hydroxyhexyl and the like.

The "$C_{1-6}$ alkyl-carbonyl" means carbonyl bonded to the above-defined "$C_{1-6}$ alkyl". Examples thereof include acetyl, propionyl, 2,2-dimethylpropionyl, butyryl, 3-methylbutyryl, 2,2-dimethylbutyryl, pentanoyl, 4-methylpentanoyl, hexanoyl and the like.

The "$C_{1-6}$ alkyl-carbonyloxy" means carbonyloxy bonded to the above-defined "$C_{1-6}$ alkyl". Examples thereof include methylcarbonyloxy, ethylcarbonyloxy, propylcarbonyloxy, isopropylcarbonyloxy, butylcarbonyloxy, isobutylcarbonyloxy, sec-butylcarbonyloxy, tert-butylcarbonyloxy, pentylcarbonyloxy, isopentylcarbonyloxy, 2-methylbutylcarbonyloxy, 1,1-dimethylpropylcarbonyloxy, neopentylcarbonyloxy, 3,3-dimethylbutylcarbonyloxy, 1-ethylpropylcarbonyloxy, hexylcarbonyloxy and the like.

The "$C_{3-7}$ cycloalkyl" means 3- to 7-membered monocyclic cycloalkyl. Examples thereof include cyclopropyl, cyclobutyl, cyclopentyl, cyclohexyl and cycloheptyl.

The "$C_{6-10}$ aryl" means 6- to 10-membered aryl. Examples thereof include phenyl, 1-naphthyl, 2-naphthyl and the like. Of these, preferred is phenyl.

The "5- or 6-membered heteroaryl containing 1, 2 or 3 nitrogen atoms, oxygen atoms or sulfur atoms" means 5- or 6-membered monocyclic heteroaryl containing, besides carbon atoms, 1, 2 or 3 hetero atoms selected from a nitrogen atom, an oxygen atom and a sulfur atom. Examples thereof include furyl, thienyl, pyrrolyl, oxazolyl, isoxazolyl, thiazolyl, isothiazolyl, imidazolyl, pyrazolyl, oxadiazolyl(1,2,5-oxadiazolyl, 1,3,4-oxadiazolyl, 1,2,4-oxadiazolyl), thiadiazolyl(1,2,5-thiadiazolyl, 1,3,4-thiadiazolyl, 1,2,4-thiadiazolyl), triazolyl(1,2,3-triazolyl, 1,2,4-triazolyl), pyridyl, pyrimidinyl, pyridazinyl, pyrazinyl, 1,3,5-triazinyl and the like. Of these, preferred is pyridyl.

The "4-, 5- or 6-membered saturated heterocyclyl containing 1, 2 or 3 nitrogen atoms, oxygen atoms or sulfur atoms" means 4-, 5- or 6-membered monocyclic saturated heterocyclyl containing, besides carbon atoms, 1, 2 or 3 hetero atoms selected from a nitrogen atom, an oxygen atom and a sulfur atom. The carbon atom of the heterocycle is optionally substituted by oxo. When a sulfur atom is contained as a hetero atom, the sulfur atom is optionally monooxidized or dioxidized. Examples thereof include oxetanyl, azetidinyl, tetrahydrofuryl, tetrahydropyranyl, tetrahydrothienyl, tetrahydrothiopyranyl, oxazolidinyl, isoxazolidinyl, thiazolidinyl, isothiazolidinyl, imidazolidinyl, pyrazolidinyl, pyrrolidinyl, piperidyl (including piperidino), morpholinyl (including morpholino), thiomorpholinyl (including thiomorpholino), piperazinyl, 1,1-dioxidoisothiazolidinyl, 1,1-dioxidotetrahydrothienyl, 1,1-dioxidotetrahydrothiopyranyl, 1,1-dioxidothiomorpholinyl (including 1,1-dioxidothiomorpholino) and the like. In addition, the saturated heterocyclyl may be partially saturated. Examples thereof include imidazolinyl, oxazolinyl, pyrazolinyl, thiazolinyl and the like. Of these, preferred is oxetanyl.

The "$C_{1-6}$ alkylsulfanyl" means sulfanyl bonded to the above-defined "$C_{1-6}$ alkyl". Examples thereof include methylsulfanyl, ethylsulfanyl, propylsulfanyl, isopropylsulfanyl, n-butylsulfanyl, isobutylsulfanyl, sec-butylsulfanyl, tert-butylsulfanyl, pentylsulfanyl, 1,1-dimethylpropylsulfanyl, 2,2-dimethylpropylsulfanyl, hexylsulfanyl and the like.

The "$C_{2-6}$ alkynyl" means straight chain or branched chain hydrocarbon having 2 to 6 carbon atoms and at least one triple bond. Examples thereof include ethynyl, 1-propynyl, 2-propynyl, 1-butynyl, 2-butynyl, 3-butynyl, 1-methyl-2-propynyl, 3,3-dimethylbutynyl (that is, 3,3-dimethylbut-1-ynyl) and the like.

The "—$(C_nH_{2n})$—" means straight chain or branched chain alkylene having n carbon atoms and 2n hydrogen atoms. Examples thereof include —$CH_2$—, —$CH_2CH_2$—, —$CH(CH_3)$—, —$CH_2CH_2CH_2$—, —$C(CH_3)_2$—, —$CH(CH_3)CH_2$— and the like.

When $R^2$ is (10) —$(C_nH_{2n})$—$R^b$ and $R^b$ is (k) —$NR^{b14}C(O)R^{b15}$, "(ii) $C_{1-8}$ alkyl (said $C_{1-8}$ alkyl is optionally substituted by 1, 2 or 3 substituents selected from the group consisting of hydroxy, halo$C_{1-4}$ alkyl, $C_{1-6}$ alkoxy and $C_{6-10}$ aryl)" for $R^{b15}$ means the above-defined "$C_{1-8}$ alkyl" substituted or not substituted by the same or different, 1, 2 or 3 substituents is selected from the group consisting of hydroxy, the above-defined "halo$C_{1-4}$ alkyl", the above-defined "$C_{1-6}$ alkoxy" and the above-defined "$C_{6-10}$ aryl", at the substitutable position(s) thereof. Examples of $R^b$ include 2-ethoxy-3-methoxypropylcarbonylamino, 1-methyl-1-methoxy-2,2,2-trifluoroethylcarbonylamino and the like.

When $R^2$ is (10) —$(C_nH_{2n})$—$R^b$ and $R^b$ is (k) —$NR^{b14}C(O)R^{b15}$, "(iv) $C_{3-7}$ cycloalkyl (said $C_{3-7}$ cycloalkyl is optionally substituted by 1, 2, 3 or 4 substituents selected from the group consisting of $C_{1-6}$ alkyl, halogen, hydroxy$C_{1-6}$ alkyl and halo$C_{1-4}$ alkyl, and/or optionally form a fused ring with a benzene ring)" for $R^{b15}$ means (1) the above-defined "$C_{3-7}$ cycloalkyl" substituted by the same or different, 1, 2, 3 or 4 substituents selected from the group consisting of the above-defined "$C_{1-6}$ alkyl", the above-defined "halogen", the above-defined "hydroxy$C_{1-6}$ alkyl" and the above-defined "halo$C_{1-4}$ alkyl", at the substitutable position(s) thereof, (2) unsubstituted $C_{3-7}$ cycloalkyl, or (3) $C_{3-7}$ cycloalkyl of (1) or (2), fused with one benzene ring at a fusible position. Examples of $R^b$ include 1,2,3,4-tetrahydro-naphthalen-2-ylcarbonylamino, 2-methyl-indan-2-ylcarbonylamino and the like.

When $R^2$ is (10) —$(C_nH_{2n})$—$R^b$ and $R^b$ is (k) —$NR^{b14}C(O)R^{b15}$, "$R^{b14}$ and $R^{b15}$ optionally form a 4-, 5- or 6-membered lactam together with the nitrogen atom that $R^{b1}$ is bonded to and the carbon atom that $R^{b15}$ is bonded to" means that $R^b$ is 2-oxo-azetidin-1-yl, 2-oxo-pyrrolidin-1-yl, 2-oxo-piperidin-1-yl or the like.

In addition, in this case, "said lactam is optionally substituted by 1, 2 or 3 $C_{1-6}$ alkyls, and/or optionally form a fused ring with a benzene ring" means that, in addition to the above-mentioned "lactam", (1) the same or different 1, 2 or 3 $C_{1-6}$ alkyls defined above are present at the substitutable position(s) of the lactam, (2) one benzene ring is fused at the fusible position of the lactam, and (3) one benzene ring is fused at the fusible position of the lactam substituted by $C_{1-6}$ alkyl(s). Examples of $R^b$ include 3,4-dimethyl-2-oxo-pyrrolidin-1-yl, 1-oxo-1,3-dihydro-isoindol-2-yl, 3,3-dimethyl-2-oxo-2,3-dihydro-indol-1-yl and the like.

In the compound represented by the formula [I], preferable embodiments of respective groups are as described below.

$R^1$ is preferably chloro, methyl, cyano or trifluoromethyl, more preferably chloro or trifluoromethyl, and further preferably chloro.

$R^2$ is preferably
(1) halogen,
(2) hydroxy,
(3) carboxy,
(5) $C_{1-6}$ alkoxy,
(6) halo$C_{1-4}$ alkoxy,
(7) halo$C_{1-4}$ alkyl,
(8) $C_{1-6}$ alkyl-carbonyl,
(9) —$C(O)NR^{a1}R^{a2}$ ($R^{a1}$ and $R^{a2}$ are as defined above) or
(10) —$(C_nH_{2n})$—$R^b$ ($R^b$ is as defined above), more preferably
(10) —$(C_nH_{2n})$—$R^b$ ($R^b$ is as defined above).

$R^b$ is preferably
(g) —$NR^{b5}C(O)NR^{b6}R^{b7}$ ($R^{b5}$, $R^{b6}$ and $R^{b7}$ are as defined above),
(h) —$NR^{b8}R^{b9}$ ($R^{b8}$ and $R^{b9}$ are as defined above),
(i) —$NR^{b10}S(O)_2R^{b11}$ ($R^{b10}$ and $R^{b11}$ are as defined above),
(j) —$NR^{b12}C(O)OR^{b13}$ ($R^{b12}$ and $R^{b13}$ are as defined above), or
(k) —$NR^{b14}C(O)R^{b15}$ ($R^{b14}$ and $R^{b15}$ are as defined above, more preferably
(k) —$NR^{b14}C(O)R^{b15}$ ($R^{b14}$ and $R^{b15}$ are as defined above).

n is preferably 1 or 2, more preferably 1.

$R^{b14}$ is preferably hydrogen or methyl, more preferably hydrogen.

$R^{b15}$ is preferably
(ii) $C_{1-4}$ alkyl (said $C_{1-4}$ alkyl is optionally substituted by 1 or 2 substituents selected from the group consisting of hydroxy, trifluoromethyl, $C_{1-4}$ alkoxy and phenyl) or
(iv) $C_{3-7}$ cycloalkyl (said $C_{3-7}$ cycloalkyl is optionally substituted by 1, 2, 3 or 4 substituents selected from the group consisting of $C_{1-4}$ alkyl, halogen, hydroxy$C_{1-4}$ alkyl and trifluoromethyl), more preferably $C_{1-4}$ alkyl optionally substituted by 1 or 2 trifluoromethyls and $C_{1-4}$ alkoxy, or $C_{3-7}$ cycloalkyl optionally substituted by one trifluoromethyl, further preferably tert-butyl, 3,3,3-trifluoro-2,2-dimethylpropyl, 3,3,3-trifluoro-2-methoxy-2-methylpropyl, 3,3,3-trifluoro-2-methyl-2-trifluoromethylpropyl, or 1-trifluoromethylcyclopropyl.

$R^3$ is preferably
(3) $C_{1-6}$ alkyl or
(4) —$OR^c$ {$R^c$ is $C_{1-6}$ alkyl optionally substituted by 1, 2 or 3 substituents selected from the group consisting of the following (a) to (f);
(a) halogen,
(b) hydroxy,
(c) $C_{1-6}$ alkoxy,
(d) —$C(O)NR^{c1}R^{c2}$ ($R^{c1}$ and $R^{c2}$ are as defined above),
(e) $C_{6-10}$ aryl (said $C_{6-10}$ aryl is optionally substituted by 1, 2 or 3 substituents selected from the group consisting of
(i) halogen,
(ii) hydroxy,
(iii) $C_{1-6}$ alkyl,
(iv) $C_{1-6}$ alkoxy, and
(v) halo$C_{1-4}$ alkyl), and
(f) 5- or 6-membered heteroaryl containing 1, 2 or 3 nitrogen atoms, oxygen atoms or sulfur atoms (said heteroaryl is optionally substituted by 1, 2 or 3 substituents selected from the group consisting of
(i) halogen,
(ii) hydroxy,
(iii) $C_{1-6}$ alkyl,
(iv) $C_{1-6}$ alkoxy, and
(v) halo$C_{1-4}$ alkyl)}.

$R^c$ is preferably methyl optionally substituted by 1 or 2 substituents selected from the following (e) and (f);
(e) $C_{6-10}$ aryl (said $C_{6-10}$ aryl is optionally substituted by 1, 2 or 3 substituents selected from the group consisting of
(i) halogen,
(ii) hydroxy,
(iii) $C_{1-6}$ alkyl,
(iv) $C_{1-6}$ alkoxy, and
(v) halo$C_{1-4}$ alkyl), and
(f) 5- or 6-membered heteroaryl containing 1, 2 or 3 nitrogen atoms, oxygen atoms or sulfur atoms (said heteroaryl is optionally substituted by 1, 2 or 3 substituents selected from the group consisting of
(i) halogen,
(ii) hydroxy,
(iii) $C_{1-6}$ alkyl,
(iv) $C_{1-6}$ alkoxy, and
(v) halo$C_{1-4}$ alkyl), more preferably methyl optionally substituted by 1 or 2 substituents selected from the following (e1) and (f1);

(e1) phenyl (said phenyl is optionally substituted by 1 or 2 substituents selected from the group consisting of
(i) halogen,
(ii) hydroxy,
(iii) $C_{1-6}$ alkyl,
(iv) $C_{1-6}$ alkoxy, and
(v) haloC$_{1-4}$ alkyl), and
(f1) pyridyl (said pyridyl is optionally substituted by 1 or 2 substituents selected from the group consisting of
(i) halogen,
(ii) hydroxy,
(iii) $C_{1-6}$ alkyl,
(iv) $C_{1-6}$ alkoxy, and
(v) haloC$_{1-4}$ alkyl).

$R^4$ is preferably hydrogen, fluoro, chloro, or methyl, more preferably hydrogen.

$R^5$ is preferably
(1) halogen,
(4) $C_{1-6}$ alkyl (said $C_{1-6}$ alkyl is optionally substituted by 1, 2 or 3 substituents selected from the group consisting of halogen, $C_{6-10}$ aryl and $C_{1-6}$ alkoxy),
(5) $C_{3-7}$ cycloalkyl,
(6) —OR$^d$ {R$^d$ is
(a) $C_{2-6}$ alkynyl,
(b) $C_{3-7}$ cycloalkyl optionally substituted by 1, 2 or 3 $C_{1-6}$ alkyls or
(c) $C_{1-8}$ alkyl (said $C_{1-8}$ alkyl is optionally substituted by 1, 2 or 3 substituents selected from the group consisting of the following (i) to (v);
(i) halogen,
(ii) $C_{6-10}$ aryl,
(iii) $C_{1-6}$ alkoxy,
(iv) $C_{3-7}$ cycloalkyl (said $C_{3-7}$ cycloalkyl is optionally substituted by 1, 2 or 3 substituents selected from the group consisting of $C_{1-6}$ alkyl and haloC$_{1-4}$ alkyl), and
(v) 4-, 5- or 6-membered saturated heterocyclyl containing one oxygen atom (said saturated heterocyclyl is optionally substituted by 1, 2 or 3 substituents selected from the group consisting of $C_{1-6}$ alkyl and haloC$_{1-4}$ alkyl))}, or
(7) the formula:

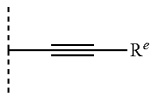

wherein R$^e$ is
(a) $C_{1-6}$ alkyl,
(b) $C_{3-7}$ cycloalkyl,
(c) 5- or 6-membered heteroaryl containing 1, 2 or 3 nitrogen atoms, oxygen atoms or sulfur atoms, or
(d) $C_{6-10}$ aryl (said $C_{6-10}$ aryl is optionally substituted by 1, 2 or 3 substituents selected from the group consisting of
(i) halogen,
(ii) $C_{1-6}$ alkyl,
(iii) haloC$_{1-4}$ alkyl,
(iv) $C_{1-6}$ alkoxy, and
(v) haloC$_{1-4}$ alkoxy).

R$^d$ is preferably $C_{1-8}$ alkyl (said $C_{1-8}$ alkyl is optionally substituted by 1, 2 or 3 substituents selected from the group consisting of the following (i) to (v);
(i) halogen,
(ii) $C_{6-10}$ aryl,
(iii) $C_{1-6}$ alkoxy,
(iv) $C_{3-7}$ cycloalkyl (said $C_{3-7}$ cycloalkyl is optionally substituted by 1, 2 or 3 substituents selected from the group consisting of $C_{1-6}$ alkyl and haloC$_{1-4}$ alkyl), and
(v) 4-, 5- or 6-membered saturated heterocyclyl containing one oxygen atom (said saturated heterocyclyl is optionally substituted by 1, 2 or 3 substituents selected from the group consisting of $C_{1-6}$ alkyl and haloC$_{1-4}$ alkyl)).

R$^e$ is preferably
(b) $C_{3-7}$ cycloalkyl,
(c) 5- or 6-membered heteroaryl containing 1, 2 or 3 nitrogen atoms, oxygen atoms or sulfur atoms, or
(d) $C_{6-10}$ aryl (said $C_{6-10}$ aryl is optionally substituted by 1, 2 or 3 substituents selected from the group consisting of
(i) halogen,
(ii) $C_{1-6}$ alkyl,
(iii) haloC$_{1-4}$ alkyl,
(iv) $C_{1-6}$ alkoxy, and
(v) haloC$_{1-4}$ alkoxy).

m1 is preferably 0, 1 or 2, more preferably 1 or 2.

In the compound represented by the formula [I], one of preferable embodiments is a compound represented by the following formula [I-A]:

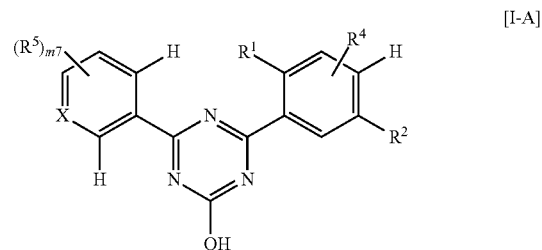

wherein
a carbon atom with a hydrogen atom is not substituted by $R^4$ and $R^5$,
X, $R^1$, $R^2$ and $R^4$ are as defined in the aforementioned formula [I],
$R^5$ is
(1) halogen,
(4) $C_{1-6}$ alkyl (said $C_{1-6}$ alkyl is optionally substituted by 1, 2 or 3 substituents selected from the group consisting of halogen, $C_{6-10}$ aryl and $C_{1-6}$ alkoxy),
(5) $C_{3-7}$ cycloalkyl, or
(6) —OR$^d$ {R$^d$ is
(a) $C_{2-6}$ alkynyl or
(c) $C_{1-8}$ alkyl (said $C_{1-8}$ alkyl is optionally substituted by 1, 2 or 3 substituents selected from the group consisting of the following (i) to (v);
(i) halogen,
(ii) $C_{6-10}$ aryl,
(iii) $C_{1-6}$ alkoxy,
(iv) $C_{3-7}$ cycloalkyl (said $C_{3-7}$ cycloalkyl is optionally substituted by 1, 2 or 3 substituents selected from the group consisting of $C_{1-6}$ alkyl and haloC$_{1-4}$ alkyl), and
(v) 4-, 5- or 6-membered saturated heterocyclyl containing 1, 2 or 3 nitrogen atoms, oxygen atoms or sulfur atoms (said saturated heterocyclyl is optionally substituted by 1, 2 or 3 substituents selected from the group consisting of $C_{1-6}$ alkyl and haloC$_{1-4}$ alkyl))}, and m7 is 0, 1 or 2 and, when m7 is 2, each $R^5$ is selected independently.

In a compound represented by the formula [I], one of the preferable other embodiments is a compound represented by the following formula [I-B]:

[I-B]

wherein
a carbon atom with a hydrogen atom is not substituted by $R^4$ and $R^5$,
X, $R^3$ and $R^4$ are as defined in the aforementioned formula [I],
$R^1$ is chloro or trifluoromethyl,
$R^5$ is
- (4) $C_{1-6}$ alkyl (said $C_{1-6}$ alkyl is optionally substituted by 1, 2 or 3 substituents selected from the group consisting of halogen, $C_{6-10}$ aryl and $C_{1-6}$ alkoxy),
- (6) —$OR^d$ {$R^d$ is $C_{1-8}$ alkyl (said $C_{1-8}$ alkyl is optionally substituted by 1, 2 or 3 substituents selected from the group consisting of the is following (i) to (iv);
  - (i) halogen,
  - (ii) $C_{6-10}$ aryl,
  - (iii) $C_{1-6}$ alkoxy, and
  - (iv) $C_{3-7}$ cycloalkyl (said $C_{3-7}$ cycloalkyl is optionally substituted by 1, 2 or 3 substituents selected from the group consisting of $C_{1-6}$ alkyl and halo$C_{1-4}$ alkyl))}, or
- (7) the formula:

$$\vdash\!\!\!\equiv\!\!\!-R^e$$

wherein $R^e$ is
- (b) $C_{3-7}$ cycloalkyl, or
- (d) $C_{6-10}$ aryl (said $C_{6-10}$ aryl is optionally substituted by 1, 2 or 3 substituents selected from the group consisting of
  - (i) halogen,
  - (ii) $C_{1-6}$ alkyl,
  - (iii) halo$C_{1-4}$ alkyl,
  - (iv) $C_{1-6}$ alkoxy, and
  - (v) halo$C_{1-4}$ alkoxy), and m7 is 0, 1 or 2 and, when m7 is 2, each $R^5$ is selected independently.

In a compound represented by the formula [I], one of the preferable other embodiments is a compound represented by the following formula [I-C]:

[I-C]

wherein
X is CH or N,
$R^{b15}$ is
- (ii) $C_{1-4}$ alkyl (said $C_{1-4}$ alkyl is optionally substituted by 1 or 2 substituents selected from trifluoromethyl and methoxy) or
- (iv) $C_{3-7}$ cycloalkyl optionally substituted by trifluoromethyl, $R^{5a}$ is
- (1) fluoro,
- (4) methyl (said methyl is optionally substituted by 3 fluoros), or
- (6) —$OR^d$ {$R^d$ is
  - (a) $C_{2-4}$ alkynyl or
  - (c) $C_{1-4}$ alkyl optionally substituted by one $C_{3-7}$ cycloalkyl (said $C_{3-7}$ cycloalkyl is optionally substituted by trifluoromethyl)}, $R^{5b}$ is
- (1) halogen,
- (4) $C_{1-4}$ alkyl, or
- (5) cyclopropyl, and m8 is 0 or 1.

A pharmaceutically acceptable salt of a compound represented by the formula [I] (hereinafter to be also referred to as the compound of the present invention) may be any salt as long as it forms a nontoxic salt with the compound of the present invention, and examples thereof include salts with inorganic acid, salts with organic acid, salts with inorganic base, salts with organic base, salts with amino acid and the like.

Various forms of pharmaceutically acceptable salts are well known in this field and, for example, they are described in the following documents.
- (a) Berge et al., J. Pharm. Sci., 66, p 1-19 (1977),
- (b) Stahl et al., "Handbook of Pharmaceutical Salt: Properties, Selection, and Use" (Wiley-VCH, Weinheim, Germany, 2002),
- (c) Paulekuhn et al., J. Med. Chem., 50, p 6665-6672 (2007)

Examples of the salts with inorganic acid include salts with hydrochloric acid, nitric acid, sulfuric acid, phosphoric acid, hydrobromic acid and the like.

Examples of the salts with organic acid include salts with oxalic acid, maleic acid, citric acid, fumaric acid, lactic acid, malic acid, succinic acid, tartaric acid, acetic acid, trifluoroacetic acid, gluconic acid, ascorbic acid, methanesulfonic acid, benzenesulfonic acid, p-toluenesulfonic acid and the like.

Examples of the salts with organic acid include salts with adipic acid, alginic acid, 4-aminosalicylic acid, anhydromethylenecitric acid, benzoic acid, calcium edetate, camphoric acid, camphor-10-sulfonic acid, carbonic acid, edetic acid, ethane-1,2-disulfonic acid, dodecylsulfuric acid, ethanesulfonic acid, glucoheptonic acid, glucuronic acid, glucoheptonic acid, glycollyarsanilic acid, hexylresorcinic acid, hydrofluoric acid, hydroiodic acid, hydroxy-naphtoic acid, 2-hydroxy-1-ethanesulfonic acid, lactobionic acid, mandelic acid, methylsulfuric acid, methylnitric acid, methylenebis (salicylic acid), galactaric acid, naphthalene-2-sulfonic acid, 2-naphtoic acid, 1,5-naphthalenedisulfonic acid, oleic acid, pamoic acid, pantothenic acid, pectin acid, picric acid, propionic acid, polygalacturonic acid, salicylic acid, stearic acid, tannic acid, teoclic acid, thiocyanic acid, undecanoic acid and the like.

Examples of the salts with inorganic base include sodium salt, potassium salt, calcium salt, magnesium salt, ammonium salt and the like.

Furthermore, examples of the salts with inorganic base include salts with aluminum, barium, bismuth, lithium, or zinc.

Examples of the salts with organic base include salts with methylamine, diethylamine, trimethylamine, triethylamine, ethanolamine, diethanolamine, triethanolamine, ethylenediamine, tris (hydroxymethyl)methylamine, dicyclohexylamine, N,N'-dibenzylethylenediamine, guanidine, pyridine, picoline, choline, cinchonine, meglumine and the like.

Furthermore, examples of the salts with organic base include salts with arecoline, betaine, clemizole, N-methylglucamine, N-benzylphenethylamine or tris (hydroxymethyl)methylamine.

Examples of the salts with amino acid include salts with lysine, arginine, aspartic acid, glutamic acid and the like.

Among the above-mentioned salts, preferred are salts with hydrochloric acid, sulfuric acid or p-toluenesulfonic acid.

Various salts can be obtained by reacting a compound represented by the formula [I] with inorganic base, organic base, inorganic acid, organic acid or amino acid according to a known method.

A compound represented by the formula [I] or a pharmaceutically acceptable salt thereof may be present as a solvate. The "solvate" is a compound represented by the formula [I] or a pharmaceutically acceptable salt thereof, which is coordinated with a solvent molecule, and also encompasses hydrates. The solvate is preferably a pharmaceutically acceptable solvate, examples thereof include a hydrate, ethanolate, dimethyl sulfoxidate and the like of a compound represented by the formula [I] or a pharmaceutically acceptable salt thereof. Specific examples include semihydrate, monohydrate, dihydrate or monoethanolate of a compound represented by the formula [I], monohydrate of sodium salt or ⅔ ethanolate of dihydrochloride of a compound represented by the formula [I], and the like.

The solvates can be obtained by a known method.

In addition, a compound represented by the formula [I] may be labeled with isotope (e.g., $^2H$, $^3H$, $^{14}C$, $^{35}S$ etc.).

The compound of the present invention may exist as a tautomer. In this case, the compound of the present invention can be a single tautomer or a mixture of individual tautomers. For example, a compound represented by the formula [I] may contain a tautomer shown below

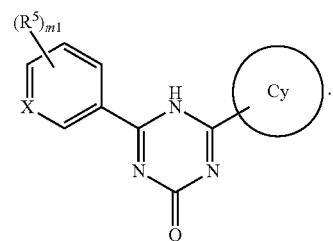

Such tautomer is also encompassed in the compound represented by the formula [I].

The compound of the present invention may have a carbon double bond. In this case, the compound of the present invention can be present as E form, Z form, or a mixture of E form and Z form.

The compound of the present invention may contain a stereoisomer that should be recognized as a cis/trans isomer. In this case, the compound of the present invention can be present as a cis form, a trans form, or mixture of a cis form and a trans form.

The compound of the present invention may contain one or more asymmetric carbons. In this case, the compound of the present invention may be present as a single enantiomer, a single diastereomer, a mixture of enantiomers or a mixture of diastereomers.

The compound of the present invention may be present as an atropisomer. In this case, the compound of the present invention may be present as an individual atropisomer or a mixture of atropisomers.

The compound of the present invention may simultaneously contain plural structural characteristics that produce the above-mentioned isomers. Moreover, the compound of the present invention may contain the above-mentioned isomers at any ratio.

In the absence of other reference such as annotation and the like, the formulae, chemical structures and compound names indicated in the present specification without specifying the stereochemistry thereof encompass all the above-mentioned isomers that may exist.

A diastereomeric mixture can be separated into each diastereomer by conventional methods such as chromatography, crystallization and the like. In addition, each diastereomer can also be formed by using a stereochemically single starting material, or by a synthesis method using a stereoselective reaction.

An enantiomeric mixture can be separated into each single enantiomer by a method well known in the pertinent field.

For example, enantiomeric mixture can be prepared by reacting the enantiomeric mixture with a substantially pure enantiomer that is known as a chiral auxiliary. The diastereomeric mixture can be separated into each diastereomer mentioned above. The diastereomer mixture can be separated into each diastereomer as mentioned above. The separated diastereomer can be converted to a desired enantiomer by removing the added chiral auxiliary by cleavage.

In addition, a mixture of enantiomers of a compound can also be directly separated by a chromatography method using a chiral solid phase well known in the pertinent field.

Alternatively, one of the enantiomers of a compound can also be obtained by using a substantially pure optically active starting material or stereoselective synthesis (asymmetric induction) of a prochiral intermediate using a chiral auxiliary and an asymmetric catalyst.

The absolute steric configuration can be determined based on the X-ray crystal analysis of the resultant crystalline product or intermediate. In this case, a resultant crystalline product or intermediate derivatized with a reagent having an asymmetric center with a known steric configuration may be used where necessary.

As a compound represented by the formula [I] or a pharmaceutically acceptable salt thereof, a substantially purified compound represented by the formula [I] or a pharmaceutically acceptable salt thereof is preferable. More preferred is a compound represented by the formula [I] or a pharmaceutically acceptable salt thereof or a solvate thereof, which is purified to have a purity of more than 80%.

Examples of the "pharmaceutical composition" include oral preparations such as tablet, capsule, granule, powder, troche, syrup, emulsion, suspension and the like, and parenteral agents such as external preparation, suppository, injection, eye drop, nasal preparations, pulmonary preparation and the like.

The pharmaceutical composition of the present invention is produced according to a method known per se in the art of pharmaceutical preparations, by mixing etc. a compound represented by the formula [I] or a pharmaceutically acceptable salt thereof, or a solvate thereof with a suitable amount of at least one kind of pharmaceutically acceptable carrier and the like as appropriate. While the content of the compound represented by the formula [I] or a pharmaceutically acceptable salt thereof, or a solvate thereof in the pharmaceutical composition varies depending on the dosage form, dose and the like, it is, for example, 0.00001 to 100 wt % of the whole composition.

Examples of the "pharmaceutically acceptable carrier" include various organic or inorganic carrier substances conventionally used as preparation materials, for example, excipient, disintegrant, binder, glidant, lubricant and the like for solid preparations, and solvent, solubilizing agent, suspending agent, isotonicity agent, buffering agent, soothing agent, surfactant, pH adjuster, thickening agent and the like for liquid preparations. Where necessary, moreover, additives such as preservative, antioxidant, colorant, sweetening agent and the like are used.

Examples of the "excipient" include lactose, sucrose, D-mannitol, D-sorbitol, cornstarch, dextrin, microcrystalline cellulose, crystalline cellulose, carmellose, carmellose calcium, sodium carboxymethyl starch, low-substituted hydroxypropylcellulose, gum arabic and the like.

Examples of the "disintegrant" include carmellose, carmellose calcium, carmellose sodium, sodium carboxymethyl starch, croscarmellose sodium, crospovidone, low-substituted hydroxypropylcellulose, hydroxypropylmethylcellulose, crystalline cellulose and the like.

Examples of the "binder" include hydroxypropylcellulose, hydroxypropylmethylcellulose, povidone, crystalline cellulose, sucrose, dextrin, starch, gelatin, carmellose sodium, gum arabic and the like.

Examples of the "glidant" include light anhydrous silicic acid, magnesium stearate and the like.

Examples of the "lubricant" include magnesium stearate, calcium stearate, talc and the like.

Examples of the "solvent" include purified water, ethanol, propylene glycol, macrogol, sesame oil, corn oil, olive oil and the like.

Examples of the "solubilizing agent" include propylene glycol, D-mannitol, benzyl benzoate, ethanol, triethanolamine, sodium carbonate, sodium citrate and the like.

Examples of the "suspending agent" include benzalkonium chloride, carmellose, hydroxypropylcellulose, propylene glycol, povidone, methylcellulose, glycerol monostearate and the like.

Examples of the "isotonicity agent" include glucose, D-sorbitol, sodium chloride, D-mannitol and the like.

Examples of the "buffering agent" include sodium hydrogenphosphate, sodium acetate, sodium carbonate, sodium citrate and the like.

Examples of the "soothing agent" include benzyl alcohol and the like.

Examples of the "surfactant" include polyoxyethylene hydrogenated castor oil, polyethylene glycol monostearate, polyoxyethylene sorbitan fatty acid ester, alkyldiaminoethylglycine, alkylbenzenesulfonate, benzethonium chloride and the like.

Examples of the "pH adjuster" include hydrochloric acid, sulfuric acid, phosphoric acid, citric acid, acetic acid, sodium hydrogen carbonate, sodium carbonate, potassium hydroxide, sodium hydroxide, monoethanolamine, triethanolamine and the like.

Examples of the "thickening agent" include polyvinyl alcohol, carboxyvinyl polymer, methylcellulose, hydroxyethylcellulose, polyethylene glycol, dextran and the like.

Examples of the "preservative" include ethyl parahydroxybenzoate, chlorobutanol, benzyl alcohol, sodium dehydroacetate, sorbic acid and the like.

Examples of the "antioxidant" include sodium sulfite, is ascorbic acid and the like.

Examples of the "colorant" include food colors (e.g., Food Color Red No. 2 or 3, Food Color Yellow No. 4 or 5 etc.), β-carotene and the like.

Examples of the "sweetening agent" include saccharin sodium, dipotassium glycyrrhizinate, aspartame and the like.

The pharmaceutical composition of the present invention can be administered orally or parenterally (e.g., topical, rectal, intravenous administration etc.) to human as well as mammals other than human (e.g., hamster, guinea pig, cat, dog, swine, bovine, horse, sheep, monkey etc.). The dose varies depending on the subject of administration, disease, symptom, dosage form, administration route and the like. For example, the daily dose for oral administration to an adult patient (body weight: about 60 kg) is generally within the range of about 0.1 μg to 10 g, based on the compound of the present invention as the active ingredient. This amount can be administered in one to several portions.

The above-mentioned compound represented by the formula [I] or a pharmaceutically acceptable salt thereof, or a solvate thereof can be used in combination with one or a plurality of other medicaments (hereinafter to be also referred to as a concomitant drug) according to a method generally employed in the medical field (hereinafter to be referred to as combined use).

The administration period of the above-mentioned compound represented by the formula [I] or a pharmaceutically acceptable salt thereof, and a concomitant drug is not limited, and they may be administered to an administration subject as combination preparation, or the both preparations may be administered simultaneously or at given intervals as individual preparations. In addition, the pharmaceutical composition of the present invention and a concomitant drug may be used in the form of a kit. The dose of the concomitant drug is similar to the clinically-employed dose and can be appropriately selected according to the subject of administration, disease, symptom, dosage form, administration route, administration time, combination and the like. The administration form of the concomitant drug is not particularly limited, and it is only required that the compound represented by the formula [I] or a pharmaceutically acceptable salt thereof, or a solvate thereof is combined with a concomitant drug.

Examples of the concomitant drug include therapeutic agents for glaucoma such as prostaglandin preparation, $ blocker, a receptor agonist, sympathetic nerve stimulation agent, a blocker, carbonic anhydrase inhibitor, anticholinesterase agent, Rho kinase inhibitor and the like.

Examples of the prostaglandin preparation include isopropyl unoprostone, latanoprost, travoprost, tafluprost, bimatoprost and the like.

Examples of the β blocker include timolol maleate, Befunolol hydrochloride, carteolol hydrochloride, betaxolol hydrochloride, nipradilol, levobunolol hydrochloride and the like.

Examples of the α receptor agonist include brimonidine tartrate and the like.

Examples of the sympathetic nerve stimulation agent include dipivefrin hydrochloride, pilocarpine hydrochloride and the like.

Examples of the α blocker include bunazosin hydrochloride and the like.

Examples of the carbonic anhydrase inhibitor include dorzolamide hydrochloride, brinzolamide and the like.

Examples of the anticholinesterase agent include distigmine bromide and the like.

Examples of the Rho kinase inhibitor include ripasudil hydrochloride hydrate and the like.

An example of the specific combination of medicaments is a combination of one medicament selected from latanoprost, travoprost, tafluprost, timolol maleate, dorzolamide hydrochloride and brinzolamide, and the above-mentioned compound represented by the formula [I] or a pharmaceutically acceptable salt thereof, or a solvate thereof.

Next, one example of the production methods of the compound to practice the present invention is explained below. However, the production method of the compound of the present invention or a pharmaceutically acceptable salt thereof is not limited thereto.

Even when no directly corresponding disclosure is found in the following Production Methods, the steps may be modified for efficient production of the compound, such as introduction of a protecting group into a functional group with deprotection in a subsequent step, changing the order of Production Methods and steps, appropriate use of reagents other than the exemplified reagents to promote progress of the reactions, and the like.

The treatment after reaction in each step may be conventional ones, where isolation and purification can be performed as necessary according to a method appropriately selected from conventional methods such as crystallization, recrystallization, distillation, partitioning, silica gel chromatography, preparative HPLC and the like, or a combination of those methods. In some cases, the next step may be conducted without isolation and purification.

An intermediate capable of forming a salt may also be obtained as a salt, or used as a salt for reactions. Examples of such salt include hydrochloride of an intermediate having an amino group.

[Production Method 1-1]

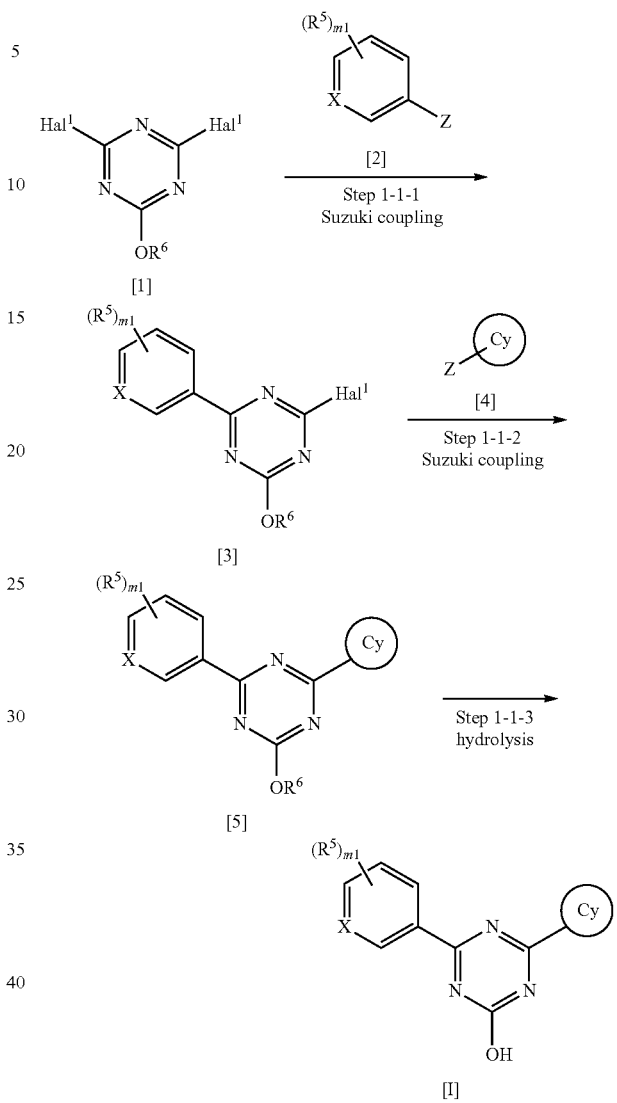

wherein $Hal^1$ is chloro or bromo;
$R^6$ is $C_{1-6}$ alkyl such as methyl, ethyl and the like or benzyl;
Z is a boron substituent used for the Suzuki coupling reaction such as $—B(OH)_2$, $—B(OR^7)_2$ (wherein $R^7$ is $C_{1-4}$ alkyl or one $R^7$ may be bonded to the other $R^7$ to form a ring), $—BF_3$, the formula

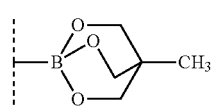

and the like; and
X, Cy, $R^5$ and m1 are as defined in the aforementioned formula [I].

(Step 1-1-1)

Compound [3] can be obtained by the Suzuki coupling reaction of compound [1] and compound [2]. For example, compound [3] can be obtained by reacting compound [1]

with compound [2] under heating in a solvent in the presence of a base and a palladium catalyst. Where necessary, a ligand may be added. Not less than 1.5 equivalents of compound [1] are preferably used relative to compound [2] to prevent the Suzuki is coupling reaction from progressing twice.

Examples of the palladium catalyst to be used for the reaction include palladium acetate, tetrakistriphenylphosphinepalladium, bis(triphenylphosphine)palladium dichloride, (bis (diphenylphosphino)ferrocene)palladium dichloride-methylene chloride complex and the like.

Examples of the base to be used for the reaction include inorganic bases such as alkali metal salts (e.g., potassium phosphate, sodium carbonate, sodium hydrogen carbonate, potassium carbonate, potassium acetate, sodium acetate, cesium fluoride etc.) and the like, and organic bases such as triethylamine and the like.

Examples of the ligand to be used for the reaction include organic phosphine ligands (e.g., triphenylphosphine, tricyclohexylphosphine, 2,2'-bis(diphenylphosphino)-1,1'-binaphthalene, 2-dicyclohexylphosphino-2',6'-dimethoxybiphenyl etc.) and the like.

Examples of the solvent to be used for the reaction include ether solvents such as 1,4-dioxane, tetrahydrofuran, diethyl ether, 1,2-dimethoxyethane, cyclopentyl methyl ether and the like; alcohol solvents such as methanol, ethanol, 1-propanol, 2-propanol and the like; hydrocarbon solvents such as toluene, xylene, hexane and the like; polar solvents such as N,N-dimethylformamide, N,N-dimethylacetamide, dimethyl sulfoxide, acetonitrile and the like; a mixed solvent thereof, and a mixed solvent thereof with water.

Compound [1] may be a commercially available product such as 2,4-dichloro-6-methoxy-1,3,5-triazine, or may be obtained by converting a commercially available product as appropriate by a method well known to those of ordinary skill in the art.

As for the Suzuki coupling reaction, for example, the following review article is known (SUZUKI, A et al. Palladium-Catalyzed Cross-Coupling Reactions of Organoboron Compounds. Chem Rev. 1995, Vol. 95, pages 2457-2483).

(Step 1-1-2)

Compound [5] can be obtained by the Suzuki coupling reaction of compound [3] and compound [4]. For example, compound [5] can be obtained by reacting compound [3] with compound [4] under heating in a solvent in the presence of a base and a palladium catalyst. Where necessary, a ligand may be added.

Examples of the palladium catalyst to be used for the reaction include palladium acetate, tetrakistriphenylphosphinepalladium, bis(triphenylphosphine)palladium dichloride, (bis (diphenylphosphino)ferrocene)palladium dichloride-methylene chloride complex and the like.

Examples of the base to be used for the reaction include inorganic bases such as alkali metal salts (e.g., potassium phosphate, sodium carbonate, sodium hydrogen carbonate, potassium carbonate, potassium acetate, sodium acetate, cesium fluoride etc.) and the like, and organic bases such as triethylamine and the like.

Examples of the ligand to be used for the reaction include organic phosphine ligands such as triphenylphosphine, tricyclohexylphosphine, 2,2'-bis(diphenylphosphino)-1,1'-binaphthalene, 2-dicyclohexylphosphino-2',6'-dimethoxybiphenyl and the like, and the like.

Examples of the solvent to be used for the reaction include ether solvents such as 1,4-dioxane, tetrahydrofuran, is diethyl ether, 1,2-dimethoxyethane, cyclopentyl methyl ether and the like; alcohol solvents such as methanol, ethanol, 1-propanol, 2-propanol and the like; hydrocarbon solvents such as toluene, xylene, hexane and the like; polar solvents such as N,N-dimethylformamide, N,N-dimethylacetamide, dimethyl sulfoxide, acetonitrile and the like; a mixed solvent thereof, and a mixed solvent thereof with water.

(Step 1-1-3)

Compound [I] can be obtained by converting the alkoxy of compound [5] to hydroxy by hydrolysis. For example, when $R^6$ is $C_{1-6}$ alkyl, compound [I] can be obtained by reacting compound [5] in a solvent in the presence of a base at room temperature to under heating, and neutralizing the obtained solution.

Examples of the base to be used for the reaction include lithium hydroxide, sodium hydroxide, potassium hydroxide, sodium methoxide and the like.

Examples of the solvent to be used for the reaction include a mixed solvent of water and alcohol solvents such as methanol, ethanol, 1-propanol, 2-propanol and the like; and a mixed solvent thereof with ether solvents such as 1,4-dioxane, tetrahydrofuran, diethyl ether, 1,2-dimethoxyethane, cyclopentyl methyl ether and the like.

[Production Method 1-2]

Compound [2] can be obtained by, for example, Production Method 1-2.

[Production Method 1-2]

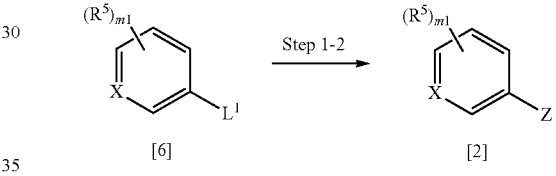

wherein $L^1$ is a leaving group such as bromo, iodo, trifluoromethanesulfonyloxy and the like, X, $R^5$ and m1 are as defined in the aforementioned formula [I], and Z is as defined in the aforementioned Production Method 1-1.

(Step 1-2)

Compound [2] can be obtained by borating compound [6]. For example, compound [2] can be obtained by reacting compound [6] with a boron reagent under heating in the presence of a base and a palladium catalyst. Where necessary, a ligand may be added Examples of the boron reagent to be used for the reaction include 4,4,4',4',5,5,5',5'-octamethyl-2,2'-bi-1,3,2-dioxaborolane, 5,5,5',5'-tetramethyl-2,2'-bi-1,3,2-dioxaborinane, tetrahydroxydiboron, 4,4,5,5-tetramethyl-1,3,2-dioxaborolane and the like.

Examples of the palladium catalyst to be used for the reaction include palladium acetate, tetrakistriphenylphosphinepalladium, bis(triphenylphosphine)palladium dichloride, (bis (diphenylphosphino)ferrocene)palladium dichloride-methylene chloride complex and the like.

Examples of the base to be used for the reaction include inorganic bases such as alkali metal salts (e.g., potassium phosphate, sodium carbonate, sodium hydrogen carbonate, potassium carbonate, potassium acetate, sodium acetate, cesium fluoride etc.) and the like, and organic bases such as triethylamine and the like.

Examples of the ligand to be used for the reaction include organic phosphorus ligands (e.g., triphenylphosphine, tricyclohexylphosphine, 2,2'-bis(diphenylphosphino)-1,1'-binaphthalene, 2-dicyclohexylphosphino-2',6'-dimethoxybiphenyl etc.) and the like.

Examples of the solvent to be used for the reaction include ether solvents such as 1,4-dioxane, tetrahydrofuran, diethyl ether, 1,2-dimethoxyethane, cyclopentyl methyl ether and the like; alcohol solvents such as methanol, ethanol, 1-propanol, 2-propanol and the like; hydrocarbon solvents such as toluene, xylene, hexane and the like; polar solvents such as N,N-dimethylformamide, N,N-dimethylacetamide, dimethyl sulfoxide, acetonitrile and the like; a mixed solvent thereof, and a mixed solvent thereof with water.

Compound [2] can also be obtained by adding an organic metal reagent to compound [6] in a solvent at −78° C. to room temperature, and reacting the product with a boron compound at −78° C. to room temperature.

Examples of the organic metal reagent to be used for the reaction include n-butyllithium, tert-butyllithium, isopropylmagnesium chloride and the like.

Examples of the boron reagent to be used for the reaction include trimethyl borate, triisopropyl borate, 2-isopropoxy-4,4,5,5-tetramethyl-1,3,2-dioxaborolane and the like.

Examples of the solvent to be used for the reaction include ether solvents such as 1,4-dioxane, tetrahydrofuran, diethyl ether, 1,2-dimethoxyethane, cyclopentyl methyl ether and the like; hydrocarbon solvents such as toluene, xylene, hexane and the like, and a mixed solvent thereof.

In one embodiment, compound [6] may be a commercially available product such as those shown below, or may be obtained by converting a commercially available product as appropriate by a method well known to those of ordinary skill in the art.

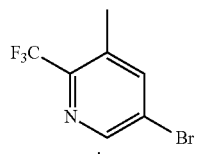
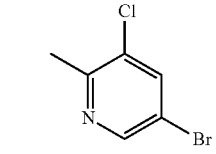
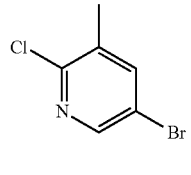
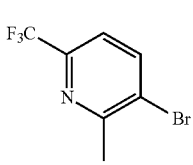
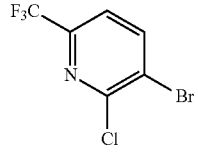

In one embodiment, compound [2] may be a commercially available product such as those shown below, or may be obtained by converting a commercially available product as appropriate by a method well known to those of ordinary skill in the art.

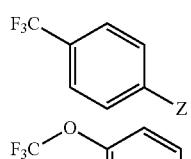
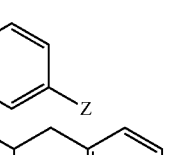

-continued

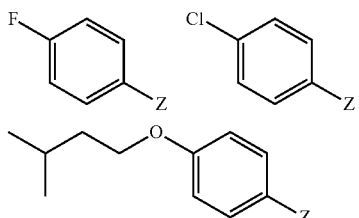
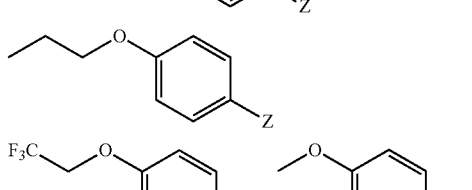
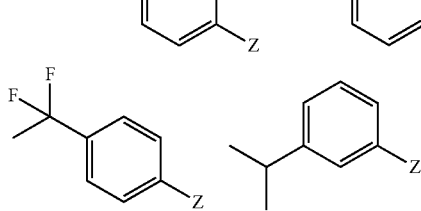
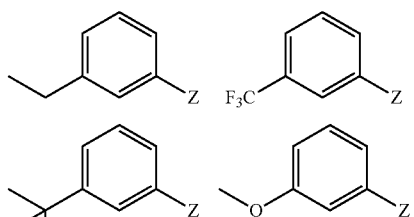
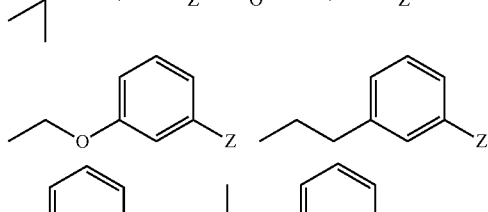
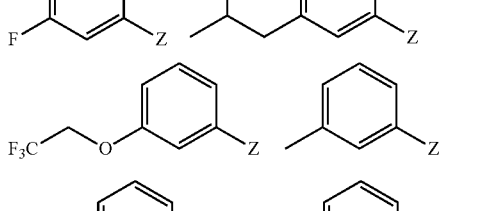
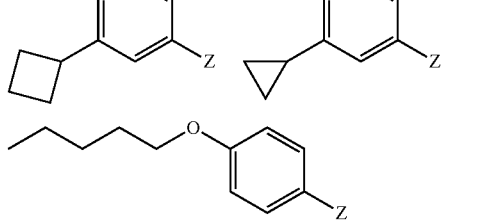
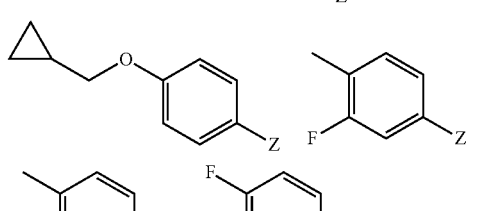
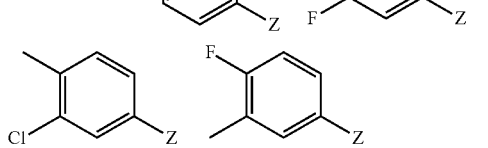

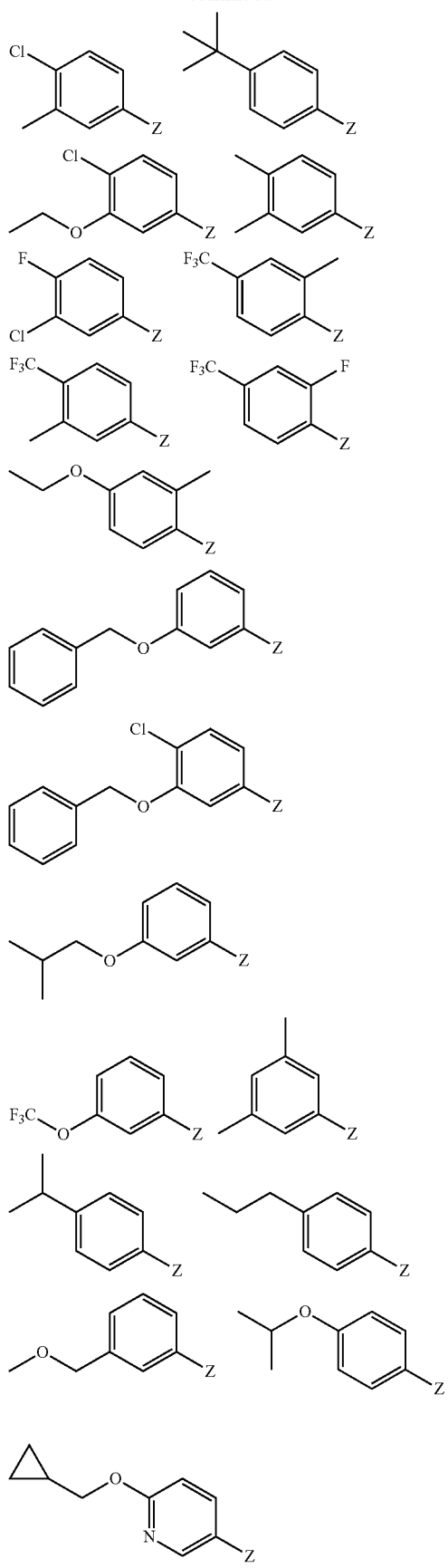
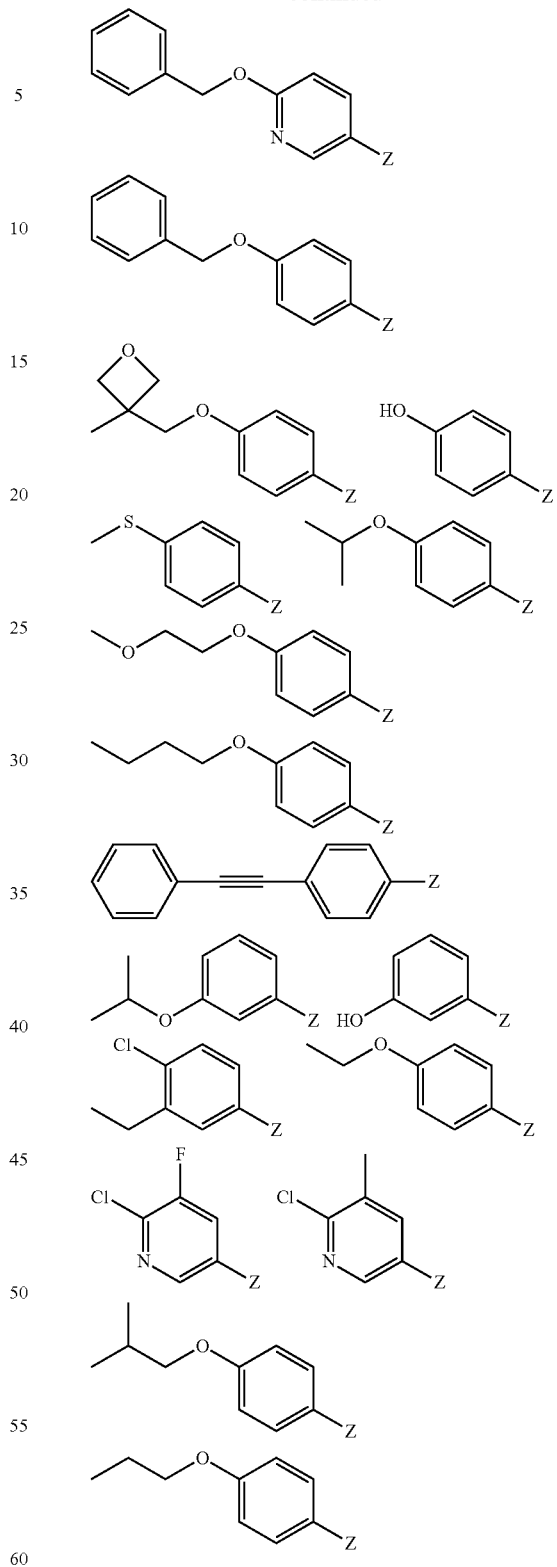
wherein Z is as defined in the aforementioned Production Method 1-1.
[Production Method 1-3]
Compound [4] can be obtained by, for example, Production Method 1-3.

[Production Method 1-3]

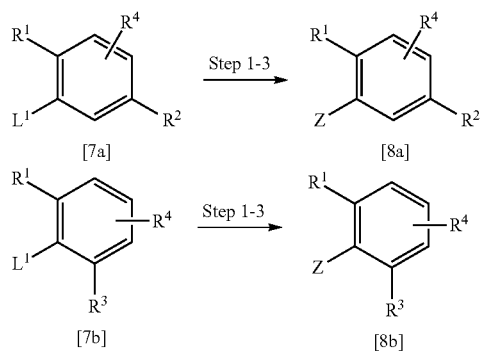

wherein $R^1$, $R^2$, $R^3$ and $R^4$ are as defined in the aforementioned formula [I], $L^1$ is as defined in the aforementioned Production Method 1-2, and Z is as defined in the aforementioned Production Method 1-1.

(Step 1-3)

Compound [4] is compound [8a] or [8b]. Compound [8a] or [8b], i.e., compound [4], can be obtained by borating compound [7a] or [7b] in the same manner as in Production Method 1-2, Step 1-2.

Compounds [7a] and [7b] may be commercially available products such as 2-bromo-4-methylbenzonitrile and 2-bromo-3-methylphenol, or may be obtained by converting a commercially available product as appropriate by a method well known to those of ordinary skill in the art.

In one embodiment, compound [4] may be a commercially available product such as those shown below, or may be obtained by converting a commercially available product as appropriate by a method well known to those of ordinary skill in the art.

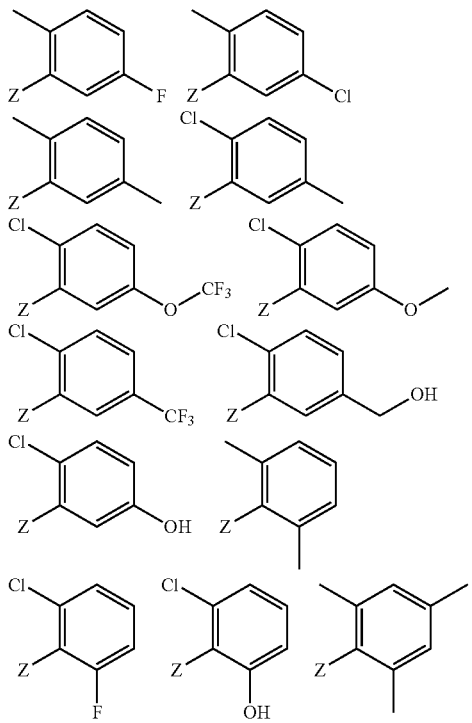

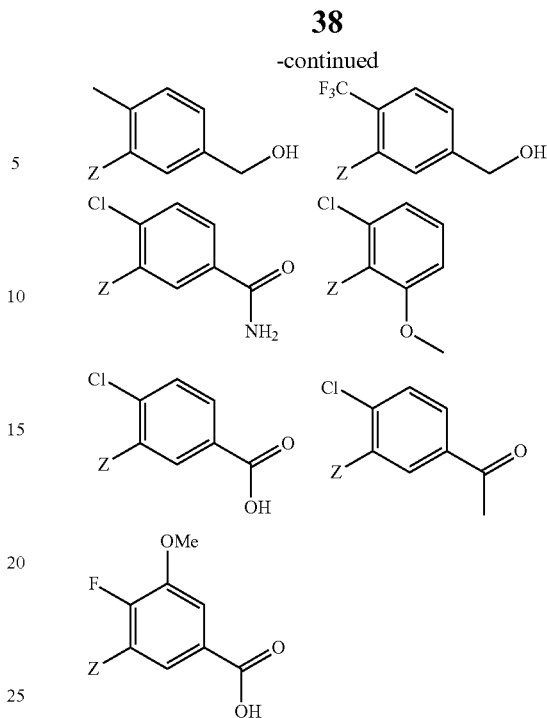

wherein Z is as defined in the aforementioned Production Method 1-1.

[Production Method 2-1] or [Production Method 2-3]

For example, compound [I-a1] which is a compound represented by the formula [I] wherein ring Cy is the formula

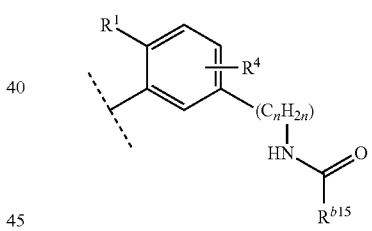

wherein $R^1$, $R^4$, $R^{b15}$ and n are as defined in the aforementioned formula [I], can be obtained by appropriately converting the substituent of ring Cy.

When $C_nH_{2n}$ is a straight chain, Production Method 2-1 is preferable, and when $C_nH_{2n}$ is a branched chain, Production Method 2-3 is preferable.

[Production Method 2-1]

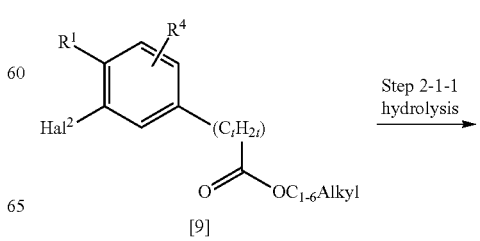

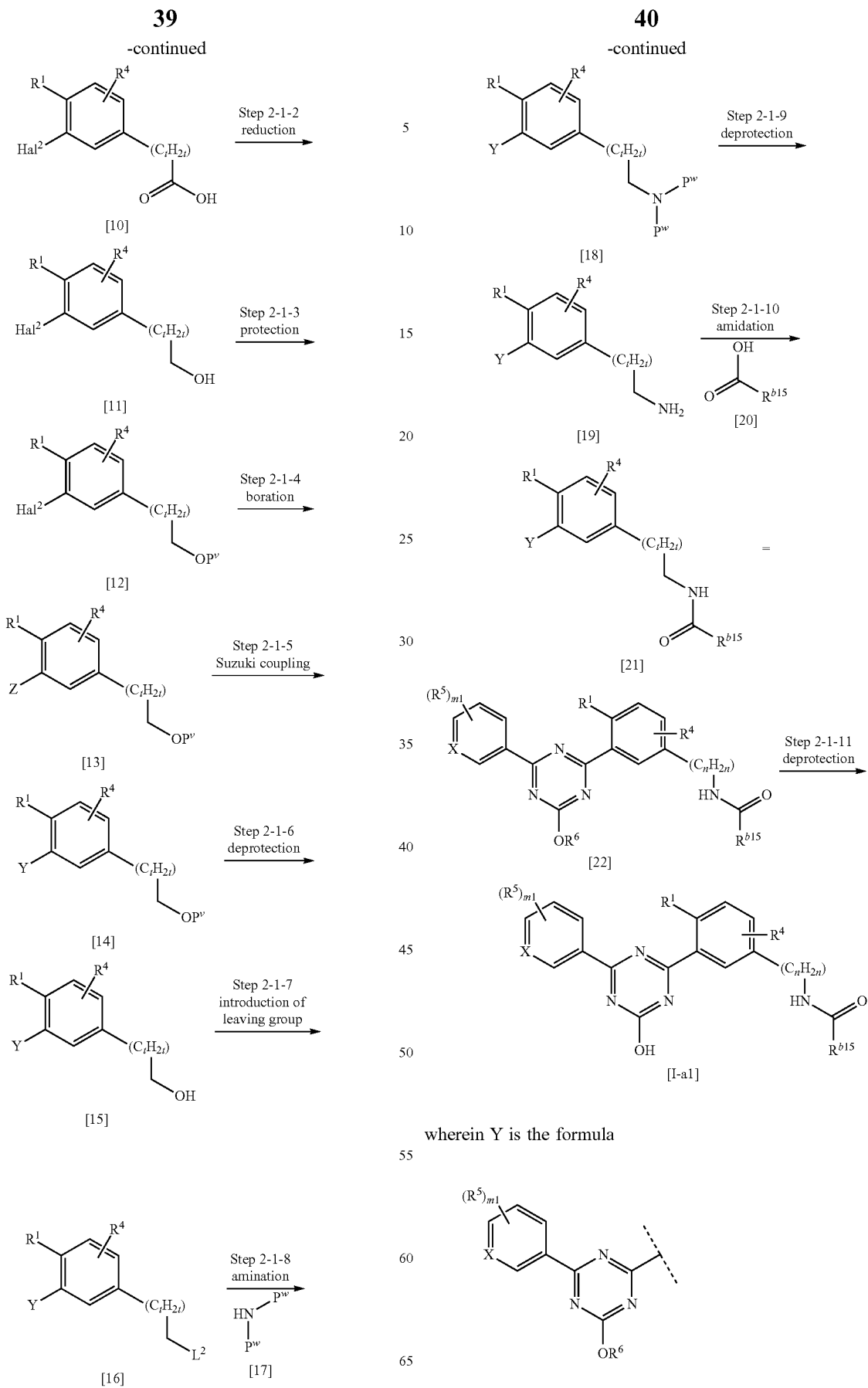

wherein $R^5$, $R^6$ and m1 are as defined in the aforementioned formula [I];

$C_{1-6}$ Alkyl is $C_{1-6}$ alkyl;

t is 0, 1, 2 or 3, —$(C_tH_{2t})$— may be a straight or branched chain;

$Hal^2$ is bromo or iodo;

$P^v$ is a hydroxy-protecting group such as methoxymethyl and the like;

$P^w$ is an amino-protecting group such as tert-butoxycarbonyl and the like;

$L^2$ is a leaving group such as halogen (e.g., chloro, bromo and the like), methanesulfonyloxy, p-toluenesulfonyloxy and the like;

$R^1$, $R^4$, $R^6$, $R^{b15}$ and n are as defined in the aforementioned formula [I], and Z is as defined in the aforementioned Production Method 1-1.

(Step 2-1-1)

Compound [10] can be obtained by converting the ester of compound [9] to carboxy by hydrolysis. For example, compound [10] can be obtained by reacting compound [9] in a solvent in the presence of a base at room temperature to under heating, and neutralizing the obtained solution.

Examples of the base to be used for the reaction include lithium hydroxide, sodium hydroxide, potassium hydroxide, sodium methoxide and the like.

Examples of the solvent to be used for the reaction include a mixed solvent of water and alcohol solvents such as methanol, ethanol, 1-propanol, 2-propanol and the like; and a mixed solvent thereof with ether solvents such as 1,4-dioxane, tetrahydrofuran, diethyl ether, 1,2-dimethoxyethane, cyclopentyl methyl ether and the like.

Compound [9] may be a commercially available product such as those shown below, or may be obtained by converting a commercially available product as appropriate by a method well known to those of ordinary skill in the art.

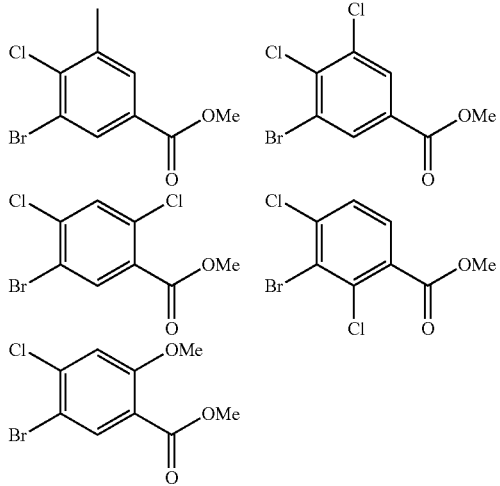

(Step 2-1-2)

Compound [11] can be obtained by converting the carboxy of compound [10] to hydroxy by reduction. For example, compound [11] can be obtained by reacting compound [10] with a reducing agent in a solvent under ice-cooling to room temperature.

Examples of the reducing agent to be used for the reaction include lithium aluminum hydride, diisobutylaluminum hydride, sodium bis(2-methoxyethoxy)aluminum hydride, borane-tetrahydrofuran complex and the like.

Examples of the solvent to be used for the reaction include tetrahydrofuran, diethyl ether, 1,2-dimethoxyethane, cyclopentyl methyl ether, toluene, xylene, hexane and the like and a mixed solvent thereof.

(Step 2-1-3)

Compound [12] can be obtained by protecting the hydroxy group of compound [11]. The protection reaction can be performed by a known method according to the protecting group to be employed.

For example, when $P^v$ is methoxymethyl, compound [12] can be obtained by reacting compound [11] with chloromethyl methyl ether in a solvent such as tetrahydrofuran, 1,2-dimethoxyethane, cyclopentyl methyl ether, N,N-dimethylformamide and the like in the presence of a base such as sodium hydride and the like from ice-cooling to room temperature.

(Step 2-1-4)

Compound [13] can be obtained by borating compound [12] in the same manner as in Production Method 1-2, Step 1-2.

(Step 2-1-5)

Compound [14] can be obtained by the Suzuki coupling reaction of compound [3] and compound [13] in the same manner as in Production Method 1-1, Step 1-1-2.

(Step 2-1-6)

Compound [15] can be obtained by removing $P^v$ of compound [14] by hydroxy-deprotection by a conventional method. The deprotection reaction can be performed by a known method according to the protecting group to be employed.

For example, when $P^v$ is methoxymethyl, a treatment with an acid such as hydrochloric acid, trifluoroacetic acid, methanesulfonic acid and the like only needs to be performed in a single or mixed solvent of chloroform, 1,4-dioxane, tetrahydrofuran, diethyl ether, 1,2-dimethoxyethane, cyclopentyl methyl ether, ethyl acetate, ethanol, methanol, water and the like.

Compound [15] can also be obtained by the Suzuki coupling reaction of compound [3] and compound [23] represented by the formula

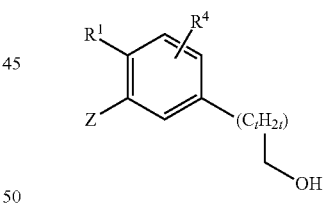

wherein $R^1$ and $R^4$ are as defined in the aforementioned formula [I], Z is as defined in the aforementioned Production Method 1-1, and t is as defined in the aforementioned Production Method 2-1, in the same manner as in Production Method 1-1, Step 1-1-2.

(Step 2-1-7)

Compound [16] can be obtained by converting the hydroxy of compound [15] to the leaving group $L^2$. For example, when $L^2$ is methanesulfonyloxy, compound [16] can be obtained by reacting compound [15] with methanesulfonyl chloride in a solvent in the presence of a base at room temperature. When $L^2$ is bromo, compound [16] can be obtained by reacting compound [15] with carbon tetrabromide in a solvent in the presence of triphenylphosphine from ice-cooling to room temperature.

Examples of the base to be used for the reaction include triethylamine, pyridine and the like.

Examples of the solvent to be used for the reaction include ether solvents such as 1,4-dioxane, tetrahydrofuran, diethyl ether, 1,2-dimethoxyethane, cyclopentyl methyl ether and the like; hydrocarbon solvents such as toluene, hexane, xylene and the like; halogenated solvents such as dichloromethane, chloroform and the like; and polar solvents such as N,N-dimethylformamide, N,N-dimethylacetamide, dimethyl sulfoxide, acetonitrile and the like.

It is possible to use dimethylsulfide instead of the above-mentioned triphenylphosphine, and N-bromosuccinimide can be used instead of the above-mentioned carbon tetrabromide.

p-Toluenesulfonyl chloride and benzenesulfonyl chloride can be used instead of the above-mentioned methanesulfonyl chloride.

(Step 2-1-8)

Compound [18] can be obtained by reacting compound [16] in a solvent in the presence of a base at room temperature to under heating compound [17]. Examples of the protecting group $P^w$ include tert-butoxycarbonyl.

Examples of the base to be used for the reaction include inorganic bases such as alkali metal salts (e.g., cesium carbonate, potassium phosphate, sodium carbonate, potassium carbonate etc.) and the like.

Examples of the solvent to be used for the reaction include polar solvents such as N,N-dimethylformamide, N,N-dimethylacetamide, dimethyl sulfoxide, acetonitrile and the like.

(Step 2-1-9)

Compound [19] can be obtained by removing $P^w$ of compound [18] by amine-deprotection by a conventional method. The deprotection reaction can be performed by a known method according to the protecting group to be employed.

For example, when $P^w$ is tert-butoxycarbonyl, a treatment with an acid such as hydrochloric acid, trifluoroacetic acid, methanesulfonic acid and the like only needs to be performed in a solvent.

Examples of the solvent to be used for the reaction include ether solvents such as 1,4-dioxane, tetrahydrofuran, diethyl ether, 1,2-dimethoxyethane, cyclopentyl methyl ether and the like; hydrocarbon solvents such as toluene, hexane, xylene and the like; halogenated solvents such as dichloromethane, chloroform and the like; ester solvents such as ethyl acetate and the like; and alcohol solvents such as methanol, ethanol, 1-propanol, 2-propanol and the like.

(Step 2-1-10)

Compound [21] can be obtained by a conventional amide bond forming reaction, for example, by reacting compound [19] with compound [20] in a solvent in the presence of a condensing agent and an additive. A base may be added as necessary.

Examples of the condensing agent to be used for the reaction include dicyclohexylcarbodiimide (DCC), 1-ethyl-3-(3-dimethylaminopropyl)carbodiimide hydrochloride (WSC·HCl), diisopropylcarbodiimide, 1,1'-carbonyldiimidazole (CDI), 0-(7-azabenzotriazol-1-yl)-N,N,N',N'-tetramethyluronium hexafluorophosphate (HATU), (benzotriazol-1-yloxy)tris(pyrrolidino)phosphonium hexafluorophosphate (PyBOP), diphenylphosphoryl azide and the like.

Examples of the additive to be used for the reaction include 1-hydroxybenzotriazole (HOBt), 1-hydroxy-7-azabenzotriazole (HOAt), N-hydroxysuccinimide (HOSu), 4-dimethylaminopyridine and the like.

Examples of the base to be used for the reaction include organic bases such as pyridine, triethylamine and the like.

Examples of the solvent to be used for the reaction include ether solvents such as 1,4-dioxane, tetrahydrofuran, diethyl ether, 1,2-dimethoxyethane, cyclopentyl methyl ether and the like; hydrocarbon solvents such as toluene, hexane, xylene and the like; halogenated solvents such as dichloromethane, chloroform and the like; and polar solvents such as N,N-dimethylformamide, N,N-dimethylacetamide, dimethyl sulfoxide, acetonitrile, pyridine and the like. These may be used singly or as a mixture of two or more kinds thereof.

Compound [20] may be a commercially available product such as cyclopentanecarboxylic acid and 1-(trifluoromethyl)cyclopropane-1-carboxylic acid, or may be obtained by converting a commercially available product as appropriate by a method well known to those of ordinary skill in the art.

(Step 2-1-11)

Compound [21] can be indicated as compound [22]. Compound [I-a1] can be obtained by converting the alkoxy of compound [22] to hydroxy by hydrolysis in the same manner as in Production Method 1-1, Step 1-1-3.

[Production Method 2-2]

Compound [10a] which is compound [10] wherein $R^1$ is $C_{1-6}$ alkyl or chloro can be obtained by [Production Method 2-2].

[Production Method 2-2]

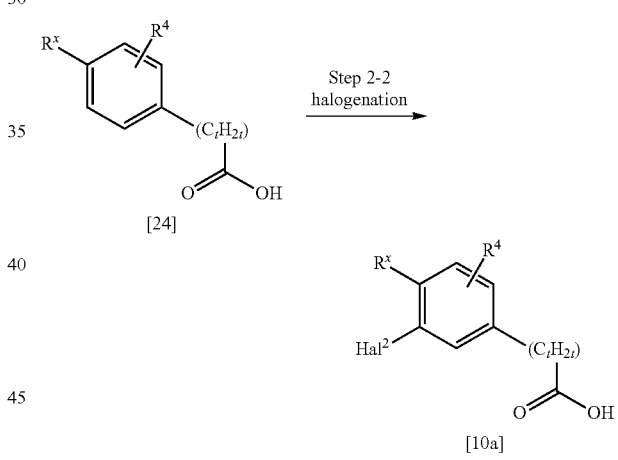

wherein $R^x$ is $C_{1-6}$ alkyl or chloro;

$R^4$ is as defined in the aforementioned formula [I], and $Hal^2$ and t are as defined in the aforementioned Production Method 2-1.

(Step 2-2)

Compound [10a] can be obtained by halogenating compound [24]. For example, when $Hal^2$ is iodo, compound [10a] can be obtained by reacting compound [24] with N-iodosuccinimide in an acid at room temperature.

Examples of the acid to be used for the reaction include concentrated sulfuric acid and the like.

Compound [24] may be a commercially available product such as 4-chlorophenylacetic acid, 3-(4-chlorophenyl)propionic acid, 4-(4-chlorophenyl)butanoic acid, 4-methylphenylacetic acid and 2-(4-methylphenyl)propionic acid, or may be obtained by converting a commercially available product as appropriate by a method well known to those of ordinary skill in the art.

[Production Method 2-3]

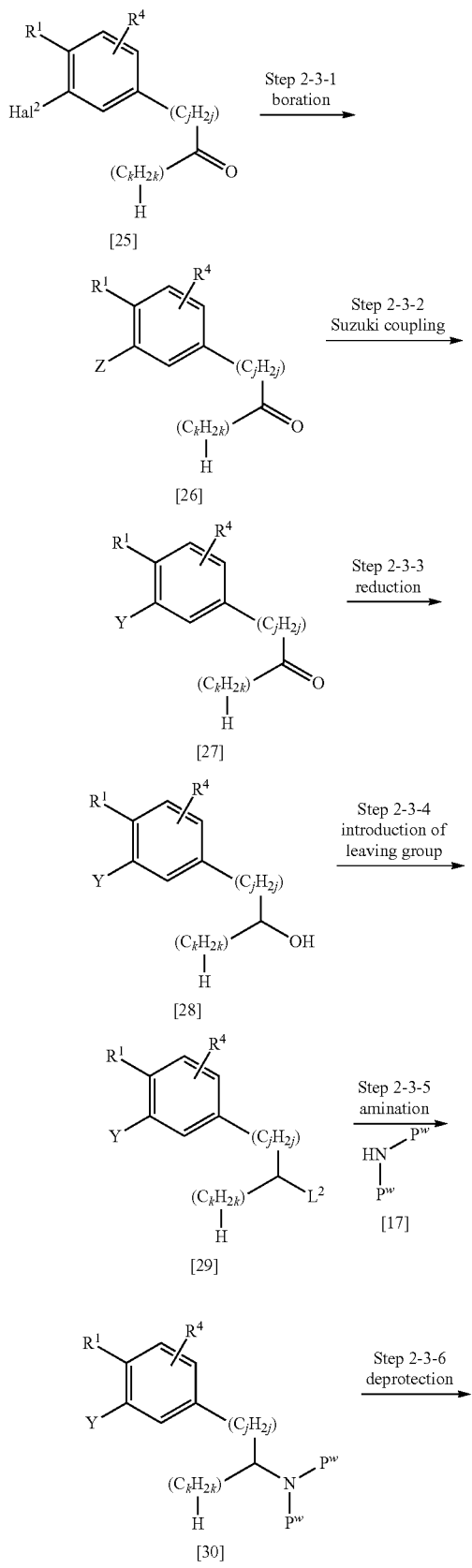

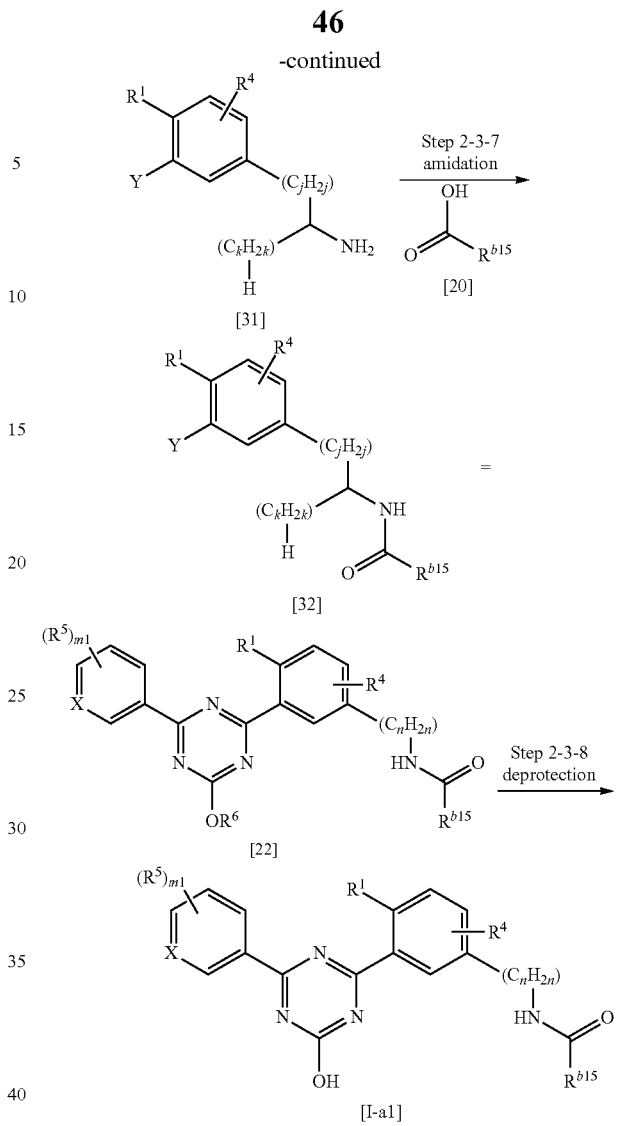

wherein j and k are each 0, 1, 2 or 3, j+k=n−1;
$R^1$, $R^4$, $R^5$, $R^{b15}$ and n are as defined in the aforementioned formula [I],
Z is as defined in the aforementioned Production Method 1-1, and
$Hal^2$, Y, $P^w$ and $L^2$ are as defined in the aforementioned Production Method 2-1.

(Step 2-3-1)

Compound [26] can be obtained by borating compound [25] in the same manner as in Production Method 1-2, Step 1-2.

Compound [25] may be a commercially available product such as 1-(3-bromo-4-chlorophenyl)propan-1-one and 1-(3-bromo-4-chlorophenyl)butan-1-one, or may be obtained by converting a commercially available product as appropriate by a method well known to those of ordinary skill in the art.

(Step 2-3-2)

Compound [27] can be obtained by the Suzuki coupling reaction of compound [3] and compound [26] in the same manner as in Production Method 1-1, Step 1-1-2.

(Step 2-3-3)

Compound [28] can be obtained by converting the carboxy of compound [27] to hydroxy by reduction. For example, compound [28] can be obtained by reacting compound [27] with a reducing agent in a solvent under ice-cooling to room temperature.

Examples of the reducing agent to be used for the reaction include sodium borohydride and the like.

Examples of the solvent to be used for the reaction include methanol, ethanol, 2-propanol, 1,4-dioxane, tetrahydrofuran, diethyl ether, 1,2-dimethoxyethane, cyclopentyl methyl ether and the like.

(Step 2-3-4)

Compound [29] can be obtained by converting the hydroxy of compound [28] to the leaving group $L^2$ in the same manner as in Production Method 2-1, Step 2-1-7.

(Step 2-3-5)

Compound [30] can be obtained by reacting compound [29] with compound [17] in the same manner as in Production Method 2-1, Step 2-1-8.

(Step 2-3-6)

Compound [31] can be obtained by removing $P^w$ of compound [30] in the same manner as in Production Method 2-1, Step 2-1-9.

(Step 2-3-7)

Compound [32] can be obtained by reacting compound [31] with compound [20] in the same manner as in Production Method 2-1, Step 2-1-10.

(Step 2-3-8)

Compound [32] can be indicated as compound [22]. Compound [I-a1] can be obtained by converting alkoxy of compound [22] to hydroxy by hydrolysis in the same manner as in Production Method 1-1, Step 1-1-3.

In Production Method 2-1, compound [I-a2] which is a compound represented by the formula [I] wherein ring Cy is the formula

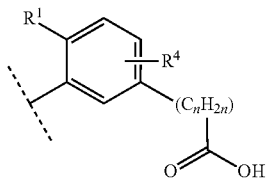

wherein $R^1$, $R^4$ and n are as defined in the aforementioned formula [I], can be obtained by subjecting compound [9] to the reactions of Step 2-1-4, Step 2-1-5 and Step 2-1-11.

In Production Method 2-1, the amide bond forming reaction is performed by using compound [10] and $HNR^{b1}R^{b2}$ such as dimethylamine, tert-butylamine and the like and in the same manner as in Step 2-1-10. Thereafter, the resultant product is subjected to the reactions of Step 2-1-4, Step 2-1-5 and Step 2-1-11, whereby compound [I-a3] which is a compound represented by the formula [I] wherein ring Cy is the formula

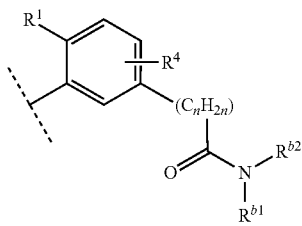

wherein $R^1$, $R^4$, $R^{b1}$, $R^{b2}$ and n are as defined in the aforementioned formula [I], can be obtained.

In Production Method 2-1, compound [I-a4] which is a compound represented by the formula [I] wherein ring Cy is the formula

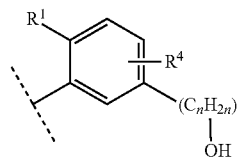

wherein $R^1$, $R^4$ and n are as defined in the aforementioned formula [I] can be obtained by subjecting compound [15] to the reaction of Step 2-1-11.

In Production Method 2-1, the reaction of Step 2-1-11 is performed by using compound [15]. Thereafter, the resultant product is reacted with a $C_{1-6}$ alkyl-carboxylic anhydride such as acetic anhydride, propionic anhydride and the like, whereby compound [I-a5] which is a compound represented by the formula [I] wherein ring Cy is the formula

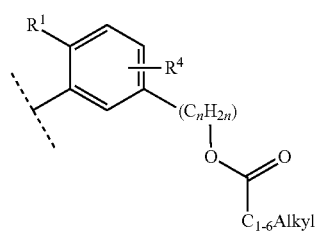

wherein $R^1$, $R^4$ and n are as defined in the aforementioned formula [I] and $C_{1-6}$ Alkyl is as defined in the aforementioned Production Method 2-1, can be obtained.

In Production Method 2-1, compound [15] is reacted with $ClC(O)NR^{b3}R^{b4}$ such as dimethylcarbamoyl chloride, diethylcarbamoyl chloride and the like in the presence of a base. Thereafter, the resultant product is subjected to the reaction of Step 2-1-11, whereby compound [I-a6] which is a compound represented by the formula [I] wherein ring Cy is the formula

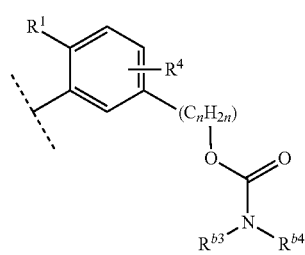

wherein $R^1$, $R^4$, $R^{b3}$, $R^{b4}$ and n are as defined in the aforementioned formula [I], can be obtained.

In Production Method 2-1, compound [15] is subjected to an alkylation reaction by using sodium hydride and a $C_{1-6}$ alkyl halide. Thereafter, the resultant product is subjected to the reaction of Step 2-1-11, whereby compound [I-a7] which is a compound represented by the formula [I] wherein ring Cy is the formula

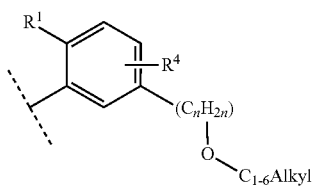

wherein $R^1$, $R^4$ and n are as defined in the aforementioned formula [I] and $C_{1-6}$ Alkyl is as defined in the aforementioned Production Method 2-1, can be obtained.

In Production Method 2-1, compound [16] is subjected to an amination reaction by using $HNR^{b8}R^{b9}$ such as dimethylamine, diethylamine and the like. Thereafter, the resultant product is subjected to the reaction of Step 2-1-11, whereby compound [I-a8] which is a compound represented by the formula [I] wherein ring Cy is the formula

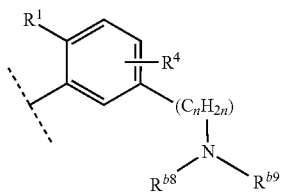

wherein $R^1$, $R^4$, $R^{b8}$, $R^{b9}$ and n are as defined in the aforementioned formula [I], can be obtained.

In Production Method 2-1, compound [16] is reacted by using sodium hydride, and $HNR^{b14}C(O)R^{b15}$ such as N-methylacetamide, 2-pyrrolidinone and the like. Thereafter, the resultant product is subjected to the reaction of Step 2-1-11, whereby compound [I-a9] which is a compound represented by the formula [I] wherein ring Cy is the formula

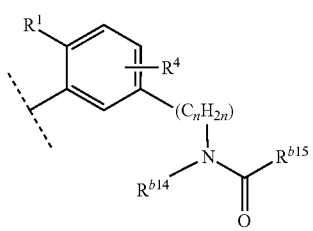

wherein $R^1$, $R^4$, $R^{b14}$, $R^{b15}$ and n are as defined in the aforementioned formula [I], can be obtained.

In Production Method 2-1, compound [16] is reacted by using sodium hydride and compound [33] represented by the formula

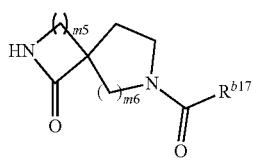

wherein $R^{b17}$, m5 and m6 are as defined in the aforementioned formula [I]. Thereafter, the resultant product is subjected to the reaction of Step 2-1-11, whereby compound [I-a10] which is is a compound represented by the formula [I] wherein ring Cy is the formula

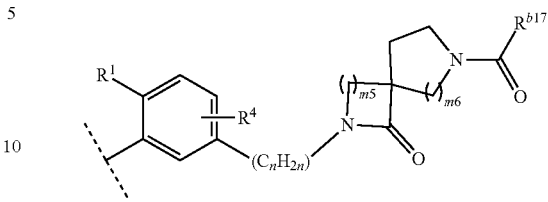

wherein $R^1$, $R^4$, $R^{b17}$, n, m5 and m6 are as defined in the aforementioned formula [I], can be obtained.

In Production Method 2-1, compound [19] is reacted with $ClC(O)NR^{b6}R^{b7}$ such as dimethylcarbamoyl chloride, diethylcarbamoyl chloride and the like in the presence of a base. Thereafter, the resultant product is subjected to the reaction of Step 2-1-11, whereby compound [I-a11] which is a compound represented by the formula [I] wherein ring Cy is the formula

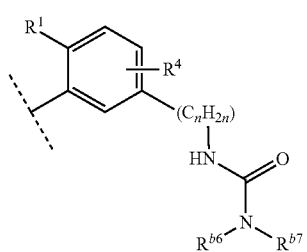

wherein $R^1$, $R^4$, $R^{b6}$, $R^{b7}$ and n are as defined in the aforementioned formula [I], can be obtained.

In Production Method 2-1, compound [19] is reacted with $R^{b11}S(O)_2Cl$ such as methanesulfonyl chloride and the like in the presence of a base. Thereafter, the resultant product is subjected to the reaction of Step 2-1-11, whereby compound [I-a12] which is a compound represented by the formula [I] wherein ring Cy is the formula

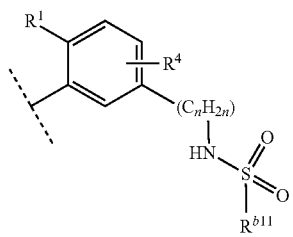

wherein $R^1$, $R^4$, $R^{b11}$ and n are as defined in the aforementioned formula [I], can be obtained.

In Production Method 2-1, compound [19] is reacted with $R^{b13}OC(O)Cl$ such as ethyl chloroformate and the like in the presence of a base. Thereafter, the resultant product is subjected to the reaction of Step 2-1-11, whereby compound [I-a13] which is a compound represented by the formula [I] wherein ring Cy is the formula

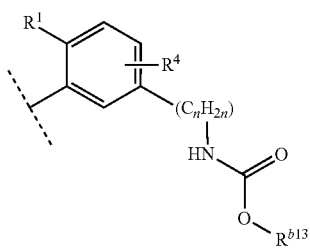

wherein $R^1$, $R^4$, $R^{b13}$ and n are as defined in the aforementioned formula [I], can be obtained.

In Production Method 2-3, compound [I-a14] which is a compound represented by the formula [I] wherein ring Cy is the formula

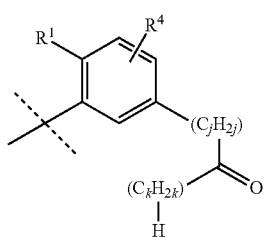

wherein $R^1$ and $R^4$ are as defined in the aforementioned formula [I], j and k are as defined in the aforementioned Production Method 2-2, can be obtained by subjecting compound [27] to the reaction of Step 2-3-8.

By Production Method 2-4, compound [I-a15] which is a compound represented by the formula [I] wherein ring Cy is the formula

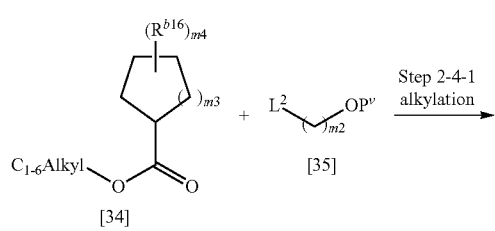

wherein $R^1$, $R^4$, $R^{b16}$, m2, m3 and m4 are as defined in the aforementioned Production Method 2-1, can be obtained.

[Production Method 2-4]

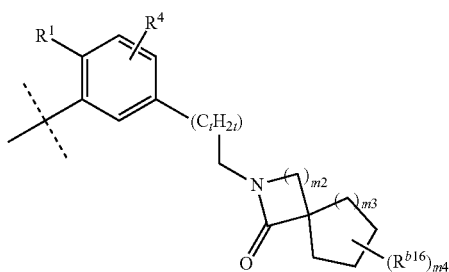

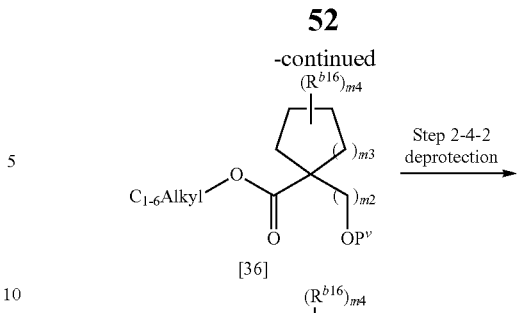

wherein $R^1$, $R^4$, $R^{b16}$, m2, m3 and m4 are as defined in the aforementioned formula [I] and $C_{1-6}$ Alkyl, $L^2$, $P^v$, t and Y are as defined in the above-mentioned Production Method 2-1.

(Step 2-4-1)

Compound [36] can be obtained by reacting compound [34] with compound [35] in a solvent in the presence of a base.

Examples of the base to be used for the reaction include, lithium diisopropylamide, lithium bis(trimethylsilyl)amide and the like base.

Examples of the solvent to be used for the reaction include ether solvents such as tetrahydrofuran, diethyl ether, 1,2-dimethoxyethane, cyclopentyl methyl ether and the like;

hydrocarbon solvents such as toluene, hexane, xylene and the like, and a mixed solvent thereof.

Compound [35] may be a commercially available product such as benzyl chloromethyl ether, or may be obtained by converting a commercially available product as appropriate by a method well known to those of ordinary skill in the art.
(Step 2-4-2)

Compound [37] can be obtained by removing $P^v$ of compound [36] in the same manner as in Production Method 2-1, Step 2-1-6.
(Step 2-4-3)

Compound [38] can be obtained by converting the ester of compound [37] to carboxy by hydrolysis in the same manner as in Production Method 2-1, Step 2-1-1.
(Step 2-4-4)

Compound [39] can be obtained by reacting compound [38] with compound [19] in a solvent in the presence of a condensing agent and an additive in the same manner as in Production Method 2-1, Step 2-1-10.
(Step 2-4-5)

Compound [40] can be obtained by cyclization of compound [39] by intramolecular Mitsunobu reaction. For example, compound [40] can be obtained by reacting compound [39] with an azodicarboxylic acid diester (e.g., diethyl azodicarboxylate, diisopropyl azodicarboxylate, bis(2-methoxyethyl) azodicarboxylate etc.) in a solvent in the presence of a phosphine such as triphenylphosphine, tributylphosphine and the like.

Examples of the solvent to be used for the reaction include dichloromethane, chloroform, 1,4-dioxane, tetrahydrofuran, diethyl ether, 1,2-dimethoxyethane, cyclopentyl methyl ether, toluene, N,N-dimethylformamide and the like. These may be used singly or as a mixture of two or more kinds thereof.

[Production Method 3-1]

Another method of appropriately converting the substituent of ring Cy is, for example, Production Method 3-1 for obtaining compound [I-b1] which is a compound represented by the formula [I] wherein ring Cy is the formula

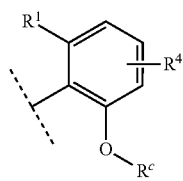

wherein $R^1$, $R^4$ and $R^c$ are as defined in the aforementioned formula [I].

[Production Method 3-1]

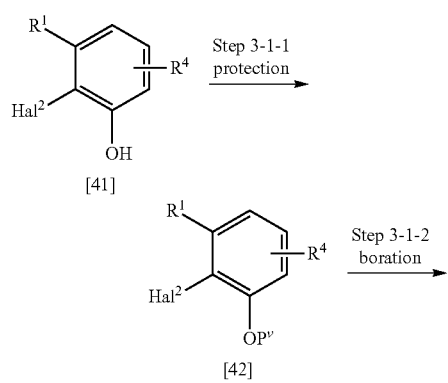

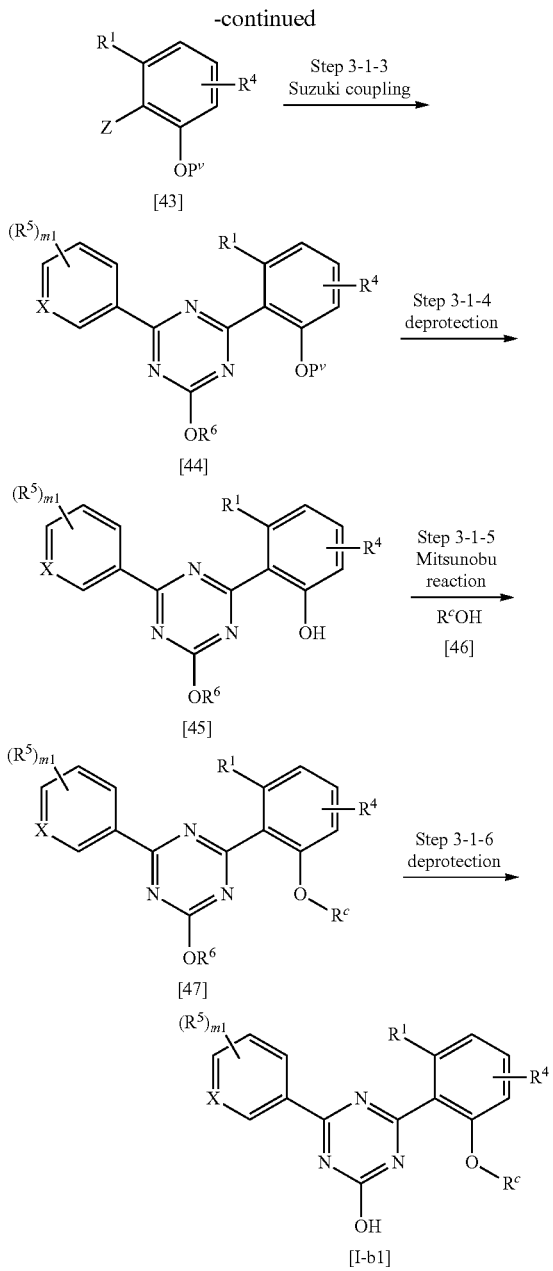

wherein $R^1$, $R^4$, $R^5$, $R^c$, m1 and X are as defined in the aforementioned formula [I], Z is as defined in the above-mentioned Production Method 1-1, and $Hal^2$ and $P^v$ are as defined in the above-mentioned Production Method 2-1.

(Step 3-1-1)

Compound [42] can be obtained by protecting the hydroxy group of compound [41] in the same manner as in Production Method 2-1, Step 2-1-3.

Compound [41] may be a commercially available product such as 2-bromo-3-methylphenol, or may be obtained by converting a commercially available product as appropriate by a is method well known to those of ordinary skill in the art.

(Step 3-1-2)

Compound [43] can be obtained by borating compound [42] in the same manner as in Production Method 1-3, Step 1-3.

(Step 3-1-3)

Compound [44] can be obtained by the Suzuki coupling reaction of compound [3] and compound [43] in the same manner as in Production Method 1-1, Step 1-1-2.

(Step 3-1-4)

Compound [45] can be obtained by removing $P^v$ of compound [44] in the same manner as in Production Method 2-1, Step 2-1-6.

(Step 3-1-5)

Compound [47] can be obtained by the Mitsunobu reaction of compound [45] and compound [46]. For example, compound [47] can be obtained by reacting compound [45] with compound [46] in a solvent in the presence of an azodicarboxylic acid diester (e.g., diethyl azodicarboxylate, diisopropyl azodicarboxylate, bis(2-methoxyethyl) azodicarboxylate etc.) and a phosphine such as triphenylphosphine, tributylphosphine and the like.

Examples of the solvent to be used for the reaction include dichloromethane, chloroform, 1,4-dioxane, tetrahydrofuran, diethyl ether, 1,2-dimethoxyethane, cyclopentyl methyl ether, toluene, N,N-dimethylformamide and the like. These may be used singly or as a mixture of two or more kinds thereof.

Compound [46] may be a commercially available product such as benzyl alcohol, 2-pyridinemethanol and the like, or may be obtained by converting a commercially available product as appropriate by a method well known to those of ordinary skill in the art.

(Step 3-1-6)

Compound [I-b1] can be obtained by converting the alkoxy of compound [47] to hydroxy by hydrolysis in the same manner as in Production Method 1-1, Step 1-1-3.

In Production Method 3-1, for example, compound [I-b2] which is a compound represented by the formula [I] wherein ring Cy is the formula

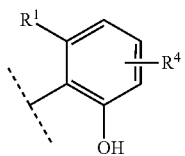

wherein $R^1$ and $R^4$ are as defined in the aforementioned formula [I], can be obtained by subjecting compound [45] to the reaction of Step 3-1-6.

[Production Method 3-2]

Compound [43a] which is compound [43] wherein $R^1$ is chloro or trifluoromethyl can also be obtained by [Production Method 3-2].

[Production Method 3-2]

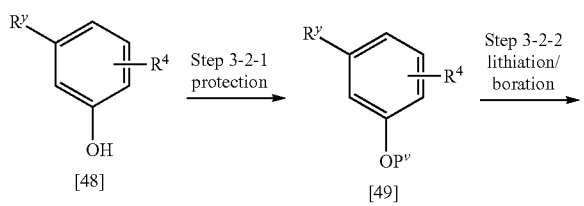

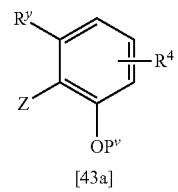

wherein $R^y$ is chloro or trifluoromethyl;

$R^4$ is as defined in the aforementioned formula [I], Z is as defined in the aforementioned Production Method 1-1, and $P^v$ is as defined in the aforementioned Production Method 2-1.

(Step 3-2-1)

Compound [49] can be obtained by protecting the hydroxy group of compound [48] in the same manner as in Production Method 2-1, Step 2-1-3.

In one embodiment, compound [48] may be a commercially available product such as those shown below, or may be obtained by converting a commercially available product as appropriate by a method well known to those of ordinary skill in the art.

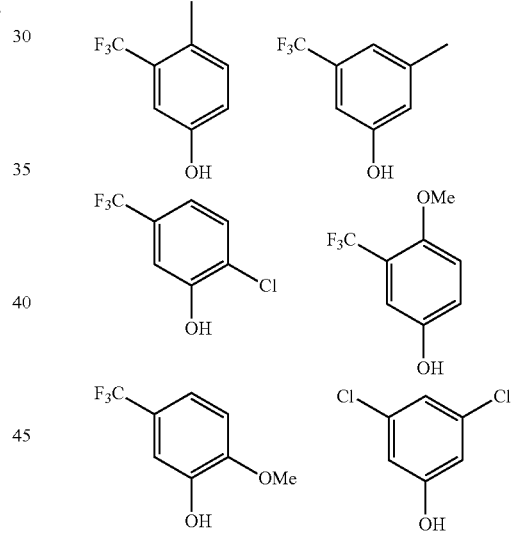

(Step 3-2-2)

Compound [43a] can be obtained by reacting compound [49] with a boron compound in a solvent in the presence of a base. For example, compound [43a] can be obtained by adding a base to compound [49] in a solvent at −78° C. to room temperature, and reacting the resultant product with a boron reagent at −78° C. to room temperature.

Examples of the base to be used for the reaction include n-butyllithium, sec-butyllithium and the like.

Examples of the boron reagent to be used for the reaction include 2-isopropoxy-4,4,5,5-tetramethyl-1,3,2-dioxaborolane, trimethyl borate and the like.

Examples of the solvent to be used for the reaction include tetrahydrofuran, diethyl ether, 1,2-dimethoxyethane, cyclopentyl methyl ether and the like.

[Production Method 4]

For example, compound [I-c1] of the formula

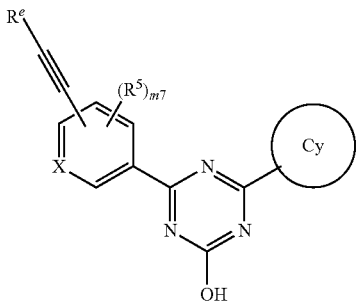

wherein $R^5$, $R^e$, X and Cy are as defined in the aforementioned formula [I], m7 is 0, 1 or 2, and when m7 is 2, each $R^5$ is selected independently, can be obtained by appropriately converting the substituent of compound [2].

[Production Method 4]

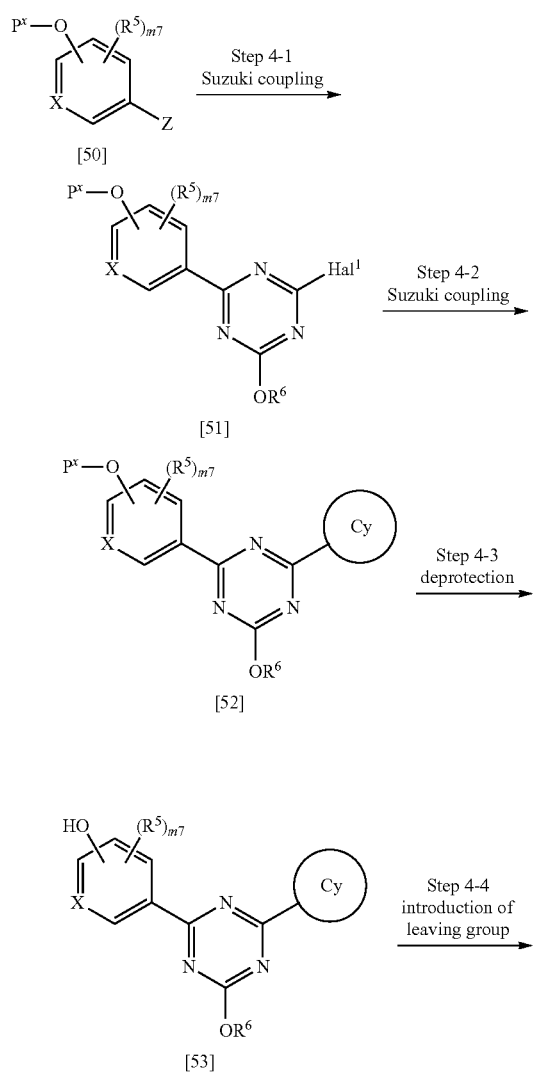

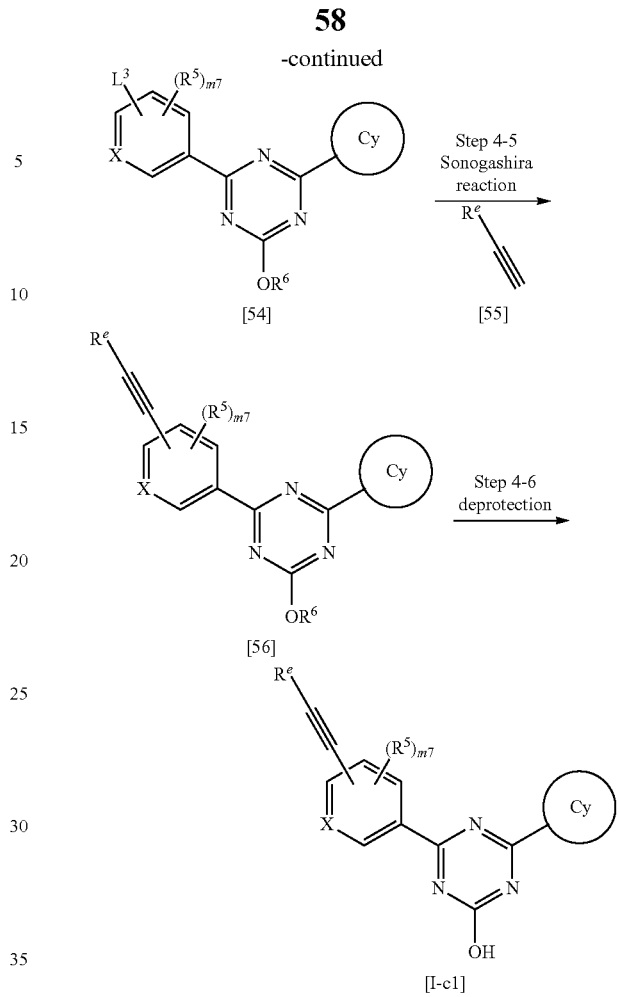

wherein $L^3$ is a leaving group such as trifluoromethanesulfonyloxy and the like;
$P^x$ is a hydroxy-protecting group such as benzyl and the like; $R^5$, $R^6$, $R^e$, X and Cy are as defined in the aforementioned formula [I], $Hal^1$ and Z are as defined in the aforementioned Production Method 1-1, and m7 is as defined in the aforementioned formula [I-A].

(Step 4-1)

Compound [51] can be obtained by the Suzuki coupling reaction of compound [1] and compound [50] in the same manner as in Production Method 1-1, Step 1-1-1.

Compound [50] may be a commercially available product such as 4-(benzyloxy)phenylboronic acid, or may be obtained by converting a commercially available product as appropriate by a method well known to those of ordinary skill in the art.

(Step 4-2)

Compound [52] can be obtained by the Suzuki coupling reaction of compound [4] and compound [51] in the same manner as in Production Method 1-1, Step 1-1-2.

(Step 4-3)

Compound [53] can be obtained by removing the phenol protecting group $P^x$ of compound [52]. The deprotection can be performed by a known method according to the protecting group to be employed.

For example, when $P^x$ is benzyl, compound [52] only needs to be subjected to a hydrogenation reaction in a single or mixed solvent of tetrahydrofuran, ethyl acetate, ethanol, methanol, water and the like in the presence of a catalyst such as palladium carbon, platinum carbon and the like.

(Step 4-4)

Compound [54] can be obtained by converting the hydroxy to a leaving group $L^3$. For example, when the leaving group is trifluoromethanesulfonyloxy, compound [54] can be obtained by reacting compound [53] with trifluoromethanesulfonic anhydride, N-phenyl bis(trifluoromethanesulfonimide) and the like in a solvent in the presence of a base from ice-cooling to room temperature.

Examples of the base to be used for the reaction include organic bases such as pyridine, 2,6-lutidine, triethylamine and the like; inorganic bases such as alkali metal salts (e.g., cesium carbonate, sodium hydride etc.) and the like.

Examples of the solvent to be used for the reaction include ether solvents such as 1,4-dioxane, tetrahydrofuran, diethyl ether, 1,2-dimethoxyethane, cyclopentyl methyl ether and the like; hydrocarbon solvents such as toluene, hexane, xylene and the like; halogenated solvents such as dichloromethane, chloroform and the like; polar solvents such as N,N-dimethylformamide, N,N-dimethylacetamide, dimethyl sulfoxide, acetonitrile, pyridine and the like, and the like. These may be used singly or as a mixture of two or more kinds thereof.

(Step 4-5)

Compound [56] can be obtained by the Sonogashira reaction of compound [54] and compound [55]. For example, compound [56] can be obtained by reacting compound [54] with compound [55] in a solvent preferably under heating in the presence of a base, a palladium catalyst and a copper catalyst.

Examples of the palladium catalyst to be used for the reaction include palladium acetate, tetrakistriphenylphosphinepalladium, bis(triphenylphosphine)palladium dichloride, (bis (diphenylphosphino)ferrocene)palladium dichloride-methylene chloride complex and the like.

Examples of the copper catalyst to be used for the reaction include copper iodide, copper bromide and the like.

Examples of the base to be used for the reaction include diethylamine, dicyclohexylamine, triethylamine, N-ethyldiisopropylamine and the like.

Examples of the solvent to be used for the reaction include ether solvents such as 1,4-dioxane, tetrahydrofuran, diethyl ether, 1,2-dimethoxyethane, cyclopentyl methyl ether and the like; hydrocarbon solvents such as toluene, hexane, xylene and the like; and polar solvents such as N,N-dimethylformamide, N,N-dimethylacetamide, dimethyl sulfoxide, acetonitrile, pyridine and the like. These may be used singly or as a mixture of two or more kinds thereof.

Compound [55] may be a commercially available product such as cyclohexylacetylene, 2-ethynylpyridine and the like, or may be obtained by converting a commercially available product as appropriate by a method well known to those of ordinary skill in the art.

As for the Sonogashira coupling reaction, for example, the following review article is known (NAJERA, C et al. The Sonogashira Reaction: A Booming Methodology in Synthetic Organic Chemistry. Chem Rev. 2007, Vol. 107, pages 874-922.).

(Step 4-6)

Compound [I-c1] can be obtained by converting the alkoxy of compound [56] to hydroxy by hydrolysis in the same manner as in Production Method 1-1, Step 1-1-3.

In Production Method 4, compound [I-c2] of the formula

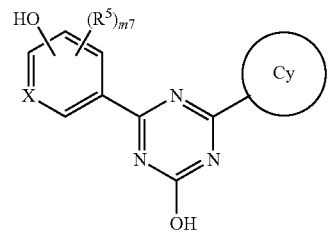

wherein $R^5$, X and Cy are as defined in the aforementioned formula [I], and m7 is as defined in the aforementioned formula [I-A], can be obtained by subjecting compound [53] to the reaction of Step 4-6.

In Production Method 4, compound [I-c3] of the formula

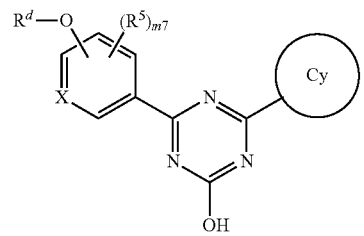

wherein $R^5$, $R^d$, X and Cy are as defined in the aforementioned formula [I], and m7 is as defined in the aforementioned formula [I-A], can be obtained by the Mitsunobu reaction of compound [53] and $R^d$OH such as cyclohexylmethanol and the like in the same manner as in Production Method 3-1, Step 3-1-5, and subjecting the resultant product to the reaction of Step 4-6.

In Production Method 4, the Suzuki coupling reaction of compound [54] and compound [57] of the formula

wherein Z is as defined in the aforementioned Production Method 1-1, is performed in the same manner as in Production Method 1-1, Step 1-1-2. The resultant product is subjected to the reaction of Step 4-6, whereby compound [I-c4] of the formula

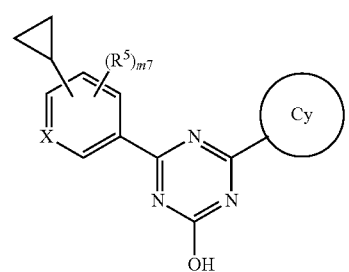

wherein $R^5$, X and Cy are as defined in the aforementioned formula [I] and m7 is as defined in the aforementioned formula [I-A], can be obtained.

In Production Method 4, the Suzuki coupling reaction of compound [54] and compound [58] of the formula

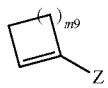

wherein m9 is 1, 2, 3, or 4, and Z is as defined in the aforementioned Production Method 1-1, is performed in the same manner as in Production Method 1-1, Step 1-1-2. After reduction of the olefin of the resultant product, the obtained product is subjected to the reaction of Step 4-6, whereby compound [I-c5] of the formula

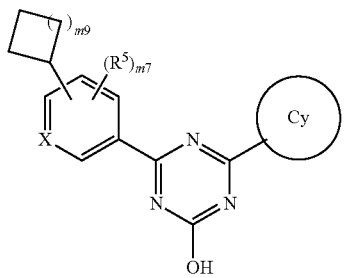

wherein m9 is as defined above, m7 is as defined in the aforementioned formula [I-A], and $R^5$, X and Cy are as defined in the aforementioned formula [I], can be obtained. For reduction reaction of the olefin, for example, a hydrogenation reaction only needs to be performed in a single or mixed solvent of tetrahydrofuran, ethyl acetate, ethanol, methanol, water and the like in the presence of a catalyst such as palladium carbon or platinum carbon and the like.

EXAMPLES

The present invention is explained in more detail in the following by referring to Examples and Experimental Examples, which are not to be construed as limitative.

The abbreviations in the Examples are as follows.
WSC·HCl: 1-ethyl-3-(3-dimethylaminopropyl)carbodiimide hydrochloride
HOBt·H$_2$O: 1-hydroxy-1H-benzotriazole monohydrate
DMSO: dimethyl sulfoxide
M: mol/L

Production Example 1

Synthesis of N-(4-chloro-3-{4-[4-(2,2-dimethylpropoxy)phenyl]-6-hydroxy-1,3,5-triazin-2-yl}benzyl)-3,3,3-trifluoro-2,2-dimethylpropionamide (Example No. 1-86)

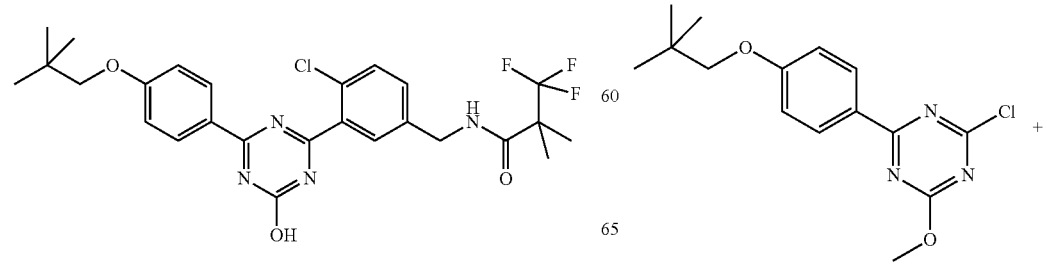

(1) 2-chloro-4-[4-(2,2-dimethylpropoxy)phenyl]-6-methoxy-1,3,5-triazine

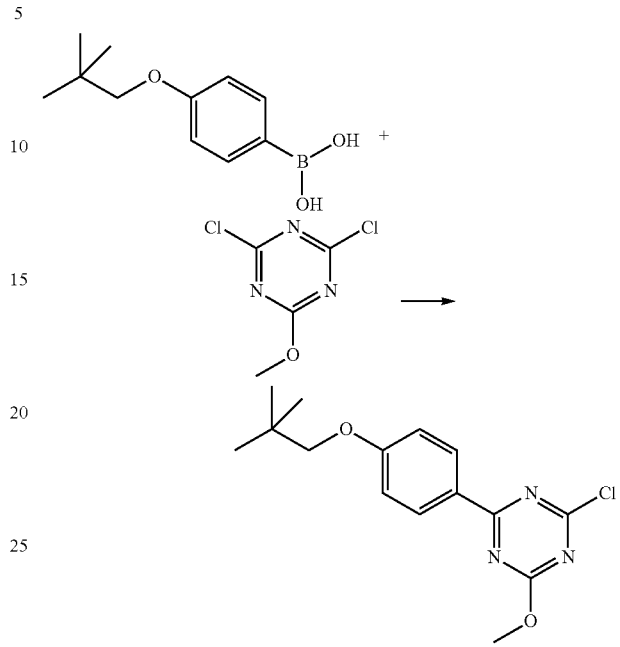

Under an argon atmosphere, a suspension of 4-(2,2-dimethylpropoxy)phenylboronic acid (2.0 g, 9.6 mmol), 2,4-dichloro-6-methoxy-1,3,5-triazine (3.5 g, 19 mmol), [1,1'-bis(diphenylphosphino)ferrocene]palladium(II)dichloride dichloromethane adduct (1.1 g, 0.96 mmol) and 2M aqueous sodium carbonate solution (14 ml, 29 mmol) in toluene (20 ml) was stirred at 100° C. for 3.5 hr. At room temperature, to the reaction mixture were added water and ethyl acetate and the mixture was partitioned. The organic layer was washed with saturated aqueous sodium hydrogen carbonate, washed with saturated brine, dried over sodium sulfate, filtered to remove sodium sulfate, and concentrated under reduced pressure. The residue was purified by silica gel column chromatography (eluent: n-hexane/ethyl acetate=19/1-4/1) to give the title compound (2.3 g, yield 77%).

$^1$H-NMR (400 MHz, CDCl$_3$) δ: 1.06 (9H, s), 3.68 (2H, s), 4.14 (3H, s), 6.94-7.02 (2H, m), 8.42-8.46 (2H, m).

(2) (4-chloro-3-{4-[4-(2,2-dimethylpropoxy)phenyl]-6-methoxy-1,3,5-triazin-2-yl}phenyl)methanol

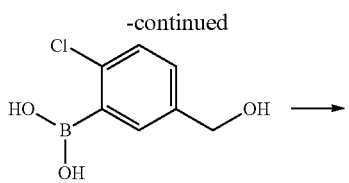

(3) tert-butyl N-(4-chloro-3-{4-[4-(2,2-dimethyl-propoxy)phenyl]-6-methoxy-1,3,5-triazin-2-yl}benzyl)-N-(tert-butoxycarbonyl)carbamate

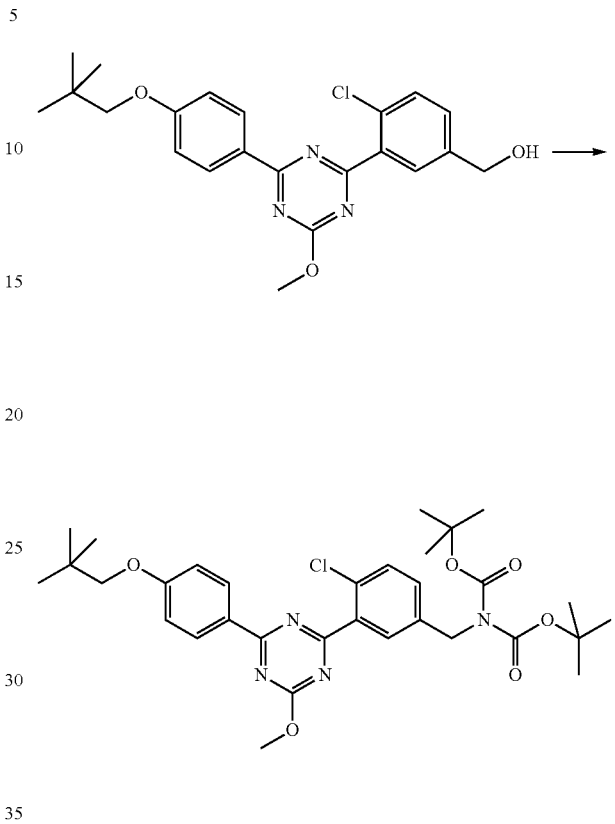

Under an argon atmosphere, a suspension of 2-chloro-4-[4-(2,2-dimethylpropoxy)phenyl]-6-methoxy-1,3,5-triazine (2.3 g, 7.4 mmol) obtained in the above-mentioned (1), 2-chloro-5-hydroxymethylphenylboronic acid (1.7 g, 8.9 mmol), [1,1'-bis(diphenylphosphino)ferrocene]palladium (II)dichloride dichloromethane adduct (0.61 g, 0.74 mmol) and 2M aqueous sodium carbonate solution (15 ml, 30 mmol) in 1,4-dioxane (23 ml) was stirred at 100° C. for 1.5 hr. At room temperature, to the reaction mixture were added water and ethyl acetate and the mixture was partitioned. The organic layer was washed with saturated aqueous sodium hydrogen carbonate, washed with saturated brine, dried over sodium sulfate, filtered to remove sodium sulfate, and concentrated under reduced pressure. The residue was purified by silica gel column chromatography (eluent: n-hexane/ethyl acetate=4/1-1/1) to give the title compound (1.3 g, yield 43%).

$^1$H-NMR (400 MHz, CDCl$_3$) δ: 1.06 (9H, s), 1.75 (1H, t, J=5.9 Hz), 3.69 (2H, s), 4.19 (3H, s), 4.77 (2H, d, J=5.9 Hz), 6.98-7.03 (2H, m), 7.46 (1H, dd, J=8.2, 2.2 Hz), 7.53 (1H, d, J=8.2 Hz), 8.00 (1H, d, J=2.2 Hz), 8.52-8.58 (2H, m).

Under an argon atmosphere, to a solution of (4-chloro-3-{4-[4-(2,2-dimethylpropoxy)phenyl]-6-methoxy-1,3,5-triazin-2-yl}phenyl)methanol (1.3 g, 3.2 mmol) obtained in the above-mentioned (2) and triethylamine (0.58 ml, 4.2 mmol) in tetrahydrofuran (13 ml) was added methanesulfonyl chloride (0.29 ml, 3.8 mmol) under ice-cooling, and the mixture was warmed to room temperature. After stirring for 0.5 hr, the reaction mixture was filtered, and the filtrate was concentrated under reduced pressure. To a solution of the residue in N,N-dimethylformamide (13 ml) were added cesium carbonate (3.1 g, 9.5 mmol) and di-tert-butyl iminodicarboxylate (0.83 g, 3.8 mmol), and the mixture is stirred for 3 hr. To the reaction mixture were added water and ethyl acetate and the mixture was partitioned. The organic layer was washed with saturated aqueous sodium hydrogen carbonate, washed with saturated brine, dried over sodium sulfate, filtered to remove sodium sulfate, and concentrated under reduced pressure. The residue was purified by silica gel column chromatography (eluent: n-hexane/ethyl acetate=9/1-7/3) to give the title compound (1.6 g, yield 82%).

$^1$H-NMR (400 MHz, CDCl$_3$) δ: 1.06 (9H, s), 1.48 (18H, s), 3.69 (2H, s), 4.18 (3H, s), 4.83 (2H, s), 6.96-7.01 (2H, m), 7.39 (1H, dd, J=8.2, 2.2 Hz), 7.48 (1H, d, J=8.2 Hz), 7.98 (1H, d, J=2.2 Hz), 8.51-8.57 (2H, m).

(4) 4-chloro-3-{4-[4-(2,2-dimethylpropoxy)phenyl]-6-methoxy-1,3,5-triazin-2-yl}benzylamine hydrochloride

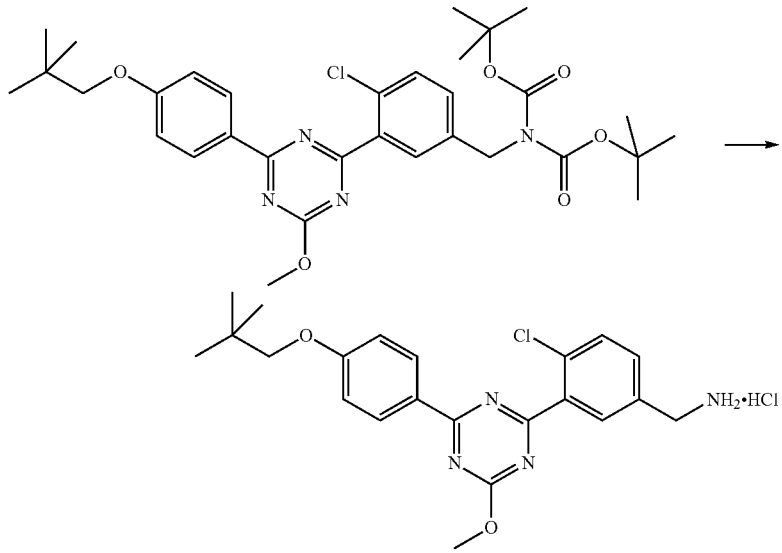

Under an argon atmosphere, to a solution of tert-butyl N-(4-chloro-3-{4-[4-(2,2-dimethylpropoxy)phenyl]-6-methoxy-1,3,5-triazin-2-yl}benzyl)-N-(tert-butoxycarbonyl)carbamate (1.3 g, 2.2 mmol) obtained in the above-mentioned (3) in 1,4-dioxane (2.8 ml) was added 4M hydrogen chloride/1,4-dioxane solution (11 ml) at room temperature, and the mixture was stirred for 3 hr. The solid was collected by filtration from the suspension, and dried under reduced pressure to give the title compound (0.97 g, yield 99%).

$^1$H-NMR (400 MHz, DMSO-$d_6$) δ: 1.03 (9H, s), 3.76 (2H, s), 4.10-4.18 (2H, m), 4.14 (3H, s), 7.11-7.17 (2H, m), 7.72 (2H, d, J=0.9 Hz), 8.13 (1H, br s), 8.40-8.58 (5H, m).

(5) N-(4-chloro-3-{4-[4-(2,2-dimethylpropoxy)phenyl]-6-methoxy-1,3,5-triazin-2-yl}benzyl)-3,3,3-trifluoro-2,2-dimethylpropionamide

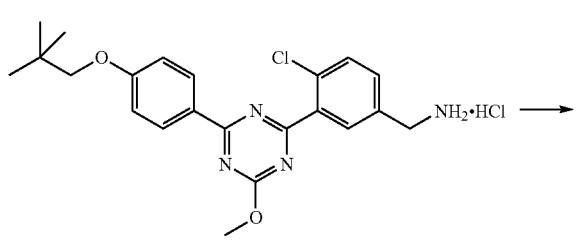

Under an argon atmosphere, to a solution of 4-chloro-3-{4-[4-(2,2-dimethylpropoxy)phenyl]-6-methoxy-1,3,5-triazin-2-yl}benzylamine hydrochloride (0.97 g, 2.2 mmol) obtained in the above-mentioned (4) and 3,3,3-trifluoro-2,2-dimethylpropionic acid (0.41 g, 2.6 mmol) in N,N-dimethylformamide (10 ml) were added HOBt·H$_2$O (0.43 g, 2.8 mmol), WSC·HCl (2.8 g, 2.8 mmol) and triethylamine (0.91 ml, 6.5 mmol) at room temperature, and the mixture was stirred for 3.5 hr. 3,3,3-Trifluoro-2,2-dimethylpropionic acid (0.067 g, 0.43 mmol), HOBt·H$_2$O (0.066 g, 0.43 mmol) and WSC·HCl (0.082 g, 0.43 mmol) were added, and the mixture was stirred for 1.5 hr. To the reaction mixture were added water and ethyl acetate and the mixture was partitioned. The organic layer was washed with saturated aqueous sodium hydrogen carbonate, washed with saturated brine, dried over sodium sulfate, filtered to remove sodium sulfate, and concentrated under reduced pressure. The residue was purified by silica gel column chromatography (eluent: n-hexane/ethyl acetate=9/1-7/3) to give the title compound (0.97 g, yield 81%).

$^1$H-NMR (400 MHz, CDCl$_3$) δ: 1.07 (9H, s), 1.44 (6H, s), 3.69 (2H, s), 4.19 (3H, s), 4.55 (2H, d, J=5.8 Hz), 6.22 (1H, br s), 6.96-7.03 (2H, m), 7.34 (1H, dd, J=8.3, 2.3 Hz), 7.51 (1H, d, J=8.3 Hz), 7.91 (1H, d, J=2.3 Hz), 8.50-8.57 (2H, m).

(6) N-(4-chloro-3-{4-[4-(2,2-dimethylpropoxy)phenyl]-6-hydroxy-1,3,5-triazin-2-yl}benzyl)-3,3,3-trifluoro-2,2-dimethylpropionamide (Example No. 1-86)

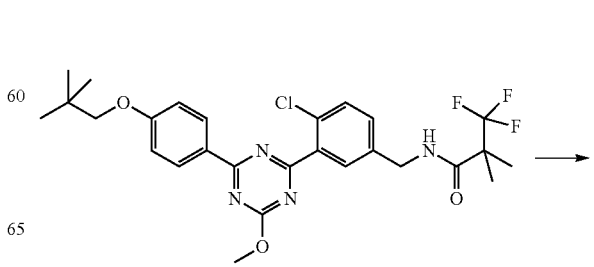

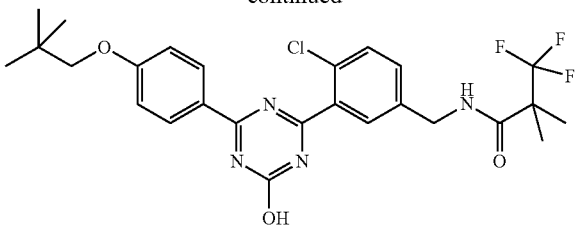

Under an argon atmosphere, to a solution of N-(4-chloro-3-{4-[4-(2,2-dimethylpropoxy)phenyl]-6-methoxy-1,3,5-triazin-2-yl}benzyl)-3,3,3-trifluoro-2,2-dimethylpropionamide (0.97 g, 1.76 mmol) obtained in the above-mentioned (5) in methanol (10 ml) was added 4M aqueous sodium hydroxide solution (3.5 ml, 14 mmol) at room temperature, and the mixture was stirred at 65° C. for 1.5 hr. To the reaction mixture were added 2M hydrochloric acid (7.0 ml, 14 mmol) and water at room temperature, and the mixture was stirred. The precipitated solid was collected by filtration, washed with water, and dried under reduced pressure to give the title compound (0.87 g, yield 92%).

$^1$H-NMR (400 MHz, DMSO-$d_6$) δ: 1.02 (9H, s), 1.37 (6H, s), 3.73 (2H, s), 4.35 (2H, d, J=5.8 Hz), 7.08 (2H, d, J=9.1 Hz), 7.40 (1H, dd, J=8.3, 2.2 Hz), 7.58 (1H, d, J=8.3 Hz), 7.62 (1H, d, J=1.9 Hz), 8.29 (2H, d, J=9.1 Hz), 8.62 (1H, t, J=5.8 Hz), 13.13 (1H, s).

Production Example 2

Synthesis of 1-[4-chloro-3-(4-hydroxy-6-phenyl-1,3,5-triazin-2-yl)-benzyl]-3,3-dimethyl-1,3-dihydroindol-2-one (Example No. 1-258)

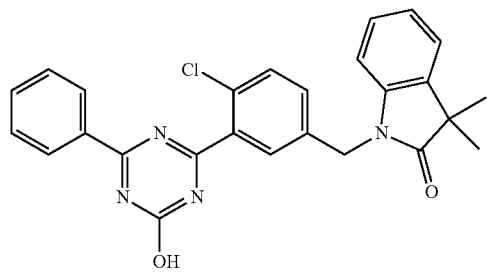 [SMILES: CC1(C)C(=O)N(Cc2ccc(Cl)c(-c3nc(O)nc(-c4ccccc4)n3)c2)c2ccccc21]

(1) 2-(5-bromomethyl-2-chlorophenyl)-4-methoxy-6-phenyl-1,3,5-triazine

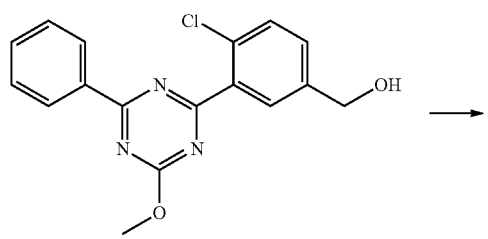

By a method similar to that in Production Example 1 (1) and (2), and using 2,4-dichloro-6-methoxy-1,3,5-triazine, 2-chloro-5-hydroxymethylphenylboronic acid, and phenylboronic acid instead of 4-(2,2-dimethylpropoxy)phenylboronic acid, [4-chloro-3-(4-methoxy-6-phenyl-1,3,5-triazin-2-yl)phenyl]methanol was obtained.

Under an argon atmosphere, to a solution of the obtained [4-chloro-3-(4-methoxy-6-phenyl-1,3,5-triazin-2-yl)phenyl]methanol (0.47 g, 1.4 mmol) and triphenylphosphine (0.56 g, 2.1 mmol) in chloroform (4.5 ml) was added carbon tetrabromide (0.71 g, 2.1 mmol) under ice-cooling. The reaction mixture was stirred at room temperature for 10 min, and concentrated under reduced pressure. The residue was purified by silica gel column chromatography (eluent: n-hexane/ethyl acetate=30/1-9/1) to give the title compound (0.49 g, yield 87%).

$^1$H-NMR (400 MHz, CDCl$_3$) δ: 4.22 (3H, s), 4.53 (2H, s), 7.45-7.64 (5H, m), 8.06 (1H, br s), 8.57-8.63 (2H, m).

(2) 1-[4-chloro-3-(4-methoxy-6-phenyl-1,3,5-triazin-2-yl)benzyl]-3,3-dimethyl-1,3-dihydroindol-2-one

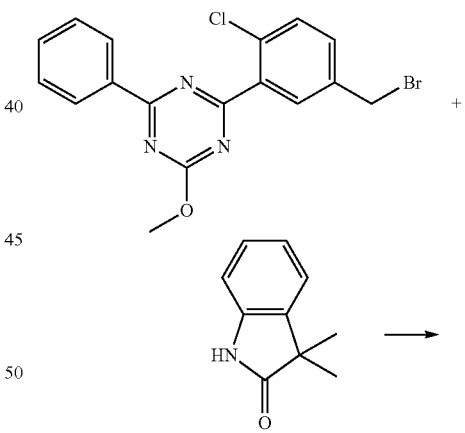

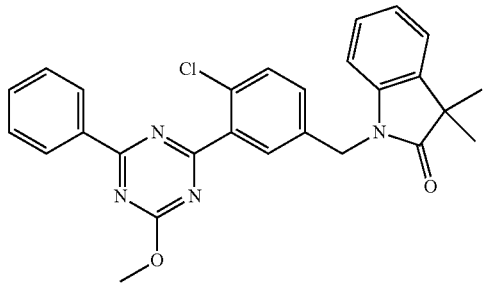

Under an argon atmosphere, to a solution of 3,3-dimethylindolin-2-one (0.050 g, 0.31 mmol) in N,N-dimethylformamide (1.0 ml) was added sodium hydride (0.012 g, 60 wt % oil dispersion) under ice-cooling. After stirring for 30 min, 2-(5-bromomethyl-2-chlorophenyl)-4-methoxy-6-phenyl-1,3,5-triazine (0.10 g, 0.26 mmol) obtained in the above-mentioned (1) was added, and the mixture was stirred at room temperature for 30 min. To the reaction mixture were added saturated aqueous ammonium chloride solution and ethyl acetate and the mixture was partitioned. The organic layer was washed with saturated aqueous sodium hydrogen carbonate, washed with saturated brine, dried over sodium sulfate, filtered to remove sodium sulfate, and concentrated under reduced pressure. The residue was purified by silica gel column chromatography (eluent: n-hexane/ethyl acetate=7/2) to give the title compound (0.11 g, yield 89%).

$^1$H-NMR (400 MHz, CDCl$_3$) δ: 1.44 (6H, s), 4.18 (3H, s), 4.98 (2H, s), 6.72-6.76 (1H, m), 7.02-7.08 (1H, m), 7.13-7.19 (1H, m), 7.21-7.25 (1H, m), 7.31-7.36 (1H, m), 7.46-7.53 (3H, m), 7.55-7.61 (1H, m), 8.00 (1H, br s), 8.51-8.58 (2H, m)

(3) 1-[4-chloro-3-(4-hydroxy-6-phenyl-1,3,5-triazin-2-yl)benzyl]-3,3-dimethyl-1,3-dihydroindol-2-one (Example No. 1-258)

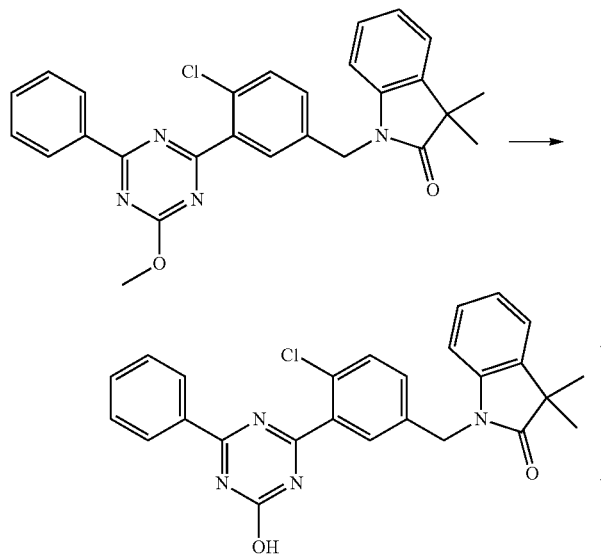

Under an argon atmosphere, to a solution of 1-[4-chloro-3-(4-methoxy-6-phenyl-1,3,5-triazin-2-yl)benzyl]-3,3-dimethyl-1,3-dihydroindol-2-one (0.11 g, 0.23 mmol) obtained in the above-mentioned (2) in methanol (10 ml) was added 4M aqueous sodium hydroxide solution (0.34 ml, 1.4 mmol) at room temperature, and the mixture was stirred at 65° C. for 2 hr. To is the reaction mixture were added 10 wt % aqueous citric acid solution (1.4 ml) and water (7.0 ml) at room temperature, and the mixture was stirred for 30 min. The precipitated solid was collected by filtration, washed with water, and dried under reduced pressure to give the title compound (0.10 g, yield 96%).

$^1$H-NMR (400 MHz, DMSO-d$_6$) δ: 1.34 (6H, s), 4.99 (2H, s), 6.97 (1H, d, J=7.6 Hz), 7.05 (1H, t, J=7.6 Hz), 7.20 (1H, t, J=7.6 Hz), 7.39 (1H, d, J=7.6 Hz), 7.48 (1H, dd, J=8.3, 1.8 Hz), 7.55 (2H, t, J=7.6 Hz), 7.59-7.68 (2H, m), 7.75 (1H, d, J=1.8 Hz), 8.29 (2H, d, J=7.6 Hz), 13.32 (1H, br s).

Production Example 3

Synthesis of N-[4-chloro-3-(4-hydroxy-6-phenyl-1,3,5-triazin-2-yl)benzyl]-N-ethyl-3,3,3-trifluoro-2,2-dimethylpropionamide (Example No. 1-263)

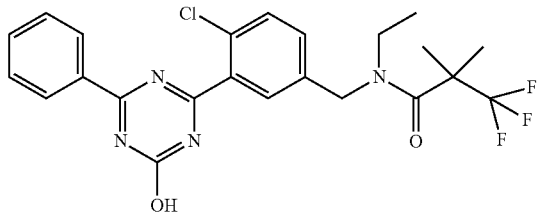 [SMILES: CCN(Cc1ccc(Cl)c(-c2nc(O)nc(-c3ccccc3)n2)c1)C(=O)C(C)(C)C(F)(F)F]

(1) [4-chloro-3-(4-methoxy-6-phenyl-1,3,5-triazin-2-yl)benzyl]ethylamine

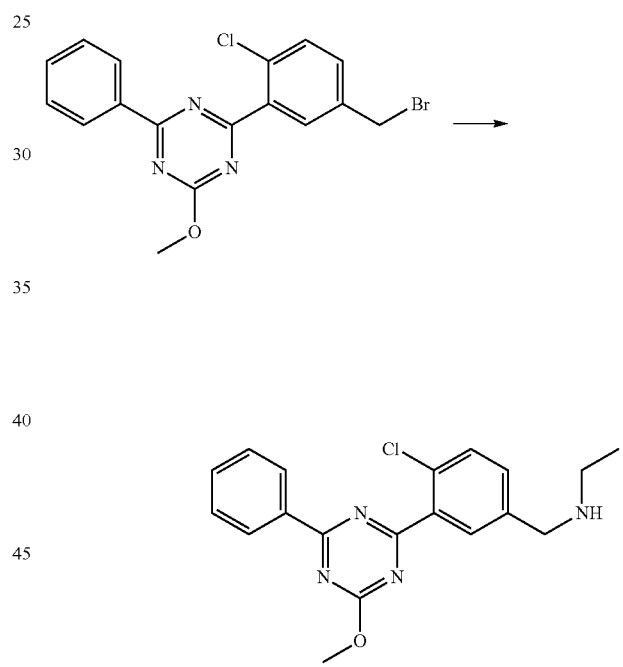

Under an argon atmosphere, to 2-(5-bromomethyl-2-chlorophenyl)-4-methoxy-6-phenyl-1,3,5-triazine (0.20 g, 0.51 mmol) obtained in the same manner as in Production Example 2 (1) was added a solution of 2M ethylamine tetrahydrofuran (2.5 ml) at room temperature, and the mixture was stirred for 1 hr. To the reaction mixture were added saturated aqueous sodium hydrogen carbonate and ethyl acetate and the mixture was partitioned. The organic layer was washed with saturated brine, dried over sodium sulfate, filtered to remove sodium sulfate, and concentrated under reduced pressure to give the title compound (0.28 g) as a crude product.

$^1$H-NMR (400 MHz, CDCl$_3$) δ: 1.14 (3H, t, J=7.2 Hz), 2.70 (2H, q, J=7.2 Hz), 3.86 (2H, s), 4.22 (3H, s), 7.44 (1H, dd, J=8.2, 2.2 Hz), 7.48-7.55 (3H, m), 7.57-7.62 (1H, m), 7.97 (1H, d, J=2.2 Hz), 8.58-8.64 (2H, m).

(2) N-[4-chloro-3-(4-methoxy-6-phenyl-1,3,5-tri-azin-2-yl)benzyl]-N-ethyl-3,3,3-trifluoro-2,2-dimethylpropionamide

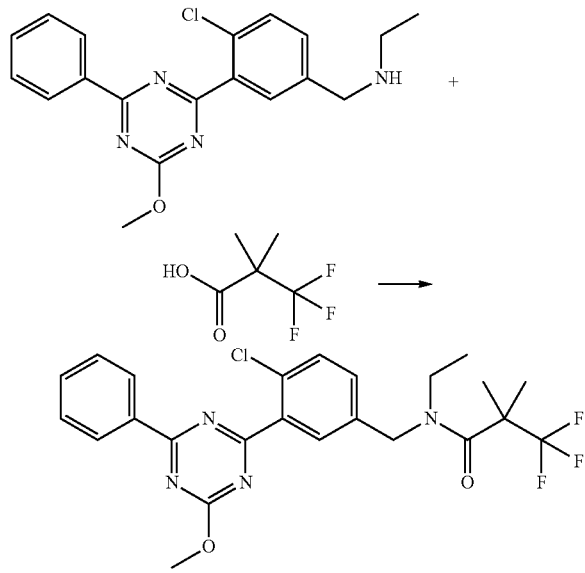

Under an argon atmosphere, to a solution of [4-chloro-3-(4-methoxy-6-phenyl-1,3,5-triazin-2-yl)benzyl]ethylamine (0.18 g, 0.38 mmol) obtained in the above-mentioned (1) and 3,3,3-trifluoro-2,2-dimethylpropionic acid (0.12 g, 0.76 mmol) in chloroform (2.0 ml) were added WSC·HCl (0.15 g, 0.76 mmol) and 4-dimethylaminopyridine (0.93 mg, 0.76 mmol) at room temperature, and the mixture was stirred for 16 hr. The residue was purified by silica gel column chromatography (eluent: n-hexane/ethyl acetate=8/3) to give the title compound (0.086 g, yield 46%).

$^1$H-NMR (400 MHz, CDCl$_3$) δ: 1.20 (3H, t, J=6.9 Hz), 1.55 (6H, s), 3.47 (2H, q, J=6.9 Hz), 4.21 (3H, s), 4.71 (2H, s), 7.24-7.30 (1H, m), 7.45-7.63 (4H, m), 7.88 (1H, br s), 8.56-8.64 (2H, m).

(3) N-[4-chloro-3-(4-hydroxy-6-phenyl-1,3,5-tri-azin-2-yl)benzyl]-N-ethyl-3,3,3-trifluoro-2,2-dimethylpropionamide (Example No. 1-263)

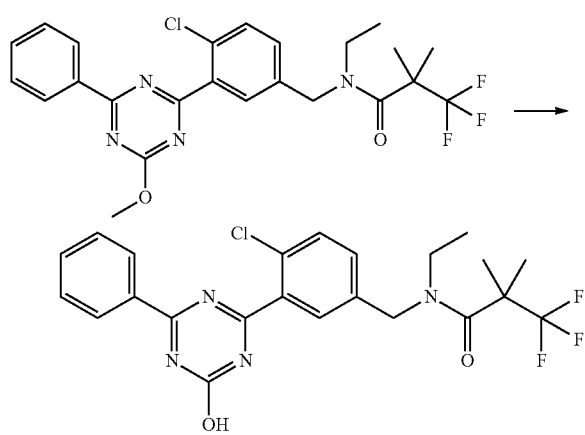

Under an argon atmosphere, to a solution of N-[4-chloro-3-(4-methoxy-6-phenyl-1,3,5-triazin-2-yl)benzyl]-N-ethyl-3,3,3-trifluoro-2,2-dimethylpropionamide (0.086 g, 0.17 mmol) obtained in the above-mentioned (2) in methanol (1.5 ml) was added 4M aqueous sodium hydroxide solution (0.26 ml, 1.0 mmol) at room temperature, and the mixture was stirred at 65° C. for 2 hr. At room temperature, 10 wt % aqueous citric acid solution (1.2 ml) and water (6 ml) were added, and the mixture was stirred for 30 min. The precipitated solid was collected by filtration, washed with water, and dried under reduced pressure to give a crude product. To a suspension of the crude product in ethyl acetate (1.5 ml) was added n-hexane (1.5 ml), and the mixture was stirred for 30 min. The solid was collected by filtration, dried under reduced pressure to give the title compound (0.067 g, yield 80%).

$^1$H-NMR (400 MHz, DMSO-d$_6$) δ:1.13 (3H, t, J=6.9 Hz), 1.50 (6H, s), 3.42 (2H, br s), 4.66 (2H, s), 7.41 (1H, dd, J=8.3, 1.8 Hz), 7.56 (2H, t, J=7.9 Hz), 7.61-7.69 (3H, m), 8.34 (2H, d, J=7.9 Hz), 13.33 (1H, br s).

Production Example 4

Synthesis of 7-tert-butyl-2-[4-chloro-3-(4-hydroxy-6-phenyl-1,3,5-triazin-2-yl)benzyl]-2-azaspiro[3.5]nonan-1-one (Example No. 1-266)

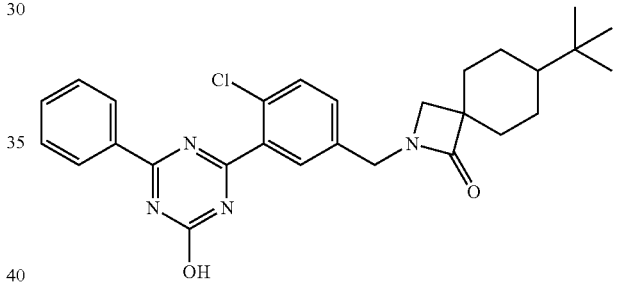

(1) methyl 1-benzyloxymethyl-4-tert-butyl-cyclohexanecarboxylate

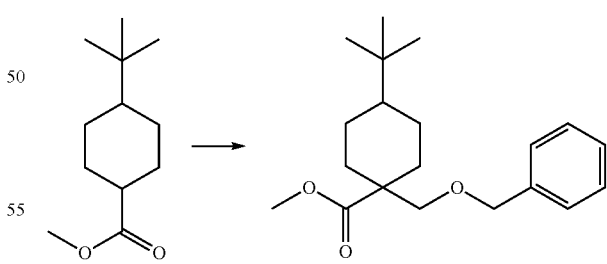

Under an argon atmosphere, to a solution of methyl 4-tert-butyl-cyclohexanecarboxylate (0.46 g, 2.3 mmol) in tetrahydrofuran (2.5 ml) was added dropwise 2M heptane/tetrahydrofuran/ethylbenzene solution (1.4 ml, 2.8 mmol) of lithium diisopropylamide at −78° C. over 5 min. After stirring for 1 hr, benzyl chloromethyl ether (0.38 ml, 2.8 mmol) was added dropwise over 1 min. Under ice-cooling, the mixture was stirred for 1 hr. To the reaction mixture were added 10 wt % aqueous citric acid solution (3.0 ml) and ethyl acetate, and the mixture was partitioned. The organic layer was washed with saturated aqueous sodium hydrogen carbonate, washed with saturated brine, dried over sodium sulfate, filtered to remove sodium sulfate, and concentrated under reduced pressure. The residue was purified by silica gel column chromatography (eluent: n-hexane/ethyl acetate=30/1) to give the title compound (0.49 g, yield 66%). While the title compound was obtained as a single stereoisomer, the relative configuration thereof is undetermined. Specifically, whether the methoxycarbonyl group is cis/trans relative to the tert-butyl group is undetermined.

$^1$H-NMR (400 MHz, CDCl$_3$) δ: 0.81 (9H, s), 0.88-0.99 (1H, m), 1.00-1.21 (4H, m), 1.68 (2H, d, J=12.0 Hz), 2.29 (2H, d, J=12.0 Hz), 3.36 (2H, s), 3.69 (3H, s), 4.48 (2H, br s), 7.22-7.38 (5H, m).

(2) methyl 4-tert-butyl-1-hydroxymethyl-cyclohexanecarboxylate

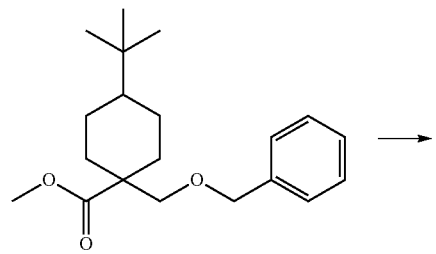

Under an argon atmosphere, to a solution of methyl 1-benzyloxymethyl-4-tert-butyl-cyclohexanecarboxylate (0.49 g, 1.5 mmol) obtained in the above-mentioned (1) in methanol (5.5 ml) was added ASCA-2 (4.5% palladium of activated carbon support-0.5% platinum catalyst (see N.E. CHEMCAT, Fine chemical Oct. 1, 2002, pages 5-14), 0.20 g) at room temperature. Under 1 atm hydrogen, the mixture was stirred for 4 hr. Under an argon atmosphere, the reaction mixture was filtered through celite, and the filtrate was eluted with ethyl acetate. The filtrate was concentrated under reduced pressure to give the title compound (0.27 g, yield 75%). While the title compound is a single stereoisomer, the relative configuration thereof is undetermined.

$^1$H-NMR (400 MHz, CDCl$_3$) δ: 0.83 (9H, s), 0.91-1.17 (5H, m), 1.64-1.78 (3H, m), 2.20-2.31 (2H, m), 3.53 (2H, d, J=6.0 Hz), 3.73 (3H, s).

(3) 4-tert-butyl-1-hydroxymethyl-cyclohexanecarboxylic acid

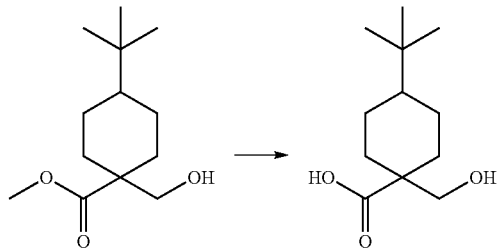 [SMILES: COC(=O)C1(CO)CCC(C(C)(C)C)CC1 ; CC(C)(C)C1CCC(CO)(C(=O)O)CC1]

Under an argon atmosphere, to a solution of methyl 4-tert-butyl-1-hydroxymethyl-cyclohexanecarboxylate (0.27 g, 1.2 mmol) obtained in the above-mentioned (2) in methanol (1.7 ml) were added tetrahydrofuran (1.7 ml) and 4M aqueous sodium hydroxide solution (1.7 ml, 7.0 mmol) at room temperature, and the mixture was stirred at 65° C. for 1.5 hr. Methanol (1.7 ml), tetrahydrofuran (1.7 ml) and 4M aqueous sodium hydroxide solution (1.7 ml, 7.0 mmol) were added, and the mixture was stirred at 65° C. for 2 hr. To the reaction mixture were added 2M hydrochloric acid (7.5 ml, 15 mmol) and water at room temperature, and the mixture was stirred. Ethyl acetate was added and the mixture was partitioned. The organic layer was washed with saturated brine, dried over sodium sulfate, filtered to remove sodium sulfate, and concentrated under reduced pressure. The residue was purified by silica gel column chromatography (eluent: n-hexane/ethyl acetate=12/1) to give the title compound (0.24 g, yield 94%). While the title compound is a single stereoisomer, the relative configuration thereof is undetermined.

$^1$H-NMR (400 MHz, DMSO-d$_6$) δ: 0.80 (9H, s), 0.86-1.12 (5H, m), 1.53-1.66 (2H, m), 2.00-2.13 (2H, m), 3.31 (2H, s)

(4) 4-tert-butyl-1-hydroxymethyl-cyclohexanecarboxylic acid 4-chloro-3-(4-methoxy-6-phenyl-1,3,5-triazin-2-yl)benzylamide

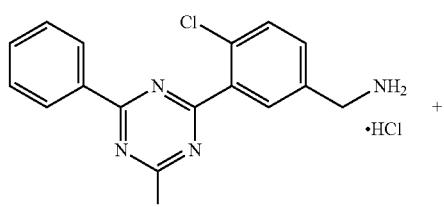

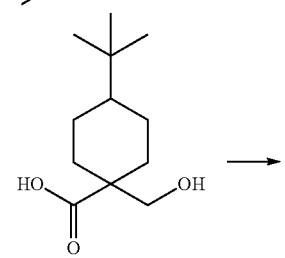

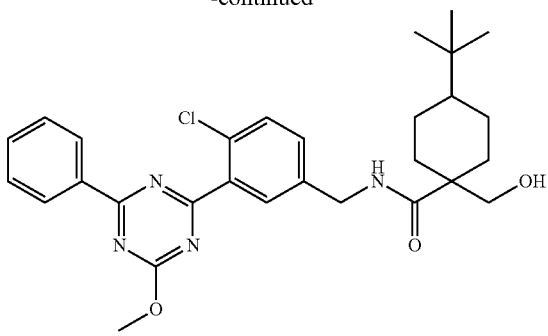

By a method similar to that in Production Example 1 (1)-(4), and using 2,4-dichloro-6-methoxy-1,3,5-triazine, 2-chloro-5-hydroxymethylphenylboronic acid, and phenylboronic acid instead of 4-(2,2-dimethylpropoxy)phenylboronic acid, 4-chloro-3-(4-methoxy-6-phenyl-1,3,5-triazin-2-yl)benzylamine hydrochloride was obtained.

Under an argon atmosphere, to a solution of the obtained 4-chloro-3-(4-methoxy-6-phenyl-1,3,5-triazin-2-yl)benzylamine hydrochloride (0.90 g, 0.25 mmol) and 4-tert-butyl-1-hydroxymethyl-cyclohexanecarboxylic acid (0.080 g, 0.37 mmol) obtained in the above-mentioned (3) in N,N-dimethylformamide (2.0 ml) were added HOBt·H$_2$O (0.057 g, 0.37 mmol), WSC·HCl (0.071 g, 0.37 mmol) and triethylamine (0.10 ml, 0.74 mmol) at room temperature, and the mixture was stirred for 13 hr. To the reaction mixture were added saturated aqueous sodium hydrogen carbonate and ethyl acetate, and the mixture was partitioned. The organic layer was washed with saturated aqueous sodium hydrogen carbonate, washed with saturated brine, dried over sodium sulfate, filtered to remove sodium sulfate, and concentrated under reduced pressure. The residue was purified by silica gel column chromatography (eluent: n-hexane/ethyl acetate=1/2-1/3) to give the title compound (0.11 g, yield 81%). While the title compound is a single stereoisomer, the relative configuration thereof is undetermined.

$^1$H-NMR (400 MHz, CDCl$_3$) δ: 0.78 (9H, s), 0.94-1.22 (5H, m), 1.66-1.75 (2H, m), 2.22-2.30 (2H, m), 2.42 (1H, t, J=5.0 Hz), 3.52 (2H, d, J=5.0 Hz), 4.21 (3H, s), 4.57 (2H, d, J=5.8 Hz), 6.46 (1H, t, J=5.8 Hz), 7.38 (1H, dd, J=8.3, 2.3 Hz), 7.47-7.55 (3H, m), 7.57-7.62 (1H, m), 7.97 (1H, d, J=2.3 Hz), 8.57-8.62 (2H, m).

(5) 7-tert-butyl-2-[4-chloro-3-(4-methoxy-6-phenyl-1,3,5-triazin-2-yl)benzyl]-2-azaspiro[3.5]nonan-1-one

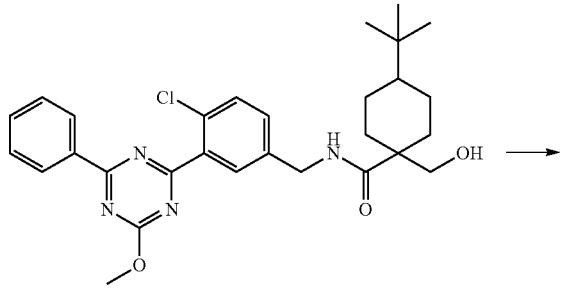

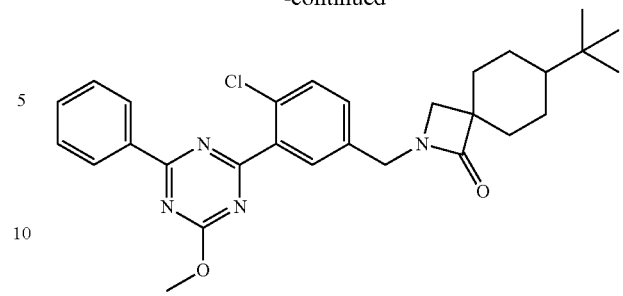

Under an argon atmosphere, to a solution of 4-tert-butyl-1-hydroxymethyl-cyclohexanecarboxylic acid 4-chloro-3-(4-methoxy-6-phenyl-1,3,5-triazin-2-yl)benzylamide (0.11 g, 0.20 mmol) obtained in the above-mentioned (4) and triphenylphosphine (0.080 g, 0.30 mmol) in tetrahydrofuran (1.0 ml) was added bis(2-methoxyethyl) azodicarboxylate (0.071 g, 0.30 mmol) at room temperature, and the mixture was stirred for 1.5 hr. To the reaction mixture were added water and ethyl acetate, and the mixture was partitioned. The organic layer was washed with saturated aqueous sodium hydrogen carbonate, washed with saturated brine, dried over sodium sulfate, filtered to remove sodium sulfate, and concentrated under reduced pressure. The residue was purified by preparative thin layer chromatography (eluent: n-hexane/ethyl acetate=4/1) to give the title compound (0.068 g, yield 66%). While the title compound is a single stereoisomer, the relative configuration of the tert-butyl group is undetermined.

$^1$H-NMR (400 MHz, CDCl$_3$) δ: 0.81-1.77 (7H, m), 0.87 (9H, s), 2.03-2.12 (2H, m), 2.87 (2H, br s), 4.21 (3H, s), 4.40 (2H, br s), 7.30-7.37 (1H, m), 7.48-7.64 (4H, m), 7.90 (1H, br s), 8.57-8.63 (2H, m).

(6) 7-tert-butyl-2-[4-chloro-3-(4-hydroxy-6-phenyl-1,3,5-triazin-2-yl)benzyl]-2-azaspiro[3.5]nonan-1-one (Example No. 1-266)

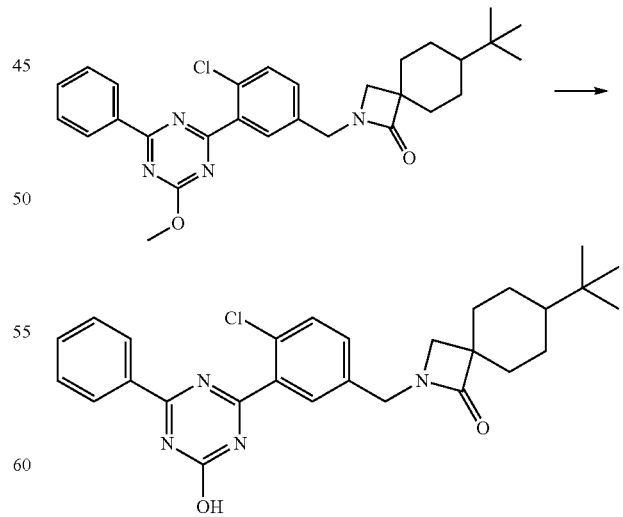

Under an argon atmosphere, to a solution of 7-tert-butyl-2-[4-chloro-3-(4-methoxy-6-phenyl-1,3,5-triazin-2-yl)benzyl]-2-azaspiro[3.5]nonan-1-one (0.068 g, 0.13 mmol) obtained in the above-mentioned (5) in methanol (1.2 ml)

was added 4M aqueous sodium hydroxide solution (0.20 ml, 0.81 mmol) at room temperature, and the mixture was stirred at 65° C. for 1.5 hr. At room temperature, to the reaction mixture were added 10 wt % aqueous citric acid solution (0.82 ml) and water (4.0 ml), and the mixture was stirred for 30 min. The precipitated solid was collected by filtration, washed with water, and dried under reduced pressure to give the title compound (0.062 g, yield 94%). While the title compound is a single stereoisomer, the relative configuration of the tert-butyl group is undetermined.

$^1$H-NMR (400 MHz, DMSO-$d_6$) δ: 0.83 (9H, s), 0.90-0.99 (1H, m), 1.41-1.67 (6H, m), 1.96-2.03 (2H, m), 2.92 (2H, s), 4.38 (2H, s), 7.47 (1H, dd, J=8.3, 1.8 Hz), 7.56 (2H, t, J=7.6 Hz), 7.63-7.69 (3H, m), 8.34 (2H, d, J=7.6 Hz), 13.34 (1H, br s).

Production Example 5

Synthesis of 4-[2-(6-methylpyridin-2-ylmethoxy)-6-trifluoromethylphenyl]-6-(4-phenylethynylphenyl)-1,3,5-triazin-2-ol hydrochloride (Example No. 2-98)

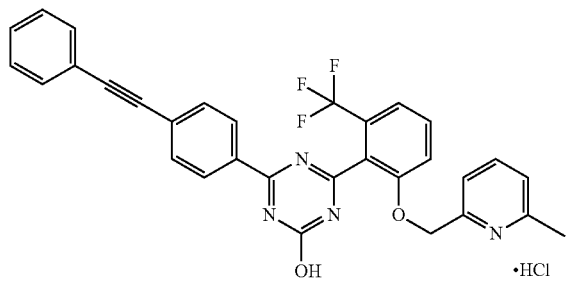 [SMILES: Cc1cccc(COc2cccc(C(F)(F)F)c2-c2nc(O)nc(-c3ccc(C#Cc4ccccc4)cc3)n2)n1 ; Cl]

(1) 2-bromo-1-methoxymethoxy-3-trifluoromethyl-benzene

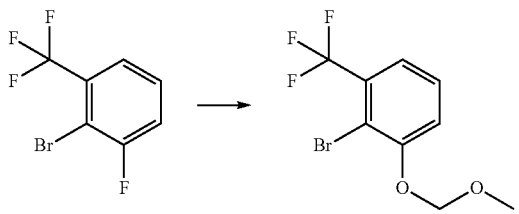

Under an argon atmosphere, to a solution of 2-bromo-3-fluorobenzotrifluoride (6.0 g, 25 mmol) and 2-(methylsulfonyl)ethanol (4.3 g, 35 mmol) in N,N-dimethylformamide (10 ml) was added sodium hydride (2.8 g, 60 wt % oil dispersion) in 3 portions under ice-cooling. After stirring at room temperature for 10 min, chloromethyl methyl ether (5.3 ml, 69 mmol) was added dropwise under ice-cooling. After stirring for 30 min, the mixture was stirred at room temperature for 15 min. Under ice-cooling, to the reaction mixture were added water and ethyl acetate, and the mixture was partitioned. The organic layer was washed with saturated aqueous sodium hydrogen carbonate, washed with saturated brine, dried over sodium sulfate, filtered to remove sodium sulfate, and concentrated under reduced pressure. The residue was purified by silica gel column chromatography (eluent: n-hexane/ethyl acetate=12/1) to give the title compound (5.0 g, yield 70%).

$^1$H-NMR (400 MHz, CDCl$_3$) δ: 3.53 (3H, s), 5.29 (2H, s), 7.31-7.38 (3H, m).

(2) 2-(2-methoxymethoxy-6-trifluoromethylphenyl)-4,4,5,5-tetramethyl-1,3,2-dioxaborolane

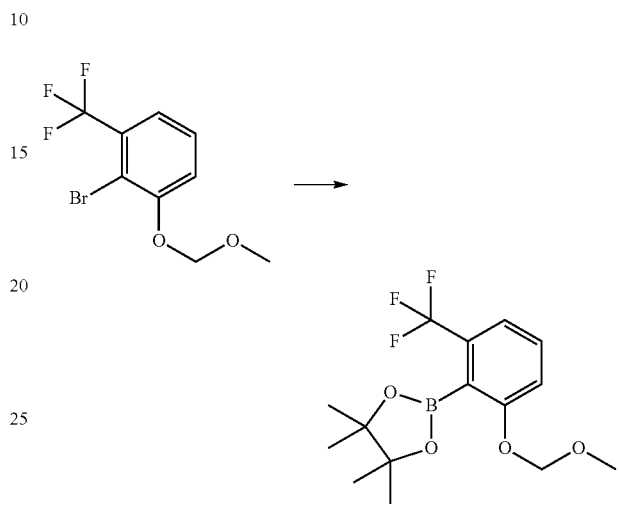

Under an argon atmosphere, to a solution of 2-bromo-1-methoxymethoxy-3-trifluoromethyl-benzene (4.9 g, 17 mmol) obtained in the above-mentioned (1) in tetrahydrofuran (90 ml) was added dropwise n-butyllithium (1.6M n-hexane solution, 11 ml, 17 mmol) at −78° C. over 30 min. 2-Isopropoxy-4,4,5,5-tetramethyl-1,3,2-dioxaborolane (3.5 ml, 17 mmol) was added dropwise over 15 min, and the mixture was warmed to room temperature and stirred for 2 hr. To the reaction mixture were added saturated ammonium chloride aqueous solution and ethyl acetate, and the mixture was partitioned. The organic layer was washed with saturated aqueous sodium hydrogen carbonate, washed with saturated brine, dried over sodium sulfate, filtered to remove sodium sulfate, and concentrated under reduced pressure. The residue was purified by silica gel column chromatography (eluent: n-hexane/ethyl acetate=9/1) to give the title compound (2.8 g, yield 48%).

$^1$H-NMR (400 MHz, CDCl$_3$) δ: 1.39 (12H, s), 3.47 (3H, s), 5.18 (2H, s), 7.20 (1H, d, J=8.4 Hz), 7.24-7.28 (1H, m), 7.36-7.42 (1H, m).

(3) 2-(4-benzyloxyphenyl)-4-methoxy-6-(2-methoxymethoxy-6-trifluoromethylphenyl)-1,3,5-triazine

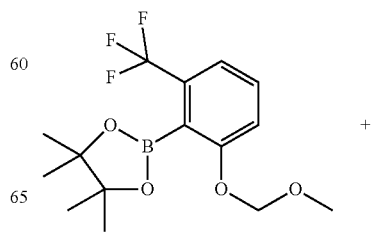

-continued

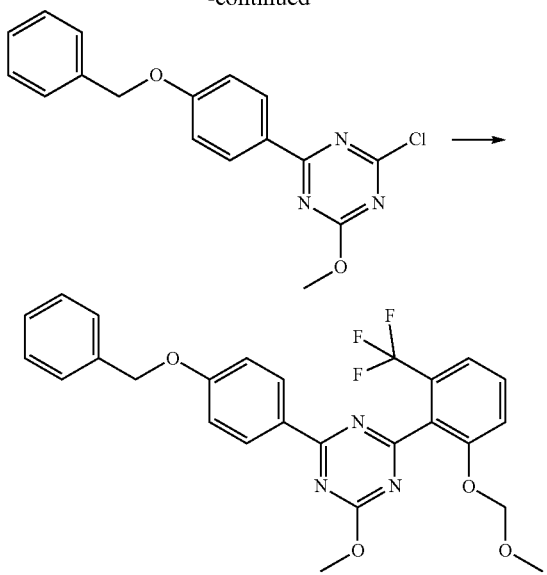

By a method similar to that in Production Example 1 (1), and using 2,4-dichloro-6-methoxy-1,3,5-triazine, and 4-(benzyloxy)phenylboronic acid instead of 4-(2,2-dimethylpropoxy)phenylboronic acid, 2-(4-benzyloxyphenyl)-4-chloro-6-methoxy-1,3,5-triazine was obtained.

Under an argon atmosphere, to a solution of the obtained 2-(4-benzyloxyphenyl)-4-chloro-6-methoxy-1,3,5-triazine (3.0 g, 9.2 mmol) and 2-(2-methoxymethoxy-6-trifluoromethylphenyl)-4,4,5,5-tetramethyl-1,3,2-dioxaborolane (2.8 g, 8.4 mmol) obtained in the above-mentioned (2) in N,N-dimethylformamide (25 ml) were added [1,1'-bis(diphenylphosphino)ferrocene]palladium(II)dichloride dichloromethane adduct (1.4 g, 1.7 mmol), copper(I) iodide (0.48 g, 2.5 mmol) and 2M aqueous sodium carbonate solution (13 ml, 25 mmol), and the mixture was stirred at 115° C. for 45 min. To the reaction mixture were added water and ethyl acetate. After stirring, the insoluble material was removed by celite filtration, and the filtrate was eluted with ethyl acetate. The filtrate was partitioned, and the organic layer was washed with saturated aqueous sodium hydrogen carbonate, washed with saturated brine, dried over sodium sulfate, filtered to remove sodium sulfate, and concentrated under reduced pressure. The is residue was purified by silica gel column chromatography (eluent: n-hexane/ethyl acetate=7/2) to give the title compound (2.0 g, yield 47%).

$^1$H-NMR (400 MHz, DMSO-$d_6$) δ: 3.39 (3H, s), 4.14 (3H, s), 5.13 (2H, s), 5.15 (2H, s), 7.02-7.08 (2H, m), 7.30-7.46 (7H, m), 7.48-7.55 (1H, m), 8.47-8.52 (2H, m).

(4) 4-[4-methoxy-6-(2-methoxymethoxy-6-trifluoromethylphenyl)-1,3,5-triazin-2-yl]phenol

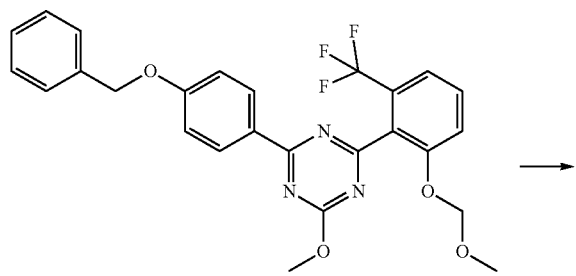

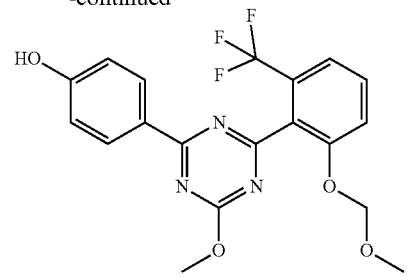

Under an argon atmosphere, to a solution of 2-(4-benzyloxyphenyl)-4-methoxy-6-(2-methoxymethoxy-6-trifluoromethylphenyl)-1,3,5-triazine (2.0 g, 4.0 mmol) obtained in the above-mentioned (3) in ethyl acetate (10 ml) were added methanol (10 ml) and 10 wt % palladium carbon (0.49 g) at room temperature. Under 1 atm hydrogen, the mixture was stirred for 2 hr. Under an argon atmosphere, the reaction mixture was filtered through celite, and the filtrate was eluted with ethyl acetate. The filtrate was concentrated under reduced pressure to give the title compound (1.6 g, yield 97%).

$^1$H-NMR (400 MHz, CDCl$_3$) δ: 3.39 (3H, s), 4.14 (4H, s), 5.13 (2H, s), 5.39 (1H, br s), 6.87-6.93 (2H, m), 7.40-7.45 (2H, m), 7.48-7.55 (1H, m), 8.43-8.48 (2H, m).

(5) trifluoromethanesulfonic acid 4-[4-methoxy-6-(2-methoxymethoxy-6-trifluoromethylphenyl)-1,3,5-triazin-2-yl]phenyl ester

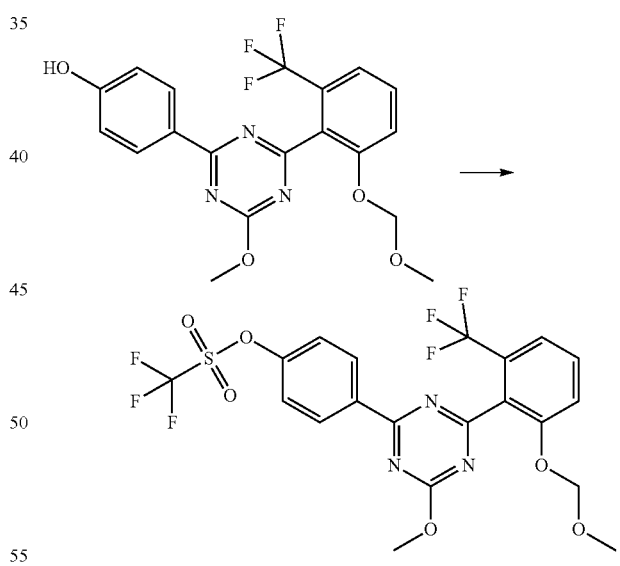

Under an argon atmosphere, to a solution of 4-[4-methoxy-6-(2-methoxymethoxy-6-trifluoromethylphenyl)-1,3,5-triazin-2-yl]phenol (1.6 g, 3.9 mmol) obtained in the above-mentioned (4) in pyridine (15 ml) was added dropwise trifluoromethanesulfonic anhydride (13 ml, 7.7 mmol) under ice-cooling, and the mixture was stirred at room temperature for 30 min. To the reaction mixture were added water and ethyl acetate, and the mixture was partitioned. The organic layer was washed with saturated aqueous sodium hydrogen carbonate, washed with saturated brine, dried over sodium sulfate, filtered to remove sodium sulfate, and concentrated under reduced pressure. The residue was purified by silica gel column chromatography (eluent: n-hexane/ethyl acetate=3/1) to give the title compound (2.0 g, yield 95%).

$^1$H-NMR (400 MHz, CDCl$_3$) δ: 3.39 (3H, s), 4.17 (3H, s), 5.13 (2H, s), 7.37-7.48 (4H, m), 7.51-7.58 (1H, m), 8.61-8.67 (2H, m).

(6) 2-methoxy-4-(2-methoxymethoxy-6-trifluoromethylphenyl)-6-(4-phenylethynylphenyl)-1,3,5-triazine

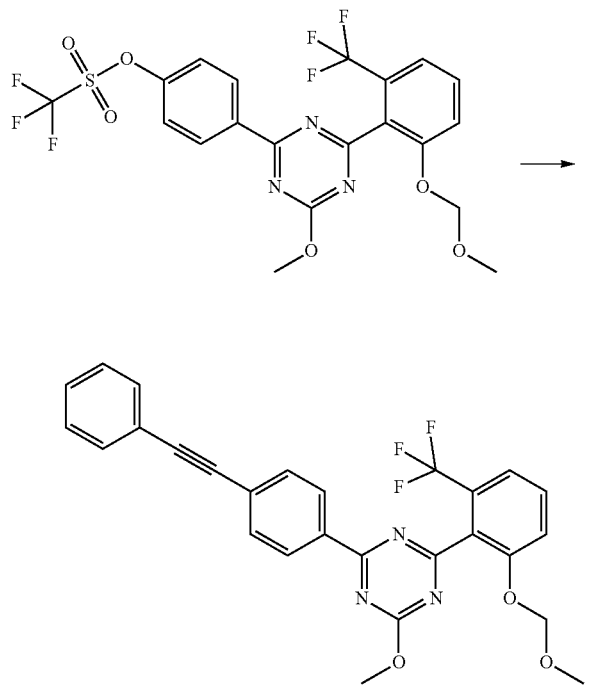

Under an argon atmosphere, to a solution of trifluoromethanesulfonic acid 4-[4-methoxy-6-(2-methoxymethoxy-6-trifluoromethylphenyl)-1,3,5-triazin-2-yl]phenyl ester (0.50 g, 0.93 mmol) obtained in the above-mentioned (5), bis(triphenylphosphine)palladium(II) dichloride (0.098 g, 0.139 mmol) and copper(I) iodide (0.053 g, 0.28 mmol) in N,N-dimethylformamide (5.0 ml) were added triethylamine (0.39 ml, 2.8 mmol) and ethynylbenzene (0.51 ml, 4.6 mmol), and the mixture was stirred at 65° C. for 2.5 hr. To the reaction mixture were added water and ethyl acetate. After stirring for 1 hr, the insoluble material was removed by celite filtration, and the filtrate was eluted with ethyl acetate. The filtrate was partitioned, and the organic layer was washed with saturated aqueous sodium hydrogen carbonate, washed with saturated brine, dried over sodium sulfate, filtered to remove sodium sulfate, and concentrated under reduced pressure. The residue was purified by silica gel column chromatography (eluent: n-hexane/ethyl acetate=5/1-4/1) to give the title compound (0.45 g, yield 98%).

$^1$H-NMR (400 MHz, DMSO-d$_6$) δ: 3.40 (3H, s), 4.17 (3H, s), 5.14 (2H, s), 7.34-7.39 (3H, m), 7.42-7.47 (2H, m), 7.50-7.59 (3H, m), 7.62-7.67 (2H, m), 8.50-8.55 (2H, m).

(7) 2-[4-methoxy-6-(4-phenylethynylphenyl)-1,3,5-triazin-2-yl]-3-trifluoromethylphenol

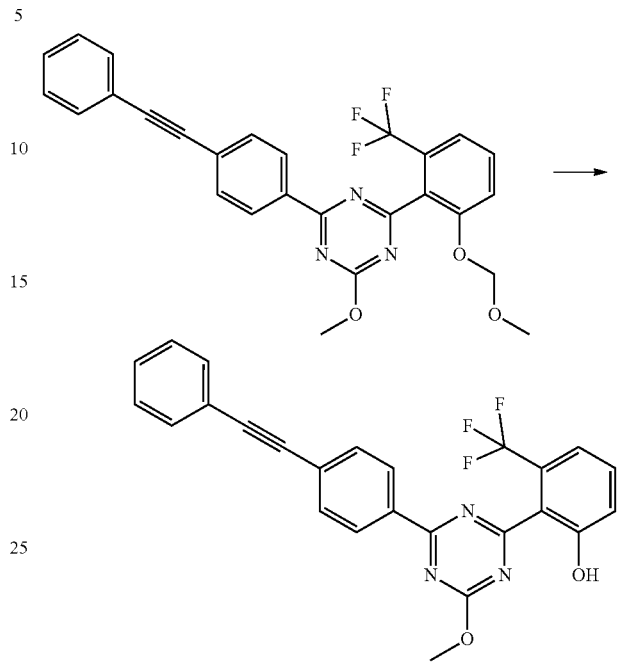

Under an argon atmosphere, to a solution of 2-methoxy-4-(2-methoxymethoxy-6-trifluoromethylphenyl)-6-(4-phenylethynylphenyl)-1,3,5-triazine (0.45 g, 0.92 mmol) obtained in the above-mentioned (6) in methanol (4.5 ml) were added 1,4-dioxane (4.5 ml) and methanesulfonic acid (0.030 ml, 0.46 mmol) at room temperature. The mixture was stirred at 70° C. for 5 hr, and triethylamine (0.13 ml, 0.92 mmol) was added to the reaction mixture at room temperature. To the reaction mixture was added water (45 ml), and the mixture was stirred for 30 min. The precipitated solid was collected by filtration and dried to give the title compound (0.38 g, yield 93%).

$^1$H-NMR (400 MHz, CDCl$_3$) δ: 4.23 (3H, s), 7.25-7.30 (1H, m), 7.36-7.40 (3H, m), 7.43-7.47 (1H, m), 7.50-7.60 (3H, m), 7.67-7.72 (2H, m), 8.48-8.52 (2H, m), 12.43 (1H, br s).

(8) 2-methoxy-4-[2-(6-methylpyridin-2-ylmethoxy)-6-trifluoromethylphenyl]-6-(4-phenylethynylphenyl)-1,3,5-triazine

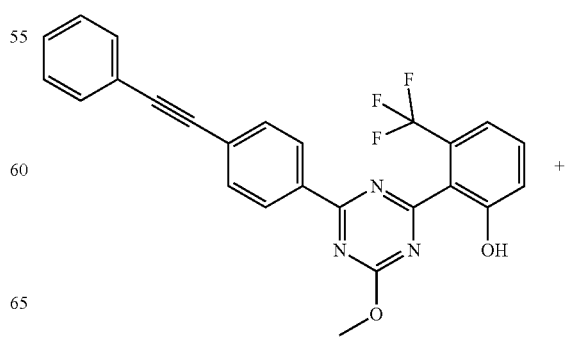

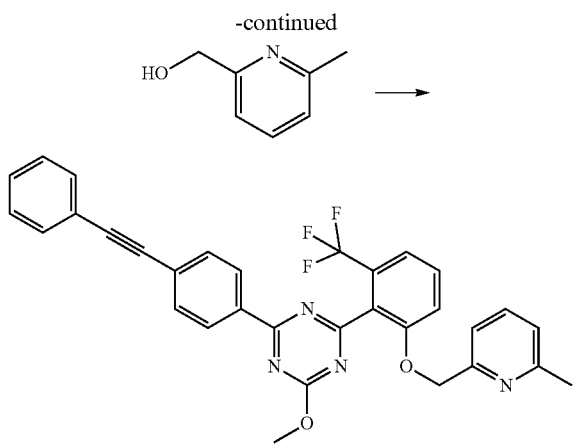
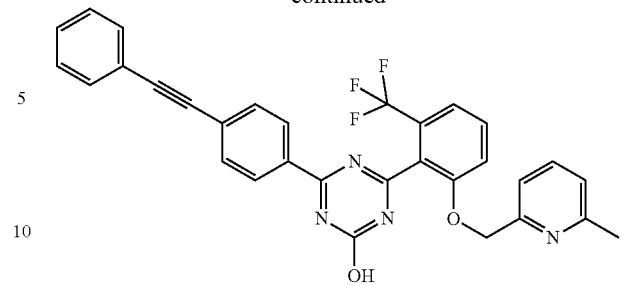

Under an argon atmosphere, to a solution of 2-[4-methoxy-6-(4-phenylethynylphenyl)-1,3,5-triazin-2-yl]-3-trifluoromethylphenol (0.24 g, 0.54 mmol) obtained in the above-mentioned (7), 6-methyl-2-pyridinemethanol (0.099 g, 0.80 mmol) and triphenylphosphine (0.21 g, 0.80 mmol) in tetrahydrofuran (6.0 ml) was added bis(2-methoxyethyl) azodicarboxylate (0.19 g, 0.80 mmol) in 3 portions under ice-cooling. The reaction mixture was stirred for 20 min and at room temperature for 20 hr. Thereafter, to the reaction mixture were added 6-methyl-2-pyridinemethanol (0.099 g, 0.80 mmol) and triphenylphosphine (0.21 g, 0.80 mmol), and bis(2-methoxyethyl) azodicarboxylate (0.19 g, 0.80 mmol) in 2 portions under ice-cooling. After stirring for 20 min, the reaction mixture was stirred for 10 min at room temperature. To the reaction mixture were added water and ethyl acetate, and the mixture was partitioned. The organic layer was washed with saturated aqueous sodium hydrogen carbonate, washed with saturated brine, dried over sodium sulfate, filtered to remove sodium sulfate, and concentrated under reduced pressure. The residue was purified by silica gel column chromatography (eluent: n-hexane/ethyl acetate=4/3) to give the title compound (0.28 g, yield 95%).

$^1$H-NMR (400 MHz, CDCl$_3$) δ: 2.51 (3H, s), 4.17 (3H, s), 5.21 (2H, s), 6.96-7.01 (1H, m), 7.02-7.07 (1H, m), 7.20-7.25 (1H, m), 7.33-7.42 (5H, m), 7.47-7.59 (3H, m), 7.62-7.68 (2H, m), 8.52-8.57 (2H, m).

(9) 4-[2-(6-methylpyridin-2-ylmethoxy)-6-trifluoromethylphenyl]-6-(4-phenylethynylphenyl)-1,3,5-triazin-2-ol

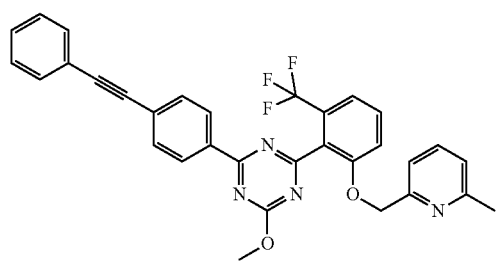

Under an argon atmosphere, to a suspension of 2-methoxy-4-[2-(6-methylpyridin-2-ylmethoxy)-6-trifluoromethylphenyl]-6-(4-phenylethynylphenyl)-1,3,5-triazine (0.28 g, 0.52 mmol) obtained in the above-mentioned (8) in methanol (4.6 ml) were added 4M aqueous sodium hydroxide solution (0.77 ml, 3.1 mmol) and tetrahydrofuran (0.46 ml) at room temperature. At 65° C., the reaction mixture was stirred for 3.5 hr. To the reaction mixture were added 10 wt % aqueous citric acid solution (3.2 ml) and water (16 ml) at room temperature, and the mixture was stirred for 30 min. The precipitated solid was collected by filtration, washed with water, and dried under reduced pressure to give the title compound (0.27 g, yield 95%).

$^1$H-NMR (400 MHz, DMSO-d$_6$) δ: 2.43 (3H, s), 5.31 (2H, s), 7.07-7.17 (2H, m), 7.43-7.49 (3H, m), 7.50-7.68 (5H, m), 7.69-7.82 (3H, m), 8.32-8.38 (2H, m), 13.63 (1H, br s)

(10) 4-[2-(6-methylpyridin-2-ylmethoxy)-6-trifluoromethylphenyl]-6-(4-phenylethynylphenyl)-1,3,5-triazin-2-ol hydrochloride (Example No. 2-98)

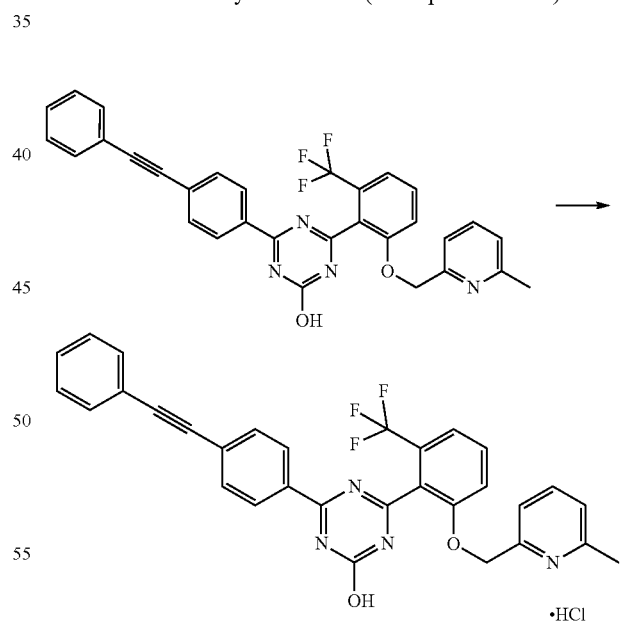

Under an argon atmosphere, to a solution of 4-[2-(6-methylpyridin-2-ylmethoxy)-6-trifluoromethylphenyl]-6-(4-phenylethynylphenyl)-1,3,5-triazin-2-ol (0.27 g, 0.49 mmol) obtained in the above-mentioned (9) in 1,4-dioxane (5.3 ml) was added 4M hydrogen chloride/1,4-dioxane solution (0.37 ml, 1.5 mmol) at room temperature. To the reaction mixture was added n-hexane (21 ml), and the mixture was stirred for 30 min. The precipitated solid was collected by filtration, washed with n-hexane, and dried under reduced pressure to give the title compound (0.26 g, yield 91%).

$^1$H-NMR (400 MHz, DMSO-$d_6$) δ: 2.48 (3H, s), 5.37 (2H, s), 7.23 (1H, d, J=7.3 Hz), 7.28 (1H, d, J=7.3 Hz), 7.48-7.45 (3H, m), 7.56 (1H, d, J=7.9 Hz), 7.64-7.59 (2H, m), 7.67 (1H, d, J=8.6 Hz), 7.82-7.72 (4H, m), 8.35 (2H, dd, J=6.8, 2.0 Hz).

Production Example 6

Synthesis of 2-[4-chloro-2-methyl-5-(4,4,5,5-tetramethyl[1,3,2]dioxaborolan-2-yl)benzyloxy]tetrahydropyran (1) 4-chloro-5-iodo-2-methylbenzoic acid

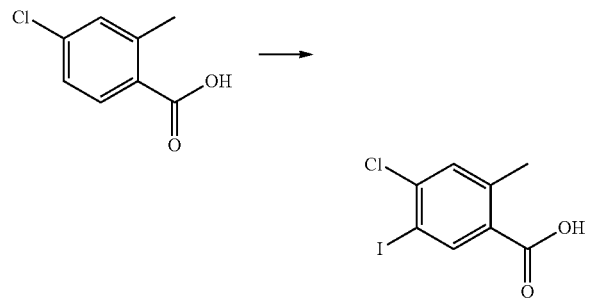

Under an argon atmosphere, to 4-chloro-2-methylbenzoic acid (1.9 g, 11 mmol) were added concentrated sulfuric acid (16 ml) and N-iodosuccinimide (2.7 g, 12 mmol) under ice-cooling, and the mixture was stirred at room temperature for 4 hr. The reaction mixture was carefully poured into ice water and the mixture was stirred. The precipitated solid was collected by filtration, washed with water, and dried under reduced pressure to give the title compound (3.3 g, yield 99%).

$^1$H-NMR (CDCl$_3$) δ: 2.58 (3H, s), 7.38 (1H, br s), 8.50 (1H, s).

(2) (4-chloro-5-iodo-2-methylphenyl)methanol

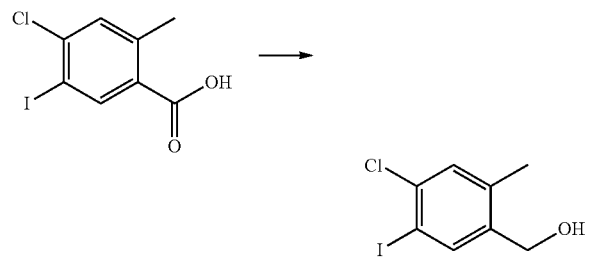

Under an argon atmosphere, to a solution of 4-chloro-5-iodo-2-methylbenzoic acid (2.4 g, 8.1 mmol) in tetrahydrofuran (12 ml) were added triethylamine (1.2 ml, 8.9 mmol) and isobutyl chloroformate (1.2 ml, 8.9 mmol) under ice-cooling, and the mixture was stirred for 30 min. At room temperature, the insoluble material was removed by filtration, and washed with tetrahydrofuran (36 ml). The filtrate was added dropwise to a solution of prepared sodium borohydride (0.92 g, 24 mmol) in water (4.5 ml) over 10 min under ice-cooling. After stirring at room temperature for 2 hr, to the reaction mixture was added sodium borohydride (0.30 g, 8.1 mmol), and the mixture was stirred for 1 hr. To the reaction mixture were added saturated aqueous ammonium chloride solution and ethyl acetate, and the mixture was partitioned. The organic layer was washed with saturated aqueous sodium hydrogen carbonate, washed with saturated brine, dried over sodium sulfate, filtered to remove sodium sulfate, and concentrated under reduced pressure. The residue was purified by silica gel column chromatography (eluent: chloroform/ethyl acetate=100/0-95/5) to give the title compound (2.0 g, yield 88%).

$^1$H-NMR (400 MHz, CDCl$_3$) δ: 1.60 (1H, t, J=5.7 Hz), 2.26 (3H, s), 4.63 (2H, d, J=5.6 Hz), 7.25-7.26 (1H, m), 7.84 (1H, br s).

(3) 2-(4-chloro-5-iodo-2-methylbenzyloxy)tetrahydropyran

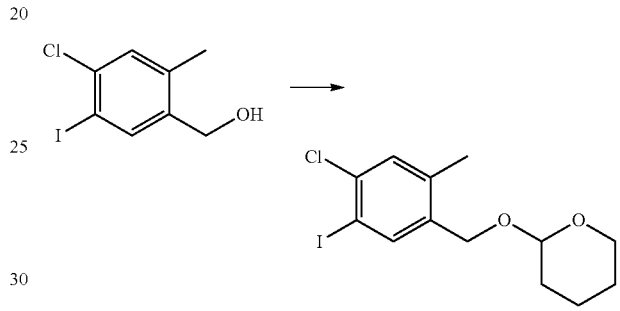

Under an argon atmosphere, to a solution of (4-chloro-5-iodo-2-methylphenyl)methanol (2.0 g, 7.1 mmol) obtained in the above-mentioned (1) in chloroform (20 ml) were added pyridinium p-toluenesulfonate (0.27 mg, 1.1 mmol) and 3,4-dihydro-2H-pyran (0.97 ml, 11 mmol) at room temperature, and the mixture was stirred for 16 hr. The reaction mixture was concentrated under reduced pressure, and the residue was purified by silica gel column chromatography (eluent: n-hexane/ethyl acetate=9/1) to give the title compound (2.6 g, yield 99%).

$^1$H-NMR (400 MHz, CDCl$_3$) δ: 1.51-1.92 (6H, m), 2.26 (3H, s), 3.52-3.59 (1H, m), 3.85-3.91 (1H, m), 4.38 (1H, d, J=12.6 Hz), 4.67-4.72 (2H, m), 7.25 (1H, br s), 7.82 (1H, br s).

(4) 2-[4-chloro-2-methyl-5-(4,4,5,5-tetramethyl[1,3,2]dioxaborolan-2-yl)benzyloxy]tetrahydropyran

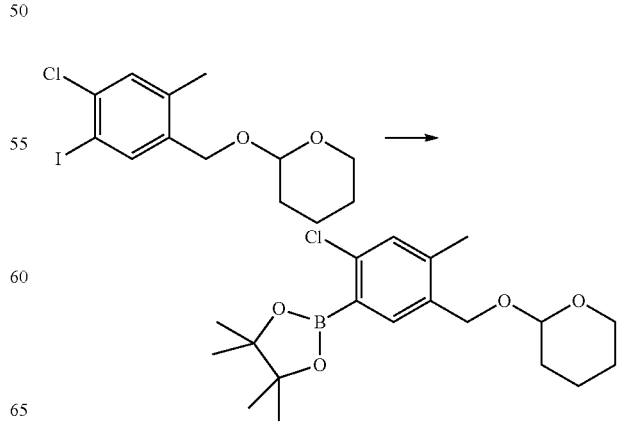

Under an argon atmosphere, to a solution of 2-(4-chloro-5-iodo-2-methylbenzyloxy)tetrahydropyran (2.3 g, 6.2 mmol) obtained in the above-mentioned (2) in 1,4-dioxane (23 ml) were is added biphenyl-2-yl-dicyclohexylphosphine (0.43 g, 1.2 mmol), palladium(II) acetate (0.070 g, 0.31 mmol), triethylamine (3.4 ml, 25 mmol) and 4,4,5,5-tetramethyl-1,3,2-dioxaborolane (2.7 ml, 18 mmol) at room temperature, and the mixture was stirred at 80° C. for 5 hr. Under ice-cooling, to the reaction mixture was added dropwise water, and ethyl acetate was added. After partitioning, the organic layer was washed with saturated aqueous sodium hydrogen carbonate, washed with saturated brine, dried over sodium sulfate, filtered to remove sodium sulfate, and concentrated under reduced pressure. The residue was purified by silica gel column chromatography (eluent: n-hexane/ethyl acetate=98/2-80/20) to give the title compound (1.3 g, yield 60%).

$^1$H-NMR (400 MHz, CDCl$_3$) δ: 1.36 (12H, s), 1.47-1.90 (6H, m), 2.34 (3H, s), 3.52-3.59 (1H, m), 3.88-3.95 (1H, m), 4.42 (1H, d, J=11.6 Hz), 4.67 (1H, t, J=3.5 Hz), 4.74 (1H, d, J=11.6 Hz), 7.18 (1H, br s), 7.63 (1H, br s)

Production Example 7

Synthesis of tert-butyl-(4-chloro-3-iodo-2-methylbenzyloxy)dimethylsilane (1) 3-(tert-butyl-dimethylsilanyloxymethyl)-6-chloro-2-methylphenylamine

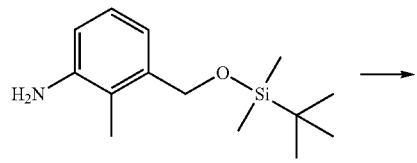

Under an argon atmosphere, to a solution of 3-(tert-butyldimethylsilanyloxymethyl)-2-methyl-phenylamine (0.91 g, 3.6 mmol) in tetrahydrofuran (5.0 ml) was added N-chlorosuccinimide (0.48 g, 3.6 mmol) at room temperature. After stirring for 22 hr, to the reaction mixture was added n-hexane (10 ml), and the insoluble material was filtered off. The filtrate was concentrated, and purified by silica gel column chromatography (eluent: n-hexane/ethyl acetate=20/1) to give the title compound (0.18 g, yield 17%).

$^1$H-NMR (400 MHz, CDCl$_3$) δ: 0.08 (6H, s), 0.92 (9H, s), 2.11 (3H, s), 4.01 (2H, br s), 4.60-4.69 (2H, m), 6.77 (1H, d, J=8.4 Hz), 7.11 (1H, d, J=8.4 Hz).

(2) tert-butyl-(4-chloro-3-iodo-2-methylbenzyloxy)dimethylsilane

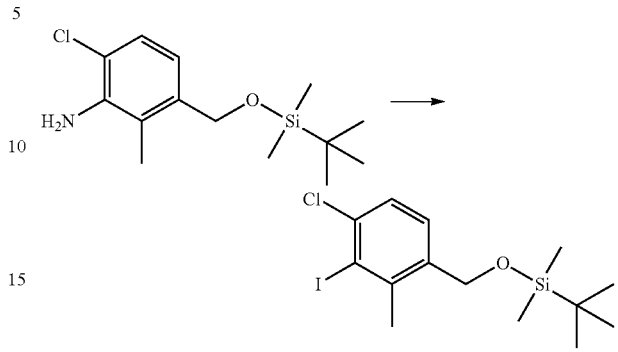

Under an argon atmosphere, to a solution of 3-(tert-butyl-dimethylsilanyloxymethyl)-6-chloro-2-methylphenylamine (0.18 g, 0.63 mmol) obtained in the above-mentioned (1) in acetonitrile (2.0 ml) were added iodine (0.19 g, 0.76 mmol) and tert-butyl nitrite (0.11 ml, 0.94 mmol) at room temperature, and the mixture was stirred at 65° C. for 30 min. At room temperature, to the reaction mixture were added water and ethyl acetate. After partitioning, the organic layer was washed with saturated aqueous sodium hydrogen carbonate, 10 wt % aqueous sodium thiosulfate solution, washed with saturated brine, dried over sodium sulfate, filtered to remove sodium sulfate, and concentrated under reduced pressure. The residue was purified by silica gel column chromatography (eluent: n-hexane/ethyl acetate=40/1) to give the title compound (0.099 g, yield 40%).

$^1$H-NMR (400 MHz, CDCl$_3$) δ: 0.10 (6H, s), 0.93 (9H, s), 2.47 (3H, s), 4.68 (2H, s), 7.30 (1H, d, J=8.4 Hz), 7.35 (1H, d, J=8.1 Hz).

Production Example 8

Synthesis of 2-(6-chloro-2-methoxymethoxy-3-methylphenyl)-4,4,5,5-tetramethyl[1,3,2]dioxaborolane (1) 4-chloro-2-methoxymethoxy-1-methylbenzene

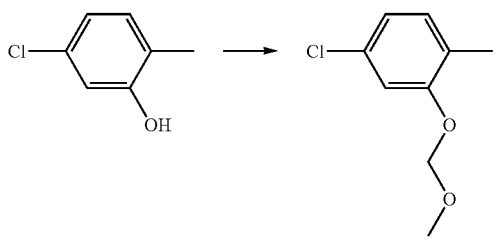

Under an argon atmosphere, to a solution of 5-chloro-2-methylphenol (1.0 g, 7.0 mmol) in N,N-dimethylformamide (20 ml) was added sodium hydride (0.34 g, 60 wt % oil dispersion) under ice-cooling. After stirring for 15 min, the mixture was stirred at room temperature for 30 min. Under ice-cooling, chloromethyl methyl ether (0.64 ml, 8.4 mmol) was added, and the mixture was stirred for 30 min. To the reaction mixture were added water and diethyl ether, and the mixture was partitioned at room temperature. The organic layer was washed with water, washed with saturated brine, dried over sodium sulfate, filtered to remove sodium sulfate, and concentrated under reduced pressure. The residue was purified by silica gel column chromatography (eluent: n-hexane/diethyl ether=25/1) to give the title compound (1.3 g, yield 96%).

¹H-NMR (400 MHz, CDCl₃) δ: 2.20 (3H, s), 3.48 (3H, s), 5.18 (2H, s), 6.89 (1H, dd, J=7.9, 2.0 Hz), 7.03-7.07 (2H, m).

(2) 2-(6-chloro-2-methoxymethoxy-3-methylphenyl)-4,4,5,5-tetramethyl[1,3,2]dioxaborolane

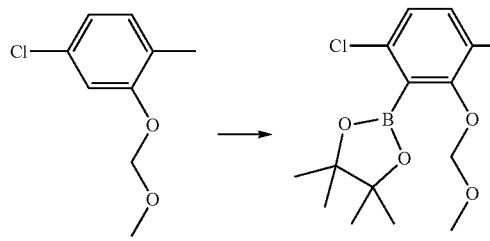

Under an argon atmosphere, to a solution of 4-chloro-2-methoxymethoxy-1-methylbenzene (0.75 g, 4.0 mmol) obtained in the above-mentioned (1) in tetrahydrofuran (20 ml) was added dropwise n-butyllithium (1.6M n-hexane solution, 2.5 ml, 4.0 mmol) at −78° C. over 5 min. After stirring for 30 min, 2-isopropoxy-4,4,5,5-tetramethyl-1,3,2-dioxaborolane (0.81 ml, 4.0 mmol) was added. After stirring for 2 hr, the stirring was discontinued, and the mixture was warmed to room temperature. After 13 hr, to the reaction mixture were added saturated aqueous ammonium chloride solution and ethyl acetate, and the mixture was partitioned. Thereafter, the organic layer was washed with water, washed with saturated brine, dried over magnesium sulfate, filtered to remove magnesium sulfate, and concentrated under reduced pressure. The residue was purified by silica gel column chromatography (eluent: n-hexane/ethyl acetate=12/1) to give the title compound (0.20 g, yield 15%).

¹H-NMR (400 MHz, CDCl₃) δ: 1.40 (12H, s), 2.27 (3H, s), 3.55 (3H, s), 5.03 (2H, s), 7.01 (1H, d, J=8.2 Hz), 7.07-7.11 (1H, m).

Production Example 9

Synthesis of N-{4-chloro-3-[4-(4-isobutylphenyl)-6-hydroxy-1,3,5-triazin-2-yl]benzyl}-2,2-dimethylpropionamide (Example No. 1-51)

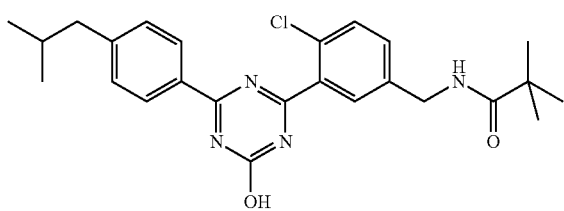 [SMILES: CC(C)Cc1ccc(-c2nc(O)nc(-c3cc(CNC(=O)C(C)(C)C)ccc3Cl)n2)cc1]

(1) 2-chloro-4-(4-isobutylphenyl)-6-methoxy-1,3,5-triazine

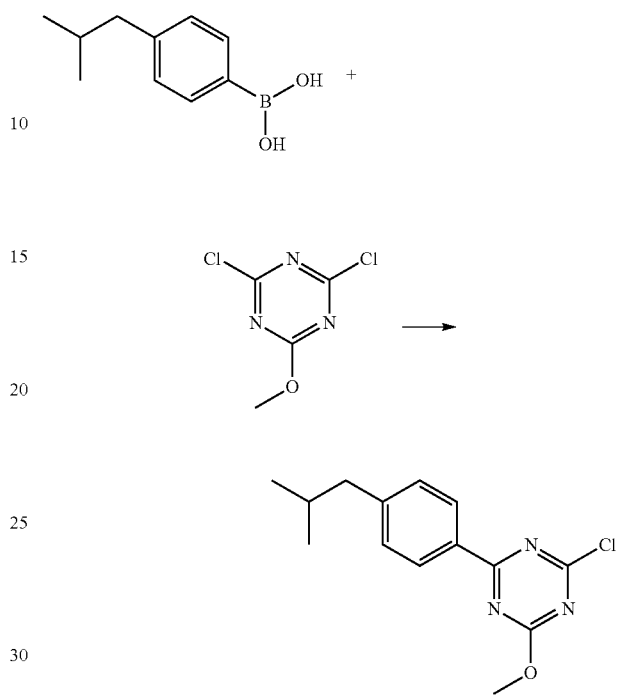

Under an argon atmosphere, a suspension of 4-(2-methylpropyl)phenylboronic acid (35 g, 200 mmol), 2,4-dichloro-6-methoxy-1,3,5-triazine (46 g, 260 mmol), tetrakis(triphenylphosphine)palladium(0) (2.3 g, 2.0 mmol) and sodium carbonate (63 g, 590 mmol) in toluene (280 ml) and distilled water (280 ml) was stirred at 70° C. for 3.5 hr. At room temperature, to the reaction mixture were added water, ethyl acetate, and n-hexane, and the mixture was partitioned. The organic layer was washed with saturated brine, dried over sodium sulfate, filtered to remove sodium sulfate, and concentrated under reduced pressure to give the title compound (60 g) as a crude product.

(2) {4-chloro-3-[4-(4-isobutylphenyl)-6-methoxy-1,3,5-triazin-2-yl]phenyl}methanol

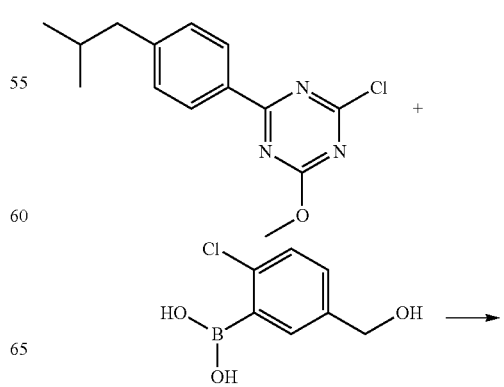

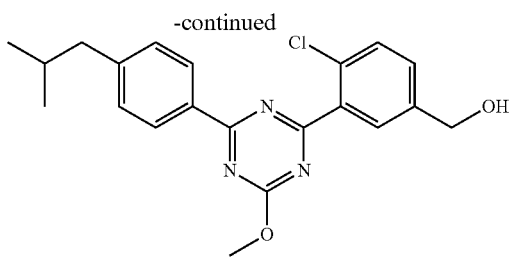

Under an argon atmosphere, a suspension of a crude product (60 g) of 2-chloro-4-(4-isobutylphenyl)-6-methoxy-1,3,5-triazine obtained in the above-mentioned (1), 2-chloro-5-hydroxymethylphenylboronic acid (44 g, 240 mmol), [1,1'-bis(diphenylphosphino)ferrocene]palladium (II)dichloride dichloromethane adduct (3.2 g, 3.9 mmol) and cesium fluoride (90 g, 590 mmol) in acetonitrile (440 ml) and distilled water (130 ml) was stirred at 67° C. for 2 hr. At room temperature, to the reaction mixture were added water and ethyl acetate, and the mixture was partitioned. The organic layer was washed with water, and the organic layer was washed with saturated brine, dried over sodium sulfate, filtered to remove sodium sulfate, and concentrated under reduced pressure. The residue was purified by silica gel column chromatography (eluent: n-hexane/ethyl acetate=7/3-6/4) to give the title compound (57 g).

$^1$H-NMR (CDCl$_3$) δ: 0.93 (6H, d, J=6.6 Hz), 1.77 (1H, t, J=6.1 Hz), 1.90-1.97 (1H, m), 2.57 (2H, d, J=7.3 Hz), 4.21 (3H, s), 4.77 (2H, d, J=6.1 Hz), 7.29 (2H, d, J=8.3 Hz), 7.47 (1H, dd, J=8.3, 2.1 Hz), 7.54 (1H, d, J=8.3 Hz), 8.01 (1H, d, J=2.1 Hz), 8.51 (2H, d, J=8.3 Hz).

(3) tert-butyl N-{4-chloro-3-[4-(4-isobutylphenyl)-6-methoxy-1,3,5-triazin-2-yl]benzyl}-N-(tert-butoxycarbonyl)carbamate

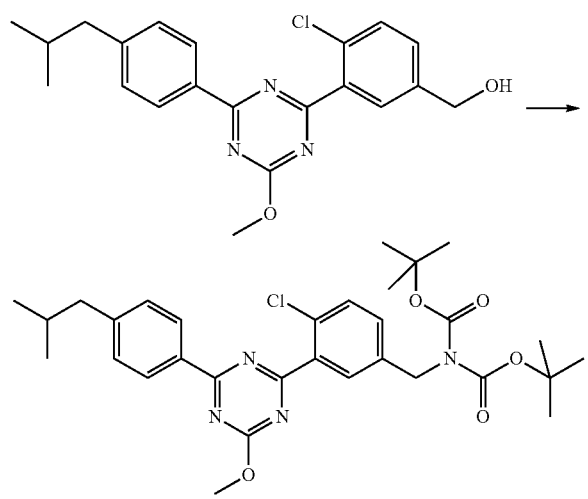

Under an argon atmosphere, to a solution of {4-chloro-3-[4-(4-isobutylphenyl)-6-methoxy-1,3,5-triazin-2-yl]phenyl}methanol (0.25 g, 0.64 mmol) obtained in the above-mentioned (2) and triphenylphosphine (0.25 g, 0.96 mmol) in chloroform (2.4 ml) was added carbon tetrabromide (0.32 g, 0.96 mmol) under ice-cooling. The reaction mixture was stirred at room temperature for 10 min. The reaction mixture was subject to silica gel column chromatography (eluent: n-hexane/ethyl acetate=30/1-10/1), and concentrated under reduced pressure. A solution of the residue in N,N-dimethylformamide (2.0 ml) was added to a solution of di-tert-butyl iminodicarboxylate (0.140 g, 0.64 mmol) and sodium hydride (0.026 g, 60 wt % oil dispersion) in N,N-dimethylformamide (1.0 ml) under ice-cooling, and the mixture was stirred at room temperature for 15 min. The reaction mixture were added water and ethyl acetate, and the mixture was partitioned. The organic layer was washed with water, and the organic layer was washed with saturated brine, dried over sodium sulfate, filtered to remove sodium sulfate, and concentrated under reduced pressure. The residue was purified by silica gel column chromatography (eluent: n-hexane/ethyl acetate=6/1) to give the title compound (0.27 g, yield 72%).

$^1$H-NMR (CDCl$_3$) δ: 0.93 (6H, d, J=6.6 Hz), 1.47 (18H, s), 1.88-1.98 (1H, m), 2.57 (2H, d, J=7.3 Hz), 4.19 (3H, s), 4.83 (2H, s), 7.28 (2H, d, J=8.4 Hz), 7.39 (1H, dd, J=8.4, 2.3 Hz), 7.48 (1H, d, J=8.4 Hz), 8.00 (1H, d, J=2.3 Hz), 8.50 (2H, dt, J=8.4, 1.8 Hz).

(4) 4-chloro-3-[4-(4-isobutylphenyl)-6-methoxy-1,3,5-triazin-2-yl]benzylamine hydrochloride

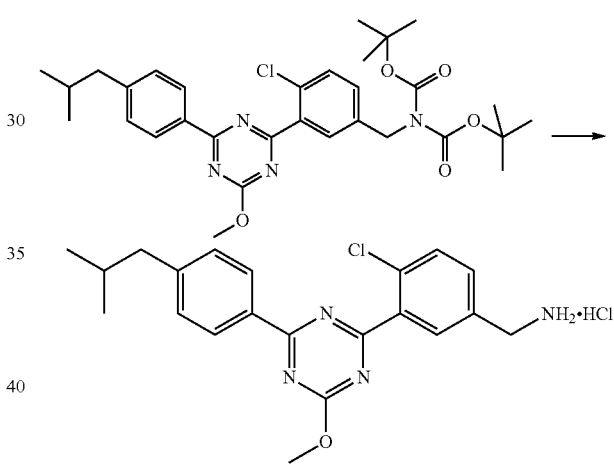

Under an argon atmosphere, to tert-butyl N-{4-chloro-3-[4-(4-isobutylphenyl)-6-methoxy-1,3,5-triazin-2-yl]benzyl}-N-(tert-butoxycarbonyl)carbamate (0.27 g, 0.46 mmol) obtained in the above-mentioned (3) was added 4M hydrogen chloride/1,4-dioxane solution (2.0 ml) at room temperature, and the mixture was stirred for 30 min. The solid was collected by filtration from the suspension, and dried under reduced pressure to give the title compound as a crude product (0.16 g).

(5) N-{4-chloro-3-[4-(4-isobutylphenyl)-6-methoxy-1,3,5-triazin-2-yl]benzyl}-2,2-dimethylpropionamide

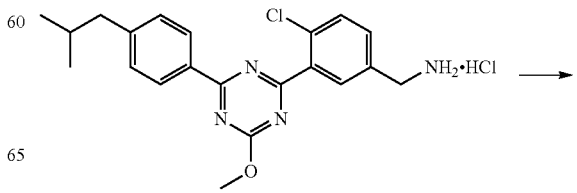

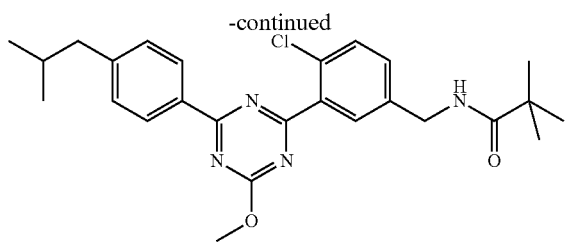

Under an argon atmosphere, to a solution of a crude product (0.035 g) of 4-chloro-3-[4-(4-isobutylphenyl)-6-methoxy-1,3,5-triazin-2-yl]benzylamine hydrochloride obtained in the above-mentioned (4), HOBt·H₂O (0.019 g, 0.12 mmol) and WSC·HCl (0.024 g, 0.13 mmol) in N,N-dimethylformamide (1.0 ml) were added 2,2-dimethylpropionic acid (0.014 ml, 0.12 mmol) and triethylamine (0.035 ml, 0.25 mmol) at room temperature, and the mixture was stirred for 3 hr. To the reaction mixture were added saturated aqueous sodium hydrogen carbonate and ethyl acetate, and the mixture was partitioned. The organic layer was washed with saturated aqueous sodium hydrogen carbonate, washed with saturated brine, dried over sodium sulfate, filtered to remove sodium sulfate, and concentrated under reduced pressure. The residue was purified by silica gel column chromatography (eluent: n-hexane/ethyl acetate=3/2) to give the title compound (0.030 g).

¹H-NMR (CDCl₃) δ: 0.93 (6H, d, J=6.6 Hz), 1.24 (9H, s), 1.88-1.99 (1H, m), 2.57 (2H, d, J=7.1 Hz), 4.20 (3H, s), 4.50 (2H, d, J=6.0 Hz), 5.98 (1H, br s), 7.29 (2H, d, J=8.3 Hz), 7.36 (1H, dd, J=8.2, 2.3 Hz), 7.51 (1H, d, J=8.2 Hz), 7.92 (1H, d, J=2.3 Hz), 8.50 (2H, d, J=8.3 Hz).

(6) N-{4-chloro-3-[4-hydroxy-6-(4-isobutylphenyl)-1,3,5-triazin-2-yl]benzyl}-2,2-dimethylpropionamide (Example No. 1-51)

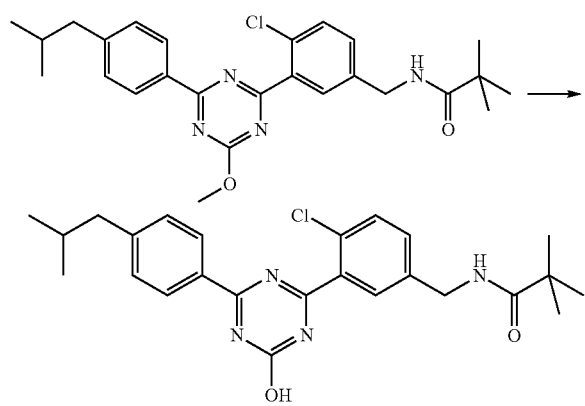

Under an argon atmosphere, to a solution of N-{4-chloro-3-[4-(4-isobutylphenyl)-6-methoxy-1,3,5-triazin-2-yl]benzyl}-2,2-dimethylpropionamide (0.030 g, 0.064 mmol) obtained in the above-mentioned (5) in methanol (10 ml) was added 4M aqueous sodium hydroxide solution (0.096 ml) at room temperature, and the mixture was stirred at room temperature for 16 hr. To the reaction mixture were added 10% aqueous citric acid solution (0.38 ml) and water (2.3 ml) at room temperature, and the mixture was stirred. The precipitated solid was collected by filtration, washed with water, and dried under reduced pressure to give the title compound (0.026 g, yield 90%). A suspension of the title compound (0.030 g) in DME (0.60 ml) was stirred at room temperature, and the solid was collected by filtration and dried to give the title compound as crystals (0.026 g).

Production Example 10

Synthesis of N-{4-chloro-3-[4-(3-fluoro-4-methylphenyl)-6-hydroxy-1,3,5-triazin-2-yl]benzyl}-3,3,3-trifluoro-2,2-dimethylpropionamide (Example No. 1-81)

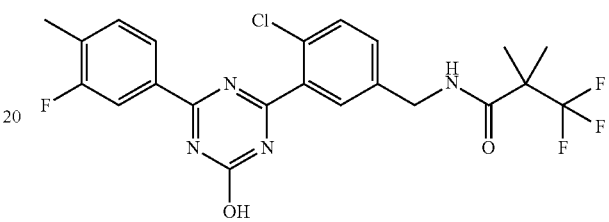

(1) 2-chloro-4-(3-fluoro-4-methylphenyl)-6-methoxy-1,3,5-triazine

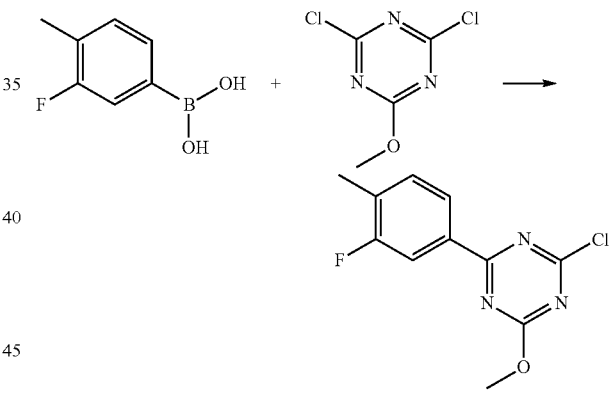

Under an argon atmosphere, to a suspension of 3-fluoro-4-methylphenylboronic acid (0.43 g, 2.8 mmol), 2,4-dichloro-6-methoxy-1,3,5-triazine (1.0 g, 5.6 mmol) and tetrakis(triphenylphosphine)palladium(0) (0.16 g, 0.14 mmol) in toluene (8 ml) was added 2M aqueous tripotassium phosphate solution (4.0 ml) at room temperature, and the mixture was stirred at 100° C. for 3 hr. At room temperature, to the reaction mixture were added water and ethyl acetate, and the mixture was partitioned. The organic layer was washed with water, partitioned, washed with saturated brine, dried over magnesium sulfate, filtered to remove magnesium sulfate, and concentrated under reduced pressure. The residue was purified by silica gel column chromatography (eluent: n-hexane/chloroform=2/3-1/2) to give the title compound (0.58 g, yield 81%).

¹H-NMR (CDCl₃) δ: 2.37 (3H, d, J=2.1 Hz), 4.17 (3H, s), 7.32 (1H, t, J=7.9 Hz), 8.12 (1H, dd, J=10.7, 1.7 Hz), 8.19 (1H, dd, J=7.9, 1.7 Hz).

(2) {4-chloro-3-[4-(3-fluoro-4-methylphenyl)-6-methoxy-1,3,5-triazin-2-yl]phenyl}methanol

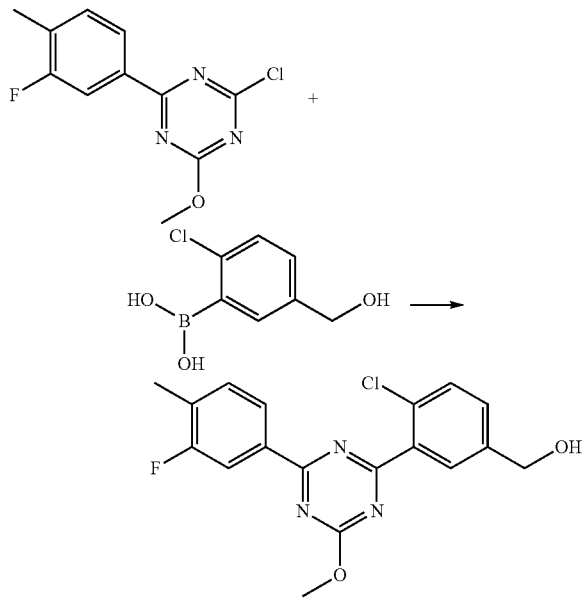

Under an argon atmosphere, to a solution of 2-chloro-4-(3-fluoro-4-methylphenyl)-6-methoxy-1,3,5-triazine (0.58 g, 2.3 mmol) obtained in the above-mentioned (1), 2-chloro-5-hydroxymethylphenylboronic acid (0.51 g, 2.7 mmol) and [1,1'-bis(diphenylphosphino)ferrocene]palladium(II)dichloride dichloromethane adduct (0.18 g, 0.23 mmol) in 1,4-dioxane (9.0 ml) was added 2M aqueous sodium carbonate solution (4.5 ml), and the mixture was stirred at 100° C. for 2 hr. At room temperature, to the reaction mixture were added water and ethyl acetate, and the mixture was partitioned. The organic layer was washed with saturated brine, dried over magnesium sulfate, filtered to remove magnesium sulfate, and concentrated under reduced pressure. The residue was purified by silica gel column chromatography (eluent: n-hexane/ethyl acetate=4/3) to give the title compound (0.44 g, yield 53%).

$^1$H-NMR (CDCl$_3$) δ: 1.76 (1H, t, J=5.8 Hz), 2.37 (3H, d, J=1.9 Hz), 4.21 (3H, s), 4.78 (2H, d, J=5.8 Hz), 7.33 (1H, t, J=7.9 Hz), 7.47 (1H, dd, J=8.1, 2.2 Hz), 7.54 (1H, d, J=8.1 Hz), 8.02 (1H, d, J=2.2 Hz), 8.23 (1H, dd, J=10.7, 1.6 Hz), 8.29 (1H, dd, J=7.9, 1.6 Hz).

(3) tert-butyl N-{4-chloro-3-[4-(3-fluoro-4-methylphenyl)-6-methoxy-1,3,5-triazin-2-yl]benzyl}-N-(tert-butoxycarbonyl)carbamate

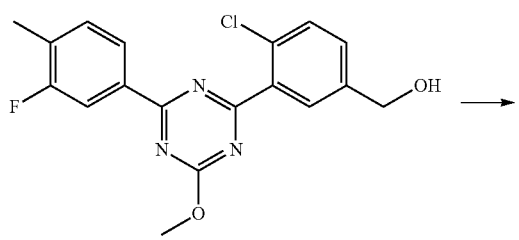

-continued

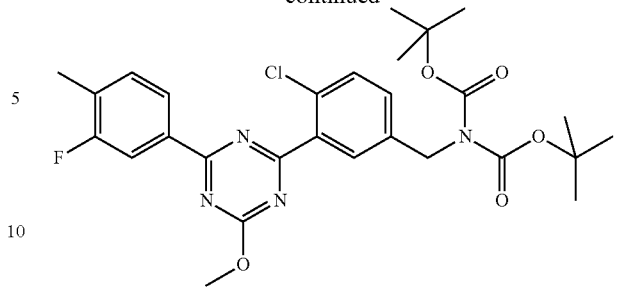

Under an argon atmosphere, to a solution of {4-chloro-3-[4-(3-fluoro-4-methylphenyl)-6-methoxy-1,3,5-triazin-2-yl]phenyl}methanol (0.44 g, 1.2 mmol) obtained in the above-mentioned (2) in tetrahydrofuran (13 ml) were added triethylamine (0.22 ml, 1.6 mmol) and methanesulfonyl chloride (0.10 ml, 1.3 mmol) under ice-cooling, and the mixture was stirred for 0.5 hr. The reaction mixture was added to a solution of di-tert-butyl iminodicarboxylate (0.32 g, 1.5 mmol) and cesium carbonate (1.2 g, 3.6 mmol) in N,N-dimethylformamide (3.0 ml) at room temperature, and the mixture was stirred for 1 hr. To the reaction mixture were added water and ethyl acetate, and the mixture was partitioned. The organic layer was washed with saturated brine, dried over magnesium sulfate, filtered to remove magnesium sulfate, and concentrated under reduced pressure. The residue was purified by silica gel column chromatography (eluent: n-hexane/ethyl acetate=6/1) to give the title compound (0.64 g, yield 94%).

$^1$H-NMR (CDCl$_3$) δ: 1.48 (18H, s), 2.37 (3H, d, J=1.6 Hz), 4.19 (3H, s), 4.83 (2H, s), 7.31 (1H, t, J=7.9 Hz), 7.40 (1H, dd, J=8.4, 2.3 Hz), 7.49 (1H, d, J=8.4 Hz), 8.00 (1H, d, J=2.3 Hz), 8.22 (1H, dd, J=10.7, 1.6 Hz), 8.28 (1H, dd, J=7.9, 1.6 Hz).

(4) 4-chloro-3-[4-(3-fluoro-4-methylphenyl)-6-methoxy-1,3,5-triazin-2-yl]benzylamine hydrochloride

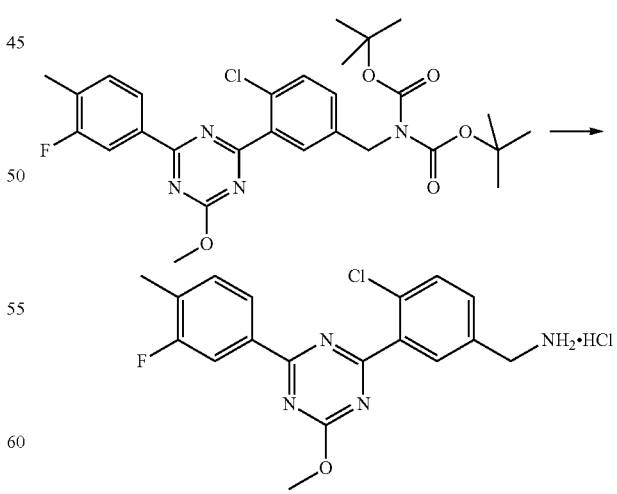

Under an argon atmosphere, to a solution of tert-butyl N-{4-chloro-3-[4-(3-fluoro-4-methylphenyl)-6-methoxy-1,3,5-triazin-2-yl]benzyl}-N-(tert-butoxycarbonyl)carbamate (0.64 g, 1.1 mmol) obtained in the above-mentioned (3) in 1,4-dioxane is (2.0 ml) was added 4M hydrogen chloride/1,4-dioxane solution (6.0 ml) at room temperature, and the mixture was stirred for 2 hr. To the reaction mixture was added n-hexane (32 ml), and the mixture was stirred for 45 min. The solid was collected by filtration from the suspension, and dried under reduced pressure to give the title compound (0.45 g, yield 99%).

$^1$H-NMR (DMSO-D$_6$) δ: 2.36 (3H, d, J=1.4 Hz), 4.13-4.19 (2H, m), 4.17 (3H, s), 7.55 (1H, t, J=8.0 Hz), 7.71 (1H, dd, J=8.1, 2.1 Hz), 7.75 (1H, d, J=8.1 Hz), 8.16-8.20 (2H, m), 8.27 (1H, dd, J=7.9, 1.6 Hz), 8.38 (3H, br s).

(5) N-{4-chloro-3-[4-(3-fluoro-4-methylphenyl)-6-methoxy-1,3,5-triazin-2-yl]benzyl}-3,3,3-trifluoro-2,2-dimethylpropionamide

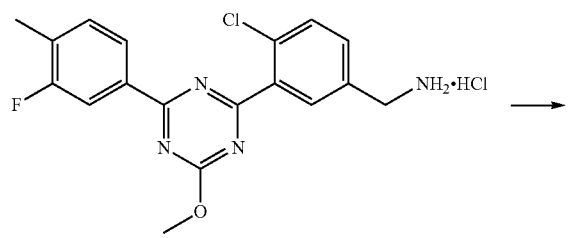

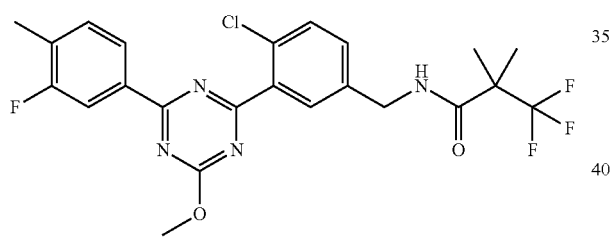

Under an argon atmosphere, to a solution of 4-chloro-3-[4-(3-fluoro-4-methylphenyl)-6-methoxy-1,3,5-triazin-2-yl]benzylamine hydrochloride (0.070 g, 0.18 mmol) obtained in the above-mentioned (4), HOBt·H$_2$O (0.041 g, 0.27 mmol) and 3,3,3-trifluoro-2,2-dimethylpropionic acid (0.042 g, 0.27 mmol) in N,N-dimethylformamide (1.0 ml) were added WSC·HCl (0.051 g, 0.27 mmol) and triethylamine (0.037 ml, 0.027 mmol) at room temperature, and the mixture was stirred for 1.5 hr. To the reaction mixture were added water and ethyl acetate, and the mixture was partitioned. The organic layer was washed with saturated aqueous sodium hydrogen carbonate, washed with saturated brine, dried over magnesium sulfate, filtered to remove magnesium sulfate, and concentrated under reduced pressure. The residue was purified by silica gel column chromatography (eluent: n-hexane/ethyl acetate=2/1) to give the title compound (0.080 g, yield 90%).

$^1$H-NMR (CDCl$_3$) δ: 1.45 (6H, s), 2.37 (3H, d, J=1.9 Hz), 4.20 (3H, s), 4.55 (2H, d, J=5.8 Hz), 6.23 (1H, br s), 7.30-7.37 (2H, m), 7.52 (1H, d, J=8.4 Hz), 7.93 (1H, d, J=2.3 Hz), 8.22 (1H, dd, J=10.7, 1.6 Hz), 8.28 (1H, dd, J=7.9, 1.6 Hz).

(6) N-{4-chloro-3-[4-(3-fluoro-4-methyl-phenyl)-6-hydroxy-1,3,5-triazin-2-yl]benzyl}-3,3,3-trifluoro-2,2-dimethylpropionamide (Example No. 1-81)

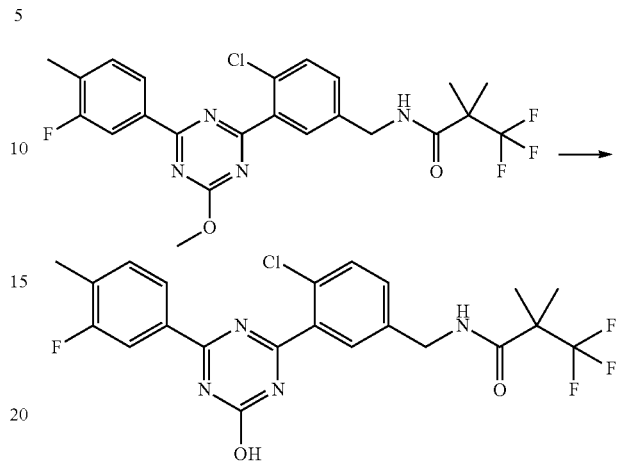

Under an argon atmosphere, to a solution of N-{4-chloro-3-[4-(3-fluoro-4-methylphenyl)-6-methoxy-1,3,5-triazin-2-yl]benzyl}-3,3,3-trifluoro-2,2-dimethylpropionamide (0.077 g, 0.16 mmol) obtained in the above-mentioned (5) in methanol (1.4 ml) was added 4M aqueous sodium hydroxide solution (0.23 ml) at room temperature, and the mixture was stirred at 60° C. for 2 hr. To the reaction mixture were added 10% aqueous citric acid solution (0.070 ml) and water at room temperature, and the mixture was stirred. The precipitated solid was collected by filtration, washed with water, and dried under reduced pressure is to give the title compound (0.070 g, yield 92%).

Production Example 11

Synthesis of N-{4-chloro-3-[4-hydroxy-6-(4-isopropylphenyl)-1,3,5-triazin-2-yl]benzyl}-3,3,3-trifluoro-2,2-dimethylpropionamide (Example No. 1-98)

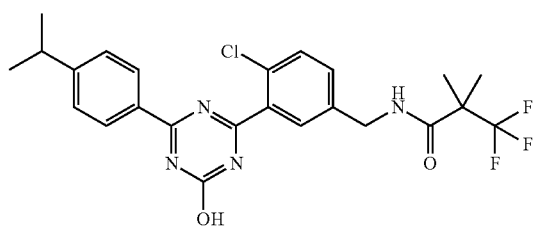 [SMILES: CC(C)c1ccc(-c2nc(O)nc(-c3cc(CNC(=O)C(C)(C)C(F)(F)F)ccc3Cl)n2)cc1]

(1) 2-chloro-4-(4-isopropylphenyl)-6-methoxy-1,3,5-triazine

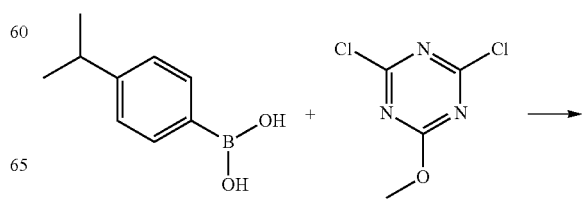

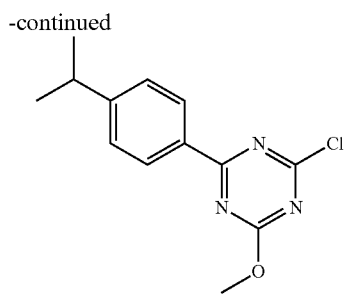

Under an argon atmosphere, to a suspension of 4-isopropylphenylboronic acid (0.30 g, 1.7 mmol), 2,4-dichloro-6-methoxy-1,3,5-triazine (0.23 g, 1.4 mmol) and [1,1'-bis(diphenylphosphino)ferrocene]palladium(II)dichloride dichloromethane adduct (0.11 g, 0.14 mmol) in 1,4-dioxane (4.0 ml) was added 2M aqueous sodium carbonate solution (2.0 ml) at room temperature, and the mixture was stirred at 100° C. for 1.5 hr. At room temperature, to the reaction mixture were added water and ethyl acetate, and the mixture was partitioned. The organic layer was washed with saturated brine, dried over sodium sulfate, filtered to remove sodium sulfate, and concentrated under reduced pressure. The residue was purified by silica gel column chromatography (eluent: n-hexane/ethyl acetate=20/1) to give the title compound (0.21 g, yield 57%).

$^1$H-NMR (CDCl$_3$) δ: 1.29 (6H, d, J=7.1 Hz), 2.99-3.02 (1H, m), 4.16 (3H, s), 7.34-7.38 (2H, m), 8.39-8.43 (2H, m).

(2) {4-chloro-3-[4-(4-isopropylphenyl)-6-methoxy-1,3,5-triazin-2-yl]phenyl}methanol

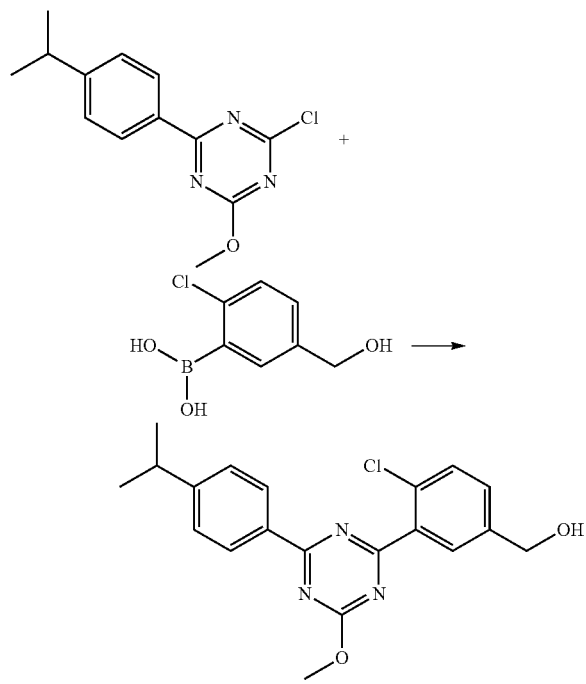

Under an argon atmosphere, to a suspension of 2-chloro-4-(4-isopropylphenyl)-6-methoxy-1,3,5-triazine (0.21 g) obtained in the above-mentioned (1), 2-chloro-5-hydroxymethylphenylboronic acid (0.15 g, 0.80 mmol) and [1,1'-bis(diphenylphosphino)ferrocene]palladium(II)dichloride dichloromethane adduct (0.066 g, 0.080 mmol) in 1,4-dioxane (2.4 ml) was added 2M aqueous sodium carbonate solution (1.2 ml) at room temperature, and the mixture was stirred at 100° C. for 2 hr. At room temperature, to the reaction mixture were added water and ethyl acetate, and the mixture was partitioned. The organic layer was washed with water, washed with saturated brine, dried over sodium sulfate, filtered to remove sodium sulfate, and concentrated under reduced pressure. The residue was purified by silica gel column chromatography (eluent: n-hexane/ethyl acetate=5/3) to give the title compound (0.15 g, yield 51%).

$^1$H-NMR (CDCl$_3$) δ: 1.30 (6H, d, J=7.1 Hz), 1.77 (1H, t, J=6.1 Hz), 2.95-3.07 (1H, m), 4.20 (3H, s), 4.77 (2H, d, J=6.1 Hz), 7.35-7.39 (2H, m), 7.46 (1H, dd, J=8.2, 2.2 Hz), 7.54 (1H, d, J=8.2 Hz), 8.01 (1H, dd, J=2.2, 0.4 Hz), 8.50-8.54 (2H, m).

(3) tert-butyl N-{4-chloro-3-[4-(4-isopropylphenyl)-6-methoxy-1,3,5-triazin-2-yl]benzyl}-N-(tert-butoxycarbonyl)carbamate

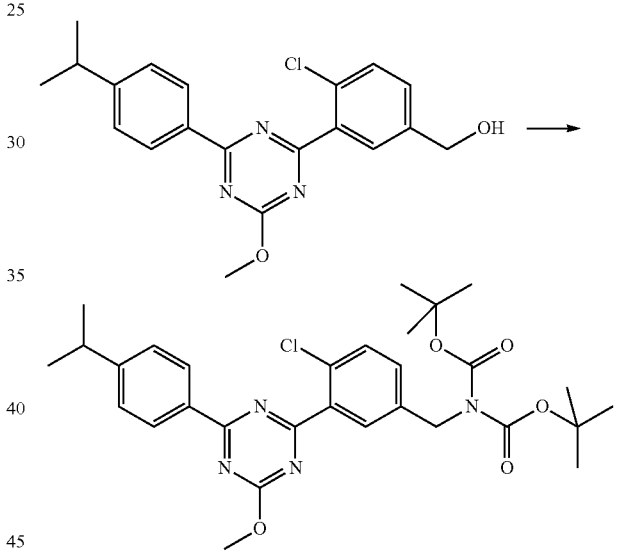

Under an argon atmosphere, to a solution of {4-chloro-3-[4-(4-isopropylphenyl)-6-methoxy-1,3,5-triazin-2-yl]phenyl}methanol (0.15 g, 0.41 mmol) obtained in the above-mentioned (2) and triphenylphosphine (0.16 g, 0.62 mmol) in chloroform (1.5 ml) was added carbon tetrabromide (0.20 g, 0.62 mmol) under ice-cooling, and the mixture was stirred at room temperature for 10 min. The reaction mixture was applied to silica gel column chromatography (eluent: n-hexane/ethyl acetate=30/1-10/1) and concentrated under reduced pressure.

A solution of the residue in N,N-dimethylformamide (1.5 ml) was added to a solution of di-tert-butyl iminodicarboxylate (0.089 g, 0.41 mmol) and sodium hydride (0.016 g, 60 wt % oil dispersion) in N,N-dimethylformamide (0.70 ml) under ice-cooling, and the mixture was stirred at room temperature for 15 min. To the reaction mixture were added water and ethyl acetate, and the mixture was partitioned. The organic layer was washed with water, washed with saturated brine, dried over sodium sulfate, filtered to remove sodium sulfate, and concentrated under reduced pressure. The residue was purified by silica gel column chromatography (eluent: n-hexane/ethyl acetate=5/1) to give the title compound (0.20 g, yield 85%).

¹H-NMR (CDCl₃) δ: 1.30 (6H, d, J=7.0 Hz), 1.47 (18H, s), 2.94-3.05 (1H, m), 4.19 (3H, s), 4.83 (2H, s), 7.34-7.41 (3H, m), 7.48 (1H, d, J=8.4 Hz), 8.00 (1H, d, J=2.3 Hz), 8.49-8.53 (2H, m).

(4) 4-chloro-3-[4-(4-isopropylphenyl)-6-methoxy-1,3,5-triazin-2-yl]benzylamine hydrochloride

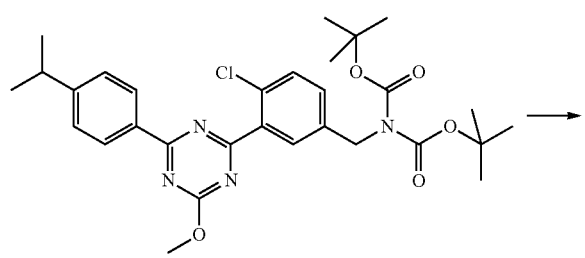

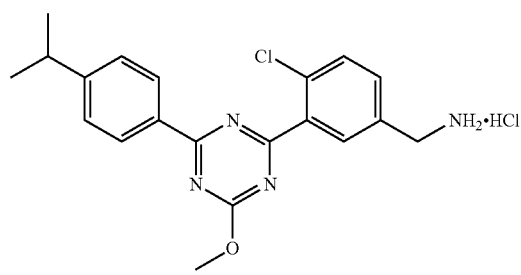

Under an argon atmosphere, to tert-butyl N-{4-chloro-3-[4-(4-isopropylphenyl)-6-methoxy-1,3,5-triazin-2-yl]benzyl}-N-(tert-butoxycarbonyl)carbamate (0.20 g, 0.35 mmol) obtained in the above-mentioned (3) was added 4M hydrogen chloride/1,4-dioxane solution (2.0 ml) at room temperature, and the mixture was stirred for 1 hr. The suspension was concentrated under reduced pressure, and azeotropically distilled with ethyl acetate (twice) to give the title compound as a crude product (0.14 g).

(5) N-{4-chloro-3-[4-(4-isopropylphenyl)-6-methoxy-1,3,5-triazin-2-yl]benzyl}-3,3,3-trifluoro-2,2-dimethylpropionamide

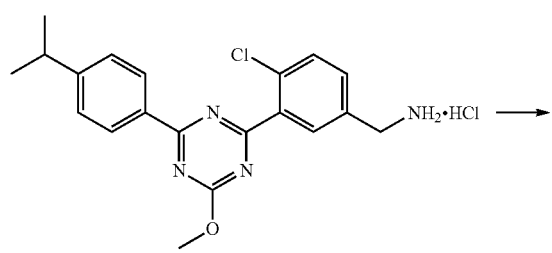

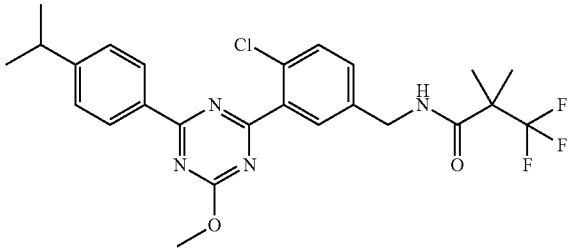

Under an argon atmosphere, to a solution of a crude product (0.10 g) of 4-chloro-3-[4-(4-isopropylphenyl)-6-methoxy-1,3,5-triazin-2-yl]benzylamine hydrochloride obtained in the above-mentioned (4), HOBt·H₂O (0.052 g, 0.34 mmol) and WSC·HCl (0.066 g, 0.34 mmol) in N,N-dimethylformamide (1.0 ml) were added 3,3,3-trifluoro-2,2-dimethylpropionic acid (0.042 g, 0.27 mmol) and triethylamine (0.069 ml, 0.49 mmol) at room temperature, and the mixture was stirred for 4 hr. To the reaction mixture were added water and ethyl acetate, and the mixture was partitioned. The organic layer was washed with saturated brine, dried over sodium sulfate, filtered to remove sodium sulfate, and concentrated under reduced pressure. The residue was purified by silica gel column chromatography (eluent: n-hexane/ethyl acetate=1/1) to give the title compound (0.054 g).

¹H-NMR (CDCl₃) δ: 1.30 (6H, d, J=6.8 Hz), 1.44 (6H, s), 2.95-3.05 (1H, m), 4.18 (3H, s), 4.53 (2H, d, J=5.7 Hz), 6.34 (1H, br s), 7.30-7.39 (3H, m), 7.50 (1H, d, J=8.4 Hz), 7.91 (1H, d, J=2.2 Hz), 8.49-8.53 (2H, m).

(6) N-{4-chloro-3-[4-hydroxy-6-(4-isopropylphenyl)-1,3,5-triazin-2-yl]benzyl}-3,3,3-trifluoro-2,2-dimethylpropionamide (Example No. 1-98)

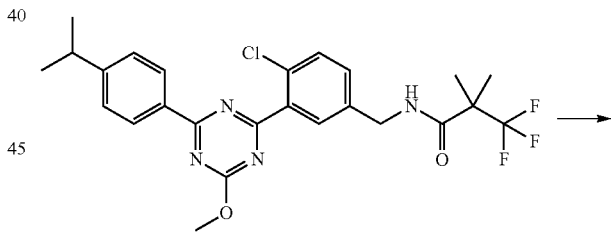

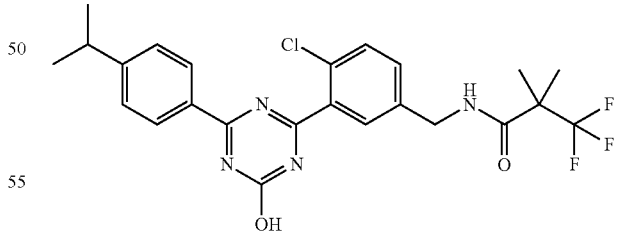

Under an argon atmosphere, to a solution of N-{4-chloro-3-[4-(4-isopropylphenyl)-6-methoxy-1,3,5-triazin-2-yl]benzyl}-3,3,3-trifluoro-2,2-dimethylpropionamide (0.050 g, 0.099 mmol) obtained in the above-mentioned (5) in methanol (0.50 ml) was added 4M aqueous sodium hydroxide solution (0.20 ml) at room temperature, and the mixture was stirred at 60° C. for 2 hr. To the reaction mixture were added 2N hydrochloric acid (0.40 ml) and water at room temperature, and the mixture was stirred. The precipitated solid was collected by filtration, washed with water, and dried under reduced pressure to give the title compound (0.043 g, yield 89%).

Production Example 12

Synthesis of N-{4-chloro-3-[4-hydroxy-6-(4-isobutoxyphenyl)-1,3,5-triazin-2-yl]benzyl}-3,3,3-trifluoro-2,2-dimethylpropionamide (Example No. 1-109)

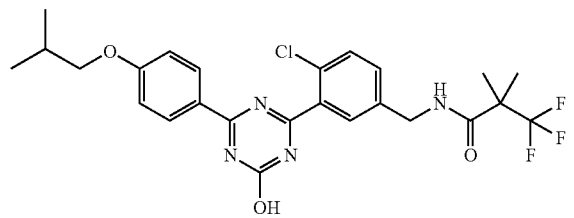 [SMILES: CC(C)COc1ccc(-c2nc(O)nc(-c3cc(CNC(=O)C(C)(C)C(F)(F)F)ccc3Cl)n2)cc1]

(1) 2-chloro-4-(4-isobutoxyphenyl)-6-methoxy-1,3,5-triazine

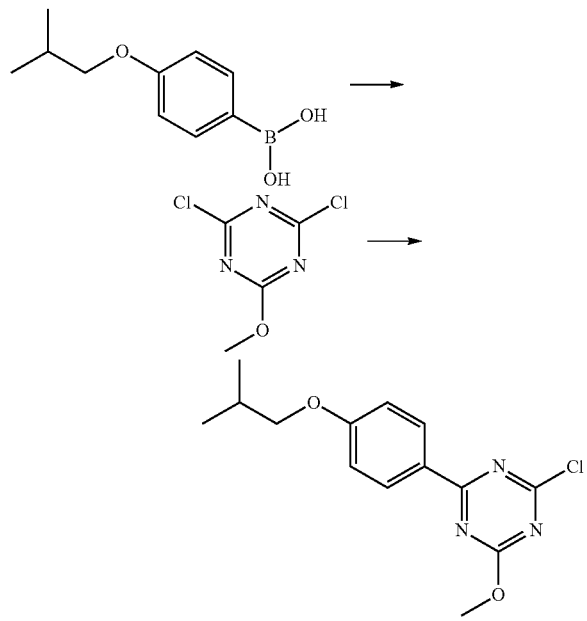

Under an argon atmosphere, to a suspension of 4-isobutoxyphenylboronic acid (0.50 g, 2.58 mmol), 2,4-dichloro-6-methoxy-1,3,5-triazine (0.93 g, 5.15 mmol), tetrakis(triphenylphosphine)palladium(0) (0.15 g, 0.129 mmol) and sodium carbonate (0.819 g, 7.73 mmol) in toluene (5.0 ml) was added distilled water (3.5 ml), and the mixture was stirred at 86° C. for 2 hr. At room temperature, to the reaction mixture were added water and ethyl acetate, and the mixture was partitioned. The organic layer was washed with saturated brine, dried over sodium sulfate, filtered to remove sodium sulfate, and concentrated under reduced pressure. The residue was purified by silica gel column chromatography (eluent: n-hexane/ethyl acetate=10/1) to give the title compound (0.606 g, yield 80%).

$^1$H-NMR (CDCl$_3$) δ: 1.05 (6H, d, J=6.7 Hz), 2.07-2.17 (1H, m), 3.81 (2H, d, J=6.5 Hz), 4.14 (3H, s), 6.95-7.00 (2H, m), 8.42-8.46 (2H, m).

(2) {4-chloro-3-[4-(4-isobutoxyphenyl)-6-methoxy-1,3,5-triazin-2-yl]phenyl}methanol

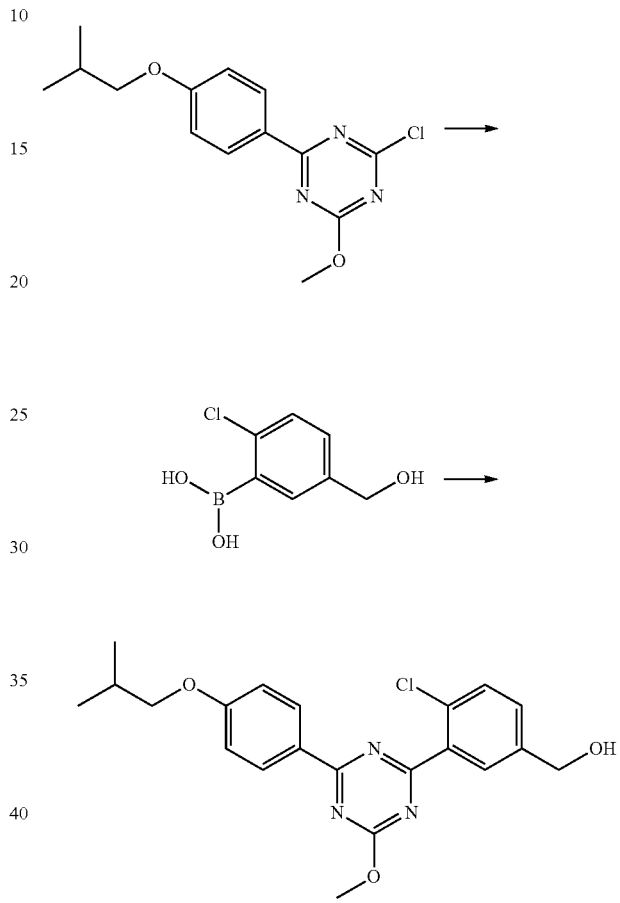

Under an argon atmosphere, a suspension of 2-chloro-4-(4-isobutoxyphenyl)-6-methoxy-1,3,5-triazine (0.60 g, 2.0 mmol) obtained in the above-mentioned (1), 2-chloro-5-hydroxymethylphenylboronic acid (0.57 g, 3.1 mmol), [1,1'-bis(diphenylphosphino)ferrocene]palladium(II)dichloride dichloromethane adduct (0.083 g, 0.10 mmol) and tripotassium phosphate (1.3 g, 6.1 mmol) in N,N-dimethylformamide (6.0 ml) was stirred at 60° C. for 1.5 hr. At room temperature, to the reaction mixture were added water and ethyl acetate, and the mixture was partitioned. The organic layer was washed with water and partitioned, washed with saturated brine, dried over sodium sulfate, filtered to remove sodium sulfate, and concentrated under reduced pressure. The residue was purified by silica gel column chromatography (eluent: n-hexane/ethyl acetate=3/2) to give the title compound (0.32 g, yield 39%).

$^1$H-NMR (CDCl$_3$) δ: 1.05 (6H, d, J=6.7 Hz), 1.77 (1H, t, J=5.9 Hz), 2.08-2.18 (1H, m), 3.82 (2H, d, J=6.5 Hz), 4.19 (3H, s), 4.77 (2H, d, J=5.9 Hz), 6.98-7.01 (2H, m), 7.46 (1H, dd, J=8.2, 2.2 Hz), 7.53 (1H, d, J=8.2 Hz), 8.00 (1H, d, J=2.2 Hz), 8.55 (2H, m).

(3) tert-butyl N-{4-chloro-3-[4-(4-isobutoxyphenyl)-6-methoxy-1,3,5-triazin-2-yl]benzyl}-N-(tert-butoxycarbonyl)carbamate

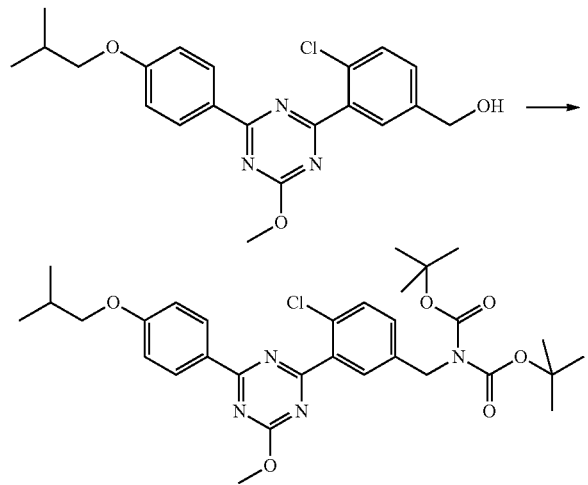

Under an argon atmosphere, to a solution of {4-chloro-3-[4-(4-isobutoxyphenyl)-6-methoxy-1,3,5-triazin-2-yl]phenyl}methanol (0.24 g, 0.61 mmol) obtained in the above-mentioned (2) in tetrahydrofuran (2.0 ml) were added triethylamine (0.11 ml, 0.79 mmol) and methanesulfonyl chloride (0.052 ml, 0.67 mmol) under ice-cooling, and the mixture was stirred for 0.5 hr. The reaction mixture was filtered, and the filtrate was concentrated under reduced pressure. To a solution of the residue in N,N-dimethylformamide (1.5 ml) were added cesium carbonate (0.59 g, 1.8 mmol) and di-tert-butyl iminodicarboxylate (0.16 g, 0.73 mmol) at room temperature, and the mixture was stirred for 1.5 hr. To the reaction mixture were added water and ethyl acetate, and the mixture was partitioned. The organic layer was washed with saturated brine, dried over magnesium sulfate, filtered to remove magnesium sulfate, and concentrated under reduced pressure. The residue was purified by silica gel column chromatography (eluent: n-hexane/ethyl acetate=6/1) to give the title compound (0.34 g, yield 92%).

$^1$H-NMR (CDCl$_3$) δ: 1.05 (6H, d, J=6.7 Hz), 1.47 (18H, s), 2.08-2.18 (1H, m), 3.82 (2H, d, J=6.5 Hz), 4.18 (3H, s), 4.82 (2H, s), 6.96-7.00 (2H, m), 7.39 (1H, dd, J=8.3, 2.3 Hz), 7.48 (1H, d, J=8.3 Hz), 7.99 (1H, d, J=2.3 Hz), 8.52-8.56 (2H, m).

(4) 4-chloro-3-[4-(4-isobutoxyphenyl)-6-methoxy-1,3,5-triazin-2-yl]benzylamine hydrochloride

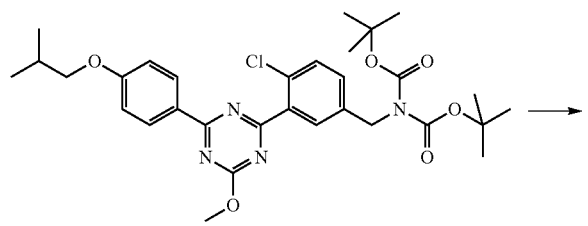

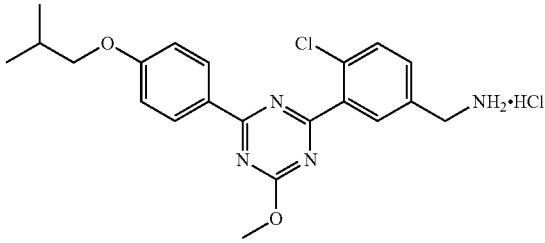

Under an argon atmosphere, to a solution of tert-butyl N-{4-chloro-3-[4-(4-isobutoxyphenyl)-6-methoxy-1,3,5-triazin-2-yl]benzyl}-N-(tert-butoxycarbonyl)carbamate (0.34 g, 0.56 mmol) obtained in the above-mentioned (3) in 1,4-dioxane (1.0 ml) was added 4M hydrogen chloride/1,4-dioxane solution (3.0 ml) at room temperature, and the mixture was stirred for 2.5 hr. To the reaction mixture was added n-hexane (20 ml), and the mixture was stirred. The solid was collected by filtration from the suspension, and dried under reduced pressure to give the title compound (0.24 g, yield 95%).

$^1$H-NMR (DMSO-D$_6$) δ: 1.01 (6H, d, J=6.8 Hz), 2.01-2.11 (1H, m), 3.88 (2H, d, J=6.4 Hz), 4.14 (3H, s), 4.12-4.17 (2H, m), 7.12-7.15 (2H, m), 7.72 (2H, br s), 8.13 (1H, br s), 8.40-8.51 (5H, m).

(5) N-{4-chloro-3-[4-(4-isobutoxyphenyl)-6-methoxy-1,3,5-triazin-2-yl]benzyl}-3,3,3-trifluoro-2,2-dimethylpropionamide

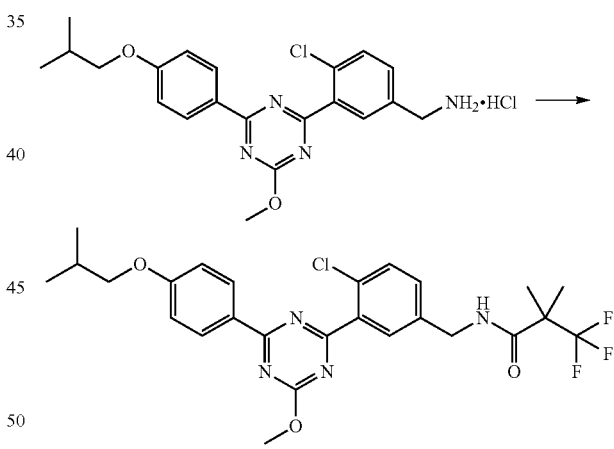

Under an argon atmosphere, to a solution of 4-chloro-3-[4-(4-isobutoxyphenyl)-6-methoxy-1,3,5-triazin-2-yl]benzylamine hydrochloride (0.065 g, 0.14 mmol) obtained in the above-mentioned (4), HOBt·H$_2$O (0.033 g, 0.22 mmol) and 3,3,3-trifluoro-2,2-dimethylpropionic acid (0.034 g, 0.22 mmol) in N,N-dimethylformamide (0.70 ml) were added WSC·HCl (0.042 g, 0.22 mmol) and triethylamine (0.030 ml, 0.22 mmol) at room temperature, and the mixture was stirred for 5 hr. To the reaction mixture were added 3,3,3-trifluoro-2,2-dimethylpropionic acid (0.034 g, 0.22 mmol), WSC·HCl (0.042 g, 0.22 mmol), HOBt·H$_2$O (0.033 g, 0.22 mmol) and triethylamine (0.030 ml, 0.22 mmol), and the mixture was stirred for 1 hr. To the reaction mixture were added water and ethyl acetate, and the mixture was partitioned. The organic layer was washed with saturated brine, dried over magnesium sulfate, filtered to remove magnesium sulfate, and concentrated under reduced pressure. The residue was purified by silica gel column chromatography (eluent: n-hexane/ethyl acetate=3/1) to give the title compound (0.068 g, yield 86%).

¹H-NMR (CDCl₃) δ: 1.06 (6H, d, J=6.8 Hz), 1.44 (6H, br s), 2.08-2.18 (1H, m), 3.82 (2H, d, J=6.6 Hz), 4.19 (3H, s), 4.55 (2H, d, J=5.7 Hz), 6.21 (1H, br s), 6.97-7.01 (2H, m), 7.34 (1H, dd, J=8.3, 2.3 Hz), 7.51 (1H, d, J=8.3 Hz), 7.91 (1H, d, J=2.3 Hz), 8.53-8.55 (2H, m).

(6) N-{4-chloro-3-[4-hydroxy-6-(4-isobutoxyphenyl)-1,3,5-triazin-2-yl]benzyl}-3,3,3-trifluoro-2,2-dimethylpropionamide (Example No. 1-109)

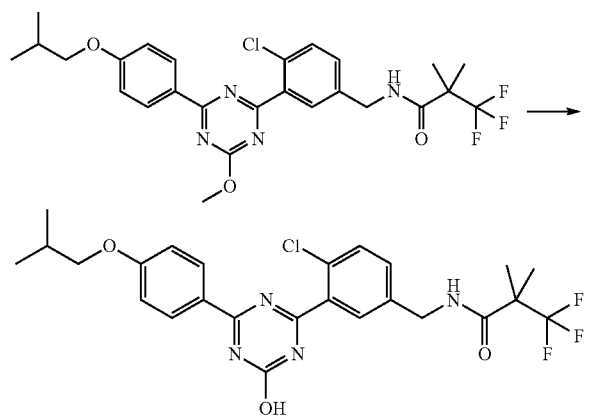

Under an argon atmosphere, to a solution of N-{4-chloro-3-[4-(4-isobutoxyphenyl)-6-methoxy-1,3,5-triazin-2-yl]benzyl}-3,3,3-trifluoro-2,2-dimethylpropionamide (0.066 g, 0.12 mmol) obtained in the above-mentioned (5) in methanol (1.1 ml) was added 4M aqueous sodium hydroxide solution (0.18 ml) at room temperature, and the mixture was stirred at 60° C. for 2 hr. To the reaction mixture were added 10% aqueous citric acid solution (0.55 ml) and water at room temperature, and the mixture was stirred. The precipitated solid was collected by filtration, washed with water, and dried under reduced pressure to give the title compound (0.057 g, yield 88%). A suspension of the title compound (0.030 g) in acetonitrile (0.60 ml) was stirred at room temperature, and the solid was collected by filtration and dried to give the title compound as crystals (0.011 g).

Production Example 13

Synthesis of N-{4-chloro-3-[4-hydroxy-6-(4-propoxyphenyl)-1,3,5-triazin-2-yl]benzyl}-3,3,3-trifluoro-2,2-dimethylpropionamide (Example No. 1-122)

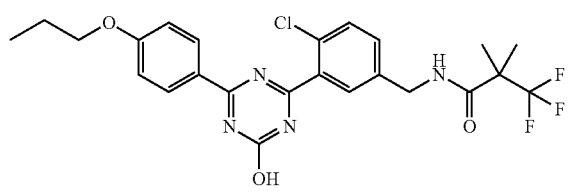 [SMILES: CCCOc1ccc(-c2nc(O)nc(-c3cc(CNC(=O)C(C)(C)C(F)(F)F)ccc3Cl)n2)cc1]

(1) 2-chloro-4-methoxy-6-(4-propoxyphenyl)-1,3,5-triazine

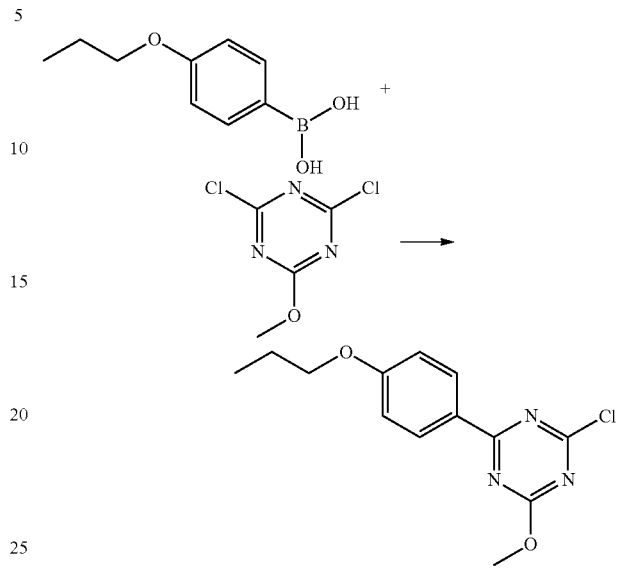

Under an argon atmosphere, to a suspension of 4-propoxyphenylboronic acid (1.0 g, 5.6 mmol), 2,4-dichloro-6-methoxy-1,3,5-triazine (2.0 g, 11 mmol) and tetrakis(triphenylphosphine)palladium(0) (0.65 g, 0.56 mmol) in toluene (25 ml) was added 2M aqueous sodium carbonate solution (8.4 ml), and the mixture was stirred at 100° C. for 1 hr. At room temperature, to the reaction mixture were added water and ethyl acetate, and the mixture was partitioned. The organic layer was washed with saturated brine, dried over magnesium sulfate, filtered to remove magnesium sulfate, and concentrated under reduced pressure. The residue was purified by silica gel column chromatography (eluent: n-hexane/ethyl acetate=20/1) to give the title compound (1.1 g, yield 70%).

¹H-NMR (CDCl₃) δ: 1.06 (3H, t, J=7.4 Hz), 1.83-1.87 (2H, m), 4.02 (2H, t, J=6.6 Hz), 4.14 (3H, s), 6.96-6.99 (2H, m), 8.43-8.45 (2H, m).

(2) {4-chloro-3-[4-methoxy-6-(4-propoxyphenyl)-1,3,5-triazin-2-yl]phenyl}methanol

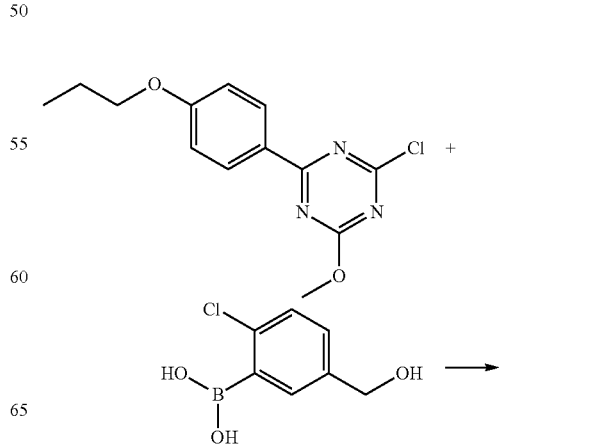

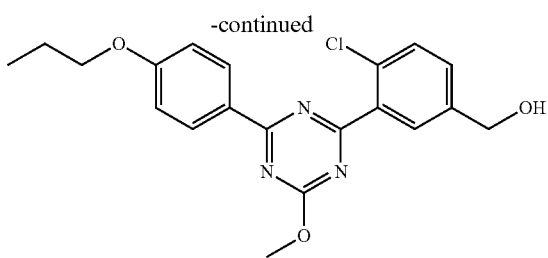

Under an argon atmosphere, to a solution of 2-chloro-4-methoxy-6-(4-propoxyphenyl)-1,3,5-triazine (0.75 g, 2.7 mmol) is obtained in the above-mentioned (1), 2-chloro-5-hydroxymethylphenylboronic acid (0.60 g, 3.2 mmol) and [1,1'-bis(diphenylphosphino)ferrocene]palladium(II)dichloride dichloromethane adduct (0.22 g, 0.27 mmol) in 1,4-dioxane (15 ml) was added 2M aqueous sodium carbonate solution (5.4 ml), and the mixture was stirred at 100° C. for 3 hr. At room temperature, to the reaction mixture were added water and ethyl acetate, and the mixture was partitioned. The organic layer was washed with water and partitioned, washed with saturated brine, dried over magnesium sulfate, filtered to remove magnesium sulfate, and concentrated under reduced pressure. The residue was purified by silica gel column chromatography (eluent: chloroform/ethyl acetate=10/1) to give the title compound (0.95 g, yield 91%).

$^1$H-NMR (CDCl$_3$) δ: 1.07 (3H, t, J=7.4 Hz), 1.77 (1H, t, J=5.8 Hz), 1.84-1.87 (2H, m), 4.02 (2H, t, J=6.6 Hz), 4.19 (3H, s), 4.77 (2H, d, J=5.8 Hz), 7.00 (2H, d, J=8.7 Hz), 7.45 (1H, dd, J=8.3, 1.9 Hz), 7.53 (1H, d, J=8.3 Hz), 8.00 (1H, d, J=1.9 Hz), 8.55 (2H, d, J=8.7 Hz).

(3) tert-butyl N-{4-chloro-3-[4-methoxy-6-(4-propoxyphenyl)-1,3,5-triazin-2-yl]benzyl}-N-(tert-butoxycarbonyl)carbamate

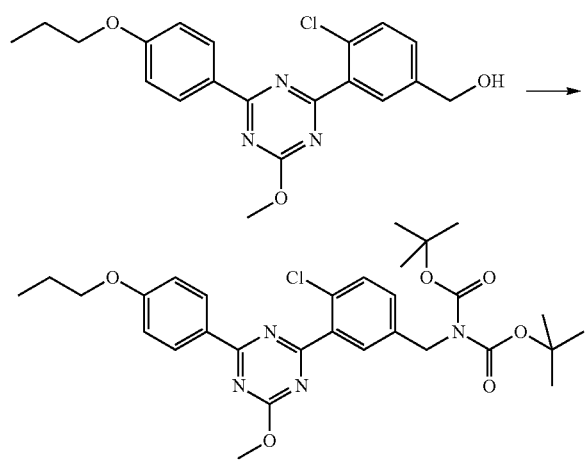

Under an argon atmosphere, to a solution of {4-chloro-3-[4-methoxy-6-(4-propoxyphenyl)-1,3,5-triazin-2-yl]phenyl}methanol (0.95 g, 2.5 mmol) obtained in the above-mentioned (2) in tetrahydrofuran (13 ml) were added triethylamine (0.45 ml, 3.2 mmol) and methanesulfonyl chloride (0.23 ml, 3.0 mmol) under ice-cooling, and the mixture was stirred for 0.5 hr. The reaction mixture was filtered, and the filtrate was concentrated under reduced pressure. To a solution of the residue in N,N-dimethylformamide (13 ml) were added cesium carbonate (2.4 g, 7.4 mmol) and di-tert-butyl iminodicarboxylate (0.64 g, 3.0 mmol) at room temperature, and the mixture was stirred for 1 hr. To the reaction mixture were added water and ethyl acetate, and the mixture was partitioned. The organic layer was washed with saturated brine, dried over magnesium sulfate, filtered to remove magnesium sulfate, and concentrated under reduced pressure. The residue was purified by silica gel column chromatography (eluent: n-hexane/ethyl acetate=10/1) to give the title compound (1.3 g, yield 90%).

(4) 4-chloro-3-[4-methoxy-6-(4-propoxyphenyl)-1,3,5-triazin-2-yl]benzylamine hydrochloride

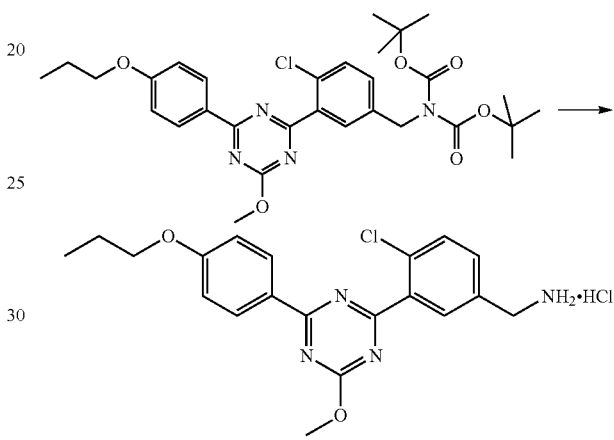

Under an argon atmosphere, to tert-butyl N-{4-chloro-3-[4-methoxy-6-(4-propoxyphenyl)-1,3,5-triazin-2-yl]benzyl}-N-(tert-butoxycarbonyl)carbamate (1.3 g, 2.2 mmol) obtained in the above-mentioned (3) was added 4M hydrogen chloride/1,4-dioxane solution (5.0 ml) at room temperature, and the mixture was stirred for 30 min. To the reaction mixture were added 1,4-dioxane (2.0 ml) and n-hexane (5.0 ml), and the mixture was stirred for 45 min. The solid was collected by filtration from the suspension, and dried under reduced pressure to give the title compound (0.68 g, yield 73%).

$^1$H-NMR (DMSO-D$_6$) δ: 1.00 (3H, t, J=7.4 Hz), 1.73-1.83 (2H, m), 4.06 (2H, t, J=6.5 Hz), 4.12-4.18 (2H, m), 4.14 (3H, s), 7.12-7.16 (2H, m), 7.69-7.74 (2H, m), 8.13 (1H, br s), 8.44 (3H, br s), 8.45-8.50 (2H, m).

(5) N-{4-chloro-3-[4-methoxy-6-(4-propoxyphenyl)-1,3,5-triazin-2-yl]benzyl}-3,3,3-trifluoro-2,2-dimethylpropionamide

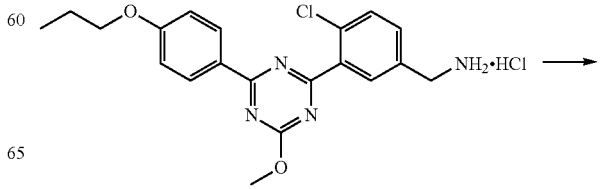

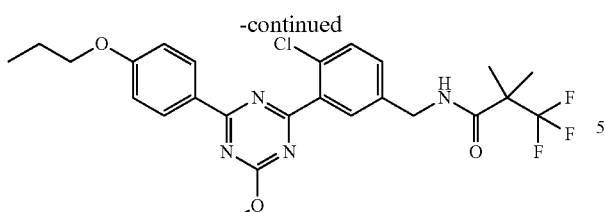

Under an argon atmosphere, to a solution of 4-chloro-3-[4-methoxy-6-(4-propoxyphenyl)-1,3,5-triazin-2-yl]benzylamine hydrochloride (0.10 g, 0.24 mmol) obtained in the above-mentioned (4), HOBt·H₂O (0.054 g, 0.36 mmol) and WSC·HCl (0.068 g, 0.36 mmol) in N,N-dimethylformamide (1.5 ml) were added 3,3,3-trifluoro-2,2-dimethylpropionic acid (0.056 g, 0.36 mmol) and triethylamine (0.099 ml, 0.71 mmol) at room temperature, and the mixture was stirred for 4 hr. To the reaction mixture were added water and ethyl acetate, and the mixture was partitioned. The organic layer was washed with saturated brine, dried over magnesium sulfate, filtered to remove magnesium sulfate, and concentrated under reduced pressure. The residue was purified by silica gel column chromatography (eluent: n-hexane/ethyl acetate=10/3) to give the title compound (0.096 g, yield 78%).

$^1$H-NMR (DMSO-D$_6$) δ: 1.00 (3H, t, J=7.3 Hz), 1.39 (6H, s), 1.73-1.83 (2H, m), 4.05 (2H, t, J=6.5 Hz), 4.11 (3H, s), 4.39 (2H, d, J=5.9 Hz), 7.10-7.14 (2H, m), 7.44 (1H, dd, J=8.1, 2.3 Hz), 7.61 (1H, d, J=8.1 Hz), 7.86 (1H, d, J=2.3 Hz), 8.42-8.47 (2H, m), 8.66 (1H, t, J=5.9 Hz).

(6) N-{4-chloro-3-[4-hydroxy-6-(4-propoxyphenyl)-1,3,5-triazin-2-yl]benzyl}-3,3,3-trifluoro-2,2-dimethylpropionamide (Example No. 1-122)

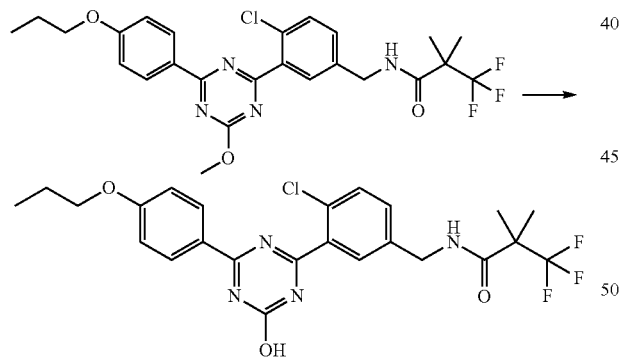

Under an argon atmosphere, to a solution of N-{4-chloro-3-[4-methoxy-6-(4-propoxyphenyl)-1,3,5-triazin-2-yl]benzyl}-3,3,3-trifluoro-2,2-dimethylpropionamide (0.094 g, 0.18 mmol) obtained in the above-mentioned (5) in methanol (0.94 ml) was added 4M aqueous sodium hydroxide solution (0.27 ml) at room temperature, and the mixture was stirred at 65° C. for 2 hr. To the reaction mixture were added 2N hydrochloric acid (0.54 ml) and water at room temperature, and the mixture was stirred. The precipitated solid was collected by filtration, washed with water, and dried under reduced pressure to give the title compound (0.069 g, yield 75%). A suspension of the title compound (0.050 g) in acetone (1.0 ml) was dissolved by heating under reflux, and the solid was collected by filtration at room temperature and dried to give the title compound as crystals (0.012 g).

Production Example 14

Synthesis of N-(4-chloro-3-{4-hydroxy-6-[4-(1-methylcyclopropylmethoxy)phenyl]-1,3,5-triazin-2-yl}benzyl)-3,3,3-trifluoro-2,2-dimethylpropionamide (Example No. 1-128)

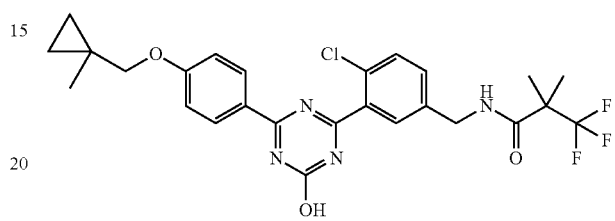

(1) 2-chloro-4-methoxy-6-(4-methoxymethoxyphenyl)-1,3,5-triazine

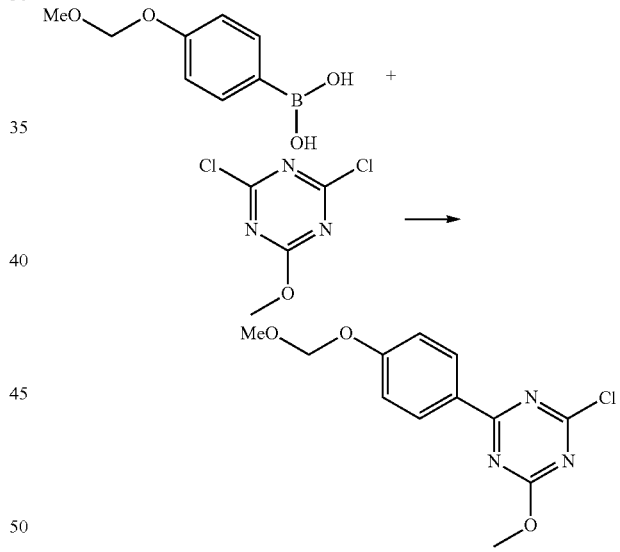

Under an argon atmosphere, to a suspension of 4-(methoxymethoxy)phenylboronic acid (1.0 g, 5.5 mmol), 2,4-dichloro-6-methoxy-1,3,5-triazine (2.0 g, 11 mmol) and tetrakis(triphenylphosphine)palladium(0) (0.64 g, 0.55 mmol) in toluene (25 ml) was added 2M aqueous sodium carbonate solution (8.3 ml), and the mixture was stirred at 100° C. for 1 hr. At room temperature, to the reaction mixture were added water and ethyl acetate, and the mixture was partitioned. The organic layer was washed with saturated brine, dried over magnesium sulfate, filtered to remove magnesium sulfate, and concentrated under reduced pressure. The residue was purified by silica gel column chromatography (eluent: n-hexane/ethyl acetate=20/1-10/1) to give the title compound (1.3 g, yield 84%).

(2) {4-chloro-3-[4-methoxy-6-(4-methoxymethoxy-phenyl)-1,3,5-triazin-2-yl]phenyl}methanol

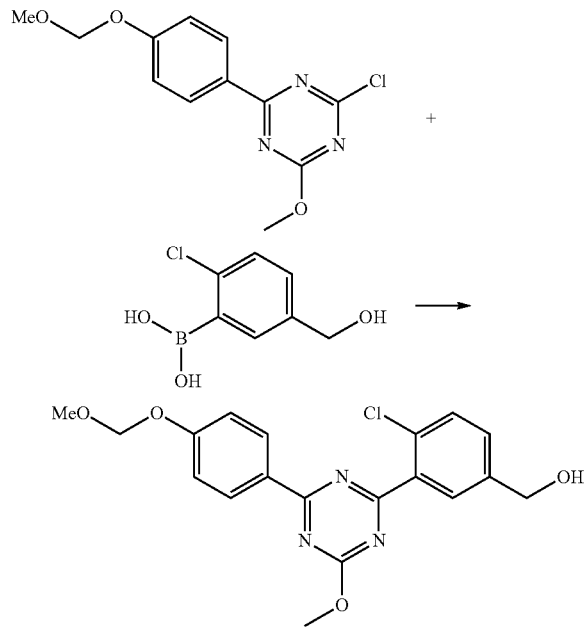

Under an argon atmosphere, to a solution of 2-chloro-4-methoxy-6-(4-methoxymethoxyphenyl)-1,3,5-triazine (1.3 g, 4.4 mmol) obtained in the above-mentioned (1), 2-chloro-5-hydroxymethylphenylboronic acid (0.99 g, 5.3 mmol) and [1,1'-bis(diphenylphosphino)ferrocene]palladium(II)dichloride dichloromethane adduct (0.36 g, 0.44 mmol) in 1,4-dioxane (25 ml) was added 2M aqueous sodium carbonate solution (8.8 ml), and the mixture was stirred at 100° C. for 3 hr. At room temperature, to the reaction mixture were added water and ethyl acetate, and the mixture was partitioned. The organic layer was washed with water, washed with saturated brine, dried over magnesium sulfate, filtered to remove magnesium sulfate, and concentrated under reduced pressure. The residue was purified by silica gel column chromatography (eluent: chloroform/ethyl acetate=10/1) to give the title compound (0.98 g, yield 56%).

(3) tert-butyl N-{4-chloro-3-[4-methoxy-6-(4-methoxymethoxyphenyl)-1,3,5-triazin-2-yl]benzyl}-N-(tert-butoxycarbonyl)carbamate

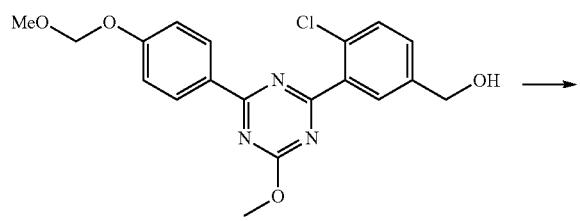

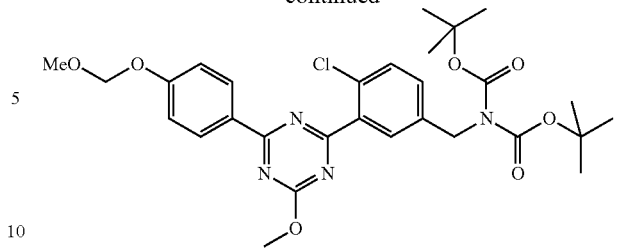

Under an argon atmosphere, to a solution of {4-chloro-3-[4-methoxy-6-(4-methoxymethoxyphenyl)-1,3,5-triazin-2-yl]phenyl}methanol (0.78 g, 2.0 mmol) obtained in the above-mentioned (2) in tetrahydrofuran (7.8 ml) were added triethylamine (0.36 ml, 2.6 mmol) and methanesulfonyl chloride (0.19 ml, 2.4 mmol) under ice-cooling, and the mixture was stirred for 0.5 hr. The reaction mixture was filtered, and the filtrate was concentrated under reduced pressure. To a solution of the residue in N,N-dimethylformamide (10 ml) were added cesium carbonate (2.0 g, 6.0 mmol) and di-tert-butyl iminodicarboxylate (0.53 g, 2.4 mmol), and the mixture was stirred for 2 hr. To the reaction mixture were added water and ethyl acetate, and the mixture was partitioned. The organic layer was washed with saturated brine, dried over magnesium sulfate, filtered to remove magnesium sulfate, and concentrated under reduced pressure. The residue was purified by silica gel column chromatography (eluent: n-hexane/ethyl acetate=10/1) to give the title compound (0.80 g, yield 68%).

$^1$H-NMR (DMSO-D$_6$) δ: 1.42 (18H, s), 3.41 (3H, s), 4.12 (3H, s), 4.77 (2H, s), 5.32 (2H, s), 7.18-7.23 (2H, m), 7.45 (1H, dd, J=8.2, 2.3 Hz), 7.65 (1H, d, J=8.2 Hz), 7.91 (1H, d, J=2.3 Hz), 8.43-8.47 (2H, m).

(4) 4-[4-(5-aminomethyl-2-chlorophenyl)-6-methoxy-1,3,5-triazin-2-yl]phenol hydrochloride

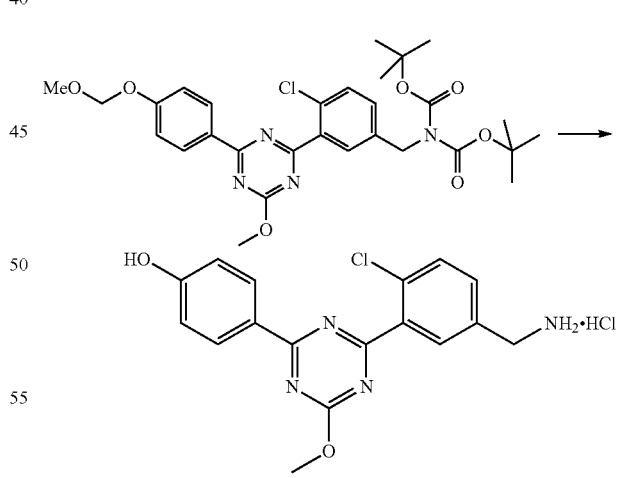

Under an argon atmosphere, to tert-butyl N-{4-chloro-3-[4-methoxy-6-(4-methoxymethoxyphenyl)-1,3,5-triazin-2-yl]benzyl}-N-(tert-butoxycarbonyl)carbamate (0.40 g, 0.68 mmol) obtained in the above-mentioned (3) was added 4M hydrogen chloride/1,4-dioxane solution (2.0 ml) at room temperature, and the mixture was stirred for 1 hr. To the reaction mixture was added n-hexane (3.0 ml), and the mixture was stirred for 45 min. The solid was collected by filtration, and dried under reduced pressure to give the title compound as a crude product (0.26 g).

(5) 4-(4-{2-chloro-5-[(3,3,3-trifluoro-2,2-dimethyl-propionylamino)methyl]phenyl}-6-methoxy-1,3,5-triazin-2-yl)phenyl 3,3,3-trifluoro-2,2-dimethylpropionate

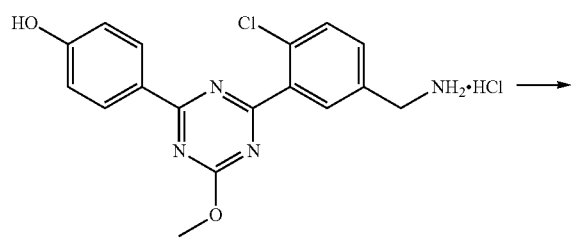

Under an argon atmosphere, to a solution of a crude product (0.10 g) of 4-[4-(5-aminomethyl-2-chlorophenyl)-6-methoxy-1,3,5-triazin-2-yl]phenol hydrochloride obtained in the above-mentioned (4), HOBt·H₂O (0.061 g, 0.40 mmol) and WSC·HCl (0.076 g, 0.40 mmol) in N,N-dimethylformamide (1.5 ml) were added 3,3,3-trifluoro-2,2-dimethylpropionic acid (0.066 g, 0.40 mmol) and triethylamine (0.11 ml, 0.79 mmol) at room temperature, and the mixture was stirred for 2 hr. To the reaction mixture were added water and ethyl acetate, and the mixture was partitioned. The organic layer was washed with saturated brine, dried over magnesium sulfate, filtered to remove magnesium sulfate, and concentrated under reduced pressure. The residue was purified by silica gel column chromatography (eluent: chloroform/ethyl acetate=10/1) to give the title compound (0.090 g).

¹H-NMR (DMSO-D₆) δ: 1.39 (6H, s), 1.59 (6H, s), 4.15 (3H, s), 4.40 (2H, d, J=6.0 Hz), 7.39-7.47 (3H, m), 7.62 (1H, d, J=8.4 Hz), 7.88 (1H, d, J=2.1 Hz), 8.55-8.60 (2H, m), 8.66 (1H, t, J=6.0 Hz).

(6) N-{4-chloro-3-[4-(4-hydroxyphenyl)-6-methoxy-1,3,5-triazin-2-yl]benzyl}-3,3,3-trifluoro-2,2-dimethylpropionamide

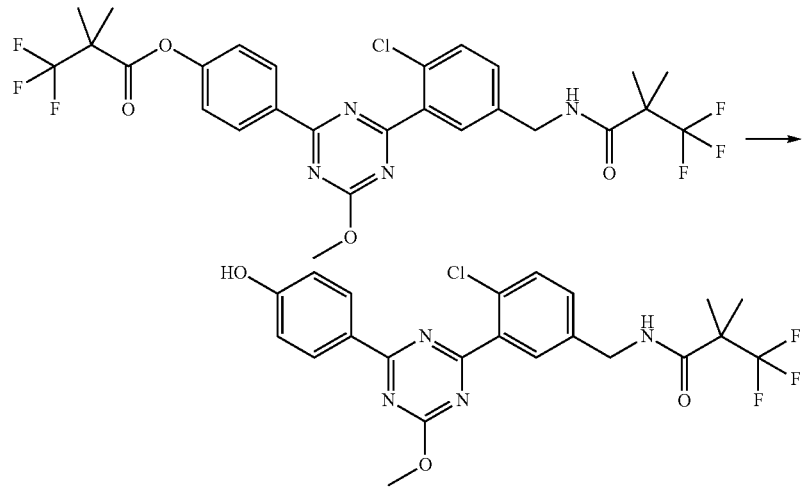

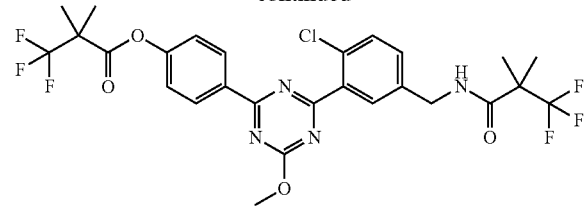

Under an argon atmosphere, to a solution of 4-(4-{2-chloro-5-[(3,3,3-trifluoro-2,2-dimethylpropionylamino)methyl]phenyl}-6-methoxy-1,3,5-triazin-2-yl)phenyl 3,3,3-trifluoro-2,2-dimethylpropionate (0.070 g, 0.15 mmol) obtained in the above-mentioned (5) in methanol (0.70 ml) was added 5M sodium methoxide/methanol solution (0.032 ml) at room temperature, and the mixture was stirred for 1 hr. The reaction mixture was adjusted to pH=2 with 2N hydrochloric acid under ice-cooling. To the reaction mixture were added water and ethyl acetate, and the mixture was partitioned. The organic layer was washed with saturated brine, dried over magnesium sulfate, filtered to remove magnesium sulfate, and concentrated under reduced pressure. The residue was purified by silica gel column chromatography (eluent: chloroform/ethyl acetate=4/1) to give the title compound (0.036 g, yield 51%).

¹H-NMR (DMSO-D₆) δ: 1.38 (6H, s), 4.10 (3H, s), 4.39 (2H, d, J=6.2 Hz), 6.91-6.95 (2H, m), 7.42 (1H, dd, J=8.3, 2.3 Hz), 7.60 (1H, d, J=8.3 Hz), 7.84 (1H, d, J=2.3 Hz), 8.34-8.39 (2H, m), 8.65 (1H, t, J=6.2 Hz), 10.38 (1H, br s).

(7) N-(4-chloro-3-{4-methoxy-6-[4-(1-methylcyclopropylmethoxy)phenyl]-1,3,5-triazin-2-yl}benzyl)-3,3,3-trifluoro-2,2-dimethylpropionamide

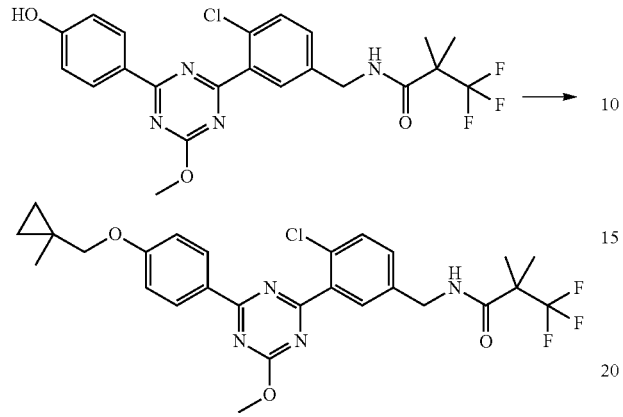

Under an argon atmosphere, to a solution of N-{4-chloro-3-[4-(4-hydroxyphenyl)-6-methoxy-1,3,5-triazin-2-yl]benzyl}-3,3,3-trifluoro-2,2-dimethylpropionamide (0.036 g, 0.075 mmol) obtained in the above-mentioned (6), 1-methyl-cyclopropanemethanol (0.0087 ml, 0.090 mmol) and triphenylphosphine (0.024 g, 0.090 mmol) in tetrahydrofuran (0.50 ml) was added 1.9M diethyl azodicarboxylate/toluene solution (0.051 ml, 0.098 mmol) under ice-cooling, and the mixture was stirred for 1 hr. The reaction mixture was stirred at room temperature for 1 hr, and 1.9M diethyl azodicarboxylate/toluene solution (0.028 ml, 0.053 mmol) was added. The reaction mixture was stirred at room temperature for 1 hr, and purified by preparative thin layer chromatography (eluent: chloroform/ethyl acetate=19/1) to give the title compound (0.029 g, yield 70%).

$^1$H-NMR (DMSO-D$_6$) δ: 0.42 (2H, dd, J=5.6, 4.0 Hz), 0.56 (2H, dd, J=5.4, 4.2 Hz), 1.20 (3H, s), 1.39 (6H, s), 3.88 (2H, s), 4.11 (3H, s), 4.39 (2H, d, J=5.9 Hz), 7.09-7.14 (2H, m), 7.43 (1H, dd, J=8.2, 2.1 Hz), 7.60 (1H, d, J=8.2 Hz), 7.85 (1H, d, J=2.1 Hz), 8.41-8.46 (2H, m), 8.66 (1H, t, J=5.9 Hz).

(8) N-(4-chloro-3-{4-hydroxy-6-[4-(1-methylcyclopropylmethoxy)phenyl]-1,3,5-triazin-2-yl}benzyl)-3,3,3-trifluoro-2,2-dimethylpropionamide (Example No. 1-128)

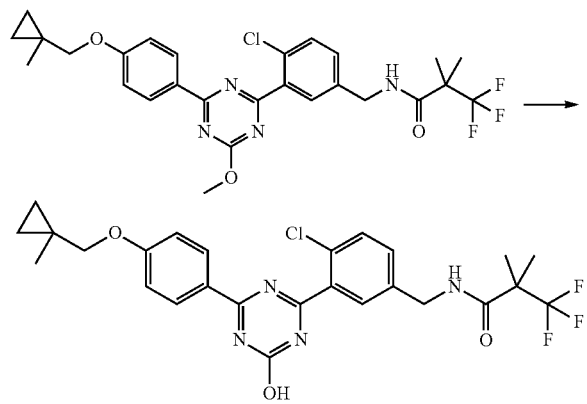

Under an argon atmosphere, to a solution of N-(4-chloro-3-{4-methoxy-6-[4-(1-methylcyclopropylmethoxy)phenyl]-1,3,5-triazin-2-yl}benzyl)-3,3,3-trifluoro-2,2-dimethylpropionamide (0.028 g, 0.051 mmol) obtained in the above-mentioned (7) in methanol (0.28 ml) was added 4M aqueous sodium hydroxide solution (0.077 ml) at room temperature, and the mixture was is stirred at 60° C. for 1 hr. To the reaction mixture were added 2N hydrochloric acid (0.16 ml) and water at room temperature, and the mixture was stirred. The precipitated solid was collected by filtration, washed with water, and dried under reduced pressure to give the title compound (0.019 g, yield 69%).

Production Example 15

Synthesis of N-{4-chloro-3-[4-(3-chloro-4-methylphenyl)-6-hydroxy-1,3,5-triazin-2-yl]benzyl}-3,3,3-trifluoro-2,2-dimethylpropionamide (Example No. 1-129)

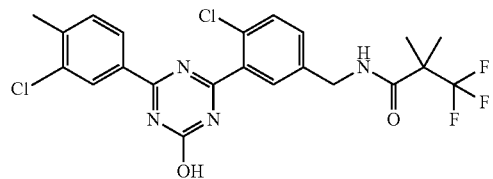 [SMILES: Cc1ccc(-c2nc(O)nc(-c3cc(CNC(=O)C(C)(C)C(F)(F)F)ccc3Cl)n2)cc1Cl]

(1) 2-chloro-4-(3-chloro-4-methylphenyl)-6-methoxy-1,3,5-triazine

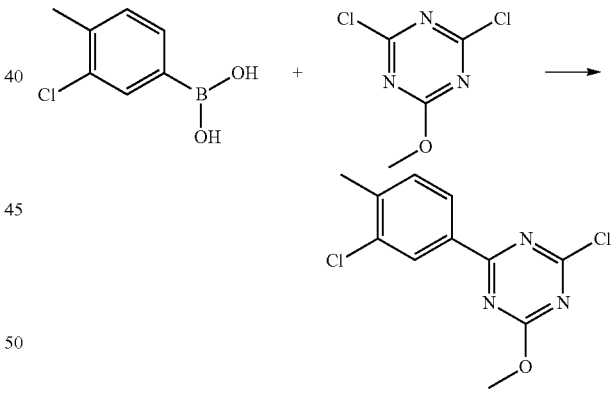

Under an argon atmosphere, to a suspension of 3-chloro-4-methylphenylboronic acid (0.47 g, 2.8 mmol), 2,4-dichloro-6-methoxy-1,3,5-triazine (1.0 g, 5.6 mmol) and tetrakis(triphenylphosphine)palladium(0) (0.32 g, 0.28 mmol) in toluene (5.0 ml) was added 2M aqueous sodium carbonate solution (4.2 ml), and the mixture was stirred at 100° C. for 2 hr. At room temperature, to the reaction mixture were added water and ethyl acetate, and the mixture was partitioned. The organic layer was washed with saturated brine, dried over sodium sulfate, filtered to remove sodium sulfate, and concentrated under reduced pressure. The residue was purified by silica gel column chromatography (eluent: n-hexane/ethyl acetate=97/3-94/6) to give the title compound (0.61 g, yield 81%).

¹H-NMR (CDCl₃) δ: 2.47 (3H, s), 4.17 (3H, s), 7.37 (1H, d, J=8.0 Hz), 8.28 (1H, dd, J=8.0, 1.8 Hz), 8.47 (1H, d, J=1.8 Hz).

(2) {4-chloro-3-[4-(3-chloro-4-methylphenyl)-6-methoxy-1,3,5-triazin-2-yl]phenyl}methanol

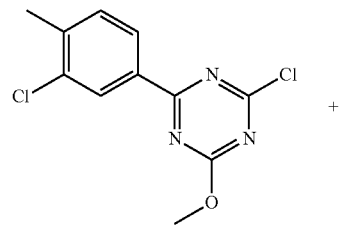

+

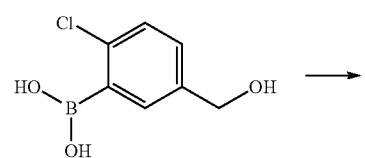

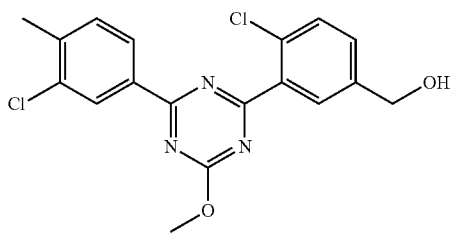

Under an argon atmosphere, to a solution of 2-chloro-4-(3-chloro-4-methylphenyl)-6-methoxy-1,3,5-triazine (0.61 g, 2.3 mmol) obtained in the above-mentioned (1), 2-chloro-5-hydroxymethylphenylboronic acid (0.51 g, 2.7 mmol) and [1,1'-bis(diphenylphosphino)ferrocene]palladium(II)dichloride dichloromethane adduct (0.19 g, 0.23 mmol) in 1,4-dioxane (6.0 ml) was added 2M aqueous sodium carbonate solution (4.5 ml), and the mixture was stirred at 100° C. for 1.5 hr. At room temperature, to the reaction mixture were added water and ethyl acetate, and the mixture was partitioned. The organic layer was washed with saturated brine, dried over sodium sulfate, filtered to remove sodium sulfate, and concentrated under reduced pressure. The residue was purified by silica gel column chromatography (eluent: n-hexane/ethyl acetate=8/2-6/4) to give the title compound (0.61 g, yield 71%).

¹H-NMR (CDCl₃) δ: 1.81 (1H, t, J=5.9 Hz), 2.47 (3H, s), 4.21 (3H, s), 4.78 (2H, d, J=5.9 Hz), 7.37 (1H, d, J=7.9 Hz), 7.47 (1H, dd, J=8.1, 2.2 Hz), 7.54 (1H, d, J=8.1 Hz), 8.01 (1H, d, J=2.2 Hz), 8.38 (1H, dd, J=7.9, 1.8 Hz), 8.57 (1H, d, J=1.8 Hz).

(3) 4-chloro-3-[4-(3-chloro-4-methylphenyl)-6-methoxy-1,3,5-triazin-2-yl]benzylamine hydrochloride

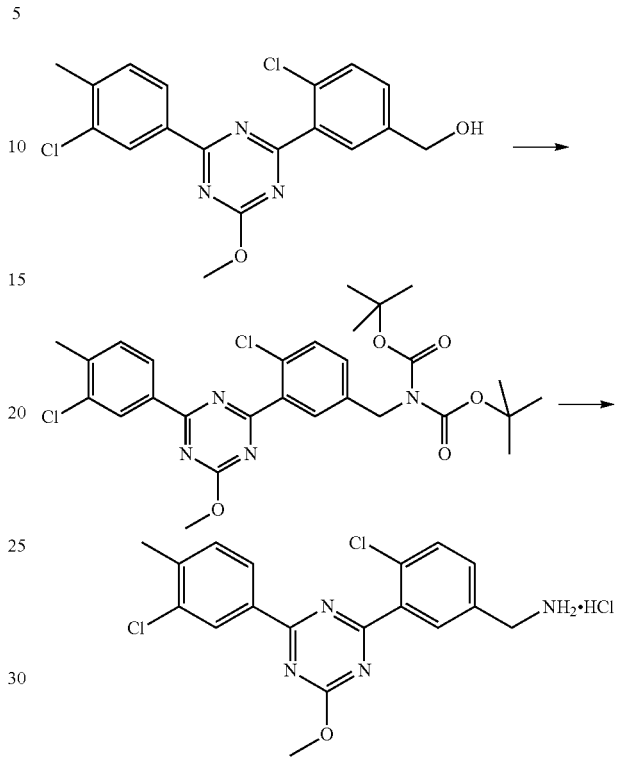

Under an argon atmosphere, to a solution of {4-chloro-3-[4-(3-chloro-4-methylphenyl)-6-methoxy-1,3,5-triazin-2-yl]phenyl}methanol (0.61 g, 1.6 mmol) obtained in the above-mentioned (2) in tetrahydrofuran (6.0 ml) were added triethylamine (0.29 ml, 2.1 mmol) and methanesulfonyl chloride (0.15 ml, 1.9 mmol) under ice-cooling, and the mixture was stirred for 1 hr. The reaction mixture was filtered, and the filtrate was concentrated under reduced pressure. To a solution of the residue in N,N-dimethylformamide (6.0 ml) were added cesium carbonate (1.6 g, 4.8 mmol) and di-tert-butyl iminodicarboxylate (0.42 g, 1.9 mmol) at room temperature, and the mixture was stirred for 2 hr. To the reaction mixture were added water and ethyl acetate, and the mixture was partitioned. The organic layer was washed with saturated brine, dried over sodium sulfate, filtered to remove sodium sulfate, and concentrated under reduced pressure. The residue was purified by silica gel column chromatography (eluent: n-hexane/ethyl acetate=95/5-80/20). Under an argon atmosphere, to a solution of the purified product in 1,4-dioxane (2.0 ml) was added 4M hydrogen chloride/1,4-dioxane solution (8.0 ml) at room temperature, and the mixture was stirred for 2.5 hr. To the reaction mixture was added n-hexane, and the solid was collected by filtration, and dried under reduced pressure to give the title compound (0.67 g, yield 99%).

¹H-NMR (DMSO-D₆) δ: 2.46 (3H, s), 4.12-4.21 (5H, m), 7.62 (1H, d, J=8.0 Hz), 7.73-7.75 (2H, m), 8.17 (1H, br s), 8.38 (1H, dd, J=8.0, 1.6 Hz), 8.47 (1H, d, J=1.6 Hz), 8.48 (3H, br s).

(4) N-{4-chloro-3-[4-(3-chloro-4-methylphenyl)-6-methoxy-1,3,5-triazin-2-yl]benzyl}-3,3,3-trifluoro-2,2-dimethylpropionamide

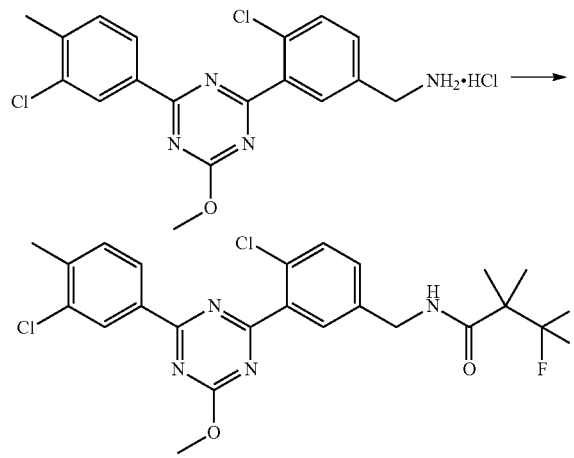

Under an argon atmosphere, to a solution of 4-chloro-3-[4-(3-chloro-4-methylphenyl)-6-methoxy-1,3,5-triazin-2-yl]benzylamine hydrochloride (0.070 g, 0.17 mmol) obtained in the above-mentioned (3), HOBt·H$_2$O (0.039 g, 0.26 mmol) and WSC·HCl (0.049 g, 0.26 mmol) in N,N-dimethylformamide (0.70 ml) were added 3,3,3-trifluoro-2,2-dimethylpropionic acid (0.037 g, 0.24 mmol) and triethylamine (0.071 ml, 0.51 mmol) at room temperature, and the mixture was stirred for 1 hr. To the reaction mixture were added water and ethyl acetate, and the mixture was partitioned. The organic layer was washed with saturated brine, dried over sodium sulfate, filtered to remove sodium sulfate, and concentrated under reduced pressure. The residue was purified by silica gel column chromatography (eluent: n-hexane/ethyl acetate=9/1-8/2) to give the title compound (0.072 g, yield 82%).

$^1$H-NMR (CDCl$_3$) δ: 1.45 (6H, s), 2.47 (3H, s), 4.21 (3H, s), 4.56 (2H, d, J=5.6 Hz), 6.24 (1H, br s), 7.34-7.39 (2H, m), 7.52 (1H, d, J=8.2 Hz), 7.92 (1H, d, J=2.3 Hz), 8.38 (1H, dd, J=8.2, 1.8 Hz), 8.56 (1H, d, J=1.8 Hz).

(5) N-{4-chloro-3-[4-(3-chloro-4-methylphenyl)-6-hydroxy-1,3,5-triazin-2-yl]benzyl}-3,3,3-trifluoro-2,2-dimethylpropionamide (Example No. 1-129)

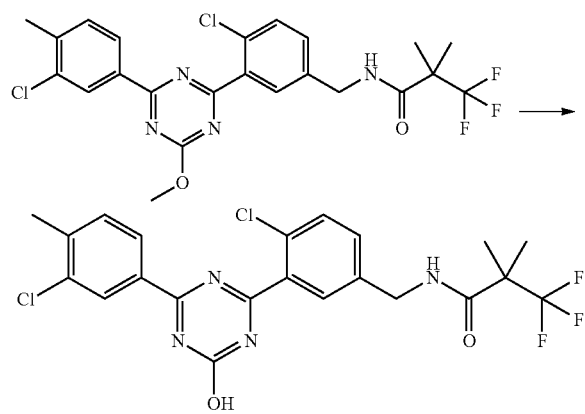

Under an argon atmosphere, to a solution of N-{4-chloro-3-[4-(3-chloro-4-methylphenyl)-6-methoxy-1,3,5-triazin-2-yl]benzyl}-3,3,3-trifluoro-2,2-dimethylpropionamide (0.072 g, 0.14 mmol) obtained in the above-mentioned (4) in methanol (0.70 ml) was added 4M aqueous sodium hydroxide solution (0.28 ml) at room temperature, and the mixture was stirred at 60° C. for 1 hr. To the reaction mixture were added 2N hydrochloric acid (0.56 ml) and water at room temperature, and the mixture was stirred. The precipitated solid was collected by filtration, washed with water, and dried under reduced pressure to give the title compound (0.057 g, yield 82%).

Production Example 16

Synthesis of N-{4-chloro-3-[4-hydroxy-6-(3-isopropyl-4-trifluoromethylphenyl)-1,3,5-triazin-2-yl]benzyl}-3,3,3-trifluoro-2,2-dimethylpropionamide (Example No. 1-130)

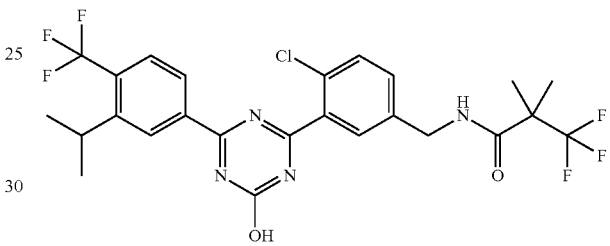

(1) 4-benzyloxy-2-bromo-1-trifluoromethylbenzene

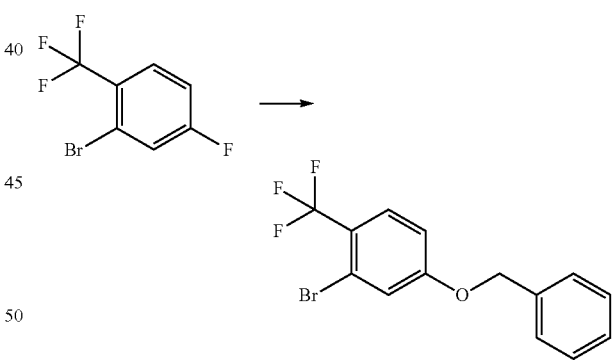

Under an argon atmosphere, to a solution of 2-bromo-4-fluoro-1-trifluoromethylbenzene (1.5 g, 6.2 mmol) and sodium hydride (0.74 g, 60 wt % oil dispersion) in N,N-dimethylformamide (15 ml) was added benzyl alcohol (0.64 ml, 6.2 mmol) under ice-cooling, and the mixture was stirred for 0.5 hr. The reaction mixture was stirred at 60° C. for 2 hr. At room temperature, to the reaction mixture were added water and ethyl acetate, and the mixture was partitioned. The organic layer was washed with saturated brine, dried over sodium sulfate, filtered to remove sodium sulfate, and concentrated under reduced pressure. The residue was purified by silica gel column chromatography (eluent: n-hexane/ethyl acetate=99/1-98/2) to give the title compound (1.3 g, yield 69%).

$^1$H-NMR (CDCl$_3$) δ: 5.08 (2H, s), 6.93 (1H, dd, J=8.8, 2.4 Hz), 7.30 (1H, d, J=2.4 Hz), 7.33-7.41 (5H, m), 7.57 (1H, d, J=8.8 Hz).

(2) 4-benzyloxy-2-isopropenyl-1-trifluoromethylbenzene

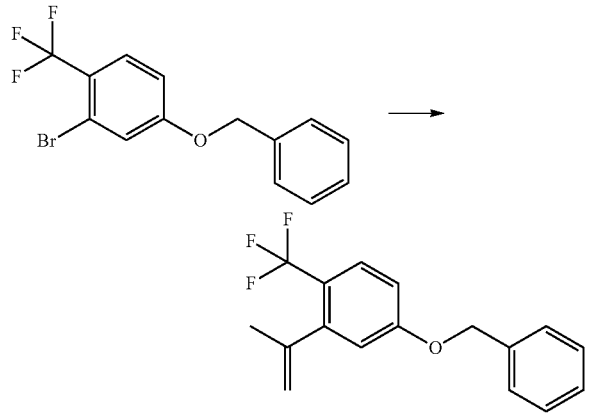

Under an argon atmosphere, to a solution of 4-benzyloxy-2-bromo-1-trifluoromethylbenzene (1.3 g, 3.9 mmol) obtained in the above-mentioned (1) in 1,4-dioxane (13 ml) were added 2-isopropenyl-4,4,5,5-tetramethyl-[1,3,2]dioxaborolane (0.99 g, 5.9 mmol), [1,1'-bis(diphenylphosphino)ferrocene]palladium(II)dichloride dichloromethane adduct (0.32 g, 0.39 mmol) and 2M aqueous sodium carbonate solution (5.9 ml) at room temperature, and the mixture was stirred at 100° C. for 2 hr. At room temperature, to the reaction mixture were added water and ethyl acetate, and the mixture was partitioned. The organic layer was washed with saturated brine, dried over sodium sulfate, filtered to remove sodium sulfate, and concentrated under reduced pressure. The residue was purified by silica gel column chromatography (eluent: n-hexane/ethyl acetate=99/1-97/3) to give the title compound (1.1 g, yield 99%).

$^1$H-NMR (CDCl$_3$) δ: 2.04 (3H, s), 4.88 (1H, br s), 5.08 (2H, s), 5.18 (1H, br s), 6.82 (1H, d, J=2.6 Hz), 6.89 (1H, dd, J=8.8, 2.6 Hz), 7.31-7.42 (5H, m), 7.54 (1H, d, J=8.8 Hz).

(3) 3-isopropyl-4-trifluoromethylphenol

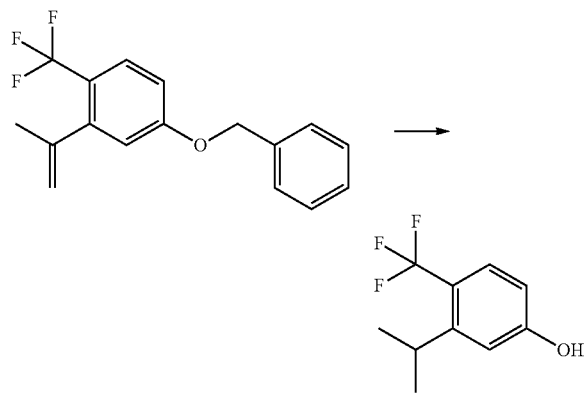

Under an argon atmosphere, to a solution of 4-benzyloxy-2-isopropenyl-1-trifluoromethylbenzene (1.2 g, 3.9 mmol) obtained in the above-mentioned (2) in tetrahydrofuran (12 ml) was added 10 wt % palladium carbon (0.23 g) at room temperature, and the mixture was stirred under 1 atm hydrogen atmosphere for hr. Under a nitrogen atmosphere, the reaction mixture was filtered through celite and eluted with ethyl acetate. The filtrate was concentrated under reduced pressure to give the title compound (0.76 g, yield 96%).

$^1$H-NMR (CDCl$_3$) δ: 1.23 (6H, d, J=6.7 Hz), 3.24-3.35 (1H, m), 5.04 (1H, br s), 6.66 (1H, dd, J=8.6, 2.6 Hz), 6.87 (1H, d, J=2.6 Hz), 7.46 (1H, d, J=8.6 Hz).

(4) 3-isopropyl-4-trifluoromethylphenyl trifluoromethanesulfonate

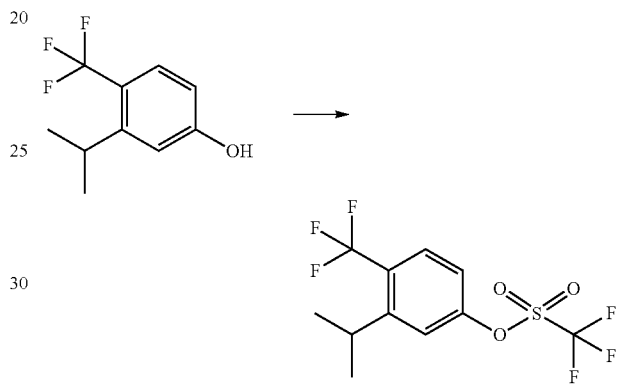

Under an argon atmosphere, to a solution of 3-isopropyl-4-trifluoromethylphenol (0.77 g, 3.8 mmol) obtained in the above-mentioned (3) in chloroform (8.0 ml) were added triethylamine (0.58 ml, 4.1 mmol) and trifluoromethanesulfonic anhydride (0.67 ml, 4.0 mmol) under ice-cooling, and the mixture was stirred for 1 hr. To the reaction mixture were added water and chloroform, and the mixture was partitioned. The organic layer was washed with saturated brine, dried over sodium sulfate, filtered to remove sodium sulfate, and concentrated under reduced pressure. The residue was purified by silica gel column chromatography (eluent: n-hexane/ethyl acetate=98/2) to give the title compound (0.78 g, yield 62%).

$^1$H-NMR (CDCl$_3$) δ: 1.28 (6H, d, J=6.7 Hz), 3.34-3.46 (1H, m), 7.19 (1H, dd, J=8.8, 2.4 Hz), 7.34 (1H, d, J=2.4 Hz), 7.70 (1H, d, J=8.8 Hz).

(5) 2-(3-isopropyl-4-trifluoromethylphenyl)-4,4,5,5-tetramethyl-[1,3,2]dioxaborolane

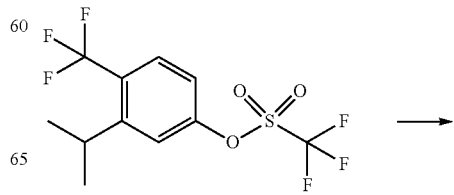

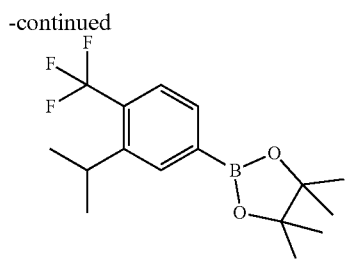

Under an argon atmosphere, to a solution of 3-isopropyl-4-trifluoromethylphenyl trifluoromethanesulfonate (0.78 g, 2.3 mmol) obtained in the above-mentioned (4) in DMSO (8.0 ml) were added bis(pinacolato)diboron (0.71 g, 2.8 mmol), potassium acetate (0.68 g, 7.0 mmol) and [1,1'-bis(diphenylphosphino)ferrocene]palladium(II)dichloride dichloromethane adduct (0.095 g, 0.12 mmol) at room temperature, and the mixture was stirred at 80° C. for 2 hr. At room temperature, to the reaction mixture were added water and ethyl acetate, and the mixture was partitioned. The organic layer was washed with saturated brine, dried over sodium sulfate, filtered to remove sodium sulfate, and concentrated under reduced pressure. The residue was purified by silica gel column chromatography (eluent: n-hexane/ethyl acetate=98/2) to give the title compound (0.48 g, yield 66%).

$^1$H-NMR (CDCl$_3$) δ: 1.29 (6H, d, J=7.0 Hz), 1.36 (12H, s), 3.29-3.40 (1H, m), 7.57 (1H, d, J=7.9 Hz), 7.68 (1H, d, J=7.9 Hz), 7.88 (1H, br s).

(6) 2-chloro-4-(3-isopropyl-4-trifluoromethylphenyl)-6-methoxy-1,3,5-triazine

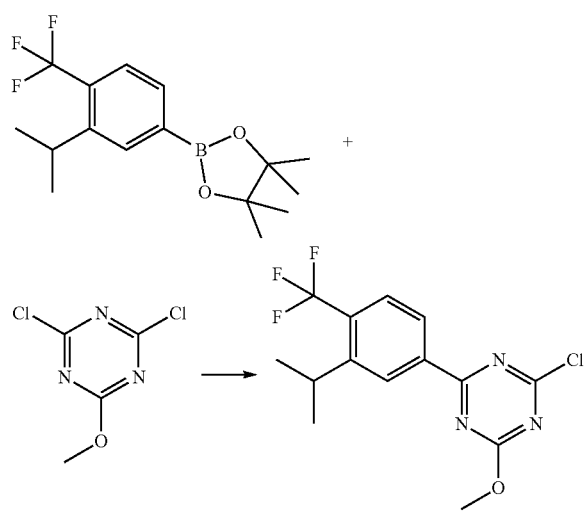

Under an argon atmosphere, to a suspension of 2-(3-isopropyl-4-trifluoromethylphenyl)-4,4,5,5-tetramethyl-[1,3,2]dioxaborolane (0.48 g, 1.5 mmol) obtained in the above-mentioned (5), 2,4-dichloro-6-methoxy-1,3,5-triazine (0.69 g, 3.8 mmol) and [1,1'-bis(diphenylphosphino)ferrocene]palladium(II)dichloride dichloromethane adduct (0.13 g, 0.15 mmol) in 1,4-dioxane (5.0 ml) was added 2M aqueous sodium carbonate solution (3.1 mL), and the mixture was stirred at 100° C. for 1 hr. At room temperature, to the reaction mixture were added water and ethyl acetate, and the mixture was partitioned. The organic layer was washed with saturated brine, dried over sodium sulfate, filtered to remove sodium sulfate, and concentrated under reduced pressure. The residue was purified by silica gel column chromatography (eluent: n-hexane/ethyl acetate=97/3-94/6) to give the title compound (0.36 g, yield 71%).

(7) {4-chloro-3-[4-(3-isopropyl-4-trifluoromethylphenyl)-6-methoxy-1,3,5-triazin-2-yl]phenyl}methanol

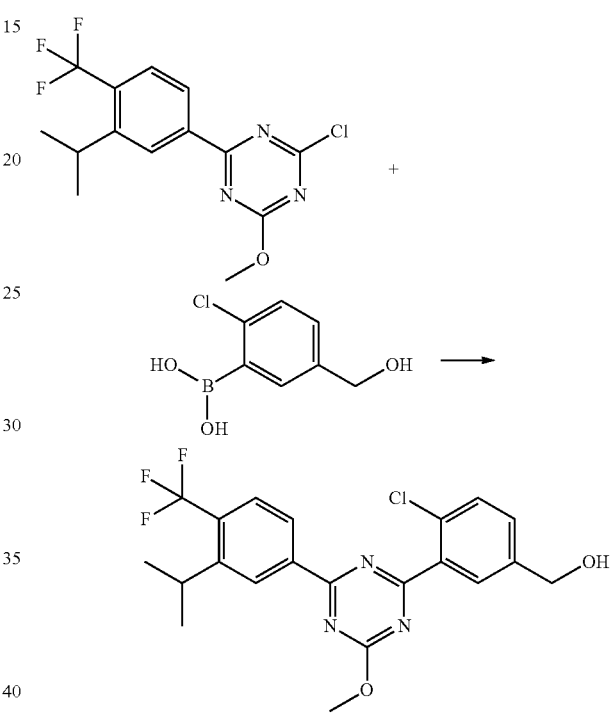

Under an argon atmosphere, to a solution of 2-chloro-4-(3-isopropyl-4-trifluoromethylphenyl)-6-methoxy-1,3,5-triazine (0.36 g, 1.1 mmol) obtained in the above-mentioned (6), 2-chloro-5-hydroxymethylphenylboronic acid (0.25 g, 1.3 mmol) and [1,1'-bis(diphenylphosphino)ferrocene]palladium(II)dichloride dichloromethane adduct (0.089 g, 0.11 mmol) in 1,4-dioxane (3.6 ml) was added 2M aqueous sodium carbonate solution (2.2 ml), and the mixture was stirred at 100° C. for 1.5 hr. At room temperature, to the reaction mixture were added water and ethyl acetate, and the mixture was partitioned. The organic layer was washed with saturated brine, dried over sodium sulfate, is filtered to remove sodium sulfate, and concentrated under reduced pressure. The residue was purified by silica gel column chromatography (eluent: n-hexane/ethyl acetate=8/2-1/1) to give the title compound (0.30 g, yield 62%).

$^1$H-NMR (CDCl$_3$) δ: 1.36 (6H, d, J=6.8 Hz), 1.79 (1H, t, J=6.0 Hz), 3.37-3.48 (1H, m), 4.24 (3H, s), 4.79 (2H, d, J=6.0 Hz), 7.49 (1H, dd, J=8.4, 2.2 Hz), 7.57 (1H, d, J=8.4 Hz), 7.75 (1H, d, J=8.4 Hz), 8.07 (1H, d, J=2.2 Hz), 8.47 (1H, d, J=8.4 Hz), 8.73 (1H, br s).

(8) 4-chloro-3-[4-(3-isopropyl-4-trifluoromethylphenyl)-6-methoxy-1,3,5-triazin-2-yl]benzylamine hydrochloride

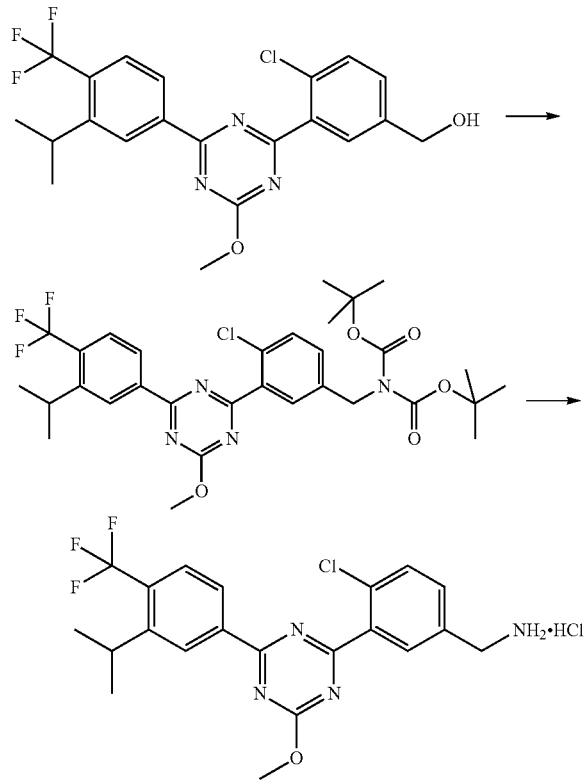

Under an argon atmosphere, to a solution of {4-chloro-3-[4-(3-isopropyl-4-trifluoromethylphenyl)-6-methoxy-1,3,5-triazin-2-yl]phenyl}methanol (0.30 g, 0.68 mmol) obtained in the above-mentioned (7) in tetrahydrofuran (3.0 ml) were added triethylamine (0.12 ml, 0.89 mmol) and methanesulfonyl chloride (0.063 ml, 0.82 mmol) under ice-cooling, and the mixture was stirred for 0.5 hr. The reaction mixture was filtered, and the filtrate was concentrated under reduced pressure. To a solution of the residue in N,N-dimethylformamide (3.0 ml) were added cesium carbonate (0.67 g, 2.0 mmol) and di-tert-butyl iminodicarboxylate (0.18 g, 0.82 mmol) at room temperature, and the mixture was stirred for 1.5 hr. To the reaction mixture were added water and ethyl acetate, and the mixture was partitioned. The organic layer was washed with saturated brine, dried over sodium sulfate, filtered to remove sodium sulfate, and concentrated under reduced pressure. The residue was purified by silica gel column chromatography (eluent: n-hexane/ethyl acetate=95/5-80/20). Under an argon atmosphere, to a solution (1.0 ml) of the purified product in 1,4-dioxane was added 4M hydrogen chloride/1,4-dioxane solution (4.0 ml) at room temperature, and the mixture was stirred for 1.5 hr. To the reaction mixture was added n-hexane, and the solid was collected by filtration and dried under reduced pressure to give the title compound (0.24 g, yield 74%).

$^1$H-NMR (DMSO-$D_6$) δ: 1.33 (6H, d, J=6.7 Hz), 3.28-3.40 (1H, m), 4.13-4.22 (5H, m), 7.73 (1H, dd, J=8.2, 2.2 Hz), 7.77 (1H, d, J=8.3 Hz), 7.92 (1H, d, J=8.3 Hz), 8.20 (1H, d, J=2.2 Hz), 8.35 (3H, br s), 8.48 (1H, d, J=8.8 Hz), 8.70 (1H, s).

(9) N-{4-chloro-3-[4-(3-isopropyl-4-trifluoromethylphenyl)-6-methoxy-1,3,5-triazin-2-yl]benzyl}-3,3,3-trifluoro-2,2-dimethylpropionamide

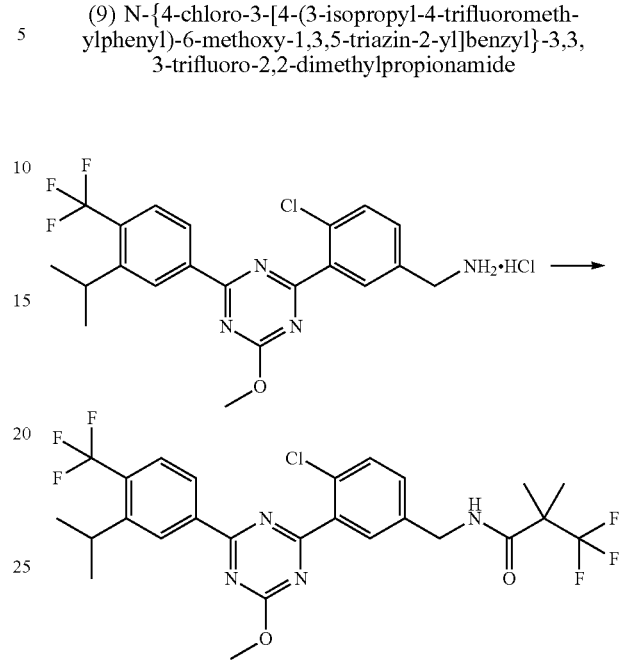

Under an argon atmosphere, to a solution of 4-chloro-3-[4-(3-isopropyl-4-trifluoromethylphenyl)-6-methoxy-1,3,5-triazin-2-yl]benzylamine hydrochloride (0.080 g, 0.17 mmol) obtained in the above-mentioned (8), HOBt·$H_2$O (0.039 g, 0.26 mmol) and WSC·HCl (0.049 g, 0.26 mmol) in N,N-dimethylformamide (0.80 ml) were added 3,3,3-trifluoro-2,2-dimethylpropionic acid (0.037 g, 0.24 mmol) and triethylamine (0.071 ml, 0.51 mmol) at room temperature, and the mixture was stirred for 1 hr. To the reaction mixture were added water and ethyl acetate, and the mixture was partitioned. The organic layer was washed with saturated brine, dried over sodium sulfate, filtered to remove sodium sulfate, and concentrated under reduced pressure. The residue was purified by silica gel column chromatography (eluent: n-hexane/ethyl acetate=19/1-8/2) to give the title compound (0.077 g, yield 79%).

$^1$H-NMR (CDCl$_3$) δ: 1.35 (6H, d, J=6.0 Hz), 1.44 (6H, br s), 3.37-3.49 (1H, m), 4.23 (3H, s), 4.56 (2H, d, J=5.8 Hz), 6.25 (1H, br s), 7.37 (1H, dd, J=8.4, 2.3 Hz), 7.54 (1H, d, J=8.4 Hz), 7.74 (1H, d, J=8.4 Hz), 7.96 (1H, d, J=2.3 Hz), 8.46 (1H, d, J=8.4 Hz), 8.72 (1H, br s).

(10) N-{4-chloro-3-[4-hydroxy-6-(3-isopropyl-4-trifluoromethylphenyl)-1,3,5-triazin-2-yl]benzyl}-3,3,3-trifluoro-2,2-dimethylpropionamide (Example No. 1-130)

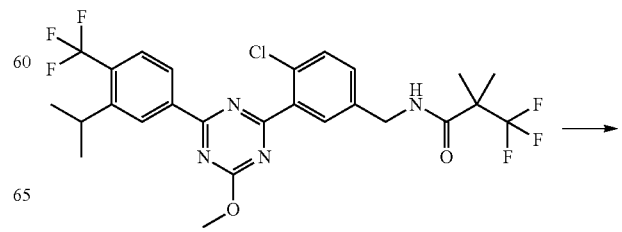

-continued

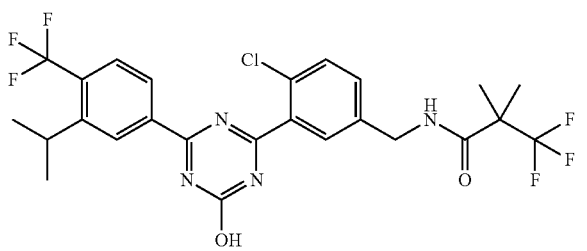 [SMILES: CC(C)c1cc(-c2nc(O)nc(-c3cc(CNC(=O)C(C)(C)C(F)(F)F)ccc3Cl)n2)ccc1C(F)(F)F]

Under an argon atmosphere, to a solution of N-{4-chloro-3-[4-(3-isopropyl-4-trifluoromethylphenyl)-6-methoxy-1,3,5-triazin-2-yl]benzyl}-3,3,3-trifluoro-2,2-dimethylpropionamide (0.077 g, 0.13 mmol) obtained in the above-mentioned (9) in methanol (0.80 ml) was added 4M aqueous sodium hydroxide solution (0.27 ml) at room temperature, and the mixture was is stirred at 60° C. for 1 hr. To the reaction mixture were added 2N hydrochloric acid (0.54 ml) and water at room temperature, and the mixture was stirred. The precipitated solid was collected by filtration, washed with water, and dried under reduced pressure to give the title compound (0.066 g, yield 88%).

Production Example 17

Synthesis of N-{3-[4-(4-butoxyphenyl)-6-hydroxy-1,3,5-triazin-2-yl]-4-chlorobenzyl}-3,3,3-trifluoro-2,2-dimethylpropionamide (Example No. 1-131)

(1) N-{3-[4-(4-butoxyphenyl)-6-methoxy-1,3,5-triazin-2-yl]-4-chlorobenzyl}-3,3,3-trifluoro-2,2-dimethylpropionamide

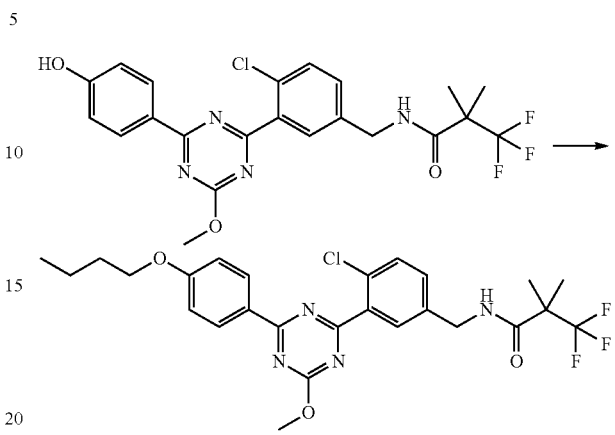

Under an argon atmosphere, to a solution of N-{4-chloro-3-[4-(4-hydroxyphenyl)-6-methoxy-1,3,5-triazin-2-yl]benzyl}-3,3,3-trifluoro-2,2-dimethylpropionamide (0.10 g, 0.21 mmol) obtained in the above-mentioned [Production Example 14] (6), n-butanol (0.023 ml, 0.25 mmol) and triphenylphosphine (0.066 g, 0.25 mmol) in tetrahydrofuran (1.0 ml) was added bis(2-methoxyethyl) azodicarboxylate (0.059 g, 0.25 mmol) under ice-cooling, and the mixture was stirred for 1 hr. To the reaction mixture were added n-butanol (0.019 ml, 0.21 mmol), triphenylphosphine (0.055 g, 0.21 mmol) and bis(2-methoxyethyl) azodicarboxylate (0.049 g, 0.21 mmol), and the mixture was stirred at room temperature for 2 hr. To the reaction mixture were added water and ethyl acetate, and the mixture was partitioned. The organic layer was washed with saturated brine, dried over magnesium sulfate, filtered to remove magnesium sulfate, and concentrated under reduced pressure. The residue was purified by silica gel column chromatography (eluent: n-hexane/ethyl acetate=1/1) to give the title compound (0.096 g, yield 85%).

(2) N-{3-[4-(4-butoxyphenyl)-6-hydroxy-1,3,5-triazin-2-yl]-4-chlorobenzyl}-3,3,3-trifluoro-2,2-dimethylpropionamide (Example No. 1-131)

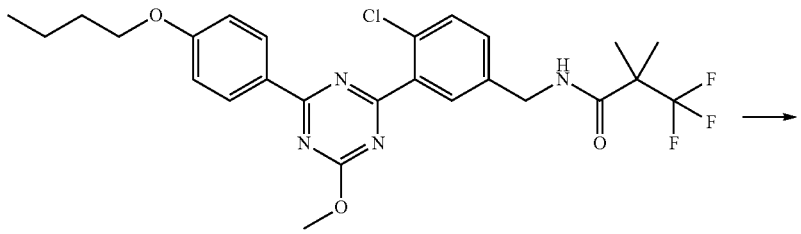

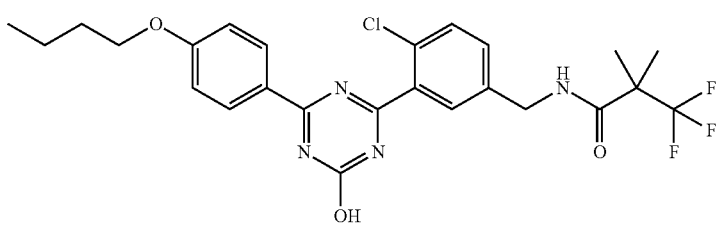

Under an argon atmosphere, to a solution of N-{3-[4-(4-butoxyphenyl)-6-methoxy-1,3,5-triazin-2-yl]-4-chlorobenzyl}-3,3,3-trifluoro-2,2-dimethylpropionamide (0.096 g, 0.18 mmol) obtained in the above-mentioned (1) in methanol (0.96 ml) was added 4M aqueous sodium hydroxide solution (0.27 ml) at room temperature, and the mixture was stirred at 65° C. for 2 hr. To the reaction mixture were added 2N hydrochloric acid (0.54 ml) and water and the mixture was stirred at room temperature. The precipitated solid was collected by filtration, washed with water, and dried under reduced pressure to give the title compound (0.086 g, yield 93%).

Production Example 18

Synthesis of N-{4-chloro-3-[4-(3-cyclopropyl-4-fluorophenyl)-6-hydroxy-1,3,5-triazin-2-yl]benzyl}-3,3,3-trifluoro-2,2-dimethylpropionamide (Example No. 1-135)

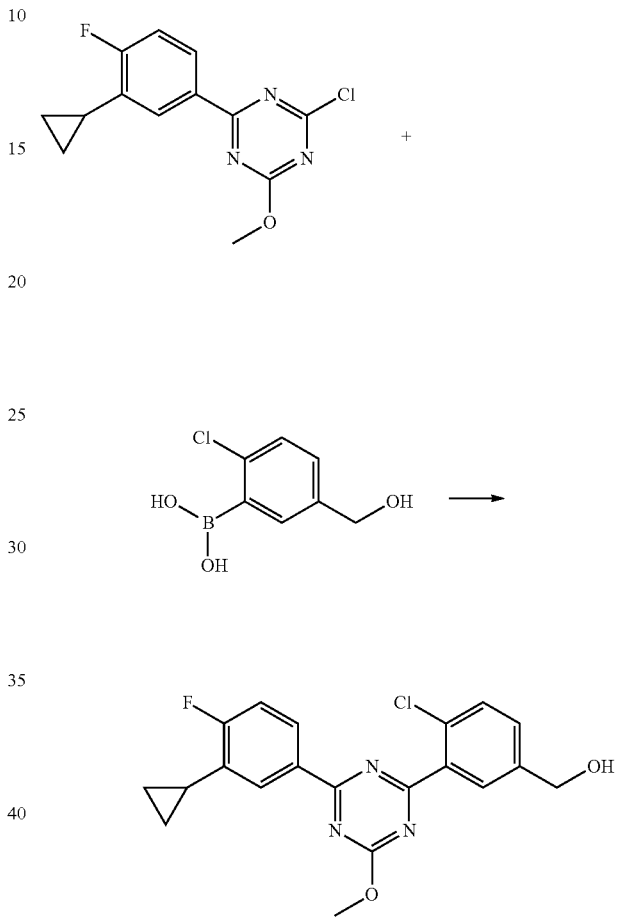

(1) 2-chloro-4-(3-cyclopropyl-4-fluorophenyl)-6-methoxy-1,3,5-triazine

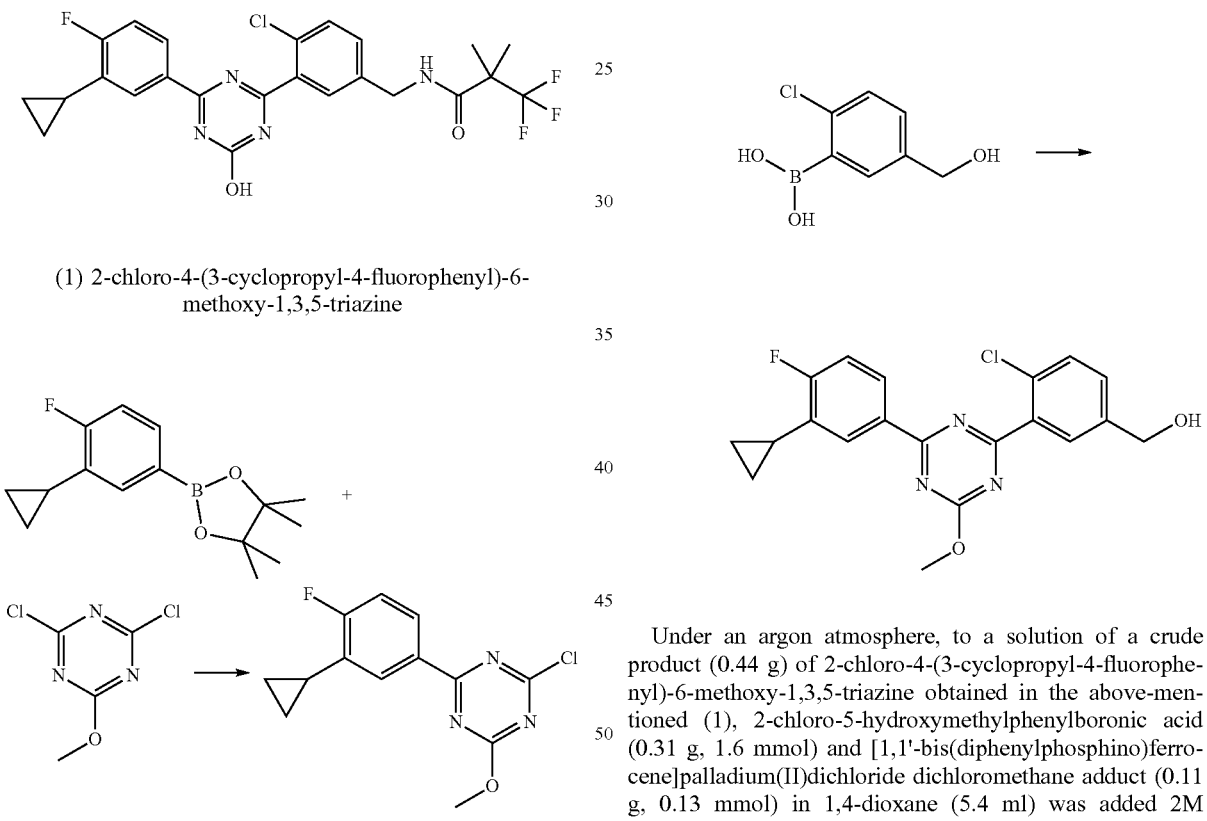

Under an argon atmosphere, to a suspension of 2-(3-cyclopropyl-4-fluorophenyl)-4,4,5,5-tetramethyl-[1,3,2]dioxaborolane (0.59 g, 2.2 mmol), 2,4-dichloro-6-methoxy-1,3,5-triazine (0.81 g, 4.5 mmol) and [1,1'-bis(diphenylphosphino)ferrocene]palladium(II)dichloride dichloromethane adduct (0.18 g, 0.22 mmol) in 1,4-dioxane (3.0 ml) was added 2M aqueous sodium carbonate solution (3.4 ml), is and the mixture was stirred at 100° C. for 1 hr. At room temperature, to the reaction mixture were added water and ethyl acetate, and the mixture was partitioned. The organic layer was washed with saturated brine, dried over sodium sulfate, filtered to remove sodium sulfate, and concentrated under reduced pressure. The residue was purified by silica gel column chromatography (eluent: n-hexane/ethyl acetate=25/1-20/1) to give the title compound as a crude product (0.44 g).

(2) {4-chloro-3-[4-(3-cyclopropyl-4-fluorophenyl)-6-methoxy-1,3,5-triazin-2-yl]phenyl}methanol Under an argon atmosphere, to a solution of a crude product (0.44 g) of 2-chloro-4-(3-cyclopropyl-4-fluorophenyl)-6-methoxy-1,3,5-triazine obtained in the above-mentioned (1), 2-chloro-5-hydroxymethylphenylboronic acid (0.31 g, 1.6 mmol) and [1,1'-bis(diphenylphosphino)ferrocene]palladium(II)dichloride dichloromethane adduct (0.11 g, 0.13 mmol) in 1,4-dioxane (5.4 ml) was added 2M aqueous sodium carbonate solution (2.7 ml), and the mixture was stirred at 100° C. for 1 hr. At room temperature, to the reaction mixture were added water and ethyl acetate, and the mixture was partitioned. The organic layer was washed with saturated brine, dried over sodium sulfate, filtered to remove sodium sulfate, and concentrated under reduced pressure. The residue was purified by silica gel column chromatography (eluent: n-hexane/ethyl acetate=5/3) to give the title compound (0.32 g).

$^1$H-NMR (CDCl$_3$) δ: 0.83-0.88 (2H, m), 1.01-1.07 (2H, m), 1.79 (1H, t, J=6.0 Hz), 2.10-2.19 (1H, m), 4.20 (3H, s), 4.77 (2H, d, J=6.0 Hz), 7.13 (1H, t, J=9.2 Hz), 7.47 (1H, d, J=8.1 Hz), 7.54 (1H, d, J=8.1 Hz), 8.01 (1H, br s), 8.20 (1H, d, J=7.6 Hz), 8.38-8.41 (1H, m).

(3) tert-butyl N-{4-chloro-3-[4-(3-cyclopropyl-4-fluorophenyl)-6-methoxy-1,3,5-triazin-2-yl]benzyl}-N-(tert-butoxycarbonyl)carbamate

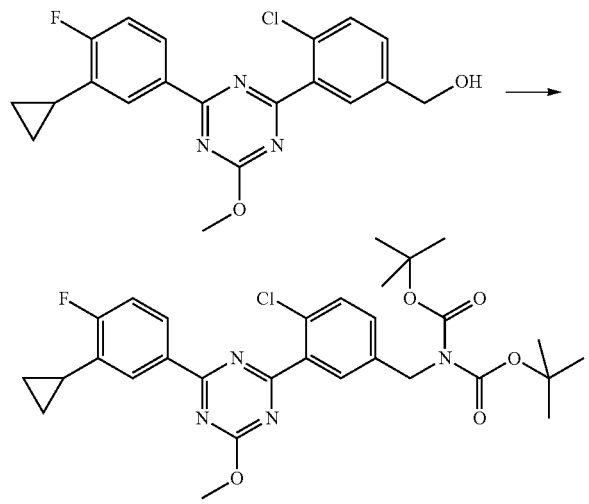

Under an argon atmosphere, to a solution of {4-chloro-3-[4-(3-cyclopropyl-4-fluorophenyl)-6-methoxy-1,3,5-triazin-2-yl]phenyl}methanol (0.32 g, 0.82 mmol) obtained in the above-mentioned (2) in tetrahydrofuran (3.3 ml) were added triethylamine (0.15 ml, 1.1 mmol) and methanesulfonyl chloride (0.076 ml, 0.98 mmol) under ice-cooling, and the mixture was stirred for 0.5 hr. The reaction mixture was filtered, and the filtrate was concentrated under reduced pressure. To a solution of the residue in N,N-dimethylformamide (3.3 ml) were added cesium carbonate (0.80 g, 2.5 mmol) and di-tert-butyl iminodicarboxylate (0.21 g, 0.98 mmol) at room temperature, and the mixture was stirred for 1 hr. To the reaction mixture were added water and ethyl acetate, and the mixture was partitioned. The organic layer was washed with saturated brine, dried over magnesium sulfate, filtered to remove magnesium sulfate, and concentrated under reduced pressure. The residue was purified by silica gel column chromatography (eluent: n-hexane/ethyl acetate=7/1) to give the title compound (0.40 g, yield 83%).

$^1$H-NMR (CDCl$_3$) δ: 0.84-0.88 (2H, m), 1.01-1.07 (2H, m), 1.47 (18H, s), 2.09-2.18 (1H, m), 4.18 (3H, s), 4.83 (2H, s), 7.11 (1H, dd, J=9.7, 8.6 Hz), 7.40 (1H, dd, J=8.3, 2.2 Hz), 7.49 (1H, d, J=8.3 Hz), 8.00 (1H, d, J=2.2 Hz), 8.19 (1H, dd, J=7.5, 2.2 Hz), 8.36-8.41 (1H, m).

(4) 4-chloro-3-[4-(3-cyclopropyl-4-fluorophenyl)-6-methoxy-1,3,5-triazin-2-yl]benzylamine hydrochloride

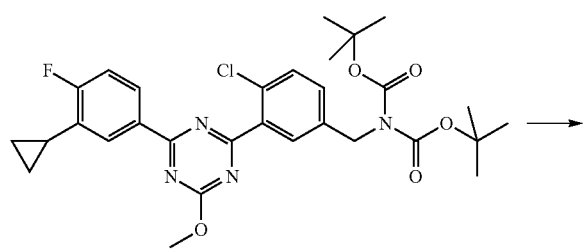

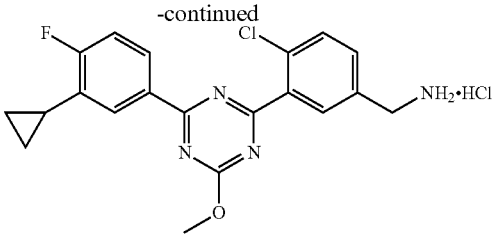

Under an argon atmosphere, to tert-butyl N-{4-chloro-3-[4-(3-cyclopropyl-4-fluorophenyl)-6-methoxy-1,3,5-triazin-2-yl]benzyl}-N-(tert-butoxycarbonyl)carbamate (0.40 g, 0.68 mmol) obtained in the above-mentioned (3) was added 4M hydrogen chloride/1,4-dioxane solution (3.3 ml) at room temperature, and the mixture was stirred for 1 hr. To the reaction mixture was added ethyl acetate (35 ml), and the mixture was stirred. The solid was collected by filtration and dried under reduced pressure to give the title compound (0.26 g, yield 89%).

$^1$H-NMR (DMSO-D$_6$) δ: 0.78-0.83 (2H, m), 1.05-1.10 (2H, m), 2.10-2.19 (1H, m), 4.16 (3H, s), 4.16 (2H, s), 7.39 (1H, dd, J=9.9, 8.7 Hz), 7.71 (1H, dd, J=8.4, 2.1 Hz), 7.75 (1H, d, J=8.4 Hz), 8.13 (1H, dd, J=7.7, 2.1 Hz), 8.16 (1H, d, J=2.1 Hz), 8.35-8.37 (4H, m).

(5) N-{4-chloro-3-[4-(3-cyclopropyl-4-fluorophenyl)-6-methoxy-1,3,5-triazin-2-yl]benzyl}-3,3,3-trifluoro-2,2-dimethylpropionamide

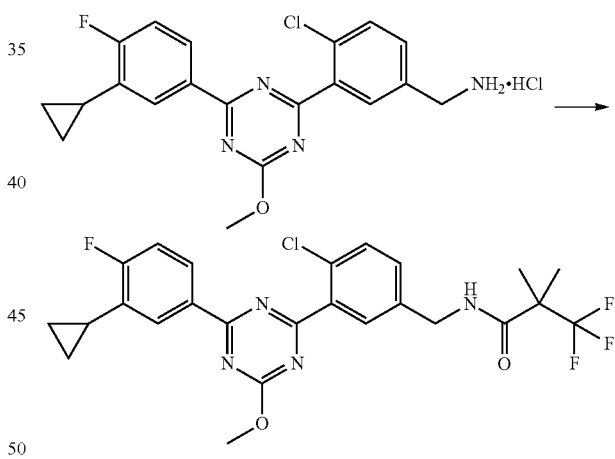

Under an argon atmosphere, to a solution of 4-chloro-3-[4-(3-cyclopropyl-4-fluorophenyl)-6-methoxy-1,3,5-triazin-2-yl]benzylamine hydrochloride (0.070 g, 0.17 mmol) obtained in the above-mentioned (4), HOBt·H$_2$O (0.033 g, 0.22 mmol) and WSC·HCl (0.041 g, 0.22 mmol) in N,N-dimethylformamide (2.0 ml) were added 3,3,3-trifluoro-2,2-dimethylpropionic acid (0.034 g, 0.22 mmol) and triethylamine (0.069 ml, 0.48 mmol) at room temperature, and the mixture was stirred for 3 hr. To the reaction mixture were added saturated aqueous sodium hydrogen carbonate and ethyl acetate, and the mixture was partitioned. The organic layer was washed with saturated brine, dried over sodium sulfate, filtered to remove sodium sulfate, and concentrated under reduced pressure. The residue was purified by silica gel column chromatography (eluent: n-hexane/ethyl acetate=5/3) to give the title compound (0.082 g, yield 94%).

¹H-NMR (CDCl₃) δ: 0.82-0.87 (2H, m), 1.01-1.05 (2H, m), 1.43 (6H, s), 2.10-2.16 (1H, m), 4.18 (3H, s), 4.54 (2H, d, J=5.6 Hz), 6.21 (1H, br s), 7.11 (1H, t, J=9.2 Hz), 7.34 (1H, d, J=8.3 Hz), 7.51 (1H, d, J=8.3 Hz), 7.90 (1H, s), 8.18 (1H, d, J=7.7 Hz), 8.36-8.40 (1H, m).

(6) N-{4-chloro-3-[4-(3-cyclopropyl-4-fluorophenyl)-6-hydroxy-1,3,5-triazin-2-yl]benzyl}-3,3,3-trifluoro-2,2-dimethylpropionamide (Example No. 1-135)

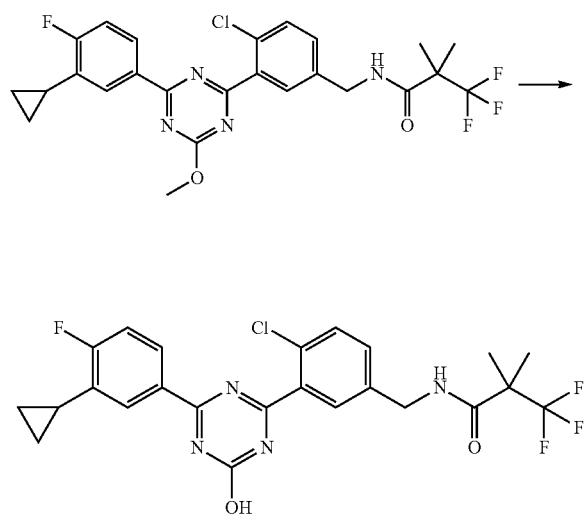

Under an argon atmosphere, to a solution of N-{4-chloro-3-[4-(3-cyclopropyl-4-fluorophenyl)-6-methoxy-1,3,5-triazin-2-yl]benzyl}-3,3,3-trifluoro-2,2-dimethylpropionamide (0.082 g, 0.16 mmol) obtained in the above-mentioned (5) in methanol (1.8 ml) was added 4M aqueous sodium hydroxide solution (0.24 ml) at room temperature, and the mixture was stirred at 60° C. for 3 hr. To the reaction mixture were added 10% aqueous citric acid solution (1.0 ml) and water, and the mixture was stirred at room temperature. The precipitated solid was collected by filtration, washed with water, and dried under reduced pressure to give the title compound (0.065 g, yield 81%).

Production Example 19

Synthesis of (R)—N-{4-chloro-3-[4-(4-chloro-3-methylphenyl)-6-hydroxy-1,3,5-triazin-2-yl]benzyl}-3,3,3-trifluoro-2-methoxy-2-methylpropionamide (Example No. 1-136)

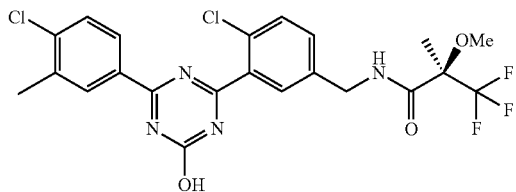 [SMILES: CO[C@](C)(C(=O)NCc1ccc(Cl)c(-c2nc(O)nc(-c3ccc(Cl)c(C)c3)n2)c1)C(F)(F)F]

(1) benzyl (R)-3,3,3-trifluoro-2-hydroxy-2-methylpropionate

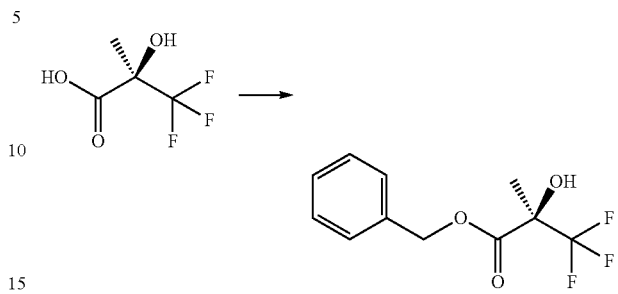

Under an argon atmosphere, to a suspension of (R)-3,3,3-trifluoro-2-hydroxy-2-methylpropionic acid (2.2 g, 14 mmol) and potassium carbonate (2.3 g, 16 mmol) in N,N-dimethylformamide (30 ml) was added benzyl bromide (1.8 ml, 15 mmol) at room temperature, and the mixture was stirred for 4 hr. To the reaction mixture were added water and ethyl acetate, and the mixture was partitioned. The organic layer was washed with saturated brine, dried over sodium sulfate, filtered to remove sodium sulfate, and concentrated under reduced pressure. The residue was purified by silica gel column chromatography (eluent: n-hexane/ethyl acetate=6/1) to give the title compound (3.0 g, yield 90%).

¹H-NMR (CDCl₃) δ: 1.60 (3H, s), 3.78 (1H, s), 5.31 (2H, s), 7.33-7.42 (5H, m).

(2) benzyl (R)-3,3,3-trifluoro-2-methoxy-2-methylpropionate

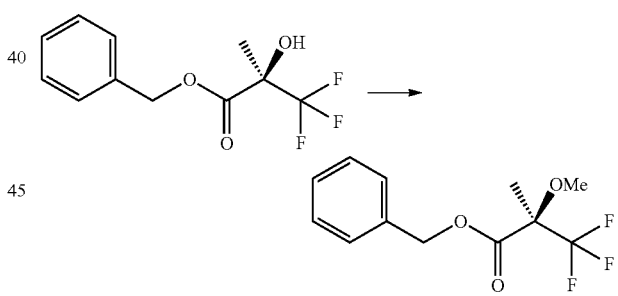

Under an argon atmosphere, to a solution of benzyl (R)-3,3,3-trifluoro-2-hydroxy-2-methylpropionate (3.4 g, 14 mmol) obtained in the above-mentioned (1) in N,N-dimethylformamide (40 ml) was added sodium hydride (0.60 g, 60 wt % oil dispersion) under ice-cooling, and the mixture was stirred for 1 hr. To the reaction mixture was added methyl iodide (1.3 ml, 20 mmol), and the mixture was stirred at room temperature for 2 hr. To the reaction mixture were added saturated aqueous ammonium chloride and ethyl acetate, and the mixture was partitioned. The organic layer was washed with saturated brine, dried over sodium sulfate, filtered to remove sodium sulfate, and concentrated under reduced pressure. The residue was purified by silica gel column chromatography (eluent: n-hexane/ethyl acetate=15/1) to give the title compound (2.8 g, yield 78%).

¹H-NMR (CDCl₃) δ: 1.59 (3H, s), 3.40 (3H, s), 5.26 (2H, s), 7.31-7.37 (5H, m).

(3) (R)-3,3,3-trifluoro-2-methoxy-2-methylpropionic acid

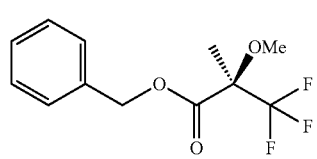

Under an argon atmosphere, to a solution of benzyl (R)-3,3,3-trifluoro-2-methoxy-2-methylpropionate (2.8 g, 11 mmol) obtained in the above-mentioned (2) in ethyl acetate (50 ml) was added 10 wt % palladium carbon (0.23 g) at room temperature, and the mixture was stirred under 1 atm hydrogen atmosphere for hr. Under a nitrogen atmosphere, the reaction mixture was filtered through celite and eluted with ethyl acetate. The filtrate was concentrated under reduced pressure to give the title compound (1.4 g, yield 78%).

$^1$H-NMR (CDCl$_3$) δ: 1.68 (3H, s), 3.54 (3H, s).

(4) 2-chloro-4-(4-chloro-3-methylphenyl)-6-methoxy-1,3,5-triazine

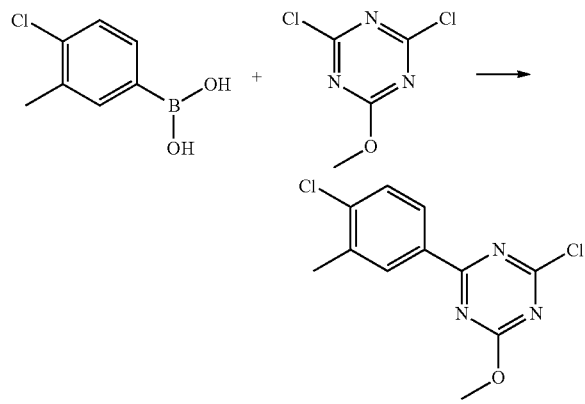

Under an argon atmosphere, to a suspension of 4-chloro-3-methylphenylboronic acid (0.47 g, 2.8 mmol), 2,4-dichloro-6-methoxy-1,3,5-triazine (1.0 g, 5.6 mmol) and tetrakis(triphenylphosphine)palladium(0) (0.32 g, 0.28 mmol) in toluene (5.0 ml) was added 2M aqueous sodium carbonate solution (4.2 ml), and the mixture was stirred at 100° C. for 2 hr. At room temperature, to the reaction mixture were added water and ethyl acetate, and the mixture was partitioned. The organic layer was washed with saturated brine, dried over sodium sulfate, filtered to remove sodium sulfate, and concentrated under reduced pressure. The residue was purified by silica gel column chromatography (eluent: n-hexane/ethyl acetate=98/2-95/5) to give the title compound (0.50 g, yield 48%).

$^1$H-NMR (CDCl$_3$) δ: 2.47 (3H, s), 4.17 (3H, s), 7.47 (1H, d, J=8.4 Hz), 8.26 (1H, dd, J=8.4, 2.1 Hz), 8.36 (1H, d, J=2.1 Hz).

(5) {4-chloro-3-[4-(4-chloro-3-methylphenyl)-6-methoxy-1,3,5-triazin-2-yl]phenyl}methanol

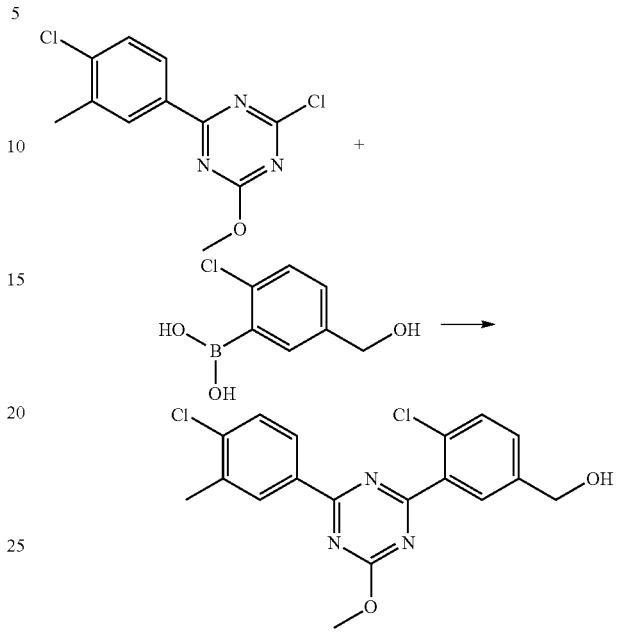

Under an argon atmosphere, to a solution of 2-chloro-4-(4-chloro-3-methylphenyl)-6-methoxy-1,3,5-triazine (0.50 g, 1.3 mmol) obtained in the above-mentioned (4), 2-chloro-5-hydroxymethylphenylboronic acid (0.30 g, 1.6 mmol) and [1,1'-bis(diphenylphosphino)ferrocene]palladium(II)dichloride dichloromethane adduct (0.11 g, 0.13 mmol) in 1,4-dioxane (5.0 ml) was added 2M aqueous sodium carbonate solution (2.6 ml), and the mixture was stirred at 100° C. for 1.5 hr. At room temperature, to the reaction mixture were added water and ethyl acetate, and the mixture was partitioned. The organic layer was washed with saturated brine, dried over sodium sulfate, filtered to remove sodium sulfate, and concentrated under reduced pressure. The residue was purified by silica gel column chromatography (eluent: n-hexane/ethyl acetate=8/2-6/4) to give the title compound (0.40 g, yield 80%).

$^1$H-NMR (CDCl$_3$) δ: 1.79 (1H, t, J=5.3 Hz), 2.48 (3H, s), 4.21 (3H, s), 4.78 (2H, d, J=5.3 Hz), 7.45-7.50 (2H, m), 7.54 (1H, d, J=8.1 Hz), 8.01 (1H, d, J=2.1 Hz), 8.37 (1H, dd, J=8.4, 2.1 Hz), 8.46 (1H, d, J=2.1 Hz).

(6) 4-chloro-3-[4-(4-chloro-3-methylphenyl)-6-methoxy-1,3,5-triazin-2-yl]benzylamine hydrochloride

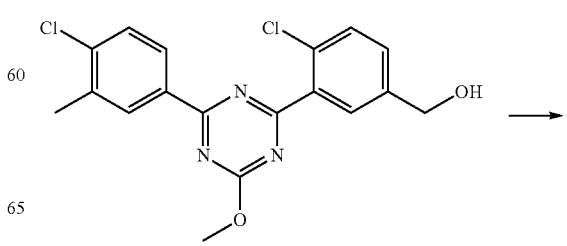

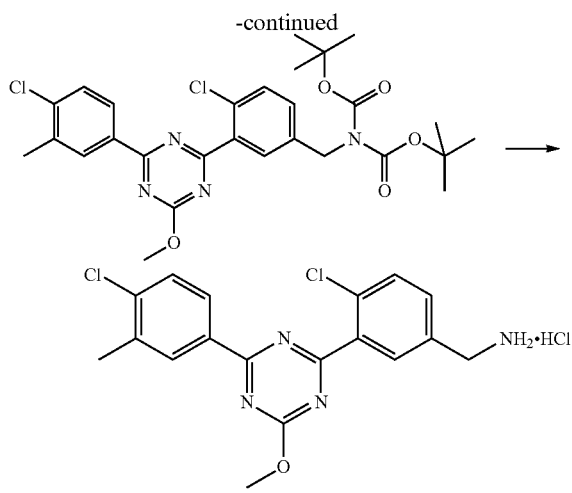

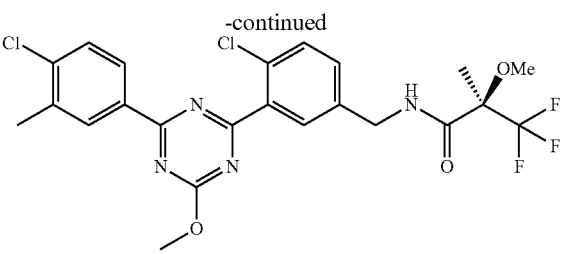

Under an argon atmosphere, to a solution of {4-chloro-3-[4-(4-chloro-3-methylphenyl)-6-methoxy-1,3,5-triazin-2-yl]phenyl}methanol (0.40 g, 1.1 mmol) obtained in the above-mentioned (5) in tetrahydrofuran (4.0 ml) were added triethylamine (0.19 ml, 1.4 mmol) and methanesulfonyl chloride (0.098 ml, 1.3 mmol) under ice-cooling, and the mixture was stirred for 1 hr. The reaction mixture was filtered, and the filtrate was concentrated under reduced pressure. To a solution of the residue in N,N-dimethylformamide (2.0 ml) were added cesium carbonate (1.0 g, 3.2 mmol) and di-tert-butyl iminodicarboxylate (0.37 g, 1.7 mmol) at room temperature, and the mixture was stirred for 3 hr. To the reaction mixture were is added water and ethyl acetate, and the mixture was partitioned. The organic layer was washed with saturated brine, dried over sodium sulfate, filtered to remove sodium sulfate, and concentrated under reduced pressure. The residue was purified by silica gel column chromatography (eluent: n-hexane/ethyl acetate=95/5-80/20). Under an argon atmosphere, to a solution (2.0 ml) of the purified product in 1,4-dioxane was added 4M hydrogen chloride/1,4-dioxane solution (4.0 ml) at room temperature, and the mixture was stirred for 2 hr. To the reaction mixture was added n-hexane, and the solid was collected by filtration and dried under reduced pressure to give the title compound (0.43 g, yield 99%).

$^1$H-NMR (DMSO-D$_6$) δ: 2.47 (3H, s), 4.13-4.19 (5H, m), 7.67 (1H, d, J=8.3 Hz), 7.71-7.76 (2H, m), 8.16 (1H, d, J=1.6 Hz), 8.35 (1H, dd, J=8.3, 1.6 Hz), 8.41-8.50 (4H, m).

(7) (R)—N-{4-chloro-3-[4-(4-chloro-3-methylphenyl)-6-methoxy-1,3,5-triazin-2-yl]benzyl}-3,3,3-trifluoro-2-methoxy-2-methylpropionamide

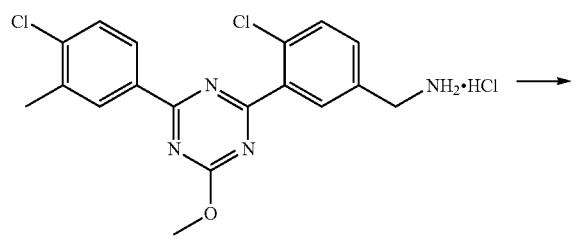

Under an argon atmosphere, to a solution of 4-chloro-3-[4-(4-chloro-3-methylphenyl)-6-methoxy-1,3,5-triazin-2-yl]benzylamine hydrochloride (0.070 g, 0.17 mmol) obtained in the above-mentioned (6), HOBt·H$_2$O (0.039 g, 0.26 mmol) and WSC·HCl (0.049 g, 0.26 mmol) in N,N-dimethylformamide (0.70 ml) were added (R)-3,3,3-trifluoro-2-methoxy-2-methylpropionic acid (0.038 g, 0.22 mmol) obtained in the above-mentioned (3) and triethylamine (0.071 ml, 0.51 mmol) at room temperature, and the mixture was stirred for 18 hr. To the reaction mixture were added saturated aqueous sodium hydrogen carbonate and ethyl acetate, and the mixture was partitioned. The organic layer was washed with saturated brine, dried over sodium sulfate, filtered to remove sodium sulfate, and concentrated under reduced pressure. The residue was purified by silica gel column chromatography (eluent: n-hexane/ethyl acetate=3/2) to give the title compound (0.058 g, yield 65%).

$^1$H-NMR (CDCl$_3$) δ: 1.66 (3H, s), 2.48 (3H, s), 3.45 (3H, s), 4.20 (3H, s), 4.48 (1H, dd, J=15.1, 5.8 Hz), 4.63 (1H, dd, J=15.1, 6.5 Hz), 7.16 (1H, br s), 7.37 (1H, dd, J=8.3, 2.3 Hz), 7.48 (1H, d, J=8.3 Hz), 7.53 (1H, d, J=8.3 Hz), 7.92 (1H, d, J=2.3 Hz), 8.36 (1H, dd, J=8.3, 2.0 Hz), 8.46 (1H, d, J=2.0 Hz).

(8) (R)—N-{4-chloro-3-[4-(4-chloro-3-methylphenyl)-6-hydroxy-1,3,5-triazin-2-yl]benzyl}-3,3,3-trifluoro-2-methoxy-2-methylpropionamide (Example No. 1-136)

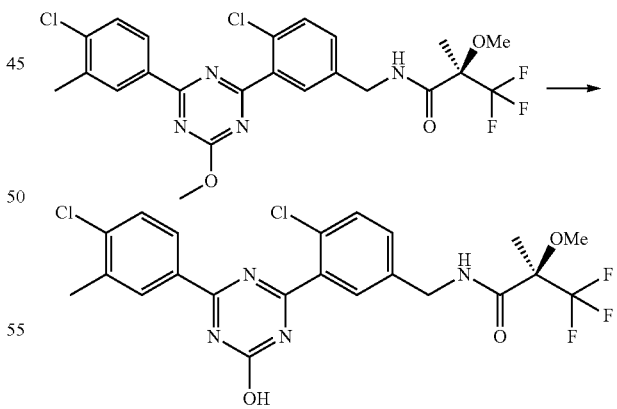

Under an argon atmosphere, to a solution of (R)—N-{4-chloro-3-[4-(4-chloro-3-methylphenyl)-6-methoxy-1,3,5-triazin-2-yl]benzyl}-3,3,3-trifluoro-2-methoxy-2-methylpropionamide (0.058 g, 0.11 mmol) obtained in the above-mentioned (7) in methanol (1.3 ml) was added 4M aqueous sodium hydroxide is solution (0.17 ml) at room temperature, and the mixture was stirred at 60° C. for 3 hr. To the reaction mixture were added 10% aqueous citric acid solution (0.68 ml) and water, and the mixture was stirred at room temperature. The precipitated solid was collected by filtration, washed with water, and dried under reduced pressure to give the title compound (0.051 g, yield 88%).

Production Example 20

Synthesis of (R)—N-{4-chloro-3-[4-hydroxy-6-(4-propoxyphenyl)-1,3,5-triazin-2-yl]benzyl}-3,3,3-trifluoro-2-methoxy-2-methylpropionamide (Example No. 1-137)

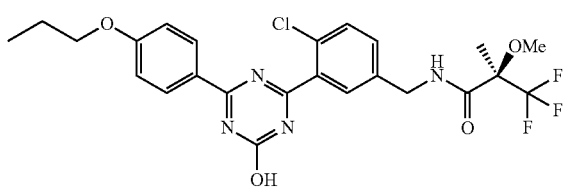 [SMILES: CCCOc1ccc(-c2nc(O)nc(-c3cc(CNC(=O)[C@@](C)(OC)C(F)(F)F)ccc3Cl)n2)cc1]

(1) (R)—N-{4-chloro-3-[4-methoxy-6-(4-propoxyphenyl)-1,3,5-triazin-2-yl]benzyl}-3,3,3-trifluoro-2-methoxy-2-methylpropionamide

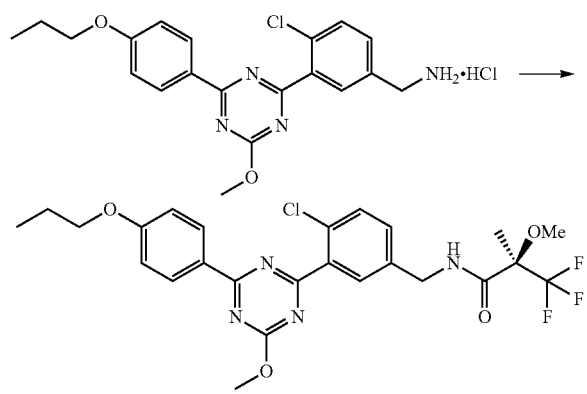

Under an argon atmosphere, to a solution of 4-chloro-3-[4-methoxy-6-(4-propoxyphenyl)-1,3,5-triazin-2-yl]benzylamine hydrochloride (0.80 g, 0.19 mmol) obtained in [Production Example 13] (4), HOBt·H₂O (0.044 g, 0.28 mmol) and WSC·HCl (0.055 g, 0.28 mmol) in N,N-dimethylformamide (1.0 ml) were added (R)-3,3,3-trifluoro-2-methoxy-2-methylpropionic acid (0.046 g, 0.27 mmol) obtained in [Production Example 19] (3) and triethylamine (0.080 ml, 0.57 mmol) at room temperature, and the mixture was stirred for 18 hr. To the reaction mixture were added water and ethyl acetate, and the mixture was partitioned. The organic layer was washed with saturated brine, dried over sodium sulfate, filtered to remove sodium sulfate, and concentrated under reduced pressure. The residue was purified by silica gel column chromatography (eluent: n-hexane/ethyl acetate=8/2-3/2) to give the title compound (0.084 g, yield 82%).

¹H-NMR (CDCl₃) δ: 1.07 (3H, t, J=7.4 Hz), 1.66 (3H, br s), 1.81-1.90 (2H, m), 3.45 (3H, br s), 4.02 (2H, t, J=6.5 Hz), 4.19 (3H, s), 4.50 (1H, dd, J=15.0, 5.8 Hz), 4.59 (1H, dd, J=15.0, 6.3 Hz), 6.97-7.02 (2H, m), 7.14 (1H, br s), 7.35 (1H, dd, J=8.3, 2.3 Hz), 7.51 (1H, d, J=8.3 Hz), 7.92 (1H, d, J=2.3 Hz), 8.52-8.56 (2H, m).

(2) (R)—N-{4-chloro-3-[4-hydroxy-6-(4-propoxyphenyl)-1,3,5-triazin-2-yl]benzyl}-3,3,3-trifluoro-2-methoxy-2-methylpropionamide (Example No. 1-137)

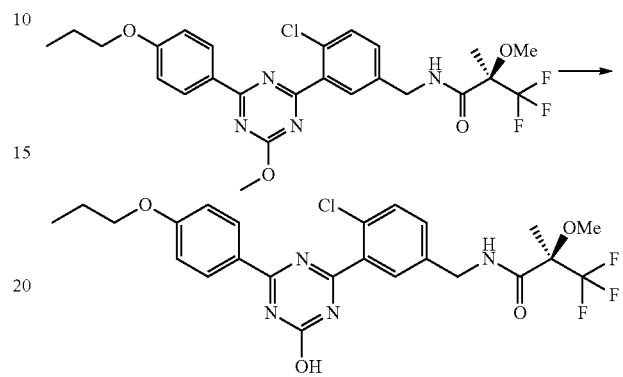

Under an argon atmosphere, to a solution of (R)—N-{4-chloro-3-[4-methoxy-6-(4-propoxyphenyl)-1,3,5-triazin-2-yl]benzyl}-3,3,3-trifluoro-2-methoxy-2-methylpropionamide (0.084 g, 0.16 mmol) obtained in the above-mentioned (1) in methanol (0.80 ml) was added 4M aqueous sodium hydroxide solution (0.30 ml) at room temperature, and the mixture was stirred at 65° C. for 1.5 hr. To the reaction mixture were added 2N hydrochloric acid (0.60 ml) and water, and the mixture was stirred at room temperature. The precipitated solid was collected by filtration, washed with water, and dried under reduced pressure to give the title compound (0.072 g, yield 89%).

Production Example 21

Synthesis of N-{4-chloro-3-[4-(3,4-dimethylphenyl)-6-hydroxy-1,3,5-triazin-2-yl]benzyl}-3,3,3-trifluoro-2,2-dimethylpropionamide (Example No. 1-150)

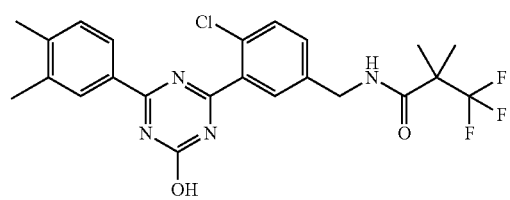 [SMILES: Cc1ccc(-c2nc(O)nc(-c3cc(CNC(=O)C(C)(C)C(F)(F)F)ccc3Cl)n2)cc1C]

(1) 2-chloro-4-(3,4-dimethylphenyl)-6-methoxy-1,3,5-triazine

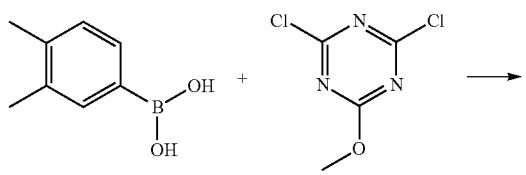

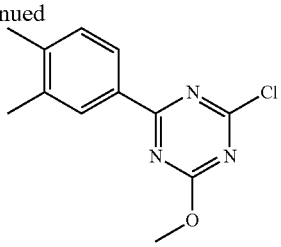

Under an argon atmosphere, to a suspension of 3,4-dimethylbenzeneboronic acid (0.42 g, 2.8 mmol), 2,4-dichloro-6-methoxy-1,3,5-triazine (1.0 g, 5.6 mmol) and tetrakis(triphenylphosphine)palladium(0) (0.32 g, 0.28 mmol) in toluene (8.4 ml) was added 2M aqueous sodium carbonate solution (4.2 ml), and the mixture was stirred at 100° C. for 2 hr. At room temperature, to the reaction mixture were added water and ethyl acetate, and the mixture was partitioned. The organic layer was washed with saturated brine, dried over sodium sulfate, filtered to remove sodium sulfate, and concentrated under reduced pressure. The residue was purified by silica gel column chromatography (eluent: n-hexane/ethyl acetate=20/1) to give the title compound (0.64 g, 92%).

$^1$H-NMR (CDCl$_3$) δ: 2.35 (6H, s), 4.16 (3H, s), 7.26 (3H, d, J=7.8 Hz), 8.22 (1H, dd, J=7.8, 2.1 Hz), 8.25 (1H, d, J=2.1 Hz).

(2) {4-chloro-3-[4-(3,4-dimethylphenyl)-6-methoxy-1,3,5-triazin-2-yl]phenyl}methanol

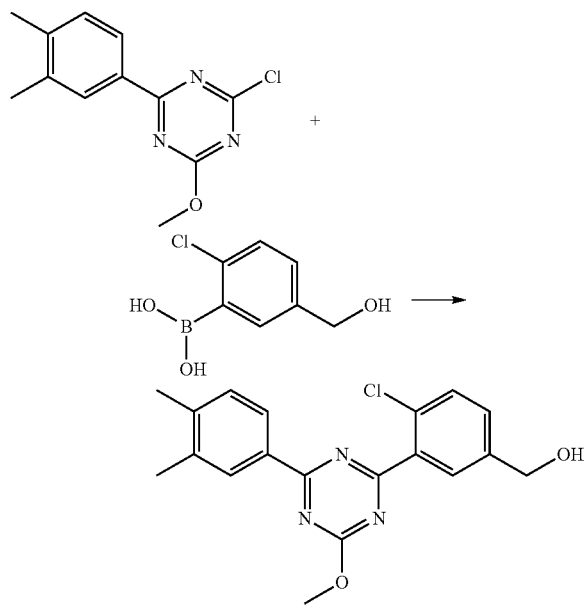

Under an argon atmosphere, to a solution of 2-chloro-4-(3,4-dimethylphenyl)-6-methoxy-1,3,5-triazine (0.64 g, 2.6 mmol) obtained in the above-mentioned (1), 2-chloro-5-hydroxymethylphenylboronic acid (0.57 g, 3.1 mmol) and [1,1'-bis(diphenylphosphino)ferrocene]palladium(II)dichloride dichloromethane adduct (0.21 g, 0.26 mmol) in 1,4-dioxane (10 ml) was added 2M aqueous sodium carbonate solution (5.1 ml), and the mixture was stirred at 100° C. for 1 hr. At room temperature, to the reaction mixture were added water and ethyl acetate, and the mixture was partitioned. The organic layer was washed with saturated brine, dried over sodium sulfate, filtered to remove sodium sulfate, and concentrated under reduced pressure. The residue was purified by silica gel column chromatography (eluent: n-hexane/ethyl acetate=5/3) to give the title compound (0.54 g, yield 59%).

$^1$H-NMR (CDCl$_3$) δ: 1.87 (1H, t, J=5.0 Hz), 2.35 (3H, s), 2.36 (3H, s), 4.20 (3H, s), 4.76 (2H, d, J=5.0 Hz), 7.27 (2H, d, J=8.2 Hz), 7.45 (1H, dd, J=8.4, 1.6 Hz), 7.53 (1H, d, J=8.4 Hz), 7.99 (1H, d, J=1.6 Hz), 8.33 (1H, d, J=8.2 Hz), 8.35 (1H, br s).

(3) 4-chloro-3-[4-(3,4-dimethylphenyl)-6-methoxy-1,3,5-triazin-2-yl]benzylamine hydrochloride

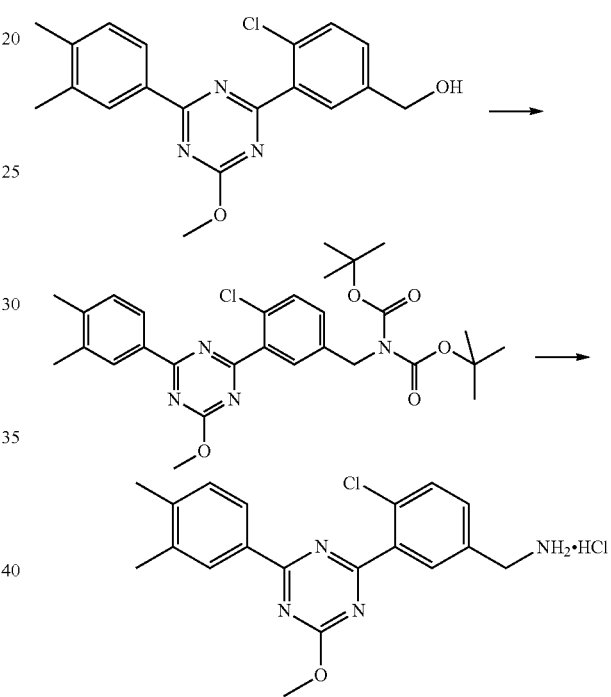

Under an argon atmosphere, to a solution of {4-chloro-3-[4-(3,4-dimethylphenyl)-6-methoxy-1,3,5-triazin-2-yl]phenyl}methanol (0.54 g, 1.5 mmol) obtained in the above-mentioned (2) in tetrahydrofuran (5.5 ml) were added triethylamine (0.28 ml, 2.0 mmol) and methanesulfonyl chloride (0.14 ml, 1.8 mmol) under ice-cooling, and the mixture was stirred for 0.5 hr. The reaction mixture was filtered, and the filtrate was concentrated under reduced pressure. To a solution of the residue in N,N-dimethylformamide (5.5 ml) were is added cesium carbonate (1.5 g, 4.6 mmol) and di-tert-butyl iminodicarboxylate (0.40 g, 1.8 mmol) under ice-cooling, and the mixture was stirred at room temperature for 1 hr. To the reaction mixture were added water and ethyl acetate, and the mixture was partitioned. The organic layer was washed with saturated brine, dried over sodium sulfate, filtered to remove sodium sulfate, and concentrated under reduced pressure. The residue was purified by silica gel column chromatography (eluent: n-hexane/ethyl acetate=7/1). Under an argon atmosphere, to the purified product was added 4M hydrogen chloride/1,4-dioxane solution (6.5 ml) at room temperature, and the mixture was stirred for 0.5 hr. To the reaction mixture was added ethyl acetate, and the solid was collected by filtration, and dried under reduced pressure to give the title compound (0.56 g, yield 94%).

$^1$H-NMR (DMSO-D$_6$) δ: 2.34 (3H, s), 2.35 (3H, s), 4.12-4.19 (5H, m), 7.38 (1H, d, J=7.9 Hz), 7.69-7.75 (2H, m), 8.12 (1H, d, J=1.9 Hz), 8.26 (1H, dd, J=7.9, 1.6 Hz), 8.29 (1H, br s), 8.44 (3H, br s).

(4) N-{4-chloro-3-[4-(3,4-dimethylphenyl)-6-methoxy-1,3,5-triazin-2-yl]benzyl}-3,3,3-trifluoro-2,2-dimethylpropionamide

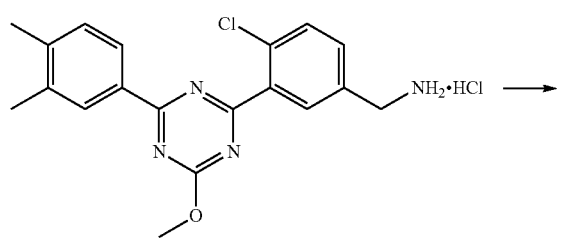

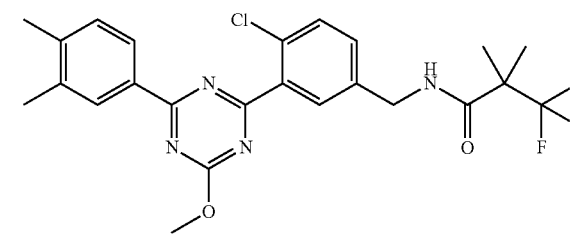

Under an argon atmosphere, to a solution of 4-chloro-3-[4-(3,4-dimethylphenyl)-6-methoxy-1,3,5-triazin-2-yl]benzylamine hydrochloride (0.070 g, 0.18 mmol) obtained in the above-mentioned (3), HOBt·H$_2$O (0.035 g, 0.23 mmol) and WSC·HCl (0.044 g, 0.23 mmol) in N,N-dimethylformamide (2.0 ml) were added 3,3,3-trifluoro-2,2-dimethylpropionic acid (0.036 g, 0.23 mmol) and triethylamine (0.075 ml, 0.54 mmol) at room temperature, and the mixture was stirred for 4 hr. To the reaction mixture were added saturated aqueous sodium hydrogen carbonate and ethyl acetate, and the mixture was partitioned. The organic layer was washed with saturated brine, dried over sodium sulfate, filtered to remove sodium sulfate, and concentrated under reduced pressure. The residue was purified by silica gel column chromatography (eluent: n-hexane/ethyl acetate=2/1) to give the title compound (0.075 g, yield 85%).

$^1$H-NMR (CDCl$_3$) δ: 1.44 (6H, s), 2.36 (3H, s), 2.37 (3H, s), 4.20 (3H, s), 4.55 (2H, d, J=5.7 Hz), 6.22 (1H, br s), 7.27 (3H, d, J=7.8 Hz), 7.35 (1H, dd, J=8.2, 2.2 Hz), 7.52 (1H, d, J=8.2 Hz), 7.91 (1H, d, J=2.2 Hz), 8.32 (1H, dd, J=7.8, 1.7 Hz), 8.35 (1H, br s).

(5) N-{4-chloro-3-[4-(3,4-dimethylphenyl)-6-hydroxy-1,3,5-triazin-2-yl]benzyl}-3,3,3-trifluoro-2,2-dimethylpropionamide (Example No. 1-150)

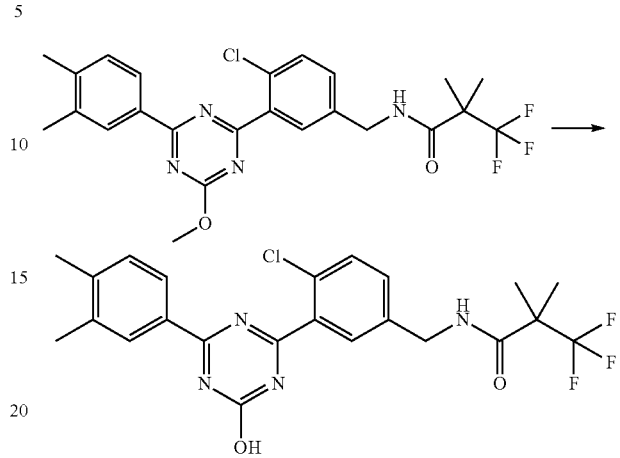

Under an argon atmosphere, to a solution of N-{4-chloro-3-[4-(3,4-dimethylphenyl)-6-methoxy-1,3,5-triazin-2-yl]benzyl}-3,3,3-trifluoro-2,2-dimethylpropionamide (0.075 g, 0.15 mmol) obtained in the above-mentioned (4) in methanol (1.8 ml) was added 4M aqueous sodium hydroxide solution (0.23 ml) at room temperature, and the mixture was stirred at 60° C. for 4 hr. To the reaction mixture were added 10% aqueous citric acid solution (1.0 ml) and water at room temperature, and the mixture was stirred. The precipitated solid was collected by filtration, washed with water, and dried under reduced pressure to give the title compound (0.063 g, yield 86%).

Production Example 22

Synthesis of N-{4-chloro-3-[4-(4-cyclopropylmethoxyphenyl)-6-hydroxy-1,3,5-triazin-2-yl]benzyl}-3,3,3-trifluoro-2-methyl-2-trifluoromethylpropionamide (Example No. 1-169)

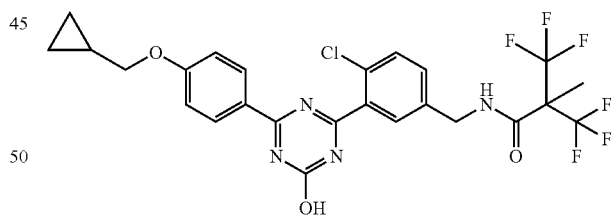

(1) 2-chloro-4-(4-cyclopropylmethoxyphenyl)-6-methoxy-1,3,5-triazine

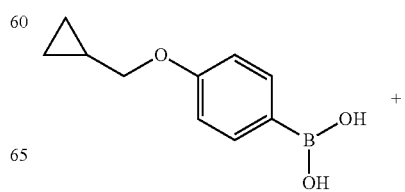

147

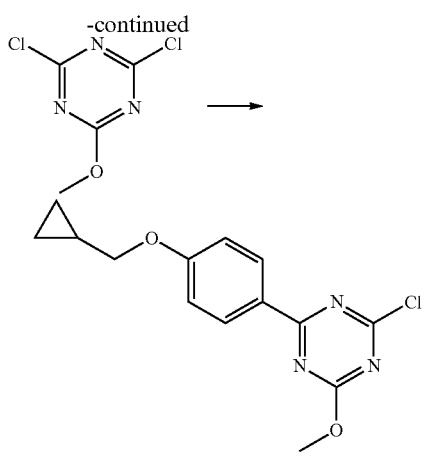

Under an argon atmosphere, to a suspension of 4-(cyclopropylmethoxy)benzeneboronic acid (2.5 g, 13 mmol), 2,4-dichloro-6-methoxy-1,3,5-triazine (4.7 g, 26 mmol) and tetrakis(triphenylphosphine)palladium(0) (1.5 g, 1.3 mmol) in toluene (25 ml) was added 2M aqueous sodium carbonate solution (20 ml), and the mixture was stirred at 100° C. for 2 hr. At room temperature, to the reaction mixture were added water and ethyl acetate, and the mixture was partitioned. The organic layer was washed with saturated brine, dried over sodium sulfate, filtered to remove sodium sulfate, and concentrated under reduced pressure. The residue was purified by silica gel column chromatography (eluent: n-hexane/ethyl acetate=90/10-80/20) to give the title compound (3.0 g, 79%).

$^1$H-NMR (CDCl$_3$) δ: 0.36-0.41 (2H, m), 0.65-0.71 (2H, m), 1.25-1.36 (1H, m), 3.90 (2H, d, J=7.0 Hz), 4.14 (3H, s), 6.96-7.00 (2H, m), 8.42-8.47 (2H, m).

(2) {4-chloro-3-[4-(4-cyclopropylmethoxyphenyl)-6-methoxy-1,3,5-triazin-2-yl]phenyl}methanol

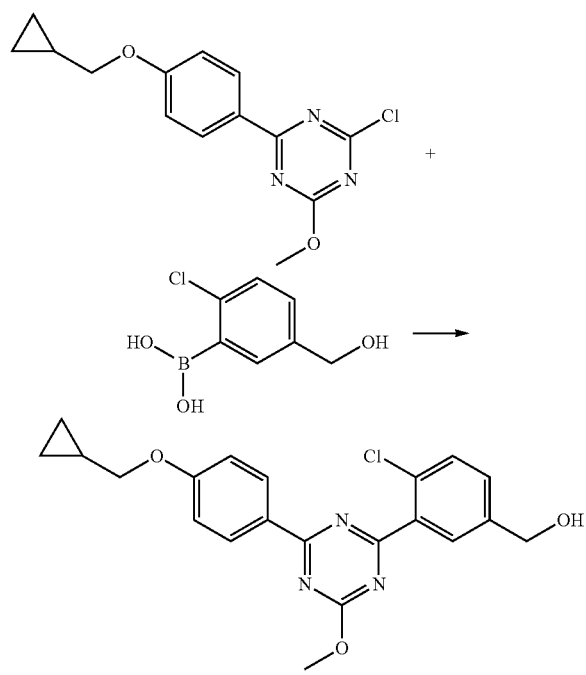

148

Under an argon atmosphere, to a solution of 2-chloro-4-(4-cyclopropylmethoxyphenyl)-6-methoxy-1,3,5-triazine (3.0 g, mmol) obtained in the above-mentioned (1), 2-chloro-5-hydroxymethylphenylboronic acid (2.3 g, 12 mmol) and [1,1'-bis(diphenylphosphino)ferrocene]palladium(II)dichloride dichloromethane adduct (0.84 g, 1.0 mmol) in 1,4-dioxane (30 ml) was added 2M aqueous sodium carbonate solution (21 ml), and the mixture was stirred at 100° C. for 3 hr. At room temperature, to the reaction mixture were added water and ethyl acetate, and the mixture was partitioned. The organic layer was washed with saturated brine, dried over sodium sulfate, filtered to remove sodium sulfate, and concentrated under reduced pressure. The residue was purified by silica gel column chromatography (eluent: n-hexane/ethyl acetate=8/2-1/1) to give the title compound (2.9 g, yield 71%).

$^1$H-NMR (CDCl$_3$) δ: 0.37-0.41 (2H, m), 0.65-0.71 (2H, m), 1.27-1.36 (1H, m), 1.76 (1H, t, J=6.0 Hz), 3.90 (2H, d, J=6.7 Hz), 4.19 (3H, s), 4.77 (2H, d, J=6.0 Hz), 6.98-7.02 (2H, m), 7.46 (1H, dd, J=8.1, 1.9 Hz), 7.53 (1H, d, J=8.1 Hz), 8.00 (1H, d, J=1.9 Hz), 8.53-8.57 (2H, m)

(3) 4-chloro-3-[4-(4-cyclopropylmethoxyphenyl)-6-methoxy-1,3,5-triazin-2-yl]benzylamine hydrochloride

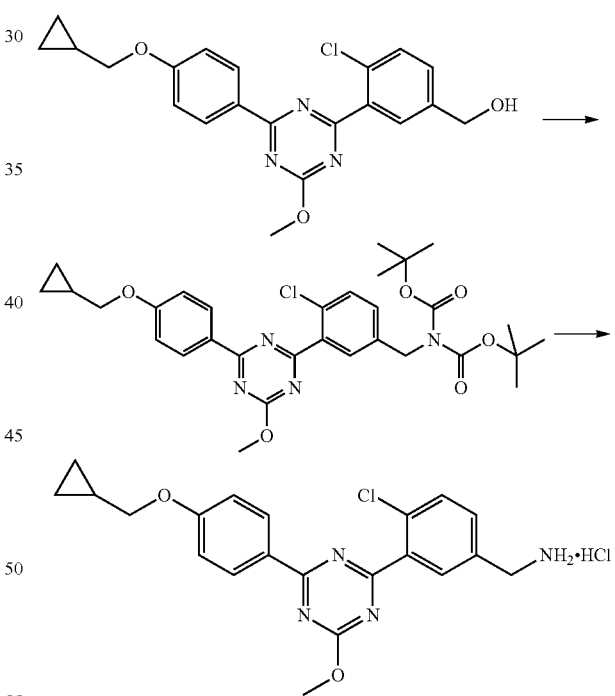

Under an argon atmosphere, to a solution of {4-chloro-3-[4-(4-cyclopropylmethoxyphenyl)-6-methoxy-1,3,5-triazin-2-yl]phenyl}methanol (2.9 g, 7.3 mmol) obtained in the above-mentioned (2) in tetrahydrofuran (29 ml) were added triethylamine (1.3 ml, 9.5 mmol) and methanesulfonyl chloride (0.68 ml, 8.7 mmol) under ice-cooling, and the mixture was stirred for 0.5 hr. The reaction mixture was filtered, and the filtrate was concentrated under reduced pressure. To a solution of the residue in N,N-dimethylformamide (29 ml) were added cesium carbonate (7.1 g, 22 mmol) and di-tert-butyl iminodicarboxylate (1.9 g, 8.7 mmol) under ice-cooling, and the mixture was stirred at room temperature for 2 hr. To the reaction mixture were added water and ethyl acetate, and the mixture was partitioned. The organic layer was washed with saturated brine, dried over sodium sulfate, filtered to remove sodium sulfate, and concentrated under reduced pressure. The residue was purified by silica gel column chromatography (eluent: n-hexane/ethyl acetate=95/5-70/30). Under an argon atmosphere, to a solution (9.3 ml) of the purified product in 1,4-dioxane was added 4M hydrogen chloride/1,4-dioxane solution (37 ml) at room temperature, and the mixture was stirred for 3 hr. To the reaction mixture was added ethyl acetate, and the solid was collected by filtration, and dried under reduced pressure to give the title compound (3.1 g, yield 97%).

$^1$H-NMR (DMSO-$D_6$) δ: 0.34-0.39 (2H, m), 0.57-0.63 (2H, m), 1.21-1.32 (1H, m), 3.95 (2H, d, J=7.0 Hz), 4.11-4.18 (5H, m), 7.11-7.15 (2H, m), 7.70-7.74 (2H, m), 8.13 (1H, br s), 8.42-8.53 (5H, m).

(4) N-{4-chloro-3-[4-(4-cyclopropylmethoxyphenyl)-6-methoxy-1,3,5-triazin-2-yl]benzyl}-3,3,3-trifluoro-2-methyl-2-trifluoromethylpropionamide

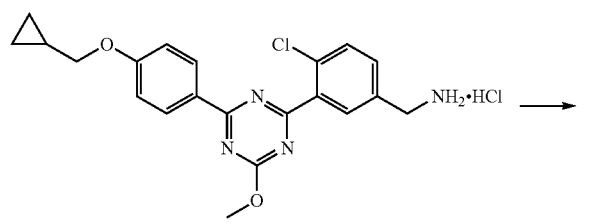

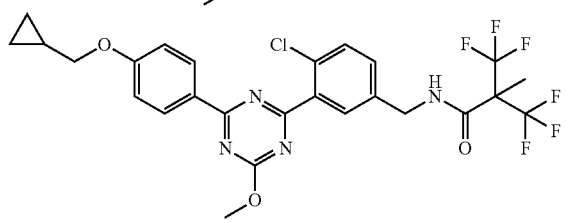

Under an argon atmosphere, to a solution of 4-chloro-3-[4-(4-cyclopropylmethoxyphenyl)-6-methoxy-1,3,5-triazin-2-yl]benzylamine hydrochloride (0.080 g, 0.18 mmol) obtained in the above-mentioned (3), HOBt·H$_2$O (0.037 g, 0.24 mmol) and WSC·HCl (0.046 g, 0.24 mmol) in N,N-dimethylformamide (2.0 ml) were added 2,2-bis(trifluoromethyl)propionic acid (0.050 g, 0.24 mmol) and triethylamine (0.077 ml, 0.55 mmol) at room temperature, and the mixture was stirred for 1.5 hr. To the reaction mixture were added HOBt·H$_2$O (0.037 g, 0.24 mmol), WSC·HCl (0.046 g, 0.24 mmol), 2,2-bis(trifluoromethyl)propionic acid (0.050 g, 0.24 mmol) and triethylamine (0.077 ml, 0.55 mmol), and the mixture was stirred for 2 hr. To the reaction mixture were added HOBt·H$_2$O (0.037 g, 0.24 mmol), WSC·HCl (0.046 g, 0.24 mmol), 2,2-bis(trifluoromethyl)propionic acid (0.050 g, 0.24 mmol) and triethylamine (0.077 ml, 0.55 mmol), and the mixture was stirred for 1.5 hr. To the reaction mixture were added saturated aqueous sodium hydrogen carbonate and ethyl acetate, and the mixture was partitioned. The organic layer was washed with saturated brine, dried over sodium sulfate, filtered to remove sodium sulfate, and concentrated under reduced pressure. The residue was purified by silica gel column chromatography (eluent: n-hexane/ethyl acetate=3/1) to give the title compound (0.045 g, yield 41%).

$^1$H-NMR (CDCl$_3$) δ: 0.36-0.41 (2H, m), 0.65-0.71 (2H, m), 1.26-1.35 (2H, m), 1.70 (3H, s), 3.90 (2H, d, J=6.7 Hz), 4.19 (3H, s), 4.61 (2H, d, J=5.8 Hz), 6.49 (1H, br s), 6.98-7.02 (2H, m), 7.32 (1H, dd, J=8.5, 2.1 Hz), 7.53 (1H, d, J=8.5 Hz), 7.92 (1H, d, J=2.1 Hz), 8.52-8.56 (2H, m).

(5) N-{4-chloro-3-[4-(4-cyclopropylmethoxyphenyl)-6-hydroxy-1,3,5-triazin-2-yl]benzyl}-3,3,3-trifluoro-2-methyl-2-trifluoromethylpropionamide
(Example No. 1-169)

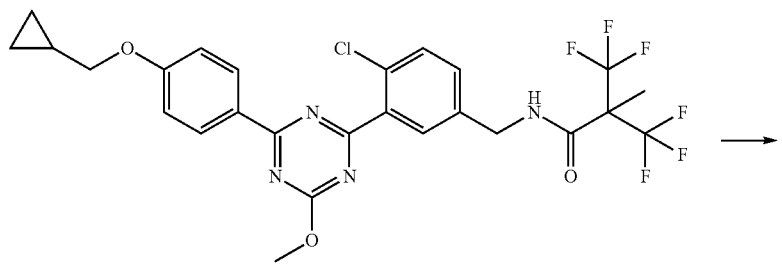

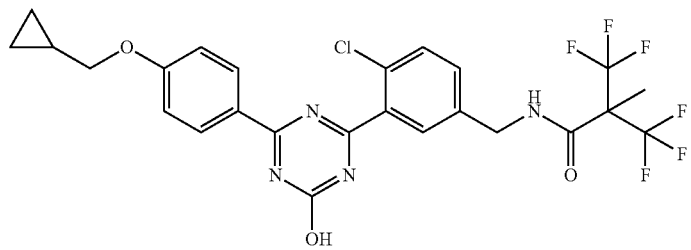

Under an argon atmosphere, to a solution of N-{4-chloro-3-[4-(4-cyclopropylmethoxyphenyl)-6-methoxy-1,3,5-triazin-2-yl]benzyl}-3,3,3-trifluoro-2-methyl-2-trifluoromethylpropionamide (0.045 g, 0.076 mmol) obtained in the above-mentioned (4) in methanol (0.70 ml) was added 4M aqueous sodium hydroxide solution (0.11 ml) at room temperature, and the mixture was stirred at 60° C. for 4 hr. To the reaction mixture were added 10% aqueous citric acid solution (0.50 ml) and water, and the mixture was stirred at room temperature. The precipitated solid was collected by filtration, washed with water, and dried under reduced pressure to give the title compound (0.039 g, yield 89%).

Production Example 23

Synthesis of 1-trifluoromethylcyclopropanecarboxylic acid 4-chloro-3-[4-hydroxy-6-(4-isobutoxyphenyl)-1,3,5-triazin-2-yl]benzylamide (Example No. 1-178)

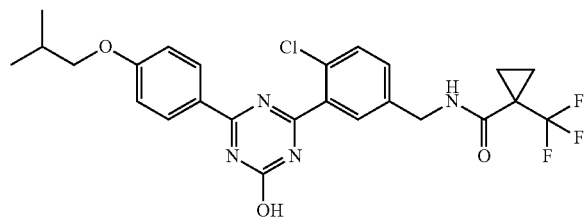 [SMILES: CC(C)COc1ccc(-c2nc(O)nc(-c3cc(CNC(=O)C4(C(F)(F)F)CC4)ccc3Cl)n2)cc1]

(1) 1-trifluoromethylcyclopropanecarboxylic acid 4-chloro-3-[4-(4-isobutoxyphenyl)-6-methoxy-1,3,5-triazin-2-yl]benzylamide

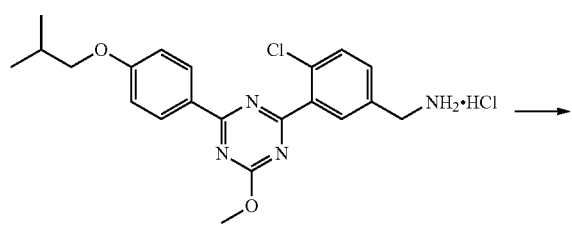

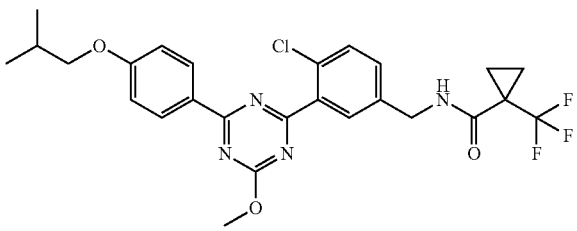

Under an argon atmosphere, to a solution of 4-chloro-3-[4-(4-isobutoxyphenyl)-6-methoxy-1,3,5-triazin-2-yl]benzylamine hydrochloride (0.10 g, 0.23 mmol) obtained in [Production Example 12] (4), HOBt·H$_2$O (0.049 g, 0.32 mmol) and WSC·HCl (0.061 g, 0.32 mmol) in N,N-dimethylformamide (0.75 ml) were added 1-trifluoromethylcyclopropane-1-carboxylic acid (0.050 g, 0.32 mmol) and triethylamine (0.064 ml, 0.46 mmol) at room temperature, and the mixture was stirred for 1.5 hr. To the reaction mixture were added water and ethyl acetate, and the mixture was partitioned. The organic layer was washed with saturated brine, dried over sodium sulfate, filtered to remove sodium sulfate, and concentrated under reduced pressure. The residue was purified by silica gel column chromatography (eluent: n-hexane/ethyl acetate=2/1, then chloroform/ethyl acetate=9/1) to give the title compound (0.068 g, yield 55%).

$^1$H-NMR (DMSO-D$_6$) δ: 1.01 (6H, d, J=6.9 Hz), 1.23-1.27 (2H, m), 1.30-1.36 (2H, m), 2.00-2.11 (1H, m), 3.87 (2H, d, J=6.4 Hz), 4.12 (3H, s), 4.37 (2H, d, J=5.9 Hz), 7.11-7.15 (2H, m), 7.43 (1H, dd, J=8.2, 2.1 Hz), 7.60 (1H, d, J=8.2 Hz), 7.85 (1H, d, J=2.1 Hz), 8.43-8.47 (2H, m), 8.50 (1H, t, J=5.9 Hz).

(2) 1-trifluoromethyl-cyclopropanecarboxylic acid 4-chloro-3-[4-hydroxy-6-(4-isobutoxyphenyl)-1,3,5-triazin-2-yl]benzylamide (Example No. 1-178)

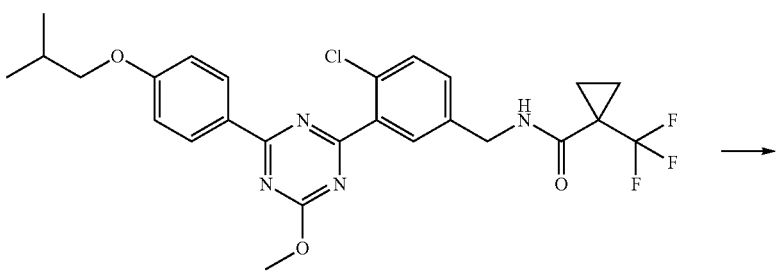

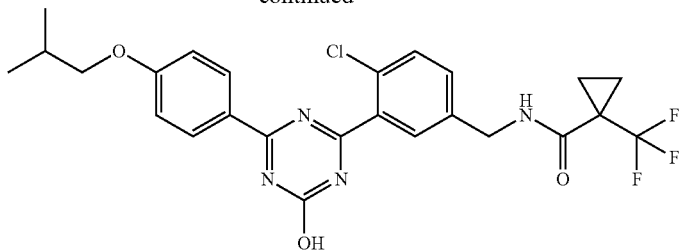

Under an argon atmosphere, to a solution of 1-trifluoromethylcyclopropanecarboxylic acid 4-chloro-3-[4-(4-isobutoxyphenyl)-6-methoxy-1,3,5-triazin-2-yl]benzylamide (0.065 g, 0.12 mmol) obtained in the above-mentioned (1) in methanol (1.0 ml) was added 4M aqueous sodium hydroxide solution (0.12 ml) at room temperature, and the mixture was stirred at 60° C. for 3 hr. To the reaction mixture were added 2N hydrochloric acid (0.24 ml) and water at room temperature, and the mixture was stirred. The precipitated solid was collected by filtration, washed with water, and dried under reduced pressure to give the title compound (0.060 g, yield 94%).

Production Example 24

Synthesis of N-(4-chloro-3-{4-[4-((S)-1-cyclopropylethoxy)phenyl]-6-hydroxy-1,3,5-triazin-2-yl}benzyl)-3,3,3-trifluoro-2,2-dimethylpropionamide (Example No. 1-184)

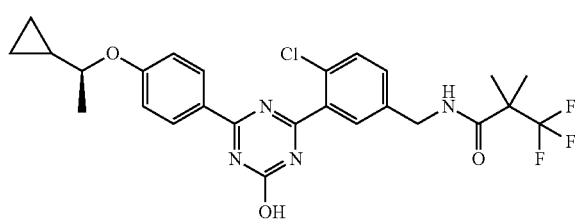 [SMILES: C[C@H](Oc1ccc(-c2nc(O)nc(-c3cc(CNC(=O)C(C)(C)C(F)(F)F)ccc3Cl)n2)cc1)C1CC1]

(1) N-(4-chloro-3-{4-[4-((S)-1-cyclopropylethoxy)phenyl]-6-methoxy-1,3,5-triazin-2-yl}benzyl)-3,3,3-trifluoro-2,2-dimethylpropionamide

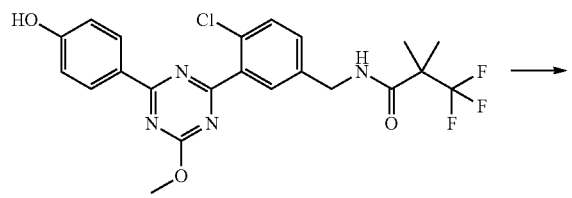

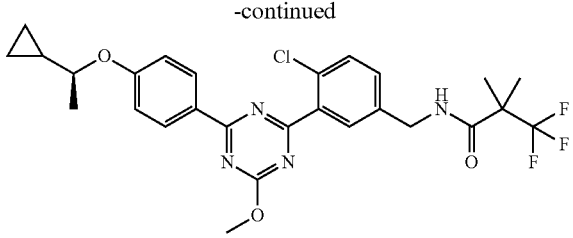

Under an argon atmosphere, to a solution of N-{4-chloro-3-[4-(4-hydroxyphenyl)-6-methoxy-1,3,5-triazin-2-yl]benzyl}-3,3,3-trifluoro-2,2-dimethylpropionamide (0.080 g, 0.17 mmol) obtained in the above-mentioned [Production Example 14] (6), (1R)-1-cyclopropylethan-1-ol (0.029 g, 0.33 mmol) and triphenylphosphine (0.087 g, 0.33 mmol) in tetrahydrofuran (1.0 ml) was added bis(2-methoxyethyl) azodicarboxylate (0.078 g, 0.33 mmol) under ice-cooling, and the mixture was stirred at room temperature for 17 hr. To the reaction mixture were added water and ethyl acetate, and the mixture was partitioned. The organic layer was washed with saturated brine, dried over sodium sulfate, filtered to remove sodium sulfate, and concentrated under reduced pressure. The residue was purified by silica gel column chromatography (eluent: n-hexane/ethyl acetate=2/1) to give the title compound (0.079 g, yield 86%).

$^1$H-NMR (CDCl$_3$) δ: 0.28-0.36 (1H, m), 0.38-0.45 (1H, m), 0.53-0.63 (2H, m), 1.12-1.21 (1H, m), 1.41 (3H, d, J=6.0 Hz), 1.44 (6H, s), 3.95-4.05 (1H, m), 4.18 (3H, s), 4.54 (2H, d, J=5.6 Hz), 6.20 (1H, br s), 6.95-7.00 (2H, m), 7.34 (1H, dd, J=8.3, 1.9 Hz), 7.51 (1H, d, J=8.3 Hz), 7.91 (1H, d, J=1.9 Hz), 8.50-8.55 (2H, m).

(2) N-(4-chloro-3-{4-[4-((S)-1-cyclopropylethoxy)phenyl]-6-hydroxy-1,3,5-triazin-2-yl}benzyl)-3,3,3-trifluoro-2,2-dimethylpropionamide (Example No. 1-184)

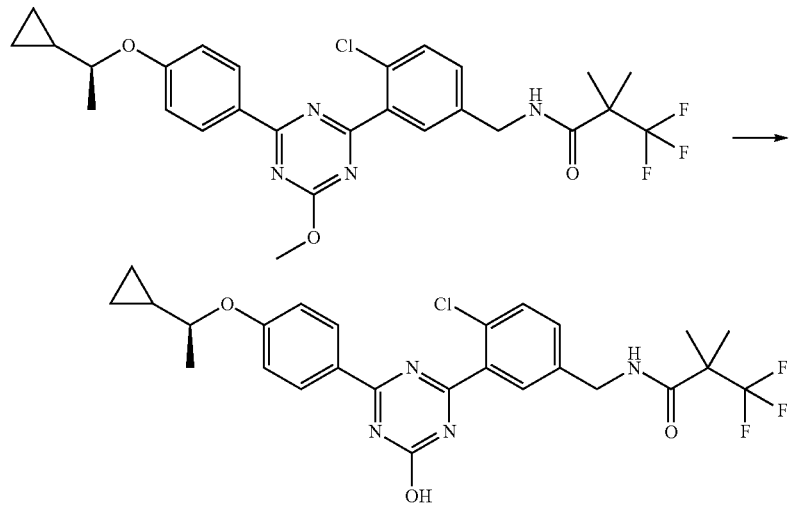

Under an argon atmosphere, to a solution of N-(4-chloro-3-{4-[4-((S)-1-cyclopropylethoxy)phenyl]-6-methoxy-1,3,5-triazin-2-yl}benzyl)-3,3,3-trifluoro-2,2-dimethylpropionamide (0.079 g, 0.14 mmol) obtained in the above-mentioned (1) in methanol (1.3 ml) was added 4M aqueous sodium hydroxide solution (0.22 ml) at room temperature, and the mixture was stirred at 65° C. for 4 hr. To the reaction mixture were added 10% aqueous citric acid solution (0.90 ml) and water at room temperature, and the mixture was stirred. The precipitated solid was collected by filtration, washed with water, and dried under reduced pressure to give the title compound (0.072 g, yield 93%).

Production Example 25

Synthesis of N-(4-chloro-3-{4-[4-((R)-1-cyclopropylethoxy)phenyl]-6-hydroxy-1,3,5-triazin-2-yl}benzyl)-3,3,3-trifluoro-2,2-dimethylpropionamide (Example No. 1-185)

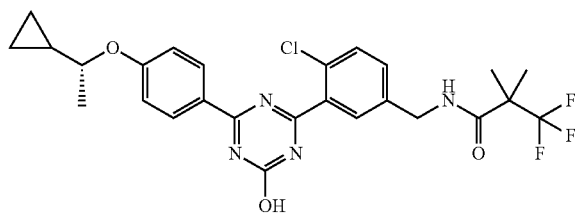 [SMILES: C[C@@H](Oc1ccc(-c2nc(O)nc(-c3cc(CNC(=O)C(C)(C)C(F)(F)F)ccc3Cl)n2)cc1)C1CC1]

(1) N-(4-chloro-3-{4-[4-((R)-1-cyclopropylethoxy)phenyl]-6-methoxy-1,3,5-triazin-2-yl}benzyl)-3,3,3-trifluoro-2,2-dimethylpropionamide

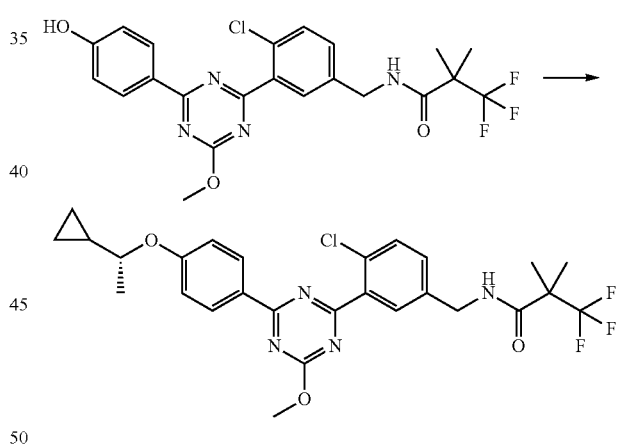

Under an argon atmosphere, to a solution of N-{4-chloro-3-[4-(4-hydroxyphenyl)-6-methoxy-1,3,5-triazin-2-yl]benzyl}-3,3,3-trifluoro-2,2-dimethylpropionamide (0.080 g, 0.17 mmol) obtained in the above-mentioned [Production Example 14] (6), (1S)-1-cyclopropylethan-1-ol (0.029 g, 0.33 mmol) and triphenylphosphine (0.087 g, 0.33 mmol) in tetrahydrofuran (1.0 ml) was added bis(2-methoxyethyl) azodicarboxylate (0.078 g, 0.33 mmol) under ice-cooling, and the mixture was stirred at room temperature for 17 hr. To the reaction mixture were added water and ethyl acetate, and the mixture was partitioned. The organic layer was washed with saturated brine, dried over sodium sulfate, filtered to remove sodium sulfate, and concentrated under reduced pressure. The residue was purified by silica gel column chromatography (eluent: n-hexane/ethyl acetate=2/1) to give the title compound (0.038 g, yield 41%).

¹H-NMR (CDCl₃) δ: 0.28-0.36 (1H, m), 0.38-0.45 (1H, m), 0.53-0.63 (2H, m), 1.12-1.21 (1H, m), 1.41 (3H, d, J=6.0 Hz), 1.44 (6H, s), 3.95-4.05 (1H, m), 4.18 (3H, s), 4.54 (2H, d, J=5.6 Hz), 6.20 (1H, br s), 6.95-7.00 (2H, m), 7.34 (1H, dd, J=8.3, 1.9 Hz), 7.51 (1H, d, J=8.3 Hz), 7.91 (1H, d, J=1.9 Hz), 8.50-8.55 (2H, m).

(2) N-(4-chloro-3-{4-[4-((R)-1-cyclopropylethoxy)phenyl]-6-hydroxy-1,3,5-triazin-2-yl}benzyl)-3,3,3-trifluoro-2,2-dimethylpropionamide (Example No. 1-185)

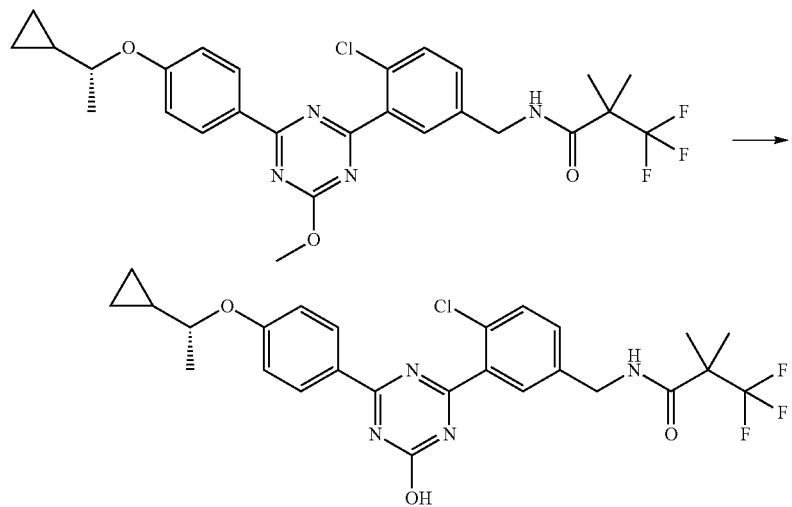

Under an argon atmosphere, to a solution of N-(4-chloro-3-{4-[4-((R)-1-cyclopropylethoxy)phenyl]-6-methoxy-1,3,5-triazin-2-yl}benzyl)-3,3,3-trifluoro-2,2-dimethylpropionamide (0.038 g, 0.069 mmol) obtained in the above-mentioned (1) in methanol (0.62 ml) was added 4M aqueous sodium hydroxide solution (0.10 ml) at room temperature, and the mixture was stirred at 65° C. for 4 hr. To the reaction mixture were added 10% aqueous citric acid solution (0.42 ml) and water at room temperature, and the mixture was stirred. The precipitated solid was collected by filtration, washed with water, and dried under reduced pressure to give the title compound (0.034 g, yield 91%).

The compounds of Example 1-1 to Example 1-267, Example 2-1 to Example 2-130, and Example 3-1 to Example 3-23 were obtained according to the above-mentioned Production Methods. The structural formulas and property data of the Example compounds are shown in Table 1-1 to Table 1-34, Table 2-1 to Table 2-15, and Table 3-1 to Table 3-3. In the Tables, the notes show the following.

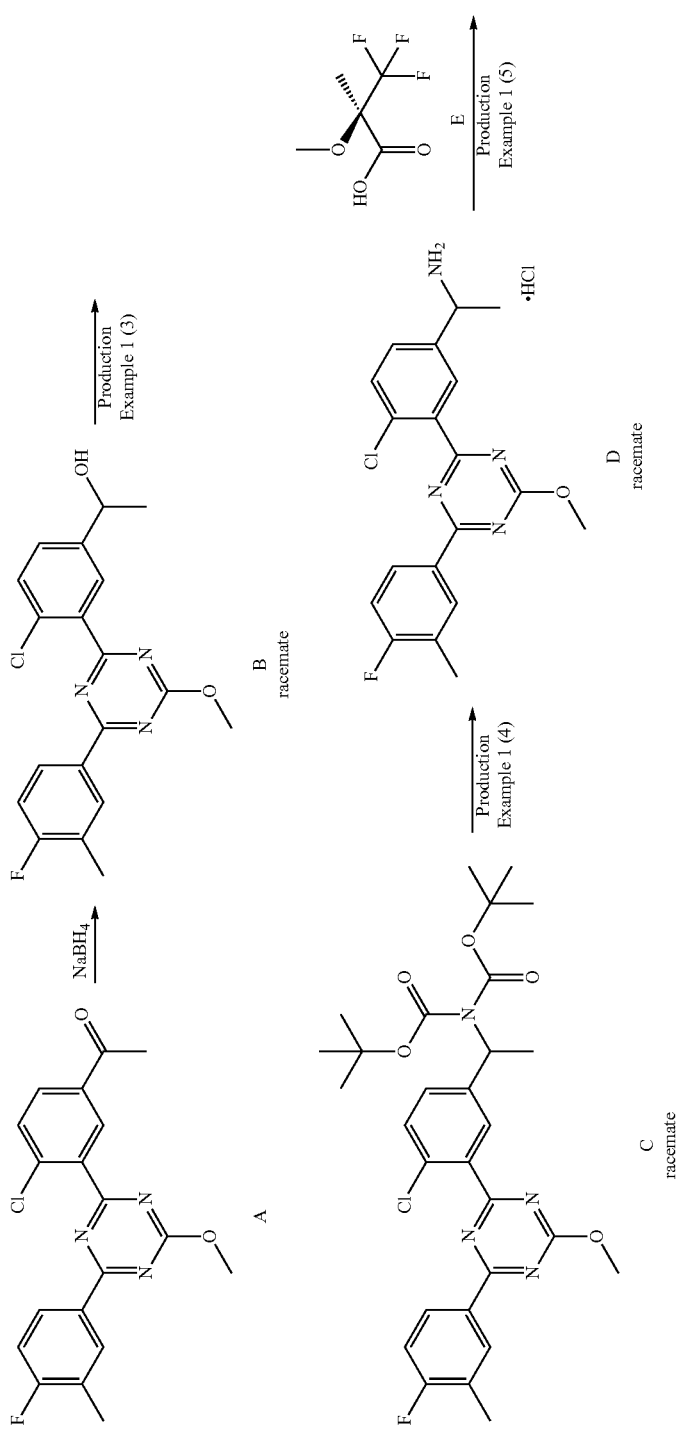

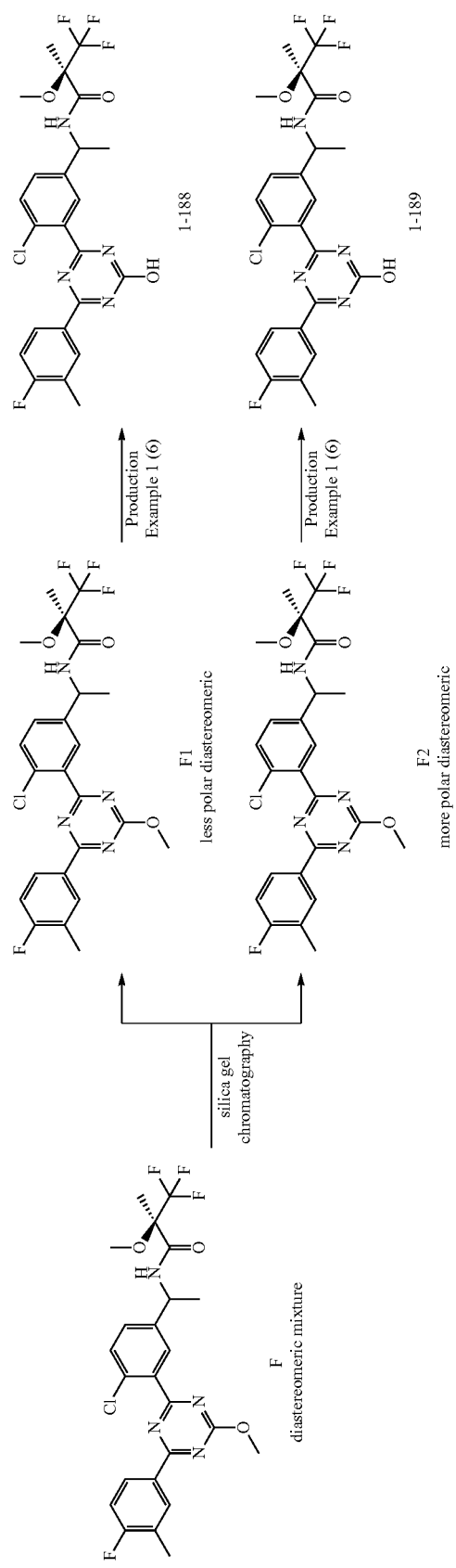

Note 1 (Example No. 1-188, 1-189)

Using 2,4-dichloro-6-methoxy-1,3,5-triazine, 4-fluoro-3-methylphenylboronic acid instead of 4-(2,2-dimethylpropoxy)phenylboronic acid, and 5-acetyl-2-chlorophenylboronic acid instead of 2-chloro-5-hydroxymethylphenylboronic acid, and by a method similar to that in Production Example 1 (1) and (2), compound A was obtained.

Racemic compound B was obtained by reducing the carbonyl group of compound A with sodium borohydride.

Racemic compound D was obtained by treating compound B in the same manner as in Production Example 1 (3) and (4).

Compound F as a diastereomer mixture was obtained by reacting racemic compound D with pure enantiomer compound E.

Compound F1 which is a less polar diastereomer (Merck TLC Silica gel 60G F254 25 Glassplates, eluent: n-hexane/ethyl acetate=2/1) and compound F2 which is a more polar diastereomer were obtained by purifying compound F by silica gel column chromatography. While compound F1 and compound F2 are single stereoisomers, the absolute configuration of the asymmetric carbon at the benzyl position is undetermined.

The compound of Example No. 1-188 was obtained by hydrolyzing compound F1 in the same manner as in Production Example 1 (6). Similarly, the compound of Example No. 1-189 was obtained from compound F2. While the compound of Example No. 1-188 and the compound of Example No. 1-189 are single stereoisomers, the absolute configuration of the asymmetric carbon at the benzyl position is undetermined.

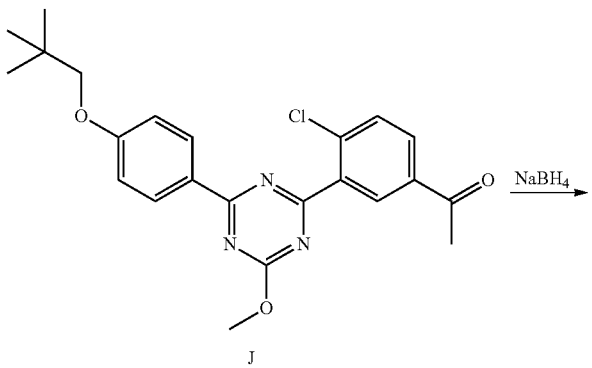

J

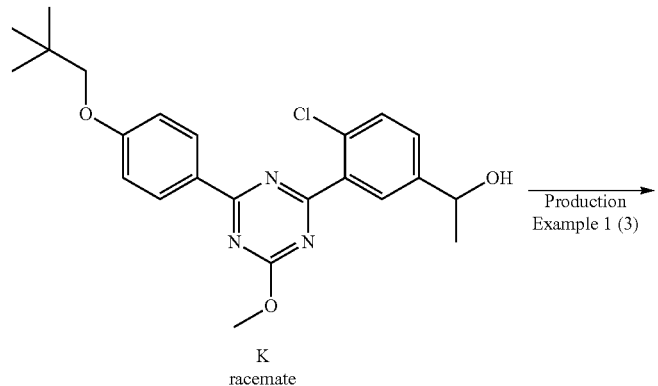

K
racemate

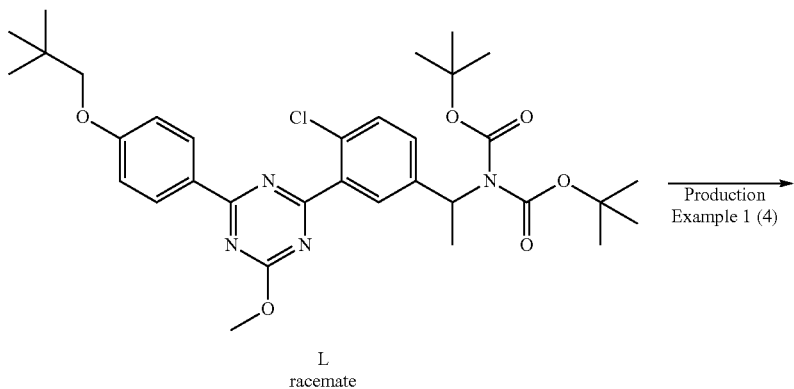

L
racemate

-continued
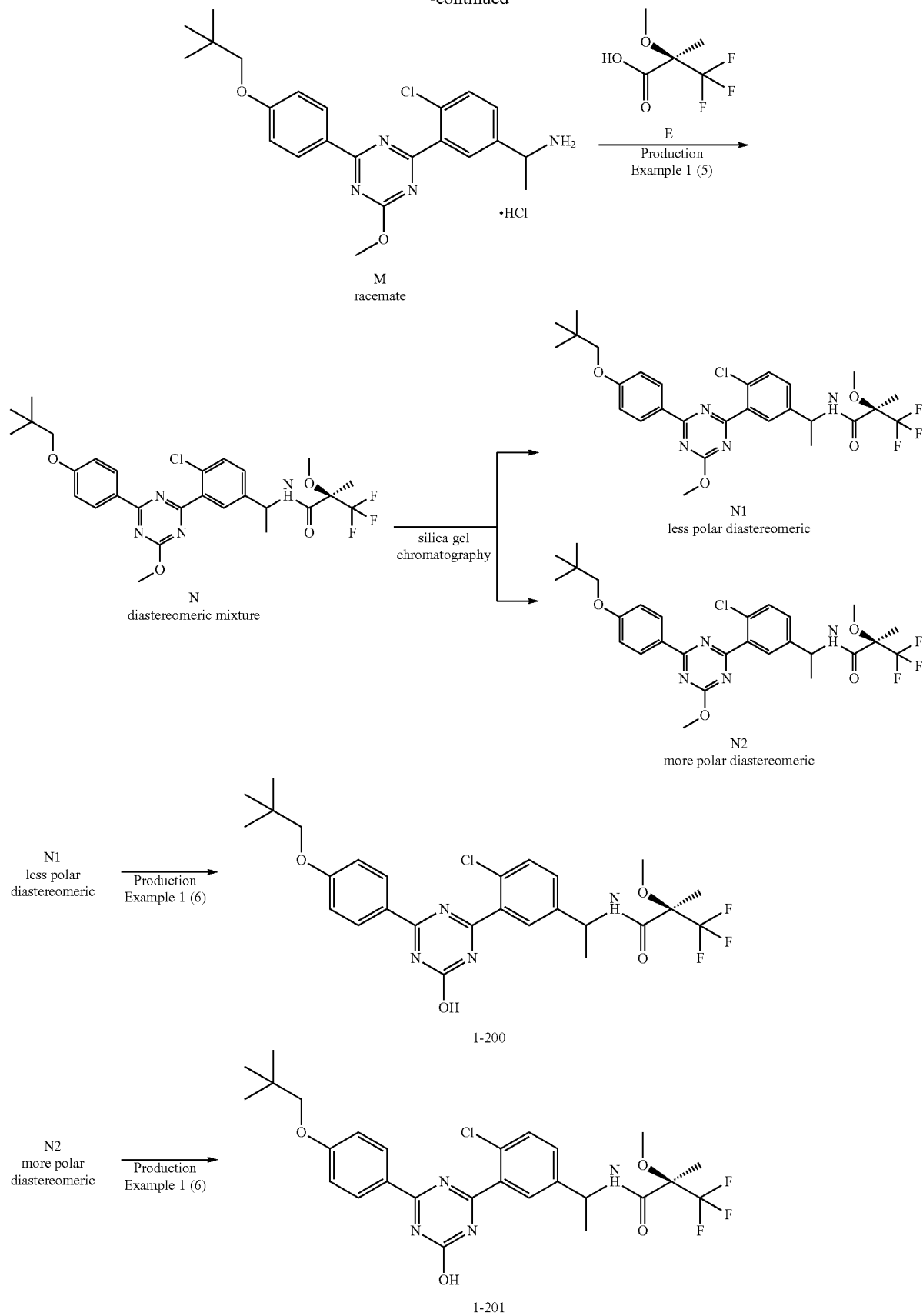

Note 2 (Example No. 1-200, 1-201)

Using 2,4-dichloro-6-methoxy-1,3,5-triazine, 4-(2,2-dimethylpropoxy)phenylboronic acid, and 5-acetyl-2-chlorophenylboronic acid instead of 2-chloro-5-hydroxymethylphenylboronic acid, and by a method similar to that in Production Example 1 (1) and (2), compound J was obtained.

Racemic compound K was obtained by reducing the carbonyl group of compound J with sodium borohydride.

Racemic compound M was obtained by treating compound K in the same manner as in Production Example 1 (3) and (4).

Compound N as a diastereomer mixture was obtained by reacting racemic compound M with pure enantiomer compound E.

Compound N was purified by silica gel column chromatography in the same manner as in note 1, by a method similar to that in Production Example 1 (6), the compound of Example No. 1-200 was obtained from compound N1 which is a less polar diastereomer (Merck TLC Silica gel 60G F254 25 Glassplates, eluent: n-hexane/ethyl acetate=2/1), and the compound of Example No. 1-201 was obtained from compound N2 which is a more polar diastereomer. While the compounds of Example Nos. 1-200 and 1-201 are single stereoisomers, the absolute configuration of the asymmetric carbon at the benzyl position is undetermined.

Note 3 (Example Nos. 1-256, 1-257)

While they are single stereoisomers, the relative configuration thereof is undetermined.

Note 4 (Example No. 1-266)

While it is a single stereoisomer, the relative configuration of the tert-butyl group is undetermined.

Note 5 (Example No. 1-267)

While it is a single stereoisomer, the relative configuration of the methoxy group is undetermined.

TABLE 1-1

| Example | Structure | NMR | MS(M + H) | MS(M − H) | Note |
|---|---|---|---|---|---|
| 1-1 | [structure] | 1H-NMR (DMSO-D6) δ: 2.50 (3H, s), 7.38 (1H, td, J = 8.3, 2.5 Hz), 7.46 (1H, dd, J = 8.4, 5.3 Hz), 7.56-7.65 (1H, br m), 7.95 (2H, d, J = 8.4 Hz), 8.55 (2H, d, J = 8.4 Hz), 13.33 (1H, br s). | 350 | 348 | |
| 1-2 | [structure] | 1H-NMR (DMSO-D6) δ: 2.35 (3H, s), 2.50 (3H, s), 7.30 (1H, d, J = 7.7 Hz), 7.34 (1H, d, J = 7.7 Hz), 7.51 (1H, br s), 7.94 (2H, d, J = 8.1 Hz), 8.55 (2H, d, J = 8.1 Hz), 13.17 (1H, br s). | 346 | 344 | |
| 1-3 | [structure] | 1H-NMR (DMSO-D6) δ: 2.50 (3H, s), 7.45 (1H, d, J = 8.4 Hz), 7.59 (1H, dd, J = 8.4, 2.3 Hz), 7.81 (1H, br s), 7.94 (2H, d, J = 8.1 Hz), 8.54 (2H, d, J = 8.1 Hz), 13.33 (1H, s). | 366 | 364 | |

TABLE 1-1-continued

| Example | Structure | NMR | MS(M + H) | MS(M − H) | Note |
|---|---|---|---|---|---|
| 1-4 | 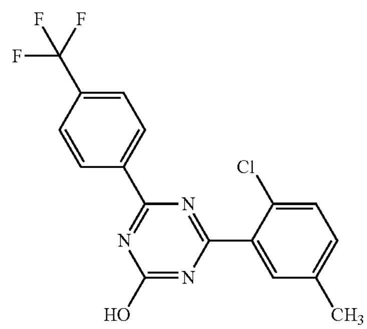 [SMILES: Cc1ccc(Cl)c(-c2nc(O)nc(-c3ccc(C(F)(F)F)cc3)n2)c1] | 1H-NMR (DMSO-D6) δ: 2.38 (3H, s), 7.46 (1H, d, J = 8.1 Hz), 7.55 (1H, d, J = 8.1 Hz), 7.64 (1H, br s), 7.94 (2H, d, J = 8.4 Hz), 8.54 (2H, d, J = 8.4 Hz), 13.49 (1H, br s). | 366 | 364 | |
| 1-5 | 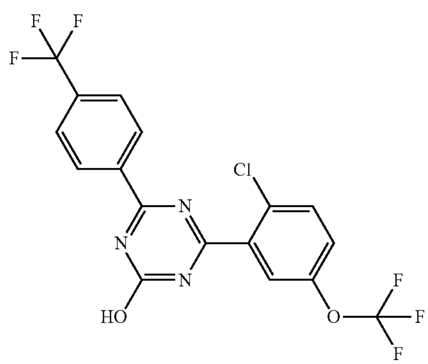 [SMILES: Oc1nc(-c2ccc(C(F)(F)F)cc2)nc(-c2cc(OC(F)(F)F)ccc2Cl)n1] | 1H-NMR (DMSO-D6) δ: 7.69 (1H, dd, J = 8.8, 2.2 Hz), 7.83 (1H, d, J = 8.8 Hz), 7.91 (1H, d, J = 2.2 Hz), 7.95 (2H, d, J = 8.2 Hz), 8.53 (2H, d, J = 8.2 Hz), 13.67 (1H, br s). | 436 | 434 | |
| 1-6 | 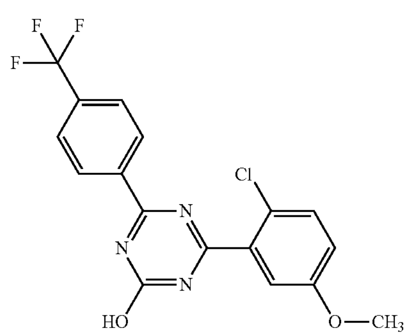 | 1H-NMR (DMSO-D6) δ: 3.83 (3H, s), 7.21 (1H, dd, J = 8.8, 3.1 Hz), 7.41 (1H, d, J = 3.1 Hz), 7.57 (1H, d, J = 8.8 Hz), 7.94 (2H, d, J = 8.4 Hz), 8.54 (2H, d, J = 8.4 Hz), 13.52 (1H, br s). | 382 | 380 | |
| 1-7 | 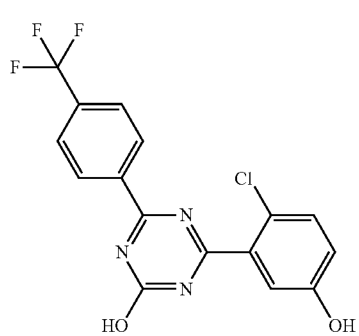 [SMILES: Oc1ccc(Cl)c(-c2nc(O)nc(-c3ccc(C(F)(F)F)cc3)n2)c1] | 1H-NMR (DMSO-D6) δ: 7.01 (1H, dd, J = 8.6, 2.9 Hz), 7.17 (1H, s), 7.44 (1H, d, J = 8.6 Hz), 7.94 (2H, d, J = 8.4 Hz), 8.53 (2H, d, J = 8.4 Hz), 10.17 (1H, s), 13.46 (1H, br s). | 368 | 366 | |

TABLE 1-1-continued

| Example | Structure | NMR | MS(M + H) | MS(M − H) | Note |
|---|---|---|---|---|---|
| 1-8 | 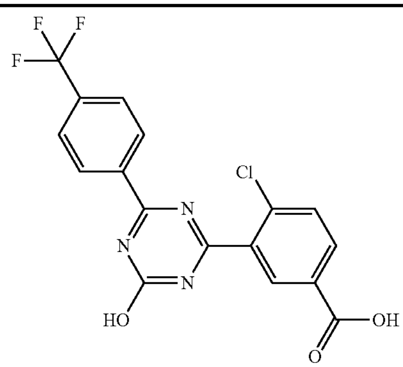 | 1H-NMR (DMSO-D6) δ: 7.81 (1H, d, J = 8.4 Hz), 7.94 (2H, d, J = 8.4 Hz), 8.12 (1H, dd, J = 8.5, 2.0 Hz), 8.36 (1H, d, J = 1.9 Hz), 8.54 (2H, d, J = 8.4 Hz), 13.53 (2H, br s). | 396 | 394 | |

TABLE 1-2

| Example | Structure | NMR | MS(M + H) | MS(M − H) | Note |
|---|---|---|---|---|---|
| 1-9 | | 1H-NMR (DMSO-D6) δ: 2.63 (3H, s), 7.66 (1H, d, J = 8.2 Hz), 7.88 (1H, dd, J = 8.3, 1.7 Hz), 7.95 (2H, d, J = 8.4 Hz), 8.11 (1H, br s), 8.54 (2H, d, J = 8.4 Hz), 13.41 (1H, br s). | 400 | 398 | |
| 1-10 | | 1H-NMR (DMSO-D6) δ: 2.61 (3H, s), 7.54 (1H, d, J = 7.9 Hz), 7.94 (2H, d, J = 8.4 Hz), 8.04 (1H, dd, J = 7.9, 1.8 Hz), 8.30 (1H, br s), 8.55 (2H, d, J = 8.4 Hz), 13.23 (2H, br s). | 376 | 374 | |
| 1-11 | | 1H-NMR (DMSO-D6) δ: 2.59 (3H, s), 7.46 (1H, br s), 7.50 (1H, d, J = 8.2 Hz), 7.94 (2H, d, J = 8.4 Hz), 8.00 (1H, dd, J = 7.9, 1.8 Hz), 8.01 (1H, br s), 8.24 (1H, br s), 8.56 (2H, d, J = 8.4 Hz), 13.28 (1H, s). | 375 | 373 | |

TABLE 1-2-continued
| 1-12 | 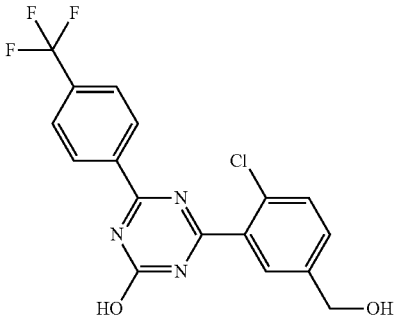 [SMILES: OCc1ccc(Cl)c(-c2nc(O)nc(-c3ccc(C(F)(F)F)cc3)n2)c1] | 1H-NMR (DMSO-D6) δ: 4.58 (2H, d, J = 5.5 Hz), 5.45 (1H, t, J = 5.6 Hz), 7.56 (1H, dd, J = 8.2, 2.0 Hz), 7.62 (1H, d, J = 8.2 Hz), 7.74 (1H, br s), 7.94 (2H, d, J = 8.4 Hz), 8.54 (2H, d, J = 8.4 Hz), 13.53 (1H, br s). | 382 | 380 |
|---|---|---|---|---|
| 1-13 | 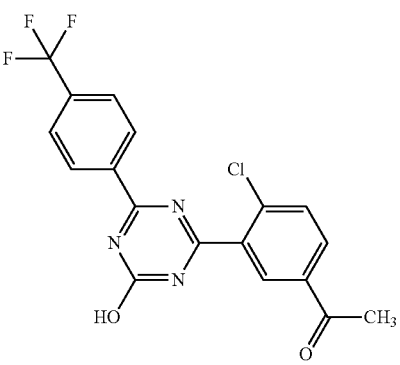 [SMILES: CC(=O)c1ccc(Cl)c(-c2nc(O)nc(-c3ccc(C(F)(F)F)cc3)n2)c1] | 1H-NMR (DMSO-D6) δ: 2.65 (3H, s), 7.84 (1H, d, J = 8.4 Hz), 7.95 (2H, d, J = 8.4 Hz), 8.16 (1H, dd, J = 8.4, 2.2 Hz), 8.38 (1H, d, J = 2.2 Hz), 8.54 (2H, d, J = 8.4 Hz), 13.65 (1H, s). | 394 | 392 |
| 1-14 | 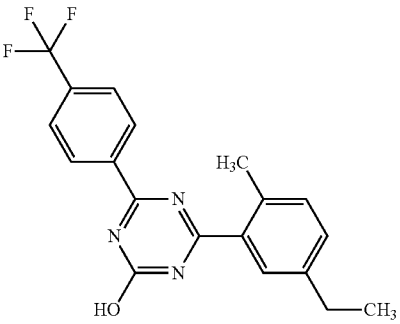 [SMILES: CCc1ccc(C)c(-c2nc(O)nc(-c3ccc(C(F)(F)F)cc3)n2)c1] | 1H-NMR (DMSO-D6) δ: 1.22 (3H, t, J = 7.7 Hz), 2.50 (3H, s), 2.66 (2H, q, J = 7.6 Hz), 7.32 (1H, d, J = 7.9 Hz), 7.37 (1H, dd, J = 7.8, 1.7 Hz), 7.55 (1H, br s), 7.94 (2H, d, J = 8.4 Hz), 8.55 (2H, d, J = 8.4 Hz), 13.19 (1H, br s). | 360 | 358 |
| 1-15 | 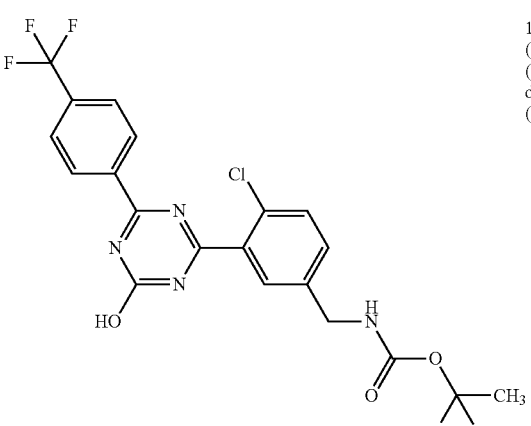 | 1H-NMR (DMSO-D6) δ: 1.39 (9H, s), 4.20 (2H, d, J = 6.0 Hz), 7.47-7.53 (2H, m), 7.62 (1H, d, J = 8.4 Hz), 7.66 (1H, br s), 7.93 (2H, d, J = 8.4 Hz), 8.53 (2H, d, J = 8.4 Hz), 13.54 (1H, s). | 481 | 479 |

TABLE 1-2-continued

| | | | | |
|---|---|---|---|---|
| 1-16 | (structure) | 1H-NMR (DMSO-D6) δ: 1.89 (3H, s), 4.32 (2H, d, J = 6.0 Hz), 7.49 (1H, dd, J = 8.3, 2.3 Hz), 7.62 (1H, d, J = 8.2 Hz), 7.67 (1H, d, J = 2.2 Hz), 7.94 (2H, d, J = 8.4 Hz), 8.46 (1H, t, J = 6.0 Hz), 8.53 (2H, d, J = 8.4 Hz), 13.55 (1H, br s). | 423 | 421 |

TABLE 1-3

| | | | | |
|---|---|---|---|---|
| 1-17 | (structure) | 1H-NMR (DMSO-D6) δ: 4.13 (2H, br s), 7.72-7.77 (2H, m), 7.93-7.97 (3H, m), 8.39 (3H, br s), 8.54 (2H, d, J = 8.4 Hz), 13.67 (1H, s). | 381 | 379 |
| 1-18 | (structure) | 1H-NMR (DMSO-D6) δ: 1.36 (3H, d, J = 6.4 Hz), 4.78-4.84 (1H, m), 5.42 (1H, d, J = 4.2 Hz), 7.57-7.62 (2H, m), 7.77 (1H, br s), 7.94 (2H, d, J = 8.2 Hz), 8.54 (2H, d, J = 8.2 Hz), 13.52 (1H, br s). | 396 | 394 |
| 1-19 | (structure) | 1H-NMR (DMSO-D6) δ: 3.34 (3H, s), 4.50 (2H, s), 7.57 (1H, dd, J = 8.3, 2.1 Hz), 7.65 (1H, d, J = 8.2 Hz), 7.76 (1H, d, J = 2.0 Hz), 7.94 (2H, d, J = 8.4 Hz), 8.54 (2H, d, J = 8.4 Hz), 13.54 (1H, br s). | 396 | 394 |

TABLE 1-3-continued

| | Structure | NMR | | |
|---|---|---|---|---|
| 1-20 | (4-(trifluoromethyl)phenyl)-triazine with 4-chloro-phenyl-CH2-NH-SO2-CH3 substituent, HO on triazine | 1H-NMR (DMSO-D6) δ: 2.93 (3H, s), 4.25 (2H, d, J = 6.4 Hz), 7.60 (1H, dd, J = 8.4, 2.0 Hz), 7.66 (1H, d, J = 8.4 Hz), 7.70 (1H, t, J = 6.4 Hz), 7.78 (1H, d, J = 2.0 Hz), 7.94 (2H, d, J = 8.4 Hz), 8.54 (2H, d, J = 8.4 Hz), 13.58 (1H, br s). | 459 | 457 |
| 1-21 | (4-(trifluoromethyl)phenyl)-triazine with 4-chloro-phenyl-CH2-N(CH3)-C(O)CH3 substituent, HO on triazine | 1H-NMR (DMSO-D6) δ: 2.07 (1.0H, s), 2.08 (2.0H, s), 2.82 (1.0H, s), 2.96 (2.0H, s), 4.56 (1.3H, s), 4.64 (0.7H, s), 7.47 (1.0H, d, J = 8.2 Hz), 7.61-7.68 (2.0H, m), 7.94 (2.0H, d, J = 8.4 Hz), 8.53 (2.0H, d, J = 8.4 Hz), 13.56 (1.0H, s). | 437 | 435 |
| 1-22 | (4-(trifluoromethyl)phenyl)-triazine with 4-chloro-phenyl-CH2-NH-C(O)-O-CH3 substituent, HO on triazine | 1H-NMR (DMSO-D6) δ: 3.56 (3H, s), 4.26 (2H, d, J = 6.2 Hz), 7.50 (1H, dd, J = 8.5, 2.1 Hz), 7.63 (1H, d, J = 8.4 Hz), 7.68 (1H, d, J = 2.0 Hz), 7.80 (1H, t, J = 6.2 Hz), 7.94 (2H, d, J = 8.4 Hz), 8.53 (2H, d, J = 8.4 Hz), 13.54 (1H, s). | 439 | 437 |
| 1-23 | (4-(trifluoromethyl)phenyl)-triazine with 4-chloro-phenyl-CH2-COOH substituent, HO on triazine | 1H-NMR (DMSO-D6) δ: 3.71 (2H, s), 7.53 (1H, dd, J = 8.3, 1.9 Hz), 7.62 (1H, d, J = 8.2 Hz), 7.71 (1H, d, J = 1.8 Hz), 7.94 (2H, d, J = 8.4 Hz), 8.54 (2H, d, J = 8.4 Hz), 12.53 (1H, br s), 13.54 (1H, br s). | 410 | 408 |

TABLE 1-3-continued
| 1-24 | 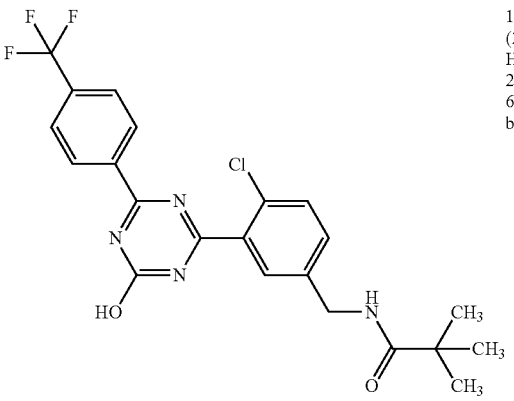 | 1H-NMR (DMSO-D6) δ: 1.13 (9H, s), 4.32 (2H, d, J = 6.0 Hz), 7.45 (1H, dd, J = 8.3, 2.1 Hz), 7.61 (1H, d, J = 8.2 Hz), 7.65 (1H, d, J = 2.0 Hz), 7.94 (2H, d, J = 8.4 Hz), 8.18 (1H, t, J = 6.1 Hz), 8.53 (2H, d, J = 8.4 Hz), 13.55 (1H, br s). | 465 | 463 |
TABLE 1-4
| 1-25 | 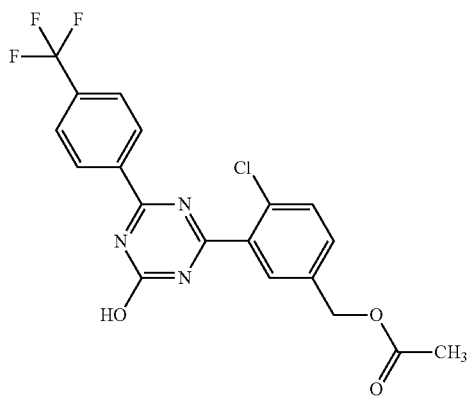 [SMILES: CC(=O)OCc1ccc(Cl)c(-c2nc(O)nc(-c3ccc(C(F)(F)F)cc3)n2)c1] | 1H-NMR (DMSO-D6) δ: 2.09 (3H, s), 5.16 (2H, s), 7.63 (1H, dd, J = 8.3, 2.1 Hz), 7.68 (1H, d, J = 8.2 Hz), 7.81 (1H, d, J = 2.0 Hz), 7.94 (2H, d, J = 8.4 Hz), 8.54 (2H, d, J = 8.4 Hz), 13.57 (1H, br s). | 424 | 422 |
| 1-26 | 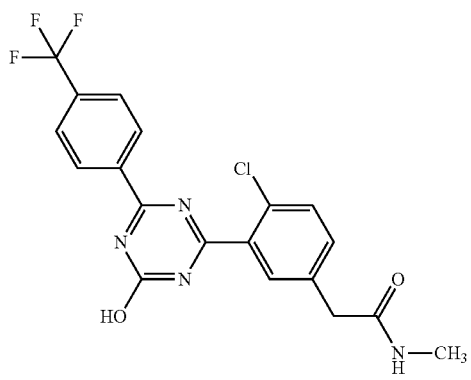 [SMILES: CNC(=O)Cc1ccc(Cl)c(-c2nc(O)nc(-c3ccc(C(F)(F)F)cc3)n2)c1] | 1H-NMR (DMSO-D6) δ: 2.59 (3H, d, J = 4.6 Hz), 3.50 (2H, s), 7.50 (1H, dd, J = 8.3, 2.1 Hz), 7.60 (1H, d, J = 8.4 Hz), 7.67 (1H, d, J = 2.0 Hz), 7.94 (2H, d, J = 8.4 Hz), 8.01-8.06 (1H, br m), 8.54 (2H, d, J = 8.4 Hz), 13.54 (1H, s). | 423 | 421 |

TABLE 1-4-continued
| 1-27 | 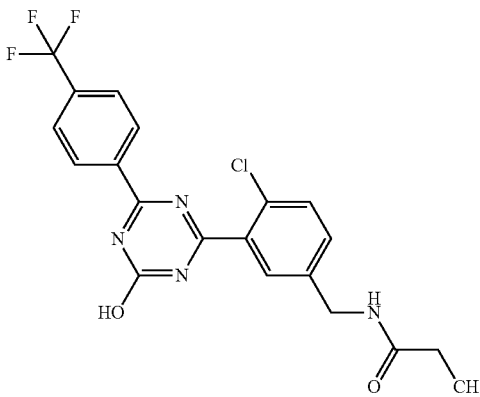 | 1H-NMR (DMSO-D6) δ: 1.02 (3H, t, J = 7.6 Hz), 2.16 (2H, q, J = 7.6 Hz), 4.32 (2H, d, J = 6.0 Hz), 7.49 (1H, dd, J = 8.4, 2.2 Hz), 7.62 (1H, d, J = 8.4 Hz), 7.67 (1H, d, J = 2.2 Hz), 7.94 (2H, d, J = 8.4 Hz), 8.39 (1H, t, J = 6.0 Hz), 8.53 (2H, d, J = 8.4 Hz), 13.55 (1H, br s). | 437 | 435 |
|---|---|---|---|---|
| 1-28 | 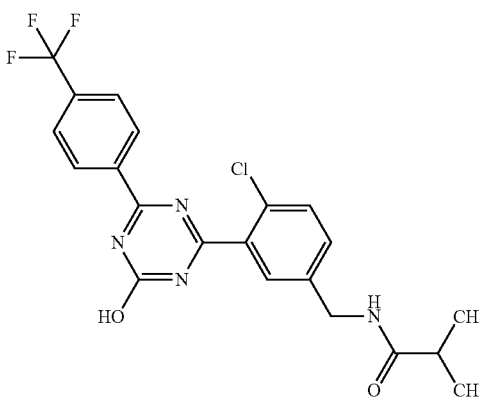 | 1H-NMR (DMSO-D6) δ: 1.04 (6H, d, J = 7.1 Hz), 2.38-2.48 (1H, m), 4.32 (2H, d, J = 6.2 Hz), 7.47 (1H, dd, J = 8.4, 2.2 Hz), 7.62 (1H, d, J = 8.4 Hz), 7.66 (1H, d, J = 2.2 Hz), 7.94 (2H, d, J = 8.4 Hz), 8.37 (1H, t, J = 6.2 Hz), 8.53 (2H, d, J = 8.4 Hz), 13.55 (1H, br s). | 451 | 449 |
| 1-29 | 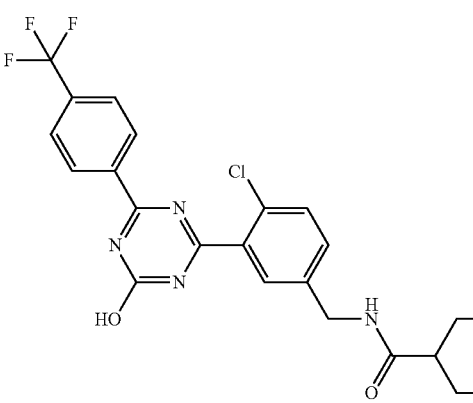 | 1H-NMR (DMSO-D6) δ: 1.11-1.40 (5H, m), 1.57-1.76 (5H, m), 2.13-2.20 (1H, m), 4.31 (2H, d, J = 6.2 Hz), 7.46 (1H, dd, J = 8.3, 2.1 Hz), 7.61 (1H, d, J = 8.2 Hz), 7.65 (1H, d, J = 2.0 Hz), 7.93 (2H, d, J = 8.4 Hz), 8.34 (1H, t, J = 6.1 Hz), 8.53 (2H, d, J = 8.4 Hz), 13.55 (1H, br s). | 491 | 489 |
| 1-30 | 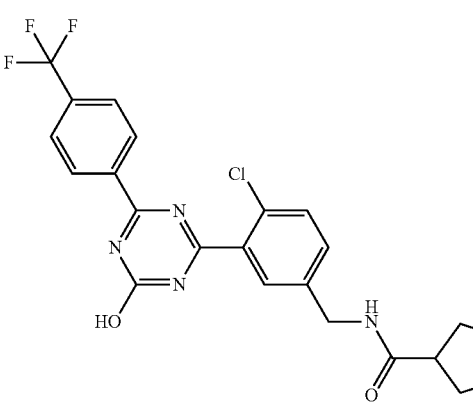 | 1H-NMR (DMSO-D6) δ: 1.44-1.82 (8H, m), 2.58-2.66 (1H, m), 4.32 (2H, d, J = 6.2 Hz), 7.47 (1H, dd, J = 8.3, 2.1 Hz), 7.62 (1H, d, J = 8.2 Hz), 7.66 (1H, d, J = 2.0 Hz), 7.93 (2H, d, J = 8.4 Hz), 8.39 (1H, t, J = 6.2 Hz), 8.53 (2H, d, J = 8.4 Hz), 13.55 (1H, br s). | 477 | 475 |

TABLE 1-4-continued
| 1-31 | 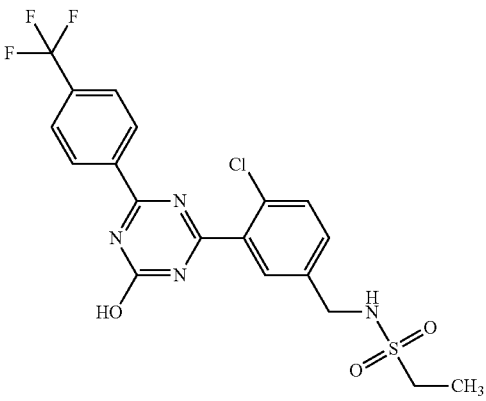 [SMILES: CCS(=O)(=O)NCc1ccc(Cl)c(-c2nc(O)nc(-c3ccc(C(F)(F)F)cc3)n2)c1] | 1H-NMR (DMSO-D6) δ: 1.20 (3H, t, J = 7.3 Hz), 3.02 (2H, q, J = 7.4 Hz), 4.23 (2H, d, J = 6.5 Hz), 7.60 (1H, dd, J = 8.4, 2.1 Hz), 7.66 (1H, d, J = 8.4 Hz), 7.72 (1H, t, J = 6.4 Hz), 7.77 (1H, d, J = 2.1 Hz), 7.94 (2H, d, J = 8.4 Hz), 8.54 (2H, d, J = 8.4 Hz), 13.57 (1H, br s). | 473 | 471 |
|---|---|---|---|---|
| 1-32 | 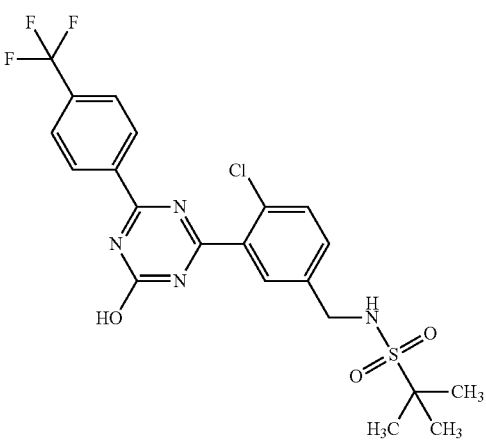 [SMILES: CC(C)(C)S(=O)(=O)NCc1ccc(Cl)c(-c2nc(O)nc(-c3ccc(C(F)(F)F)cc3)n2)c1] | 1H-NMR (DMSO-D6) δ: 1.31 (9H, s), 4.32 (2H, d, J = 6.4 Hz), 7.60-7.66 (3H, m), 7.76 (1H, br s), 7.94 (2H, d, J = 8.4 Hz), 8.53 (2H, d, J = 8.4 Hz), 13.58 (1H, br s). | 501 | 499 |
45
TABLE 1-5
| 1-33 | 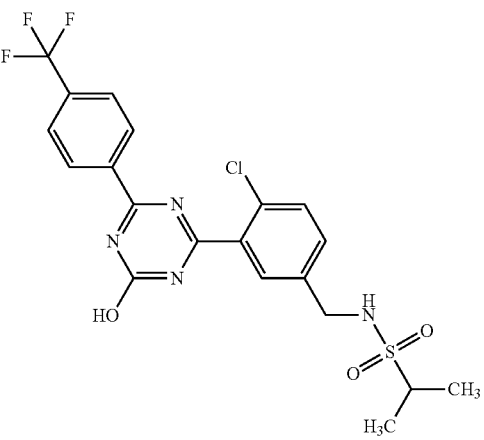 [SMILES: CC(C)S(=O)(=O)NCc1ccc(Cl)c(-c2nc(O)nc(-c3ccc(C(F)(F)F)cc3)n2)c1] | 1H-NMR (DMSO-D6) δ: 1.24 (6H, d, J = 6.8 Hz), 3.14-3.20 (1H, m), 4.25 (2H, d, J = 6.4 Hz), 7.60 (1H, dd, J = 8.5, 1.9 Hz), 7.66 (1H, d, J = 8.4 Hz), 7.70 (1H, t, J = 6.5 Hz), 7.77 (1H, d, J = 1.8 Hz), 7.94 (2H, d, J = 8.2 Hz), 8.53 (2H, d, J = 8.2 Hz), 13.58 (1H, br s). | 487 | 485 |
|---|---|---|---|---|

TABLE 1-5-continued

| | Structure | NMR | | |
|---|---|---|---|---|
| 1-34 | (structure) | 1H-NMR (DMSO-D6) δ: 2.81 (6H, s), 4.28 (2H, d, J = 5.8 Hz), 6.98 (1H, t, J = 5.9 Hz), 7.50 (1H, dd, J = 8.3, 2.0 Hz), 7.59 (1H, d, J = 8.4 Hz), 7.68 (1H, d, J = 1.9 Hz), 7.94 (2H, d, J = 8.4 Hz), 8.53 (2H, d, J = 8.4 Hz), 13.54 (1H, br s). | 452 | 450 |
| 1-35 | (structure) | 1H-NMR (DMSO-D6) δ: 2.56 (3H, d, J = 4.6 Hz), 4.26 (2H, d, J = 6.2 Hz), 5.90 (1H, q, J = 4.6 Hz), 6.52 (1H, t, J = 6.2 Hz), 7.49 (1H, dd, J = 8.3, 2.1 Hz), 7.60 (1H, d, J = 8.4 Hz), 7.66 (1H, d, J = 2.0 Hz), 7.94 (2H, d, J = 8.4 Hz), 8.53 (2H, d, J = 8.4 Hz), 13.55 (1H, br s). | 438 | 436 |
| 1-36 | (structure) | 1H-NMR (DMSO-D6) δ: 0.85 (3H, t, J = 7.4 Hz), 1.54 (2H, sextet, J = 7.4 Hz), 2.13 (2H, t, J = 7.4 Hz), 4.33 (2H, d, J = 6.2 Hz), 7.48 (1H, dd, J = 8.2, 2.0 Hz), 7.62 (1H, d, J = 8.2 Hz), 7.66 (1H, d, J = 2.0 Hz), 7.94 (2H, d, J = 8.2 Hz), 8.41 (1H, t, J = 6.1 Hz), 8.53 (2H, d, J = 8.2 Hz), 13.55 (1H, br s). | 451 | 449 |
| 1-37 | (structure) | 1H-NMR (DMSO-D6) δ: 0.87 (6H, d, J = 6.4 Hz), 1.96-2.06 (3H, m), 4.33 (2H, d, J = 6.0 Hz), 7.48 (1H, dd, J = 8.2, 2.0 Hz), 7.61 (1H, d, J = 8.2 Hz), 7.66 (1H, d, J = 2.0 Hz), 7.93 (2H, d, J = 8.4 Hz), 8.42 (1H, t, J = 6.1 Hz), 8.53 (2H, d, J = 8.4 Hz), 13.55 (1H, br s). | 465 | 463 |

| | | | | |
|---|---|---|---|---|
| 1-38 | 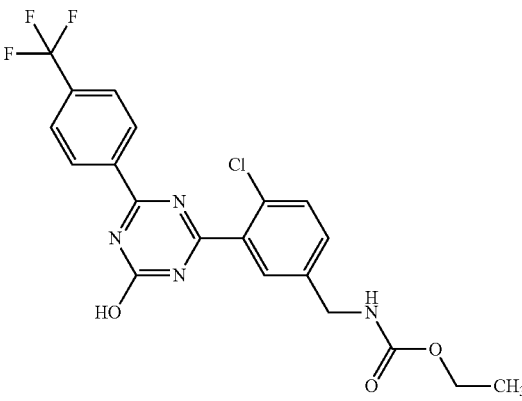 [SMILES: CCOC(=O)NCc1ccc(Cl)c(-c2nc(O)nc(-c3ccc(C(F)(F)F)cc3)n2)c1] | 1H-NMR (DMSO-D6) δ: 1.16 (3H, t, J = 7.1 Hz), 4.01 (2H, q, J = 7.1 Hz), 4.25 (2H, d, J = 6.2 Hz), 7.50 (1H, dd, J = 8.4, 2.0 Hz), 7.63 (1H, d, J = 8.4 Hz), 7.68 (1H, d, J = 2.0 Hz), 7.76 (1H, t, J = 6.3 Hz), 7.94 (2H, d, J = 8.4 Hz), 8.53 (2H, d, J = 8.4 Hz), 13.55 (1H, br s). | 453 | 451 |
| 1-39 | 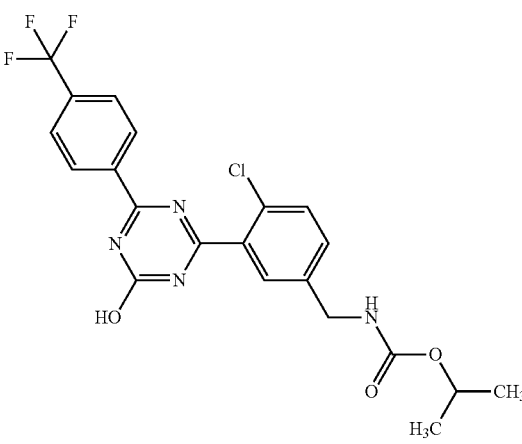 [SMILES: CC(C)OC(=O)NCc1ccc(Cl)c(-c2nc(O)nc(-c3ccc(C(F)(F)F)cc3)n2)c1] | 1H-NMR (DMSO-D6) δ: 1.17 (6H, d, J = 6.2 Hz), 4.24 (2H, d, J = 6.2 Hz), 4.73-4.80 (1H, m), 7.49 (1H, dd, J = 8.4, 2.0 Hz), 7.63 (1H, d, J = 8.4 Hz), 7.66-7.71 (2H, m), 7.93 (2H, d, J = 8.4 Hz), 8.53 (2H, d, J = 8.4 Hz), 13.55 (1H, br s). | 467 | 465 |
| 1-40 | 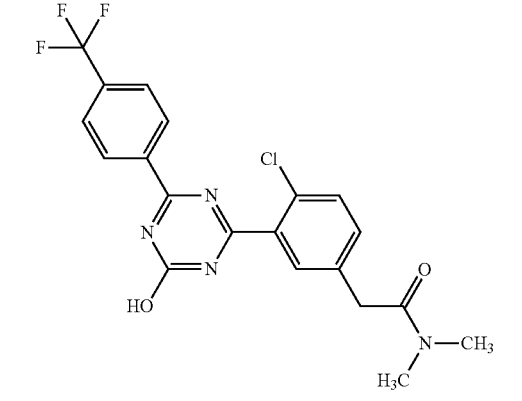 [SMILES: CN(C)C(=O)Cc1ccc(Cl)c(-c2nc(O)nc(-c3ccc(C(F)(F)F)cc3)n2)c1] | 1H-NMR (DMSO-D6) δ: 2.85 (3H, s), 3.05 (3H, s), 3.80 (2H, s), 7.47 (1H, dd, J = 8.4, 2.2 Hz), 7.59 (1H, d, J = 8.4 Hz), 7.65 (1H, d, J = 2.2 Hz), 7.94 (2H, d, J = 8.4 Hz), 8.54 (2H, d, J = 8.4 Hz), 13.54 (1H, br s). | 437 | 435 |

TABLE 1-6

| | | | | |
|---|---|---|---|---|
| 1-41 | (structure) | 1H-NMR (DMSO-D6) δ: 1.25 (9H, s), 3.47 (2H, s), 7.49 (1H, dd, J = 8.5, 2.1 Hz), 7.59 (1H, d, J = 8.4 Hz), 7.66 (1H, d, J = 2.0 Hz), 7.77 (1H, s), 7.94 (2H, d, J = 8.4 Hz), 8.54 (2H, d, J = 8.4 Hz), 13.54 (1H, s). | 465 | 463 |
| 1-42 | (structure) | 1H-NMR (DMSO-D6) δ: 1.51-1.71 (4H, m), 1.83-1.92 (4H, m), 3.47-3.54 (1H, m), 4.26 (2H, d, J = 6.4 Hz), 7.59 (1H, d, J = 8.3 Hz), 7.66 (1H, d, J = 8.3 Hz), 7.72 (1H, t, J = 6.3 Hz), 7.77 (1H, s), 7.94 (2H, d, J = 8.3 Hz), 8.53 (2H, d, J = 8.3 Hz), 13.58 (1H, br s). | 513 | 511 |
| 1-43 | (structure) | 1H-NMR (DMSO-D6) δ: 1.13 (9H, s), 4.31 (2H, d, J = 6.0 Hz), 7.44 (1H, dd, J = 8.2, 2.0 Hz), 7.56-7.58 (3H, m), 7.64-7.69 (2H, m), 8.18 (1H, t, J = 6.0 Hz), 8.34 (2H, d, J = 7.1 Hz), 13.34 (1H, br s). | 397 | 395 |
| 1-44 | (structure) | 1H-NMR (DMSO-D6) δ: 0.91 (3H, t, J = 7.4 Hz), 1.13 (9H, s), 1.62-1.65 (2H, m), 2.65 (2H, t, J = 7.5 Hz), 4.31 (2H, d, J = 6.0 Hz), 7.38 (2H, d, J = 8.2 Hz), 7.43 (1H, dd, J = 8.4, 2.0 Hz), 7.59 (1H, d, J = 8.4 Hz), 7.64 (1H, br s), 8.17 (1H, t, J = 6.1 Hz), 8.26 (2H, d, J = 8.2 Hz), 13.25 (1H, br s). | 439 | 437 |

| | | | | |
|---|---|---|---|---|
| 1-45 | 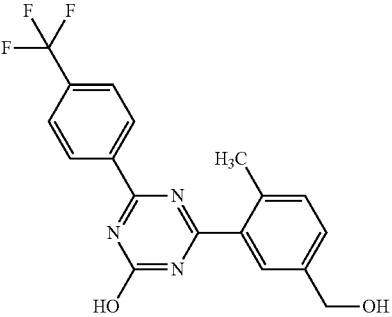 | 1H-NMR (DMSO-D6) δ: 2.51 (3H, s), 4.55 (2H, d, J = 5.5 Hz), 5.29 (1H, t, J = 5.6 Hz), 7.36 (1H, d, J = 7.9 Hz), 7.46 (1H, dd, J = 7.8, 1.7 Hz), 7.65 (1H, br s), 7.94 (2H, d, J = 8.4 Hz), 8.55 (2H, d, J = 8.4 Hz), 13.22 (1H, br s). | 362 | 360 |
| 1-46 | 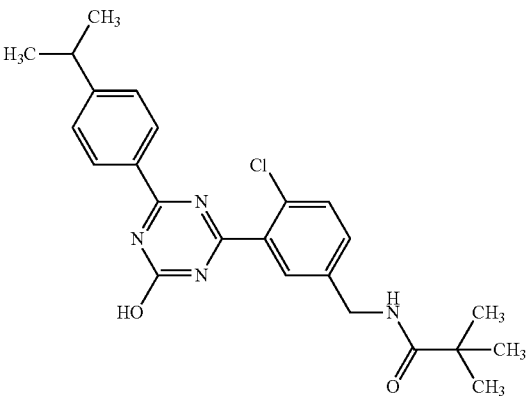 [SMILES: CC(C)c1ccc(-c2nc(O)nc(-c3cc(CNC(=O)C(C)(C)C)ccc3Cl)n2)cc1] | 1H-NMR (DMSO-D6) δ: 1.13 (9H, s), 1.24 (6H, d, J = 6.8 Hz), 2.96-3.03 (1H, m), 4.31 (2H, d, J = 6.0 Hz), 7.41-7.46 (3H, m), 7.58 (1H, d, J = 8.4 Hz), 7.64 (1H, br s), 8.17 (1H, t, J = 6.0 Hz), 8.27 (2H, d, J = 8.2 Hz), 13.26 (1H, br s). | 439 | 437 |
| 1-47 | 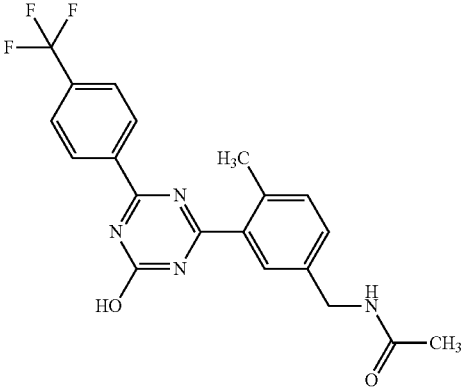 [SMILES: CC(=O)NCc1ccc(C)c(-c2nc(O)nc(-c3ccc(C(F)(F)F)cc3)n2)c1] | 1H-NMR (DMSO-D6) δ: 1.88 (3H, s), 2.50 (3H, s), 4.29 (2H, d, J = 6.0 Hz), 7.35 (1H, d, J = 7.9 Hz), 7.39 (1H, dd, J = 7.9, 1.8 Hz), 7.59 (1H, br s), 7.94 (2H, d, J = 8.2 Hz), 8.37 (1H, t, J = 6.0 Hz), 8.54 (2H, d, J = 8.2 Hz), 13.26 (1H, br s). | 403 | 401 |
| 1-48 | 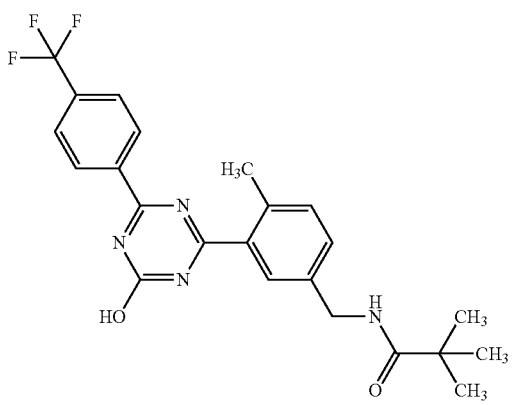 [SMILES: Cc1ccc(CNC(=O)C(C)(C)C)cc1-c1nc(O)nc(-c2ccc(C(F)(F)F)cc2)n1] | 1H-NMR (DMSO-D6) δ: 1.13 (9H, s), 2.50 (3H, s), 4.30 (2H, d, J = 6.0 Hz), 7.34-7.35 (2H, br m), 7.57 (1H, br s), 7.93 (2H, d, J = 8.4 Hz), 8.09 (1H, t, J = 6.1 Hz), 8.54 (2H, d, J = 8.4 Hz), 13.24 (1H, br s). | 445 | 443 |

TABLE 1-7
| | | | | |
|---|---|---|---|---|
| 1-49 | 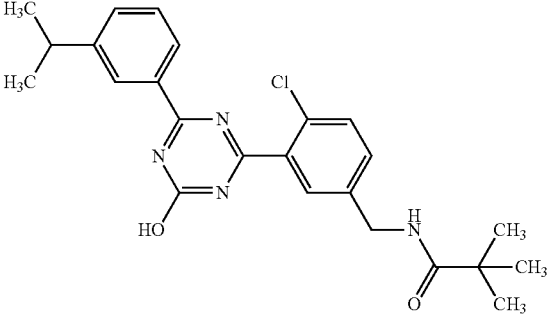 [SMILES: CC(C)c1cccc(-c2nc(O)nc(-c3cc(CNC(=O)C(C)(C)C)ccc3Cl)n2)c1] | 1H-NMR (DMSO-D6) δ: 1.13 (9H, s), 1.25 (6H, d, J = 7.0 Hz), 2.96-3.03 (1H, m), 4.32 (2H, d, J = 5.8 Hz), 7.44 (1H, dd, J = 8.1, 1.2 Hz), 7.48 (1H, t, J = 7.7 Hz), 7.56 (1H, d, J = 7.7 Hz), 7.59 (1H, d, J = 8.1 Hz), 7.65 (1H, br s), 8.16-8.20 (3H, m), 13.30 (1H, br s). | 439 | 437 |
| 1-50 | 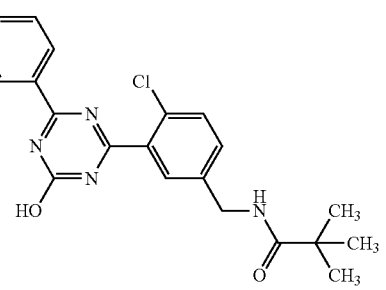 | 1H-NMR (DMSO-D6) δ: 0.91 (3H, t, J = 7.3 Hz), 1.13 (9H, s), 1.61-1.65 (2H, m), 2.65 (2H, t, J = 7.5 Hz), 4.31 (2H, d, J = 6.2 Hz), 7.43-7.50 (3H, m), 7.59 (1H, d, J = 8.2 Hz), 7.64 (1H, br s), 8.16-8.18 (3H, m), 13.30 (1H, s). | 439 | 437 |
| 1-51 | 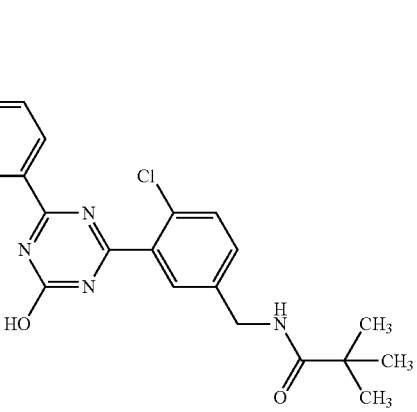 | 1H-NMR (DMSO-D6) δ: 0.88 (6H, d, J = 6.6 Hz), 1.13 (9H, s), 1.88-1.92 (1H, m), 2.55 (2H, d, J = 7.1 Hz), 4.31 (2H, d, J = 6.2 Hz), 7.35 (2H, d, J = 8.2 Hz), 7.43 (1H, dd, J = 8.4, 2.0 Hz), 7.58 (1H, d, J = 8.2 Hz), 7.64 (1H, br s), 8.17 (1H, t, J = 6.1 Hz), 8.26 (2H, d, J = 8.4 Hz), 13.25 (1H, br s). | 439 | 437 |
| 1-52 | 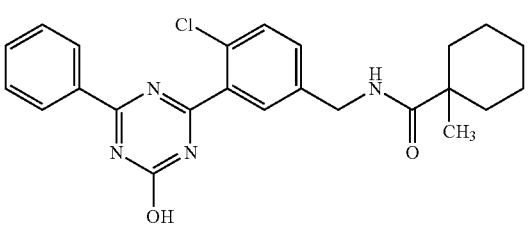 [SMILES: CC1(C(=O)NCc2ccc(Cl)c(-c3nc(O)nc(-c4ccccc4)n3)c2)CCCCC1] | 1H-NMR (DMSO-D6) δ: 1.06 (3H, s), 1.14-1.49 (8H, m), 1.91-1.98 (2H, m), 4.32 (2H, d, J = 5.8 Hz), 7.43 (1H, d, J = 8.1 Hz), 7.52-7.59 (3H, m), 7.62-7.67 (2H, m), 8.16 (1H, t, J = 5.9 Hz), 8.32 (2H, d, J = 8.1 Hz), 13.31 (1H, br s). | 437 | 435 |
| 1-53 | 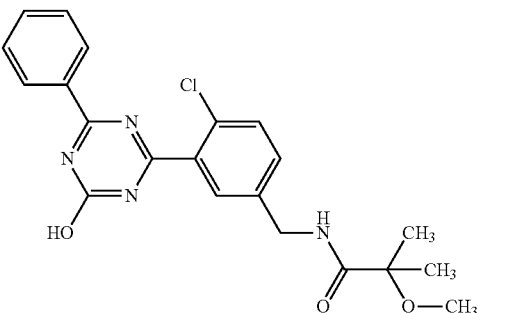 | 1H-NMR (DMSO-D6) δ: 1.26 (6H, s), 3.15 (3H, s), 4.32 (2H, d, J = 6.3 Hz), 7.45 (1H, d, J = 7.2 Hz), 7.53-7.59 (3H, m), 7.63-7.68 (2H, m), 8.32 (2H, d, J = 7.9 Hz), 8.46 (1H, t, J = 6.3 Hz), 13.31 (1H, br s). | 413 | 411 |

TABLE 1-7-continued
| | | | | |
|---|---|---|---|---|
| 1-54 | 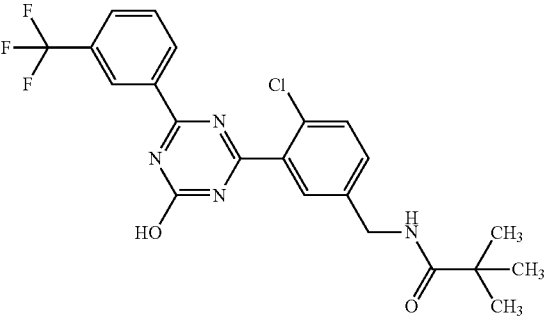 [SMILES: CC(C)(C)C(=O)NCc1ccc(Cl)c(-c2nc(O)nc(-c3cccc(C(F)(F)F)c3)n2)c1] | 1H-NMR (DMSO-D6) δ: 1.12 (9H, s), 4.31 (2H, d, J = 6.0 Hz), 7.45 (1H, d, J = 8.4 Hz), 7.60 (1H, d, J = 8.4 Hz), 7.63 (1H, s), 7.81 (1H, t, J = 7.9 Hz), 8.03 (1H, d, J = 7.4 Hz), 8.16 (1H, t, J = 5.9 Hz), 8.57-8.63 (2H, m), 13.51 (1H, br s). | 465 | 463 |
| 1-55 | 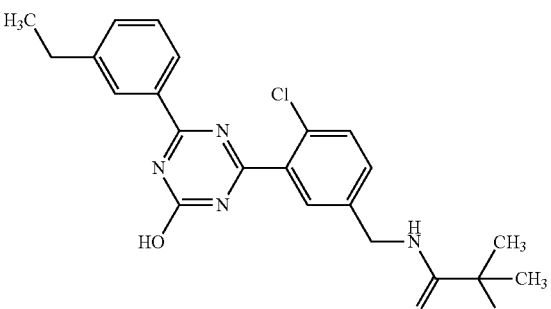 | 1H-NMR (DMSO-D6) δ: 1.13 (9H, s), 1.22 (3H, t, J = 7.6 Hz), 2.70 (2H, q, J = 7.6 Hz), 4.31 (2H, d, J = 6.0 Hz), 7.42-7.53 (3H, m), 7.59 (1H, d, J = 8.2 Hz), 7.64 (1H, s), 8.15-8.19 (3H, m), 13.31 (1H, br s). | 425 | 423 |
| 1-56 | 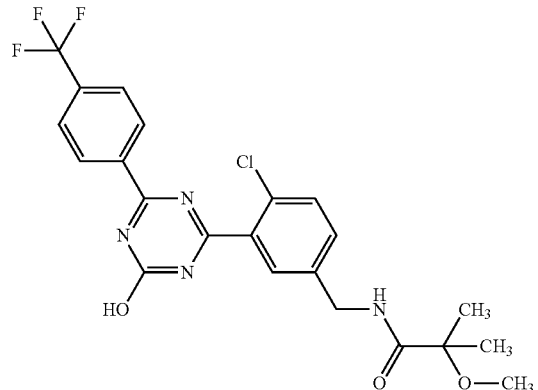 | 1H-NMR (DMSO-D6) δ: 1.28 (6H, s), 3.17 (3H, s), 4.33 (2H, d, J = 6.2 Hz), 7.48 (1H, dd, J = 8.4, 2.1 Hz), 7.61 (1H, d, J = 8.3 Hz), 7.67 (1H, s), 7.94 (2H, d, J = 8.3 Hz), 8.48 (1H, t, J = 6.3 Hz), 8.52 (2H, d, J = 8.3 Hz), 13.55 (1H, br s). | 481 | 479 |
TABLE 1-8
| | | | | |
|---|---|---|---|---|
| 1-57 | 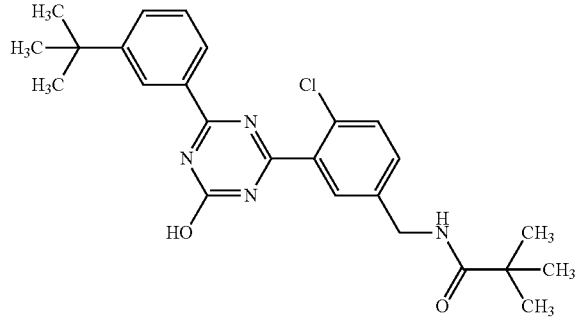 [SMILES: CC(C)(C)C(=O)NCc1ccc(Cl)c(-c2nc(O)nc(-c3cccc(C(C)(C)C)c3)n2)c1] | 1H-NMR (DMSO-D6) δ: 1.13 (9H, s), 1.34 (9H, s), 4.31 (2H, d, J = 6.0 Hz), 7.43 (1H, dd, J = 8.2, 2.0 Hz), 7.49 (1H, t, J = 7.8 Hz), 7.59 (1H, d, J = 8.2 Hz), 7.66 (1H, s), 7.72 (1H, d, J = 8.2 Hz), 8.15-8.18 (2H, m), 8.38 (1H, s), 13.33 (1H, br s). | 453 | 451 |

TABLE 1-8-continued

| | | | | |
|---|---|---|---|---|
| 1-58 | (structure) | 1H-NMR (DMSO-D6) δ: 0.72 (3H, t, J = 7.4 Hz), 1.08 (6H, s), 1.49 (2H, q, J = 7.4 Hz), 4.32 (2H, d, J = 6.0 Hz), 7.47 (1H, dd, J = 8.2, 2.0 Hz), 7.61 (1H, d, J = 8.2 Hz), 7.65 (1H, s), 7.82 (1H, t, J = 7.8 Hz), 8.04 (1H, d, J = 7.9 Hz), 8.15 (1H, t, J = 6.1 Hz), 8.59-8.63 (2H, m), 13.54 (1H, s). | 479 | 477 |
| 1-59 | (structure) | 1H-NMR (DMSO-D6) δ: 1.37 (6H, s), 4.36 (2H, d, J = 5.6 Hz), 7.45 (1H, d, J = 8.4 Hz), 7.62 (1H, d, J = 8.4 Hz), 7.64 (1H, s), 7.81 (1H, t, J = 7.7 Hz), 8.03 (1H, d, J = 7.9 Hz), 8.58-8.66 (3H, m), 13.53 (1H, br s). | 519 | 517 |
| 1-60 | (structure) | 1H-NMR (DMSO-D6) δ: 1.13 (9H, s), 4.31 (2H, d, J = 6.0 Hz), 7.45 (1H, d, J = 8.4 Hz), 7.55 (2H, d, J = 8.7 Hz), 7.61 (1H, d, J = 8.4 Hz), 7.64 (1H, s), 8.18 (1H, t, J = 6.0 Hz), 8.46 (2H, d, J = 8.7 Hz), 13.45 (1H, br s). | 481 | 479 |
| 1-61 | (structure) | 1H-NMR (DMSO-D6) δ: 1.13 (9H, s), 4.31 (2H, d, J = 6.0 Hz), 7.45 (1H, dd, J = 8.4, 2.2 Hz), 7.60 (1H, d, J = 8.4 Hz), 7.63-7.73 (3H, m), 8.18 (1H, t, J = 6.0 Hz), 8.21 (1H, s), 8.37 (1H, dt, J = 7.4, 1.5 Hz), 13.50 (1H, br s). | 481 | 479 |
| 1-62 | (structure) | 1H-NMR (DMSO-D6) δ: 1.12 (9H, s), 1.34 (3H, t, J = 7.0 Hz), 4.09 (2H, q, J = 7.0 Hz), 4.30 (2H, d, J = 6.0 Hz), 7.20 (1H, dd, J = 8.1, 2.3 Hz), 7.41-7.46 (2H, m), 7.57 (1H, d, J = 8.4 Hz), 7.63 (1H, s), 7.84 (1H, s), 7.91 (1H, d, J = 7.7 Hz), 8.16 (1H, t, J = 6.0 Hz), 13.30 (1H, br s). | 441 | 439 |

TABLE 1-8-continued

| No. | Structure | 1H-NMR | MS1 | MS2 |
|---|---|---|---|---|
| 1-63 | (4-methylphenyl)-triazine-Cl-phenyl-CH2NH-C(O)-C(CH3)2-H, triazine-OH | 1H-NMR (DMSO-D6) δ: 1.13 (9H, s), 2.41 (3H, s), 4.31 (2H, d, J = 6.0 Hz), 7.37 (2H, d, J = 8.1 Hz), 7.43 (1H, d, J = 8.1 Hz), 7.59 (1H, d, J = 8.1 Hz), 7.64 (1H, s), 8.17 (1H, t, J = 6.0 Hz), 8.24 (2H, d, J = 8.1 Hz), 13.24 (1H, br s). | 411 | 409 |
| 1-64 | (3-methylphenyl)-triazine-Cl-phenyl-CH2NH-C(O)-C(CH3)2-H, triazine-OH | 1H-NMR (DMSO-D6) δ: 1.14 (9H, s), 2.40 (3H, s), 4.32 (2H, d, J = 6.0 Hz), 7.41-7.51 (3H, m), 7.60 (1H, d, J = 8.4 Hz), 7.64 (1H, s), 8.11-8.20 (3H, m), 13.30 (1H, br s). | 411 | 409 |

TABLE 1-9

| No. | Structure | 1H-NMR | MS1 | MS2 |
|---|---|---|---|---|
| 1-65 | phenyl-triazine-OH, Cl-phenyl-CH2NH-C(O)-adamantyl | 1H-NMR (DMSO-D6) δ: 1.60-1.71 (6H, m), 1.79-1.83 (6H, m), 1.94-1.98 (3H, m), 4.30 (2H, d, J = 6.0 Hz), 7.42 (1H, d, J = 8.6 Hz), 7.53-7.59 (3H, m), 7.63-7.68 (2H, m), 8.10 (1H, t, J = 6.1 Hz), 8.34 (2H, d, J = 7.5 Hz), 13.34 (1H, br s). | 475 | 473 |
| 1-66 | phenyl-triazine-OH, Cl-phenyl-CH2NH-C(O)-cyclobutyl | 1H-NMR (DMSO-D6) δ: 1.72-1.94 (2H, m), 1.99-2.08 (2H, m), 2.10-2.20 (2H, m), 3.03-3.11 (1H, m), 4.31 (2H, d, J = 6.0 Hz), 7.45 (1H, dd, J = 8.4, 2.0 Hz), 7.54-7.69 (5H, m), 8.28 (1H, t, J = 6.0 Hz), 8.34 (2H, d, J = 7.3 Hz), 13.34 (1H, br s). | 395 | 393 |
| 1-67 | phenyl-triazine-OH, Cl-phenyl-CH2NH-C(O)-cyclopentyl | 1H-NMR (DMSO-D6) δ: 1.46-1.81 (8H, m), 2.58-2.66 (1H, m), 4.32 (2H, d, J = 6.0 Hz), 7.45 (1H, dd, J = 8.4, 2.2 Hz), 7.56 (2H, t, J = 7.6 Hz), 7.60 (1H, d, J = 8.2 Hz), 7.64-7.69 (2H, m), 8.34 (2H, d, J = 7.5 Hz), 8.40 (1H, t, J = 6.1 Hz), 13.34 (1H, br s). | 409 | 407 |

TABLE 1-9-continued

| | Structure | NMR | MW | MS |
|---|---|---|---|---|
| 1-68 | 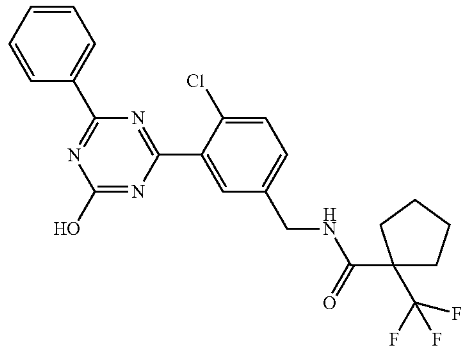 [SMILES: O=C(NCc1ccc(Cl)c(-c2nc(O)nc(-c3ccccc3)n2)c1)C1(C(F)(F)F)CCCC1] | 1H-NMR (DMSO-D6) δ: 1.50-1.68 (4H, m), 1.82-1.91 (2H, m), 2.29-2.36 (2H, m), 4.37 (2H, d, J = 5.8 Hz), 7.41 (1H, d, J = 8.8 Hz), 7.54 (2H, t, J = 7.7 Hz), 7.59 (1H, d, J = 8.4 Hz), 7.62-7.67 (2H, m), 8.32 (2H, d, J = 7.7 Hz), 8.69 (1H, t, J = 5.9 Hz), 13.33 (1H, br s). | 477 | 475 |
| 1-69 | 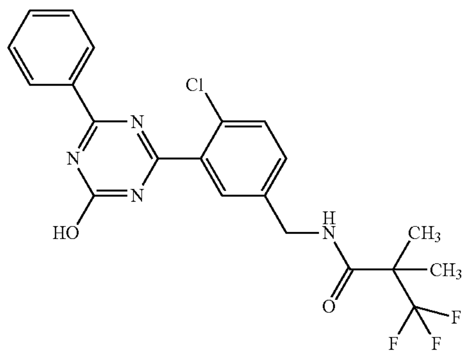 [SMILES: CC(C)(C(=O)NCc1ccc(Cl)c(-c2nc(O)nc(-c3ccccc3)n2)c1)C(F)(F)F] | 1H-NMR (DMSO-D6) δ: 1.38 (6H, s), 4.37 (2H, d, J = 6.0 Hz), 7.44 (1H, dd, J = 8.3, 2.1 Hz), 7.56 (2H, t, J = 7.6 Hz), 7.61 (1H, d, J = 8.4 Hz), 7.64-7.69 (2H, m), 8.34 (2H, d, J = 7.5 Hz), 8.64 (1H, t, J = 6.0 Hz), 13.35 (1H, br s). | 451 | 449 |
| 1-70 | 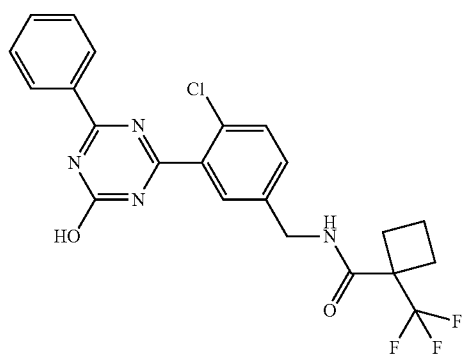 [SMILES: O=C(NCc1ccc(Cl)c(-c2nc(O)nc(-c3ccccc3)n2)c1)C1(C(F)(F)F)CCC1] | 1H-NMR (DMSO-D6) δ: 1.77-1.94 (2H, m), 2.30-2.39 (2H, m), 2.45-2.57 (2H, m), 4.39 (2H, d, J = 5.8 Hz), 7.44 (1H, d, J = 7.4 Hz), 7.54 (2H, t, J = 7.7 Hz), 7.60 (1H, d, J = 8.4 Hz), 7.63-7.68 (2H, m), 8.33 (2H, d, J = 7.7 Hz), 8.78 (1H, t, J = 5.9 Hz), 13.32 (1H, br s). | 463 | 461 |
| 1-71 | 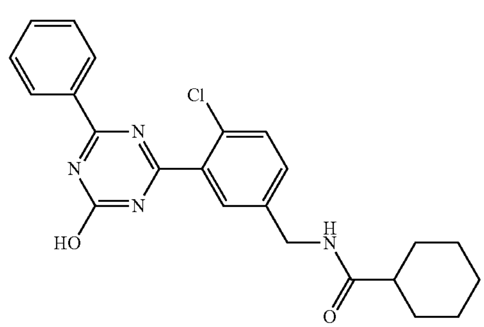 [SMILES: O=C(NCc1ccc(Cl)c(-c2nc(O)nc(-c3ccccc3)n2)c1)C1CCCCC1] | 1H-NMR (DMSO-D6) δ: 1.08-1.42 (5H, m), 1.57-1.77 (5H, m), 2.13-2.21 (1H, m), 4.31 (2H, d, J = 6.0 Hz), 7.44 (1H, dd, J = 8.2, 2.2 Hz), 7.54-7.60 (3H, m), 7.65-7.69 (2H, m), 8.33-8.35 (3H, m), 13.34 (1H, br s). | 423 | 421 |

TABLE 1-9-continued

| | | | | |
|---|---|---|---|---|
| 1-72 | (structure) | 1H-NMR (DMSO-D6) δ: 1.35 (3H, s), 1.63-1.76 (3H, m), 1.84-1.93 (1H, m), 2.30-2.37 (2H, m), 4.32 (2H, d, J = 6.2 Hz), 7.45 (1H, dd, J = 8.4, 2.0 Hz), 7.56 (2H, t, J = 7.6 Hz), 7.60 (1H, d, J = 8.4 Hz), 7.64-7.68 (2H, m), 8.18 (1H, t, J = 6.1 Hz), 8.34 (2H, d, J = 7.5 Hz), 13.35 (1H, br s). | 409 | 407 |

TABLE 1-10

| | | | | |
|---|---|---|---|---|
| 1-73 | (structure) | 1H-NMR (DMSO-D6) δ: 1.19 (3H, s), 1.35-1.43 (2H, m), 1.51-1.62 (4H, m), 1.98-2.05 (2H, m), 4.32 (2H, d, J = 6.0 Hz), 7.44 (1H, dd, J = 8.3, 2.1 Hz), 7.54-7.60 (3H, m), 7.64-7.69 (2H, m), 8.20 (1H, t, J = 6.1 Hz), 8.34 (2H, d, J = 7.3 Hz), 13.34 (1H, br s). | 423 | 421 |
| 1-74 | (structure) | 1H-NMR (DMSO-D6) δ: 1.12 (9H, s), 4.30 (2H, d, J = 6.0 Hz), 7.37 (1H, d, J = 8.8 Hz), 7.39 (1H, d, J = 8.8 Hz), 7.42 (1H, dd, J = 8.5, 2.0 Hz), 7.58 (1H, d, J = 8.4 Hz), 7.62 (1H, s), 8.16 (1H, t, J = 5.9 Hz), 8.38 (1H, d, J = 8.8 Hz), 8.40 (1H, d, J = 8.8 Hz), 13.33 (1H, br s). | 415 | 413 |
| 1-75 | (structure) | 1H-NMR (DMSO-D6) δ: 1.13 (9H, s), 3.32 (3H, s), 4.31 (2H, d, J = 6.0 Hz), 4.50 (2H, s), 7.43 (1H, d, J = 8.6 Hz), 7.53 (1H, t, J = 7.7 Hz), 7.59 (2H, d, J = 8.1 Hz), 7.63 (1H, s), 8.18 (1H, t, J = 6.0 Hz), 8.26 (1H, d, J = 7.7 Hz), 8.30 (1H, s), 13.34 (1H, br s). | 441 | 439 |

TABLE 1-10-continued

| | | | | |
|---|---|---|---|---|
| 1-76 | (structure) | 1H-NMR (DMSO-D6) δ: 1.14 (9H, s), 4.32 (2H, d, J = 6.0 Hz), 7.45 (1H, dd, J = 8.4, 2.1 Hz), 7.52 (1H, td, J = 8.4, 2.7 Hz), 7.59-7.63 (2H, m), 7.65 (1H, d, J = 2.1 Hz), 8.05 (1H, dt, J = 9.8, 2.0 Hz), 8.16-8.20 (2H, m), 13.43 (1H, br s). | 415 | 413 |
| 1-77 | (structure) | 1H-NMR (DMSO-D6) δ: 1.38 (6H, s), 4.37 (2H, d, J = 5.8 Hz), 7.41 (1H, d, J = 8.4 Hz), 7.58 (1H, d, J = 8.4 Hz), 7.61-7.65 (2H, m), 7.69 (1H, t, J = 7.8 Hz), 8.21 (1H, s), 8.36 (1H, d, J = 7.7 Hz), 8.63 (1H, t, J = 5.8 Hz), 13.52 (1H, br s). | 535 | 533 |
| 1-78 | (structure) | 1H-NMR (DMSO-D6) δ: 1.48-1.71 (4H, m), 1.81-1.94 (2H, m), 2.30-2.39 (2H, m), 4.39 (2H, d, J = 5.9 Hz), 7.45 (1H, dd, J = 8.3, 1.4 Hz), 7.59-7.75 (4H, m), 8.22 (1H, br s), 8.35-8.39 (1H, m), 8.72 (1H, t, J = 5.9 Hz), 13.51 (1H, br s). | 561 | 559 |
| 1-79 | (structure) | 1H-NMR (DMSO-D6) δ: 1.50-1.69 (4H, m), 1.83-1.93 (2H, m), 2.29-2.39 (2H, m), 4.39 (2H, d, J = 6.0 Hz), 7.44 (1H, dd, J = 8.3, 1.9 Hz), 7.60-7.66 (2H, m), 7.82 (1H, t, J = 7.7 Hz), 8.03 (1H, d, J = 7.7 Hz), 8.59-8.65 (2H, m), 8.71 (1H, t, J = 6.0 Hz), 13.54 (1H, br s). | 545 | 543 |

TABLE 1-10-continued

| | | | | |
|---|---|---|---|---|
| 1-80 | [structure] | 1H-NMR (DMSO-D6) δ: 1.34 (9H, s), 1.49-1.69 (4H, m), 1.83-1.92 (2H, m), 2.29-2.38 (2H, m), 4.38 (2H, d, J = 6.0 Hz), 7.42 (1H, d, J = 8.3 Hz), 7.49 (1H, t, J = 7.8 Hz), 7.61 (1H, d, J = 8.3 Hz), 7.65 (1H, s), 7.71 (1H, d, J = 7.8 Hz), 8.15 (1H, d, J = 7.8 Hz), 8.38 (1H, s), 8.71 (1H, t, J = 6.0 Hz), 13.35 (1H, br s). | 533 | 531 |

TABLE 1-11

| | | | | |
|---|---|---|---|---|
| 1-81 | [structure] | 1H-NMR (DMSO-D6) δ: 1.37 (6H, s), 2.32 (3H, d, J = 1.2 Hz), 4.36 (2H, d, J = 5.9 Hz), 7.50-7.43 (2H, m), 7.60 (1H, d, J = 8.4 Hz), 7.64 (1H, br s), 7.99 (1H, d, J = 10.9 Hz), 8.08 (1H, dd, J = 7.8, 1.5 Hz), 8.63 (1H, t, J = 5.9 Hz), 13.36 (1H, s). | 483 | 481 |
| 1-82 | [structure] | 1H-NMR (DMSO-D6) δ: 1.13 (9H, s), 1.31 (6H, d, J = 6.0 Hz), 4.31 (2H, d, J = 6.0 Hz), 4.72-4.82 (1H, m), 7.06 (2H, d, J = 8.9 Hz), 7.42 (1H, d, J = 8.4 Hz), 7.58 (1H, d, J = 8.4 Hz), 7.63 (1H, s), 8.17 (1H, t, J = 6.0 Hz), 8.29 (2H, d, J = 8.9 Hz), 13.12 (1H, br s). | 455 | 453 |
| 1-83 | [structure] | 1H-NMR (DMSO-D6) δ: 1.17 (6H, d, J = 6.3 Hz), 1.34 (9H, s), 4.23 (2H, d, J = 6.0 Hz), 4.72-4.80 (1H, m), 7.43-7.52 (2H, m), 7.60 (1H, d, J = 8.4 Hz), 7.65-7.73 (3H, m), 8.15 (1H, d, J = 7.7 Hz), 8.38 (1H, s), 13.33 (1H, br s). | 455 | 453 |

TABLE 1-11-continued

| | | | | |
|---|---|---|---|---|
| 1-84 | [structure] | 1H-NMR (DMSO-D6) δ: 1.27 (6H, s), 1.34 (9H, s), 3.16 (3H, s), 4.33 (2H, d, J = 6.3 Hz), 7.42-7.46 (1H, m), 7.49 (1H, d, J = 7.9 Hz), 7.57 (1H, d, J = 8.1 Hz), 7.66-7.71 (2H, m), 8.14 (1H, d, J = 7.9 Hz), 8.38 (1H, s), 8.47 (1H, t, J = 6.3 Hz), 13.32 (1H, br s). | 469 | 467 |
| 1-85 | [structure] | 1H-NMR (DMSO-D6) δ: 1.36 (3H, t, J = 7.0 Hz), 1.51-1.69 (4H, m), 1.84-1.91 (2H, m), 2.30-2.38 (2H, m), 4.10 (2H, q, J = 7.0 Hz), 4.38 (2H, d, J = 6.0 Hz), 7.20 (1H, dd, J = 8.3, 2.4 Hz), 7.39-7.43 (1H, m), 7.46 (1H, d, J = 7.9 Hz), 7.59 (1H, d, J = 8.3 Hz), 7.63 (1H, s), 7.85 (1H, d, J = 2.4 Hz), 7.89-7.96 (1H, m), 8.71 (1H, t, J = 6.0 Hz), 13.33 (1H, br s). | 521 | 519 |
| 1-86 | [structure] | 1H-NMR (DMSO-D6) δ: 1.02 (9H, s), 1.37 (6H, s), 3.73 (2H, s), 4.35 (2H, d, J = 5.8 Hz), 7.08 (2H, d, J = 9.1 Hz), 7.40 (1H, dd, J = 8.3, 2.2 Hz), 7.58 (1H, d, J = 8.3 Hz), 7.62 (1H, d, J = 1.9 Hz), 8.29 (2H, d, J = 9.1 Hz), 8.62 (1H, t, J = 5.8 Hz), 13.13 (1H, s). | 537 | 535 |
| 1-87 | [structure] | 1H-NMR (DMSO-D6) δ: 1.54 (3H, s), 3.36 (3H, s), 4.32-4.44 (2H, m), 7.46 (1H, d, J = 8.2 Hz), 7.53-7.71 (5H, m), 8.34 (2H, d, J = 7.5 Hz), 9.04 (1H, t, J = 6.3 Hz), 13.35 (1H, br s). | 467 | 465 |

TABLE 1-11-continued

| 1-88 | [structure] | 1H-NMR (DMSO-D6) δ: 1.00 (6H, d, J = 6.8 Hz), 1.38 (6H, s), 1.99-2.10 (1H, m), 3.83 (2H, d, J = 6.4 Hz), 4.37 (2H, d, J = 6.0 Hz), 7.23 (1H, dd, J = 8.2, 2.6 Hz), 7.41-7.49 (2H, m), 7.61 (1H, d, J = 8.2 Hz), 7.66 (1H, s), 7.84-7.88 (1H, m), 7.93 (1H, d, J = 7.9 Hz), 8.64 (1H, t, J = 6.0 Hz), 13.33 (1H, br s). | 523 | 521 |

TABLE 1-12

| 1-89 | [structure] | 1H-NMR (DMSO-D6) δ: 1.54 (3H, s), 3.36 (3H, s), 4.32-4.44 (2H, m), 7.46 (1H, d, J = 8.2 Hz), 7.53-7.71 (5H, m), 8.34 (2H, d, J = 7.5 Hz), 9.04 (1H, t, J = 6.3 Hz), 13.35 (1H, br s). | 467 | 465 |
| 1-90 | [structure] | 1H-NMR (DMSO-D6) δ: 1.38 (6H, s), 2.31 (3H, s), 4.37 (2H, d, J = 5.8 Hz), 7.31 (1H, t, J = 9.1 Hz), 7.43 (1H, dd, J = 8.4, 2.0 Hz), 7.60 (1H, d, J = 8.4 Hz), 7.63 (1H, s), 8.21 (1H, s), 8.28 (1H, d, J = 7.4 Hz), 8.64 (1H, t, J = 5.8 Hz), 13.32 (1H, br s). | 483 | 481 |
| 1-91 | [structure] | 1H-NMR (DMSO-D6) δ: 1.30 (6H, d, J = 6.0 Hz), 1.38 (6H, s), 4.37 (2H, d, J = 5.8 Hz), 4.66-4.72 (1H, m), 7.20 (1H, dd, J = 8.4, 2.1 Hz), 7.42-7.47 (2H, m), 7.60 (1H, d, J = 8.4 Hz), 7.66 (1H, s), 7.84-7.86 (1H, m), 7.90 (1H, d, J = 7.7 Hz), 8.64 (1H, t, J = 5.8 Hz), 13.32 (1H, br s). | 509 | 507 |

TABLE 1-12-continued
| 1-92 | 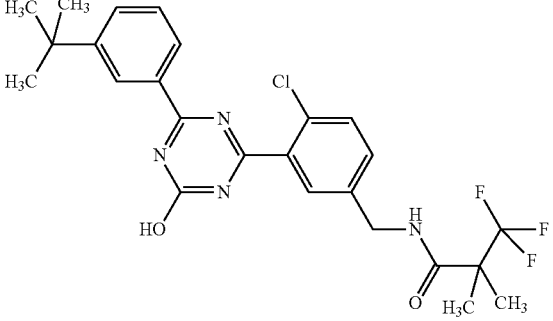 [SMILES: CC(C)(C)c1cccc(-c2nc(O)nc(-c3cc(CNC(=O)C(C)(C)C(F)(F)F)ccc3Cl)n2)c1] | 1H-NMR (DMSO-D6) δ: 1.34 (9H, s), 1.38 (6H, s), 4.37 (2H, d, J = 6.0 Hz), 7.42 (1H, d, J = 8.4 Hz), 7.48 (1H, t, J = 7.9 Hz), 7.59 (1H, d, J = 8.4 Hz), 7.66 (1H, s), 7.70 (1H, d, J = 7.7 Hz), 8.15 (1H, d, J = 7.7 Hz), 8.37-8.39 (1H, m), 8.63 (1H, t, J = 6.0 Hz), 13.33 (1H, br s). | 507 | 505 |
| --- | --- | --- | --- | --- |
| 1-93 | 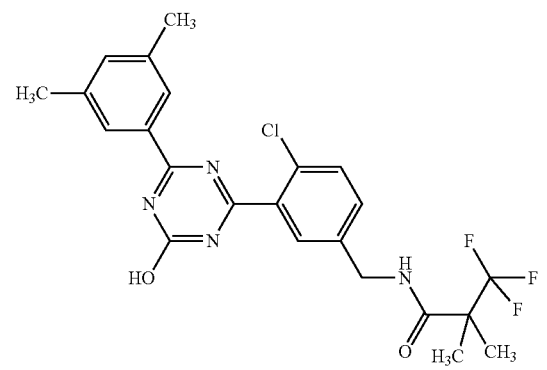 [SMILES: Cc1cc(C)cc(-c2nc(O)nc(-c3cc(CNC(=O)C(C)(C)C(F)(F)F)ccc3Cl)n2)c1] | 1H-NMR (DMSO-D6) δ: 1.38 (6H, s), 2.35 (6H, s), 4.37 (2H, d, J = 5.8 Hz), 7.30 (1H, s), 7.44 (1H, d, J = 8.4 Hz), 7.60 (1H, d, J = 8.4 Hz), 7.63 (1H, s), 7.96 (2H, s), 8.64 (1H, t, J = 5.8 Hz), 13.27 (1H, br s). | 479 | 477 |
| 1-94 | 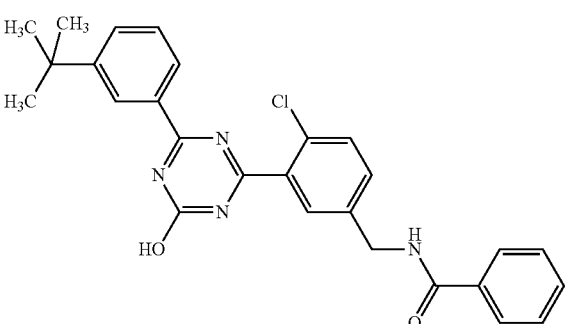 | 1H-NMR (DMSO-D6) δ: 1.33 (9H, s), 4.55 (2H, d, J = 5.8 Hz), 7.45-7.50 (3H, m), 7.52-7.56 (2H, m), 7.61 (1H, d, J = 8.4 Hz), 7.71 (1H, d, J = 8.4 Hz), 7.78 (1H, s), 7.89-7.91 (2H, m), 8.14 (1H, d, J = 7.7 Hz), 8.37 (1H, s), 9.15 (1H, t, J = 5.8 Hz), 13.33 (1H, br s). | 473 | 471 |
| 1-95 | 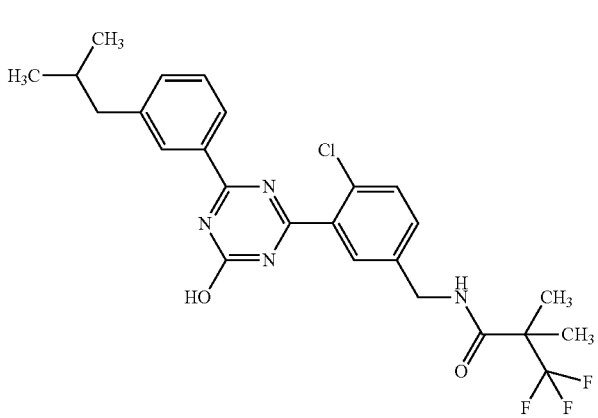 [SMILES: CC(C)Cc1cccc(-c2nc(O)nc(-c3cc(CNC(=O)C(C)(C)C(F)(F)F)ccc3Cl)n2)c1] | 1H-NMR (DMSO-D6) δ: 0.88 (6H, d, J = 6.6 Hz), 1.38 (6H, s), 1.82-1.94 (1H, m), 2.55 (2H, d, J = 7.1 Hz), 4.37 (2H, d, J = 6.0 Hz), 7.42-7.50 (3H, m), 7.59-7.67 (2H, m), 8.12-8.20 (2H, m), 8.64 (1H, t, J = 6.0 Hz), 13.31 (1H, br s). | 507 | 505 |

TABLE 1-12-continued
| 1-96 | 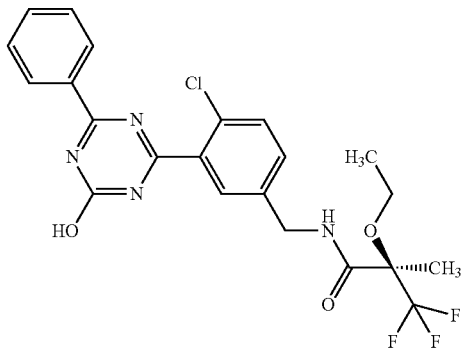 [SMILES: CCO[C@](C)(C(=O)NCc1ccc(Cl)c(-c2nc(O)nc(-c3ccccc3)n2)c1)C(F)(F)F] | 1H-NMR (DMSO-D6) δ: 1.19 (3H, t, J = 7.1 Hz), 1.54 (3H, s), 3.46-3.54 (1H, m), 3.57-3.66 (1H, m), 4.40 (2H, d, J = 6.2 Hz), 7.46 (1H, d, J = 8.4 Hz), 7.54-7.70 (5H, m), 8.34 (2H, d, J = 7.5 Hz), 8.86 (1H, t, J = 6.2 Hz), 13.35 (1H, br s). | 481 | 479 |
TABLE 1-13
| 1-97 | 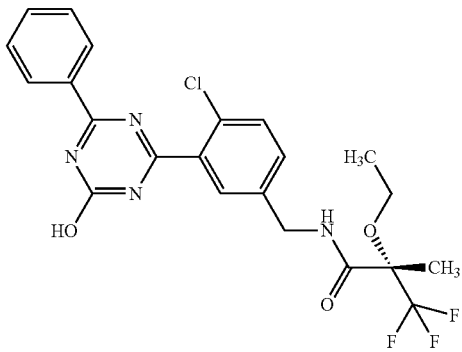 [SMILES: CCO[C@@](C)(C(=O)NCc1ccc(Cl)c(-c2nc(O)nc(-c3ccccc3)n2)c1)C(F)(F)F] | 1H-NMR (DMSO-D6) δ: 1.19 (3H, t, J = 7.1 Hz), 1.54 (3H, s), 3.46-3.54 (1H, m), 3.57-3.66 (1H, m), 4.40 (2H, d, J = 6.2 Hz), 7.46 (1H, d, J = 8.4 Hz), 7.54-7.70 (5H, m), 8.34 (2H, d, J = 7.5 Hz), 8.86 (1H, t, J = 6.2 Hz), 13.35 (1H, br s). | 481 | 479 |
| 1-98 | 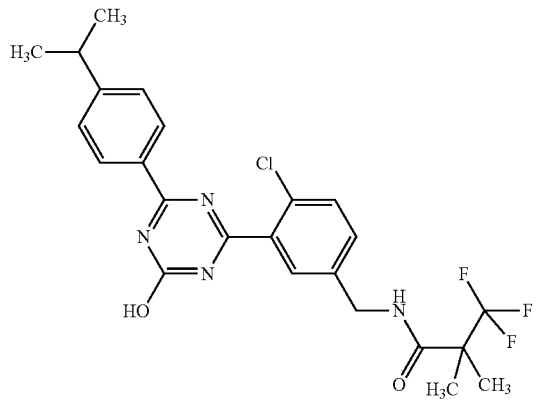 [SMILES: CC(C)c1ccc(-c2nc(O)nc(-c3cc(CNC(=O)C(C)(C)C(F)(F)F)ccc3Cl)n2)cc1] | 1H-NMR (DMSO-D6) δ: 1.24 (6H, d, J = 7.0 Hz), 1.38 (6H, s), 4.36 (2H, d, J = 5.8 Hz), 7.35-7.40 (3H, m), 7.54 (1H, d, J = 8.4 Hz), 7.61 (1H, d, J = 2.1 Hz), 8.25 (2H, d, J = 8.4 Hz), 8.62 (1H, t, J = 5.8 Hz), 13.26 (1H, br s). | 493 | 491 |
| 1-99 | 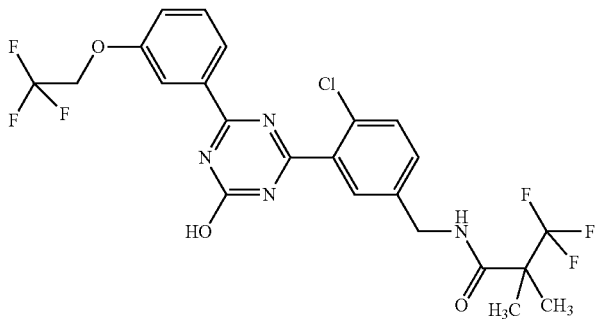 [SMILES: CC(C)(C(=O)NCc1ccc(Cl)c(-c2nc(O)nc(-c3cccc(OCC(F)(F)F)c3)n2)c1)C(F)(F)F] | 1H-NMR (DMSO-D6) δ: 1.38 (6H, s), 4.37 (2H, d, J = 5.8 Hz), 4.86 (2H, q, J = 8.8 Hz), 7.36 (1H, dd, J = 8.0, 2.4 Hz), 7.43 (1H, dd, J = 8.0, 2.4 Hz), 7.53 (1H, t, J = 8.0 Hz), 7.60 (1H, d, J = 8.0 Hz), 7.65 (1H, s), 7.93-7.95 (1H, m), 8.03 (1H, d, J = 7.7 Hz), 8.64 (1H, t, J = 5.8 Hz), 13.35 (1H, br s). | 549 | 547 |

TABLE 1-13-continued

| | | | | |
|---|---|---|---|---|
| 1-100 | | 1H-NMR (DMSO-D6) δ: 1.36 (6H, s), 1.79-1.87 (1H, m), 1.93-2.05 (1H, m), 2.07-2.18 (2H, m), 2.29-2.36 (2H, m), 3.55-3.64 (1H, m), 4.35 (2H, d, J = 6.0 Hz), 7.37-7.48 (3H, m), 7.56 (1H, d, J = 8.1 Hz), 7.61 (1H, s), 8.13 (1H, d, J = 7.0 Hz), 8.18 (1H, s), 8.61 (1H, t, J = 6.0 Hz), 13.31 (1H, br s). | 505 | 503 |
| 1-101 | | 1H-NMR (DMSO-D6) δ: 0.88 (6H, d, J = 6.5 Hz), 1.25 (9H, s), 1.84-1.95 (1H, m), 2.55 (2H, d, J = 7.2 Hz), 3.45 (2H, s), 7.35 (2H, d, J = 8.1 Hz), 7.46 (1H, d, J = 8.4 Hz), 7.57 (1H, d, J = 8.4 Hz), 7.65 (1H, s), 7.76 (1H, s), 8.26 (2H, d, J = 8.1 Hz), 13.24 (1H, br s). | 453 | 451 |
| 1-102 | | 1H-NMR (DMSO-D6) δ: 0.91 (3H, t, J = 7.6 Hz), 1.38 (6H, s), 1.58-1.69 (2H, m), 2.64 (2H, t, J = 7.6 Hz), 4.37 (2H, d, J = 6.0 Hz), 7.40-7.46 (3H, m), 7.58 (1H, d, J = 8.1 Hz), 7.63 (1H, d, J = 1.9 Hz), 8.14-8.18 (2H, m), 8.63 (1H, t, J = 6.0 Hz), 13.32 (1H, br s). | 493 | 491 |
| 1-103 | | 1H-NMR (DMSO-D6) δ: 1.54 (3H, s), 3.36 (3H, s), 4.32-4.46 (2H, m), 7.48 (1H, d, J = 7.7 Hz), 7.60-7.75 (4H, m), 8.22 (1H, s), 8.37 (1H, d, J = 7.3 Hz), 9.04 (1H, t, J = 6.3 Hz), 13.52 (1H, br s). | 551 | 549 |

TABLE 1-13-continued

| | | | | |
|---|---|---|---|---|
| 1-104 | [structure] | 1H-NMR (DMSO-D6) δ: 0.91 (3H, t, J = 7.4 Hz), 1.54 (3H, s), 1.58-1.69 (2H, m), 2.65 (2H, t, J = 7.6 Hz), 3.36 (3H, s), 4.32-4.45 (2H, m), 7.43-7.52 (3H, m), 7.61 (1H, d, J = 8.4 Hz), 7.67 (1H, s), 8.13-8.19 (2H, m), 9.04 (1H, t, J = 6.2 Hz), 13.31 (1H, br s). | 509 | 507 |

TABLE 1-14

| | | | | |
|---|---|---|---|---|
| 1-105 | [structure] | 1H-NMR (DMSO-D6) δ: 1.54 (3H, s), 2.34 (3H, d, J = 1.1 Hz), 3.36 (3H, s), 4.33-4.45 (2H, m), 7.44-7.52 (2H, m), 7.61 (1H, d, J = 8.2 Hz), 7.67 (1H, s), 8.00 (1H, d, J = 11.0 Hz), 8.09 (1H, dd, J = 7.9, 1.5 Hz), 9.04 (1H, t, J = 6.2 Hz), 13.38 (1H, br s). | 499 | 497 |
| 1-106 | [structure] | 1H-NMR (DMSO-D6) δ: 1.54 (3H, s), 2.32 (3H, d, J = 1.3 Hz), 3.36 (3H, s), 4.32-4.44 (2H, m), 7.32 (1H, t, J = 9.0 Hz), 7.46 (1H, d, J = 8.3 Hz), 7.61 (1H, d, J = 8.3 Hz), 7.65 (1H, s), 8.19-8.25 (1H, m), 8.28 (1H, d, J = 7.3 Hz), 9.03 (1H, t, J = 6.3 Hz), 13.33 (1H, br s). | 499 | 497 |
| 1-107 | [structure] | 1H-NMR (DMSO-D6) δ: 1.25 (6H, d, J = 6.9 Hz), 1.38 (6H, s), 2.94-3.06 (1H, m), 4.37 (2H, d, J = 5.9 Hz), 7.41-7.68 (5H, m), 8.13-8.19 (1H, m), 8.22 (1H, br s), 8.64 (1H, t, J = 5.9 Hz), 13.33 (1H, br s). | 493 | 491 |

TABLE 1-14-continued

| 1-108 | 1H-NMR (DMSO-D6) δ: 1.25 (6H, d, J = 7.3 Hz), 1.54 (3H, s), 2.94-3.07 (1H, m), 3.36 (3H, s), 4.31-4.46 (2H, m), 7.42-7.71 (5H, m), 8.16 (1H, d, J = 7.7 Hz), 8.22 (1H, br s), 9.04 (1H, t, J = 6.0 Hz), 13.32 (1H, br s). | 509 | 507 |

| 1-109 | 1H-NMR (DMSO-D6) δ: 0.98 (6H, d, J = 6.5 Hz), 1.37 (6H, s), 2.07-2.00 (1H, m), 3.85 (2H, d, J = 6.5 Hz), 4.35 (2H, d, J = 6.0 Hz), 7.07 (2H, d, J = 9.1 Hz), 7.41 (1H, dd, J = 8.1, 2.1 Hz), 7.58 (1H, d, J = 8.1 Hz), 7.62 (1H, s), 8.29 (2H, d, J = 9.1 Hz), 8.63 (1H, t, J = 5.9 Hz), 13.13 (1H, br s). | 523 | 521 |

| 1-110 | 1H-NMR (DMSO-D6) δ: 1.22 (3H, t, J = 7.6 Hz), 1.38 (6H, s), 2.70 (2H, q, J = 7.6 Hz), 4.37 (2H, d, J = 6.0 Hz), 7.42-7.54 (3H, m), 7.61 (1H, d, J = 8.4 Hz), 7.65 (1H, s), 8.16 (1H, d, J = 7.7 Hz), 8.19 (1H, s), 8.65 (1H, t, J = 6.0 Hz), 13.32 (1H, br s). | 479 | 477 |

| 1-111 | 1H-NMR (DMSO-D6) δ: 1.38 (6H, s), 2.40 (3H, s), 4.37 (2H, d, J = 6.0 Hz), 7.41-7.50 (3H, m), 7.61 (1H, d, J = 8.4 Hz), 7.65 (1H, s), 8.11-8.18 (2H, m), 8.65 (1H, t, J = 6.0 Hz), 13.32 (1H, br s). | 465 | 463 |

TABLE 1-14-continued

| No. | Structure | 1H-NMR | MS1 | MS2 |
|---|---|---|---|---|
| 1-112 | (4-chloro-3-methylphenyl triazine structure) | 1H-NMR (DMSO-D6) δ: 1.38 (6H, s), 2.42 (3H, s), 4.37 (2H, d, J = 6.0 Hz), 7.44 (1H, dd, J = 8.4, 2.1 Hz), 7.61 (2H, dd, J = 8.4, 2.1 Hz), 7.64 (1H, d, J = 2.1 Hz), 8.17 (1H, dd, J = 8.4, 2.1 Hz), 8.30 (1H, d, J = 2.1 Hz), 8.65 (1H, t, J = 6.0 Hz), 13.39 (1H, br s). | 499 | 497 |

TABLE 1-15

| No. | Structure | 1H-NMR | MS1 | MS2 |
|---|---|---|---|---|
| 1-113 | (2,2,2-trifluoroethoxyphenyl triazine structure) | 1H-NMR (DMSO-D6) δ: 1.38 (6H, s), 4.36 (2H, d, J = 6.0 Hz), 4.89 (2H, q, J = 8.8 Hz), 7.20 (2H, d, J = 9.1 Hz), 7.39 (1H, dd, J = 8.3, 2.0 Hz), 7.56 (1H, d, J = 8.3 Hz), 7.62 (1H, d, J = 2.0 Hz), 8.33 (2H, d, J = 9.1 Hz), 8.64 (1H, t, J = 6.0 Hz), 13.24 (1H, br s). | 549 | 547 |
| 1-114 | (isopentyloxyphenyl triazine structure) | 1H-NMR (DMSO-D6) δ: 0.94 (6H, d, J = 6.6 Hz), 1.37 (6H, s), 1.63 (2H, q, J = 6.6 Hz), 1.79 (1H, m), 4.04 (2H, t, J = 6.6 Hz), 4.33 (2H, d, J = 6.0 Hz), 6.95 (2H, d, J = 8.9 Hz), 7.23 (1H, d, J = 8.3 Hz), 7.42 (1H, d, J = 8.3 Hz), 7.50 (1H, d, J = 2.0 Hz), 8.22 (2H, d, J = 8.9 Hz), 8.59 (1H, t, J = 6.0 Hz). | 537 | 535 |

TABLE 1-15-continued

| | | | | |
|---|---|---|---|---|
| 1-115 | (structure) | 1H-NMR (DMSO-D6) δ: 1.38 (6H, s), 2.55 (3H, s), 4.36 (2H, d, J = 6.0 Hz), 7.39 (2H, d, J = 8.7 Hz), 7.40 (1H, d, J = 8.3 Hz), 7.58 (1H, d, J = 8.3 Hz), 7.63 (1H, s), 8.26 (2H, d, J = 8.7 Hz), 8.64 (1H, t, J = 6.0 Hz), 13.26 (1H, s). | 497 | 495 |
| 1-116 | (structure) | 1H-NMR (DMSO-D6) δ: 1.37 (6H, s), 1.94-1.80 (4H, m), 2.11-2.04 (2H, m), 2.77-2.69 (1H, m), 4.05 (2H, d, J = 6.7 Hz), 4.35 (2H, d, J = 5.8 Hz), 7.07 (2H, d, J = 9.1 Hz), 7.40 (1H, dd, J = 8.4, 2.1 Hz), 7.57 (1H, d, J = 8.4 Hz), 7.62 (1H, s), 8.28 (2H, d, J = 9.1 Hz), 8.62 (1H, t, J = 5.8 Hz), 13.13 (1H, s). | 535 | 533 |
| 1-117 | (structure) | 1H-NMR (DMSO-D6) δ: 1.27 (6H, d, J = 7.1 Hz), 1.38 (6H, s), 3.19-3.28 (1H, m), 4.37 (2H, d, J = 6.0 Hz), 7.33 (1H, t, J = 9.5 Hz), 7.44 (1H, d, J = 8.4 Hz), 7.59-7.68 (2H, m), 8.21-8.26 (1H, m), 8.33 (1H, dd, J = 7.5, 2.2 Hz), 8.64 (1H, t, J = 6.0 Hz), 13.36 (1H, br s). | 511 | 509 |
| 1-118 | (structure) | 1H-NMR (DMSO-D6) δ: 0.92 (3H, t, J = 7.3 Hz), 1.38 (6H, s), 1.56-1.67 (2H, m), 2.67 (2H, t, J = 7.7 Hz), 4.37 (2H, d, J = 6.0 Hz), 7.33 (1H, t, J = 9.3 Hz), 7.44 (1H, d, J = 8.4 Hz), 7.59-7.66 (2H, m), 8.21-8.30 (2H, m), 8.65 (1H, t, J = 6.0 Hz), 13.34 (1H, br s). | 511 | 509 |

TABLE 1-15-continued

| | | | | |
|---|---|---|---|---|
| 1-119 | (structure) | 1H-NMR (DMSO-D6) δ: 1.38 (6H, s), 2.01 (3H, t, J = 19.0 Hz), 4.37 (2H, d, J = 5.8 Hz), 7.44 (1H, dd, J = 8.4, 2.1 Hz), 7.61 (2H, d, J = 8.1 Hz), 7.65 (2H, d, J = 2.1 Hz), 7.74 (2H, d, J = 8.4 Hz), 8.43 (2H, d, J = 8.1 Hz), 8.64 (1H, t, J = 5.8 Hz), 13.46 (1H, br s). | 515 | 513 |
| 1-120 | (structure) | 1H-NMR (DMSO-D6) δ: 1.01 (6H, d, J = 6.7 Hz), 1.37 (6H, s), 2.04-2.10 (1H, m), 3.95 (2H, d, J = 6.7 Hz), 4.33 (2H, d, J = 6.0 Hz), 7.25 (1H, dd, J = 8.3, 2.2 Hz), 7.29 (1H, d, J = 8.3 Hz), 7.44 (1H, d, J = 8.3 Hz), 7.51 (1H, d, J = 2.2 Hz), 8.49-8.53 (2H, m), 8.56-8.62 (1H, m). | 591 | 589 |

TABLE 1-16

| | | | | |
|---|---|---|---|---|
| 1-121 | (structure) | 1H-NMR (DMSO-D6) δ: 1.23 (3H, t, J = 7.7 Hz), 1.54 (3H, s), 2.70 (2H, q, J = 7.7 Hz), 3.36 (3H, S), 4.32-4.45 (2H, m), 7.44-7.54 (3H, m), 7.61 (1H, d, J = 8.4 Hz), 7.67 (1H, s), 8.13-8.19 (2H, m), 9.03 (1H, t, J = 6.3 Hz), 13.31 (1H, br s). | 495 | 493 |

TABLE 1-16-continued
| 1-122 | 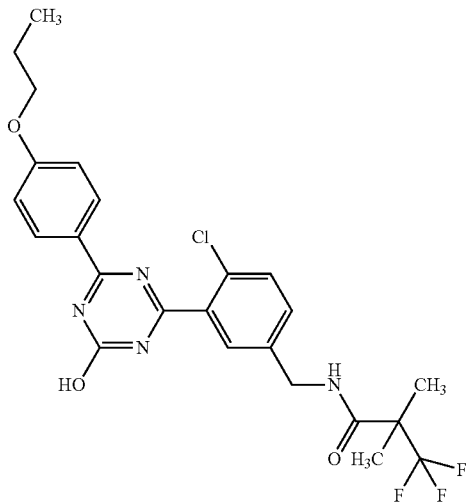 [SMILES: CCCOc1ccc(-c2nc(O)nc(-c3cc(CNC(=O)C(C)(C)C(F)(F)F)ccc3Cl)n2)cc1] | 1H-NMR (DMSO-D6) δ: 0.99 (3H, t, J = 7.4 Hz), 1.38 (6H, s), 1.76 (2H, m), 4.04 (2H, t, J = 6.6 Hz), 4.36 (2H, d, J = 5.8 Hz), 7.07 (2H, d, J = 8.8 Hz), 7.40 (1H, d, J = 6.0 Hz), 7.57 (1H, d, J = 6.0 Hz), 7.62 (1H, s), 8.29 (2H, d, J = 8.8 Hz), 8.63 (1H, s), 13.14 (1H, s). | 509 | 507 |
| --- | --- | --- | --- | --- |
| 1-123 | 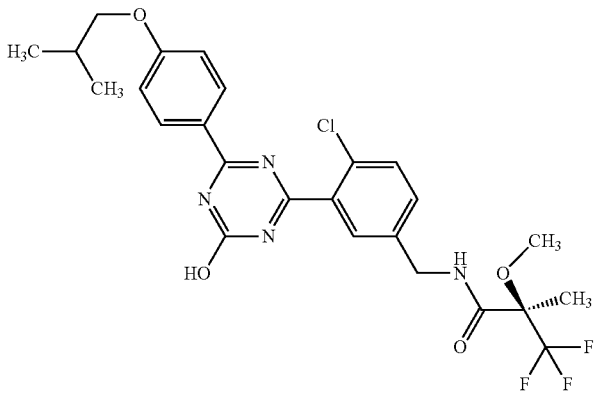 [SMILES: CO[C@](C)(C(=O)NCc1ccc(Cl)c(-c2nc(O)nc(-c3ccc(OCC(C)C)cc3)n2)c1)C(F)(F)F] | 1H-NMR (DMSO-D6) δ: 1.00 (6H, d, J = 6.9 Hz), 1.54 (3H, s), 1.98-2.12 (1H, m), 3.36 (3H, s), 3.86 (2H, d, J = 6.2 Hz), 4.30-4.45 (2H, m), 7.09 (2H, d, J = 8.5 Hz), 7.44 (1H, d, J = 8.5 Hz), 7.59 (1H, d, J = 8.5 Hz), 7.66 (1H, br s), 8.30 (2H, d, J = 8.9 Hz), 9.03 (1H, t, J = 6.2 Hz), 13.14 (1H, br s). | 539 | 537 |
| 1-124 | 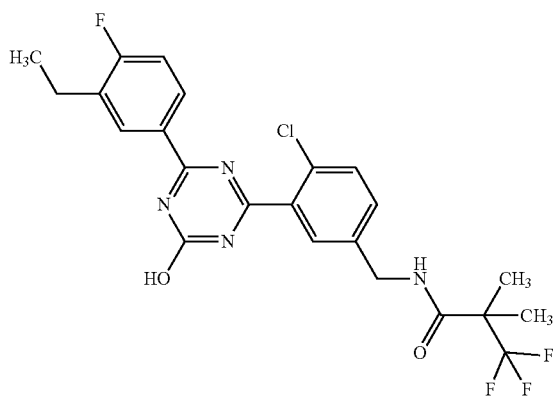 [SMILES: CCc1cc(-c2nc(O)nc(-c3cc(CNC(=O)C(C)(C)C(F)(F)F)ccc3Cl)n2)ccc1F] | 1H-NMR (DMSO-D6) δ: 1.21 (3H, t, J = 7.6 Hz), 1.38 (6H, s), 2.71 (2H, q, J = 7.6 Hz), 4.37 (2H, d, J = 6.0 Hz), 7.33 (1H, t, J = 9.3 Hz), 7.44 (1H, dd, J = 8.5, 2.1 Hz), 7.59-7.66 (2H, m), 8.21-8.26 (1H, m), 8.30 (1H, dd, J = 7.7, 2.2 Hz), 8.65 (1H, t, J = 6.0 Hz), 13.35 (1H, br s). | 497 | 495 |

TABLE 1-16-continued

| | | | | |
|---|---|---|---|---|
| 1-125 | [structure] | 1H-NMR (DMSO-D6) δ: 1.75-2.00 (2H, m), 2.28-2.43 (5H, m), 2.45-2.61 (2H, m), 4.40 (2H, d, J = 5.7 Hz), 7.33 (1H, t, J = 9.1 Hz), 7.46 (1H, dd, J = 8.4,1.8 Hz), 7.63 (1H, d, J = 8.4 Hz), 7.66 (1H, br s), 8.19-8.32 (2H, m), 8.81 (1H, t, J = 5.7 Hz), 13.33 (1H, br s). | 495 | 493 |
| 1-126 | [structure] | 1H-NMR (DMSO-D6) δ: 1.54 (3H, s), 3.36 (3H, s), 4.32-4.46 (2H, m), 7.48 (1H, dd, J = 8.4, 1.6 Hz), 7.63 (1H, d, J = 8.4 Hz), 7.68 (1H, br s), 7.94 (2H, d, J = 8.4 Hz), 8.53 (2H, d, J = 8.4 Hz), 9.04 (1H, t, J = 6.0 Hz), 13.56 (1H, br s). | 535 | 533 |
| 1-127 | [structure] | 1H-NMR (DMSO-D6) δ: 1.20-1.39 (4H, m), 2.32 (3H, s), 4.35 (2H, d, J = 5.9 Hz), 7.33 (1H, t, J = 9.1 Hz), 7.45 (1H, dd, J = 8.4, 1.8 Hz), 7.61 (1H, d, J = 8.4 Hz), 7.64 (1H, s), 8.18-8.31 (2H, m), 8.48 (1H, t, J = 5.9 Hz), 13.32 (1H, br s). | 481 | 479 |
| 1-128 | [structure] | 1H-NMR (DMSO-D6) δ: 0.41 (2H, dd, J = 5.8, 4.0 Hz), 0.55 (2H, dd, J = 5.2, 4.0 Hz), 1.19 (3H, s), 1.38 (6H, s), 3.87 (2H, s), 4.36 (2H, d, J = 5.8 Hz), 7.07 (2H, d, J = 8.9 Hz), 7.41 (1H, d, J = 7.3 Hz), 7.58 (1H, d, J = 7.3 Hz), 7.63 (1H, s), 8.29 (2H, d, J = 8.9 Hz), 8.64 (1H, t, J = 5.8 Hz), 13.14 (1H, s). | 535 | 533 |

TABLE 1-17
| 1-129 | 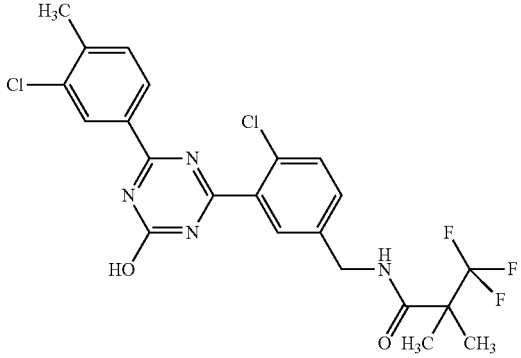 [SMILES: Cc1ccc(-c2nc(O)nc(-c3cc(CNC(=O)C(C)(C)C(F)(F)F)ccc3Cl)n2)cc1Cl] | 1H-NMR (DMSO-D6) δ: 1.39 (6H, s), 2.43 (3H, s), 4.37 (2H, d, J = 6.0 Hz), 7.44 (1H, d, J = 8.4 Hz), 7.55 (1H, d, J = 8.4 Hz), 7.61 (1H, d, J = 8.4 Hz), 7.64 (1H, s), 8.20 (1H, dd, J = 8.4, 1.5 Hz), 8.31 (1H, d, J = 1.5 Hz), 8.64 (1H, t, J = 6.0 Hz), 13.39 (1H, br s). | 499 | 497 |
|---|---|---|---|---|
| 1-130 | 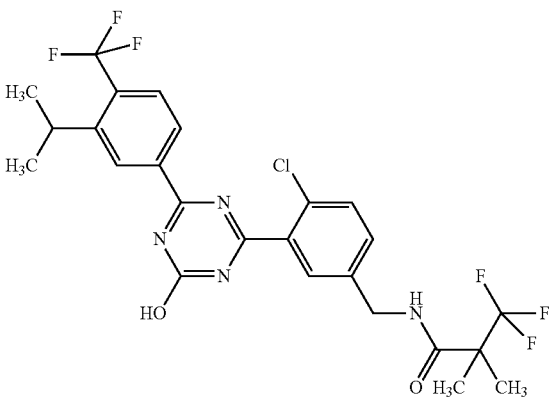 [SMILES: CC(C)c1cc(-c2nc(O)nc(-c3cc(CNC(=O)C(C)(C)C(F)(F)F)ccc3Cl)n2)ccc1C(F)(F)F] | 1H-NMR (DMSO-D6) δ: 1.30 (6H, d, J = 6.7 Hz), 1.38 (6H, s), 4.37 (2H, d, J = 5.8 Hz), 7.43 (1H, dd, J = 8.4, 2.0 Hz), 7.60 (1H, d, J = 8.4 Hz), 7.65 (1H, d, J = 2.0 Hz), 7.83 (1H, d, J = 8.4 Hz), 8.29 (1H, d, J = 8.4 Hz), 8.52 (1H, s), 8.63 (1H, t, J = 5.8 Hz), 13.55 (1H, br s). | 561 | 559 |
| 1-131 | 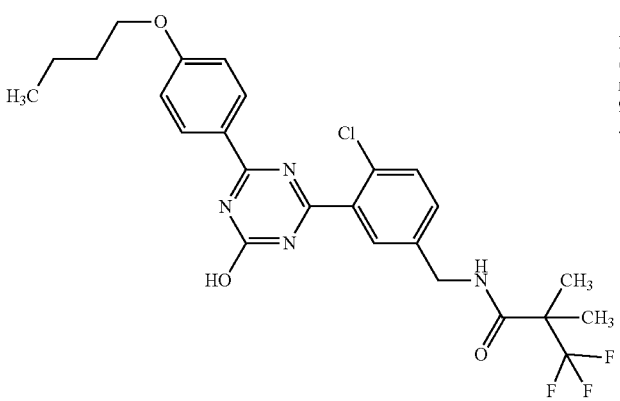 | 1H-NMR (DMSO-D6) δ: 0.94 (3H, t, J = 7.3 Hz), 1.38 (6H, s), 1.45 (2H, m), 1.69-1.76 (2H, m), 3.17 (2H, d, J = 5.1 Hz), 4.08 (2H, m), 4.37 (2H, d, J = 5.8 Hz), 7.10 (2H, d, J = 9.1 Hz), 7.44 (1H, s), 7.60 (m, s), 8.31 (2H, d, J = 9.1 Hz), 8.64 (1H, s), 13.14 (1H, s). | 523 | 521 |
| 1-132 | 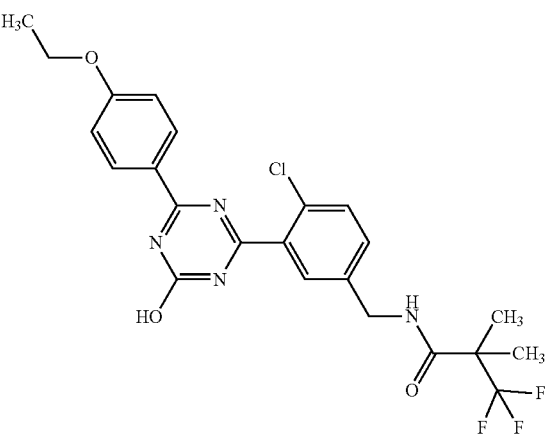 [SMILES: CCOc1ccc(-c2nc(O)nc(-c3cc(CNC(=O)C(C)(C)C(F)(F)F)ccc3Cl)n2)cc1] | 1H-NMR (DMSO-D6) δ: 1.35 (3H, t, J = 7.1 Hz), 1.37 (6H, s), 4.13(2H, q, J = 7.1 Hz), 4.35 (2H, d, J = 6.0 Hz), 7.07 (2H, d, J = 8.8 Hz), 7.42 (aH, brs), 7.60 (2H, brs), 8.29 (2H, d, J = 8.8 Hz), 8.62 (1H, t, J = 6.0 Hz), 13.13 (1H, s). | 495 | 493 |

TABLE 1-17-continued

| | | | | |
|---|---|---|---|---|
| 1-133 | [structure] | 1H-NMR (DMSO-D6) δ: 0.34 (2H, m), 0.57 (2H, m), 1.23 (1H, m), 1.37 (6H, s), 3.92 (2H, d, J = 6.7 Hz), 4.35 (2H, d, J = 6.0 Hz), 7.07 (2H, s), 7.42 (1H, s), 7.59 (2H, s), 8.28 (2H, d, J = 9.1 Hz), 8.62 (1H, t, J = 6.0 Hz), 13.13 (1H, s). | 521 | 519 |
| 1-134 | [structure] | 1H-NMR (DMSO-D6) δ: 1.38 (6H, s), 4.36 (2H, d, J = 5.8 Hz), 6.90 (2H, d, J = 8.8 Hz), 7.42 (1H, d, J = 8.6 Hz), 7.59 (1H, d, J = 8.6 Hz), 7.64 (1H, s), 8.23 (2H, d, J = 8.8 Hz), 8.64 (1H, t, J = 5.8 Hz), 10.46 (1H, s). | 467 | 465 |
| 1-135 | [structure] | 1H-NMR (DMSO-D6) δ: 0.74-0.87 (2H, m), 1.01-1.09 (2H, m), 1.38 (6H, s), 2.07-2.15 (1H, m), 4.37 (2H, d, J = 6.0 Hz), 7.33 (1H, t, J = 9.3 Hz), 7.44 (1H, d, J = 8.2 Hz), 7.61 (1H, d, J = 8.2 Hz), 7.65 (1H, s), 7.96 (1H, dd, J = 7.4,1.9 Hz), 8.15-8.21 (1H, m), 8.64 (1H, t, J = 6.0 Hz), 13.33 (1H, br s). | 509 | 507 |

TABLE 1-17-continued
| 1-136 | 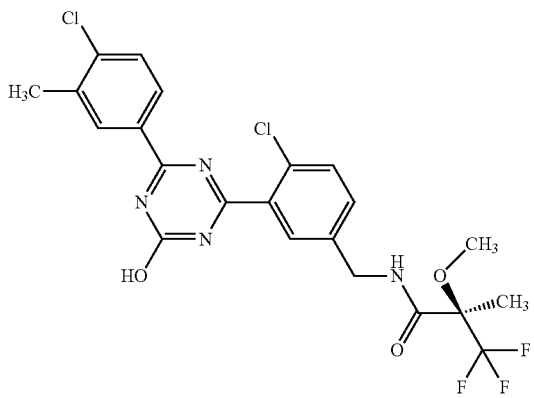 [SMILES: CO[C@](C)(C(=O)NCc1ccc(Cl)c(-c2nc(O)nc(-c3ccc(Cl)c(C)c3)n2)c1)C(F)(F)F] | 1H-NMR (DMSO-D6) δ: 1.54 (3H, s), 2.42 (3H, s), 3.36 (3H, s), 4.32-4.45 (2H, m), 7.46 (1H, dd, J = 8.4, 2.0 Hz), 7.58-7.68 (3H, m), 8.16 (1H, dd, J = 8.4, 2.0 Hz), 8.30 (1H, d, J = 2.0 Hz), 9.04 (1H, t, J = 6.2 Hz), 13.39 (1H, br s). | 515 | 513 |
TABLE 1-18
| 1-137 | 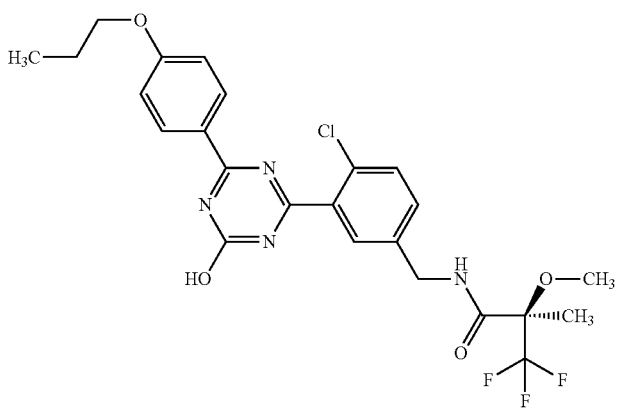 [SMILES: CCCOc1ccc(-c2nc(O)nc(-c3cc(CNC(=O)[C@@](C)(OC)C(F)(F)F)ccc3Cl)n2)cc1] | 1H-NMR (DMSO-D6) δ: 0.99 (3H, t, J = 7.4 Hz), 1.54 (3H, s), 1.71-1.81 (2H, m), 3.36 (3H, s), 4.04 (2H, t, J = 6.6 Hz), 4.32-4.43 (2H, m), 7.07 (2H, d, J = 9.0 Hz), 7.42 (1H, dd, J = 8.3, 1.9 Hz), 7.58 (1H, d, J = 8.3 Hz), 7.65 (1H, d, J = 1.9 Hz), 8.29 (2H, d, J = 9.0 Hz), 9.03 (1H, t, J = 6.6 Hz), 13.15 (1H, br s). | 525 | 523 |
| 1-138 | 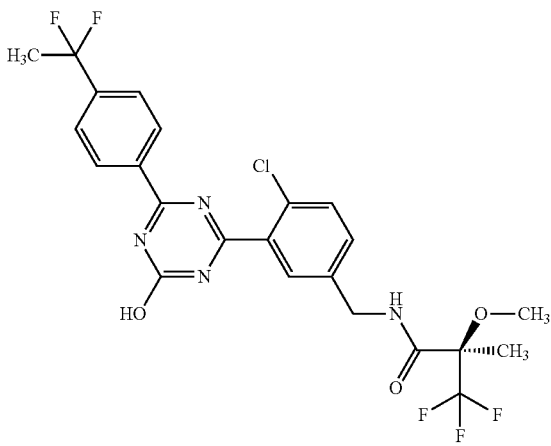 [SMILES: CO[C@](C)(C(=O)NCc1ccc(Cl)c(-c2nc(O)nc(-c3ccc(C(C)(F)F)cc3)n2)c1)C(F)(F)F] | 1H-NMR (DMSO-D6) δ: 1.54 (3H, s), 2.01 (3H, t, J = 19.0 Hz), 3.36 (3H, s, J = 8.8 Hz), 4.38 (2H, dd, J = 6.3, 2.8 Hz), 7.44 (1H, dd, J = 8.4, 2.1 Hz), 7.60 (1H, d, J = 8.4 Hz), 7.66 (1H, d, J = 2.1 Hz), 7.73 (2H, d, J = 8.4 Hz), 8.42 (2H, d, J = 8.4 Hz), 9.03 (1H, t, J = 6.3 Hz), 13.47 (1H, s). | 531 | 529 |

TABLE 1-18-continued

| | | | | |
|---|---|---|---|---|
| 1-139 | (structure) | 1H-NMR (DMSO-D6) δ: 1.38 (6H, s), 3.86 (3H, s), 4.37 (2H, d, J = 6.0 Hz), 7.10 (2H, d, J = 8.8 Hz), 7.42 (1H, d, J = 8.6 Hz), 7.59 (1H, d, J = 8.6 Hz), 7.64 (1H, s), 8.32 (2H, d, J = 8.8 Hz), 8.63 (1H, t, J = 6.0 Hz), 13.15 (1H, s). | 481 | 479 |
| 1-140 | (structure) | 1H-NMR (DMSO-D6) δ: 1.31 (6H, d, J = 6.0 Hz), 1.38 (6H, s), 4.37 (2H, d, J = 5.8 Hz), 4.77 (1H, m), 7.06 (2H, d, J = 8.8 Hz), 7.41 (1H, d, J = 8.4 Hz), 7.59 (1H, d, J = 8.4 Hz), 7.64 (1H, s), 8.29 (2H, d, J = 8.8 Hz), 8.63 (1H, t, J = 5.8 Hz), 13.13 (1H, s). | 509 | 507 |
| 1-141 | (structure) | 1H-NMR (DMSO-D6) δ: 1.38 (6H, s), 1.66 (2H, m), 1.85 (2H, m), 2.07 (2H, m), 4.36 (2H, d, J = 5.8 Hz), 4.81 (1H, m), 6.98 (2H, d, J = 8.8 Hz), 7.40 (1H, d, J = 7.9 Hz), 7.57 (1H, d, J = 7.9 Hz), 7.62 (1H, s), 8.28 (2H, d, J = 8.8 Hz), 8.63 (1H, t, J = 5.8 Hz), 13.14 (1H, s). | 521 | 519 |

| | | | |
|---|---|---|---|---|
| 1-142 | 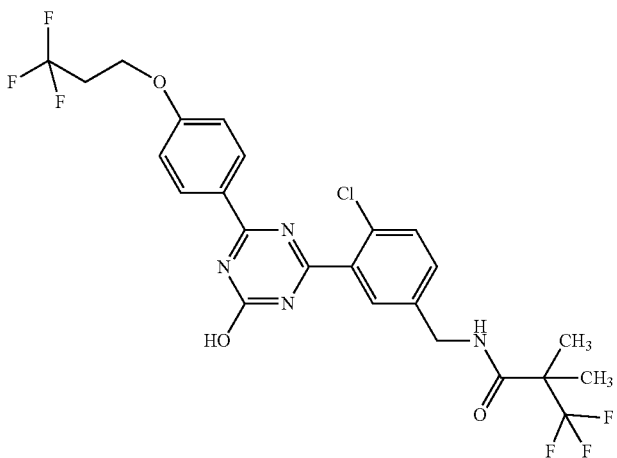 [SMILES: CC(C)(C(=O)NCc1ccc(Cl)c(-c2nc(O)nc(-c3ccc(OCCC(F)(F)F)cc3)n2)c1)C(F)(F)F] | 1H-NMR (DMSO-D6) δ: 1.38 (6H, s), 2.83 (2H, td, J = 11.3, 5.5 Hz), 4.33 (2H, t, J = 5.8 Hz), 4.37 (2H, d, J = 6.0 Hz), 7.12 (2H, d, J = 8.8 Hz), 7.43 (1H, s), 7.58 (1H, s), 7.64 (1H, s), 8.32 (2H, d, J = 8.8 Hz), 8.64 (1H, d, J = 6.0 Hz), 13.18 (1H, s). | 563 | 561 |
| 1-143 | 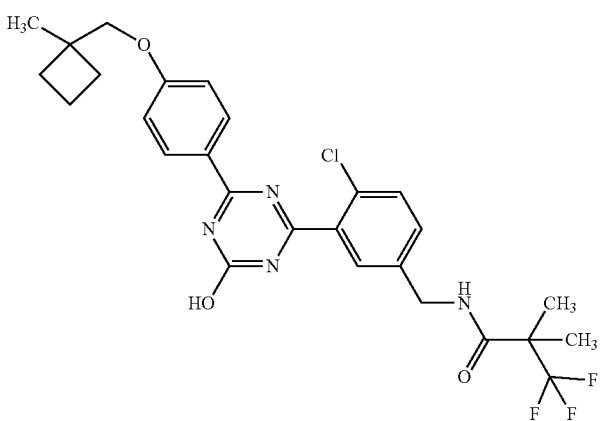 [SMILES: CC1(COc2ccc(-c3nc(O)nc(-c4cc(CNC(=O)C(C)(C)C(F)(F)F)ccc4Cl)n3)cc2)CCC1] | 1H-NMR (DMSO-D6) δ: 1.38 (3H, s), 1.39 (6H, s), 4.18 (2H, s), 4.32 (2H, d, J = 5.8 Hz), 4.37 (2H, d, J = 5.8 Hz), 4.51 (2H, d, J = 5.8 Hz), 7.15 (2H, d, J = 8.8 Hz), 7.43 (1H, d, J = 7.7 Hz), 7.60 (1H, d, J = 7.7 Hz), 7.64 (1H, s), 8.33 (2H, d, J = 8.8 Hz), 8.64 (1H, t, J = 5.8 Hz), 13.17 (1H, s). | 551 | 549 |
| 1-144 | 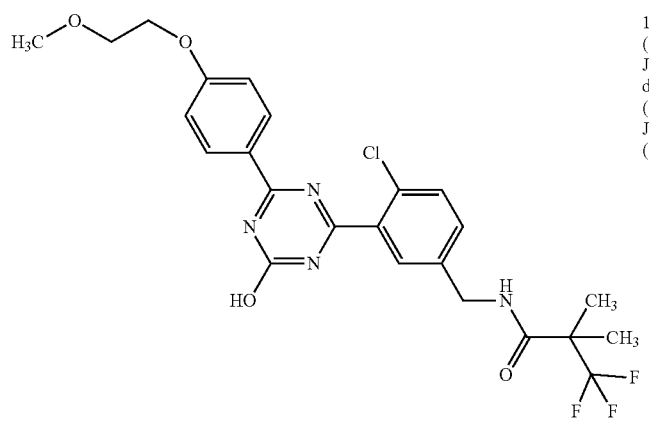 | 1H-NMR (DMSO-D6) δ: 1.38 (6H, s), 3.32 (3H, s), 3.69 (2H, t, J = 4.4 Hz), 4.21 (2H, t, J = 4.4 Hz), 4.37 (2H, d, J = 5.8 Hz), 7.11 (2H, d, J = 8.8 Hz), 7.42 (1H, d, J = 8.1 Hz), 7.60 (1H, d, J = 8.1 Hz), 7.64 (1H, s), 8.31 (2H, d, J = 8.8 Hz), 8.63 (1H, d, J = 5.8 Hz), 13.15 (1H, s). | 525 | 523 |

TABLE 1-19
| | | | | |
|---|---|---|---|---|
| 1-145 | 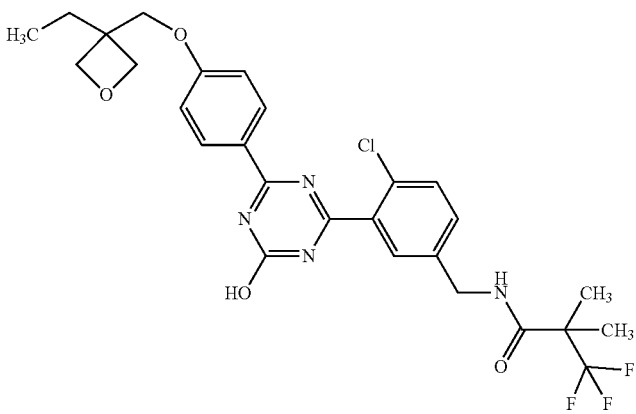 [SMILES: CCC1(COc2ccc(-c3nc(O)nc(-c4cc(CNC(=O)C(C)(C)C(F)(F)F)ccc4Cl)n3)cc2)COC1] | 1H-NNR (DMSO-D6) δ: 0.91 (3H, t, J = 7.6 Hz), 1.38 (6H, s), 1.80 (2H, q, J = 7.6 Hz), 4.21 (2H, s), 4.35 (2H, d, J = 6.0 Hz), 4.37 (2H, d, J = 5.8 Hz), 4.46 (2H, d, J = 6.0 Hz), 7.15 (2H, d, J = 8.8 Hz), 7.42 (1H, d, J = 8.4 Hz), 7.59 (1H, d, J = 8.4 Hz), 7.64 (1H, s), 8.32 (2H, d, J = 8.8 Hz), 8.64 (1H, t, J = 5.8 Hz), 13.17 (1H, s). | 565 | 563 |
| 1-146 | 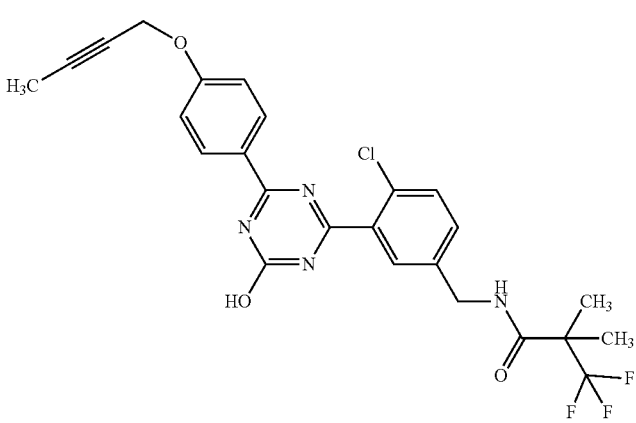 [SMILES: CC#CCOc1ccc(-c2nc(O)nc(-c3cc(CNC(=O)C(C)(C)C(F)(F)F)ccc3Cl)n2)cc1] | 1H-NNR (DMSO-D6) δ: 1.38 (6H, s), 1.84 (3H, t, J = 2.2 Hz), 4.37 (2H, d, J = 5.8 Hz), 4.87 (2H, d, J = 2.2 Hz), 7.12 (2H, d, J = 8.8 Hz), 7.43 (1H, d, J = 8.4 Hz), 7.60 (1H, d, J = 8.4 Hz), 7.65 (1H, s), 8.32 (2H, d, J = 8.8 Hz), 8.64 (1H, t, J = 5.8 Hz), 13.17 (1H, s). | 519 | 517 |
| 1-147 | 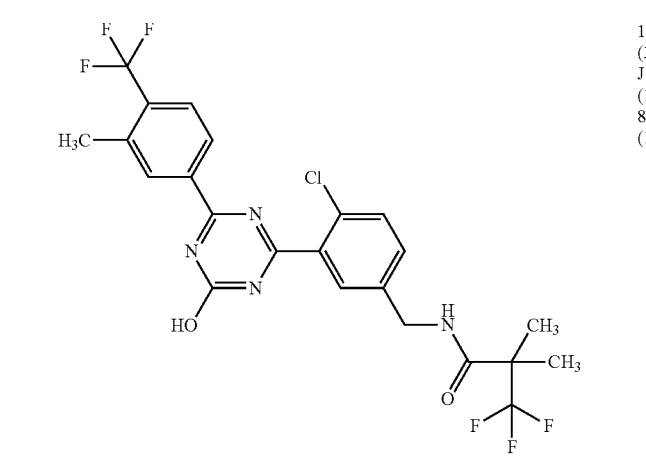 | 1H-NNR (DMSO-D6) δ: 1.38 (6H, s), 2.53 (3H, s), 4.37 (2H, d, J = 6.0 Hz), 7.42 (1H, dd, J = 8.1, 2.1 Hz), 7.59 (1H, d, J = 8.1 Hz), 7.63 (1H, d, J = 2.1 Hz), 7.84 (1H, d, J = 8.1 Hz), 8.30 (1H, d, J = 8.1 Hz), 8.34 (1H, s), 8.64 (1H, t, J = 6.0 Hz), 13.53 (1H, br s). | 533 | 531 |

TABLE 1-19-continued

| | | | | |
|---|---|---|---|---|
| 1-148 | (structure) | 1H-NNR (DMSO-D6) δ: 1.54 (3H, s), 2.54 (3H, s), 3.36 (3H, s), 4.33-4.44 (2H, m), 7.47 (1H, dd, J = 8.3, 2.0 Hz), 7.62 (1H, d, J = 8.3 Hz), 7.66 (1H, d, J = 2.0 Hz), 7.86 (1H, d, J = 8.3 Hz), 8.31 (1H, d, J = 8.3 Hz), 8.35 (1H, s), 9.04 (1H, t, J = 6.4 Hz), 13.53 (1H, br s). | 549 | 547 |
| 1-149 | (structure) | 1H-NNR (DMSO-D6) δ: 1.22-1.36 (4H, m), 2.53 (3H, s), 4.34 (2H, d, J = 6.0 Hz), 7.40 (1H, dd, J = 8.4, 2.1 Hz), 7.57 (1H, d, J = 8.4 Hz), 7.61 (1H, d, J = 2.1 Hz), 7.82 (1H, d, J = 8.4 Hz), 8.30 (1H, d, J = 8.4Hz), 8.34 (1H, s), 8.47 (1H, t, J = 6.0 Hz), 13.53 (1H, br s). | 531 | 529 |
| 1-150 | (structure) | 1H-NNR (DMSO-D6) δ: 1.38 (6H, s), 2.31 (3H, s), 2.32 (3H, s), 4.37 (2H, d, J = 6.0 Hz), 7.33 (1H, d, J = 8.2 Hz), 7.43 (1H, d, J = 8.2 Hz), 7.58-7.67 (2H, m), 8.07 (1H, d, J = 8.2 Hz), 8.12 (1H, s), 8.65 (1H, t, J = 6.0 Hz), 13.23 (1H, br s). | 479 | 477 |
| 1-151 | (structure) | 1H-NNR (DMSO-D6) δ: 1.21 (3H, t, J = 7.5 Hz), 1.54 (3H, s), 2.71 (2H, q, J = 7.5 Hz), 3.36 (3H, s), 4.32-4.45 (2H, m), 7.33 (1H, t, J = 9.3 Hz), 7.46 (1H, dd, J = 8.4, 2.0 Hz), 7.61 (1H, d, J = 8.4 Hz), 7.66 (1H, s), 8.20-8.26 (1H, m), 8.29 (1H, dd, J = 7.6, 2.3 Hz), 9.04 (1H, t, J = 6.3 Hz), 13.35 (1H, br s). | 513 | 511 |

TABLE 1-19-continued
| 1-152 | 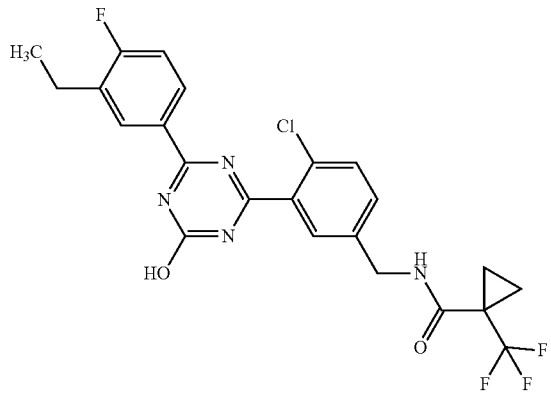 [SMILES: CCc1cc(-c2nc(O)nc(-c3cc(CNC(=O)C4(C(F)(F)F)CC4)ccc3Cl)n2)ccc1F] | 1H-NNR (DMSO-D6) δ: 1.19-1.27 (5H, m), 1.32-1.37 (2H, m), 2.71 (2H, q, J = 7.5 Hz), 4.35 (2H, d, J = 6.0 Hz), 7.33 (1H, t, J = 9.2 Hz), 7.45 (1H, dd, J = 8.4, 2.0 Hz), 7.61 (1H, d, J = 8.4 Hz), 7.65 (1H, s), 8.21-8.26 (1H, m), 8.30 (1H, dd, J = 7.5, 2.0 Hz), 8.48 (1H, t, J = 6.0 Hz), 13.34 (1H, br s). | 495 | 493 |
TABLE 1-20
| 1-153 | 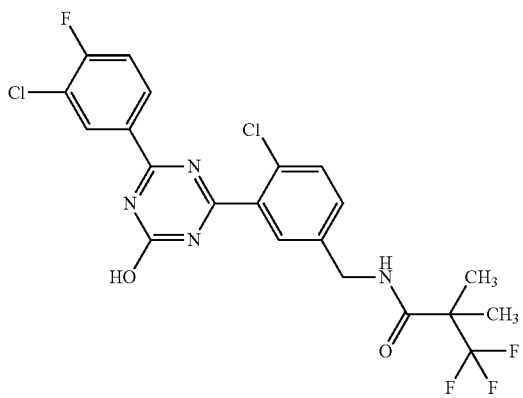 [SMILES: CC(C)(C(=O)NCc1ccc(Cl)c(-c2nc(O)nc(-c3ccc(F)c(Cl)c3)n2)c1)C(F)(F)F] | 1H-NMR (DMSO-D6) δ: 1.39 (6H, s), 4.37 (2H, d, J = 6.0 Hz), 7.45 (1H, dd, J = 8.3, 2.1 Hz), 7.59-7.66 (3H, m), 8.32-8.38 (1H, m), 8.45 (1H, dd, J = 7.4, 2.1 Hz), 8.65 (1H, t, J = 6.0 Hz), 13.48 (0H, br s). | 503 | 501 |
| 1-154 | 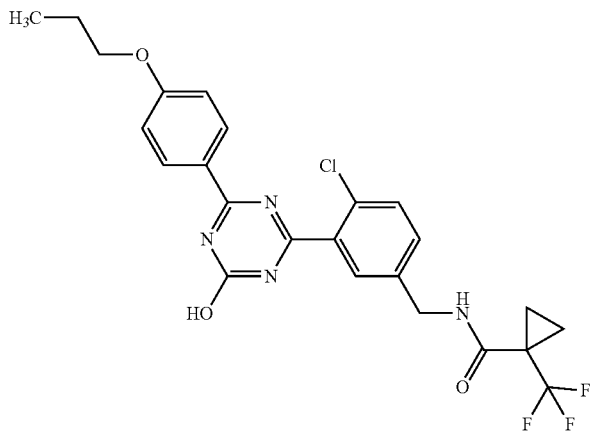 [SMILES: CCCOc1ccc(-c2nc(O)nc(-c3cc(CNC(=O)C4(C(F)(F)F)CC4)ccc3Cl)n2)cc1] | 1H-NMR (DMSO-D6) δ: 0.99 (3H, t, J = 7.4 Hz), 1.22-1.27 (2H, m), 1.31-1.37 (2H, m), 1.71-1.81 (2H, m), 4.04 (2H, t, J = 6.5 Hz), 4.34 (2H, d, J = 6.0 Hz), 7.09 (2H, d, J = 9.0 Hz), 7.43 (1H, dd, J = 8.4, 2.0 Hz), 7.59 (1H, d, J = 8.4 Hz), 7.64 (1H, s), 8.31 (2H, d, J = 9.0 Hz), 8.47 (1H, t, J = 6.0 Hz), 13.14 (1H, br s). | 507 | 505 |

| | | | |
|---|---|---|---|
| 1-155 | 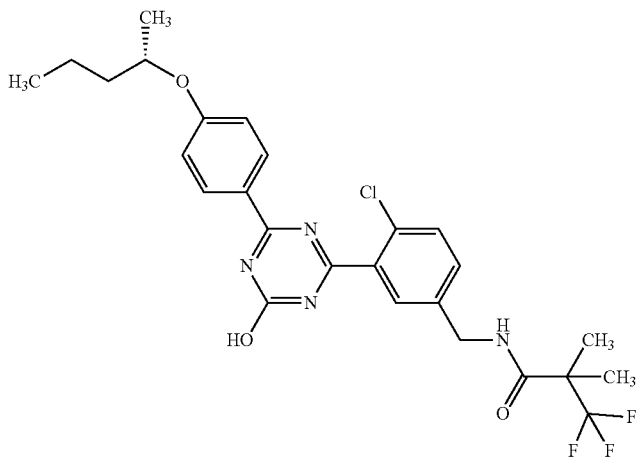 [SMILES: CCC[C@H](C)Oc1ccc(-c2nc(O)nc(-c3cc(CNC(=O)C(C)(C)C(F)(F)F)ccc3Cl)n2)cc1] | 1H-NMR (DMSO-D6) δ: 0.90 (3H, t, J = 7.3 Hz), 1.27 (3H, d, J = 6.0 Hz), 1.37 (6H, s), 1.43 (2H, m), 1.52-1.60 (1H, m), 1.67 (1H, m), 4.37 (2H, d, J = 5.8 Hz), 4.62 (1H, m), 7.07 (2H, d, J = 9.1 Hz), 7.42 (1H, d, J = 8.1 Hz), 7.59 (1H, d, J = 8.1 Hz), 7.64 (1H, s), 8.29 (2H, d, J = 9.1 Hz), 8.63 (1H, t, J = 5.8 Hz), 13.13 (1H, s). | 537 535 |
| 1-156 | 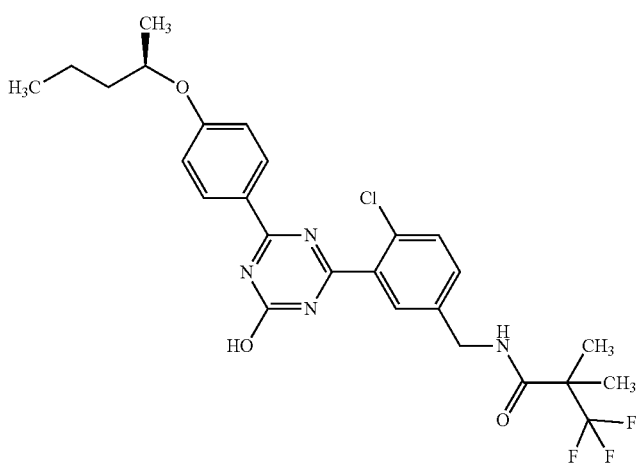 [SMILES: CCC[C@@H](C)Oc1ccc(-c2nc(O)nc(-c3cc(CNC(=O)C(C)(C)C(F)(F)F)ccc3Cl)n2)cc1] | 1H-NMR (DMSO-D6) δ: 0.90 (3H, t, J = 7.3 Hz), 1.27 (3H, d, J = 6.0 Hz), 1.36 (6H, s), 1.43 (2H, m), 1.51-1.60 (1H, m), 1.65 (1H, m), 4.37 (2H, d, J = 5.8 Hz), 4.62 (1H, m), 7.06 (2H, d, J = 8.8 Hz), 7.41 (1H, d, J = 8.1 Hz), 7.59 (1H, d, J = 8.1 Hz), 7.64 (1H, s), 8.29 (2H, d, J = 8.8 Hz), 8.63 (1H, t, J = 5.8 Hz), 13.13 (1H, s). | 537 535 |
| 1-157 | 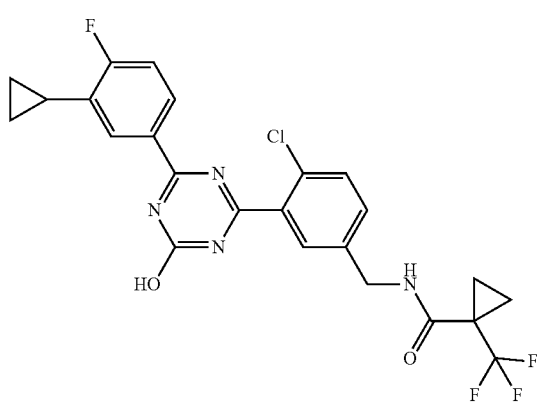 [SMILES: O=C(NCc1ccc(Cl)c(-c2nc(O)nc(-c3ccc(F)c(C4CC4)c3)n2)c1)C1(C(F)(F)F)CC1] | 1H-NMR (DMSO-D6) δ: 0.77-0.83 (2H, m), 1.02-1.08 (2H, m), 1.22-1.27 (2H, m), 1.31-1.36 (2H, m), 2.07-2.15 (1H, m), 4.34 (2H, d, J = 5.8 Hz), 7.33 (1H, t, J = 9.3 Hz), 7.44 (1H, d, J = 8.4 Hz), 7.60 (1H, d, J = 8.4 Hz), 7.65 (1H, s), 7.96 (1H, d, J = 7.9 Hz), 8.15-8.20 (1H, m), 8.47 (1H, t, J = 5.8 Hz), 13.31 (1H, br s). | 507 505 |

TABLE 1-20-continued

| | | | | |
|---|---|---|---|---|
| 1-158 | (structure) | 1H-NMR (DMSO-D6) δ: 0.99 (3H, t, J = 7.5 Hz), 1.21 (6H, s), 1.76 (2H, m), 3.03 (2H, s), 4.04 (2H, t, J = 6.5 Hz), 4.40 (2H, s), 7.09 (2H, d, J = 8.9 Hz), 7.47 (1H, d, J = 8.3 Hz), 7.65 (1H, d, J = 8.3 Hz), 7.67 (1H, s), 8.31 (2H, d, J = 8.9 Hz), 13.14 (1H, s). | 453 | 451 |
| 1-159 | (structure) | 1H-NMR (DMSO-D6) δ: 0.72-0.77 (2H, m), 0.97-1.04 (2H, m), 1.38 (6H, s), 1.99-2.07 (1H, m), 4.37 (2H, d, J = 6.0 Hz), 7.34-7.45 (3H, m), 7.59 (1H, d, J = 8.4 Hz), 7.65 (1H, s), 8.03 (1H, s), 8.10 (1H, d, J = 7.7 Hz), 8.64 (1H, t, J = 6.0 Hz), 13.32 (1H, br s). | 491 | 489 |
| 1-160 | (structure) | 1H-NMR (DMSO-D6) δ: 0.72-0.78 (2H, m), 0.98-1.04 (2H, m), 1.21-1.27 (2H, m), 1.31-1.36 (2H, m), 2.00-2.07 (1H, m), 4.34 (2H, d, J = 5.8 Hz), 7.35-7.46 (3H, m), 7.60 (1H, d, J = 8.1 Hz), 7.66 (1H, s), 8.03 (1H, s), 8.10 (1H, d, J = 7.4 Hz), 8.47 (1H, t, J = 5.8 Hz), 13.30 (1H, br s). | 489 | 487 |

TABLE 1-21

| | | | | |
|---|---|---|---|---|
| 1-161 | (structure) | 1H-NMR (DMSO-D6) δ: 1.32-1.38 (9H, m), 2.55 (3H, s), 4.10 (2H, q, J = 12 Hz), 4.35 (2H, d, J = 5.8 Hz), 6.86-6.92 (2H, m), 7.39 (1H, d, J = 8.6 Hz), 7.56 (1H, d, J = 8.6 Hz), 7.62 (1H, s), 7.81 (1H, br s), 8.61 (1H, t, J = 5.8 Hz), 13.08 (1H, br s). | 509 | 507 |

TABLE 1-21-continued
| | | | | |
|---|---|---|---|---|
| 1-162 | 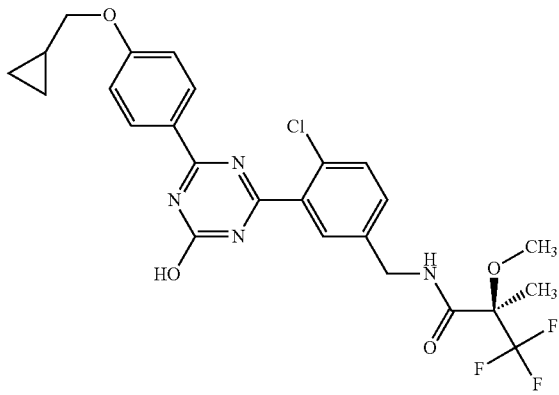 [SMILES: CO[C@](C)(C(=O)NCc1ccc(Cl)c(-c2nc(O)nc(-c3ccc(OCC4CC4)cc3)n2)c1)C(F)(F)F] | 1H-NMR (DMSO-D6) δ: 0.35 (2H, q, J = 5.1 Hz), 0.57-0.60 (2H, m), 1.22-1.30 (1H, m), 1.54 (3H, s), 3.36 (3H, s), 3.93 (2H, d, J = 7.0 Hz), 4.37 (2H, dd, J = 5.9, 2.9 Hz), 7.07 (2H, d, J = 8.8 Hz), 7.42 (1H, d, J = 8.4 Hz), 7.58 (1H, d, J = 8.4 Hz), 7.65 (1H, s), 8.29 (2H, d, J = 8.8 Hz), 9.02 (1H, t, J = 5.9 Hz), 13.14 (1H, br s). | 537 | 535 |
| 1-163 | 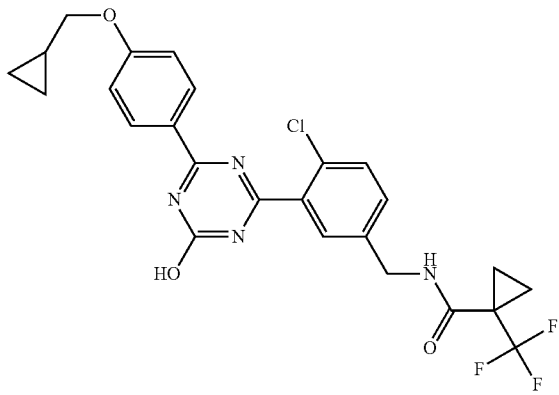 [SMILES: O=C(NCc1ccc(Cl)c(-c2nc(O)nc(-c3ccc(OCC4CC4)cc3)n2)c1)C1(C(F)(F)F)CC1] | 1H-NMR (DMSO-D6) δ: 0.33-0.37 (2H, m), 0.57-0.61 (2H, m), 1.22-1.35 (5H, m), 3.92 (2H, d, J = 7.0 Hz), 4.33 (2H, d, J = 5.8 Hz), 7.05 (2H, d, J = 8.8 Hz), 7.39 (1H, dd, J = 8.3, 1.9 Hz), 7.55 (1H, d, J = 8.3 Hz), 7.61 (1H, d, J = 1.9 Hz), 8.28 (2H, d, J = 8.8 Hz), 8.46 (1H, t, J = 5.8 Hz), 13.15 (1H, br s). | 519 | 517 |
| 1-164 | 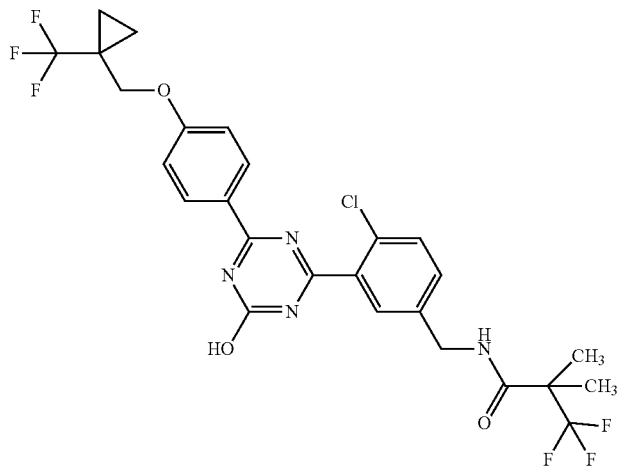 [SMILES: CC(C)(C(=O)NCc1ccc(Cl)c(-c2nc(O)nc(-c3ccc(OCC4(C(F)(F)F)CC4)cc3)n2)c1)C(F)(F)F] | 1H-NMR(DMSO-D6) δ: 1.05 (2H, m), 1.10 (2H, m), 1.38 (6H, s), 4.20 (2H, s), 4.34 (2H, d, J = 5.6 Hz), 7.02 (2H, d, J = 7.9 Hz), 7.32 (1H, d, J = 7.5 Hz), 7.49 (1H, d, J = 7.5 Hz), 7.56 (1H, s), 8.26 (2H, d, J = 7.9 Hz), 8.61 (1H, t, J = 5.6 Hz), 13.18 (1H, s). | 589 | 587 |

| 1-165 | 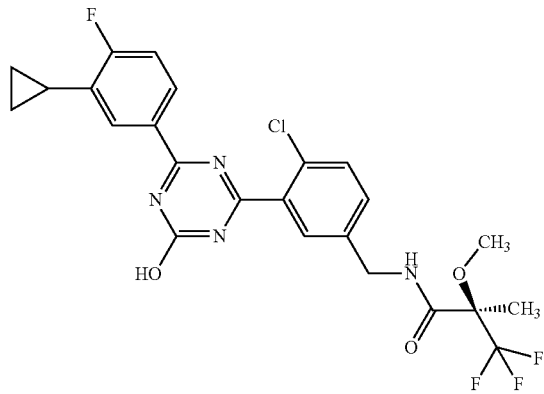 [SMILES: CO[C@](C)(C(=O)NCc1ccc(Cl)c(-c2nc(O)nc(-c3ccc(F)c(C4CC4)c3)n2)c1)C(F)(F)F] | 1H-NMR (DMSO-D6) δ: 0.77-0.82 (2H, m), 1.01-1.07 (2H, m), 1.54 (3H, s), 2.07-2.15 (1H, m), 3.35 (3H, s), 4.31-4.44 (2H, m), 7.32 (1H, t, J = 9.3 Hz), 7.44 (1H, d, J = 8.4 Hz), 7.60 (1H, d, J = 8.4 Hz), 7.67 (1H, s), 7.95 (1H, d, J = 7.2 Hz), 8.14-8.19 (1H, m), 9.02 (1H, t, J = 6.3 Hz), 13.31 (1H, br s). | 525 | 523 |
|---|---|---|---|---|
| 1-166 | 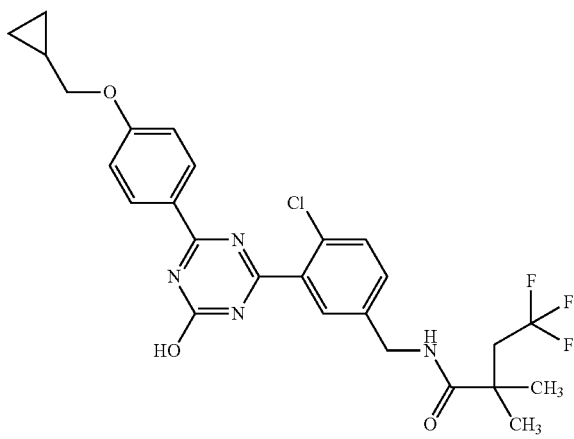 [SMILES: CC(C)(CC(F)(F)F)C(=O)NCc1ccc(Cl)c(-c2nc(O)nc(-c3ccc(OCC4CC4)cc3)n2)c1] | 1H-NMR (DMSO-D6) δ: 0.33-0.38 (2H, m), 0.56-0.62 (2H, m), 1.19-1.31 (7H, m), 2.59 (2H, q, J = 12.1 Hz), 3.93 (2H, d, J = 7.1 Hz), 4.33 (2H, d, J = 6.0 Hz), 7.07 (2H, d, J = 9.0 Hz), 7.42 (1H, d, J = 8.4 Hz), 7.58 (1H, d, J = 8.4 Hz), 7.63 (1H, s), 8.29 (2H, d, J = 9.0 Hz), 8.35 (1H, t, J = 6.0 Hz), 13.14 (1H, br s). | 535 | 533 |
| 1-167 | 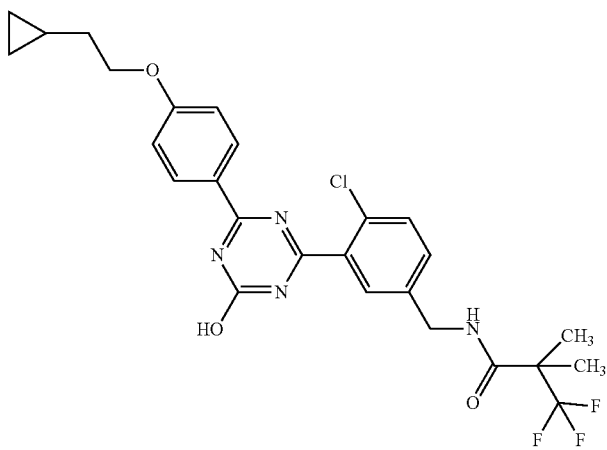 [SMILES: CC(C)(C(=O)NCc1ccc(Cl)c(-c2nc(O)nc(-c3ccc(OCCC4CC4)cc3)n2)c1)C(F)(F)F] | 1H-NMR (DMSO-D6) δ: 0.11-0.16 (2H, m), 0.41-0.48 (2H, m), 0.79-0.90 (1H, m), 1.38 (6H, s), 1.65 (2H, q, J = 6.5 Hz), 4.14 (2H, t, J = 6.5 Hz), 4.37 (2H, d, J = 6.0 Hz), 7.09 (2H, d, J = 9.0 Hz), 7.41 (1H, dd, J = 8.4, 2.0 Hz), 7.59 (1H, d, J = 8.4 Hz), 7.64 (1H, d, J = 2.0 Hz), 8.30 (2H, d, J = 9.0 Hz), 8.64 (1H, t, J = 6.0 Hz), 13.15 (1H, br s). | 535 | 533 |

TABLE 1-21-continued
| | | | | |
|---|---|---|---|---|
| 1-168 | 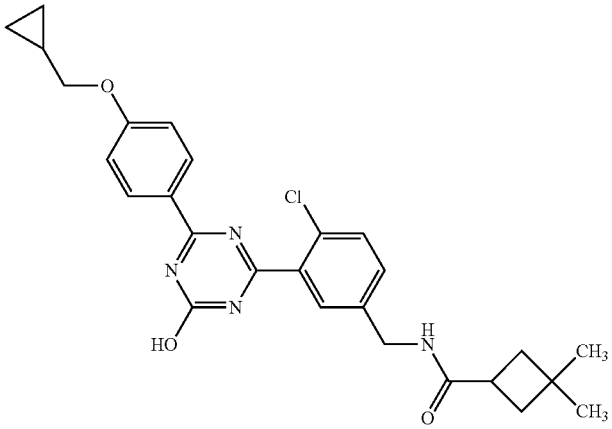 [SMILES: CC1(C)CC(C(=O)NCc2ccc(Cl)c(-c3nc(O)nc(-c4ccc(OCC5CC5)cc4)n3)c2)C1] | 1H-NMR (DMSO-D6) δ: 0.32-0.38 (2H, m), 0.56-0.62 (2H, m), 1.01 (3H, s), 1.12 (3H, s), 1.19-1.30 (1H, m), 1.78-1.85 (2H, m), 1.90-1.97 (2H, m), 2.95-3.05 (1H, m), 3.93 (2H, d, J = 7.0 Hz), 4.30 (2H, d, J = 6.0 Hz), 7.08 (2H, d, J = 8.6 Hz), 7.43 (1H, d, J = 8.4 Hz), 7.58 (1H, d, J = 8.4 Hz), 7.62 (1H, s), 8.25-8.32 (3H, m), 13.13 (1H, br s). | 493 | 491 |
TABLE 1-22
| | | | | |
|---|---|---|---|---|
| 1-169 | 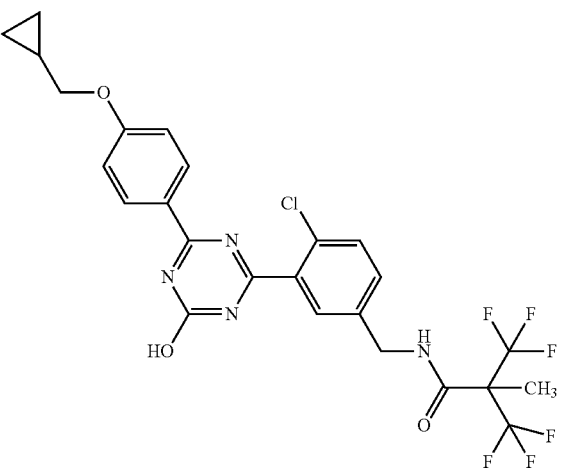 [SMILES: CC(C(=O)NCc1ccc(Cl)c(-c2nc(O)nc(-c3ccc(OCC4CC4)cc3)n2)c1)(C(F)(F)F)C(F)(F)F] | 1H-NMR (DMSO-D6) δ: 0.32-0.38 (2H, m), 0.55-0.62 (2H, m), 1.20-1.29 (1H, m), 1.74 (3H, s), 3.93 (2H, d, J = 6.7 Hz), 4.43 (2H, d, J = 6.0 Hz), 7.07 (2H, d, J = 8.4 Hz), 7.41 (1H, d, J = 8.4 Hz), 7.60 (1H, d, J = 8.4 Hz), 7.65 (1H, s), 8.29 (2H, d, J = 8.4 Hz), 9.10 (1H, t, J = 6.0 Hz), 13.14 (1H, br s). | 575 | 573 |
| 1-170 | 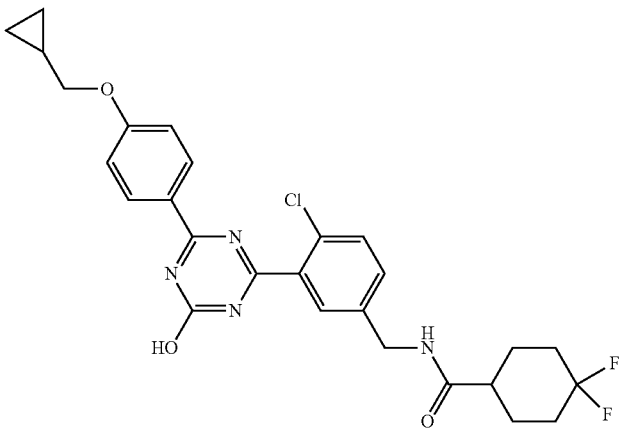 [SMILES: O=C(NCc1ccc(Cl)c(-c2nc(O)nc(-c3ccc(OCC4CC4)cc3)n2)c1)C1CCC(F)(F)CC1] | 1H-NMR (DMSO-D6) δ: 0.33-0.38 (2H, m), 0.56-0.62 (2H, m), 1.20-1.31 (1H, m), 1.57-1.90 (6H, m), 1.97-2.09 (2H, m), 2.29-2.39 (1H, m), 3.93 (2H, d, J = 7.1 Hz), 4.31-4.33 (2H, br m), 7.08 (2H, d, J = 8.8 Hz), 7.44 (1H, d, J = 8.4 Hz), 7.58 (1H, d, J = 8.4 Hz), 7.64 (1H, s), 8.29 (2H, d, J = 8.8 Hz), 8.50 (1H, t, J = 6.0 Hz), 13.14 (1H, br s). | 529 | 527 |

TABLE 1-22-continued

| | | | | |
|---|---|---|---|---|
| 1-171 | (structure) | 1H-NMR (DMSO-D6) δ: 0.33-0.38 (2H, m), 0.56-0.62 (2H, m), 0.79 (6H, t, J = 7.5 Hz), 1.20-1.54 (5H, m), 1.98-2.07 (1H, m), 3.94 (2H, d, J = 7.1 Hz), 4.34 (2H, d, J = 6.0 Hz), 7.08 (2H, d, J = 9.0 Hz), 7.46 (1H, d, J = 8.2 Hz), 7.60 (1H, d, J = 8.2 Hz), 7.66 (1H, s), 8.29 (2H, d, J = 9.0 Hz), 8.46 (1H, t, J = 5.7 Hz), 13.14 (1H, br s). | 481 | 479 |
| 1-172 | (structure) | 1H-NMR (DMSO-D6) δ: 0.99-1.33 (5H, m), 1.38 (6H, s), 1.62-1.86 (6H, m), 3.89 (2H, d, J = 6.2 Hz), 4.36 (2H, d, J = 6.0 Hz), 7.06 (2H, d, J = 9.0 Hz), 7.40 (1H, dd, J = 8.4, 2.0 Hz), 7.57 (1H, d, J = 8.4 Hz), 7.62 (1H, d, J = 2.0 Hz), 8.29 (2H, d, J = 9.0 Hz), 8.64 (1H, t, J = 6.0 Hz), 13.15 (1H, br s). | 563 | 561 |
| 1-173 | (structure) | 1H-NMR (DMSO-D6)δ: 0.33-0.37 (2H, m), 0.56-0.62 (2H, m), 1.11 (6H, s), 1.17 (6H, s), 1.20-1.29 (2H, m), 3.93 (2H, d, J = 7.1 Hz), 4.29 (2H, d, J = 6.0 Hz), 7.07 (2H, d, J = 8.8 Hz), 7.43 (1H, dd, J = 8.4, 2.0 Hz), 7.57 (1H, d, J = 8.4 Hz), 7.62 (1H, d, J = 2.0 Hz), 8.29 (2H, d, J = 8.8 Hz), 8.37 (1H, t, J = 6.0 Hz), 13.14 (1H, br s). | 507 | 505 |
| 1-174 | (structure) | 1H-NMR (DMSO-D6) δ: 2.51 (3H, s), 7.49-7.46 (3H, m), 7.63-7.60 (2H, m), 7.66 (1H, d, J = 7.9 Hz), 7.77 (2H, d, J = 8.6 Hz), 7.96 (1H, d, J = 7.9 Hz), 8.22 (1H, s), 8.53 (2H, d, J = 8.6 Hz), 13.46 (1H, s). | 389 | 387 |

TABLE 1-22-continued

| 1-175 | (structure) | 1H-NMR (DMSO-D6) δ: 0.36 (2H, td, J = 5.2, 3.9 Hz), 0.56-0.60 (2H, m), 1.23-1.30 (1H, m), 1.38 (6H, s), 2.21 (3H, s), 3.91 (2H, d, J = 6.7 Hz), 4.34 (2H, d, J = 5.8 Hz), 6.97 (1H, d, J = 8.6 Hz), 7.29 (1H, dd, J = 8.3, 1.9 Hz), 7.47 (1H, d, J = 8.4 Hz), 7.53 (1H, d, J = 1.9 Hz), 8.08-8.14 (2H, m), 8.61 (1H, t, J = 5.8 Hz). | 535 | 533 |

TABLE 1-23

| 1-176 | (structure) | 1H-NMR (DMSO-D6) δ: 0.30 (2H, td, J = 5.3, 4.0 Hz), 0.56 (2H, ddd, J = 9.2, 5.3, 3.1 Hz), 1.22-1.27 (1H, m), 1.38 (6H, s), 2.29 (6H, s), 3.69 (2H, d, J = 7.0 Hz), 4.36 (2H, d, J = 5.8 Hz), 7.41 (1H, dd, J = 8.4, 1.9 Hz), 7.58 (1H, d, J = 8.4 Hz), 7.61 (1H, d, J = 1.9 Hz), 8.02 (2H, s), 8.64 (1H, t, J = 5.8 Hz), 13.18 (1H, br s). | 549 | 547 |
| 1-177 | (structure) | 1H-NMR (DMSO-D6) δ: 0.88 (6H, d, J = 6.4 Hz), 1.54 (3H, s), 1.83-1.98 (1H, m), 2.55 (2H, d, J = 7.3 Hz), 3.36 (3H, s), 4.31-4.45 (2H, m), 7.35 (2H, d, J = 8.3 Hz), 7.45 (1H, dd, J = 8.1, 2.0 Hz), 7.60 (1H, d, J = 8.1 Hz), 7.67 (1H, br s), 8.26 (2H, d, J = 8.3 Hz), 9.03 (1H, t, J = 6.2 Hz), 13.26 (1H, br s). | 523 | 521 |

TABLE 1-23-continued
| | | | | |
|---|---|---|---|---|
| 1-178 | 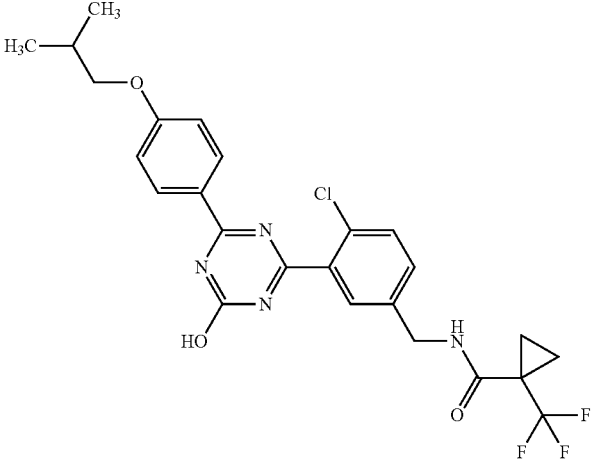 [SMILES: CC(C)COc1ccc(-c2nc(O)nc(-c3cc(CNC(=O)C4(C(F)(F)F)CC4)ccc3Cl)n2)cc1] | 1H-NMR (DMSO-D6) δ: 0.99 (6H, d, J = 6.4 Hz), 1.20-1.39 (4H, m), 1.96-2.13 (1H, m), 3.84 (2H, d, J = 6.4 Hz), 4.33 (2H, d, J = 6.0 Hz), 7.05 (2H, d, J = 9.1 Hz), 7.37 (1H, dd, J = 8.3, 2.0 Hz), 7.54 (1H, d, J = 8.3 Hz), 7.60 (1H, d, J = 2.0 Hz), 8.28 (2H, d, J = 9.1 Hz), 8.46 (1H, t, J = 5.8 Hz), 13.15 (1H, br s). | 521 | 519 |
| 1-179 | 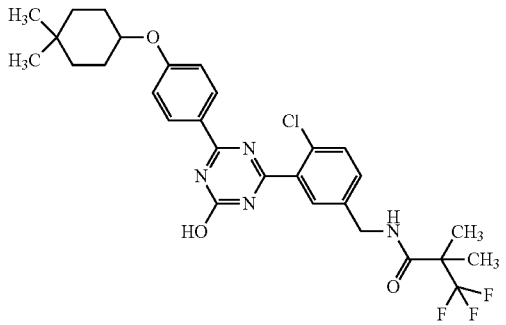 [SMILES: CC1(C)CCC(Oc2ccc(-c3nc(O)nc(-c4cc(CNC(=O)C(C)(C)C(F)(F)F)ccc4Cl)n3)cc2)CC1] | 1H-NMR (DMSO-D6) δ: 0.94 (3H, s), 0.95 (3H, s), 1.27-1.36 (2H, m), 1.38 (6H, s), 1.41-1.49 (2H, m), 1.56-1.66 (2H, m), 1.80-1.89 (2H, m), 4.36 (2H, d, J = 5.7 Hz), 4.45-4.53 (1H, m), 7.07 (2H, d, J = 9.0 Hz), 7.40 (1H, dd, J = 8.2, 2.0 Hz), 7.58 (1H, d, J = 8.2 Hz), 7.63 (1H, d, J = 2.0 Hz), 8.28 (2H, d, J = 9.0 Hz), 8.63 (1H, t, J = 6.1 Hz), 13.13 (1H, br s). | 577 | 575 |
| 1-180 | 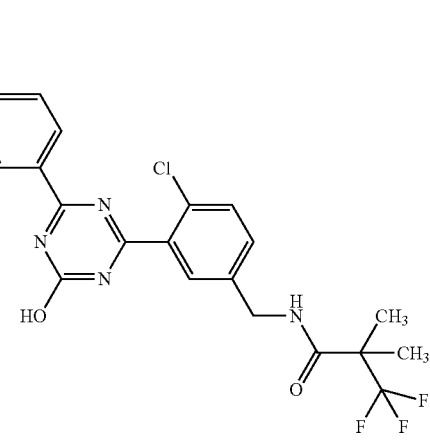 | 1H-NMR (DMSO-D6) δ: 0.91 (3H, t, J = 7.3 Hz), 1.27-1.37 (2H, m), 1.38 (6H, s), 1.55-1.64 (2H, m), 2.67 (2H, t, J = 7.7 Hz), 4.37 (2H, d, J = 6.0 Hz), 7.38 (2H, d, J = 8.2 Hz), 7.42 (1H, d, J = 8.4 Hz), 7.59 (1H, d, J = 8.4 Hz), 7.64 (1H, s), 8.25 (2H, d, J = 8.2 Hz), 8.64 (1H, t, J = 6.0 Hz), 13.27 (1H, br s). | 507 | 505 |
| 1-181 | 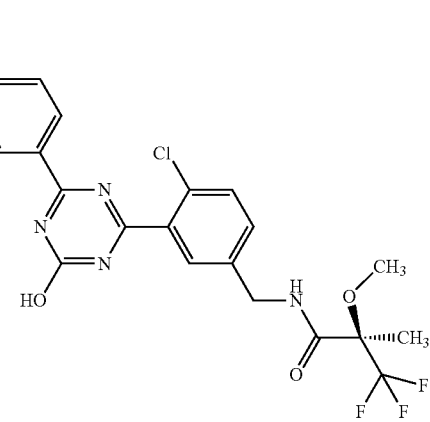 | 1H-NMR (DMSO-D6) δ: 0.90 (3H, t, J = 7.7 Hz), 1.26-1.37 (2H, m), 1.54 (3H, s), 1.55-1.64 (2H, m), 2.67 (2H, t, J = 7.7 Hz), 3.36 (3H, s), 4.32-4.44 (2H, m), 7.38 (2H, d, J = 7.5 Hz), 7.44 (1H, d, J = 8.4 Hz), 7.59 (1H, d, J = 8.4 Hz), 7.66 (1H, s), 8.25 (2H, d, J = 7.5 Hz), 9.03 (1H, t, J = 6.2 Hz), 13.27 (1H, br s). | 523 | 521 |

TABLE 1-23-continued
| 1-182 | 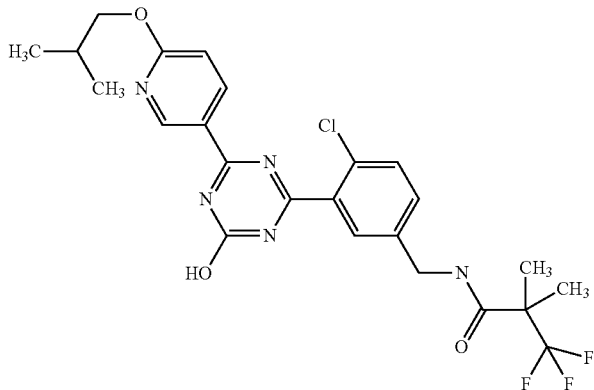 [SMILES: CC(C)COc1ccc(-c2nc(O)nc(-c3cc(CNC(=O)C(C)(C)C(F)(F)F)ccc3Cl)n2)cn1] | 1H-NMR (DMSO-D6) δ: 0.99 (6H, t, J = 6.0 Hz), 1.37 (6H, s), 2.00-2.10 (1H, m), 4.11 (2H, d, J = 6.5 Hz), 4.34 (2H, d, J = 6.0 Hz), 6.88 (1H, d, J = 8.7 Hz), 7.30 (1H, dd, J = 8.1, 2.1 Hz), 7.48 (1H, d, J = 8.1 Hz), 7.57 (1H, d, J = 2.1 Hz), 8.47 (1H, dd, J = 8.7, 2.4 Hz), 8.60 (1H, t, J = 6.0 Hz), 9.02 (1H, d, J = 2.4 Hz). | 524 | 522 |
| --- | --- | --- | --- | --- |
| 1-183 | 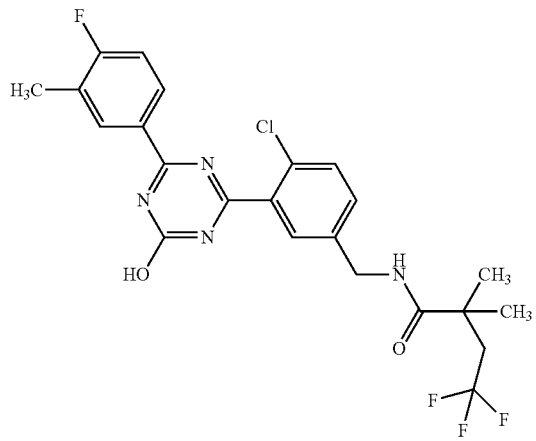 [SMILES: Cc1cc(-c2nc(O)nc(-c3cc(CNC(=O)C(C)(C)CC(F)(F)F)ccc3Cl)n2)ccc1F] | 1H-NMR (DMSO-D6) δ: 1.24 (6H, s), 2.32 (3H, d, J = 1.3 Hz), 2.59 (2H, q, J = 12.1 Hz), 4.34 (2H, d, J = 6.2 Hz), 7.32 (1H, t, J = 9.2 Hz), 7.44 (1H, dd, J = 8.4, 2.0 Hz), 7.59 (1H, d, J = 8.4 Hz), 7.63 (1H, d, J = 2.0 Hz), 8.19-8.25 (1H, m), 8.28 (1H, d, J = 7.7 Hz), 8.35 (1H, t, J = 5.8 Hz), 13.33 (1H, br s). | 497 | 495 |
TABLE 1-24
| 1-184 | 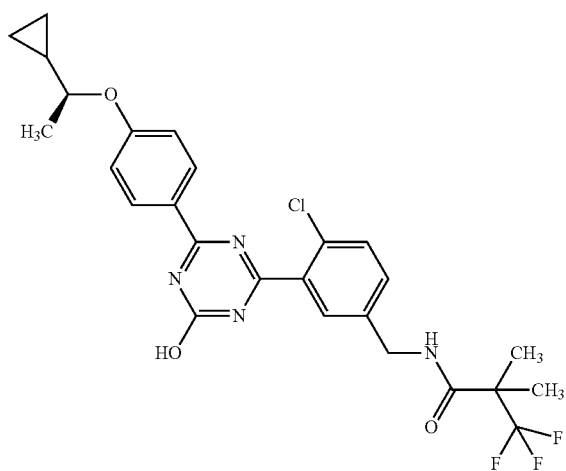 [SMILES: C[C@H](Oc1ccc(-c2nc(O)nc(-c3cc(CNC(=O)C(C)(C)C(F)(F)F)ccc3Cl)n2)cc1)C1CC1] | 1H-NMR (DMSO-D6) δ: 0.29-0.39 (2H, m), 0.47-0.55 (2H, m), 1.08-1.17 (1H, m), 1.32 (3H, d, J = 6.3 Hz), 1.38 (6H, s), 4.10-4.18 (1H, m), 4.36 (2H, d, J = 6.0 Hz), 7.05 (2H, d, J = 8.8 Hz), 7.41 (1H, d, J = 8.0 Hz), 7.58 (1H, d, J = 8.0 Hz), 7.63 (1H, s), 8.27 (2H, d, J = 8.8 Hz), 8.63 (1H, t, J = 6.0 Hz), 13.13 (1H, br s). | 535 | 533 |
| --- | --- | --- | --- | --- |

TABLE 1-24-continued
| 1-185 | 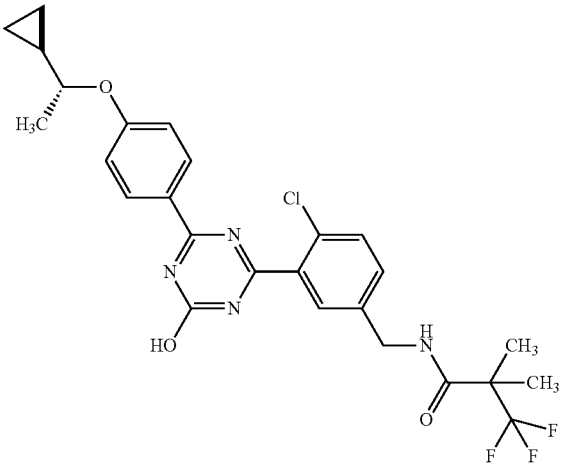 | 1H-NMR (DMSO-D6) δ: 0.29-0.39 (2H, m), 0.47-0.55 (2H, m), 1.08-1.17 (1H, m), 1.32 (3H, d, J = 6.3 Hz), 1.38 (6H, s), 4.10-4.18 (1H, m), 4.36 (2H, d, J = 6.0 Hz), 7.05 (2H, d, J = 8.8 Hz), 7.41 (1H, d, J = 8.0 Hz), 7.58 (1H, d, J = 8.0 Hz), 7.63 (1H, s), 8.27 (2H, d, J = 8.8 Hz), 8.63 (1H, t, J = 6.0 Hz), 13.13 (1H, br s). | 535 | 533 | |
| 1-186 | 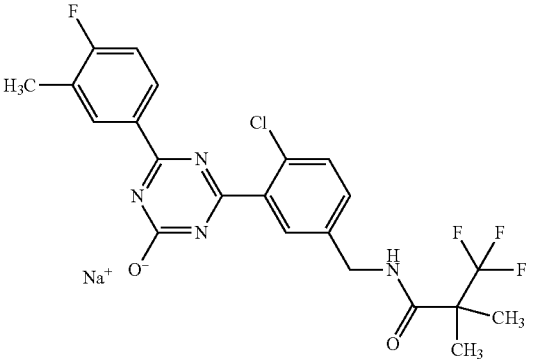 [SMILES: Cc1cc(-c2nc([O-])nc(-c3cc(CNC(=O)C(C)(C)C(F)(F)F)ccc3Cl)n2)ccc1F ; [Na+]] | 1H-NMR (DMSO-D6) δ: 1.37 (6H, s), 2.28 (3H, d, J = 1.2 Hz), 4.33 (2H, d, J = 6.0 Hz), 7.15 (1H, t, J = 9.1 Hz), 7.22 (1H, dd, J = 8.4, 2.3 Hz), 7.41 (1H, d, J = 8.4 Hz), 7.49 (1H, d, J = 2.3 Hz), 8.10-8.16 (1H, m), 8.19 (1H, dd, J = 8.1, 1.6 Hz), 8.59 (1H, t, J = 6.0 Hz). | 505 | 503 | |
| 1-187 | 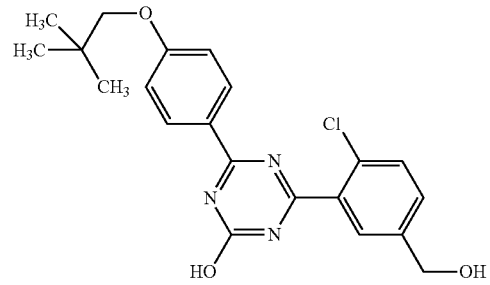 [SMILES: CC(C)(C)COc1ccc(-c2nc(O)nc(-c3cc(CO)ccc3Cl)n2)cc1] | 1H-NMR (DMSO-D6) δ: 1.02 (9H, s), 3.75 (2H, s), 4.57 (2H, d, J = 5.7 Hz), 5.42 (1H, t, J = 5.7 Hz), 7.10 (2H, d, J = 8.8 Hz), 7.53 (1H, d, J = 8.4 Hz), 7.59 (1H, d, J = 8.4 Hz), 7.71 (1H, s), 8.31 (2H, d, J = 8.8 Hz), 13.13 (1H, br s). | 400 | 398 | |
| 1-188 | 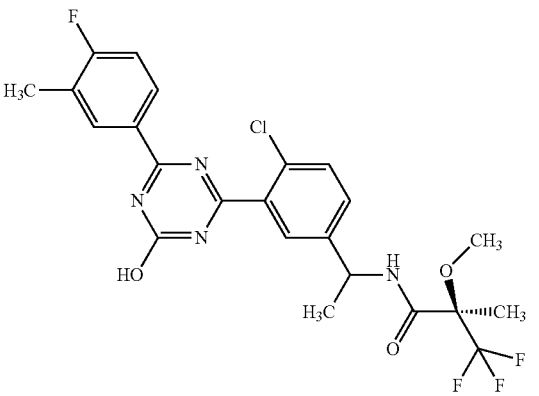 [SMILES: CO[C@](C)(C(=O)NC(C)c1ccc(Cl)c(-c2nc(O)nc(-c3ccc(F)c(C)c3)n2)c1)C(F)(F)F] | 1H-NMR (DMSO-D6) δ: 1.45 (3H, d, J = 6.8 Hz), 1.49 (3H, s), 2.32 (3H, s), 3.33 (3H, s), 5.02-5.10 (1H, m), 7.32 (1H, t, J = 9.3 Hz), 7.60 (2H, s), 7.76 (1H, s), 8.18-8.24 (1H, m), 8.27 (1H, d, J = 6.8 Hz), 8.81 (1H, d, J = 8.4 Hz), 13.32 (1H, s). | 513 | 511 | 1 |

TABLE 1-24-continued

| No. | Structure | NMR | MS1 | MS2 | — |
|---|---|---|---|---|---|
| 1-189 | 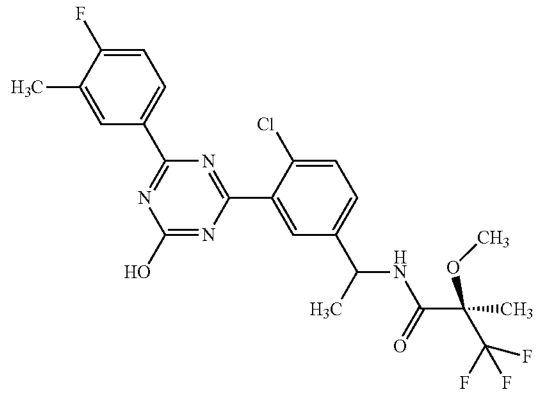 [SMILES: CO[C@](C)(C(=O)NC(C)c1ccc(Cl)c(-c2nc(O)nc(-c3ccc(F)c(C)c3)n2)c1)C(F)(F)F] | 1H-NMR (DMSO-D6) δ: 1.46 (3H, d, J = 6.8 Hz), 1.54 (3H, s), 2.31 (3H, s), 3.37 (3H, s), 5.02-5.11 (1H, m), 7.32 (1H, t, J = 9.2 Hz), 7.54 (1H, d, J = 8.4 Hz), 7.61 (1H, d, J = 8.4 Hz), 7.72 (1H, s), 8.19-8.25 (1H, m), 8.28 (1H, d, J = 7.3 Hz), 8.83 (1H, d, J = 8.2 Hz), 13.33 (1H, br s). | 513 | 511 | 1 |
| 1-190 | 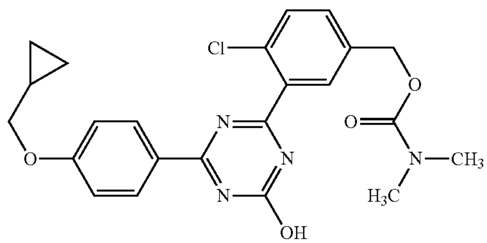 [SMILES: CN(C)C(=O)OCc1ccc(Cl)c(-c2nc(O)nc(-c3ccc(OCC4CC4)cc3)n2)c1] | 1H-NMR (DMSO-D6) δ: 0.33-0.37 (2H, m), 0.56-0.62 (2H, m), 1.21-1.30 (1H, m), 2.85 (3H, br s), 2.90 (3H, br s), 3.94 (2H, d, J = 7.1 Hz), 5.13 (2H, s), 7.09 (2H, d, J = 8.6 Hz), 7.56-7.67 (2H, br m), 7.78 (1H, br s), 8.30 (2H, d, J = 8.6 Hz), 13.15 (1H, br s). | 455 | 453 | |
| 1-191 | 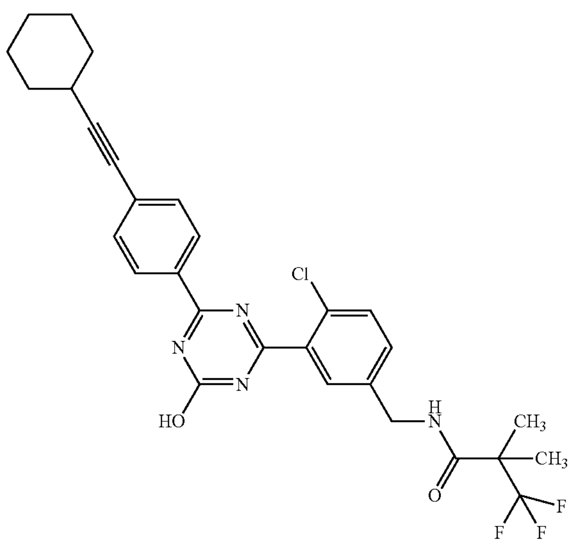 [SMILES: CC(C)(C(=O)NCc1ccc(Cl)c(-c2nc(O)nc(-c3ccc(C#CC4CCCCC4)cc3)n2)c1)C(F)(F)F] | 1H-NMR (DMSO-D6) δ: 1.30-1.40 (9H, m), 1.44-1.55 (3H, m), 1.64-1.74 (2H, m), 1.80-1.88 (2H, m), 2.63-2.70 (1H, m), 4.33 (2H, d, J = 6.0 Hz), 7.25 (1H, dd, J = 8.6, 2.1 Hz), 7.40-7.46 (3H, m), 7.52 (1H, d, J = 2.1 Hz), 8.25 (2H, d, J = 8.1 Hz), 8.59 (1H, t, J = 6.0 Hz). | 557 | 555 | |

TABLE 1-25

| No. | Structure | NMR | MS1 | MS2 |
|---|---|---|---|---|
| 1-192 | 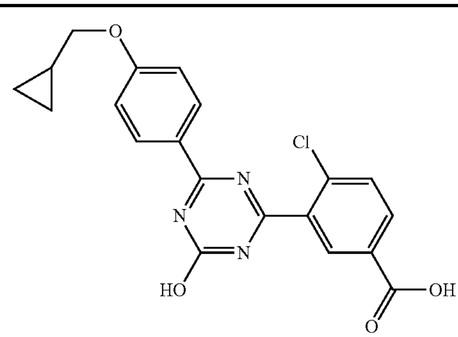 | 1H-NMR (DMSO-D6) δ: 0.35 (2H, dt, J = 7.9, 2.8 Hz), 0.57-0.61 (2H, m), 1.21-1.30 (1H, m), 3.94 (2H, d, J = 7.0 Hz), 7.09 (2H, d, J = 8.8 Hz), 7.77 (1H, d, J = 8.4 Hz), 8.09 (1H, dd, J = 8.4, 1.6 Hz), 8.30 (2H, d, J = 9.0 Hz), 8.33 (1H, s), 13.31 (1H, s). | 398 | 396 |

TABLE 1-25-continued
| 1-193 | 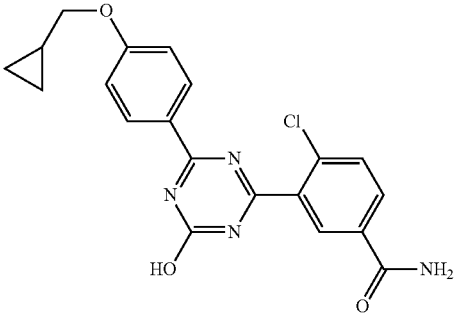 [SMILES: NC(=O)c1ccc(Cl)c(-c2nc(O)nc(-c3ccc(OCC4CC4)cc3)n2)c1] | 1H-NMR (DMSO-D6) δ: 0.35 (2H, td, J = 5.2, 4.1 Hz), 0.56-0.62 (2H, m), 1.21-1.29 (1H, m), 3.94 (2H, d, J = 7.0 Hz), 7.08 (2H, d, J = 8.8 Hz), 7.58 (1H, s), 7.74 (1H, d, J = 8.4 Hz), 8.06 (1H, d, J = 8.4 Hz), 8.17 (1H, s), 8.27 (1H, d, J = 2.1 Hz), 8.31 (2H, d, J = 8.8 Hz), 13.14 (1H, s). | 397 | 395 |
| --- | --- | --- | --- | --- |
| 1-194 | 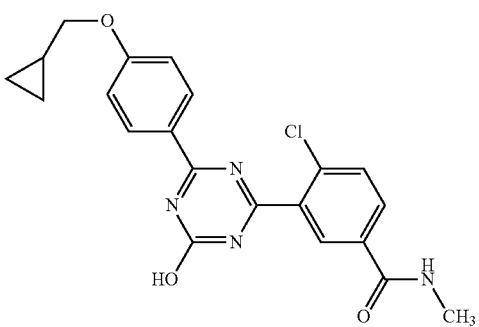 [SMILES: CNC(=O)c1ccc(Cl)c(-c2nc(O)nc(-c3ccc(OCC4CC4)cc3)n2)c1] | 1H-NMR (DMSO-D6) δ: 0.35 (2H, q, J = 4.8 Hz), 0.57-0.61 (2H, m), 1.22-1.29 (1H, m), 2.81 (3H, d, J = 4.4 Hz), 3.94 (2H, d, J = 7.0 Hz), 7.09 (2H, d, J = 8.8 Hz), 7.75 (1H, d, J = 8.4 Hz), 8.02 (1H, d, J = 8.1 Hz), 8.24 (1H, s), 8.31 (2H, d, J = 8.8 Hz), 8.63-8.67 (1H, m), 13.19 (1H, s). | 411 | 409 |
| 1-195 | 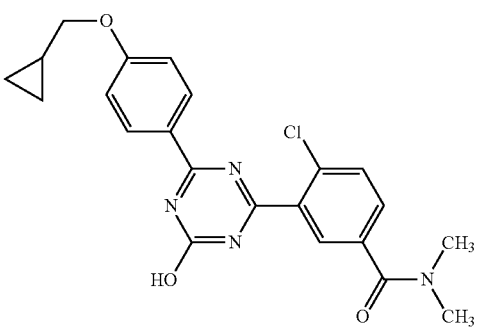 [SMILES: CN(C)C(=O)c1ccc(Cl)c(-c2nc(O)nc(-c3ccc(OCC4CC4)cc3)n2)c1] | 1H-NMR (DMSO-D6) δ: 0.33-0.37 (2H, m), 0.57-0.61 (2H, m), 1.20-1.30 (1H, m), 2.95 (3H, s), 3.00 (3H, s), 3.94 (2H, d, J = 7.0 Hz), 7.09 (2H, d, J = 8.8 Hz), 7.63 (1H, d, J = 9.1 Hz), 7.70 (1H, d, J = 8.1 Hz), 7.83 (1H, d, J = 1.9 Hz), 8.30 (2H, d, J = 9.1 Hz), 13.16 (1H, s). | 425 | 423 |
| 1-196 | 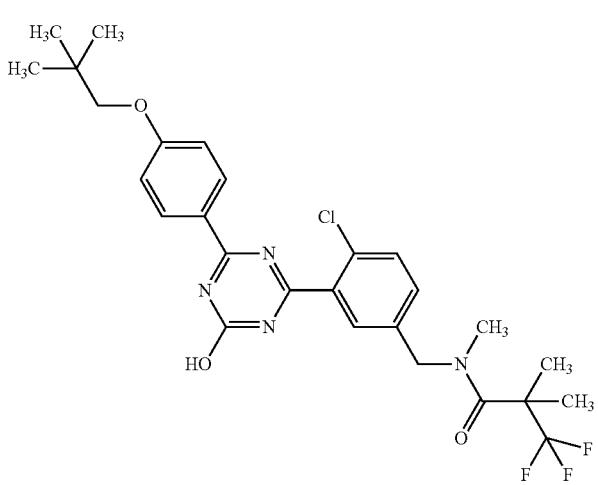 [SMILES: CN(Cc1ccc(Cl)c(-c2nc(O)nc(-c3ccc(OCC(C)(C)C)cc3)n2)c1)C(=O)C(C)(C)C(F)(F)F] | 1H-NMR (DMSO-D6) δ: 1.02 (9H, s), 1.51 (6H, s), 3.05 (3H, s), 3.75 (2H, s), 4.65 (2H, s), 7.10 (2H, d, J = 8.8 Hz), 7.41 (1H, d, J = 8.6 Hz), 7.61-7.66 (2H, m), 8.31 (2H, d, J = 8.8 Hz), 13.15 (1H, br s). | 551 | 549 |

TABLE 1-25-continued
| | | | | | |
|---|---|---|---|---|---|
| 1-197 | 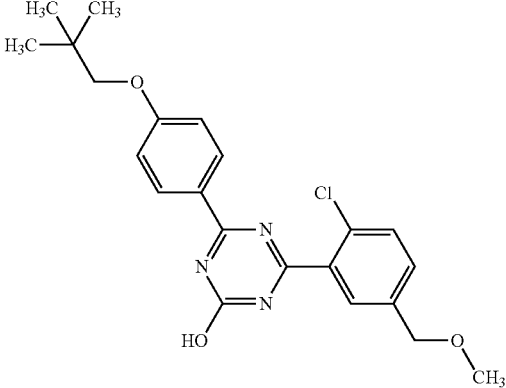 [SMILES: COCc1ccc(Cl)c(-c2nc(O)nc(-c3ccc(OCC(C)(C)C)cc3)n2)c1] | 1H-NMR (DMSO-D6) δ: 1.02 (9H, s), 3.34 (3H, s), 3.75 (2H, s), 4.49 (2H, s), 7.10 (2H, d, J = 8.8 Hz), 7.53 (1H, dd, J = 8.2, 2.0 Hz), 7.62 (1H, d, J = 8.2 Hz), 7.72 (1H, d, J = 2.0 Hz), 8.31 (2H, d, J = 8.8 Hz), 13.14 (1H, br s). | 414 | 412 | |
| 1-198 | 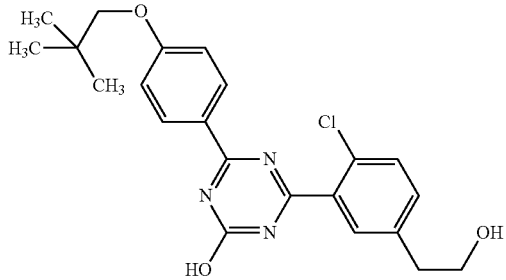 [SMILES: CC(C)(C)COc1ccc(-c2nc(O)nc(-c3cc(CCO)ccc3Cl)n2)cc1] | 1H-NMR (DMSO-D6) δ: 1.02 (9H, s), 2.79 (2H, t, J = 6.6 Hz), 3.65 (2H, td, J = 6.6, 5.1 Hz), 3.75 (2H, s), 4.69 (1H, t, J = 5.1 Hz), 7.10 (2H, d, J = 8.8 Hz), 7.47 (1H, s), 7.54 (1H, d, J = 8.1 Hz), 7.63 (1H, s), 8.31 (2H, d, J = 8.8 Hz), 13.10 (1H, br s). | 414 | 412 | |
| 1-199 | 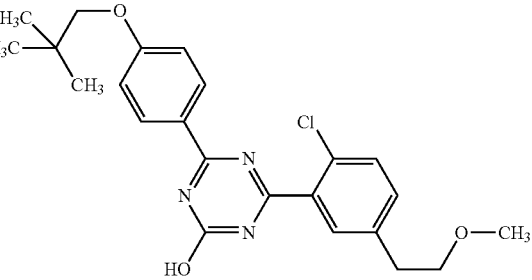 | 1H-NMR (DMSO-D6) δ: 1.02 (9H, s), 2.89 (2H, t, J = 6.5 Hz), 3.25 (3H, s), 3.58 (2H, t, J = 6.5 Hz), 3.75 (2H, s), 7.10 (2H, d, J = 8.8 Hz), 7.47 (1H, d, J = 8.1 Hz), 7.55 (1H, d, J = 8.1 Hz), 7.65 (1H, d, J = 1.9 Hz), 8.31 (2H, d, J = 8.8 Hz), 13.10 (1H, s). | 428 | 426 | |
TABLE 1-26
| | | | | | |
|---|---|---|---|---|---|
| 1-200 | 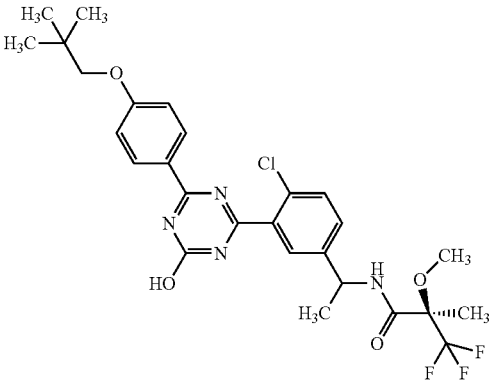 [SMILES: CO[C@](C)(C(=O)NC(C)c1ccc(Cl)c(-c2nc(O)nc(-c3ccc(OCC(C)(C)C)cc3)n2)c1)C(F)(F)F] | 1H-NMR (DMSO-D6) δ: 1.02 (9H, s), 1.45 (3H, d, J = 7.1 Hz), 1.49 (3H, s), 3.33 (3H, s), 3.75 (2H, s), 5.02-5.11 (1H, m), 7.09 (2H, d, J = 8.8 Hz), 7.58 (2H, s), 7.76 (1H, s), 8.29 (2H, d, J = 8.8 Hz), 8.82 (1H, d, J = 8.2 Hz), 13.14 (1H, br s). | 567 | 565 | 2 |

TABLE 1-26-continued

| | | | | | |
|---|---|---|---|---|---|
| 1-201 | (structure) | 1H-NMR (DMSO-D6) δ: 1.02 (9H, s), 1.47 (3H, d, J = 7.1 Hz), 1.54 (3H, s), 3.37 (3H, s), 3.75 (2H, s), 5.02-5.11 (1H, m), 7.09 (2H, d, J = 8.2 Hz), 7.51 (1H, d, J = 8.4 Hz), 7.59 (1H, d, J = 8.4 Hz), 7.72 (1H, s), 8.31 (2H, d, J = 8.2 Hz), 8.83 (1H, d, J = 8.2 Hz), 13.15 (1H, br s). | 567 | 565 | 2 |
| 1-202 | (structure) | 1H-NMR (DMSO-D6) δ: 1.48 (6H, s), 4.29 (2H, d, J = 6.0 Hz), 7.08 (1H, t, J = 7.6 Hz), 7.21 (2H, t, J = 7.6 Hz), 7.30 (2H, d, J = 8.4 Hz), 7.33-7.41 (2H, m), 7.52-7.60 (3H, m), 7.68 (1H, t, J = 7.2 Hz), 8.03 (1H, t, J = 6.0 Hz), 8.34 (2H, d, J = 8.1 Hz), 13.33 (1H, br s). | 459 | 457 | |
| 1-203 | (structure) | 1H-NMR (DMSO-D6) δ: 1.00 (9H, t, J = 16.5 Hz), 1.29 (6H, s), 2.80 (2H, t, J = 7.0 Hz), 3.30 (4H, s), 3.34 (3H, q, J = 6.7 Hz), 3.73 (2H, s), 7.07 (2H, d, J = 8.8 Hz), 7.37 (1H, dd, J = 8.4, 2.0 Hz), 7.51 (1H, d, J = 8.4 Hz), 7.57 (1H, d, J = 2.1 Hz), 8.00 (1H, t, J = 5.6 Hz), 8.29 (2H, d, J = 8.8 Hz), 13.10 (1H, br s). | 551 | 549 | |
| 1-204 | (structure) | 1H-NMR (DMSO-D6) δ: 0.89 (6H, d, J = 6.7 Hz), 1.02 (9H, s), 1.81-1.91 (1H, m), 3.25 (2H, d, J = 6.5 Hz), 3.75 (2H, s), 4.53 (2H, s), 7.10 (2H, d, J = 8.8 Hz), 7.54 (1H, d, J = 8.4 Hz), 7.62 (1H, d, J = 8.1 Hz), 7.73 (1H, s), 8.31 (2H, d, J = 8.8 Hz), 13.12 (1H, s). | 456 | 454 | |
| 1-205 | (structure) | 1H-NMR (DMSO-D6) δ: 0.91 (3H, t, J = 7.3 Hz), 1.02 (9H, s), 1.28-1.37 (2H, m), 1.55-1.62 (2H, m), 2.65 (2H, t, J = 7.7 Hz), 3.75 (2H, s), 7.10 (2H, d, J = 9.1 Hz), 7.43 (1H, d, J = 8.1 Hz), 7.53 (1H, d, J = 8.1 Hz), 7.61 (1H, d, J = 2.1 Hz), 8.31 (2H, d, J = 9.1 Hz), 13.09 (1H, s). | 426 | 424 | |

TABLE 1-26-continued
| | | | | |
|---|---|---|---|---|
| 1-206 | 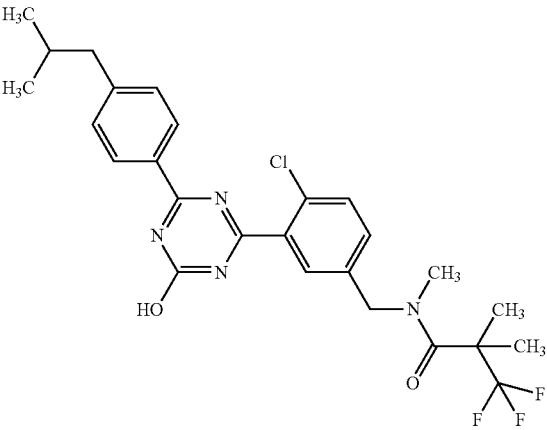 [SMILES: CC(C)Cc1ccc(-c2nc(O)nc(-c3cc(CN(C)C(=O)C(C)(C)C(F)(F)F)ccc3Cl)n2)cc1] | 1H-NMR (DMSO-D6) δ: 0.88 (6H, d, J = 6.6 Hz), 1.51 (6H, s), 1.84-1.95 (1H, m), 2.55 (2H, d, J = 7.3 Hz), 3.05 (3H, s), 4.65 (2H, s), 7.35 (2H, d, J = 8.4 Hz), 7.41 (1H, d, J = 8.2 Hz), 7.62-7.66 (2H, m), 8.26 (2H, d, J = 8.4 Hz), 13.26 (1H, br s). | 521 | 519 |
| 1-207 | 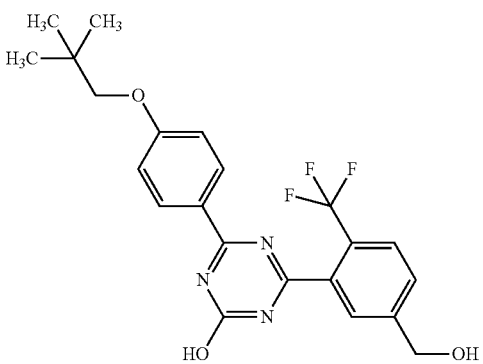 [SMILES: CC(C)(C)COc1ccc(-c2nc(O)nc(-c3cc(CO)ccc3C(F)(F)F)n2)cc1] | 1H-NMR (DMSO-D6) δ: 1.01 (9H, s), 3.75 (2H, s), 4.67 (2H, d, J = 5.5 Hz), 5.55 (1H, t, J = 5.5 Hz), 7.10 (2H, d, J = 8.8 Hz), 7.73 (1H, d, J = 7.9 Hz), 7.78 (1H, s), 7.90 (1H, d, J = 7.9 Hz), 8.29 (2H, d, J = 8.8 Hz), 13.21 (1H, br s). | 434 | 432 |
TABLE 1-27
| | | | | |
|---|---|---|---|---|
| 1-208 | 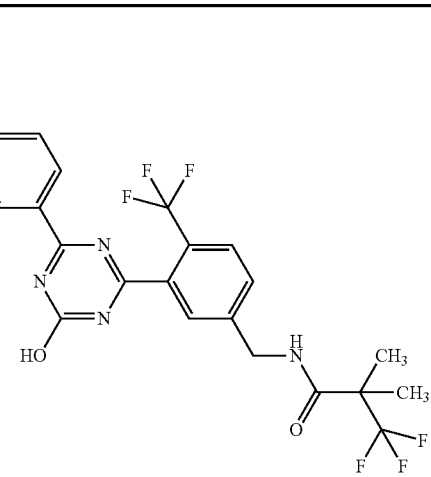 | 1H-NMR (DMSO-D6) δ: 1.01 (9H, s), 1.39 (6H, s), 3.74 (2H, s), 4.44 (2H, d, J = 6.0 Hz), 7.08 (2H, d, J = 8.6 Hz), 7.57 (1H, d, J = 8.1 Hz), 7.68 (1H, s), 7.88 (1H, d, J = 8.1 Hz), 8.28 (2H, d, J = 8.6 Hz), 8.69 (1H, t, J = 6.0 Hz), 13.23 (1H, br s). | 571 | 569 |

TABLE 1-27-continued

| 1-209 | (structure) | 1H-NMR (CDCl3) δ: 1.07 (9H, s), 1.12 (3H, t, J = 5.8 Hz), 1.48 (9H, br s), 3.27 (2H, br s), 3.70 (2H, s), 4.48 (2H, s), 7.02 (2H, d, J = 8.6 Hz), 7.41 (1H, br s), 7.50 (1H, d, J = 8.1 Hz), 7.89 (1H, s), 8.50 (2H, d, J = 8.4 Hz). | 527 | 525 |
| 1-210 | (structure) | 1H-NMR (DMSO-D6) δ: 1.02 (9H, s), 1.23 (3H, t, J = 7.2 Hz), 2.99 (2H, dt, J = 19.7, 7.2 Hz), 3.76 (2H, s), 4.23 (2H, t, J = 6.0 Hz), 7.13 (2H, d, J = 9.1 Hz), 7.74 (2H, s), 7.97 (1H, s), 8.33 (2H, d, J = 9.1 Hz), 9.05 (2H, s). | 427 | 425 |
| 1-211 | (structure) | 1H-NMR (DMSO-D6) δ: 1.00-1.32 (5H, m), 1.51 (6H, s), 1.61-1.85 (6H, m), 3.05 (3H, s), 3.89 (2H, d, J = 6.2 Hz), 4.65 (2H, s), 7.08 (2H, d, J = 9.0 Hz), 7.40 (1H, d, J = 8.2 Hz), 7.61-7.65 (2H, m), 8.30 (2H, d, J = 9.0 Hz), 13.14 (1H, br s). | 577 | 575 |
| 1-212 | (structure) | 1H-NMR (DMSO-D6) δ: 1.02 (9H, s), 3.24 (2H, q, J = 9.5 Hz), 3.75 (2H, s), 3.86 (2H, s), 7.10 (2H, d, J = 8.6 Hz), 7.54-7.63 (2H, m), 7.74 (1H, s), 8.32 (2H, d, J = 8.6 Hz), 13.11 (1H, s). | 481 | 479 |

TABLE 1-27-continued
| No. | Structure | 1H-NMR | MW | MS |
|---|---|---|---|---|
| 1-213 | 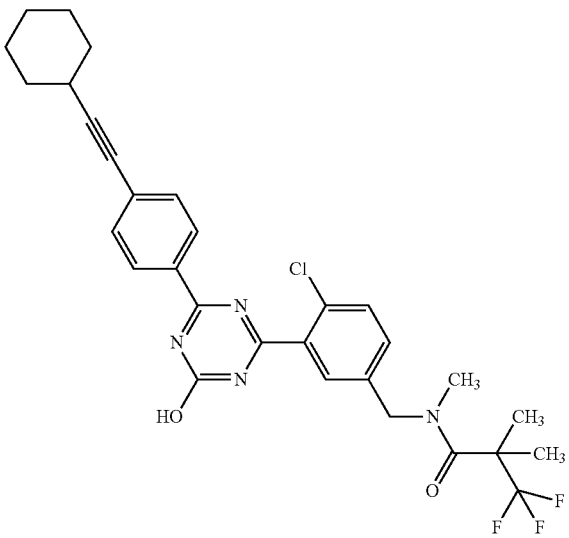 [SMILES: CN(Cc1ccc(Cl)c(-c2nc(O)nc(-c3ccc(C#CC4CCCCC4)cc3)n2)c1)C(=O)C(C)(C)C(F)(F)F] | 1H-NMR (DMSO-D6) δ: 1.30-1.41 (3H, m), 1.44-1.56 (9H, m), 1.65-1.73 (2H, m), 1.81-1.88 (2H, m), 2.66-2.73 (1H, m), 3.05 (3H, s), 4.65 (2H, s), 7.42 (1H, d, J = 8.6 Hz), 7.54 (2H, d, J = 8.4 Hz), 7.62-7.66 (2H, m), 8.30 (2H, d, J = 8.4 Hz), 13.36 (1H, br s). | 571 | 569 |
| 1-214 | 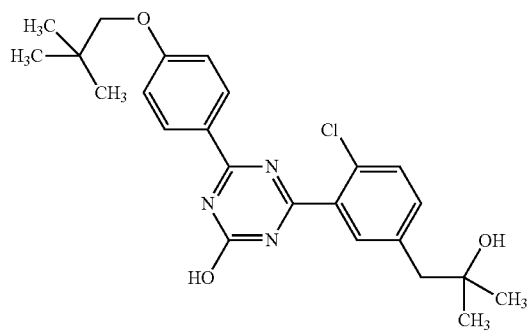 [SMILES: CC(C)(C)COc1ccc(-c2nc(O)nc(-c3cc(CC(C)(C)O)ccc3Cl)n2)cc1] | 1H-NMR (DMSO-D6) δ: 1.02 (9H, s), 1.09 (6H, s), 2.72 (2H, s), 3.75 (2H, s), 4.40 (1H, s), 7.10 (2H, d, J = 8.8 Hz), 7.44 (1H, d, J = 8.8 Hz), 7.53 (1H, d, J = 8.1 Hz), 7.61 (1H, s), 8.31 (2H, d, J = 8.8 Hz), 13.10 (1H, br s). | 442 | 440 |
| 1-215 | 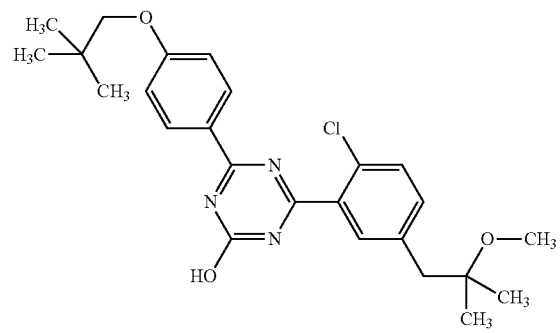 [SMILES: COC(C)(C)Cc1ccc(Cl)c(-c2nc(O)nc(-c3ccc(OCC(C)(C)C)cc3)n2)c1] | 1H-NMR (DMSO-D6) δ: 1.02 (9H, s), 1.10 (6H, s), 2.81 (2H, s), 3.17 (3H, s), 3.75 (2H, s), 7.10 (2H, d, J = 8.8 Hz), 7.41 (1H, dd, J = 8.5, 1.7 Hz), 7.53 (1H, d, J = 8.5 Hz), 7.58 (1H, d, J = 1.7 Hz), 8.31 (2H, d, J = 8.8 Hz), 13.10 (1H, s). | 456 | 454 |
TABLE 1-28
| No. | Structure | 1H-NMR | MW | MS |
|---|---|---|---|---|
| 1-216 | 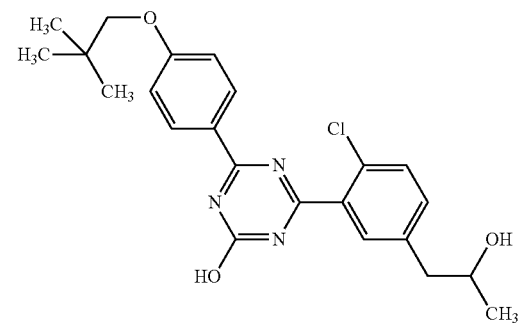 [SMILES: CC(O)Cc1ccc(Cl)c(-c2nc(O)nc(-c3ccc(OCC(C)(C)C)cc3)n2)c1] | 1H-NMR (DMSO-D6) δ: 1.00 (9H, s), 1.06 (3H, d, J = 6.3 Hz), 2.68 (2H, d, J = 6.0 Hz), 3.73 (2H, s), 3.82-3.88 (1H, m), 4.60 (1H, d, J = 4.9 Hz), 7.09 (2H, d, J = 9.1 Hz), 7.42 (1H, d, J = 9.3 Hz), 7.51 (1H, d, J = 8.1 Hz), 7.59 (1H, s), 8.30 (2H, d, J = 9.1 Hz), 13.08 (1H, s). | 428 | 426 |

TABLE 1-28-continued

| | | | | |
|---|---|---|---|---|
| 1-217 | (structure) | 1H-NMR (DMSO-D6) δ: 1.02 (9H, s), 1.20 (9H, s), 2.36 (2H, t, J = 7.6 Hz), 2.86 (2H, t, J = 7.6 Hz), 3.75 (2H, s), 7.10 (2H, d, J = 8.8 Hz), 7.40-7.46 (2H, m), 7.53 (1H, d, J = 8.2 Hz), 7.61 (1H, s), 8.31 (2H, d, J = 8.8 Hz), 13.11 (1H, br s). | 497 | 495 |
| 1-218 | (structure) | 1H-NMR (DMSO-D6) δ: 1.02 (9H, s), 2.66 (2H, t, J = 7.6 Hz), 2.81 (3H, s), 2.87 (2H, t, J = 7.6 Hz), 2.95 (3H, s), 3.75 (2H, s), 7.10 (2H, d, J = 8.8 Hz), 7.46-7.56 (2H, m), 7.66 (1H, d, J = 2.0 Hz), 8.31 (2H, d, J = 9.0 Hz), 13.11 (1H, br s). | 469 | 467 |
| 1-219 | (structure) | 1H-NMR (DMSO-D6) δ: 0.89 (6H, d, J = 6.5 Hz), 1.30-1.40 (3H, m), 1.46-1.55 (3H, m), 1.65-1.73 (2H, m), 1.80-1.90 (3H, m), 2.67-2.72 (1H, m), 3.25 (2H, d, J = 6.5 Hz), 4.53 (2H, s), 7.54 (2H, d, J = 8.4 Hz), 7.57 (1H, d, J = 1.6 Hz), 7.64 (1H, d, J = 8.1 Hz), 7.73 (1H, s), 8.31 (2H, d, J = 8.4 Hz), 13.33 (1H, br s). | 476 | 474 |
| 1-220 | (structure) | 1H-NMR (DMSO-D6) δ: 1.51 (6H, s), 3.06 (3H, s), 4.65 (2H, s), 7.42 (1H, d, J = 8.4 Hz), 7.56 (2H, t, J = 7.7 Hz), 7.62-7.69 (3H, m), 8.34 (2H, d, J = 7.7 Hz), 13.34 (1H, br s). | 465 | 463 |

TABLE 1-28-continued
| 1-221 | 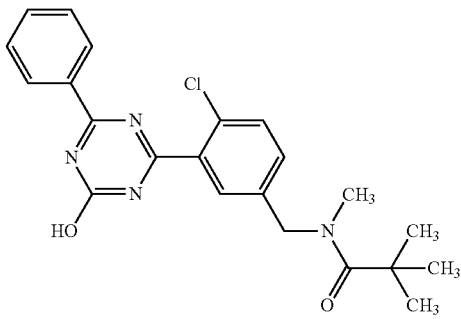 [SMILES: CN(Cc1ccc(Cl)c(-c2nc(O)nc(-c3ccccc3)n2)c1)C(=O)C(C)(C)C] | 1H-NMR (DMSO-D6) δ: 1.24 (9H, s), 3.02 (3H, s), 4.62 (2H, s), 7.40 (1H, dd, J = 8.4, 1.8 Hz), 7.56 (2H, t, J = 7.6 Hz), 7.61-7.69 (3H, m), 8.34 (2H, d, J = 7.6 Hz), 13.34 (1H, br s). | 465 | 463 |
|---|---|---|---|---|
| 1-222 | 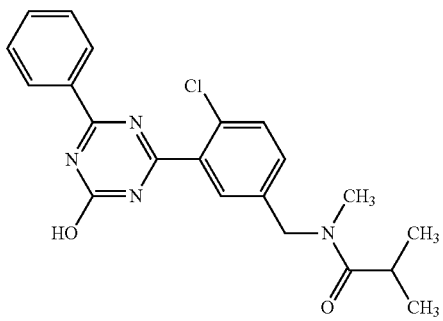 [SMILES: CC(C)C(=O)N(C)Cc1ccc(Cl)c(-c2nc(O)nc(-c3ccccc3)n2)c1] | 1H-NMR (DMSO-D6) δ: 1.01 (1.8H, d, J = 6.7 Hz), 1.04 (4.2H, d, J = 6.7 Hz), 2.84 (0.9H, s), 2.84-2.88 (0.3H, m), 2.90-2.97 (0.7H, m), 3.01 (2.1H, s), 4.57 (1.4H, s), 4.71 (0.6H, s), 7.42 (1H, dd, J = 8.3, 1.9 Hz), 7.57 (2H, t, J = 7.6 Hz), 7.60-7.69 (3H, m), 8.34 (2H, d, J = 7.6 Hz), 13.34 (1H, br s). | 397 | 395 |
| 1-223 | 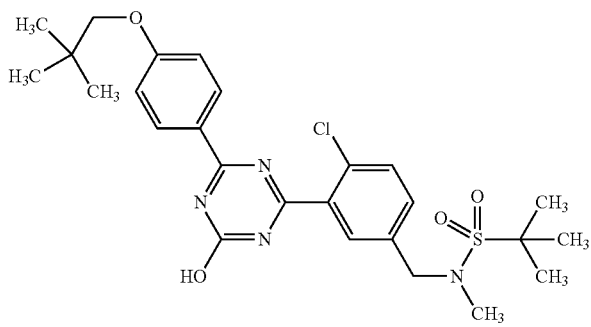 [SMILES: CN(Cc1ccc(Cl)c(-c2nc(O)nc(-c3ccc(OCC(C)(C)C)cc3)n2)c1)S(=O)(=O)C(C)(C)C] | 1H-NMR (DMSO-D6) δ: 1.02 (9H, s), 1.37 (9H, s), 2.79 (3H, s), 3.75 (2H, s), 4.50 (2H, s), 7.11 (2H, d, J = 8.9 Hz), 7.55 (1H, dd, J = 8.1, 1.6 Hz), 7.68 (1H, d, J = 8.1 Hz), 7.72 (1H, s), 8.31 (2H, d, J = 8.9 Hz), 13.17 (1H, br s). | 533 | 531 |
TABLE 1-29
| 1-224 | 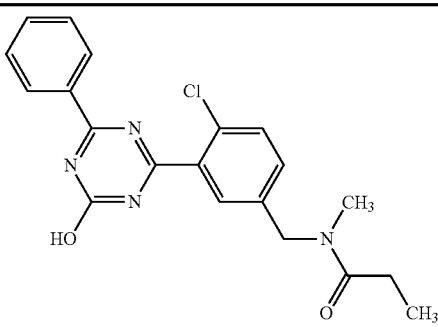 | 1H-NMR (DMSO-D6) δ: 0.97-1.05 (3H, m), 2.34-2.43 (2H, m), 2.85 (0.9H, s), 2.96 (2.1H, s), 4.57 (1.4H, s), 4.65 (0.6H, s), 7.44 (1H, d, J = 8.4 Hz), 7.54-7.69 (5H, m), 8.34 (2H, d, J = 8.4 Hz), 13.35 (1H, br s). | 383 | 381 |

TABLE 1-29-continued

| | | | | |
|---|---|---|---|---|
| 1-225 | | 1H-NMR (DMSO-D6) δ: 0.84-0.93 (3H, m), 1.50-1.60 (2H, m), 2.31-2.38 (2H, m), 2.84 (0.9H, s), 2.96 (2.1H, s), 4.57 (1.4H, s), 4.66 (0.6H, s), 7.41-7.46 (1H, m), 7.54-7.69 (5H, m), 8.34 (2H, d, J = 7.6 Hz), 13.34 (1H, br s). | 397 | 395 |
| 1-226 | | 1H-NMR (DMSO-D6) δ: 0.87-0.93 (6H, m), 1.99-2.10 (1H, m), 2.22-2.28 (2H, m), 2.84 (0.9H, s), 2.97 (2.1H, s), 4.58 (1.4H, s), 4.66 (0.6H, s), 7.40-7.46 (1H, m), 7.56 (2H, t, J = 7.6 Hz), 7.60-7.70 (3H, m), 8.34 (2H, d, J = 7.6 Hz), 13.34 (1H, br s). | 411 | 409 |
| 1-227 | | 1H-NMR (DMSO-D6) δ: 1.02 (9H, s), 1.43 (6H, s), 2.88 (2H, t, J = 7.5 Hz), 3.03 (3H, s), 3.55 (2H, t, J = 7.5 Hz), 3.74 (2H, s), 7.09 (2H, d, J = 9.0 Hz), 7.45 (1H, dd, J = 8.0, 2.0 Hz), 7.55 (1H, d, J = 8.0 Hz), 7.64 (1H, d, J = 2.0 Hz), 8.30 (2H, d, J = 9.0 Hz), 13.11 (1H, br s). | 565 | 563 |
| 1-228 | | 1H-NMR (DMSO-D6) δ: 1.46-1.86 (8H, m), 2.83 (0.9H, s), 2.96-3.10 (1H, m), 3.01 (2.1H, s), 4.57 (1.4H, s), 4.72 (0.6H, s), 7.42 (1H, d, J = 8.3 Hz), 7.56 (2H, t, J = 7.6 Hz), 7.60-7.69 (3H, m), 8.34 (2H, d, J = 7.6 Hz), 13.33 (1H, br s). | 423 | 421 |
| 1-229 | | 1H-NMR (DMSO-D6) δ: 1.10-1.43 (5H, m), 1.58-1.77 (5H, m), 2.56-2.68 (1H, m), 2.81 (0.9H, s), 3.01 (2.1H, s), 4.56 (1.4H, s), 4.70 (0.6H, s), 7.38-7.43 (1H, m), 7.56 (2H, t, J = 7.6 Hz), 7.59-7.69 (3H, m), 8.34 (2H, d, J = 7.6 Hz), 13.34 (1H, br s). | 437 | 435 |

TABLE 1-29-continued

| 1-230 | [structure] | 1H-NMR (DMSO-D6) δ: 2.87-2.97 (3H, m), 4.54 (0.8H, s), 4.75 (1.2H, s), 7.39-7.51 (5.4H, m), 7.54-7.61 (2.6H, m), 7.62-7.70 (2.4H, m), 7.74-7.83 (0.6H, m), 8.35 (2H, d, J = 7.6 Hz), 13.35 (1H, br s). | 431 | 429 |
| --- | --- | --- | --- | --- |
| 1-231 | [structure] | 1H-NMR (DMSO-D6) δ: 0.79 (3H, t, J = 7.4 Hz), 1.19 (6H, s), 1.64 (2H, q, J = 7.4 Hz), 3.02 (3H, s), 4.61 (2H, s), 7.43 (1H, d, J = 8.3 Hz), 7.56 (2H, t, J = 7.6 Hz), 7.61-7.69 (3H, m), 8.34 (2H, d, J = 7.6 Hz), 13.33 (1H, br s). | 425 | 423 |

TABLE 1-30

| 1-232 | [structure] | 1H-NMR (DMSO-D6) δ: 0.88 (6H, d, J = 6.7 Hz), 1.35 (9H, s), 1.84-1.95 (1H, m), 2.55 (2H, d, J = 7.4 Hz), 2.90 (3H, s), 3.77 (2H, s), 7.35 (2H, d, J = 8.1 Hz), 7.41 (1H, d, J = 8.3 Hz), 7.57 (1H, d, J = 8.3 Hz), 7.62 (1H, s), 8.26 (2H, d, J = 8.1 Hz), 13.24 (1H, br s). | 467 | 465 |
| --- | --- | --- | --- | --- |
| 1-233 | [structure] | 1H-NMR (DMSO-D6) δ: 0.75-0.84 (6H, m), 1.33-1.46 (2H, m), 1.47-1.60 (2H, m), 2.62-2.71 (1H, m), 2.88 (0.9H, s), 3.03 (2.1H, s), 4.61 (1.4H, s), 4.72 (0.6H, s), 7.41-7.47 (1H, m), 7.56 (2H, t, J = 7.6 Hz), 7.61-7.69 (3H, m), 8.33 (2H, d, J = 7.6 Hz), 13.35 (1H, br s). | 425 | 423 |

TABLE 1-30-continued
| | | | | |
|---|---|---|---|---|
| 1-234 | 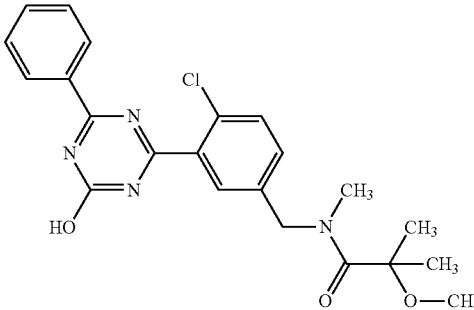 | 1H-NMR (DMSO-D6) δ: 1.37 (6H, s), 2.78 (0.6H, br s), 3.14 (3H, s), 3.23 (2.4H, br s), 4.59 (1.6H, s), 5.09 (0.4H, br s), 7.45 (1H, d, J = 7.9 Hz), 7.56 (2H, t, J = 7.9 Hz), 7.61-7.69 (3H, m), 8.33 (2H, d, J = 7.9 Hz), 13.33 (1H, br s). | 427 | 425 |
| 1-235 | 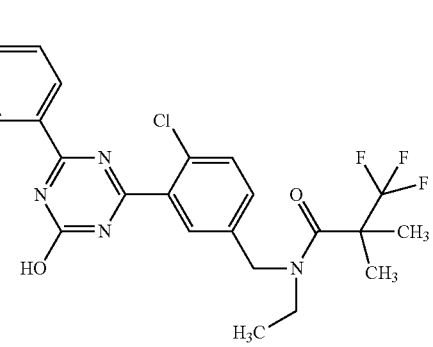 | 1H-NMR (DMSO-D6) δ: 1.02 (9H, s), 1.12 (3H, t, J = 6.8 Hz), 1.50 (6H, s), 3.42 (2H, br s), 3.75 (2H, s), 4.66 (2H, s), 7.09 (2H, d, J = 8.8 Hz), 7.40 (1H, d, J = 8.3 Hz), 7.61 (1H, d, J = 8.3 Hz), 7.62 (1H, s), 8.30 (2H, d, J = 8.8 Hz), 13.14 (1H, s). | 565 | 563 |
| 1-236 | 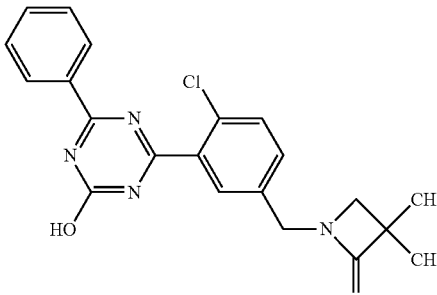 | 1H-NMR (DMSO-D6) δ: 1.21 (6H, s), 3.04 (2H, s), 4.41 (2H, s), 7.48 (1H, d, J = 8.6 Hz), 7.57 (2H, t, J = 7.6 Hz), 7.64-7.71 (3H, m), 8.35 (2H, d, J = 7.6 Hz), 13.34 (1H, br s). | 395 | 393 |
| 1-237 | 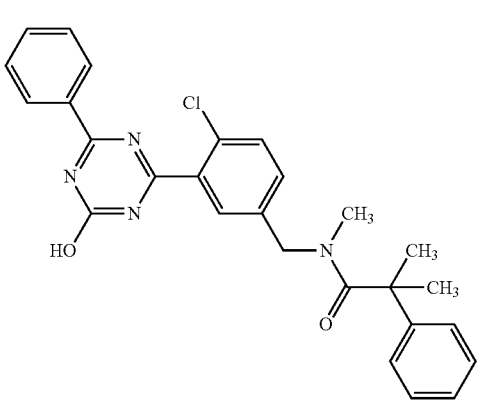 [SMILES: CN(Cc1ccc(Cl)c(-c2nc(O)nc(-c3ccccc3)n2)c1)C(=O)C(C)(C)c1ccccc1] | 1H-NMR (DMSO-D6) δ: 1.48 (6H, s), 2.45 (3H, br s), 4.55 (2H, br s), 7.18 (1H, t, J = 7.2 Hz), 7.22-7.26 (2H, m), 7.28-7.34 (2H, m), 7.41 (1H, br s), 7.53-7.68 (5H, m), 8.35 (2H, d, J = 8.1 Hz), 13.34 (1H, br s). | 473 | 471 |

TABLE 1-30-continued
| 1-238 | 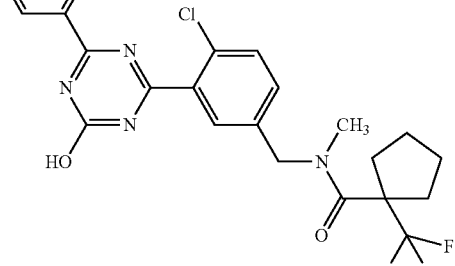 | 1H-NMR (DMSO-D6) δ: 1.56-1.67 (4H, m), 2.08-2.17 (2H, m), 2.37-2.46 (2H, m), 3.02 (3H, s), 4.65 (2H, s), 7.39 (1H, d, J = 8.3 Hz), 7.55 (2H, t, J = 8.0 Hz), 7.60-7.68 (3H, m), 8.34 (2H, d, J = 8.0 Hz), 13.34 (1H, br s). | 491 | 489 |
| --- | --- | --- | --- | --- |
| 1-239 | 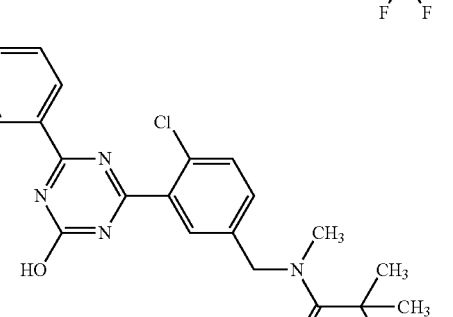 | 1H-NMR (DMSO-D6) δ: 1.23 (6H, s), 3.02 (3H, s), 3.20 (3H, s), 3.43 (2H, s), 4.63 (2H, s), 7.42 (1H, d, J = 8.3 Hz), 7.54-7.70 (5H, m), 8.34 (2H, d, J = 7.6 Hz), 13.36 (1H, br s). | 441 | 439 |
TABLE 1-31
| 1-240 | 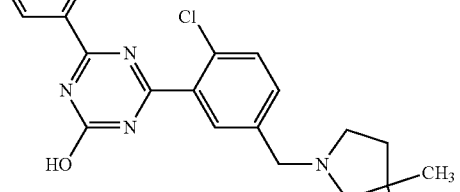 | 1H-NMR (DMSO-D6) δ: 1.07 (6H, s), 1.83 (2H, t, J = 6.9 Hz), 3.21 (2H, t, J = 6.9 Hz), 4.44 (2H, s), 7.42 (1H, d, J = 8.3 Hz), 7.57 (2H, t, J = 7.6 Hz), 7.62-7.69 (3H, m), 8.34 (2H, d, J = 7.6 Hz), 13.34 (1H, br s). | 409 | 407 |
| --- | --- | --- | --- | --- |
| 1-241 | 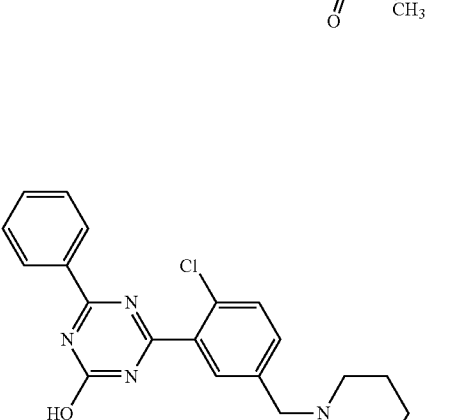 | 1H-NMR (DMSO-D6) δ: 1.15 (6H, s), 1.64-1.69 (2H, m), 1.74-1.81 (2H, m), 3.26 (2H, t, J = 6.0 Hz), 4.53 (2H, s), 7.42 (1H, d, J = 8.1 Hz), 7.56 (2H, t, J = 7.4 Hz), 7.60-7.69 (3H, m), 8.35 (2H, d, J = 7.4 Hz), 13.33 (1H, br s). | 423 | 421 |

TABLE 1-31-continued
| 1-242 | 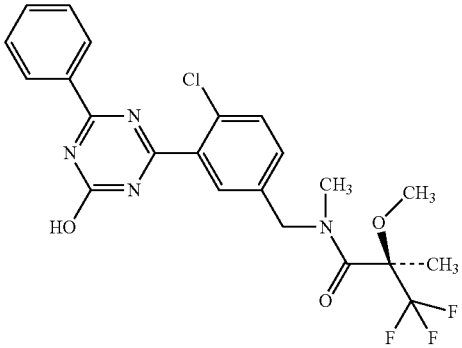 [SMILES: CO[C@](C)(C(=O)N(C)Cc1ccc(Cl)c(-c2nc(O)nc(-c3ccccc3)n2)c1)C(F)(F)F] | 1H-NMR (DMSO-D6) δ: 1.61 (3H, s), 2.82 (0.6H, br s), 3.23 (2.4H, s), 3.37 (3H, s), 4.64 (1.6H, s), 4.87-5.12 (0.4H, m), 7.46 (1H, d, J = 8.3 Hz), 7.56 (2H, t, J = 7.6 Hz), 7.63-7.71 (3H, m), 8.34 (2H, d, J = 7.6 Hz), 13.34 (1H, br s). | 481 | 479 |
|---|---|---|---|---|
| 1-243 | 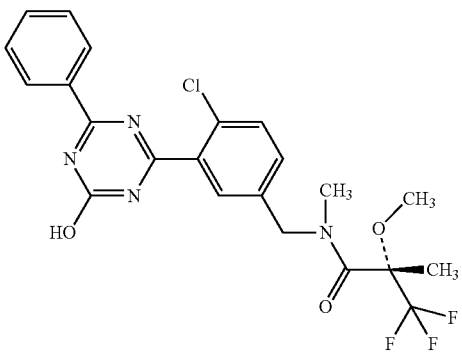 [SMILES: CO[C@@](C)(C(=O)N(C)Cc1ccc(Cl)c(-c2nc(O)nc(-c3ccccc3)n2)c1)C(F)(F)F] | 1H-NMR (DMSO-D6) δ: 1.61 (3H, s), 2.82 (0.6H, br s), 3.23 (2.4H, s), 3.37 (3H, s), 4.64 (1.6H, s), 4.87-5.12 (0.4H, m), 7.46 (1H, d, J = 8.3 Hz), 7.56 (2H, t, J = 7.6 Hz), 7.63-7.71 (3H, m), 8.34 (2H, d, J = 7.6 Hz), 13.34 (1H, br s). | 481 | 479 |
| 1-244 | 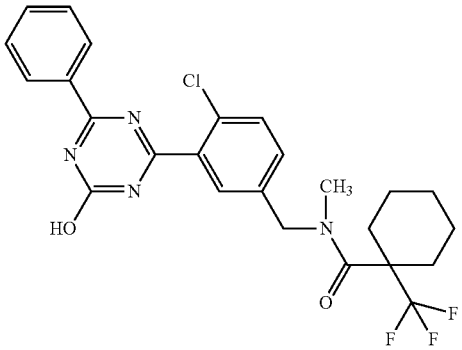 [SMILES: CN(Cc1ccc(Cl)c(-c2nc(O)nc(-c3ccccc3)n2)c1)C(=O)C1(C(F)(F)F)CCCCC1] | 1H-NMR (DMSO-D6) δ: 1.18-1.31 (3H, m), 1.46-1.59 (3H, m), 1.63-1.72 (2H, m), 2.51-2.58 (2H, m), 3.15 (3H, s), 4.71 (2H, s), 7.43 (1H, dd, J = 8.1, 1.8 Hz), 7.56 (2H, t, J = 7.5 Hz), 7.63-7.69 (3H, m), 8.34 (2H, d, J = 7.5 Hz), 13.36 (1H, br s). | 505 | 503 |
| 1-245 | 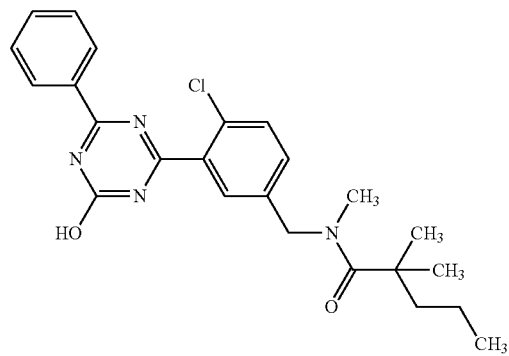 | 1H-NMR (DMSO-D6) δ: 0.81 (3H, t, J = 7.4 Hz), 1.15-1.25 (8H, m), 1.54-1.60 (2H, m), 3.02 (3H, s), 4.61 (2H, s), 7.42 (1H, d, J = 8.6 Hz), 7.56 (2H, t, J = 7.4 Hz), 7.60-7.69 (3H, m), 8.34 (2H, d, J = 7.4 Hz), 13.34 (1H, br s). | 439 | 437 |

TABLE 1-31-continued

| | | | | |
|---|---|---|---|---|
| 1-246 | | 1H-NMR (DMSO-D6) δ: 2.88 (0.9H, s), 3.04-3.22 (6.1 H, m), 3.63-3.77 (1H, m), 4.62 (1.4H, s), 4.80 (0.6H, s), 7.42-7.48 (1H, m), 7.52-7.58 (2H, m), 7.60-7.69 (3H, m), 8.34 (2H, d, J = 7.9 Hz), 13.35 (1H, br s). | 471 | 469 |
| 1-247 | | 1H-NMR (DMSO-D6) δ: 1.14-1.36 (5H, m), 1.38-1.50 (3H, m), 1.89-1.97 (2H, m), 3.37 (2H, s), 4.36 (2H, d, J = 6.0 Hz), 4.75 (1H, br s), 7.49 (1H, d, J = 8.3 Hz), 7.53-7.59 (3H, m), 7.64-7.70 (2H, m), 8.09 (1H, t, J = 6.0 Hz), 8.34 (2H, d, J = 7.4 Hz), 13.32 (1H, br s). | 453 | 451 |

TABLE 1-32

| | | | | |
|---|---|---|---|---|
| 1-248 | | 1H-NMR (DMSO-D6) δ: 1.26-1.37 (3H, m), 1.42-1.50 (1H, m), 1.59-1.71 (6H, m), 3.02 (2H, s), 4.40 (2H, s), 7.47 (1H, dd, J = 8.1, 2.1 Hz), 7.56 (2H, t, J = 7.9 Hz), 7.63-7.69 (3H, m), 8.34 (2H, d, J = 7.9 Hz), 13.33 (1H, br s). | 435 | 433 |
| 1-249 | | 1H-NMR (DMSO-D6) δ: 1.21 (6H, s), 2.94 (2H, s), 3.11 (3H, s), 4.63 (2H, s), 7.06-7.10 (2H, m), 7.11-7.16 (1H, m), 7.16-7.22 (2H, m), 7.39 (1H, dd, J = 7.9, 1.8 Hz), 7.55 (2H, t, J = 7.4 Hz), 7.59-7.67 (3H, m), 8.34 (2H, d, J = 7.4 Hz), 13.35 (1H, br s). | 453 | 451 |

TABLE 1-32-continued
| | | | | |
|---|---|---|---|---|
| 1-250 | 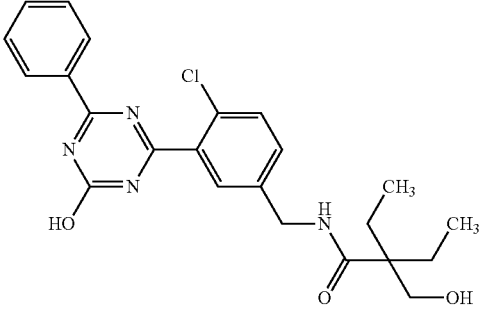 [SMILES: CCC(CC)(CO)C(=O)NCc1ccc(Cl)c(-c2nc(O)nc(-c3ccccc3)n2)c1] | 1H-NMR (DMSO-D6) δ: 0.71 (6H, t, J = 7.4 Hz), 1.51 (4H, q, J = 7.4 Hz), 3.47 (2H, d, J = 4.0 Hz), 4.34 (2H, d, J = 5.7 Hz), 4.62 (1H, br s), 7.48 (1H, d, J = 7.7 Hz), 7.53-7.61 (3H, m), 7.64-7.71 (2H, m), 8.11 (1H, t, J = 5.7 Hz), 8.34 (2H, d, J = 7.3 Hz), 13.34 (1H, br s). | 441 | 439 |
| 1-251 | 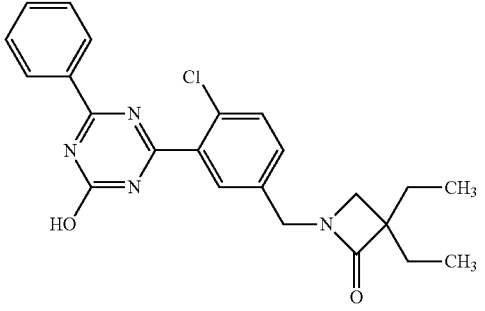 [SMILES: CCC1(CC)CN(Cc2ccc(Cl)c(-c3nc(O)nc(-c4ccccc4)n3)c2)C1=O] | 1H-NMR (DMSO-D6) δ: 0.87 (6H, t, J = 7.4 Hz), 1.52-1.63 (4H, m), 3.01 (2H, s), 4.40 (2H, s), 7.49 (1H, d, J = 8.3 Hz), 7.57 (2H, t, J = 7.9 Hz), 7.64-7.72 (3H, m), 8.34 (2H, d, J = 7.9 Hz), 13.35 (1H, br s). | 423 | 421 |
| 1-252 | 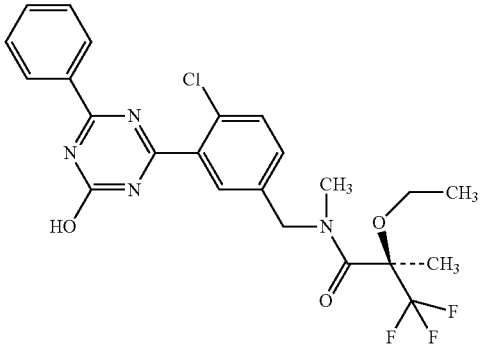 [SMILES: CCO[C@](C)(C(=O)N(C)Cc1ccc(Cl)c(-c2nc(O)nc(-c3ccccc3)n2)c1)C(F)(F)F] | 1H-NMR (DMSO-D6) δ: 1.02 (0.6H, br s), 1.17 (2.4H, t, J = 6.9 Hz), 1.62 (3H, s), 2.81 (0.6H, s), 3.25 (2.4H, s), 3.54-3.67 (2H, m), 4.63 (1.6H, s), 4.90-5.17 (0.4H, m), 7.45 (1H, dd, J = 8.2, 1.8 Hz), 7.56 (2H, t, J = 7.6 Hz), 7.63-7.69 (3H, m), 8.34 (2H, d, J = 7.6 Hz), 13.34 (1H, br s). | 495 | 493 |
| 1-253 | 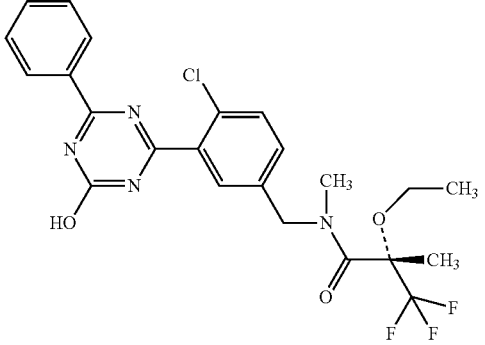 [SMILES: CCO[C@@](C)(C(=O)N(C)Cc1ccc(Cl)c(-c2nc(O)nc(-c3ccccc3)n2)c1)C(F)(F)F] | 1H-NMR (DMSO-D6) δ: 1.02 (0.6H, br s), 1.17 (2.4H, t, J = 6.9 Hz), 1.62 (3H, s), 2.81 (0.6H, s), 3.25 (2.4H, s), 3.54-3.67 (2H, m), 4.63 (1.6H, s), 4.90-5.17 (0.4H, m), 7.45 (1H, dd, J = 8.2, 1.8 Hz), 7.56 (2H, t, J = 7.6 Hz), 7.63-7.69 (3H, m), 8.34 (2H, d, J = 7.6 Hz), 13.34 (1H, br s). | 495 | 493 |
| 1-254 | 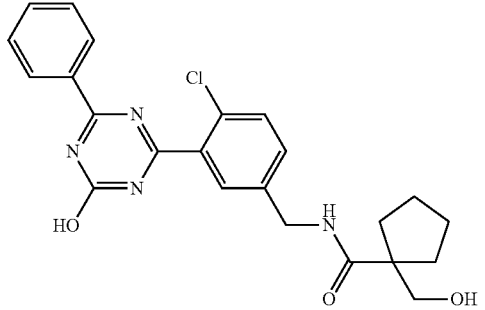 [SMILES: O=C(NCc1ccc(Cl)c(-c2nc(O)nc(-c3ccccc3)n2)c1)C1(CO)CCCC1] | 1H-NMR (DMSO-D6) δ: 1.51-1.55 (6H, m), 1.86-1.95 (2H, m), 3.46 (2H, s), 4.35 (2H, d, J = 6.0 Hz), 4.99 (1H, br s), 7.47 (1H, dd, J = 8.4, 2.0 Hz), 7.54-7.60 (3H, m), 7.64-7.69 (2H, m), 8.12 (1H, t, J = 6.0 Hz), 8.34 (2H, d, J = 7.7 Hz), 13.34 (1H, br s). | 439 | 437 |

TABLE 1-32-continued
| 1-255 | 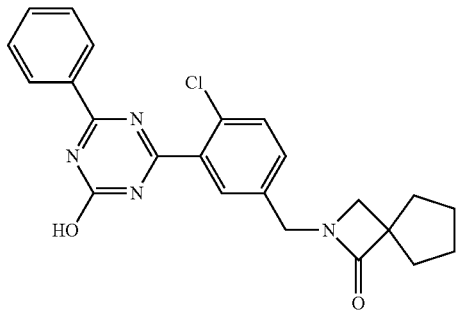 [SMILES: O=C1N(Cc2ccc(Cl)c(-c3nc(O)nc(-c4ccccc4)n3)c2)CC12CCCC2] | 1H-NMR (DMSO-D6) δ: 1.53-1.68 (4H, m), 1.77-1.89 (4H, m), 3.17 (2H, s), 4.42 (2H, s), 7.47 (1H, dd, J = 8.3, 2.1 Hz), 7.56 (2H, t, J = 7.6 Hz), 7.64-7.69 (3H, m), 8.35 (2H, d, J = 7.6 Hz). | 421 | 419 | |
TABLE 1-33
| 1-256 | 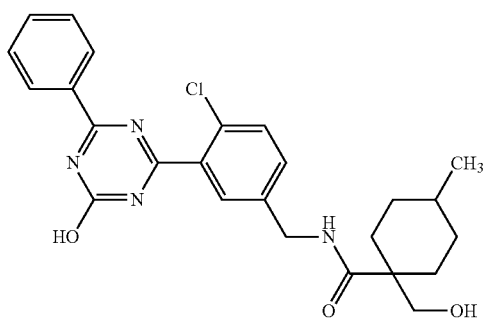 [SMILES: CC1CCC(CO)(C(=O)NCc2ccc(Cl)c(-c3nc(O)nc(-c4ccccc4)n3)c2)CC1] | 1H-NMR (DMSO-D6) δ: 0.69 (3H, d, J = 6.2 Hz), 0.85-0.98 (2H, m), 1.06-1.28 (3H, m), 1.42-1.50 (2H, m), 2.05-2.12 (2H, m), 3.28 (2H, s), 4.36 (2H, d, J = 6.0 Hz), 4.73 (1H, br s), 7.49 (1H, d, J = 8.1 Hz), 7.53-7.59 (3H, m), 7.63-7.69 (2H, m), 8.10 (1H, t, J = 6.0 Hz), 8.34 (2H, d, J = 7.9 Hz), 13.34 (1H, br s). | 467 | 465 | 3 |
| 1-257 | 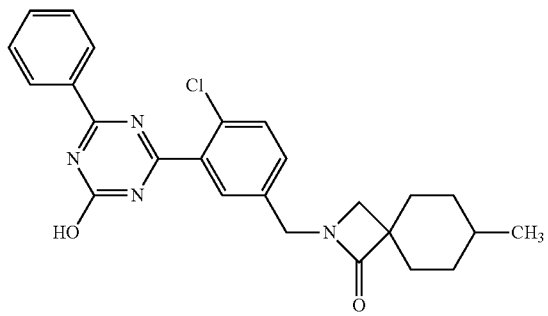 [SMILES: CC1CCC2(CC1)CN(Cc1ccc(Cl)c(-c3nc(O)nc(-c4ccccc4)n3)c1)C2=O] | 1H-NMR (DMSO-D6) δ: 0.89 (3H, d, J = 5.5 Hz), 1.33-1.46 (3H, m), 1.51-1.62 (4H, m), 1.87-1.94 (2H, m), 2.94 (2H, s), 4.39 (2H, s), 7.47 (1H, dd, J = 8.3, 2.3 Hz), 7.56 (2H, t, J = 7.9 Hz), 7.63-7.69 (3H, m), 8.34 (2H, d, J = 7.9 Hz), 13.33 (1H, br s). | 449 | 447 | 3 |
| 1-258 | 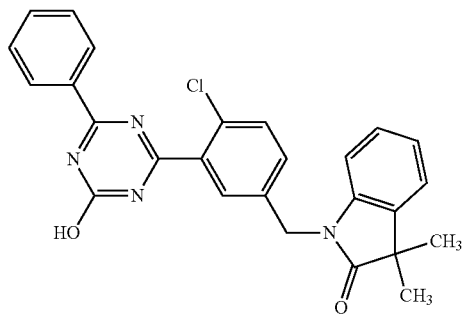 [SMILES: CC1(C)C(=O)N(Cc2ccc(Cl)c(-c3nc(O)nc(-c4ccccc4)n3)c2)c2ccccc21] | 1H-NMR (DMSO-D6) δ: 1.34 (6H, s), 4.99 (2H, s), 6.97 (1H, d, J = 7.6 Hz), 7.05 (1H, t, J = 7.6 Hz), 7.20 (1H, t, J = 7.6 Hz), 7.39 (1H, d, J = 7.6 Hz), 7.48 (1H, dd, J = 8.3, 1.8 Hz), 7.55 (2H, t, J = 7.6 Hz), 7.59-7.68 (2H, m), 7.75 (1H, d, J = 1.8 Hz), 8.29 (2H, d, J = 7.6 Hz), 13.32 (1H, br s). | 457 | 455 | |

TABLE 1-33-continued
| 1-259 | 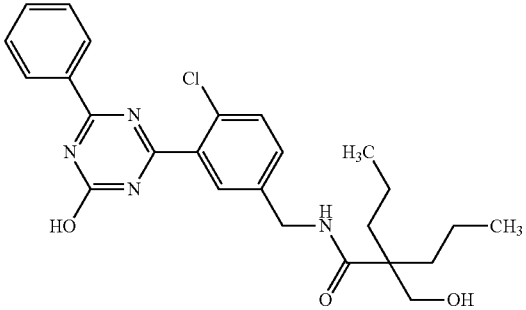 [SMILES: CCCC(CO)(CCC)C(=O)NCc1ccc(Cl)c(-c2nc(O)nc(-c3ccccc3)n2)c1] | 1H-NMR (DMSO-D6) δ: 0.77 (6H, t, J = 7.3 Hz), 1.03-1.19 (4H, m), 1.36-1.50 (4H, m), 3.46 (2H, s), 4.33 (2H, d, J = 6.0 Hz), 4.62 (1H, br s), 7.47 (1H, d, J = 8.4 Hz), 7.53-7.60 (3H, m), 7.61-7.69 (2H, m), 8.12 (1H, t, J = 6.0 Hz), 8.34 (2H, d, J = 7.6 Hz), 13.35 (1H, br s). | 469 | 467 |
| --- | --- | --- | --- | --- |
| 1-260 | 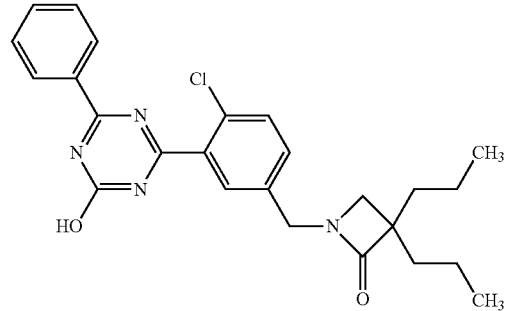 [SMILES: CCCC1(CCC)CN(Cc2ccc(Cl)c(-c3nc(O)nc(-c4ccccc4)n3)c2)C1=O] | 1H-NMR (DMSO-D6) δ: 0.84 (6H, t, J = 7.2 Hz), 1.14-1.29 (2H, m), 1.30-1.58 (6H, m), 3.02 (2H, s), 4.39 (2H, s), 7.48 (1H, dd, J = 8.3, 2.1 Hz), 7.57 (2H, t, J = 7.9 Hz), 7.64-7.70 (3H, m), 8.34 (2H, d, J = 7.9 Hz), 13.36 (1H, br s). | 451 | 449 |
| 1-261 | 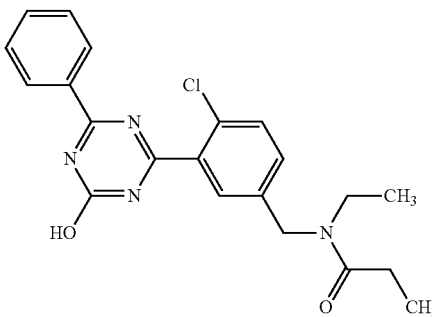 | 1H-NMR (DMSO-D6) δ: 0.96-1.06 (3.9H, m), 1.10 (2.1H, t, J = 7.2 Hz), 2.31 (0.6H, q, J = 7.2 Hz), 2.42 (1.4H, q, J = 7.2 Hz), 3.29-3.35 (2H, m), 4.56 (1.4H, s), 4.63 (0.6H, s), 7.45 (1H, d, J = 8.3 Hz), 7.54-7.69 (5H, m), 8.34 (2H, d, J = 7.9 Hz), 13.33 (1H, br s). | 397 | 395 |
| 1-262 | 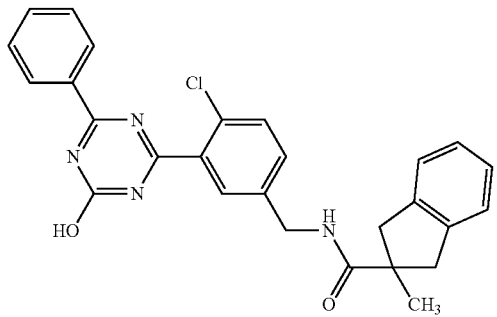 [SMILES: CC1(C(=O)NCc2ccc(Cl)c(-c3nc(O)nc(-c4ccccc4)n3)c2)Cc2ccccc2C1] | 1H-NMR (DMSO-D6) δ: 1.28 (3H, s), 2.75 (2H, d, J = 15.7 Hz), 3.36 (2H, d, J = 15.7 Hz), 4.37 (2H, d, J = 6.0 Hz), 7.06-7.11 (2H, m), 7.14-7.18 (2H, m), 7.44 (1H, dd, J = 8.3, 2.1 Hz), 7.52-7.62 (4H, m), 7.66 (1H, t, J = 7.4 Hz), 8.34 (2H, d, J = 7.4 Hz), 8.41 (1H, t, J = 6.0 Hz), 13.32 (1H, br s). | 471 | 469 |
| 1-263 | 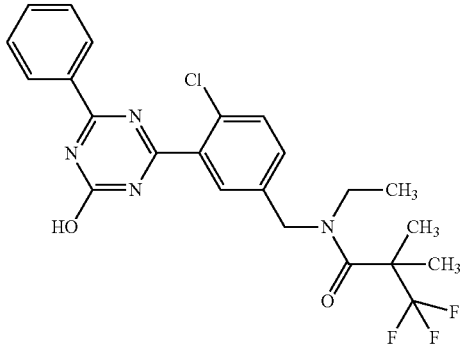 [SMILES: CCN(Cc1ccc(Cl)c(-c2nc(O)nc(-c3ccccc3)n2)c1)C(=O)C(C)(C)C(F)(F)F] | 1H-NMR (DMSO-D6) δ: 1.13 (3H, t, J = 6.9 Hz), 1.50 (6H, s), 3.42 (2H, br s), 4.66 (2H, s), 7.41 (1H, dd, J = 8.3, 1.8 Hz), 7.56 (2H, t, J = 7.9 Hz), 7.61-7.69 (3H, m), 8.34 (2H, d, J = 7.9 Hz), 13.33 (1H, br s). | 479 | 477 |

TABLE 1-34
| | | | | | |
|---|---|---|---|---|---|
| 1-264 | 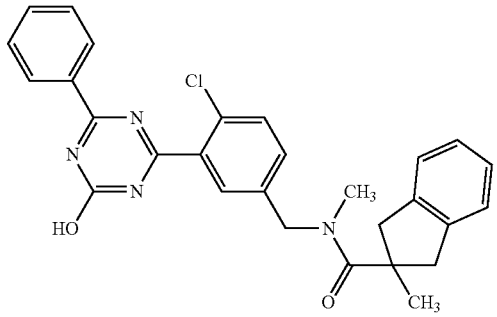 [SMILES: CN(Cc1ccc(Cl)c(-c2nc(O)nc(-c3ccccc3)n2)c1)C(=O)C1(C)Cc2ccccc2C1] | 1H-NMR (DMSO-D6) δ: 1.31 (3H, s), 2.91 (2H, d, J = 16.0 Hz), 3.04 (3H, br s), 3.51 (2H, d, J = 16.0 Hz), 4.66 (2H, br s), 7.11-7.15 (2H, m), 7.17-7.21 (2H, m), 7.45 (1H, dd, J = 8.3, 2.1 Hz), 7.54 (2H, t, J = 7.9 Hz), 7.61-7.67 (3H, m), 8.33 (2H, d, J = 7.9 Hz), 13.33 (1H, br s). | 485 | 483 | |
| 1-265 | 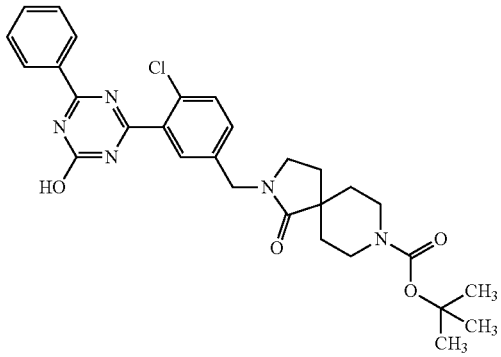 [SMILES: CC(C)(C)OC(=O)N1CCC2(CC1)CCN(Cc1ccc(Cl)c(-c3nc(O)nc(-c4ccccc4)n3)c1)C2=O] | 1H-NMR (DMSO-D6) δ: 1.34-1.42 (2H, m), 1.40 (9H, s), 1.53-1.63 (2H, m), 1.96 (2H, t, J = 6.8 Hz), 2.86-3.00 (2H, m), 3.25 (2H, t, J = 6.8 Hz), 3.78-3.87 (2H, m), 4.46 (2H, s), 7.42 (1H, dd, J = 8.3, 2.1 Hz), 7.54-7.59 (2H, m), 7.60-7.69 (3H, m), 8.34 (2H, d, J = 7.7 Hz), 13.34 (1H, br s). | 550 | 548 | |
| 1-266 | 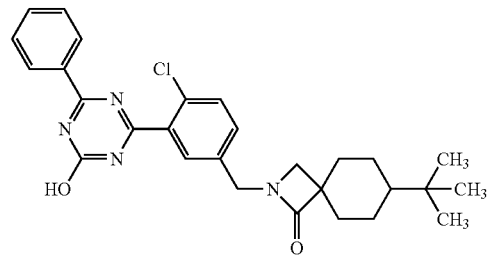 [SMILES: CC(C)(C)C1CCC2(CC1)CN(Cc1ccc(Cl)c(-c3nc(O)nc(-c4ccccc4)n3)c1)C2=O] | 1H-NMR (DMSO-D6) δ: 0.83 (9H, s), 0.90-0.99 (1H, m), 1.41-1.67 (6H, m), 1.96-2.03 (2H, m), 2.92 (2H, s), 4.38 (2H, s), 7.47 (1H, dd, J = 8.3, 1.8 Hz), 7.56 (2H, t, J = 7.6 Hz), 7.63-7.69 (3H, m), 8.34 (2H, d, J = 7.6 Hz), 13.34 (1H, br s). | 491 | 489 | 4 |
| 1-267 | 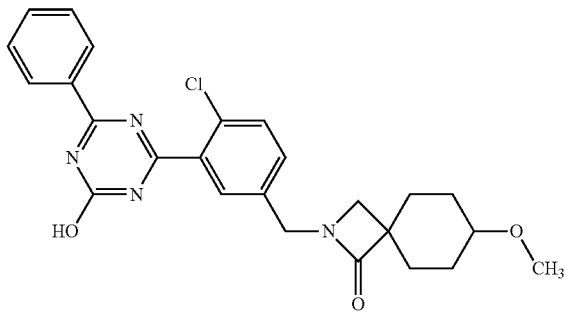 [SMILES: COC1CCC2(CC1)CN(Cc1ccc(Cl)c(-c3nc(O)nc(-c4ccccc4)n3)c1)C2=O] | 1H-NMR (DMSO-D6) δ: 1.48-1.65 (4H, m), 1.67-1.77 (2H, m), 1.82-1.91 (2H, m), 3.03 (2H, s), 3.21 (3H, s), 3.23-3.29 (1H, m), 4.40 (2H, s), 7.48 (1H, dd, J = 8.1, 1.8 Hz), 7.56 (2H, t, J = 7.6 Hz), 7.63-7.70 (3H, m), 8.34 (2H, d, J = 7.6 Hz), 13.34 (1H, br s). | 465 | 463 | 5 |

TABLE 2-1
| Example | Structure | NMR | MS (M + H) | MS (M − H) | Note |
|---|---|---|---|---|---|
| 2-1 | 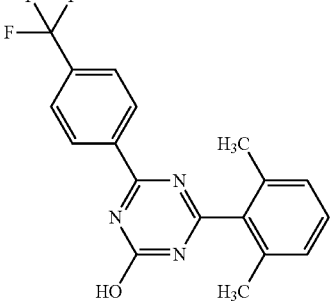 | 1H-NMR (DMSO-D6) δ: 2.24 (6H, s), 7.21 (2H, d, J = 7.6 Hz), 7.37 (1H, t, J = 7.6 Hz), 7.91 (2H, d, J = 8.4 Hz), 8.53 (2H, d, J = 8.4 Hz), 13.35 (1H, br s). | 346 | 344 | |
| 2-2 | 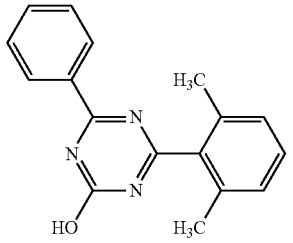 [SMILES: Cc1cccc(C)c1-c1nc(O)nc(-c2ccccc2)n1] | 1H-NMR (CDCl3) δ: 2.34 (6H, s), 7.17 (2H, d, J = 7.7 Hz), 7.33 (1H, t, J = 7.7 Hz), 7.49 (2H, t, J = 7.7 Hz), 7.60 (1H, t, J = 7.7 Hz), 8.52 (2H, dd, J = 7.7, 1.2 Hz), 11.87 (1H, s). | 278 | 276 | |
| 2-3 | 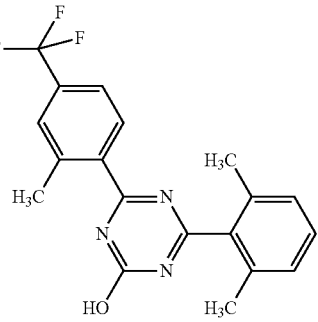 | 1H-NMR (CDCl3) δ: 2.32 (6H, s), 2.72 (3H, s), 7.17 (2H, d, J = 7.7 Hz), 7.34 (1H, t, J = 7.7 Hz), 7.53-7.56 (2H, m), 8.12-8.16 (1H, m), 11.29 (1H, s). | 360 | 358 | |
| 2-4 | 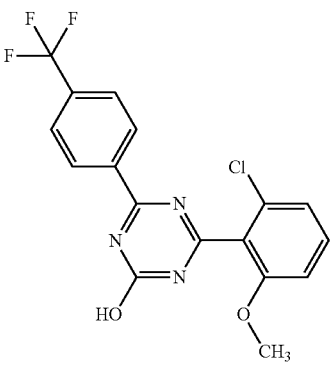 [SMILES: COc1cccc(Cl)c1-c1nc(O)nc(-c2ccc(C(F)(F)F)cc2)n1] | 1H-NMR (DMSO-D6) δ: 3.84 (3H, s), 7.25 (2H, d, J = 8.3 Hz), 7.59 (1H, t, J = 8.3 Hz), 7.92 (2H, d, J = 8.3 Hz), 8.51 (2H, d, J = 8.3 Hz), 13.59 (1H, br s). | 382 | 380 | |
| 2-5 | 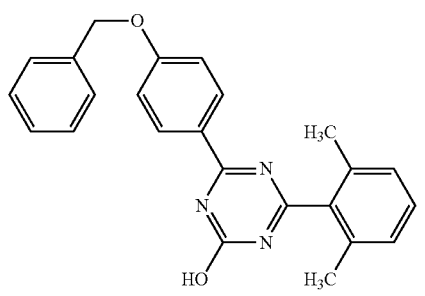 [SMILES: Cc1cccc(C)c1-c1nc(O)nc(-c2ccc(OCc3ccccc3)cc2)n1] | 1H-NMR (DMSO-D6) δ: 2.22 (6H, s), 5.22 (2H, s), 7.13-7.21 (2H, m), 7.32-7.37 (2H, m), 7.38-7.43 (2H, m), 7.46-7.48 (2H, m), 8.28-8.32 (2H, m), 12.98 (1H, br s). | 384 | 382 | |

TABLE 2-1-continued

| Example | Structure | NMR | MS (M + H) | MS (M − H) | Note |
|---|---|---|---|---|---|
| 2-6 | 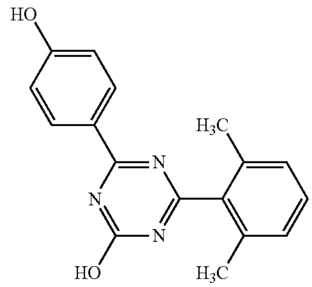 [SMILES: Cc1cccc(C)c1-c1nc(O)nc(-c2ccc(O)cc2)n1] | 1H-NMR (DMSO-D6) δ: 2.20 (6H, s), 6.86 (2H, dt, J = 9.4, 2.4 Hz), 7.17 (2H, d, J = 7.7 Hz), 7.32 (1H, t, J = 7.6 Hz), 8.19 (2H, dt, J = 9.5, 2.3 Hz), 10.32 (1H, br s), 12.87 (1H, br s). | 294 | 292 | |
| 2-7 | 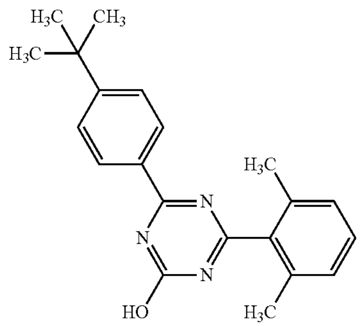 [SMILES: Cc1cccc(C)c1-c1nc(O)nc(-c2ccc(C(C)(C)C)cc2)n1] | 1H-NMR (DMSO-D6) δ: 1.32 (9H, s), 2.22 (6H, s), 7.20 (2H, d, J = 7.7 Hz), 7.35 (1H, t, J = 7.7 Hz), 7.56 (2H, d, J = 8.5 Hz), 8.28 (2H, d, J = 8.5 Hz), 13.08 (1H, br s). | 334 | 332 | |
| 2-8 | 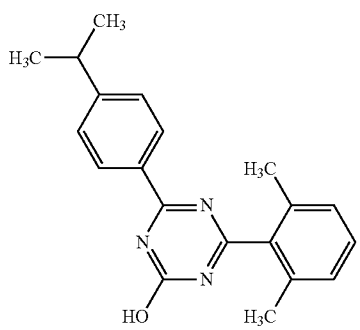 [SMILES: Cc1cccc(C)c1-c1nc(O)nc(-c2ccc(C(C)C)cc2)n1] | 1H-NMR (DMSO-D6) δ: 1.23 (6H, d, J = 7.3 Hz), 2.22 (6H, s), 2.90-3.05 (1H, m), 7.20 (2H, d, J = 7.7 Hz), 7.35 (1H, t, J = 7.7 Hz), 7.41 (2H, d, J = 8.3 Hz), 8.27 (2H, d, J = 8.3 Hz), 13.09 (1H, br s). | 320 | 318 | |
| 2-9 | 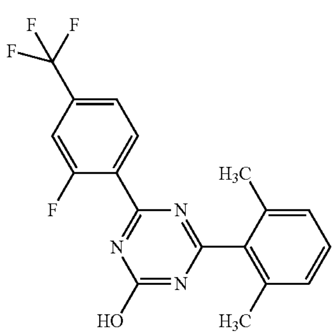 [SMILES: Cc1cccc(C)c1-c1nc(O)nc(-c2ccc(C(F)(F)F)cc2F)n1] | 1H-NMR (DMSO-D6) δ: 2.24 (6H, s), 7.19 (2H, d, J = 7.7 Hz), 7.34 (1H, t, J = 7.7 Hz), 7.73 (1H, d, J = 8.1 Hz), 7.85 (1H, d, J = 10.7 Hz), 8.24 (1H, t, J = 7.9 Hz), 13.42 (1H, br s). | 364 | 362 | |

TABLE 2-2

| | | | | |
|---|---|---|---|---|
| 2-10 | (structure) | 1H-NMR (DMSO-D6) δ: 7.50 (1H, t, J = 8.8 Hz), 7.57 (1H, d, J = 8.4 Hz), 7.67-7.73 (1H, m), 7.94 (2H, d, J = 8.1 Hz), 8.51 (2H, d, J = 8.1 Hz), 13.90 (1H, br s). | 370 | 368 |
| 2-11 | (structure) | 1H-NMR (DMSO-D6) δ: 2.24 (6H, s), 7.20 (2H, d, J = 7.7 Hz), 7.35 (1H, t, J = 7.7 Hz), 7.45-7.47 (3H, m), 7.59-7.63 (2H, m), 7.71 (2H, dd, J = 6.9, 2.0 Hz), 8.37 (2H, dd, J = 6.9, 2.0 Hz), 13.20 (1H, br s). | 378 | 376 |
| 2-12 | (structure) | 1H-NMR (DMSO-D6) δ: 2.22 (6H, s), 2.89-3.00 (4H, m), 7.16-7.29 (7H, m), 7.33 (1H, d, J = 7.7 Hz), 7.38 (2H, d, J = 8.4 Hz), 8.24 (2H, d, J = 8.4 Hz), 13.09 (1H, br s). | 382 | 380 |
| 2-13 | (structure) | 1H-NMR (DMSO-D6) δ: 2.23 (6H, s), 2.39 (3H, s), 7.20 (2H, d, J = 7.6 Hz), 7.35 (1H, t, J = 7.6 Hz), 7.40-7.48 (2H, m), 8.11-8.18 (2H, m), 13.14 (1H, br s). | 292 | 290 |
| 2-14 | (structure) | 1H-NMR (DMSO-D6) δ: 2.23 (6H, s), 3.83 (3H, s), 7.18-7.24 (3H, m), 7.36 (1H, t, J = 7.8 Hz), 7.45 (1H, t, J = 7.8 Hz), 7.83-7.86 (1H, m), 7.94 (1H, d, J = 7.8 Hz), 13.17 (1H, br s). | 308 | 306 |

TABLE 2-2-continued
| 2-15 | 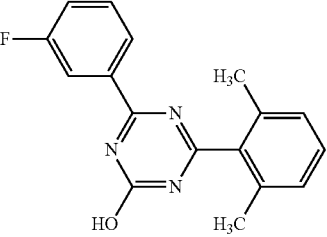 [SMILES: Cc1cccc(C)c1-c1nc(O)nc(-c2cccc(F)c2)n1] | 1H-NMR (DMSO-D6) δ: 2.23 (6H, s), 7.21 (2H, d, J = 7.6 Hz), 7.36 (1H, t, J = 7.6 Hz), 7.47-7.53 (1H, m), 7.57-7.63 (1H, m), 8.00-8.05 (1H, m), 8.19 (1H, dt, J = 7.9, 1.3 Hz), 13.27 (1H, br s). | 296 | 294 |
| --- | --- | --- | --- | --- |
| 2-16 | 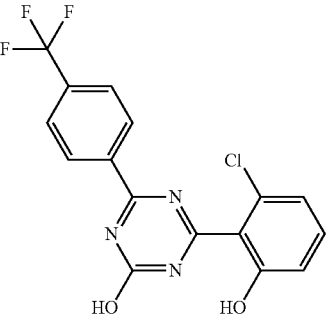 [SMILES: Oc1nc(-c2ccc(C(F)(F)F)cc2)nc(-c2c(O)cccc2Cl)n1] | 1H-NMR (DMSO-D6) δ: 6.97 (1H, dd, J = 8.1, 0.7 Hz), 7.05 (1H, dd, J = 8.1, 0.7 Hz), 7.39 (1H, t, J = 8.1 Hz), 7.90 (2H, d, J = 8.4 Hz), 8.50 (2H, d, J = 8.4 Hz), 10.74 (1H, br s), 13.38 (1H, br s). | 368 | 366 |
| 2-17 | 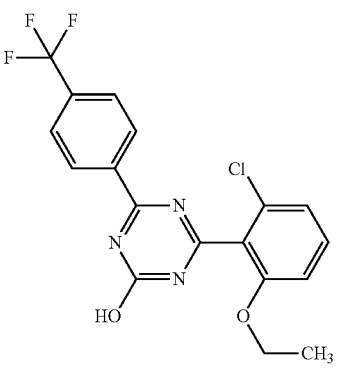 [SMILES: CCOc1cccc(Cl)c1-c1nc(O)nc(-c2ccc(C(F)(F)F)cc2)n1] | 1H-NMR (DMSO-D6) δ: 1.20 (3H, t, J = 7.0 Hz), 4.12 (2H, q, J = 7.0 Hz), 7.21 (2H, d, J = 8.3 Hz), 7.55 (1H, t, J = 8.3 Hz), 7.91 (2H, d, J = 8.3 Hz), 8.50 (2H, d, J = 8.3 Hz), 13.53 (1H, br s). | 396 | 394 |
| 2-18 | 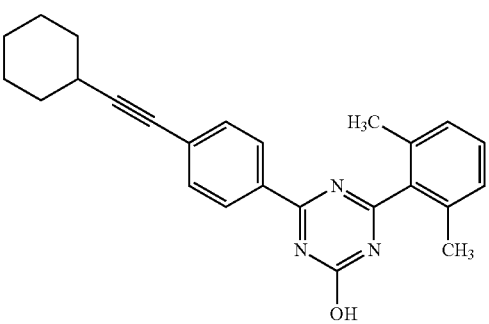 [SMILES: Cc1cccc(C)c1-c1nc(O)nc(-c2ccc(C#CC3CCCCC3)cc2)n1] | 1H-NMR (DMSO-D6) δ: 1.31-1.40 (3H, m), 1.45-1.54 (3H, m), 1.65-1.72 (2H, m), 1.81-1.88 (2H, m), 2.22 (6H, s), 2.67-2.71 (1H, m), 7.20 (2H, d, J = 7.7 Hz), 7.35 (1H, t, J = 7.7 Hz), 7.51 (2H, dd, J = 6.7, 1.9 Hz), 8.29 (2H, dd, J = 6.7, 1.9 Hz), 13.16 (1H, br s). | 384 | 382 |

TABLE 2-3
| 2-19 | 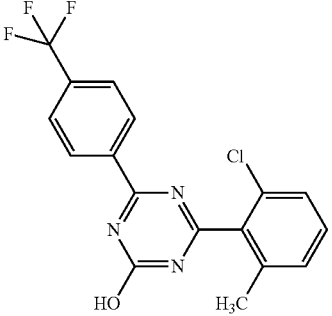 [SMILES: Cc1cccc(Cl)c1-c1nc(O)nc(-c2ccc(C(F)(F)F)cc2)n1] | 1H-NMR (DMSO-D6) δ: 2.29 (3H, s), 7.38-7.41 (1H, m), 7.47-7.52 (2H, m), 7.92 (2H, d, J = 8.1 Hz), 8.52 (2H, d, J = 8.1 Hz), 13.61 (1H, br s). | 366 | 364 |
| --- | --- | --- | --- | --- |
| 2-20 | 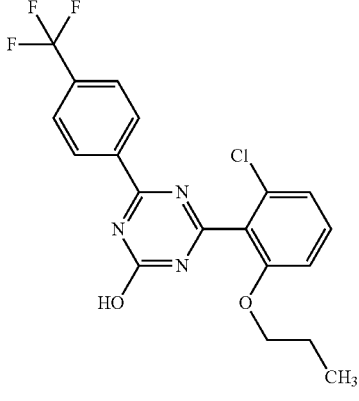 | 1H-NMR (DMSO-D6) δ: 0.80 (3H, t, J = 7.3 Hz), 1.55-1.63 (2H, m), 4.02 (2H, t, J = 6.3 Hz), 7.22 (2H, t, J = 8.3 Hz), 7.55 (1H, t, J = 8.3 Hz), 7.90 (2H, d, J = 8.3 Hz), 8.50 (2H, d, J = 8.3 Hz), 13.54 (1H, br s). | 410 | 408 |
| 2-21 | 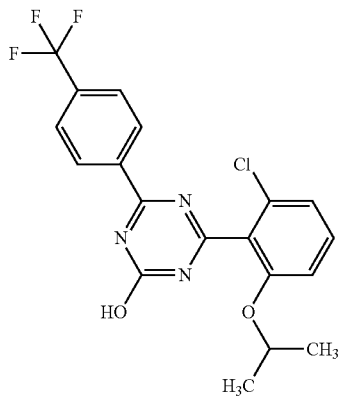 [SMILES: CC(C)Oc1cccc(Cl)c1-c1nc(O)nc(-c2ccc(C(F)(F)F)cc2)n1] | 1H-NMR (DMSO-D6) δ: 1.18 (6H, d, J = 6.0 Hz), 4.65-4.71 (1H, m), 7.20 (1H, d, J = 8.4 Hz), 7.25 (1H, d, J = 8.4 Hz), 7.54 (1H, t, J = 8.4 Hz), 7.91 (2H, d, J = 8.4 Hz), 8.50 (2H, d, J = 8.4 Hz), 13.49 (1H, br s). | 410 | 408 |
| 2-22 | 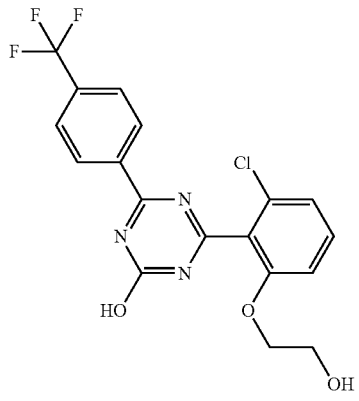 [SMILES: OCCOc1cccc(Cl)c1-c1nc(O)nc(-c2ccc(C(F)(F)F)cc2)n1] | 1H-NMR (DMSO-D6) δ: 3.59-3.62 (2H, br m), 4.09 (2H, t, J = 5.0 Hz), 4.81 (1H, br s), 7.24 (2H, t, J = 8.3 Hz), 7.56 (1H, t, J = 8.3 Hz), 7.92 (2H, d, J = 8.4 Hz), 8.52 (2H, d, J = 8.4 Hz), 13.49 (1H, s). | 412 | 410 |

TABLE 2-3-continued

| | | | | |
|---|---|---|---|---|
| 2-23 | (structure) | 1H-NMR (DMSO-D6) δ: 1.71-1.77 (2H, m), 3.39 (2H, t, J = 6.2 Hz), 4.14 (2H, t, J = 6.2 Hz), 4.45 (1H, br s), 7.23 (1H, d, J = 8.3 Hz), 7.24 (1H, d, J = 8.3 Hz), 7.56 (1H, t, J = 8.3 Hz), 7.92 (2H, d, J = 8.4 Hz), 8.52 (2H, d, J = 8.4 Hz), 13.56 (1H, br s). | 426 | 424 |
| 2-24 | (structure) | 1H-NMR (DMSO-D6) δ: 2.23 (6H, s), 7.20 (2H, d, J = 7.7 Hz), 7.35 (1H, t, J = 7.7 Hz), 7.60 (2H, d, J = 8.6 Hz), 8.34 (2H, d, J = 8.6 Hz), 13.21 (1H, br s). | 296 | 294 |
| 2-25 | (structure) | 1H-NMR (DMSO-D6) δ: 2.23 (6H, s), 7.20 (2H, d, J = 7.6 Hz), 7.35 (1H, t, J = 7.6 Hz), 7.60 (2H, d, J = 8.6 Hz), 8.34 (2H, d, J = 8.6 Hz), 13.21 (1H, br s). | 312 | 310 |
| 2-26 | (structure) | 1H-NMR (DMSO-D6) δ: 2.22 (6H, s), 2.40 (3H, s), 7.20 (2H, d, J = 7.5 Hz), 7.32-7.37 (3H, m), 8.23 (2H, d, J = 8.2 Hz), 13.08 (1H, br s). | 292 | 290 |
| 2-27 | (structure) | 1H-NMR (DMSO-D6) δ: 2.22 (6H, s), 3.85 (3H, s), 7.07 (2H, d, J = 9.0 Hz), 7.19 (2H, d, J = 7.6 Hz), 7.34 (1H, t, J = 7.6 Hz), 8.31 (2H, d, J = 9.0 Hz), 12.98 (1H, s). | 308 | 306 |

TABLE 2-4

| | Structure | NMR | | |
|---|---|---|---|---|
| 2-28 | 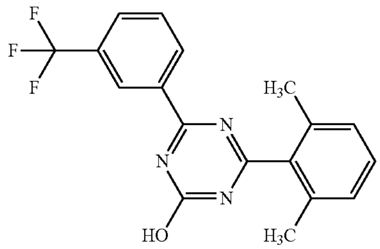 [SMILES: Cc1cccc(C)c1-c1nc(O)nc(-c2cccc(C(F)(F)F)c2)n1] | 1H-NMR (DMSO-D6) δ: 2.24 (6H, s), 7.21 (2H, d, J = 7.7 Hz), 7.37 (1H, t, J = 7.7 Hz), 7.80 (1H, t, J = 7.9 Hz), 8.03 (1H, d, J = 7.9 Hz), 8.57 (1H, s), 8.62 (1H, d, J = 7.9 Hz), 13.33 (1H, br s). | 346 | 344 |
| 2-29 | 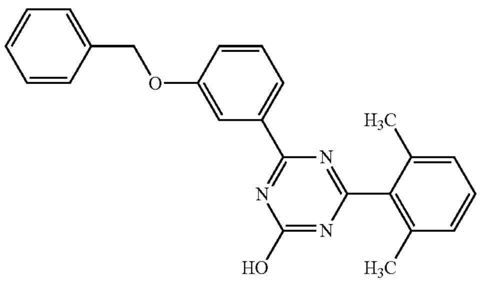 [SMILES: Cc1cccc(C)c1-c1nc(O)nc(-c2cccc(OCc3ccccc3)c2)n1] | 1H-NMR (DMSO-D6) δ: 2.22 (6H, s), 5.19 (2H, s), 7.20 (2H, d, J = 7.5 Hz), 7.27-7.42 (5H, m), 7.43-7.49 (3H, m), 7.92-7.96 (2H, m), 13.17 (1H, br s). | 384 | 382 |
| 2-30 | 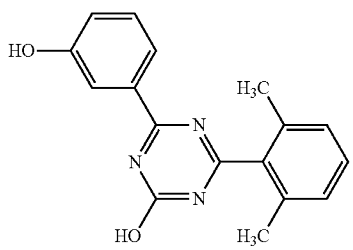 [SMILES: Cc1cccc(C)c1-c1nc(O)nc(-c2cccc(O)c2)n1] | 1H-NMR (DMSO-D6) δ: 2.22 (6H, s), 6.99-7.03 (1H, m), 7.20 (2H, d, J = 7.7 Hz), 7.30-7.37 (2H, m), 7.76-7.80 (2H, m), 9.69 (1H, s), 13.12 (1H, br s). | 294 | 292 |
| 2-31 | 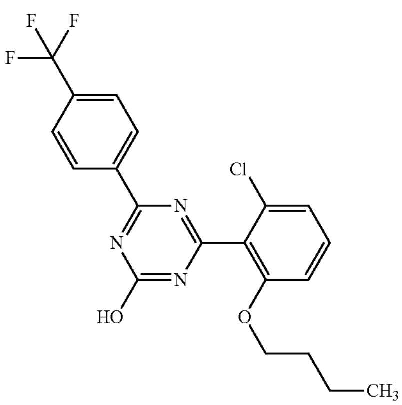 | 1H-NMR (DMSO-D6) δ: 0.76 (3H, t, J = 7.4 Hz), 1.22-1.31 (2H, m), 1.53-1.60 (2H, m), 4.07 (2H, t, J = 6.2 Hz), 7.23 (2H, dd, J = 8.4, 2.2 Hz), 7.56 (1H, t, J = 8.4 Hz), 7.92 (2H, d, J = 8.4 Hz), 8.51 (2H, d, J = 8.4 Hz), 13.56 (1H, br s). | 424 | 422 |
| 2-32 | 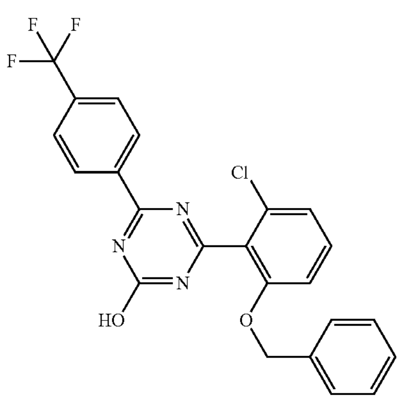 [SMILES: Oc1nc(-c2ccc(C(F)(F)F)cc2)nc(-c2c(Cl)cccc2OCc2ccccc2)n1] | 1H-NMR (DMSO-D6) δ: 5.24 (2H, s), 7.35-7.24 (7H, m), 7.57 (1H, t, J = 8.3 Hz), 7.93 (2H, d, J = 8.2 Hz), 8.52 (2H, d, J = 8.2 Hz), 13.66 (1H, br s). | 458 | 456 |

TABLE 2-4-continued

| | Structure | NMR | | |
|---|---|---|---|---|
| 2-33 | (structure) | 1H-NMR (DMSO-D6) δ: 0.80 (6H, d, J = 6.7 Hz), 1.82-1.92 (1H, m), 3.83 (2H, d, J = 6.0 Hz), 7.20 (2H, dd, J = 8.3, 3.5 Hz), 7.54 (1H, t, J = 8.3 Hz), 7.90 (2H, d, J = 8.4 Hz), 8.50 (2H, d, J = 8.4 Hz), 13.56 (1H, br s). | 424 | 422 |
| 2-34 | (structure) | 1H-NMR (DMSO-D6) δ: 3.12 (3H, s), 3.53 (2H, t, J = 4.5 Hz), 4.18 (2H, t, J = 4.5 Hz), 7.24 (2H, dd, J = 8.3, 3.8 Hz), 7.55 (1H, t, J = 8.3 Hz), 7.90 (2H, d, J = 8.4 Hz), 8.50 (2H, d, J = 8.4 Hz), 13.54 (1H, br s). | 426 | 424 |
| 2-35 | (structure) | 1H-NMR (DMSO-D6) δ: 3.83 (3H, s), 5.22 (2H, s), 7.16 (2H, d, J = 8.8 Hz), 7.22 (2H, d, J = 8.8 Hz), 7.37-7.32 (1H, m), 7.43-7.38 (2H, m), 7.50-7.45 (2H, m), 7.61-7.53 (1H, m), 8.28 (2H, d, J = 8.8 Hz), 13.17 (1H, s). | 420 | 418 |
| 2-36 | (structure) | 1H-NMR (DMSO-D6) δ: 4.90 (2H, q, J = 8.7 Hz), 7.38 (2H, dd, J = 8.4, 2.4 Hz), 7.64 (1H, t, J = 8.4 Hz), 7.93 (2H, d, J = 8.2 Hz), 8.51 (2H, d, J = 8.2 Hz), 13.68 (1H, br s). | 450 | 448 |

TABLE 2-5

| | | | | |
|---|---|---|---|---|
| 2-37 | (structure) | 1H-NMR (DMSO-D6) δ: 0.99-1.10 (2H, m), 1.13-1.30 (3H, m), 1.61-1.83 (6H, m), 2.20 (6H, s), 3.86 (2H, d, J = 6.3 Hz), 7.04 (2H, d, J = 9.1 Hz), 7.17 (2H, d, J = 7.7 Hz), 7.32 (1H, t, J = 7.7 Hz), 8.26 (2H, d, J = 9.1 Hz), 12.95 (1H, br s). | 390 | 388 |
| 2-38 | (structure) | 1H-NMR (DMSO-D6) δ: 1.28 (6H, d, J = 6.0 Hz), 2.20 (6H, s), 4.70-4.76 (1H, m), 7.02 (2H, d, J = 8.8 Hz), 7.18 (2H, d, J = 7.6 Hz), 7.32 (1H, t, J = 7.6 Hz), 8.26 (2H, d, J = 8.8 Hz), 12.94 (1H, br s). | 336 | 334 |
| 2-39 | (structure) | 1H-NMR (DMSO-D6) δ: 0.88 (6H, d, J = 6.4 Hz), 1.84-1.94 (1H, m), 2.23 (6H, s), 2.54 (2H, d, J = 6.9 Hz), 7.20 (2H, d, J = 7.7 Hz), 7.30-7.38 (3H, m), 8.26 (2H, d, J = 8.5 Hz), 13.09 (1H, br s). | 334 | 332 |
| 2-40 | (structure) | 1H-NMR (DMSO-D6) δ: 1.35 (3H, t, J = 6.9 Hz), 2.22 (6H, s), 4.13 (2H, q, J = 6.9 Hz), 7.05 (2H, d, J = 8.8 Hz), 7.20 (2H, d, J = 7.5 Hz), 7.34 (1H, t, J = 7.5 Hz), 8.29 (2H, d, J = 8.8 Hz), 12.97 (1H, br s). | 322 | 320 |
| 2-41 | (structure) | 1H-NMR (DMSO-D6) δ: 0.99 (3H, t, J = 7.4 Hz), 1.71-1.80 (2H, m), 2.22 (6H, s), 4.03 (2H, t, J = 6.6 Hz), 7.06 (2H, d, J = 9.0 Hz), 7.20 (2H, d, J = 7.5 Hz), 7.34 (1H, t, J = 7.5 Hz), 8.29 (2H, d, J = 9.0 Hz), 12.98 (1H, br s). | 336 | 334 |

TABLE 2-5-continued
| | | | | |
|---|---|---|---|---|
| 2-42 | 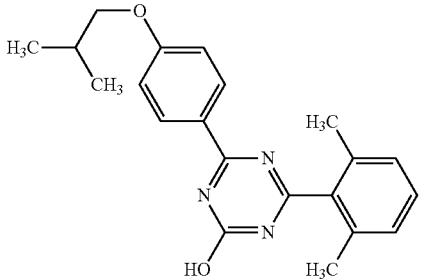 [SMILES: Cc1cccc(C)c1-c1nc(O)nc(-c2ccc(OCC(C)C)cc2)n1] | 1H-NMR (DMSO-D6) δ: 0.99 (6H, d, J = 6.8 Hz), 2.01-2.08 (1H, m), 2.22 (6H, s), 3.85 (2H, d, J = 6.6 Hz), 7.06 (2H, d, J = 8.8 Hz), 7.20 (2H, d, J = 7.5 Hz), 7.35 (1H, t, J = 7.5 Hz), 8.29 (2H, d, J = 8.8 Hz), 12.97 (1H, br s). | 350 | 348 |
| 2-43 | 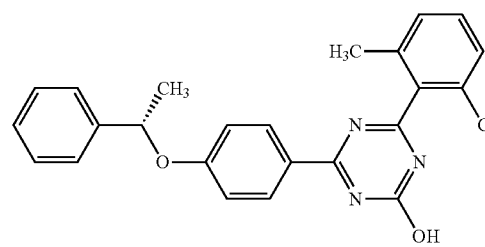 | 1H-NMR (DMSO-D6) δ: 1.58 (3H, d, J = 6.4 Hz), 2.19 (6H, s), 5.66 (1H, q, J = 6.4 Hz), 7.04 (2H, d, J = 9.0 Hz), 7.17 (2H, d, J = 7.7 Hz), 7.23-7.28 (1H, m), 7.30-7.37 (3H, m), 7.41-7.43 (2H, m), 8.20 (2H, d, J = 9.0 Hz), 12.96 (1H, br s). | 398 | 396 |
| 2-44 | 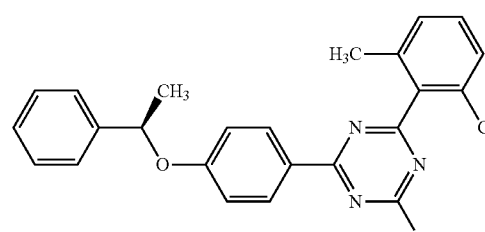 | 1H-NMR (DMSO-D6) δ: 1.58 (3H, d, J = 6.4 Hz), 2.19 (6H, s), 5.66 (1H, q, J = 6.4 Hz), 7.04 (2H, d, J = 9.0 Hz), 7.18 (2H, d, J = 7.7 Hz), 7.24-7.28 (1H, m), 7.30-7.37 (3H, m), 7.41-7.43 (2H, m), 8.20 (2H, d, J = 9.0 Hz), 12.96 (1H, br s). | 398 | 396 |
| 2-45 | 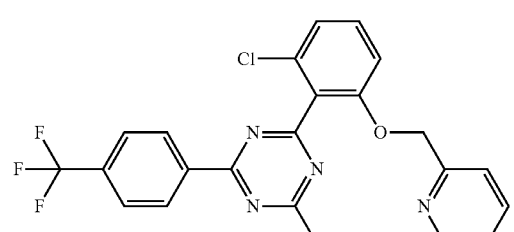 | 1H-NMR (DMSO-D6) δ: 5.32 (2H, s), 7.34-7.27 (4H, m), 7.57 (1H, t, J = 8.2 Hz), 7.71 (1H, td, J = 7.7, 1.7 Hz), 7.93 (2H, d, J = 8.2 Hz), 8.55-8.51 (3H, m), 13.74 (1H, s). | 459 | 457 |
TABLE 2-6
| | | | | |
|---|---|---|---|---|
| 2-46 | 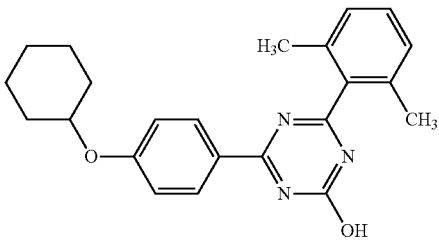 [SMILES: Cc1cccc(C)c1-c1nc(O)nc(-c2ccc(OC3CCCCC3)cc2)n1] | 1H-NMR (DMSO-D6) δ: 1.23-1.32 (1H, m), 1.35-1.57 (5H, m), 1.68-1.75 (2H, m), 1.92-1.98 (2H, m), 2.22 (6H, s), 4.47-4.51 (1H, m), 7.06 (2H, d, J = 8.8 Hz), 7.19 (2H, d, J = 7.6 Hz), 7.34 (1H, t, J = 7.6 Hz), 8.27 (2H, d, J = 8.8 Hz), 12.96 (1H, br s). | 376 | 374 |

TABLE 2-6-continued

| | Structure | 1H-NMR | | |
|---|---|---|---|---|
| 2-47 | 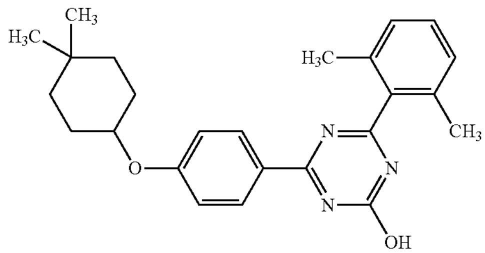 | 1H-NMR (DMSO-D6) δ: 0.94 (6H, d, J = 4.2 Hz), 1.26-1.35 (2H, m), 1.41-1.48 (2H, m), 1.56-1.65 (2H, m), 1.81-1.87 (2H, m), 2.22 (6H, s), 4.46-4.50 (1H, m), 7.06 (2H, d, J = 8.8 Hz), 7.19 (2H, d, J = 7.5 Hz), 7.34 (1H, t, J = 7.5 Hz), 8.27 (2H, d, J = 8.8 Hz), 12.96 (1H, br s). | 404 | 402 |
| 2-48 | 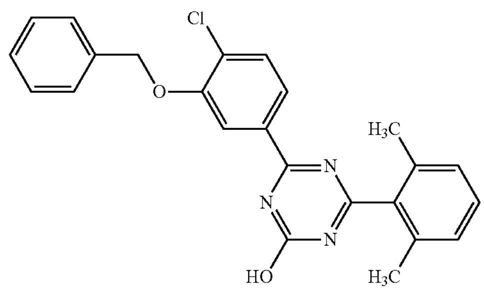 [SMILES: Cc1cccc(C)c1-c1nc(O)nc(-c2ccc(Cl)c(OCc3ccccc3)c2)n1] | 1H-NMR (DMSO-D6) δ: 2.23 (6H, s), 5.31 (2H, s), 7.19-7.23 (2H, m), 7.32-7.43 (4H, m), 7.48-7.53 (2H, m), 7.63 (1H, d, J = 8.4 Hz), 7.97 (1H, dd, J = 8.4, 1.7 Hz), 8.10 (1H, d, J = 1.7 Hz), 13.22 (1H, br s). | 418 | 416 |
| 2-49 | 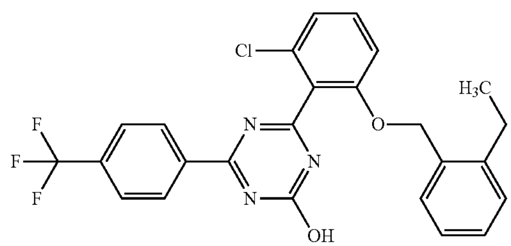 [SMILES: CCc1ccccc1COc1cccc(Cl)c1-c1nc(O)nc(-c2ccc(C(F)(F)F)cc2)n1] | 1H-NMR (DMSO-D6) δ: 0.99 (3H, t, J = 7.5 Hz), 2.55 (2H, q, J = 7.5 Hz), 5.22 (2H, s), 7.07 (1H, t, J = 6.8 Hz), 7.16 (1H, d, J = 6.8 Hz), 7.22 (1H, t, J = 6.8 Hz), 7.27 (1H, d, J = 8.2 Hz), 7.31 (1H, d, J = 6.8 Hz), 7.42 (1H, d, J = 8.2 Hz), 7.60 (1H, t, J = 8.2 Hz), 7.91 (2H, d, J = 8.6 Hz), 8.48 (2H, d, J = 8.6 Hz), 13.63 (1H, s). | 486 | 484 |
| 2-50 | 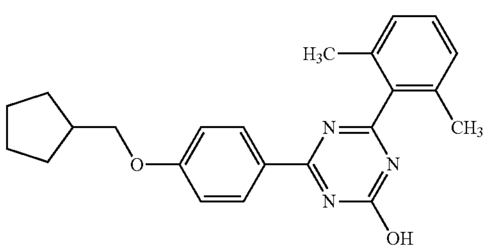 [SMILES: Cc1cccc(C)c1-c1nc(O)nc(-c2ccc(OCC3CCCC3)cc2)n1] | 1H-NMR (DMSO-D6) δ: 1.30-1.38 (2H, m), 1.50-1.65 (4H, m), 1.74-1.82 (2H, m), 2.22 (6H, s), 2.29-2.36 (1H, m), 3.95 (2H, d, J = 7.1 Hz), 7.06 (2H, d, J = 8.8 Hz), 7.20 (2H, d, J = 7.7 Hz), 7.34 (1H, t, J = 7.7 Hz), 8.28 (2H, d, J = 8.8 Hz), 12.97 (1H, br s). | 376 | 374 |
| 2-51 | 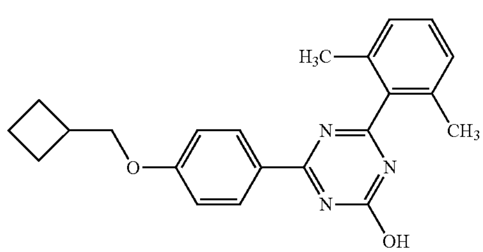 [SMILES: Cc1cccc(C)c1-c1nc(O)nc(-c2ccc(OCC3CCC3)cc2)n1] | 1H-NMR (DMSO-D6) δ: 1.81-1.94 (4H, m), 2.05-2.12 (2H, m), 2.22 (6H, s), 2.70-2.78 (1H, m), 4.05 (2H, d, J = 6.6 Hz), 7.06 (2H, d, J = 8.8 Hz), 7.20 (2H, d, J = 7.5 Hz), 7.34 (1H, t, J = 7.5 Hz), 8.29 (2H, d, J = 8.8 Hz), 12.97 (1H, br s). | 362 | 360 |
| 2-52 | 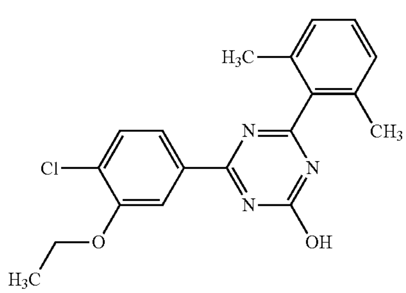 [SMILES: CCOc1cc(-c2nc(O)nc(-c3c(C)cccc3C)n2)ccc1Cl] | 1H-NMR (DMSO-D6) δ: 1.38 (3H, t, J = 6.9 Hz), 2.22 (6H, s), 4.19 (2H, q, J = 6.9 Hz), 7.19 (2H, d, J = 7.6 Hz), 7.34 (1H, t, J = 7.6 Hz), 7.58 (1H, d, J = 8.3 Hz), 7.92 (1H, dd, J = 8.3, 1.7 Hz), 7.96 (1H, d, J = 1.7 Hz), 13.19 (1H, br s). | 356 | 354 |

TABLE 2-6-continued

| | | | | |
|---|---|---|---|---|
| 2-53 | 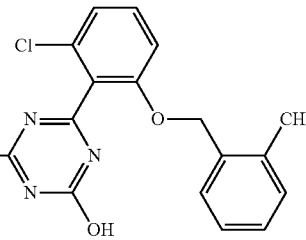 | 1H-NMR (DMSO-D6) δ: 2.18 (3H, s), 5.18 (2H, s), 7.04 (1H, t, J = 7.4 Hz), 7.16-7.09 (2H, m), 7.21 (1H, d, J = 7.9 Hz), 7.28 (1H, d, J = 7.4 Hz), 7.34 (1H, d, J = 8.4 Hz), 7.57-7.49 (1H, m), 7.88 (2H, d, J = 8.4 Hz), 8.47 (2H, d, J = 8.4 Hz), 13.63 (1H, s). | 472 | 470 |
| 2-54 | 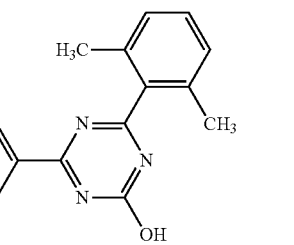 | 1H-NMR (DMSO-D6) δ: 1.20 (3H, t, J = 7.5 Hz), 2.23 (6H, s), 2.80 (2H, q, J = 7.5 Hz), 7.21 (2H, d, J = 7.6 Hz), 7.36 (1H, t, J = 7.6 Hz), 7.58 (1H, d, J = 8.4 Hz), 8.17 (1H, dd, J = 8.4, 2.0 Hz), 8.29 (1H, d, J = 2.0 Hz), 13.20 (1H, br s). | 340 | 338 |

TABLE 2-7

| | | | | |
|---|---|---|---|---|
| 2-55 | 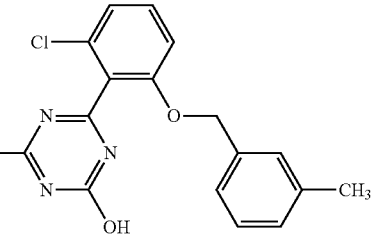 | 1H-NMR (DMSO-D6) δ: 2.11 (3H, s), 5.17 (2H, s), 7.04 (1H, d, J = 7.7 Hz), 7.17-7.06 (3H, m), 7.25 (1H, d, J = 8.3 Hz), 7.29 (1H, d, J = 8.3 Hz), 7.57 (1H, t, J = 8.3 Hz), 7.91 (2H, d, J = 8.1 Hz), 8.52 (2H, d, J = 8.1 Hz), 13.64 (1H, br s). | 472 | 470 |
| 2-56 | 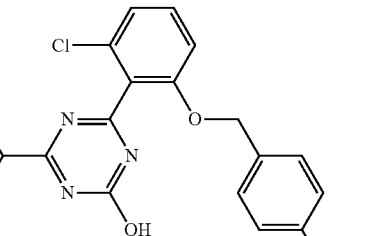 | 1H-NMR (DMSO-D6) δ: 2.22 (3H, s), 5.16 (2H, s), 7.06 (2H, d, J = 7.9 Hz), 7.20 (2H, d, J = 7.9 Hz), 7.23 (1H, d, J = 7.9 Hz), 7.28 (1H, d, J = 7.9 Hz), 7.55 (1H, t, J = 8.4 Hz), 7.92 (2H, d, J = 8.4 Hz), 8.49 (2H, d, J = 8.4 Hz), 13.62 (1H, br s). | 472 | 470 |
| 2-57 | 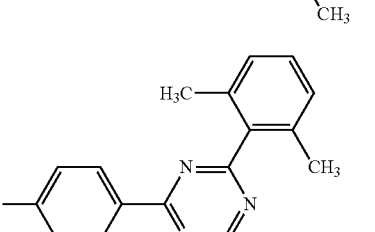 | 1H-NMR (DMSO-D6) δ: 1.34-1.23 (2H, m), 1.62-1.38 (6H, m), 1.72-1.63 (2H, m), 1.86-1.77 (2H, m), 2.00-1.88 (1H, m), 2.22 (6H, s), 3.86 (2H, d, J = 6.8 Hz), 7.06 (2H, d, J = 8.8 Hz), 7.20 (2H, d, J = 7.6 Hz), 7.34 (1H, t, J = 7.6 Hz), 8.28 (2H, d, J = 8.8 Hz), 12.97 (1H, br s). | 404 | 402 |
| 2-58 | 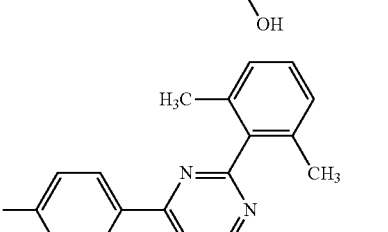 | 1H-NMR (DMSO-D6) δ: 1.01 (9H, s), 2.22 (6H, s), 3.74 (2H, s), 7.07 (2H, d, J = 8.8 Hz), 7.20 (2H, d, J = 7.7 Hz), 7.35 (1H, t, J = 7.7 Hz), 8.29 (2H, d, J = 8.8 Hz), 12.97 (1H, br s). | 364 | 362 |

TABLE 2-7-continued

| 2-59 | 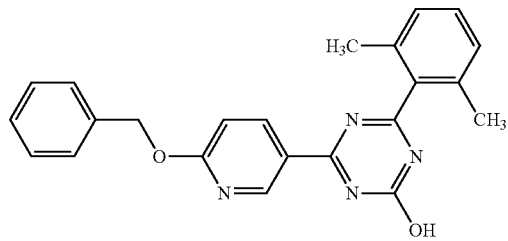 [SMILES: Cc1cccc(C)c1-c1nc(O)nc(-c2ccc(OCc3ccccc3)nc2)n1] | 1H-NMR (DMSO-D6) δ: 2.24 (6H, s), 5.46 (2H, s), 7.02 (1H, d, J = 8.8 Hz), 7.20 (2H, d, J = 7.7 Hz), 7.31-7.41 (4H, m), 7.46-7.49 (2H, m), 8.53 (1H, dd, J = 8.8, 2.0 Hz), 9.10 (1H, d, J = 2.0 Hz), 13.13 (1H, br s). | 385 | 383 |
|---|---|---|---|---|
| 2-60 | 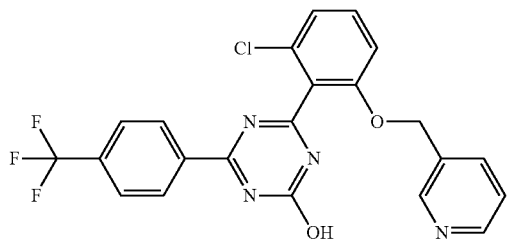 [SMILES: Oc1nc(-c2ccc(C(F)(F)F)cc2)nc(-c2c(Cl)cccc2OCc2cccnc2)n1] | 1H-NMR (DMSO-D6) δ: 5.30 (2H, s), 7.28 (1H, d, J = 7.9 Hz), 7.30-7.35 (2H, m), 7.59 (1H, t, J = 8.4 Hz), 7.73 (1H, dt, J = 7.9, 1.5 Hz), 7.93 (2H, d, J = 8.4 Hz), 8.48 (1H, dd, J = 4.9, 1.5 Hz), 8.51 (2H, d, J = 8.4 Hz), 8.56 (1H, d, J = 1.5 Hz), 13.67 (1H, br s). | 459 | 457 |
| 2-61 | 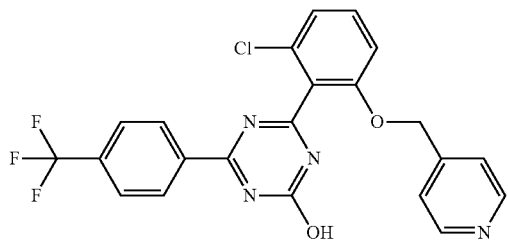 [SMILES: Oc1nc(-c2ccc(C(F)(F)F)cc2)nc(-c2c(Cl)cccc2OCc2ccncc2)n1] | 1H-NMR (DMSO-D6) δ: 5.33 (2H, s), 7.23-7.32 (4H, m), 7.57 (1H, t, J = 8.4 Hz), 7.94 (2H, d, J = 8.4 Hz), 8.48 (2H, d, J = 5.3 Hz), 8.54 (2H, d, J = 8.4 Hz), 13.72 (1H, br s). | 459 | 457 |
| 2-62 | 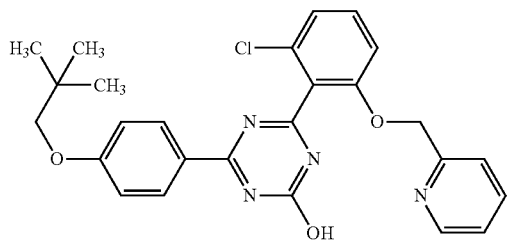 [SMILES: CC(C)(C)COc1ccc(-c2nc(O)nc(-c3c(Cl)cccc3OCc3ccccn3)n2)cc1] | 1H-NMR (DMSO-D6) δ: 1.00 (9H, s), 3.73 (2H, s), 5.30 (2H, s), 7.08 (2H, t, J = 4.5 Hz), 7.30-7.20 (3H, m), 7.33 (1H, d, J = 7.7 Hz), 7.52 (1H, t, J = 8.1 Hz), 7.69 (1H, td, J = 7.7, 1.7 Hz), 8.28 (2H, d, J = 8.8 Hz), 8.53-8.49 (1H, m), 13.27 (1H, br s). | 477 | 475 |
| 2-63 | 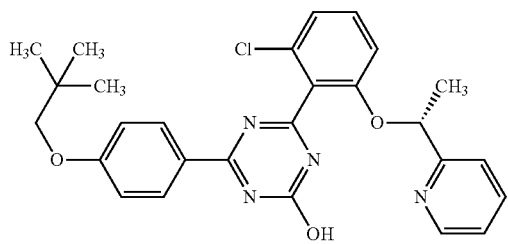 [SMILES: C[C@@H](Oc1cccc(Cl)c1-c1nc(O)nc(-c2ccc(OCC(C)(C)C)cc2)n1)c1ccccn1] | 1H-NMR (DMSO-D6) δ: 1.01 (9H, s), 1.46 (3H, d, J = 6.2 Hz), 3.74 (2H, s), 5.60 (1H, q, J = 6.2 Hz), 7.04-7.11 (3H, m), 7.17 (1H, d, J = 7.7 Hz), 7.27 (1H, dd, J = 7.0, 5.1 Hz), 7.37-7.44 (2H, m), 7.72 (1H, t, J = 7.0 Hz), 8.30 (2H, d, J = 8.8 Hz), 8.51 (1H, d, J = 4.2 Hz), 13.32 (1H, br s). | 491 | 489 |

TABLE 2-8

| 2-64 | 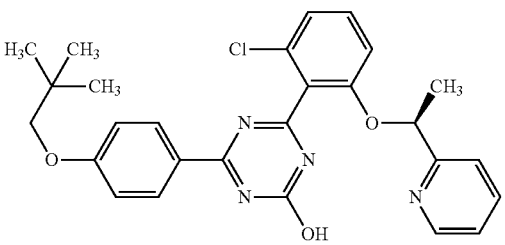 [SMILES: C[C@H](Oc1cccc(Cl)c1-c1nc(O)nc(-c2ccc(OCC(C)(C)C)cc2)n1)c1ccccn1] | 1H-NMR (DMSO-D6) δ: 1.01 (9H, s), 1.47 (3H, d, J = 6.3 Hz), 3.74 (2H, s), 5.60 (1H, q, J = 6.3 Hz), 7.13-7.02 (3H, m), 7.18 (1H, d, J = 7.7 Hz), 7.27 (1H, dd, J = 7.1, 5.2 Hz), 7.48-7.36 (2H, m), 7.72 (1H, t, J = 7.1 Hz), 8.31 (2H, d, J = 8.8 Hz), 8.51 (1H, d, J = 4.2 Hz), 13.32 (1H, br s). | 491 | 489 |
|---|---|---|---|---|

TABLE 2-8-continued

| | | | | |
|---|---|---|---|---|
| 2-65 | (structure) | 1H-NMR (DMSO-D6) δ: 1.01 (9H, s), 1.40 (3H, d, J = 6.2 Hz), 3.74 (2H, s), 5.62 (1H, q, J = 6.2 Hz), 7.05-7.15 (4H, m), 7.21-7.41 (6H, m), 8.31 (2H, d, J = 8.8 Hz), 13.21 (1H, br s). | 490 | 488 |
| 2-66 | (structure) | 1H-NMR (DMSO-D6) δ: 0.99 (6H, d, J = 6.6 Hz), 2.04 (1H, td, J = 13.3, 6.6 Hz), 3.86 (2H, d, J = 6.6 Hz), 5.31 (2H, s), 7.08 (2H, d, J = 8.8 Hz), 7.31-7.21 (3H, m), 7.34 (1H, d, J = 7.7 Hz), 7.57-7.48 (1H, m), 7.70 (1H, td, J = 7.7, 1.6 Hz), 8.30 (2H, d, J = 8.8 Hz), 8.53 (1H, d, J = 4.9 Hz), 13.29 (1H, br s). | 463 | 461 |
| 2-67 | (structure) | 1H-NMR (DMSO-D6) δ: 1.00 (6H, d, J = 6.6 Hz), 1.48 (3H, d, J = 6.2 Hz), 2.09-2.02 (1H, m), 3.87 (2H, d, J = 6.6 Hz), 5.61 (1H, q, J = 6.2 Hz), 7.14-7.04 (3H, m), 7.19 (1H, d, J = 7.9 Hz), 7.31-7.25 (1H, m), 7.48-7.37 (2H, m), 7.73 (1H, td, J = 7.9, 1.6 Hz), 8.32 (2H, d, J = 9.0 Hz), 8.53 (1H, d, J = 4.9 Hz), 13.33 (1H, br s). | 477 | 475 |
| 2-68 | (structure) | 1H-NMR (DMSO-D6) δ: 1.02 (9H, s), 3.74 (2H, s), 5.40 (2H, s), 7.08 (2H, d, J = 8.8 Hz), 7.24 (2H, d, J = 7.7 Hz), 7.44 (1H, t, J = 4.9 Hz), 7.51 (1H, br s), 8.27 (2H, d, J = 8.8 Hz), 8.78 (2H, d, J = 4.9 Hz), 13.19 (1H, br s). | 478 | 476 |
| 2-69 | (structure) | 1H-NMR (DMSO-D6) δ: 0.88 (3H, t, J = 7.2 Hz), 1.31-1.42 (4H, m), 1.69-1.76 (2H, m), 2.21 (6H, s), 4.05 (2H, t, J = 6.5 Hz), 7.04 (2H, d, J = 8.8 Hz), 7.18 (2H, d, J = 7.4 Hz), 7.33 (1H, t, J = 7.4 Hz), 8.27 (2H, d, J = 8.8 Hz), 12.96 (1H, br s). | 364 | 362 |
| 2-70 | (structure) | 1H-NMR (DMSO-D6) δ: 0.92 (3H, t, J = 7.3 Hz), 1.38-1.48 (2H, m), 1.67-1.74 (2H, m), 2.21 (6H, s), 4.06 (2H, t, J = 6.5 Hz), 7.05 (2H, d, J = 8.8 Hz), 7.18 (2H, d, J = 7.7 Hz), 7.33 (1H, t, J = 7.7 Hz), 8.27 (2H, d, J = 8.8 Hz), 12.96 (1H, br s). | 350 | 348 |

TABLE 2-8-continued

| | Structure | 1H-NMR | | |
|---|---|---|---|---|
| 2-71 | 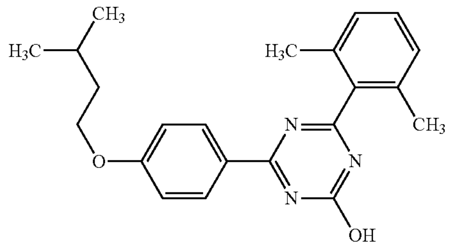 [SMILES: Cc1cccc(C)c1-c1nc(O)nc(-c2ccc(OCCC(C)C)cc2)n1] | 1H-NMR (DMSO-D6) δ: 0.92 (6H, d, J = 6.6 Hz), 1.63 (2H, q, J = 6.6 Hz), 1.72-1.82 (1H, m), 2.21 (6H, s), 4.08 (2H, t, J = 6.6 Hz), 7.05 (2H, d, J = 8.8 Hz), 7.18 (2H, d, J = 7.4 Hz), 7.33 (1H, t, J = 7.4 Hz), 8.27 (2H, d, J = 8.8 Hz), 12.96 (1H, br s). | 364 | 362 |
| 2-72 | 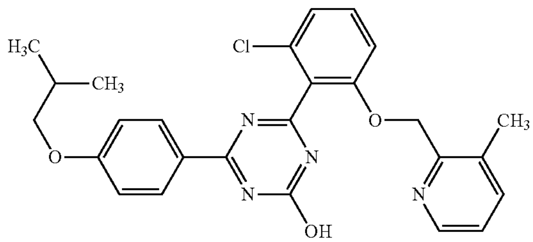 [SMILES: Cc1cccnc1COc1cccc(Cl)c1-c1nc(O)nc(-c2ccc(OCC(C)C)cc2)n1] | 1H-NMR (DMSO-D6) δ: 0.98 (6H, d, J = 6.5 Hz), 2.00-2.07 (1H, m), 2.19 (3H, s), 3.84 (2H, d, J = 6.5 Hz), 5.31 (2H, s), 7.05 (2H, d, J = 8.8 Hz), 7.20-7.26 (2H, m), 7.40 (1H, d, J = 8.1 Hz), 7.50-7.57 (2H, m), 8.23 (2H, d, J = 8.8 Hz), 8.33 (1H, d, J = 3.7 Hz), 13.25 (1H, br s). | 477 | 475 |

TABLE 2-9

| | Structure | 1H-NMR | | |
|---|---|---|---|---|
| 2-73 | 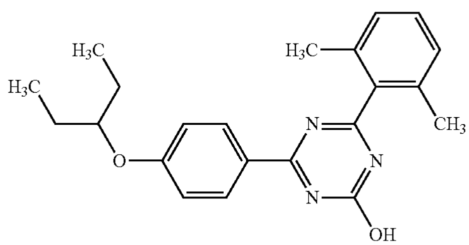 [SMILES: CCC(CC)Oc1ccc(-c2nc(O)nc(-c3c(C)cccc3C)n2)cc1] | 1H-NMR (DMSO-D6) δ: 0.90 (6H, t, J = 7.4 Hz), 1.60-1.69 (4H, m), 2.22 (6H, s), 4.36-4.42 (1H, m), 7.06 (2H, d, J = 8.8 Hz), 7.20 (2H, d, J = 7.5 Hz), 7.35 (1H, t, J = 7.5 Hz), 8.28 (2H, d, J = 8.8 Hz), 12.97 (1H, br s). | 364 | 362 |
| 2-74 | 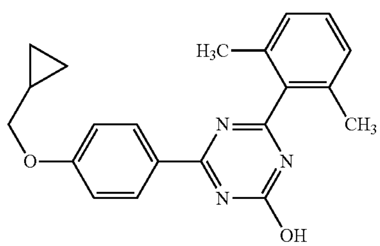 [SMILES: Cc1cccc(C)c1-c1nc(O)nc(-c2ccc(OCC3CC3)cc2)n1] | 1H-NMR (DMSO-D6) δ: 0.31-0.35 (2H, m), 0.55-0.59 (2H, m), 1.20-1.27 (1H, m), 2.21 (6H, s), 3.91 (2H, d, J = 7.0 Hz), 7.04 (2H, d, J = 8.8 Hz), 7.18 (2H, d, J = 7.4 Hz), 7.33 (1H, t, J = 7.4 Hz), 8.27 (2H, d, J = 8.8 Hz), 12.95 (1H, br s). | 348 | 346 |
| 2-75 | 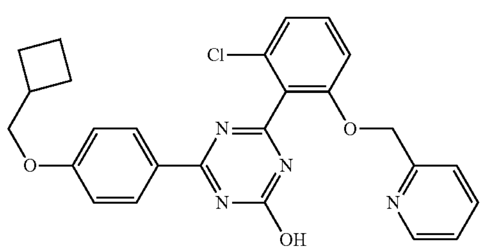 [SMILES: Oc1nc(-c2ccc(OCC3CCC3)cc2)nc(-c2c(Cl)cccc2OCc2ccccn2)n1] | 1H-NMR (DMSO-D6) δ: 1.94-1.80 (4H, m), 2.11-2.03 (2H, m), 2.76-2.69 (1H, m), 4.05 (2H, d, J = 6.7 Hz), 5.29 (2H, s), 7.07 (2H, d, J = 8.8 Hz), 7.29-7.23 (3H, m), 7.32 (1H, d, J = 7.9 Hz), 7.56-7.48 (1H, m), 7.71-7.66 (1H, m), 8.28 (2H, d, J = 8.8 Hz), 8.52-8.50 (1H, m), 13.28 (1H, br s). | 475 | 473 |
| 2-76 | 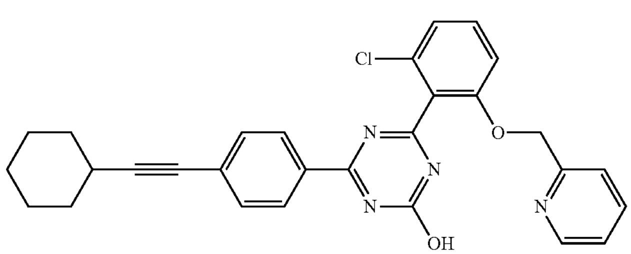 [SMILES: Oc1nc(-c2ccc(C#CC3CCCCC3)cc2)nc(-c2c(Cl)cccc2OCc2ccccn2)n1] | 1H-NMR (DMSO-D6) δ: 1.40-1.31 (3H, m), 1.54-1.45 (3H, m), 1.73-1.65 (2H, m), 1.88-1.80 (2H, m), 2.73-2.66 (1H, m), 5.31 (2H, s), 7.31-7.25 (3H, m), 7.33 (1H, d, J = 7.7 Hz), 7.57-7.51 (3H, m), 7.70 (1H, td, J = 7.7, 1.7 Hz), 8.30 (2H, d, J = 8.4 Hz), 8.52 (1H, d, J = 4.6 Hz), 13.53 (1H, br s). | 497 | 495 |

TABLE 2-9-continued

| 2-77 | (structure) | 1H-NMR (DMSO-D6) δ: 1.30-0.99 (5H, m), 1.83-1.60 (6H, m), 3.87 (2H, d, J = 6.3 Hz), 5.29 (2H, s), 7.06 (2H, d, J = 8.8 Hz), 7.29-7.23 (3H, m), 7.32 (1H, d, J = 7.7 Hz), 7.55-7.49 (1H, m), 7.68 (1H, t, J = 7.7 Hz), 8.27 (2H, d, J = 8.8 Hz), 8.51 (1H, d, J = 4.9 Hz), 13.27 (1H, br s). | 503 | 501 |
|---|---|---|---|---|
| 2-78 | (structure) | 1H-NMR (DMSO-D6) δ: 0.90 (3H, t, J = 7.3 Hz), 1.27 (3H, d, J = 6.0 Hz), 1.47-1.31 (2H, m), 1.60-1.51 (1H, m), 1.72-1.63 (1H, m), 4.65-4.59 (1H, m), 5.31 (2H, s), 7.06 (2H, d, J = 9.0 Hz), 7.31-7.24 (3H, m), 7.34 (1H, d, J = 7.7 Hz), 7.53 (1H, t, J = 7.7 Hz), 7.70 (1H, td, J = 7.7, 1.5 Hz), 8.28 (2H, d, J = 9.0 Hz), 8.53 (1H, d, J = 4.2 Hz), 13.28 (1H, br s). | 477 | 475 |
| 2-79 | (structure) | 1H-NMR (DMSO-D6) δ: 0.90 (3H, t, J = 7.3 Hz), 1.27 (3H, d, J = 6.0 Hz), 1.47-1.33 (2H, m), 1.61-1.51 (1H, m), 1.72-1.62 (1H, m), 4.65-4.59 (1H, m), 5.31 (2H, s), 7.06 (2H, d, J = 9.0 Hz), 7.31-7.24 (3H, m), 7.34 (1H, d, J = 7.9 Hz), 7.53 (1H, t, J = 7.9 Hz), 7.72-7.68 (1H, m), 8.28 (2H, d, J = 9.0 Hz), 8.53 (1H, d, J = 4.0 Hz), 13.28 (1H, br s). | 477 | 475 |
| 2-80 | (structure) | 1H-NMR (DMSO-D6) δ: 5.31 (2H, s), 7.30-7.25 (3H, m), 7.33 (1H, d, J = 7.7 Hz), 7.47-7.43 (3H, m), 7.54 (1H, t, J = 8.5 Hz), 7.62-7.57 (2H, m), 7.73-7.67 (3H, m), 8.36 (2H, d, J = 8.4 Hz), 8.52 (1H, d, J = 4.0 Hz), 13.56 (1H, br s). | 491 | 489 |

TABLE 2-10

| 2-81 | (structure) | 1H-NMR (DMSO-D6) δ: 1.76-1.54 (6H, m), 2.04-1.95 (2H, m), 2.95-2.88 (1H, m), 5.31 (2H, s), 7.34-7.25 (4H, m), 7.58-7.51 (3H, m), 7.70 (1H, td, J = 7.7, 1.8 Hz), 8.29 (2H, d, J = 8.4 Hz), 8.54-8.52 (1H, m), 13.53 (1H, br s). | 483 | 481 |
|---|---|---|---|---|
| 2-82 | (structure) | 1H-NMR (DMSO-D6) δ: 0.81-0.76 (2H, m), 0.96-0.90 (2H, m), 1.64-1.55 (1H, m), 5.31 (2H, s), 7.33-7.25 (4H, m), 7.58-7.50 (3H, m), 7.70 (1H, td, J = 7.7, 1.7 Hz), 8.28 (2H, d, J = 8.4 Hz), 8.53 (1H, d, J = 4.0 Hz), 13.52 (1H, br s). | 455 | 453 |

TABLE 2-10-continued

| No. | Structure | NMR | MW1 | MW2 |
|---|---|---|---|---|
| 2-83 | [structure] | 1H-NMR (DMSO-D6) δ: 1.31-1.40 (3H, m), 1.45-1.54 (3H, m), 1.65-1.72 (2H, m), 1.81-1.87 (2H, m), 2.67-2.72 (1H, m), 5.44 (2H, s), 7.25-7.30 (2H, m), 7.51-7.56 (4H, m), 8.14 (1H, d, J = 8.2 Hz), 8.29 (2H, d, J = 8.6 Hz), 8.94 (1H, s), 13.52 (1H, br s). | 565 | 563 |
| 2-84 | [structure] | 1H-NMR (DMSO-D6) δ: 0.94 (6H, d, J = 4.2 Hz), 1.35-1.25 (2H, m), 1.49-1.40 (2H, m), 1.66-1.55 (2H, m), 1.89-1.79 (2H, m), 4.53-4.44 (1H, m), 5.30 (2H, s), 7.07 (2H, d, J = 8.8 Hz), 7.31-7.21 (3H, m), 7.34 (1H, d, J = 7.7 Hz), 7.56-7.48 (1H, m), 7.70 (1H, t, J = 7.1 Hz), 8.27 (2H, d, J = 8.8 Hz), 8.53 (1H, d, J = 4.6 Hz), 13.28 (1H, s). | 517 | 515 |
| 2-85 | [structure] | 1H-NMR (DMSO-D6) δ: 5.38 (2H, s), 7.28 (1H, d, J = 8.1 Hz), 7.31 (1H, d, J = 8.1 Hz), 7.47-7.40 (5H, m), 7.55 (1H, d, J = 8.4 Hz), 7.61-7.57 (2H, m), 7.72 (2H, d, J = 8.8 Hz), 7.88-7.84 (1H, m), 8.36 (2H, d, J = 8.8 Hz), 8.58 (1H, d, J = 4.4 Hz). | 491 | 489 |
| 2-86 | [structure] | 1H-NMR (DMSO-D6) δ: 1.51 (3H, d, J = 6.4 Hz), 5.65 (1H, q, J = 6.4 Hz), 7.11 (1H, d, J = 8.6 Hz), 7.22 (1H, d, J = 7.7 Hz), 7.32 (1H, dd, J = 6.9, 5.4 Hz), 7.50-7.41 (5H, m), 7.63-7.59 (2H, m), 7.81-7.73 (3H, m), 8.40 (2H, d, J = 8.6 Hz), 8.55 (1H, d, J = 4.2 Hz). | 505 | 503 |
| 2-87 | [structure] | 1H-NMR (DMSO-D6) δ: 2.53 (3H, s), 5.40 (2H, s), 7.30 (1H, d, J = 8.2 Hz), 7.33 (1H, d, J = 8.2 Hz), 7.42-7.35 (2H, m), 7.49-7.44 (3H, m), 7.64-7.56 (3H, m), 7.73 (2H, d, J = 8.8 Hz), 7.91-7.88 (1H, m), 8.37 (2H, d, J = 8.8 Hz). | 505 | 503 |
| 2-88 | [structure] | 1H-NMR (CDCl3) δ: 5.50 (0.90H, s), 5.60 (1.10H, s), 7.43-7.30 (5.45H, m), 7.69-7.54 (5.00H, m), 7.90-7.78 (2.00H, m), 8.05 (0.45H, d, J = 7.9 Hz), 8.71-8.60 (2.55H, m), 8.88 (0.55H, d, J = 4.2 Hz), 11.44 (0.45H, s), 14.69 (0.55H, br s). | 482 | 480 |

TABLE 2-10-continued

| | | | | |
|---|---|---|---|---|
| 2-89 | (structure) | 1H-NMR (DMSO-D6) δ: 0.38-0.32 (2H, m), 0.62-0.56 (2H, m), 1.30-1.20 (1H, m), 3.93 (2H, d, J = 6.8 Hz), 5.32 (2H, s), 7.08 (2H, d, J = 7.5 Hz), 7.36-7.24 (4H, m), 7.54 (1H, t, J = 8.4 Hz), 7.71 (1H, t, J = 7.6 Hz), 8.29 (2H, d, J = 7.5 Hz), 8.53 (1H, d, J = 4.6 Hz). | 461 | 459 |

TABLE 2-11

| | | | | |
|---|---|---|---|---|
| 2-90 | (structure) | 1H-NMR (DMSO-D6) δ: 0.32-0.35 (2H, m), 0.55-0.59 (2H, m), 1.20-1.25 (1H, m), 2.79 (3H, s), 2.91 (3H, s), 3.91 (2H, d, J = 7.0 Hz), 4.98 (2H, s), 7.05 (2H, d, J = 8.8 Hz), 7.16 (1H, d, J = 8.4 Hz), 7.23 (1H, d, J = 8.4 Hz), 7.51 (1H, t, J = 8.4 Hz), 8.26 (2H, d, J = 8.8 Hz), 13.15 (1H, br s). | 455 | 453 |
| 2-91 | (structure) | 1H-NMR (DMSO-D6) δ: 1.76-1.53 (6H, m), 2.05-1.93 (2H, m), 2.95-2.88 (1H, m), 5.36 (2H, s), 7.28 (1H, dd, J = 7.9, 0.7 Hz), 7.30 (1H, d, J = 7.9 Hz), 7.43-7.36 (2H, m), 7.59-7.50 (3H, m), 7.81 (1H, td, J = 7.7, 1.8 Hz), 8.29 (2H, d, J = 8.6 Hz), 8.57 (1H, dq, J = 5.0, 0.8 Hz). | 483 | 481 |
| 2-92 | (structure) | 1H-NMR (DMSO-D6) δ: 1.41-1.30 (3H, m), 1.56-1.45 (3H, m), 1.74-1.64 (2H, m), 1.89-1.80 (2H, m), 2.74-2.65 (1H, m), 5.37 (2H, s), 7.28 (1H, dd, J = 8.0, 0.6 Hz), 7.31 (1H, d, J = 8.0 Hz), 7.46-7.40 (2H, m), 7.59-7.52 (3H, m), 7.85 (1H, td, J = 7.8, 1.6 Hz), 8.29 (2H, d, J = 8.6 Hz), 8.59-8.58 (1H, m). | 497 | 495 |
| 2-93 | (structure) | 1H-NMR (DMSO-D6) δ: 0.33-0.37 (2H, m), 0.54-0.59 (2H, m), 1.23-1.30 (1H, m), 4.21 (2H, d, J = 7.3 Hz), 5.23 (2H, s), 6.97 (1H, d, J = 8.8 Hz), 7.23-7.35 (7H, m), 7.55 (1H, t, J = 8.0 Hz), 8.48 (1H, dd, J = 8.8, 2.2 Hz), 9.05 (1H, d, J = 2.2 Hz), 13.41 (1H, br s). | 461 | 459 |

TABLE 2-11-continued

| | | | | |
|---|---|---|---|---|
| 2-94 | 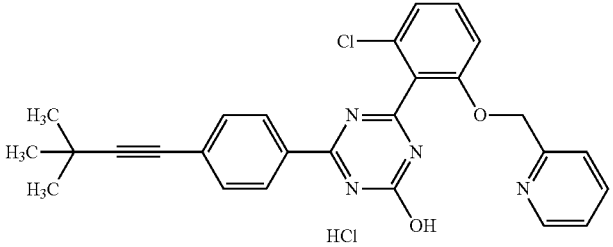 [SMILES: CC(C)(C)C#Cc1ccc(-c2nc(O)nc(-c3c(Cl)cccc3OCc3ccccn3)n2)cc1 ; Cl] | 1H-NMR (DMSO-D6) δ: 1.31 (9H, s), 5.38 (2H, s), 7.28 (1H, d, J = 8.2 Hz), 7.31 (1H, d, J = 8.2 Hz), 7.47-7.41 (2H, m), 7.52 (2H, d, J = 8.8 Hz), 7.56 (1H, t, J = 8.4 Hz), 7.86 (1H, td, J = 7.7, 1.5 Hz), 8.29 (2H, d, J = 8.8 Hz), 8.59 (1H, dd, J = 5.0, 0.8 Hz). | 471 | 469 |
| 2-95 | 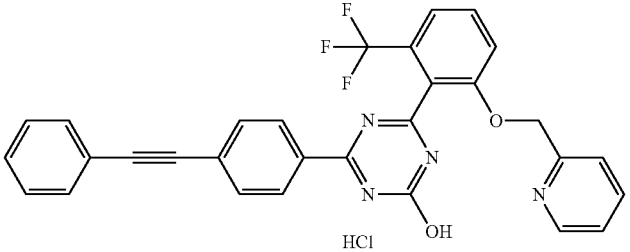 [SMILES: Oc1nc(-c2ccc(C#Cc3ccccc3)cc2)nc(-c2c(OCc3ccccn3)cccc2C(F)(F)F)n1 ; Cl] | 1H-NMR (DMSO-D6) δ: 5.38 (2H, s), 7.39-7.34 (2H, m), 7.46-7.43 (3H, m), 7.54 (1H, d, J = 7.9 Hz), 7.61-7.57 (2H, m), 7.66 (1H, d, J = 8.6 Hz), 7.72 (2H, d, J = 8.4 Hz), 7.82-7.76 (2H, m), 8.34 (2H, d, J = 8.4 Hz), 8.56 (1H, d, J = 4.9 Hz). | 525 | 523 |
| 2-96 | 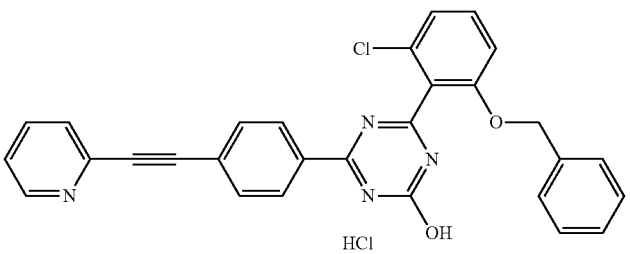 [SMILES: Oc1nc(-c2ccc(C#Cc3ccccn3)cc2)nc(-c2c(Cl)cccc2OCc2ccccc2)n1 ; Cl] | 1H-NMR (DMSO-D6) δ: 5.25 (2H, s), 7.36-7.24 (8H, m), 7.46 (1H, ddd, J = 7.8, 4.9, 1.0 Hz), 7.57 (1H, t, J = 8.3 Hz), 7.72 (1H, dt, J = 7.8, 1.0 Hz), 7.79 (2H, d, J = 8.6 Hz), 7.90 (1H, td, J = 7.8, 1.8 Hz), 8.40 (2H, d, J = 8.6 Hz), 8.65 (1H, dq, J = 4.9, 0.9 Hz). | 491 | 489 |
| 2-97 | 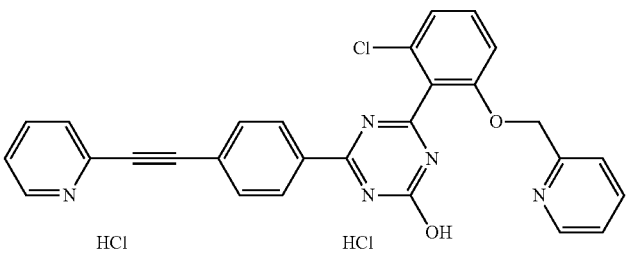 [SMILES: Oc1nc(-c2ccc(C#Cc3ccccn3)cc2)nc(-c2c(Cl)cccc2OCc2ccccn2)n1 ; Cl ; Cl] | 1H-NMR (DMSO-D6) δ: 5.40 (2H, s), 7.30 (1H, dd, J = 8.2, 0.7 Hz), 7.33 (1H, d, J = 8.2 Hz), 7.51-7.43 (3H, m), 7.58 (1H, t, J = 8.2 Hz), 7.75 (1H, dt, J = 7.8, 1.0 Hz), 7.80 (2H, dd, J = 6.7, 1.9 Hz), 7.95-7.87 (2H, m), 8.40 (2H, dd, J = 6.7, 1.9 Hz), 8.61 (1H, d, J = 5.0 Hz), 8.66 (1H, dq, J = 5.0, 0.9 Hz). | 492 | 490 |
| 2-98 | 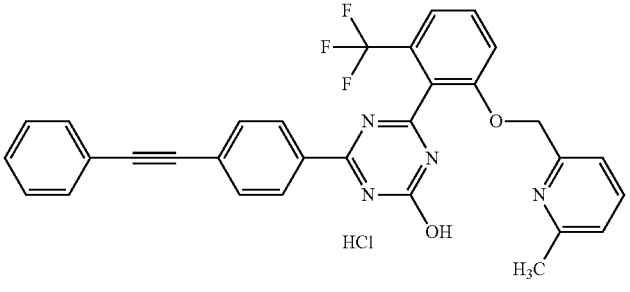 [SMILES: Cc1cccc(COc2cccc(C(F)(F)F)c2-c2nc(O)nc(-c3ccc(C#Cc4ccccc4)cc3)n2)n1 ; Cl] | 1H-NMR (DMSO-D6) δ: 2.48 (3H, s), 5.37 (2H, s), 7.23 (1H, d, J = 7.3 Hz), 7.28 (1H, d, J = 7.3 Hz), 7.48-7.45 (3H, m), 7.56 (1H, d, J = 7.9 Hz), 7.64-7.59 (2H, m), 7.67 (1H, d, J = 8.6 Hz), 7.82-7.72 (4H, m), 8.35 (2H, dd, J = 6.8, 2.0 Hz). | 539 | 537 |

TABLE 2-12

| | | | | |
|---|---|---|---|---|
| 2-99 | (structure) | 1H-NMR (DMSO-D6) δ: 2.41 (3H, s), 5.30 (2H, s), 7.09 (1H, d, J = 7.7 Hz), 7.14 (1H, d, J = 7.7 Hz), 7.51-7.45 (3H, m), 7.54 (1H, d, J = 7.7 Hz), 7.60 (1H, t, J = 7.7 Hz), 7.66-7.64 (3H, m), 7.78 (1H, d, J = 8.2 Hz), 7.81 (1H, dd, J = 8.2, 0.8 Hz), 8.61 (1H, dd, J = 8.2, 0.8 Hz), 9.40-9.39 (1H, m), 13.78 (1H, br s). | 540 | 538 |
| 2-100 | (structure) | 1H-NMR (DMSO-D6) δ: 2.50 (3H, s), 5.41 (2H, s), 7.29-7.24 (1H, m), 7.35 (2H, dd, J = 4.9, 1.1 Hz), 7.43-7.39 (2H, m), 7.56 (2H, dd, J = 7.7, 4.2 Hz), 7.67 (1H, d, J = 8.6 Hz), 7.73 (2H, d, J = 8.6 Hz), 7.86-7.78 (2H, m), 8.36 (2H, d, J = 8.6 Hz), 8.59-8.57 (1H, m). | 539 | 537 |
| 2-101 | (structure) | 1H-NMR (DMSO-D6) δ: 2.34 (3H, s), 5.41 (2H, s), 7.27 (1H, d, J = 7.7 Hz), 7.34 (1H, t, J = 7.7 Hz), 7.43-7.39 (4H, m), 7.56 (1H, d, J = 7.7 Hz), 7.68 (1H, d, J = 8.4 Hz), 7.72 (2H, dd, J = 6.7, 1.9 Hz), 7.87-7.78 (2H, m), 8.35 (2H, dd, J = 6.7, 1.9 Hz), 8.59 (1H, d, J = 4.4 Hz). | 539 | 537 |
| 2-102 | (structure) | 1H-NMR (DMSO-D6) δ: 2.35 (3H, s), 5.40 (2H, s), 7.27 (2H, d, J = 7.9 Hz), 7.42-7.37 (2H, m), 7.49 (2H, d, J = 7.9 Hz), 7.56 (1H, d, J = 7.9 Hz), 7.67 (1H, d, J = 8.6 Hz), 7.71 (2H, d, J = 8.6 Hz), 7.85-7.77 (2H, m), 8.34 (2H, d, J = 8.6 Hz), 8.58 (1H, dq, J = 4.9, 0.9 Hz). | 539 | 537 |
| 2-103 | (structure) | 1H-NMR (DMSO-D6) δ: 5.39 (2H, s), 7.39-7.35 (2H, m), 7.56 (1H, d, J = 7.9 Hz), 7.69-7.64 (2H, m), 7.72 (2H, dd, J = 6.7, 1.9 Hz), 7.83-7.75 (3H, m), 7.89-7.85 (2H, m), 8.39 (2H, dd, J = 6.7, 1.9 Hz), 8.57 (1H, d, J = 4.9 Hz). | 593 | 591 |
| 2-104 | (structure) | 1H-NMR (DMSO-D6) δ: 5.40 (2H, s), 7.40-7.36 (2H, m), 7.56 (1H, d, J = 7.9 Hz), 7.67 (1H, d, J = 8.6 Hz), 7.72 (1H, d, J = 7.9 Hz), 7.84-7.76 (5H, m), 7.92 (1H, d, J = 7.7 Hz), 7.99 (1H, br s), 8.37 (2H, dd, J = 6.8, 2.0 Hz), 8.57 (1H, dq, J = 4.9, 0.9 Hz). | 593 | 591 |

TABLE 2-12-continued

| | | | | |
|---|---|---|---|---|
| 2-105 | | 1H-NMR (DMSO-D6) δ: 5.40 (2H, s), 7.41-7.36 (2H, m), 7.56 (1H, d, J = 7.9 Hz), 7.68 (1H, d, J = 8.6 Hz), 7.84-7.77 (8H, m), 8.37 (2H, dd, J = 6.7, 1.9 Hz), 8.57 (1H, d, J = 4.9 Hz). | 593 | 591 |
| 2-106 | | 1H-NMR (DMSO-D6) δ: 5.40 (2H, s), 7.41-7.36 (2H, m), 7.51-7.45 (3H, m), 7.57 (1H, d, J = 7.7 Hz), 7.64-7.60 (2H, m), 7.68 (1H, d, J = 8.4 Hz), 7.84-7.79 (3H, m), 8.10 (1H, dd, J = 10.5, 1.4 Hz), 8.19 (1H, dd, J = 8.2, 1.5 Hz), 8.57 (1H, dq, J = 4.9, 0.9 Hz). | 543 | 541 |
| 2-107 | | 1H-NMR (DMSO-D6) δ: 2.54 (3H, s), 5.45 (2H, s), 7.30 (1H, td, J = 7.6, 1.1 Hz), 7.44-7.35 (3H, m), 7.56-7.50 (1H, m), 7.58 (1H, d, J = 7.9 Hz), 7.71-7.67 (2H, m), 7.75 (2H, dd, J = 6.7, 1.9 Hz), 7.81 (1H, t, J = 7.9 Hz), 7.92 (1H, br s), 8.36 (2H, dd, J = 6.7, 1.9 Hz). | 557 | 555 |

TABLE 2-13

| | | | | |
|---|---|---|---|---|
| 2-108 | | 1H-NMR (DMSO-D6) δ: 2.52 (3H, s), 5.43 (2H, s), 7.33 (1H, d, J = 7.7 Hz), 7.38 (1H, d, J = 7.7 Hz), 7.43 (1H, td, J = 7.7, 1.4 Hz), 7.48 (1H, td, J = 7.7, 1.9 Hz), 7.57 (1H, d, J = 8.0 Hz), 7.63 (1H, dd, J = 8.0, 1.2 Hz), 7.68 (1H, d, J = 8.3 Hz), 7.76-7.72 (3H, m), 7.81 (1H, t, J = 8.3 Hz), 7.90-7.84 (1H, m), 8.37 (2H, dd, J = 6.7, 1.9 Hz). | 573 | 571 |
| 2-109 | | 1H-NMR (DMSO-D6) δ: 2.51 (3H, s), 3.88 (3H, s), 5.41 (2H, s), 7.00 (1H, td, J = 7.5, 0.9 Hz), 7.12 (1H, d, J = 7.9 Hz), 7.29 (1H, d, J = 7.9 Hz), 7.34 (1H, d, J = 7.5 Hz), 7.43 (1H, ddd, J = 8.8, 7.1, 1.3 Hz), 7.52 (1H, dd, J = 7.5, 1.7 Hz), 7.57 (1H, d, J = 7.9 Hz), 7.69-7.66 (3H, m), 7.85-7.78 (2H, m), 8.34 (2H, dd, J = 6.8, 2.0 Hz). | 569 | 567 |

TABLE 2-13-continued

| 2-110 | [structure] | 1H-NMR (DMSO-D6) δ: 2.24 (3H, s), 2.49 (3H, s), 5.41 (2H, s), 7.22 (1H, br s), 7.31 (1H, br s), 7.46-7.43 (3H, m), 7.60-7.57 (3H, m), 7.72-7.68 (3H, m), 7.82 (1H, t, J = 8.3 Hz), 8.33 (2H, dd, J = 6.7, 1.8 Hz). | 553 | 551 |
| --- | --- | --- | --- | --- |
| 2-111 | [structure] | 1H-NMR (DMSO-D6) δ: 5.42 (2H, d, J = 1.6 Hz), 7.42-7.48 (4H, m), 7.54 (1H, t, J = 4.2 Hz), 7.59-7.63 (2H, m), 7.64-7.73 (3H, m), 7.81 (2H, d, J = 4.2 Hz), 8.29 (2H, d, J = 8.6 Hz), 8.35-8.37 (1H, m). | 543 | 541 |
| 2-112 | [structure] | 1H-NMR (DMSO-D6) δ: 5.37 (2H, s), 7.37 (1H, d, J = 8.3 Hz), 7.44-7.48 (3H, m), 7.55 (1H, d, J = 7.6 Hz), 7.58-7.66 (3H, m), 7.73 (2H, d, J = 8.6 Hz), 7.79 (1H, t, J = 8.1 Hz), 7.88 (1H, dd, J = 8.6, 2.3 Hz), 8.34 (2H, d, J = 8.6 Hz), 8.59 (1H, d, J = 2.3 Hz). | 559 | 557 |
| 2-113 | [structure] | 1H-NMR (DMSO-D6) δ: 2.27 (3H, s), 5.43 (2H, s), 7.35 (1H, s), 7.39 (1H, d, J = 5.8 Hz), 7.44-7.48 (3H, m), 7.57-7.63 (3H, m), 7.69-7.75 (3H, m), 7.83 (1H, t, J = 8.1 Hz), 8.35 (2H, d, J = 8.3 Hz), 8.51 (1H, d, J = 5.3 Hz). | 539 | 537 |
| 2-114 | [structure] | 1H-NMR (DMSO-D6) δ: 7.36 (1H, d, J = 7.9 Hz), 7.44-7.48 (3H, m), 7.56 (1H, d, J = 7.9 Hz), 7.59-7.63 (2H, m), 7.66-7.75 (4H, m), 7.79 (1H, t, J = 8.1 Hz), 8.34 (2H, d, J = 8.6 Hz), 8.44 (1H, s). | 539 | 537 |
| 2-115 | [structure] | 1H-NMR (DMSO-D6) δ: 5.36 (2H, s), 7.41 (1H, dd, J = 8.8, 4.4 Hz), 7.44-7.48 (3H, m), 7.55 (1H, d, J = 7.9 Hz), 7.58-7.63 (2H, m), 7.65-7.75 (4H, m), 7.79 (1H, t, J = 8.1 Hz), 8.34 (2H, d, J = 8.6 Hz), 8.53 (1H, d, J = 3.0 Hz). | 543 | 541 |

TABLE 2-13-continued

| | | |
|---|---|---|
| 2-116 | [structure] HCl | 1H-NMR (DMSO-D6) δ: 2.53 (3H, s), 5.44 (2H, s), 7.54-7.30 (6H, m), 7.58 (1H, d, J = 7.7 Hz), 7.69 (1H, d, J = 8.0 Hz), 7.74 (2H, dd, J = 6.8, 1.8 Hz), 7.81 (1H, t, J = 8.0 Hz), 7.90 (1H, br s), 8.35 (2H, dd, J = 6.8, 1.8 Hz). | 557 555 |

TABLE 2-14

| | | |
|---|---|---|
| 2-117 | [structure] HCl | 1H-NMR (DMSO-D6) δ: 2.51 (3H, s), 5.42 (2H, s), 7.33-7.29 (3H, m), 7.37 (1H, d, J = 7.9 Hz), 7.57 (1H, d, J = 7.9 Hz), 7.69-7.65 (3H, m), 7.72 (2H, dd, J = 6.8, 1.8 Hz), 7.89-7.78 (2H, m), 8.34 (2H, dd, J = 6.8, 1.8 Hz). | 557 555 |
| 2-118 | [structure] | 1H-NMR (CDCl3) δ: 3.87 (3H, s), 5.27 (2H, s), 6.61 (1H, d, J = 8.2 Hz), 6.86 (1H, d, J = 7.3 Hz), 7.31 (1H, d, J = 8.6 Hz), 7.35-7.39 (3H, m), 7.43-7.51 (2H, m), 7.53-7.60 (3H, m), 7.64 (2H, d, J = 8.4 Hz), 8.50 (2H, d, J = 8.4 Hz). | 555 553 |
| 2-119 | [structure] | 1H-NMR (DMSO-D6) δ: 5.10 (2H, s), 6.16-6.32 (2H, m), 7.32-7.38 (1H, m), 7.44-7.48 (3H, m), 7.54-7.63 (4H, m), 7.70-7.75 (2H, m), 7.77-7.84 (1H, m), 8.34 (2H, d, J = 8.6 Hz). | 541 539 |
| 2-120 | [structure] HCl | 1H-NMR (DMSO-D6) δ: 3.89 (3H, s), 5.48 (2H, s), 7.20-7.26 (2H, m), 7.44-7.49 (3H, m), 7.58-7.64 (3H, m), 7.69-7.75 (3H, m), 7.84 (1H, t, J = 8.2 Hz), 8.33 (2H, d, J = 8.6 Hz), 8.56 (1H, d, J = 6.0 Hz). | 555 553 |

TABLE 2-14-continued

| | | | | |
|---|---|---|---|---|
| 2-121 | | 1H-NMR (DMSO-D6) δ: 5.47 (2H, s), 7.44-7.48 (3H, m), 7.55-7.63 (4H, m), 7.68 (1H, d, J = 8.6 Hz), 7.73 (2H, d, J = 8.6 Hz), 7.78-7.84 (2H, m), 8.03 (1H, t, J = 8.1 Hz), 8.35 (2H, d, J = 8.6 Hz), 13.58 (1H, br s). | 593 | 591 |
| 2-122 | | 1H-NMR (DMSO-D6) δ: 5.47 (2H, s), 7.44-7.51 (4H, m), 7.56-7.63 (3H, m), 7.67-7.74 (4H, m), 7.82 (1H, t, J = 8.1 Hz), 8.34 (2H, d, J = 8.6 Hz), 8.83 (1H, d, J = 5.1 Hz). | 593 | 591 |
| 2-123 | | 1H-NMR (DMSO-D6) δ: 2.50 (3H, s), 5.40 (2H, s), 7.29 (1H, d, J = 7.7 Hz), 7.33 (1H, d, J = 7.7 Hz), 7.59-7.46 (4H, m), 7.68 (1H, d, J = 8.4 Hz), 7.71-7.69 (1H, m), 7.75 (2H, dd, J = 6.7, 1.9 Hz), 7.84-7.78 (2H, m), 8.36 (2H, dd, J = 6.7, 1.9 Hz). | 573 | 571 |
| 2-124 | | 1H-NMR (DMSO-D6) δ: 2.49 (3H, s), 5.39 (2H, s), 7.26 (1H, d, J = 7.5 Hz), 7.31 (1H, d, J = 7.5 Hz), 7.53 (2H, dt, J = 8.7, 2.2 Hz), 7.56 (1H, d, J = 7.9 Hz), 7.63 (2H, dt, J = 8.7, 2.2 Hz), 7.67 (1H, d, J = 8.4 Hz), 7.74 (2H, dd, J = 6.7, 1.9 Hz), 7.83-7.76 (2H, m), 8.35 (2H, dd, J = 6.7, 1.9 Hz). | 573 | 571 |
| 2-125 | | 1H-NMR (DMSO-D6) δ: 2.50 (3H, s), 3.80 (3H, s), 5.40 (2H, s), 7.03 (1H, dq, J = 8.6, 1.2 Hz), 7.19-7.14 (2H, m), 7.29 (1H, d, J = 7.3 Hz), 7.39-7.32 (2H, m), 7.57 (1H, d, J = 7.9 Hz), 7.67 (1H, d, J = 8.6 Hz), 7.73 (2H, dd, J = 6.7, 1.9 Hz), 7.85-7.77 (2H, m), 8.34 (2H, dd, J = 6.7, 1.9 Hz). | 569 | 567 |

TABLE 2-15

| | | | | |
|---|---|---|---|---|
| 2-126 | (structure) | 1H-NMR (DMSO-D6) δ: 2.49 (3H, s), 3.81 (3H, s), 5.40 (2H, s), 7.01 (2H, dt, J = 9.5, 2.4 Hz), 7.28 (1H, d, J = 6.8 Hz), 7.32 (1H, d, J = 7.5 Hz), 7.57-7.53 (3H, m), 7.70-7.66 (3H, m), 7.80 (2H, t, J = 7.9 Hz), 8.33 (2H, dd, J = 6.8, 2.0 Hz). | 569 | 567 |
| 2-127 | (structure) | 1H-NMR (DMSO-D6) δ: 2.35 (3H, s), 2.51 (3H, s), 5.42 (2H, s), 7.27 (2H, d, J = 7.7 Hz), 7.32 (1H, d, J = 7.7 Hz), 7.36 (1H, d, J = 7.7 Hz), 7.49 (2H, d, J = 8.2 Hz), 7.57 (1H, d, J = 7.7 Hz), 7.72-7.66 (3H, m), 7.88-7.77 (2H, m), 8.33 (2H, dd, J = 6.7, 1.9 Hz). | 553 | 551 |
| 2-128 | (structure) | 1H-NMR (DMSO-D6) δ: 1.19 (3H, t, J = 7.5 Hz), 2.52 (3H, s), 2.65 (2H, q, J = 7.6 Hz), 5.43 (2H, s), 7.30 (2H, d, J = 8.4 Hz), 7.34 (1H, d, J = 7.7 Hz), 7.39 (1H, d, J = 7.7 Hz), 7.52 (2H, d, J = 8.4 Hz), 7.57 (1H, d, J = 7.7 Hz), 7.72-7.67 (3H, m), 7.81 (1H, t, J = 8.3 Hz), 7.87 (1H, br s), 8.33 (2H, dd, J = 6.7, 1.9 Hz). | 567 | 565 |
| 2-129 | (structure) | 1H-NMR (DMSO-D6) δ: 2.51 (3H, s), 5.42 (2H, s), 7.32 (1H, d, J = 7.1 Hz), 7.37 (1H, d, J = 7.7 Hz), 7.63-7.48 (4H, m), 7.72-7.67 (3H, m), 7.89-7.77 (3H, m), 8.37 (2H, dd, J = 6.8, 2.0 Hz). | 623 | 621 |
| 2-130 | (structure) | 1H-NMR (DMSO-D6) δ: 2.55 (3H, s), 5.47 (2H, s), 7.40 (1H, d, J = 7.1 Hz), 7.48-7.43 (3H, m), 7.58 (1H, d, J = 7.7 Hz), 7.69 (1H, d, J = 8.5 Hz), 7.77-7.72 (4H, m), 7.82 (1H, t, J = 8.5 Hz), 7.95 (1H, br s), 8.35 (2H, dd, J = 6.7, 1.9 Hz). | 623 | 621 |

TABLE 3-1
| Example | Structure | NMR | MS (M + H) | MS (M − H) | Note |
|---|---|---|---|---|---|
| 3-1 | 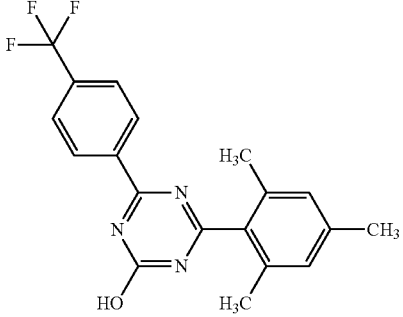 [SMILES: Cc1cc(C)c(-c2nc(O)nc(-c3ccc(C(F)(F)F)cc3)n2)c(C)c1] | 1H-NMR (DMSO-D6) δ: 2.19 (6H, s), 2.30 (3H, s), 7.01 (2H, s), 7.90 (2H, d, J = 8.4 Hz), 8.51 (2H, d, J = 8.4 Hz), 13.26 (1H, br s). | 360 | 358 | |
| 3-2 | 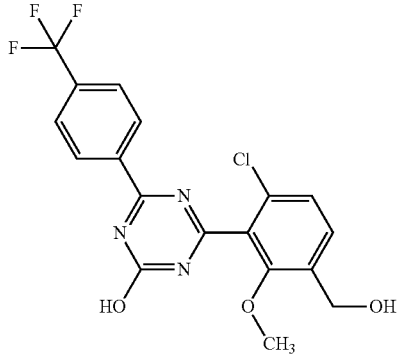 [SMILES: COc1c(CO)ccc(Cl)c1-c1nc(O)nc(-c2ccc(C(F)(F)F)cc2)n1] | 1H-NMR (DMSO-D6) δ: 3.72 (3H, s), 4.59 (2H, d, J = 5.5 Hz), 5.41 (1H, t, J = 5.5 Hz), 7.45 (1H, d, J = 8.4 Hz), 7.67 (1H, d, J = 8.4 Hz), 7.92 (2H, d, J = 8.4 Hz), 8.53 (2H, d, J = 8.4 Hz), 13.70 (1H, br s). | 412 | 410 | |
| 3-3 | 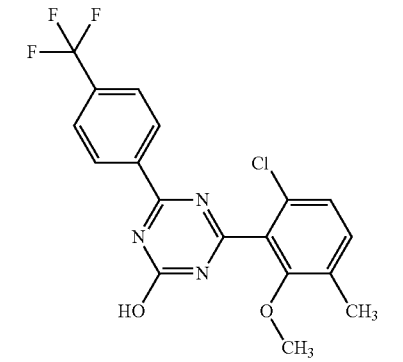 [SMILES: COc1c(C)ccc(Cl)c1-c1nc(O)nc(-c2ccc(C(F)(F)F)cc2)n1] | 1H-NMR (DMSO-D6) δ: 2.31 (3H, s), 3.71 (3H, s), 7.36 (1H, d, J = 8.4 Hz), 7.49 (1H, d, J = 8.4 Hz), 7.93 (2H, d, J = 8.3 Hz), 8.53 (2H, d, J = 8.3 Hz), 13.67 (1H, br s). | 396 | 394 | |
| 3-4 | 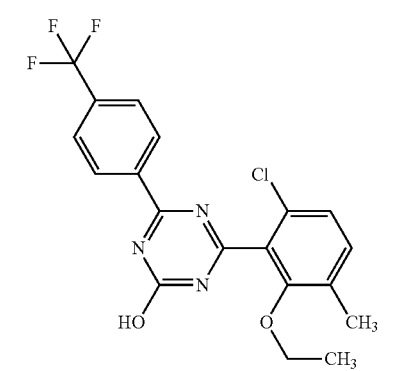 [SMILES: CCOc1c(C)ccc(Cl)c1-c1nc(O)nc(-c2ccc(C(F)(F)F)cc2)n1] | 1H-NMR (DMSO-D6) δ: 1.09 (3H, t, J = 7.0 Hz), 2.30 (3H, s), 3.94 (2H, q, J = 7.0 Hz), 7.34 (1H, d, J = 8.2 Hz), 7.48 (1H, d, J = 8.2 Hz), 7.93 (2H, d, J = 8.2 Hz), 8.53 (2H, d, J = 8.2 Hz), 13.66 (1H, br s). | 410 | 408 | |

TABLE 3-1-continued

| Example | Structure | NMR | MS (M + H) | MS (M − H) | Note |
|---|---|---|---|---|---|
| 3-5 | 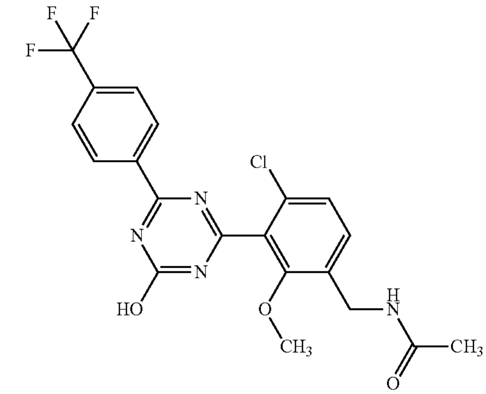 [SMILES: COc1c(CNC(C)=O)ccc(Cl)c1-c1nc(O)nc(-c2ccc(C(F)(F)F)cc2)n1] | 1H-NMR (DMSO-D6) δ: 1.91 (3H, s), 3.74 (3H, s), 4.32 (2H, d, J = 5.8 Hz), 7.43 (1H, d, J = 8.4 Hz), 7.49 (1H, d, J = 8.4 Hz), 7.92 (2H, d, J = 8.4 Hz), 8.42 (1H, t, J = 5.8 Hz), 8.53 (2H, d, J = 8.4 Hz), 13.73 (1H, br s). | 453 | 451 | |
| 3-6 | 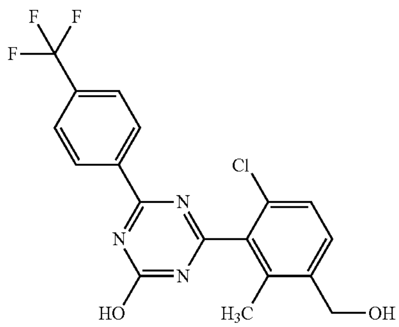 [SMILES: Cc1c(CO)ccc(Cl)c1-c1nc(O)nc(-c2ccc(C(F)(F)F)cc2)n1] | 1H-NMR (DMSO-D6) δ: 2.17 (3H, s), 4.55 (2H, d, J = 5.1 Hz), 5.35 (1H, t, J = 5.2 Hz), 7.48 (1H, d, J = 8.4 Hz), 7.60 (1H, d, J = 8.4 Hz), 7.91 (2H, d, J = 8.6 Hz), 8.51 (2H, d, J = 8.6 Hz), 13.61 (1H, br s). | 396 | 394 | |
| 3-7 | 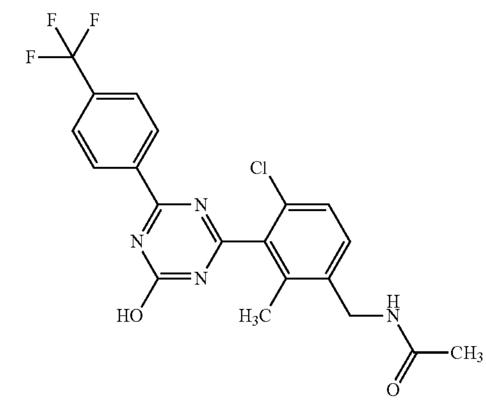 [SMILES: CC(=O)NCc1ccc(Cl)c(-c2nc(O)nc(-c3ccc(C(F)(F)F)cc3)n2)c1C] | 1H-NMR (DMSO-D6) δ: 1.90 (3H, s), 2.21 (3H, s), 4.28 (2H, d, J = 5.7 Hz), 7.41 (1H, d, J = 8.4 Hz), 7.47 (1H, d, J = 8.4 Hz), 7.91 (2H, d, J = 8.2 Hz), 8.37 (1H, t, J = 5.8 Hz), 8.51 (2H, d, J = 8.2 Hz), 13.62 (1H, br s). | 437 | 435 | |
| 3-8 | 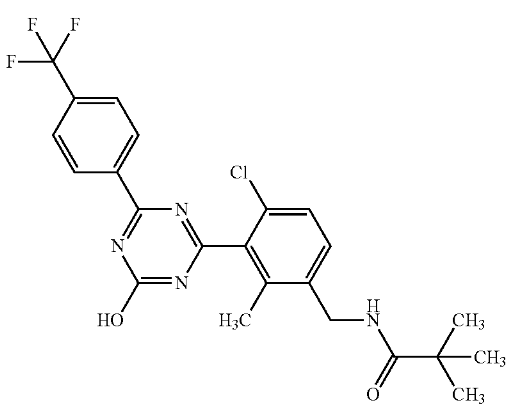 [SMILES: Cc1c(CNC(=O)C(C)(C)C)ccc(Cl)c1-c1nc(O)nc(-c2ccc(C(F)(F)F)cc2)n1] | 1H-NMR (DMSO-D6) δ: 1.16 (9H, s), 2.21 (3H, s), 4.27 (2H, d, J = 5.7 Hz), 7.34 (1H, d, J = 8.4 Hz), 7.46 (1H, d, J = 8.4 Hz), 7.91 (2H, d, J = 8.2 Hz), 8.09 (1H, t, J = 5.6 Hz), 8.51 (2H, d, J = 8.2 Hz), 13.64 (1H, br s). | 479 | 477 | |

TABLE 3-2
| 3-9 | 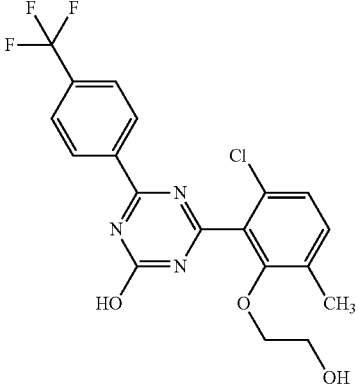 [SMILES: Cc1ccc(Cl)c(-c2nc(O)nc(-c3ccc(C(F)(F)F)cc3)n2)c1OCCO] | 1H-NMR (DMSO-D6) δ: 2.32 (3H, s), 3.47 (2H, t, J = 4.9 Hz), 3.88 (2H, t, J = 4.8 Hz), 4.70 (1H, br s), 7.34 (1H, d, J = 8.1 Hz), 7.47 (1H, d, J = 8.1 Hz), 7.92 (2H, d, J = 8.4 Hz), 8.51 (2H, d, J = 8.4 Hz), 13.56 (1H, br s). | 426 | 424 |
|---|---|---|---|---|
| 3-10 | 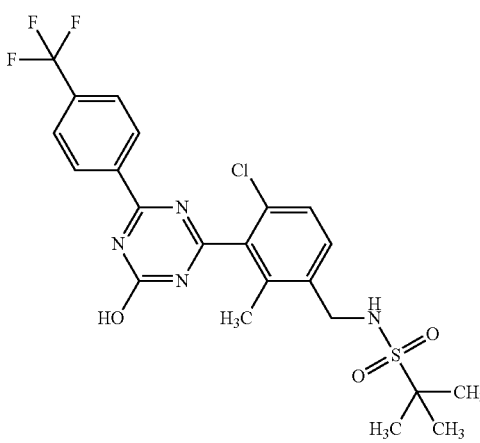 | 1H-NMR (DMSO-D6) δ: 1.33 (9H, s), 2.22 (3H, s), 4.30 (2H, d, J = 6.0 Hz), 7.52-7.54 (2H, m), 7.60 (1H, d, J = 8.4 Hz), 7.91 (2H, d, J = 8.4 Hz), 8.51 (2H, d, J = 8.4 Hz), 13.65 (1H, br s). | 515 | 513 |
| 3-11 | 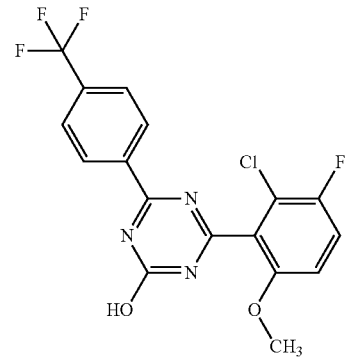 [SMILES: COc1ccc(F)c(Cl)c1-c1nc(O)nc(-c2ccc(C(F)(F)F)cc2)n1] | 1H-NMR (DMSO-D6) δ: 3.79-3.87 (3H, m), 7.28 (1H, dd, J = 9.3, 3.7 Hz), 7.67 (1H, t, J = 9.2 Hz), 7.93 (2H, d, J = 8.6 Hz), 8.51 (2H, d, J = 8.6 Hz), 13.68 (1H, br s). | 400 | 398 |
| 3-12 | 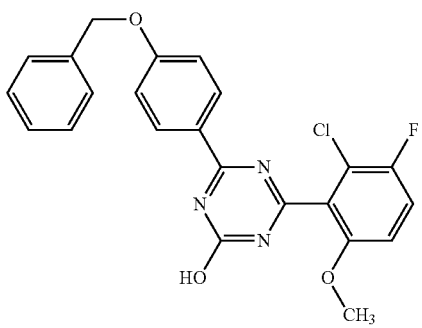 [SMILES: COc1ccc(F)c(Cl)c1-c1nc(O)nc(-c2ccc(OCc3ccccc3)cc2)n1] | 1H-NMR (DMSO-D6) δ: 3.82 (3H, s), 5.22 (2H, s), 7.17 (2H, d, J = 9.0 Hz), 7.24-7.27 (1H, br m), 7.35 (1H, t, J = 7.2 Hz), 7.41 (2H, t, J = 7.3 Hz), 7.47 (2H, d, J = 7.1 Hz), 7.63-7.66 (1H, br m), 8.28 (2H, d, J = 9.0 Hz), 13.26 (1H, br s). | 438 | 436 |

TABLE 3-2-continued
| | | | | |
|---|---|---|---|---|
| 3-13 | 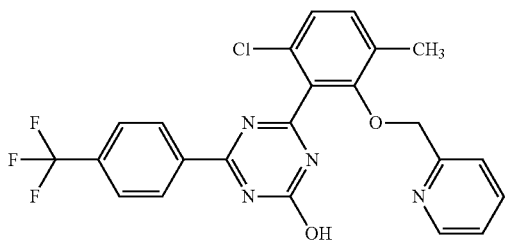 [SMILES: Cc1ccc(Cl)c(-c2nc(O)nc(-c3ccc(C(F)(F)F)cc3)n2)c1OCc1ccccn1] | 1H-NMR (DMSO-D6) δ: 2.36 (3H, s), 5.01 (2H, s), 7.11-7.15 (1H, m), 7.22 (1H, d, J = 7.7 Hz), 7.39 (1H, d, J = 8.4 Hz), 7.52 (1H, d, J = 8.4 Hz), 7.60 (1H, td, J = 7.7, 1.7 Hz), 7.86 (2H, d, J = 8.4 Hz), 8.31 (1H, d, J = 4.0 Hz), 8.41 (2H, d, J = 8.4 Hz), 13.61 (1H, br s). | 473 | 471 |
| 3-14 | 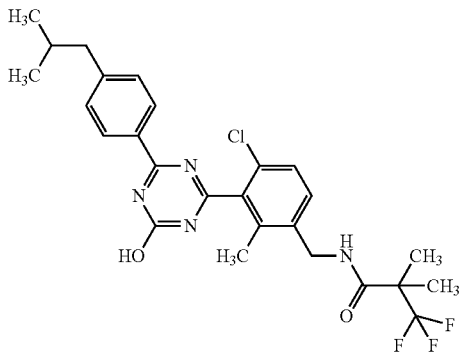 [SMILES: Cc1c(CNC(=O)C(C)(C)C(F)(F)F)ccc(Cl)c1-c1nc(O)nc(-c2ccc(CC(C)C)cc2)n1] | 1H-NMR (DMSO-D6) δ: 0.88 (6H, d, J = 6.6 Hz), 1.41 (6H, s), 1.83-1.95 (1H, m), 2.19 (3H, s), 2.54 (2H, d, J = 7.3 Hz), 4.33 (2H, d, J = 5.5 Hz), 7.28-7.38 (3H, m), 7.46 (1H, d, J = 8.4 Hz), 8.24 (2H, d, J = 8.2 Hz), 8.52-8.60 (1H, m), 13.35 (1H, br s). | 521 | 519 |
| 3-15 | 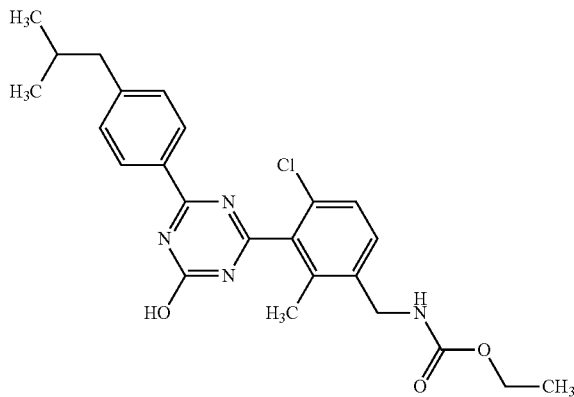 [SMILES: CCOC(=O)NCc1ccc(Cl)c(-c2nc(O)nc(-c3ccc(CC(C)C)cc3)n2)c1C] | 1H-NMR (DMSO-D6) δ: 0.88 (6H, d, J = 6.6 Hz), 1.18 (3H, t, J = 7.1 Hz), 1.83-1.94 (1H, m), 2.19 (3H, s), 2.54 (2H, d, J = 7.1 Hz), 4.02 (2H, q, J = 7.1 Hz), 4.21 (2H, d, J = 5.7 Hz), 7.33 (2H, d, J = 8.4 Hz), 7.39 (1H, d, J = 8.2 Hz), 7.46 (1H, d, J = 8.2 Hz), 7.69-7.75 (1H, m), 8.24 (2H, d, J = 8.4 Hz), 13.33 (1H, br s). | 455 | 453 |
| 3-16 | 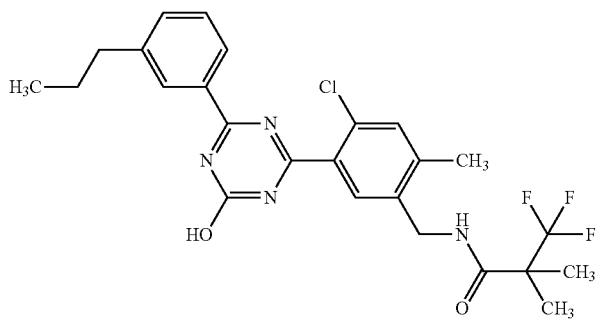 [SMILES: CCCc1cccc(-c2nc(O)nc(-c3cc(CNC(=O)C(C)(C)C(F)(F)F)c(C)cc3Cl)n2)c1] | 1H-NMR (DMSO-D6) δ: 0.91 (3H, t, J = 7.3 Hz), 1.37 (6H, s), 1.60-1.67 (2H, m), 2.33 (3H, s), 2.62 (2H, t, J = 7.6 Hz), 4.31 (2H, d, J = 5.7 Hz), 7.30-7.38 (3H, m), 7.52 (1H, s), 8.10-8.15 (2H, m), 8.48 (1H, t, J = 5.7 Hz). | 507 | 505 |

TABLE 3-3
| 3-17 | 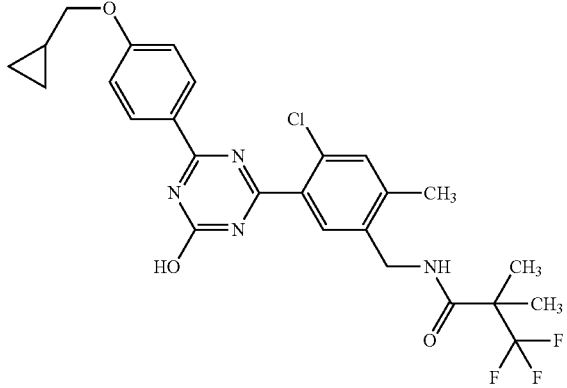 [SMILES: Cc1cc(Cl)c(-c2nc(O)nc(-c3ccc(OCC4CC4)cc3)n2)cc1CNC(=O)C(C)(C)C(F)(F)F] | 1H-NMR (DMSO-D6) δ: 0.35 (2H, dt, J = 8.0, 2.9 Hz), 0.59 (2H, ddd, J = 9.1, 5.0, 2.9 Hz), 1.20-1.29 (1H, m), 1.38 (6H, s), 2.35 (3H, s), 3.93 (2H, d, J = 7.0 Hz), 4.32 (2H, d, J = 5.6 Hz), 7.05 (2H, d, J = 8.8 Hz), 7.44 (1H, s), 7.56 (1H, s), 8.29 (2H, d, J = 8.8 Hz), 8.49 (1H, t, J = 5.6 Hz), 13.08 (1H, br s). | 535 | 533 |
| --- | --- | --- | --- | --- |
| 3-18 | 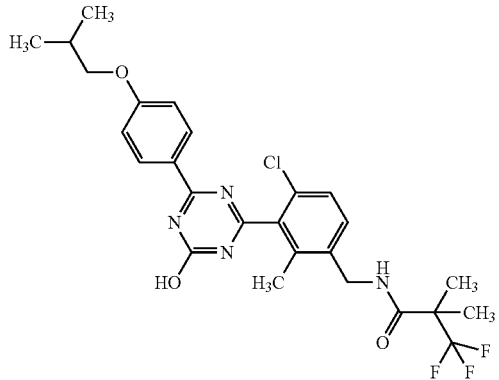 [SMILES: Cc1c(CNC(=O)C(C)(C)C(F)(F)F)ccc(Cl)c1-c1nc(O)nc(-c2ccc(OCC(C)C)cc2)n1] | 1H-NMR (DMSO-D6) δ: 0.99 (6H, d, J = 6.6 Hz), 1.41 (6H, s), 1.98-2.10 (1H, m), 2.18 (3H, s), 3.85 (2H, d, J = 6.6 Hz), 4.32 (2H, d, J = 5.7 Hz), 7.06 (2H, d, J = 8.4 Hz), 7.30 (1H, d, J = 8.2 Hz), 7.44 (1H, d, J = 8.2 Hz), 8.27 (2H, d, J = 8.4 Hz), 8.52-8.59 (1H, m), 13.23 (1H, br s). | 537 | 535 |
| 3-19 | 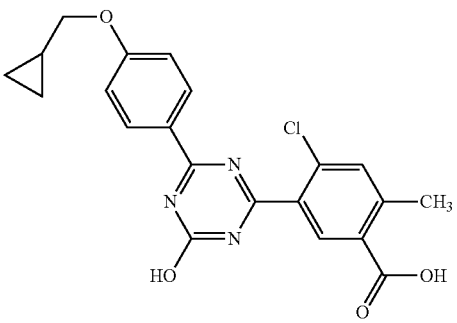 [SMILES: Cc1cc(Cl)c(-c2nc(O)nc(-c3ccc(OCC4CC4)cc3)n2)cc1C(=O)O] | 1H-NMR (DMSO-D6) δ: 0.35 (2H, td, J = 5.2, 4.1 Hz), 0.57-0.62 (2H, m), 1.24-1.27 (1H, m), 2.61 (3H, s), 3.94 (2H, d, J = 7.2 Hz), 7.09 (2H, d, J = 8.8 Hz), 7.64 (1H, s), 8.27 (1H, s), 8.30 (2H, d, J = 8.8 Hz), 13.20 (2H, br s). | 412 | 410 |
| 3-20 | 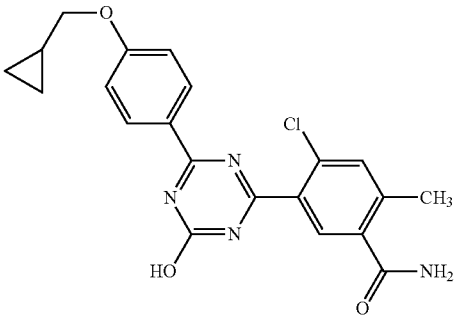 [SMILES: Cc1cc(Cl)c(-c2nc(O)nc(-c3ccc(OCC4CC4)cc3)n2)cc1C(N)=O] | 1H-NMR (DMSO-D6) δ: 0.35 (2H, td, J = 5.1, 4.1 Hz), 0.58-0.60 (2H, m), 1.22-1.30 (1H, m), 2.45 (3H, s), 3.94 (2H, d, J = 7.2 Hz), 7.09 (2H, d, J = 9.1 Hz), 7.56 (2H, s), 7.81 (1H, s), 7.85 (1H, s), 8.32 (2H, d, J = 8.8 Hz), 13.06 (1H, br s). | 411 | 409 |

TABLE 3-3-continued

| | | | | |
|---|---|---|---|---|
| 3-21 | (structure) | 1H-NMR (DMSO-D6) δ: 0.35 (2H, td, J = 5.2, 4.0 Hz), 0.57-0.62 (2H, m), 1.22-1.27 (1H, m), 2.42 (3H, s), 2.77 (3H, d, J = 4.7 Hz), 3.94 (2H, d, J = 7.0 Hz), 7.09 (2H, d, J = 9.1 Hz), 7.56 (1H, s), 7.77 (1H, s), 8.31 (2H, d, J = 9.1 Hz), 8.32 (1H, s), 13.09 (1H, br s). | 425 | 423 |
| 3-22 | (structure) | 1H-NMR (DMSO-D6) δ: 0.35 (2H, td, J = 5.6, 4.4 Hz), 0.57-0.61 (2H, m), 1.21-1.29 (1H, m), 2.28 (3H, s), 2.81 (3H, s), 3.02 (3H, s), 3.93 (2H, d, J = 7.2 Hz), 7.08 (2H, d, J = 9.1 Hz), 7.59 (1H, s), 7.62 (1H, s), 8.30 (2H, d, J = 9.1 Hz), 13.10 (1H, br s). | 439 | 437 |
| 3-23 | (structure) | 1H-NMR (DMSO-D6) δ: 0.35 (2H, td, J = 5.3, 4.0 Hz), 0.57-0.61 (2H, m), 0.90 (3H, t, J = 7.3 Hz), 1.20-1.30 (2H, m), 1.30-1.40 (2H, m), 1.46-1.53 (2H, m), 2.41 (3H, s), 3.24 (2H, q, J = 6.9 Hz), 3.94 (2H, d, J = 7.2 Hz), 7.09 (2H, d, J = 9.1 Hz), 7.56 (1H, s), 7.74 (1H, s), 8.31 (2H, d, J = 9.1 Hz), 8.37 (1H, t, J = 5.5 Hz), 13.09 (1H, br s). | 467 | 465 |

Experimental Example 1: Evaluation of Human mPGES-1 Enzyme Inhibitory Activity

The human mPGES-1 enzyme inhibitory activity of a test article was evaluated according to the report of Xu et al. (XU, D et al. MF63 [2-(6-chloro-1H-phenanthro[9,10-d]imidazol-2-yl)-isophthalonitrile], a selective microsomal prostaglandin E synthase-1 inhibitor, relieves pyresis and pain in preclinical models of inflammation. J Pharmacol Exp Ther. Sep 2008, Vol. 326, No. 3, pages 754-763). That is, the amount of PGE2 produced by human mPGES-1 in the presence of a test article was measured by the HTRF (homogeneous time resolved fluorescence) method, based on which the human mPGES-1 enzyme inhibitory activity of the test article was determined.

1) Preparation of Human mPGES-1 Expressing Cell Microsome Fraction

A DNA fragment containing human mPGES-1, which is added with a BamHI recognition cleavage sequence immediately before the translation initiation codon and an EcoRI recognition cleavage sequence immediately after the translation termination codon was amplified by the PCR (Polymerase Chain Reaction) method using a human mPGES-1 expression plasmid DNA (pME-18S/iPGES-1) prepared in-house as a template. The purified DNA fragment was digested with BamHI and EcoRI, and ligated to pcDNA3.1 (+) (Invitrogen, model number V790-20), similarly digested with BamHI and EcoRI, by using a DNA Ligation kit ver.2.1 (Takara Bio, model number 6022). The human mPGES-1 expression plasmid DNA was isolated from *Escherichia coli* DH5a (TOYOBO, model number DNA-903) transformed with the obtained ligation product. The base sequence of human mPGES-1 cloned to a vector was determined by the Dye Terminator method by using BigDye Terminator v3.1 Cycle Sequencing Kit (Applied Biosystems, #4337455). The determined sequence was identical with the sequence of the protein translational region of human mPGES-1 (Accession number NM 004878) registered in the NCBI Reference Database.

Human mPGES-1 expression plasmid DNA was transfected into Chinese hamster ovary-derived cells (FreeStyle CHO-S Cell, Invitrogen, #R800-07) by using a transgene reagent (FreeStyle MAX Reagent (Invitrogen, #16447-100)), and cultured with shaking (8% $CO_2$, 37° C.) in a medium containing 8 mmol/L L-glutamine (GIBCO FreeStyle CHO Expression Medium, Invitrogen, #12651-022) for 48 hr.

The CHO-S cells were suspended in Homogenate Buffer (100 mmol/L potassium phosphate (pH 7.4), 250 mmol/L Sucrose, 100 mmol/L EDTA, complete EDTA free (Roche,

1873580)). Using an ultrasonic disruptor UD-201 (Tomy Seiko), the suspended cells were disrupted at output:3, duty cycle:50 for 30 seconds. The precipitate was removed by centrifugation (1,000×g, 5 min, 4° C.), is and the supernatant was centrifuged (5,000×g, 10 min, 4° C.). The supernatant was further centrifuged (105,000×g, 60 min, 4° C.). The obtained precipitate was suspended in Resuspension Buffer (100 mmol/L potassium phosphate (pH 7.4), 250 mmol/L sucrose, 100 mmol/L EDTA, 10% glycerol) to give a microsome fraction.

The protein concentration of the microsome fraction was measured by the Bradford method (Protein Assay Kit, Bio-Rad). The microsome fraction was rapidly frozen in liquid nitrogen and preserved at −80° C. Human mPGES-1 in the microsome fraction was detected by Western Blot using rabbit anti-mPGES-1 polyclonal antibody (ThermoFisher Scientific, #PA1-10264).

2) Evaluation of Human mPGES-1 Enzyme Inhibitory Activity

A test article solution diluted with 0.1 mol/L potassium phosphate, pH 7.4 (hereinafter to be referred to as KPB) or DMSO (Nacalai Tesque, #13407-45) was added at 5 μL/well to 96 well V-bottom plate (Corning, #3363). The final DMSO concentration during the reaction was set to 2% (v/v). Furthermore, a microsome fraction of CHO-S cells expressing human mPGES-1, which was diluted with reduced GSH (12.5 mmol/L KPB solution, SIGMA, #G6529-25G) such that the protein concentration was 5 μg/mL, was added at 20 μL/well. The amount of the microsome fraction used is the amount of microsome fraction within a range where the amount of PGE2 produced under the reaction conditions shown below and the amount of microsome fraction used show linearity. To the blank was added reduced GSH (12.5 mmol/L KPB solution) at 20 μL/well. After stirring at room temperature for 10 min, PGH2 (PGH2 dissolved in cold acetone to 100 μg/mL and diluted with D-PBS(−) (Nikken biomedical laboratory, #CM6201) to 10 μg/mL, Cayman Chemical, #17020) was added at 25 μL/well, and the mixture was stood at room temperature for 45 seconds. Tin(II) chloride dihydrate (2 mg/mL 10 mmol/L citric acid solution, Wako Pure Chemical Industries, Ltd., #204-01562) was added at 50 μL/well, and the plate was gently shaken to discontinue the enzyme reaction. The concentration of PGE2 in the above-mentioned enzyme reaction mixture was measured using Prostaglandin E2 assay (CISbio Bioassays, #62P2APEC) according to the manual. As the reference standard for analytical curve, PGE2 (Cayman Chemical, #14010) was used. Using RUBYstar (BMG Labtech), the time-resolved fluorescence at 620 nm and 665 nm relative to the excitation light at 337 nm was measured. PGE2 concentration was extrapolated from the PGE2 analytical curve. Average of the PGE2 concentrations of the respectively-treated wells was used as the data.

The mPGES-1 enzyme inhibitory activity (%) of the test article was calculated according to the following formula 1.

mPGES-1 enzyme inhibitory activity (%)=(PGE2$_A$−PGE2$_X$)/(PGE2$_A$−PGE2$_B$)×100  [formula 1]

PGE2$_A$: PGE2 concentration of vehicle-treated well
PGE2$_B$: PGE2 concentration of blank well
PGE2$_X$: PGE2 concentration of test article-treated well The IC$_{50}$ value (50% inhibitory concentration) of the test article was calculated according to the following formula 2.

IC$_{50}$ value=10$^{\{log\ 10(D/E)\times(50-G)/(F-G)+log\ 10(E)\}}$  [formula 2]

D: concentration of test article that shows activity of not less than 50% inhibition between two points across 50% inhibition E: concentration of test article that shows activity of not more than 50% inhibition between two points across 50% inhibition F: mPGES-1 enzyme inhibitory activity (%) when concentration of test article is D G: mPGES-1 enzyme inhibitory activity (%) when concentration of test article is E The results are shown in Table 4-1 to Table 4-9.

TABLE 4-1

| Example | Human mPGES-1 enzyme inhibitory activity (μM) |
|---|---|
| 1-1 | 0.813 |
| 1-2 | 0.138 |
| 1-3 | 0.164 |
| 1-4 | 0.025 |
| 1-5 | 0.672 |
| 1-6 | 0.163 |
| 1-7 | 0.652 |
| 1-8 | 27.0 |
| 1-9 | 0.601 |
| 1-10 | 5% inhibition (at 30 μM) |
| 1-11 | 42% inhibition (at 30 μM) |
| 1-12 | 0.015 |
| 1-13 | 0.397 |
| 1-14 | 1.413 |
| 1-15 | 0.0074 |
| 1-16 | 0.010 |
| 1-17 | 0.735 |
| 1-18 | 0.114 |
| 1-19 | 0.411 |
| 1-20 | 0.0016 |
| 1-21 | 0.988 |
| 1-22 | 0.0027 |
| 1-23 | 0.134 |
| 1-24 | 0.0006 |
| 1-25 | 0.108 |
| 1-26 | 0.018 |
| 1-27 | 0.0010 |
| 1-28 | 0.0006 |
| 1-29 | 0.0011 |
| 1-30 | 0.0006 |
| 1-31 | 0.0010 |
| 1-32 | 0.0007 |
| 1-33 | 0.0008 |
| 1-34 | 0.0059 |
| 1-35 | 0.022 |
| 1-36 | 0.0007 |
| 1-37 | 0.0008 |
| 1-38 | 0.0015 |
| 1-39 | 0.0019 |
| 1-40 | 2.231 |
| 1-41 | 0.0023 |
| 1-42 | 0.0010 |
| 1-43 | 0.0020 |
| 1-44 | 0.0006 |
| 1-45 | 0.138 |
| 1-46 | 0.0007 |
| 1-47 | 0.043 |
| 1-48 | 0.0009 |
| 1-49 | 0.0009 |
| 1-50 | 0.0009 |
| 1-51 | 0.0010 |

TABLE 4-2

| Example | Human mPGES-1 enzyme inhibitory activity (μM) |
|---|---|
| 1-52 | 0.0006 |
| 1-53 | 0.0045 |
| 1-54 | 0.0009 |
| 1-55 | 0.0011 |
| 1-56 | 0.0006 |
| 1-57 | 0.0005 |
| 1-58 | 0.0005 |
| 1-59 | 0.0006 |
| 1-60 | 0.0004 |
| 1-61 | 0.0007 |
| 1-62 | 0.0010 |
| 1-63 | 0.0005 |
| 1-64 | 0.0019 |
| 1-65 | 0.0086 |
| 1-66 | 0.0041 |
| 1-67 | 0.0010 |
| 1-68 | 0.0003 |
| 1-69 | 0.0003 |
| 1-70 | 0.0007 |
| 1-71 | 0.0025 |
| 1-72 | 0.0013 |
| 1-73 | 0.0006 |
| 1-74 | 0.0006 |
| 1-75 | 0.0067 |
| 1-76 | 0.0017 |
| 1-77 | 0.0009 |
| 1-78 | 0.0022 |
| 1-79 | 0.0012 |
| 1-80 | 0.0031 |
| 1-81 | 0.0006 |
| 1-82 | 0.0008 |
| 1-83 | 0.011 |
| 1-84 | 0.0006 |
| 1-85 | 0.0005 |
| 1-86 | 0.0058 |
| 1-87 | 0.0008 |
| 1-88 | 0.0012 |
| 1-89 | 0.0009 |
| 1-90 | 0.0004 |
| 1-91 | 0.0004 |
| 1-92 | 0.0005 |
| 1-93 | 0.0007 |
| 1-94 | 0.0046 |
| 1-95 | 0.0021 |
| 1-96 | 0.081 |
| 1-97 | 0.0091 |
| 1-98 | 0.0009 |
| 1-99 | 0.0007 |
| 1-100 | 0.0009 |
| 1-101 | 0.0058 |
| 1-102 | 0.0009 |

TABLE 4-3

| Example | Human mPGES-1 enzyme inhibitory activity (μM) |
|---|---|
| 1-103 | 0.0013 |
| 1-104 | 0.0015 |
| 1-105 | 0.0007 |
| 1-106 | 0.0007 |
| 1-107 | 0.0012 |
| 1-108 | 0.0006 |
| 1-109 | 0.0025 |
| 1-110 | 0.0009 |
| 1-111 | 0.0012 |
| 1-112 | 0.0009 |
| 1-113 | 0.0009 |
| 1-114 | 0.0059 |
| 1-115 | 0.0006 |
| 1-116 | 0.0020 |
| 1-117 | 0.0016 |
| 1-118 | 0.0019 |
| 1-119 | 0.0010 |
| 1-120 | 0.048 |
| 1-121 | 0.0012 |
| 1-122 | 0.0013 |
| 1-123 | 0.0023 |
| 1-124 | 0.0009 |
| 1-125 | 0.0008 |
| 1-126 | 0.0008 |
| 1-127 | 0.0008 |
| 1-128 | 0.0013 |
| 1-129 | 0.0006 |
| 1-130 | 0.009 |
| 1-131 | 0.0009 |
| 1-132 | 0.0003 |
| 1-133 | 0.0005 |
| 1-134 | 0.004 |
| 1-135 | 0.0005 |
| 1-136 | 0.0005 |
| 1-137 | 0.0005 |
| 1-138 | 0.0005 |
| 1-139 | 0.0006 |
| 1-140 | 0.0005 |
| 1-141 | 0.0011 |
| 1-142 | 0.0005 |
| 1-143 | 0.0010 |
| 1-144 | 0.0009 |
| 1-145 | 0.0005 |
| 1-146 | 0.0004 |
| 1-147 | 0.0008 |
| 1-148 | 0.0017 |
| 1-149 | 0.0008 |
| 1-150 | 0.0004 |
| 1-151 | 0.0004 |
| 1-152 | 0.0004 |
| 1-153 | 0.0005 |

TABLE 4-4

| Example | Humanm PGES-1 enzyme inhibitory activity (μM) |
|---|---|
| 1-154 | 0.0005 |
| 1-155 | 0.0035 |
| 1-156 | 0.0041 |
| 1-157 | 0.0007 |
| 1-158 | 0.012 |
| 1-159 | 0.0007 |
| 1-160 | 0.0014 |
| 1-161 | 0.0013 |
| 1-162 | 0.0012 |
| 1-163 | 0.0010 |
| 1-164 | 0.0037 |
| 1-165 | 0.0009 |
| 1-166 | 0.0011 |
| 1-167 | 0.0019 |
| 1-168 | 0.0021 |
| 1-169 | 0.0020 |
| 1-170 | 0.0015 |
| 1-171 | 0.0005 |
| 1-172 | 0.017 |
| 1-173 | 0.0054 |
| 1-174 | 0.0031 |
| 1-175 | 0.0013 |
| 1-176 | 0.0018 |
| 1-177 | 0.0013 |
| 1-178 | 0.0014 |
| 1-179 | 0.016 |
| 1-180 | 0.0041 |
| 1-181 | 0.0024 |
| 1-182 | 0.0016 |
| 1-183 | 0.0013 |

TABLE 4-4-continued

| Example | Humanm PGES-1 enzyme inhibitory activity (μM) |
|---|---|
| 1-184 | 0.0019 |
| 1-185 | 0.0017 |
| 1-186 | 0.0014 |
| 1-187 | 0.0053 |
| 1-188 | 0.0016 |
| 1-189 | 1.1 |
| 1-190 | 0.047 |
| 1-191 | 0.015 |
| 1-192 | 41% inhibition (at 30 μM) |
| 1-193 | 8.7 |
| 1-194 | 10.5 |
| 1-195 | 6.0 |
| 1-196 | 0.042 |
| 1-197 | 0.289 |
| 1-198 | 0.014 |
| 1-199 | 0.031 |
| 1-200 | 0.010 |
| 1-201 | 0.306 |
| 1-202 | 0.0082 |
| 1-203 | 0.020 |
| 1-204 | 0.034 |

TABLE 4-5

| Example | Human mPGES-1 enzyme inhibitory activity (μM) |
|---|---|
| 1-205 | 0.367 |
| 1-206 | 0.014 |
| 1-207 | 0.0043 |
| 1-208 | 0.016 |
| 1-209 | 0.059 |
| 1-210 | 0.288 |
| 1-211 | 0.063 |
| 1-212 | 0.032 |
| 1-213 | 0.088 |
| 1-214 | 0.024 |
| 1-215 | 0.452 |
| 1-216 | 0.039 |
| 1-217 | 0.126 |
| 1-218 | 0.070 |
| 1-219 | 0.041 |
| 1-220 | 0.016 |
| 1-221 | 0.079 |
| 1-222 | 0.165 |
| 1-223 | 0.007 |
| 1-224 | 5.8 |
| 1-225 | 4.2 |
| 1-226 | 2.2 |
| 1-227 | 0.050 |
| 1-228 | 0.672 |
| 1-229 | 0.532 |
| 1-230 | 0.750 |
| 1-231 | 0.045 |
| 1-232 | 0.521 |
| 1-233 | 0.848 |
| 1-234 | 1.0 |
| 1-235 | 0.070 |
| 1-236 | 0.263 |
| 1-237 | 1.3 |
| 1-238 | 0.0074 |
| 1-239 | 0.428 |
| 1-240 | 0.428 |
| 1-241 | 0.278 |
| 1-242 | 0.082 |
| 1-243 | 0.120 |
| 1-244 | 0.021 |
| 1-245 | 0.108 |
| 1-246 | 0.307 |
| 1-247 | 0.011 |

TABLE 4-5-continued

| Example | Human mPGES-1 enzyme inhibitory activity (μM) |
|---|---|
| 1-248 | 0.016 |
| 1-249 | 0.226 |
| 1-250 | 0.012 |
| 1-251 | 0.018 |
| 1-252 | 0.511 |
| 1-253 | 0.791 |
| 1-254 | 0.030 |
| 1-255 | 0.045 |

TABLE 4-6

| Example | Human mPGES-1 enzyme inhibitory activity (μM) |
|---|---|
| 1-256 | 0.098 |
| 1-257 | 0.017 |
| 1-258 | 1.9 |
| 1-259 | 0.176 |
| 1-260 | 0.147 |
| 1-261 | 44% inhibition (at 30 μM) |
| 1-262 | 0.007 |
| 1-263 | 0.702 |
| 1-264 | 0.163 |
| 1-265 | 0.056 |
| 1-266 | 0.011 |
| 1-267 | 0.150 |
| 2-1 | 0.283 |
| 2-2 | 21.3 |
| 2-3 | 14.7 |
| 2-4 | 0.066 |
| 2-5 | 0.101 |
| 2-6 | 28% inhibition (at 30 μM) |
| 2-7 | 3.5 |
| 2-8 | 1.9 |
| 2-9 | 6.4 |
| 2-10 | 0.073 |
| 2-11 | 0.0060 |
| 2-12 | 0.141 |
| 2-13 | 23.1 |
| 2-14 | 14.3 |
| 2-15 | 16.4 |
| 2-16 | 0.412 |
| 2-17 | 0.039 |
| 2-18 | 0.0080 |
| 2-19 | 0.211 |
| 2-20 | 0.052 |
| 2-21 | 0.341 |
| 2-22 | 0.219 |
| 2-23 | 0.155 |
| 2-24 | 2.4 |
| 2-25 | 0.249 |
| 2-26 | 2.7 |
| 2-27 | 7.7 |
| 2-28 | 3.7 |
| 2-29 | 0.503 |
| 2-30 | 43% inhibition (at 30 μM) |
| 2-31 | 0.031 |
| 2-32 | 0.014 |
| 2-33 | 0.102 |
| 2-34 | 0.163 |
| 2-35 | 0.017 |
| 2-36 | 0.053 |
| 2-37 | 0.041 |
| 2-38 | 1.0 |
| 2-39 | 0.450 |

TABLE 4-7

| Example | Human mPGES-1 enzyme inhibitory activity (μM) |
|---|---|
| 2-40 | 1.3 |
| 2-41 | 0.429 |
| 2-42 | 0.239 |
| 2-43 | 0.570 |
| 2-44 | 0.563 |
| 2-45 | 0.012 |
| 2-46 | 0.494 |
| 2-47 | 0.295 |
| 2-48 | 0.019 |
| 2-49 | 0.014 |
| 2-50 | 0.061 |
| 2-51 | 0.090 |
| 2-52 | 0.100 |
| 2-53 | 0.011 |
| 2-54 | 0.170 |
| 2-55 | 0.010 |
| 2-56 | 0.018 |
| 2-57 | 0.025 |
| 2-58 | 0.145 |
| 2-59 | 0.095 |
| 2-60 | 0.121 |
| 2-61 | 0.092 |
| 2-62 | 0.0093 |
| 2-63 | 0.259 |
| 2-64 | 0.012 |
| 2-65 | 0.151 |
| 2-66 | 0.016 |
| 2-67 | 0.027 |
| 2-68 | 0.672 |
| 2-69 | 0.084 |
| 2-70 | 0.158 |
| 2-71 | 0.172 |
| 2-72 | 0.283 |
| 2-73 | 0.402 |
| 2-74 | 0.424 |
| 2-75 | 0.0037 |
| 2-76 | 0.0058 |
| 2-77 | 0.0037 |
| 2-78 | 0.0068 |
| 2-79 | 0.0037 |
| 2-80 | 0.0016 |
| 2-81 | 0.0027 |
| 2-82 | 0.0017 |
| 2-83 | 0.051 |
| 2-84 | 0.017 |
| 2-85 | 0.0016 |
| 2-86 | 0.0022 |
| 2-87 | 0.0018 |
| 2-88 | 0.0020 |
| 2-89 | 0.018 |
| 2-90 | 2.1 |

TABLE 4-8

| Example | Human mPGES-1 enzyme inhibitory activity (μM) |
|---|---|
| 2-91 | 0.0016 |
| 2-92 | 0.0044 |
| 2-93 | 0.038 |
| 2-94 | 0.0041 |
| 2-95 | 0.0050 |
| 2-96 | 0.021 |
| 2-97 | 0.0089 |
| 2-98 | 0.0037 |
| 2-99 | 0.0017 |
| 2-100 | 0.0056 |
| 2-101 | 0.0065 |
| 2-102 | 0.0059 |
| 2-103 | 0.010 |
| 2-104 | 0.018 |
| 2-105 | 0.018 |
| 2-106 | 0.0050 |
| 2-107 | 0.0038 |
| 2-108 | 0.0064 |
| 2-109 | 0.0028 |
| 2-110 | 0.0074 |
| 2-111 | 0.0044 |
| 2-112 | 0.0059 |
| 2-113 | 0.0051 |
| 2-114 | 0.0049 |
| 2-115 | 0.0030 |
| 2-116 | 0.0055 |
| 2-117 | 0.0047 |
| 2-118 | 0.0071 |
| 2-119 | 0.0018 |
| 2-120 | 0.0041 |
| 2-121 | 0.014 |
| 2-122 | 0.015 |
| 2-123 | 0.012 |
| 2-124 | 0.012 |
| 2-125 | 0.0043 |
| 2-126 | 0.0046 |
| 2-127 | 0.0062 |
| 2-128 | 0.013 |
| 2-129 | 0.032 |
| 2-130 | 0.035 |
| 3-1 | 0.484 |
| 3-2 | 0.148 |
| 3-3 | 0.141 |
| 3-4 | 0.202 |
| 3-5 | 0.341 |
| 3-6 | 0.056 |
| 3-7 | 0.019 |
| 3-8 | 0.0010 |
| 3-9 | 0.776 |
| 3-10 | 0.016 |
| 3-11 | 0.093 |

TABLE 4-9

| Example | Human mPGES-1 enzyme inhibitory activity (μM) |
|---|---|
| 3-12 | 0.028 |
| 3-13 | 0.034 |
| 3-14 | 0.002 |
| 3-15 | 0.0051 |
| 3-16 | 0.0021 |
| 3-17 | 0.0008 |
| 3-18 | 0.0012 |
| 3-19 | 24.6 |
| 3-20 | 1.1 |
| 3-21 | 0.611 |
| 3-22 | 6.9 |
| 3-23 | 0.041 |

Experimental Example 2: Evaluation of Action of mPGES-1 Inhibitor on Normal Intraocular Pressure of *Macaca fascicularis*

This test was performed using male *Macaca fascicularis*. To eliminate interindividual difference and an influence of the difference in administration days, a crossover test was used for the evaluation as shown in Table 5.

TABLE 5

| Animal No. | First course | Second course | Third course |
|---|---|---|---|
| SX1M01 | test article 10 mg/kg | reference article | vehicle |
| SX1M02 | reference article | vehicle | test article 30 mg/kg |
| SX1M03 | reference article | vehicle | test article 30 mg/kg |
| SX1M04 | vehicle | test article 30 mg/kg | reference article |
| SX1M05 | vehicle | test article 30 mg/kg | reference article |

To exclude the influence of the remaining test article, a 1-week washout period was set between tests. On the day of test, the monkeys were fed after the final measurement.

The test article (compound of Examples 2-98) was suspended in 0.5% methylcellulose (Wako Pure Chemical Industries, Ltd.), and administered by gavage by using a polypropylene syringe (sterilized disposable product, Nipro Corporation) and a stomach catheter (nelaton type A No. 9, Izumo health). The dose was set to 10 mg/kg/5 mL (N=1) or 30 mg/kg/5 mL (N=4) based on the body weight of each individual the day before the administration. To the vehicle group was administered the vehicle (0.5% methylcellulose (MC)) by a method similar to that for the test article. As a reference is article, Xalatan (registered trade mark) ophthalmic solution 0.005% (Pfizer Inc., general name: latanoprost) was used. The reference article was administered by instillation of 20 µL thereof to one eye by using a micropipette. After instillation, the lacrimal part was lightly fixed by gently pressing the lower eyelid for about 15 seconds. The opposite eye was treated in the same manner. The intraocular pressure was measured immediately before administration, and 2, 4, 8, 12 and 24 hr after administration. Before measurement of the intraocular pressure, the animal was fixed on a monkey chair, and topically anesthetized by instillation of an ophthalmic surface anesthetic (Benoxyl (registered trade mark) ophthalmic solution 0.4%, Santen Pharmaceutical Co., Ltd., general name: oxybuprocaine hydrochloride). A lid rectactor (Handaya Co., Ltd.) was set, and the intraocular pressure of the both eyes was measured using a pneumatic applanation tonometer (Model30 Classic, Reichert Inc.).

To confirm disappearance of the test article, after an intraocular pressure measurement at 24 hr after the third course administration, blood samples (1 mL) were collected from the femoral vein under unanesthetized condition by using polypropylene syringe and 23 gauge injection needle (both sterilized disposable products) treated with heparin sodium, and the concentration of unaltered compound in the plasma containing the test article was measured.

An intraocular pressure difference (ΔmmHg; in first decimal place) from the value immediately before administration was determined for each measurement eye at each measurement time point, an average of the both eyes was calculated and taken as the evaluation data of the individual. The mean and standard deviation (in second decimal place) of the intraocular pressure difference was calculated for each group, and the test article administration group or reference article administration group was subjected to a homoscedasticity test (significance level 5%) based on F-test with the vehicle group. When the dispersion was equal, Student's t-test was performed and, when the dispersion was not equal, Aspin-Welch's t-test was performed. In addition, the maximum ocular hypotensive effect (ΔmmHg; maximum descent value from value immediately before administration, in first decimal place) was determined for each group, and the groups were compared in the same manner. The two-sided test was performed. It is a significant variation when a difference from the vehicle group was found at a 5% significance level and shown in FIG. 1 separately as 5% and 1%. Since the test article 10 mg/kg administration group contained only one animal, it was excluded from the statistical analysis.

The intraocular pressure of *Macaca fascicularis* used for this test before administration of a test article was 19.6±1.7 mmHg. After the measurement of intraocular pressure at 24 hr after the third course administration, the concentration of an unaltered test article in the plasma of the vehicle group and the reference article administration group was less than the lower detection limit. The results are shown in FIG. 1.

Experimental Example 3: Evaluation of Effect on Prostaglandin Composition in Guinea Pig Aqueous Humor A test article was dissolved in saline containing 0.5% polysorbate80 (Fluka) and 0.003% ophthalmic solution (pH 7.0-8.0) was prepared. The test article was administered to Hartley male guinea pig by instillation of 20 µL thereof to one eye by using a micropipette. After instillation, the lacrimal part was lightly fixed by gently pressing the lower eyelid for about 15 seconds. The opposite eye was treated in the same manner. To the vehicle group was administered the medium (0.5% polysorbate-containing saline) by a method similar to that for the test article. After 23 hr from the instillation, Mydrin P (registered trade mark) 0.5% ophthalmic solution (Santen Pharmaceutical Co., Ltd., general name: tropicamide/phenylephrine hydrochloride) was dropwisely added by one drop to the both eyes of a guinea pig to cause mydriasis. The guinea pig was anesthetized with Escain (registered trade mark) inhalation anesthetics (Pfizer Inc., general name: isoflurane), the cornea of the both eyes was tapped with a 30G injection needle, and the leaked aqueous humor (primary aqueous humor) was collected. One hour later (24 hr after instillation), the guinea pig was anesthetized again with isoflurane, and the secondary aqueous humor was collected in the same manner. The concentration of prostaglandins in the secondary aqueous humor obtained from each group (4 guinea pigs, 8 eyes) was measured by the LC/MS/MS system (Ultra high performance liquid chromatography: Nexera (registered trademark) manufactured by Shimadzu Corporation, mass spectrometer: AB SCIEX manufactured by QTRAP (registered trademark) 5500), and the concentration ratio of each prostaglandin concentration relative to the total of all prostaglandin concentrations was calculated. The results are shown in Table 6.

TABLE 6

| Example | PGE2 (%) | PGF2α (%) | 6-keto-PGF1α (%) | PGD2 (%) | TXB2 (%) |
|---|---|---|---|---|---|
| vehicle | 80.8 | 7 | 6.8 | 4.7 | 0.7 |
| 1-51 | 50.7 | 14 | 21.7 | 13.2 | 0.4 |
| 1-81 | 60 | 9.8 | 15.7 | 13.2 | 1.3 |
| 1-98 | 38 | 14.2 | 31.2 | 16.3 | 0.3 |
| 1-109 | 29.5 | 14.1 | 37.5 | 18.9 | 0.1 |
| 1-122 | 37.3 | 11.7 | 27.7 | 23 | 0.2 |
| 1-128 | 36.2 | 13.9 | 29.7 | 19.3 | 0.8 |
| 1-129 | 62.5 | 10.2 | 18.1 | 9.2 | 0 |
| 1-130 | 73.6 | 8 | 11.2 | 6.2 | 1 |
| 1-131 | 42.9 | 9.8 | 27.9 | 18.8 | 0.6 |
| 1-135 | 56.1 | 12.7 | 19.4 | 10.9 | 0.9 |

TABLE 6-continued

| Example | PGE2 (%) | PGF2α (%) | 6-keto-PGF1α (%) | PGD2 (%) | TXB2 (%) |
|---|---|---|---|---|---|
| 1-136 | 66.7 | 7.9 | 17.3 | 7.4 | 0.7 |
| 1-137 | 49.5 | 11.3 | 24.8 | 14.1 | 0.3 |
| 1-150 | 69 | 8.9 | 14 | 8 | 0.2 |
| 1-169 | 28.7 | 13.5 | 40.3 | 17 | 0.5 |
| 1-178 | 30 | 13 | 36.6 | 20.1 | 0.3 |
| 1-184 | 57 | 10.3 | 21.2 | 10.7 | 0.8 |
| 1-185 | 50 | 11 | 25.4 | 12.1 | 1.6 |
| 2-98 | 37.8 | 14.8 | 27.3 | 20.1 | 0 |

Experimental Example 4: Evaluation of Action of mPGES-1 Inhibitor on Normal Intraocular Pressure of *Macaca fascicularis*

This test is performed using male *Macaca fascicularis*. To eliminate interindividual difference and an influence of the difference in administration days, a crossover test is used for the evaluation as shown in Table 7.

TABLE 7

| Animal No. | First course | Second course | Third course | Fourth course |
|---|---|---|---|---|
| SX1M01 | vehicle | test article | test article + reference article | reference article |
| SX1M02 | test article | vehicle | reference article | test article + reference article |
| SX1M03 | reference article | test article + reference article | test article | vehicle |
| SX1M04 | test article + reference article | test article | vehicle | reference article |
| SX1M05 | vehicle | reference article | test article + reference article | test article |
| SX1M06 | test article | vehicle | reference article | test article + reference article |

To exclude the influence of the remaining test article, a 1-week washout period is set between tests. On the day of test, the monkeys are fed after the final measurement.

A test article is dissolved in saline containing 0.5% polysorbate80 (Fluka) and 0.1% ophthalmic solution (pH 7.9-8.1) is prepared. To the vehicle group is administered the medium (0.5% polysorbate-containing saline) by a method similar to that for the test article. As a reference article, Xalatan (registered trademark) ophthalmic solution 0.005% (Pfizer Inc., general name: latanoprost) is used. The test article is administered by instillation of 30 μL thereof to one eye 5 times and 1 time of vehicle at 5-min intervals by using a micropipette (total 6 times instillation for each eye). Each of vehicle and reference article is administered 1 time and then vehicle is instilled 5 times (total 6 times instillation for each eye). In the test article+reference article combination group, the test article is instilled 5 times after instillation of the reference article (total 6 times instillation for each eye). After instillation at each time, the lacrimal part is lightly fixed by gently pressing the lower eyelid for about 15 seconds. The intraocular pressure is measured immediately before administration, and 2, 4, 8, 12 and 24 hr after administration. Before measurement of the intraocular pressure, the animal is fixed on a monkey chair, and topically anesthetized by instillation of an ophthalmic surface anesthetic (Benoxyl (registered trademark) ophthalmic solution 0.4%, Santen Pharmaceutical Co., Ltd., general name: oxybuprocaine hydrochloride). A lid rectactor (Handaya Co., Ltd.) is set, and the intraocular pressure of the both eyes is measured using a pneumatic applanation tonometer (Model30 Classic, Reichert Inc.).

An intraocular pressure difference (ΔmmHg; in first is decimal place) from the value immediately before administration is determined for each measurement eye at each measurement time point, an average of the both eyes is calculated and taken as the evaluation data of the individual. The mean and standard deviation (in second decimal place) of the intraocular pressure difference is calculated for each group, and the test article administration group or reference article administration group is subjected to a homoscedasticity test (significance level 5%) based on F-test with the vehicle group. When the dispersion is equal, Student's t-test is performed and, when the dispersion is not equal, Aspin-Welch's t-test is performed. In addition, the maximum ocular hypotensive effect (ΔmmHg; maximum descent value from value immediately before administration, in first decimal place) is determined for each group, and the groups are compared in the same manner. The two-sided test is performed. It is a significant variation when a difference from the vehicle group is found at a 5% significance level.

The Formulation Examples of the present invention include the following formulations. However, the present invention is not limited by such Formulation Examples.

Formulation Example 1 (Production of Capsule)

| 1) compound of Example 1-86 | 30 mg |
|---|---|
| 2) microcrystalline cellulose | 10 mg |
| 3) lactose | 19 mg |
| 4) magnesium stearate | 1 mg |

1), 2), 3) and 4) are mixed and filled in a gelatin capsule.

Formulation Example 2 (Production of Tablet)

| 1) compound of Example 86 | 10 g |
|---|---|
| 2) lactose | 50 g |
| 3) cornstarch | 15 g |
| 4) carmellose calcium | 44 g |
| 5) magnesium stearate | 1 g |

The total amount of 1), 2), 3) and 30 g of 4) are kneaded with water, vacuum dried and sieved. The sieved powder is mixed with 14 g of 4) and 1 g of 5), and the mixture is tableted by a tableting machine. In this way, 1000 tablets containing 10 mg of the compound of Example 1-86 per tablet are obtained.

Formulation Example 3 (Production of Eye Drop)

in 100 mL of eye drop

| 1) compound of Example 1-86 | 100 mg |
|---|---|
| 2) polysorbate80 | 500 mg |
| 3) sodium chloride | 900 mg |

-continued

| | |
|---|---|
| 4) sodium hydroxide | q.s. |
| 5) sterilized purified water | q.s. |
| The above components are aseptically blended to pH 7.9-8.1 to give an eye drop. | |

Formulation Example 4 (Production of Eye Drop)

in 100 mL of eye drop

| | |
|---|---|
| 1) compound of Example 1-86 | 100 mg |
| 2) polysorbate80 | 100 mg |
| 3) sodium dihydrogen phosphate dehydrate | 100 mg |
| 4) sodium chloride | 900 mg |
| 5) benzalkonium chloride | 5 mg |
| 6) sodium hydroxide | q.s. |
| 7) sterilized purified water | q.s. |
| The above components are aseptically blended to pH 7.9-8.1 to give an eye drop. | |

Formulation Example 5 (Production of Eye Drop)

in 100 mL of eye drop

| | |
|---|---|
| 1) compound of Example 1-86 | 100 mg |
| 2) boric acid | 700 mg |
| 3) borax | q.s. |
| 4) sodium chloride | 500 mg |
| 5) sodium edetate | 0.05 mg |
| 6) benzalkonium chloride | 0.0005 mg |
| 7) sterilized purified water | q.s. |
| The above components are aseptically blended to pH 7.9-8.1 to give an eye drop. | |

INDUSTRIAL APPLICABILITY

Since the compound of the present invention and a pharmaceutically acceptable salt thereof have an mPGES-1 inhibitory activity, they can afford a medicament effective for the prophylaxis or treatment of pain, rheumatism, osteoarthritis, fever, Alzheimer's disease, multiple sclerosis, arteriosclerosis, glaucoma, ocular hypertension, ischemic retinal disease, systemic scleroderma, cancer including colorectal cancer and diseases for which suppression of PGE2 production is effective.

This application is based on a patent application No. 2014-031035 filed in Japan on Feb. 20, 2014, the contents of which are incorporated in full herein.

The invention claimed is:

1. A compound represented by the formula [I] or a pharmaceutically acceptable salt thereof:

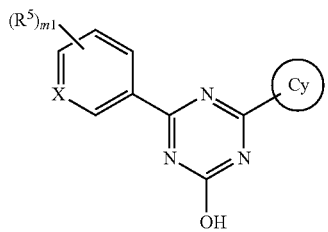

[I]

wherein
X is CH,
ring Cy is
the formula:

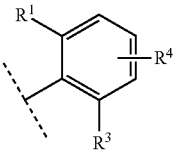

wherein $R^1$ is
(1) halogen,
(2) $C_{1-6}$ alkyl,
(3) cyano or
(4) halo$C_{1-4}$ alkyl,
$R^3$ is
(1) halogen,
(2) hydroxy,
(3) $C_{1-6}$ alkyl or
(4) —$OR^c$, wherein the $R^c$ is $C_{1-6}$ alkyl optionally substituted by 1, 2 or 3 substituents selected from the group consisting of the following (a) to (f);
(a) halogen,
(b) hydroxy,
(c) $C_{1-6}$ alkoxy,
(d) —$C(O)NR^{c1}R^{c2}$, wherein the $R^{c1}$ and the $R^{c2}$ are each independently hydrogen or $C_{1-6}$ alkyl,
(e) $C_{6-10}$ aryl, wherein the $C_{6-10}$ aryl is optionally substituted by 1, 2 or 3 substituents selected from the group consisting of
(i) halogen,
(ii) hydroxy,
(iii) $C_{1-6}$ alkyl,
(iv) $C_{1-6}$ alkoxy, and
(v) halo$C_{1-4}$ alkyl, and
(f) 5- or 6-membered heteroaryl containing 1, 2 or 3 nitrogen atoms, oxygen atoms or sulfur atoms, wherein the heteroaryl is optionally substituted by 1, 2 or 3 substituents selected from the group consisting of
(i) halogen,
(ii) hydroxy,
(iii) $C_{1-6}$ alkyl,
(iv) $C_{1-6}$ alkoxy, and
(v) halo$C_{1-4}$ alkyl, and
$R^4$ is
(1) hydrogen,
(2) halogen,
(3) $C_{1-6}$ alkyl or
(4) $C_{1-6}$ alkoxy,
$R^5$ is
(1) halogen,
(2) hydroxy,
(3) $C_{1-6}$ alkylsulfanyl,
(4) $C_{1-6}$ alkyl, wherein the $C_{1-6}$ alkyl is optionally substituted by 1, 2 or 3 substituents selected from the group consisting of halogen, $C_{6-10}$ aryl and $C_{1-6}$ alkoxy,
(5) $C_{3-7}$ cycloalkyl,
(6) —$OR^d$, wherein the $R^d$ is
(a) $C_{2-6}$ alkynyl,
(b) $C_{3-7}$ cycloalkyl optionally substituted by 1, 2 or 3 $C_{1-6}$ alkyls or (c) $C_{1-8}$ alkyl, wherein the $C_{1-8}$ alkyl is optionally substituted by 1, 2 or 3 substituents selected from the group consisting of the following (i) to (v);
  (i) halogen,
  (ii) $C_{6-10}$ aryl,
  (iii) $C_{1-6}$ alkoxy,
  (iv) $C_{3-7}$ cycloalkyl, wherein the $C_{3-7}$ cycloalkyl is optionally substituted by 1, 2 or 3 substituents selected from the group consisting of $C_{1-6}$ alkyl and haloC$_{1-4}$ alkyl, and
  (v) 4-, 5- or 6-membered saturated heterocyclyl containing 1, 2 or 3 nitrogen atoms, oxygen atoms or sulfur atoms, wherein the saturated heterocyclyl is optionally substituted by 1, 2 or 3 substituents selected from the group consisting of $C_{1-6}$ alkyl and haloC$_{1-4}$ alkyl or
(7) the formula:

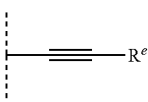

wherein $R^e$ is
(a) $C_{1-6}$ alkyl,
(b) $C_{3-7}$ cycloalkyl,
(c) 5- or 6-membered heteroaryl containing 1, 2 or 3 nitrogen atoms, oxygen atoms or sulfur atoms, or
(d) $C_{6-10}$ aryl, wherein the $C_{6-10}$ aryl is optionally substituted by 1, 2 or 3 substituents selected from the group consisting of
  (i) halogen,
  (ii) $C_{1-6}$ alkyl,
  (iii) haloC$_{1-4}$ alkyl,
  (iv) $C_{1-6}$ alkoxy, and
  (v) haloC$_{1-4}$ alkoxy, and m1 is 0, 1, 2 or 3 and, when m1 is 2 or 3, each $R^5$ is selected independently,
excluding 4,6-bis-(2,5-dimethyl-phenyl)-1,3,5-triazin-2-ol.

2. The compound according to claim 1 or a pharmaceutically acceptable salt thereof, wherein $R^1$ is
(1) chloro,
(2) methyl,
(3) cyano or
(4) trifluoromethyl.

3. The compound according to claim 1 or a pharmaceutically acceptable salt thereof, wherein $R^4$ is hydrogen.

4. The compound according to claim 1 or a pharmaceutically acceptable salt thereof, wherein $R^3$ is
(1) halogen,
(2) hydroxy,
(3) $C_{1-6}$ alkyl or
(4) —OR$^c$, wherein the $R^c$ is $C_{1-6}$ alkyl optionally substituted by 1, 2 or 3 substituents selected from the group consisting of the following (a) to (f)
  (a) halogen,
  (b) hydroxy,
  (c) $C_{1-6}$ alkoxy,
  (d) —C(O)NR$^{c1}$R$^{c2}$, wherein the R$^{c1}$ and the R$^{c2}$ are each independently hydrogen or $C_{1-6}$ alkyl,
  (e) phenyl, wherein the phenyl is optionally substituted by 1, 2 or 3 substituents selected from the group consisting of
    (i) halogen,
    (ii) hydroxy,
    (iii) $C_{1-6}$ alkyl,
    (iv) $C_{1-6}$ alkoxy, and
    (v) haloC$_{1-4}$ alkyl, and
  (f) pyridyl, wherein the pyridyl is optionally substituted by 1, 2 or 3 substituents selected from the group consisting of
    (i) halogen,
    (ii) hydroxy,
    (iii) $C_{1-6}$ alkyl,
    (iv) $C_{1-6}$ alkoxy, and
    (v) haloC$_{1-4}$ alkyl.

5. The compound according to claim 1 or a pharmaceutically acceptable salt thereof, wherein m1 is 1, and $R^5$ is the formula:

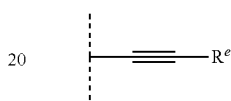

wherein $R^e$ is as defined in claim 1.

6. A pharmaceutical composition comprising the compound according to claim 1 or a pharmaceutically acceptable salt thereof, and a pharmaceutically acceptable carrier.

7. A method of inhibiting mPGES-1, comprising administering a therapeutically effective amount of the compound according to claim 1 or a pharmaceutically acceptable salt thereof to a human in need thereof.

8. A method of treating pain, rheumatism, fever, osteoarthritis, glaucoma, or ocular hypertension, comprising administering a therapeutically effective amount of the compound according to claim 1 or a pharmaceutically acceptable salt thereof to a human in need thereof.

9. A compound of the following formula or a pharmaceutically acceptable salt thereof:

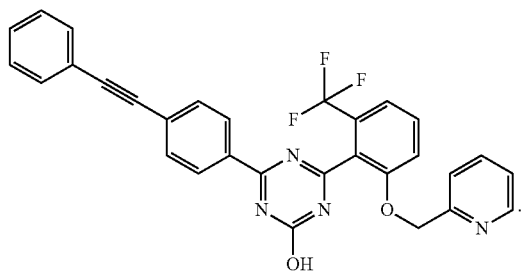 [SMILES: Oc1nc(-c2ccc(C#Cc3ccccc3)cc2)nc(-c2c(OCc3ccccn3)cccc2C(F)(F)F)n1]

10. A compound of the following formula:

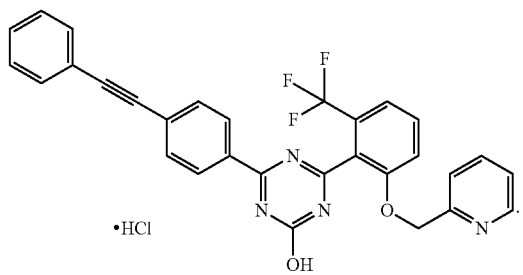 [SMILES: Oc1nc(-c2ccc(C#Cc3ccccc3)cc2)nc(-c2c(OCc3ccccn3)cccc2C(F)(F)F)n1 ; Cl]

* * * * *